(12) United States Patent
Haider et al.

(10) Patent No.: US 10,105,149 B2
(45) Date of Patent: Oct. 23, 2018

(54) ON-BOARD TOOL TRACKING SYSTEM AND METHODS OF COMPUTER ASSISTED SURGERY

(71) Applicants: Board of Regents of the University of Nebraska, Lincoln, NE (US); TRAK SURGICAL, INC., San Jose, CA (US)

(72) Inventors: Hani Haider, Carter Lake, IA (US); Ibrahim Al-Shawi, Amman (JO); Osvaldo Andres Barrera, Omaha, NE (US); David Scott Saunders, Redwood City, CA (US)

(73) Assignees: Board of Regents of the University of Nebraska, Lincoln, NE (US); Trak Surgical, Inc., San Jose, CA (US)

( * ) Notice: Subject to any disclaimer, the term of this patent is extended or adjusted under 35 U.S.C. 154(b) by 217 days.

(21) Appl. No.: 14/776,755

(22) PCT Filed: Mar. 14, 2014

(86) PCT No.: PCT/US2014/029334
§ 371 (c)(1),
(2) Date: Sep. 15, 2015

(87) PCT Pub. No.: WO2014/144780
PCT Pub. Date: Sep. 8, 2014

(65) Prior Publication Data
US 2016/0022374 A1   Jan. 28, 2016

Related U.S. Application Data

(60) Provisional application No. 61/799,656, filed on Mar. 15, 2013.

(51) Int. Cl.
*A61B 19/00* (2006.01)
*A61B 17/16* (2006.01)
(Continued)

(52) U.S. Cl.
CPC .......... *A61B 17/17* (2013.01); *A61B 17/142* (2016.11); *A61B 34/20* (2016.02); *A61B 17/16* (2013.01);
(Continued)

(58) Field of Classification Search
CPC .......................... A61B 17/17–17/1796; A61B 34/20–2034/258
See application file for complete search history.

(56) References Cited

U.S. PATENT DOCUMENTS

| 3,730,277 A | 5/1973 | Brugler |
| 3,752,161 A | 8/1973 | Bent |

(Continued)

FOREIGN PATENT DOCUMENTS

| CN | 1162251 A | 10/1997 |
| CN | 1689518 A | 11/2005 |

(Continued)

OTHER PUBLICATIONS

Agus et al.; A multiprocessor decoupled system for the simulation of temporal bone surgery; Computing and Visualization in Science, vol. 5, Issue 1, pp. 35-43; Jul. 2002 (author manuscript, 10 pgs.).

(Continued)

*Primary Examiner* — Zade Coley
(74) *Attorney, Agent, or Firm* — Shay Glenn LLP

(57) ABSTRACT

A number of improvements are provided relating to computer aided surgery utilizing an on tool tracking system. The various improvements relate generally to both the methods used during computer aided surgery and the devices used during such procedures. Other improvements relate to the structure of the tools used during a procedure and how the tools can be controlled using the OTT device. Still other improvements relate to methods of providing feedback during a procedure to improve either the efficiency or (Continued)

OTT ON SURGICAL TOOL quality, or both, for a procedure including the rate of and type of data processed depending upon a CAS mode.

20 Claims, 214 Drawing Sheets

(51) Int. Cl.
*A61B 17/17* (2006.01)
*A61B 17/14* (2006.01)
A61B 17/00 (2006.01)
A61B 34/20 (2016.01)
A61B 34/10 (2016.01)

(52) U.S. Cl.
CPC ............... *A61B 2017/00734* (2013.01); *A61B 2034/105* (2016.02); *A61B 2034/2055* (2016.02)

(56) References Cited

U.S. PATENT DOCUMENTS

| | | | |
|---|---|---|---|
| 3,932,923 A | 1/1976 | DiMatteo | |
| 4,089,084 A | 5/1978 | Droz | |
| 4,204,145 A | 5/1980 | Hevenor, Jr. et al. | |
| 4,269,615 A | 5/1981 | Zboralski et al. | |
| 4,291,708 A | 9/1981 | Frei et al. | |
| 4,337,566 A | 7/1982 | DiMatteo et al. | |
| 4,423,075 A | 12/1983 | Dvornik et al. | |
| 4,436,684 A | 3/1984 | White | |
| 4,458,694 A | 7/1984 | Sollish et al. | |
| 4,476,609 A | 10/1984 | Loudin | |
| 4,640,120 A | 2/1987 | Garritano et al. | |
| 4,660,573 A | 4/1987 | Brumbach | |
| 4,660,970 A | 4/1987 | Ferrano | |
| 4,668,087 A | 5/1987 | Strandell et al. | |
| 4,725,965 A | 2/1988 | Keenan | |
| 4,742,819 A | 5/1988 | George | |
| 4,899,095 A | 2/1990 | Kishi et al. | |
| 4,907,169 A | 3/1990 | Lovoi | |
| 4,963,147 A | 10/1990 | Agee et al. | |
| 4,977,886 A | 12/1990 | Takehana et al. | |
| 4,995,877 A | 2/1991 | Ams et al. | |
| 5,006,999 A | 4/1991 | Kuno et al. | |
| 5,086,401 A | 2/1992 | Glassman et al. | |
| 5,152,799 A | 10/1992 | Lyons | |
| 5,188,093 A | 2/1993 | Lafferty et al. | |
| 5,190,549 A | 3/1993 | Miller et al. | |
| 5,190,550 A | 3/1993 | Miller et al. | |
| 5,230,623 A | 7/1993 | Guthrie et al. | |
| 5,261,404 A | 11/1993 | Mick et al. | |
| 5,263,988 A | 11/1993 | Huebner | |
| 5,283,642 A | 2/1994 | Sarr | |
| 5,321,353 A | 6/1994 | Furness | |
| 5,383,454 A | 1/1995 | Bucholz | |
| 5,389,101 A | 2/1995 | Heilbrun et al. | |
| 5,411,500 A | 5/1995 | Lafferty et al. | |
| 5,429,502 A | 7/1995 | Cooper et al. | |
| 5,433,717 A | 7/1995 | Rubinsky et al. | |
| 5,449,363 A | 9/1995 | Brust et al. | |
| 5,458,443 A | 10/1995 | Belge et al. | |
| 5,524,180 A | 6/1996 | Wang et al. | |
| 5,548,694 A | 8/1996 | Gibson | |
| 5,562,448 A | 10/1996 | Mushabac | |
| 5,601,561 A | 2/1997 | Terry et al. | |
| 5,603,318 A | 2/1997 | Heilbrun et al. | |
| 5,611,025 A | 3/1997 | Lorensen et al. | |
| 5,617,857 A | 4/1997 | Chader et al. | |
| 5,622,170 A | 4/1997 | Schulz | |
| 5,626,594 A | 5/1997 | Smith | |
| 5,632,758 A | 5/1997 | Sklar | |
| 5,668,061 A | 9/1997 | Herko et al. | |
| 5,669,921 A | 9/1997 | Berman et al. | |
| 5,676,673 A | 10/1997 | Ferre et al. | |
| 5,682,886 A | 11/1997 | Delp et al. | |
| 5,688,281 A | 11/1997 | Cripe et al. | |
| 5,694,013 A | 12/1997 | Stewart et al. | |
| 5,706,408 A | 1/1998 | Pryor | |
| 5,715,836 A | 2/1998 | Kliegis et al. | |
| 5,725,580 A | 3/1998 | Cloutier et al. | |
| 5,732,992 A | 3/1998 | Mauldin | |
| 5,735,283 A | 4/1998 | Snook | |
| 5,740,802 A | 4/1998 | Nafis et al. | |
| 5,748,767 A | 5/1998 | Raab | |
| 5,751,011 A | 5/1998 | McLaughlin et al. | |
| RE35,816 E | 6/1998 | Schulz | |
| 5,769,087 A | 6/1998 | Westphal et al. | |
| 5,769,092 A | 6/1998 | Williamson | |
| 5,776,136 A | 7/1998 | Sahay et al. | |
| 5,777,720 A | 7/1998 | Shapiro et al. | |
| 5,781,195 A | 7/1998 | Marvin | |
| 5,788,636 A | 8/1998 | Curley | |
| 5,792,147 A | 8/1998 | Evans et al. | |
| 5,806,518 A | 9/1998 | Mittelstadt | |
| 5,817,105 A | 10/1998 | Van Der Brug | |
| 5,820,627 A | 10/1998 | Rosen et al. | |
| 5,824,085 A | 10/1998 | Sahay et al. | |
| 5,827,178 A | 10/1998 | Berall | |
| 5,838,882 A | 11/1998 | Gan et al. | |
| 5,846,244 A | 12/1998 | Cripe | |
| 5,880,976 A | 3/1999 | DiGioia, III et al. | |
| 5,882,206 A | 3/1999 | Gillio | |
| 5,902,239 A | 5/1999 | Buurman | |
| 5,907,395 A | 5/1999 | Schulz et al. | |
| 5,920,395 A | 7/1999 | Schulz | |
| 5,921,992 A | 7/1999 | Costales et al. | |
| 5,925,064 A | 7/1999 | Meyers et al. | |
| 5,928,137 A | 7/1999 | Green | |
| 5,951,475 A | 9/1999 | Gueziec et al. | |
| 5,954,648 A | 9/1999 | Van Der Brug | |
| 5,956,253 A | 9/1999 | Gottschalk | |
| 5,971,767 A | 10/1999 | Kaufman et al. | |
| 5,973,678 A | 10/1999 | Stewart et al. | |
| 5,987,960 A | 11/1999 | Messner et al. | |
| 5,995,738 A | 11/1999 | DiGioia, III et al. | |
| 6,002,859 A | 12/1999 | DiGioia, III et al. | |
| 6,003,415 A | 12/1999 | Turner et al. | |
| 6,006,126 A | 12/1999 | Cosman | |
| 6,006,127 A | 12/1999 | Van Der Brug et al. | |
| 6,011,581 A | 1/2000 | Swift et al. | |
| 6,014,145 A | 1/2000 | Bardon et al. | |
| 6,021,343 A | 2/2000 | Foley et al. | |
| 6,033,415 A | 3/2000 | Mittelstadt et al. | |
| 6,038,467 A | 3/2000 | De Bliek et al. | |
| 6,054,992 A | 4/2000 | Gibson | |
| 6,059,494 A | 5/2000 | Susnjara | |
| 6,063,095 A | 5/2000 | Wang et al. | |
| 6,069,634 A | 5/2000 | Gibson | |
| 6,080,162 A | 6/2000 | Dye et al. | |
| 6,080,181 A | 6/2000 | Jensen et al. | |
| 6,083,163 A | 7/2000 | Wegner et al. | |
| 6,084,979 A | 7/2000 | Kanade et al. | |
| 6,086,544 A | 7/2000 | Hibner et al. | |
| 6,091,453 A | 7/2000 | Coan et al. | |
| 6,094,007 A | 7/2000 | Faul et al. | |
| 6,097,168 A | 8/2000 | Katoh et al. | |
| 6,106,457 A | 8/2000 | Perkins et al. | |
| 6,112,113 A | 8/2000 | Van Der Brug et al. | |
| 6,120,462 A | 9/2000 | Hibner et al. | |
| 6,131,097 A | 10/2000 | Peurach et al. | |
| 6,141,104 A | 10/2000 | Schulz et al. | |
| 6,151,009 A | 11/2000 | Kanade et al. | |
| 6,158,136 A | 12/2000 | Gotz et al. | |
| 6,159,200 A | 12/2000 | Verdura et al. | |
| 6,167,292 A | 12/2000 | Badano et al. | |
| 6,167,295 A | 12/2000 | Cosman | |
| 6,167,296 A | 12/2000 | Shahidi | |
| 6,176,837 B1 | 1/2001 | Foxtin | |
| 6,187,012 B1 | 2/2001 | Masini | |
| 6,190,395 B1 | 2/2001 | Williams | |
| 6,192,777 B1 | 2/2001 | Williams et al. | |
| 6,198,794 B1 | 3/2001 | Peshkin et al. | |
| 6,203,497 B1 | 3/2001 | Dekel et al. | |
| 6,205,411 B1 | 3/2001 | DiGioia, III et al. | |

(56) References Cited

U.S. PATENT DOCUMENTS

| | | |
|---|---|---|
| 6,214,018 B1 | 4/2001 | Kreizman et al. |
| 6,216,029 B1 | 4/2001 | Paltieli |
| 6,226,548 B1 | 5/2001 | Foley et al. |
| 6,228,089 B1 | 5/2001 | Wahrburg |
| 6,236,875 B1 | 5/2001 | Bucholz et al. |
| 6,245,084 B1 | 6/2001 | Mark et al. |
| 6,262,738 B1 | 7/2001 | Gibson et al. |
| 6,263,230 B1 | 7/2001 | Haynor et al. |
| 6,273,862 B1 | 8/2001 | Privitera et al. |
| 6,285,902 B1 | 9/2001 | Kienzle, III et al. |
| 6,298,262 B1 | 10/2001 | Franck et al. |
| 6,314,310 B1 | 11/2001 | Ben Haim et al. |
| 6,314,311 B1 | 11/2001 | Williams et al. |
| 6,317,616 B1 | 11/2001 | Glossop |
| 6,319,286 B1 | 11/2001 | Fernandez et al. |
| 6,322,567 B1 | 11/2001 | Mittelstadt et al. |
| 6,329,778 B1 | 12/2001 | Culp et al. |
| 6,332,891 B1 | 12/2001 | Himes |
| 6,336,931 B1 | 1/2002 | Hsu et al. |
| 6,347,460 B1 | 2/2002 | Forrer et al. |
| 6,351,573 B1 | 2/2002 | Schneider |
| 6,368,354 B2 | 4/2002 | Burstein et al. |
| 6,390,982 B1 | 5/2002 | Bova et al. |
| 6,423,063 B1 | 7/2002 | Bonutti |
| 6,424,885 B1 | 7/2002 | Niemeyer et al. |
| 6,428,547 B1 | 8/2002 | Vilsmeier et al. |
| 6,430,434 B1 | 8/2002 | Mittelstadt |
| 6,432,112 B2 | 8/2002 | Brock et al. |
| 6,434,416 B1 | 8/2002 | Mizoguchi et al. |
| 6,442,416 B1 | 8/2002 | Schultz |
| 6,442,417 B1 | 8/2002 | Shahidi et al. |
| 6,450,978 B1 | 9/2002 | Brosseau et al. |
| 6,453,190 B1 | 9/2002 | Acker et al. |
| 6,456,868 B2 | 9/2002 | Saito et al. |
| 6,468,289 B1 | 10/2002 | Bonutti |
| 6,470,207 B1 | 10/2002 | Simon |
| 6,474,159 B1 | 11/2002 | Foxlin et al. |
| 6,478,802 B2 | 11/2002 | Kienzle, III et al. |
| 6,491,701 B2 | 12/2002 | Tierney et al. |
| 6,497,134 B1 | 12/2002 | Faul et al. |
| 6,501,997 B1 | 12/2002 | Kakino |
| 6,503,195 B1 | 1/2003 | Keller et al. |
| 6,503,267 B2 | 1/2003 | Bonutti et al. |
| 6,503,277 B2 | 1/2003 | Bonutti |
| 6,511,323 B1 | 1/2003 | Wilkinson |
| 6,514,259 B2 | 2/2003 | Picard et al. |
| 6,520,228 B1 | 2/2003 | Kennedy et al. |
| 6,522,906 B1 | 2/2003 | Salisbury et al. |
| 6,529,765 B1 | 3/2003 | Franck et al. |
| 6,546,277 B1 | 4/2003 | Franck et al. |
| 6,546,279 B1 | 4/2003 | Bova et al. |
| 6,550,997 B1 | 4/2003 | King et al. |
| 6,552,722 B1 | 4/2003 | Shih et al. |
| 6,575,969 B1 | 6/2003 | Rittman, III et al. |
| 6,575,982 B1 | 6/2003 | Bonutti |
| 6,584,339 B2 | 6/2003 | Galloway et al. |
| 6,591,698 B1 | 7/2003 | Carlsson et al. |
| 6,599,247 B1 * | 7/2003 | Stetten .................. A61B 8/00 128/916 |
| 6,608,688 B1 | 8/2003 | Faul et al. |
| 6,620,181 B1 | 9/2003 | Bonutti |
| 6,620,198 B2 | 9/2003 | Burstein et al. |
| 6,635,073 B2 | 10/2003 | Bonutti |
| 6,638,233 B2 | 10/2003 | Caryl et al. |
| 6,640,127 B1 | 10/2003 | Kosaka et al. |
| 6,640,128 B2 | 10/2003 | Vilsmeier et al. |
| 6,647,840 B2 | 11/2003 | Luik |
| 6,659,939 B2 | 12/2003 | Moll et al. |
| 6,662,036 B2 | 12/2003 | Cosman |
| 6,669,635 B2 | 12/2003 | Kessman et al. |
| 6,669,710 B2 | 12/2003 | Moutafis et al. |
| 6,676,669 B2 | 1/2004 | Charles et al. |
| 6,678,552 B2 | 1/2004 | Pearlman |
| 6,681,129 B2 | 1/2004 | Matsuzaki et al. |
| 6,685,711 B2 | 2/2004 | Axelson, Jr. et al. |
| 6,690,964 B2 | 2/2004 | Bieger et al. |
| 6,702,821 B2 | 3/2004 | Bonutti |
| 6,711,432 B1 | 3/2004 | Krause et al. |
| 6,718,194 B2 | 4/2004 | Kienzle, III |
| 6,725,080 B2 | 4/2004 | Melkent et al. |
| 6,730,128 B2 | 5/2004 | Burstein |
| 6,738,657 B1 | 5/2004 | Franklin et al. |
| 6,747,651 B1 | 6/2004 | Tan et al. |
| 6,757,582 B2 | 6/2004 | Brisson et al. |
| 6,770,078 B2 | 8/2004 | Bonutti |
| 6,780,007 B1 | 8/2004 | Coffin |
| 6,782,287 B2 | 8/2004 | Grzeszczuk et al. |
| 6,788,999 B2 | 9/2004 | Green |
| 6,796,988 B2 | 9/2004 | Melkent et al. |
| 6,816,755 B2 | 11/2004 | Habibi et al. |
| 6,823,207 B1 | 11/2004 | Jensen et al. |
| 6,827,723 B2 | 12/2004 | Carson |
| 6,829,384 B2 | 12/2004 | Schneiderman et al. |
| 6,837,892 B2 | 1/2005 | Shoham |
| 6,847,394 B1 | 1/2005 | Hansen et al. |
| 6,859,661 B2 | 2/2005 | Tuke |
| 6,892,090 B2 | 5/2005 | Verard et al. |
| 6,917,827 B2 | 7/2005 | Kienzle, III |
| 6,920,347 B2 | 7/2005 | Simon et al. |
| 6,923,817 B2 | 8/2005 | Carson et al. |
| 6,932,823 B2 | 8/2005 | Grimm et al. |
| 6,947,786 B2 | 9/2005 | Simon et al. |
| 6,960,894 B2 | 11/2005 | Carusillo et al. |
| 6,963,792 B1 | 11/2005 | Green |
| 6,977,356 B2 | 12/2005 | Vaidyanathan et al. |
| 6,978,167 B2 | 12/2005 | Dekel et al. |
| 6,980,229 B1 | 12/2005 | Ebersole |
| 6,990,368 B2 | 1/2006 | Simon et al. |
| 6,993,374 B2 | 1/2006 | Sasso |
| 6,994,004 B2 | 2/2006 | Gass et al. |
| 7,005,606 B2 | 2/2006 | Legge et al. |
| 7,022,123 B2 | 4/2006 | Heldreth |
| 7,027,083 B2 | 4/2006 | Kanade et al. |
| 7,032,458 B2 | 4/2006 | Tanaka |
| 7,034,821 B2 | 4/2006 | Bamberg |
| RE39,102 E | 5/2006 | Schulz et al. |
| 7,084,867 B1 | 8/2006 | Ho et al. |
| 7,102,666 B2 | 9/2006 | Kanade et al. |
| 7,104,996 B2 | 9/2006 | Bonutti |
| 7,106,361 B2 | 9/2006 | Kanade et al. |
| 7,107,091 B2 | 9/2006 | Jutras et al. |
| 7,130,676 B2 | 10/2006 | Barrick |
| 7,139,601 B2 | 11/2006 | Bucholz et al. |
| 7,166,114 B2 | 1/2007 | Moctezuma De La Barrera et al. |
| 7,203,277 B2 | 4/2007 | Birkenbach et al. |
| 7,204,805 B2 | 4/2007 | Dean |
| 7,206,626 B2 | 4/2007 | Quaid et al. |
| 7,206,627 B2 | 4/2007 | Abovitz et al. |
| 7,213,598 B2 | 5/2007 | Zeiss et al. |
| 7,217,276 B2 | 5/2007 | Henderson et al. |
| 7,220,283 B2 | 5/2007 | Terrill |
| 7,226,456 B2 | 6/2007 | O'Neil et al. |
| 7,232,409 B2 | 6/2007 | Hale et al. |
| 7,239,940 B2 | 7/2007 | Wang et al. |
| 7,258,668 B2 | 8/2007 | Hirooka et al. |
| 7,302,288 B1 | 11/2007 | Schellenberg |
| 7,313,430 B2 | 12/2007 | Urquhart et al. |
| 7,317,955 B2 | 1/2008 | McGreevy |
| 7,324,915 B2 | 1/2008 | Altmann et al. |
| 7,361,018 B2 | 4/2008 | Imgrund et al. |
| 7,366,562 B2 | 4/2008 | Dukesherer et al. |
| 7,371,068 B2 | 5/2008 | Lloyd et al. |
| 7,377,429 B2 | 5/2008 | Anderson et al. |
| 7,377,924 B2 | 5/2008 | Raistrick et al. |
| 7,383,073 B1 | 6/2008 | Abovitz et al. |
| 7,399,946 B2 | 7/2008 | Hertzberg et al. |
| 7,422,605 B2 | 9/2008 | Burstein et al. |
| 7,463,823 B2 | 12/2008 | Birkenbach et al. |
| 7,485,882 B2 | 2/2009 | Zombo et al. |
| 7,492,930 B2 | 2/2009 | Leitner et al. |
| 7,509,899 B2 | 3/2009 | Gass et al. |
| 7,556,652 B2 | 7/2009 | Angibaud et al. |
| 7,558,617 B2 | 7/2009 | Vilsmeier |
| 7,559,940 B2 | 7/2009 | McGuire et al. |

(56) References Cited

U.S. PATENT DOCUMENTS

| | | |
|---|---|---|
| 7,561,733 B2 | 7/2009 | Vilsmeier et al. |
| 7,567,834 B2 | 7/2009 | Clayton et al. |
| 7,570,986 B2 | 8/2009 | Huang et al. |
| 7,574,250 B2 | 8/2009 | Niemeyer |
| 7,594,933 B2 | 9/2009 | Kammerzell et al. |
| 7,599,730 B2 | 10/2009 | Hunter et al. |
| 7,636,595 B2 | 12/2009 | Marquart et al. |
| 7,638,958 B2 | 12/2009 | Philipp et al. |
| 7,641,660 B2 | 1/2010 | Lakin et al. |
| 7,643,862 B2 | 1/2010 | Schoenefeld |
| 7,657,300 B2 | 2/2010 | Hunter et al. |
| 7,665,647 B2 | 2/2010 | Shelton, IV et al. |
| 7,697,972 B2 | 4/2010 | Verard et al. |
| 7,697,973 B2 | 4/2010 | Strommer et al. |
| 7,706,683 B2 | 4/2010 | Rossner et al. |
| 7,708,782 B2 | 5/2010 | Burstein et al. |
| 7,715,602 B2 | 5/2010 | Richard |
| 7,726,564 B2 | 6/2010 | Goldbach |
| 7,728,868 B2 | 6/2010 | Razzaque et al. |
| 7,747,311 B2 | 6/2010 | Quaid et al. |
| 7,747,312 B2 | 6/2010 | Barrick et al. |
| 7,758,495 B2 | 7/2010 | Pease et al. |
| 7,760,909 B2 | 7/2010 | Manus |
| 7,766,971 B2 | 8/2010 | Gladdish et al. |
| 7,771,444 B2 | 8/2010 | Patel et al. |
| 7,774,044 B2 | 8/2010 | Sauer et al. |
| 7,794,396 B2 | 9/2010 | Gattani et al. |
| 7,796,789 B2 | 9/2010 | Salgo et al. |
| 7,835,778 B2 | 11/2010 | Foley et al. |
| 7,835,785 B2 | 11/2010 | Scully et al. |
| 7,837,621 B2 | 11/2010 | Krause et al. |
| 7,853,058 B2 | 12/2010 | Gauldie et al. |
| 7,857,756 B2 | 12/2010 | Warren et al. |
| 7,876,942 B2 | 1/2011 | Gilboa |
| 7,885,705 B2 | 2/2011 | Murphy |
| 7,894,872 B2 | 2/2011 | Sherman |
| 7,909,831 B2 | 3/2011 | Axelson, Jr. et al. |
| 7,933,341 B2 | 4/2011 | Agazzi et al. |
| 7,933,782 B2 | 4/2011 | Reiner |
| 7,935,134 B2 | 5/2011 | Reglos et al. |
| 7,937,277 B2 | 5/2011 | Marx |
| 7,949,544 B2 | 5/2011 | Miglietta et al. |
| 7,962,348 B2 | 6/2011 | Dew et al. |
| 7,983,733 B2 | 7/2011 | Viswanathan |
| 7,987,001 B2 | 7/2011 | Teichman et al. |
| 7,993,353 B2 | 8/2011 | Rossner et al. |
| 8,007,437 B2 | 8/2011 | Lombaert et al. |
| 8,010,180 B2 | 8/2011 | Quaid et al. |
| 8,010,181 B2 | 8/2011 | Smith et al. |
| 8,025,680 B2 | 9/2011 | Hayes et al. |
| 8,031,190 B2 | 10/2011 | Smith et al. |
| 8,041,459 B2 | 10/2011 | Sutherland et al. |
| 8,046,050 B2 | 10/2011 | Govari et al. |
| 8,050,938 B1 | 11/2011 | Green et al. |
| 8,057,482 B2 | 11/2011 | Stone et al. |
| 8,074,662 B2 | 12/2011 | Hunter et al. |
| 8,095,237 B2 | 1/2012 | Habibi et al. |
| 8,096,996 B2 | 1/2012 | Gutierrez et al. |
| 8,108,025 B2 | 1/2012 | Csavoy et al. |
| 8,114,086 B2 | 2/2012 | Claypool et al. |
| 8,114,092 B2 | 2/2012 | Altarac et al. |
| 8,116,847 B2 | 2/2012 | Gattani et al. |
| 8,117,549 B2 | 2/2012 | Reiner |
| 8,123,675 B2 | 2/2012 | Funda et al. |
| 8,126,226 B2 | 2/2012 | Bernard et al. |
| 8,131,343 B2 | 3/2012 | Burgkart |
| 8,147,503 B2 | 4/2012 | Zhao et al. |
| 8,157,826 B2 | 4/2012 | Deng et al. |
| 8,160,325 B2 | 4/2012 | Zug et al. |
| 8,160,677 B2 | 4/2012 | Gielen et al. |
| 8,165,658 B2 | 4/2012 | Waynik et al. |
| 8,180,429 B2 | 5/2012 | Sasso |
| 8,193,931 B2 | 6/2012 | Rapaport et al. |
| 8,206,293 B2 | 6/2012 | Reglos et al. |
| 8,207,863 B2 | 6/2012 | Neubauer et al. |
| 8,224,024 B2 | 7/2012 | Foxlin et al. |
| 8,226,690 B2 | 7/2012 | Altarac et al. |
| 8,229,548 B2 | 7/2012 | Frangioni |
| 8,233,963 B2 | 7/2012 | Hartmann et al. |
| 8,238,631 B2 | 8/2012 | Hartmann et al. |
| 8,241,366 B2 | 8/2012 | Roche et al. |
| 8,248,413 B2 | 8/2012 | Gattani et al. |
| 8,248,414 B2 | 8/2012 | Gattani et al. |
| 8,265,790 B2 | 9/2012 | Amiot et al. |
| 8,267,969 B2 | 9/2012 | Altarac et al. |
| 8,282,487 B2 | 10/2012 | Wilson et al. |
| 8,285,363 B2 | 10/2012 | Malackowski et al. |
| 8,287,600 B2 | 10/2012 | Angibaud |
| 8,290,570 B2 | 10/2012 | Hoppe et al. |
| 8,311,611 B2 | 11/2012 | Csavoy et al. |
| 8,315,689 B2 | 11/2012 | Jenkins et al. |
| 8,317,869 B2 | 11/2012 | Cloutier et al. |
| 8,320,612 B2 | 11/2012 | Knobel et al. |
| 8,320,996 B2 | 11/2012 | Panasyuk et al. |
| 8,323,320 B2 | 12/2012 | Lowry et al. |
| 8,337,563 B2 | 12/2012 | Roche et al. |
| 8,494,608 B2 | 7/2013 | Markowitz et al. |
| 8,532,734 B2 | 9/2013 | Markowitz et al. |
| 8,560,047 B2 | 10/2013 | Haider et al. |
| 8,771,304 B1 | 7/2014 | Jurbala |
| 8,961,536 B2 | 2/2015 | Nikon et al. |
| 2001/0034530 A1* | 10/2001 | Malackowski ........ A61B 90/36 606/130 |
| 2001/0053907 A1 | 12/2001 | Ota |
| 2002/0016624 A1 | 2/2002 | Patterson et al. |
| 2002/0019644 A1 | 2/2002 | Hastings et al. |
| 2002/0040220 A1 | 4/2002 | Zvuloni et al. |
| 2002/0082865 A1 | 6/2002 | Bianco et al. |
| 2002/0122038 A1 | 9/2002 | Cowperthwaite |
| 2002/0156365 A1 | 10/2002 | Tsekos |
| 2002/0170399 A1 | 11/2002 | Gass et al. |
| 2003/0004519 A1 | 1/2003 | Torode et al. |
| 2003/0069591 A1 | 4/2003 | Carson et al. |
| 2003/0076413 A1 | 4/2003 | Kanade et al. |
| 2003/0078485 A1 | 4/2003 | Hartlep |
| 2003/0153978 A1 | 8/2003 | Whiteside |
| 2003/0209096 A1* | 11/2003 | Pandey ................. A61B 90/36 73/865.9 |
| 2003/0210812 A1 | 11/2003 | Khamene et al. |
| 2003/0218720 A1 | 11/2003 | Morita et al. |
| 2003/0229279 A1 | 12/2003 | Amstutz et al. |
| 2004/0015070 A1 | 1/2004 | Liang et al. |
| 2004/0043368 A1 | 3/2004 | Hsieh et al. |
| 2004/0068173 A1 | 4/2004 | Viswanathan |
| 2004/0068187 A1 | 4/2004 | Krause et al. |
| 2004/0091462 A1 | 5/2004 | Lin et al. |
| 2004/0092933 A1 | 5/2004 | Shaolian et al. |
| 2004/0106916 A1* | 6/2004 | Quaid .................... A61B 34/71 606/1 |
| 2004/0138556 A1 | 7/2004 | Cosman |
| 2004/0171924 A1 | 9/2004 | Mire et al. |
| 2004/0201857 A1 | 10/2004 | Foxlin |
| 2005/0015005 A1 | 1/2005 | Kockro |
| 2005/0020909 A1* | 1/2005 | Moctezuma de la Barrera .......... A61B 17/62 600/424 |
| 2005/0065617 A1 | 3/2005 | Moctezuma de la Barrera et al. |
| 2005/0107920 A1 | 5/2005 | Ban et al. |
| 2005/0108052 A1 | 5/2005 | Omaboe |
| 2005/0116673 A1 | 6/2005 | Carl et al. |
| 2005/0119550 A1 | 6/2005 | Serra et al. |
| 2005/0131426 A1 | 6/2005 | Moctezuma de la Barrera et al. |
| 2005/0154296 A1 | 7/2005 | Lechner et al. |
| 2005/0156876 A1 | 7/2005 | Kong |
| 2005/0159759 A1 | 7/2005 | Harbaugh et al. |
| 2005/0192583 A1 | 9/2005 | Walker et al. |
| 2005/0197569 A1 | 9/2005 | McCombs |
| 2005/0215879 A1 | 9/2005 | Chuanggui |
| 2005/0216032 A1 | 9/2005 | Hayden |
| 2005/0228250 A1 | 10/2005 | Bitter et al. |
| 2005/0228266 A1 | 10/2005 | McCombs |
| 2005/0251030 A1 | 11/2005 | Azar et al. |
| 2005/0251065 A1 | 11/2005 | Henning et al. |
| 2005/0279368 A1 | 12/2005 | McCombs |

(56) References Cited

U.S. PATENT DOCUMENTS

| | | |
|---|---|---|
| 2005/0288575 A1 | 12/2005 | De La Barrera et al. |
| 2006/0011001 A1 | 1/2006 | Showalter |
| 2006/0063998 A1 | 3/2006 | von Jako et al. |
| 2006/0142656 A1 | 6/2006 | Malackowski et al. |
| 2006/0142739 A1 | 6/2006 | DiSilestro et al. |
| 2006/0176242 A1 | 8/2006 | Jaramaz et al. |
| 2006/0200025 A1 | 9/2006 | Elliott et al. |
| 2006/0224151 A1 | 10/2006 | Waaler |
| 2006/0235849 A1 | 10/2006 | Schmidt et al. |
| 2006/0241388 A1 | 10/2006 | Lavallee |
| 2006/0258938 A1 | 11/2006 | Hoffman et al. |
| 2006/0293557 A1 | 12/2006 | Chuanggui et al. |
| 2007/0018975 A1 | 1/2007 | Chuanggui et al. |
| 2007/0033073 A1 | 2/2007 | Tajaliawal et al. |
| 2007/0043375 A1 | 2/2007 | Anissian |
| 2007/0046661 A1 | 3/2007 | Ma et al. |
| 2007/0055131 A1 | 3/2007 | Deinzer et al. |
| 2007/0055142 A1 | 3/2007 | Webler |
| 2007/0066917 A1 | 3/2007 | Hodorek et al. |
| 2007/0118140 A1 | 5/2007 | Baur et al. |
| 2007/0142917 A1 | 6/2007 | Roche et al. |
| 2007/0161907 A1 | 7/2007 | Goldman et al. |
| 2007/0192133 A1 | 8/2007 | Morgan |
| 2007/0213692 A1 | 9/2007 | Neubauer et al. |
| 2007/0219559 A1 | 9/2007 | Heavener et al. |
| 2007/0219561 A1 | 9/2007 | Lavallee et al. |
| 2007/0225595 A1 | 9/2007 | Malackowski et al. |
| 2007/0236514 A1 | 10/2007 | Agusanto et al. |
| 2007/0238981 A1* | 10/2007 | Zhu .................. A61B 90/36 600/424 |
| 2007/0239159 A1 | 10/2007 | Altarac et al. |
| 2007/0244563 A1 | 10/2007 | Roche et al. |
| 2007/0270660 A1 | 11/2007 | Caylor et al. |
| 2007/0274577 A1 | 11/2007 | De Font Reaulx Rojas |
| 2007/0299334 A1 | 12/2007 | Vilsmeier |
| 2008/0004516 A1 | 1/2008 | DiSilvestro et al. |
| 2008/0004533 A1 | 1/2008 | Jansen et al. |
| 2008/0008366 A1 | 1/2008 | Desh et al. |
| 2008/0009697 A1* | 1/2008 | Haider .................. A61B 17/15 600/407 |
| 2008/0010706 A1 | 1/2008 | Moses et al. |
| 2008/0013809 A1 | 1/2008 | Zhu et al. |
| 2008/0051908 A1 | 2/2008 | Angibaud et al. |
| 2008/0077158 A1 | 3/2008 | Haider et al. |
| 2008/0077200 A1 | 3/2008 | Bendett et al. |
| 2008/0103509 A1 | 5/2008 | Goldbach |
| 2008/0109012 A1 | 5/2008 | Falco et al. |
| 2008/0123910 A1 | 5/2008 | Zhu |
| 2008/0125630 A1 | 5/2008 | Caylor |
| 2008/0132882 A1 | 6/2008 | DeMaria et al. |
| 2008/0132909 A1 | 6/2008 | Jascob |
| 2008/0147075 A1 | 6/2008 | Bonutti |
| 2008/0147529 A1 | 6/2008 | Kreiner et al. |
| 2008/0161682 A1 | 7/2008 | Kendrick et al. |
| 2008/0183068 A1 | 7/2008 | Carls et al. |
| 2008/0183074 A1 | 7/2008 | Carls et al. |
| 2008/0183188 A1 | 7/2008 | Carls et al. |
| 2008/0183190 A1 | 7/2008 | Adcox et al. |
| 2008/0183215 A1 | 7/2008 | Altarac et al. |
| 2008/0195109 A1 | 8/2008 | Hunter et al. |
| 2008/0200794 A1 | 8/2008 | Teichman et al. |
| 2008/0200926 A1 | 8/2008 | Verard et al. |
| 2008/0228195 A1 | 9/2008 | von Jako et al. |
| 2008/0235052 A1 | 9/2008 | Node-Langlois et al. |
| 2008/0243125 A1 | 10/2008 | Guzman et al. |
| 2008/0252726 A1 | 10/2008 | Chan et al. |
| 2008/0269596 A1 | 10/2008 | Revie et al. |
| 2008/0269755 A1 | 10/2008 | Malackowski et al. |
| 2008/0281989 A1 | 11/2008 | Hager et al. |
| 2008/0291219 A1 | 11/2008 | Morita et al. |
| 2008/0302226 A1 | 12/2008 | Fischer |
| 2008/0319313 A1 | 12/2008 | Boivin et al. |
| 2009/0017430 A1 | 1/2009 | Muller-Daniels et al. |
| 2009/0018465 A1 | 1/2009 | Hessel et al. |
| 2009/0024140 A1 | 1/2009 | Allen et al. |
| 2009/0036902 A1 | 2/2009 | DiMaio et al. |
| 2009/0051763 A1 | 2/2009 | Adler et al. |
| 2009/0118742 A1 | 5/2009 | Hartmann et al. |
| 2009/0124891 A1 | 5/2009 | Shechter et al. |
| 2009/0125047 A1 | 5/2009 | Reglos et al. |
| 2009/0143828 A1 | 6/2009 | Stad et al. |
| 2009/0183740 A1 | 7/2009 | Sheffer et al. |
| 2009/0187393 A1 | 7/2009 | Van Lierde et al. |
| 2009/0204222 A1 | 8/2009 | Burstein et al. |
| 2009/0216113 A1 | 8/2009 | Meier et al. |
| 2009/0228045 A1 | 9/2009 | Hayes et al. |
| 2009/0234360 A1 | 9/2009 | Alexander |
| 2009/0264940 A1 | 10/2009 | Beale et al. |
| 2009/0281419 A1 | 11/2009 | Troesken et al. |
| 2009/0285465 A1 | 11/2009 | Haimerl et al. |
| 2009/0299439 A1 | 12/2009 | Mire et al. |
| 2009/0309874 A1 | 12/2009 | Salganicoff et al. |
| 2009/0322867 A1 | 12/2009 | Carrey et al. |
| 2009/0326322 A1 | 12/2009 | Diolaiti |
| 2009/0326556 A1 | 12/2009 | Diolaiti et al. |
| 2010/0022871 A1 | 1/2010 | De Beni et al. |
| 2010/0030063 A1 | 2/2010 | Lee et al. |
| 2010/0036384 A1 | 2/2010 | Gorek et al. |
| 2010/0036393 A1 | 2/2010 | Unsworth |
| 2010/0036423 A1 | 2/2010 | Hayes et al. |
| 2010/0069758 A1 | 3/2010 | Barnes et al. |
| 2010/0094656 A1 | 4/2010 | Conant |
| 2010/0100081 A1 | 4/2010 | Tuma et al. |
| 2010/0114597 A1 | 5/2010 | Shreiber et al. |
| 2010/0130853 A1 | 5/2010 | Chandonnet et al. |
| 2010/0141961 A1 | 6/2010 | Knobel et al. |
| 2010/0156906 A1 | 6/2010 | Montgomery et al. |
| 2010/0174410 A1 | 7/2010 | Greer et al. |
| 2010/0174558 A1 | 7/2010 | Smith et al. |
| 2010/0179418 A1 | 7/2010 | Mueller et al. |
| 2010/0211179 A1 | 8/2010 | Angibaud et al. |
| 2010/0228117 A1 | 9/2010 | Hartmann |
| 2010/0231509 A1 | 9/2010 | Boillot et al. |
| 2010/0234857 A1 | 9/2010 | Itkowitz et al. |
| 2010/0241129 A1 | 9/2010 | Markey et al. |
| 2010/0245549 A1 | 9/2010 | Allen et al. |
| 2010/0249571 A1 | 9/2010 | Jensen et al. |
| 2010/0256504 A1 | 10/2010 | Moreau-Gaudry et al. |
| 2010/0262150 A1 | 10/2010 | Lian |
| 2010/0280363 A1 | 11/2010 | Skarda et al. |
| 2010/0292703 A1 | 11/2010 | Couture |
| 2011/0007069 A1 | 1/2011 | Lee |
| 2011/0009694 A1* | 1/2011 | Schultz .............. A61B 1/00052 600/109 |
| 2011/0015647 A1 | 1/2011 | Salisbury et al. |
| 2011/0026794 A1 | 2/2011 | Sundar et al. |
| 2011/0060341 A1 | 3/2011 | Angibaud et al. |
| 2011/0064286 A1 | 3/2011 | Chien et al. |
| 2011/0066143 A1 | 3/2011 | Bischoff |
| 2011/0119089 A1 | 5/2011 | Carlisle |
| 2011/0125149 A1 | 5/2011 | Ei-Galley et al. |
| 2011/0130761 A1 | 6/2011 | Plaskos et al. |
| 2011/0137156 A1 | 6/2011 | Razzaque et al. |
| 2011/0144658 A1 | 6/2011 | Wenderow et al. |
| 2011/0160569 A1 | 6/2011 | Cohen et al. |
| 2011/0160593 A1 | 6/2011 | Deno et al. |
| 2011/0161110 A1 | 6/2011 | Mau It |
| 2011/0166883 A1 | 7/2011 | Palmer et al. |
| 2011/0190637 A1 | 8/2011 | Knobel et al. |
| 2011/0224688 A1 | 9/2011 | Larkin et al. |
| 2011/0230894 A1 | 9/2011 | Simaan et al. |
| 2011/0242097 A1 | 10/2011 | Miyamoto |
| 2011/0257653 A1 | 10/2011 | Hughes et al. |
| 2011/0270084 A1 | 11/2011 | Choi et al. |
| 2011/0301654 A1 | 12/2011 | Wozencroft et al. |
| 2011/0301732 A1 | 12/2011 | Gao |
| 2012/0015329 A1 | 1/2012 | Gross et al. |
| 2012/0016269 A1 | 1/2012 | Moctezuma de la Barrera |
| 2012/0019511 A1 | 1/2012 | Chandrasekhar |
| 2012/0035417 A1 | 2/2012 | Möllstam et al. |
| 2012/0040305 A1 | 2/2012 | Karazivan et al. |
| 2012/0046521 A1 | 2/2012 | Hunter et al. |
| 2012/0046536 A1 | 2/2012 | Cheung et al. |
| 2012/0046668 A1 | 2/2012 | Gantes |

(56) References Cited

U.S. PATENT DOCUMENTS

| | | | |
|---|---|---|---|
| 2012/0046914 A1 | 2/2012 | Gao | |
| 2012/0078236 A1 | 3/2012 | Schoepp | |
| 2012/0087558 A1 | 4/2012 | Meyer | |
| 2012/0088965 A1* | 4/2012 | Stokes | A61B 1/00087 600/104 |
| 2012/0100517 A1 | 4/2012 | Bowditch et al. | |
| 2012/0101847 A1 | 4/2012 | Johnson et al. | |
| 2012/0108900 A1 | 5/2012 | Viola et al. | |
| 2012/0113223 A1 | 5/2012 | Hilliges et al. | |
| 2012/0120091 A1 | 5/2012 | Koudijs et al. | |
| 2012/0123418 A1 | 5/2012 | Giurgi et al. | |
| 2012/0143213 A1 | 6/2012 | Myrman | |
| 2012/0157841 A1 | 6/2012 | Glaenzer et al. | |
| 2012/0165652 A1 | 6/2012 | Dempsey | |
| 2012/0209392 A1 | 8/2012 | Angibaud et al. | |
| 2012/0215094 A1 | 8/2012 | Rahimian et al. | |
| 2012/0220859 A1 | 8/2012 | Amiot et al. | |
| 2012/0222323 A1 | 9/2012 | Tait | |
| 2012/0223970 A1 | 9/2012 | Cortés Provencio | |
| 2012/0226150 A1 | 9/2012 | Balicki et al. | |
| 2012/0232377 A1 | 9/2012 | Nottmeier | |
| 2012/0253200 A1* | 10/2012 | Stolka | A61B 1/041 600/459 |
| 2012/0259204 A1 | 10/2012 | Carrat et al. | |
| 2012/0274631 A1 | 11/2012 | Friedland et al. | |
| 2012/0289825 A1 | 11/2012 | Rai et al. | |
| 2013/0010081 A1 | 1/2013 | Tenney et al. | |
| 2013/0030250 A1 | 1/2013 | Findeisen et al. | |
| 2013/0039732 A1 | 2/2013 | Brewer et al. | |
| 2013/0041292 A1 | 2/2013 | Cunningham | |
| 2013/0116574 A1 | 5/2013 | Knobel et al. | |
| 2014/0030669 A1 | 1/2014 | Hey et al. | |
| 2014/0039520 A1 | 2/2014 | Haider et al. | |
| 2014/0107471 A1 | 4/2014 | Haider et al. | |
| 2014/0236159 A1 | 8/2014 | Haider et al. | |
| 2017/0281280 A1 | 10/2017 | Haider et al. | |

FOREIGN PATENT DOCUMENTS

| | | | |
|---|---|---|---|
| CN | 1806771 A | 7/2006 | |
| CN | 101011280 A | 8/2007 | |
| CN | 101797182 A | 8/2010 | |
| CN | 102905641 A | 1/2013 | |
| DE | 10008806 | 12/2001 | |
| DE | 20321068 U1 | 1/2006 | |
| DE | 202005015438 | 3/2006 | |
| EP | 0674881 B1 | 5/2000 | |
| EP | 1219259 B1 | 7/2003 | |
| EP | 1374793 A1 | 1/2004 | |
| EP | 1504726 A1 | 2/2005 | |
| EP | 1442729 B1 | 3/2006 | |
| EP | 1994882 A1 | 11/2008 | |
| EP | 2138280 B1 | 3/2011 | |
| EP | 1404212 B1 | 4/2011 | |
| EP | 1153292 B1 | 8/2011 | |
| EP | 1523951 B1 | 10/2012 | |
| EP | 2508118 A1 | 10/2012 | |
| GB | 1003153 A | 9/1965 | |
| GB | 1499812 A | 2/1978 | |
| GB | 2298931 A | 9/1996 | |
| GB | 2417222 B | 9/2008 | |
| JP | 2000510362 A | 8/2000 | |
| JP | 2002514448 A | 5/2002 | |
| JP | 2006102100 A | 4/2006 | |
| WO | WO89/01192 A1 | 2/1989 | |
| WO | WO89/07910 A1 | 9/1989 | |
| WO | WO94/24933 A1 | 11/1994 | |
| WO | WO95/01757 A1 | 1/1995 | |
| WO | WO96/11624 A2 | 4/1996 | |
| WO | WO99/49280 A1 | 9/1999 | |
| WO | WO00/21442 A1 | 4/2000 | |
| WO | WO00/63719 A1 | 10/2000 | |
| WO | WO01/01845 A2 | 1/2001 | |
| WO | WO01/37743 A1 | 5/2001 | |
| WO | WO02/060653 A2 | 8/2002 | |
| WO | WO2004/001569 A2 | 12/2003 | |
| WO | WO2004/069036 A2 | 8/2004 | |
| WO | WO2005/000139 A1 | 1/2005 | |
| WO | WO2005/072629 A1 | 8/2005 | |
| WO | WO2005/074303 A1 | 8/2005 | |
| WO | WO2005/076033 A1 | 8/2005 | |
| WO | WO2007/073551 A1 | 6/2007 | |
| WO | WO2007/085909 A2 | 8/2007 | |
| WO | WO2007/113815 A2 | 10/2007 | |
| WO | WO2008/064126 A2 | 5/2008 | |
| WO | WO2008/076079 A1 | 6/2008 | |
| WO | WO2009/047629 A1 | 4/2009 | |
| WO | WO2009/111682 A1 | 9/2009 | |
| WO | WO2010/067267 A1 | 6/2010 | |
| WO | WO2010/123858 A2 | 10/2010 | |
| WO | WO2011/020505 A1 | 2/2011 | |
| WO | WO2011/028575 A2 | 3/2011 | |
| WO | WO2011/063266 A2 | 5/2011 | |
| WO | WO 2011063266 A2 * | 5/2011 | A61B 1/041 |
| WO | WO2011/116347 A1 | 9/2011 | |
| WO | WO 2011116347 A1 * | 9/2011 | A61B 5/0077 |
| WO | WO2011/133927 A2 | 10/2011 | |
| WO | WO2011/133946 A2 | 10/2011 | |
| WO | WO2011/134083 A1 | 11/2011 | |
| WO | WO2012/013304 A1 | 2/2012 | |
| WO | WO2012/045626 A1 | 4/2012 | |
| WO | WO2012/078989 A1 | 6/2012 | |
| WO | WO2012/171555 A1 | 12/2012 | |
| WO | WO2013/080124 A1 | 6/2013 | |

OTHER PUBLICATIONS

Amstutz et al.; Press-fit prosthesis: Principle, Results, and Techniques (Chap. 20); pp. 261-270. In: Amstutz, H.C. (Ed.): Hip Arthroplasty. 1st ed.; Elsevier Health Sciences, Aug. 1991.

Azuma et al.; Recent Advances in Augmented Reality; IEEE Computer Graphics and Applications; 21(6); pp. 34-47; Nov./Dec. 2001.

B Braun / Aesculap AG; OrthoPilot®, Orthopaedic Navigation System; 1 pg.; printed from: http://www.orthopilot.com/cps/rde/xchg/ae-orthopilot-en-int/hs.xsl/7218.html on Oct. 24, 2013 (This web address was available to applicant(s) at least as of Jun. 2008).

Bach et al.: Scoring systems in total knee arthroplasty, Clin Orthop Relat Res.; 399; pp. 184-196; Jun. 2002.

Barrera et al., "Comparison of Distal Femoral TKR Bone Cuts by Freehand Navigation vs. Conventional Cutting Jigs", The Fourth Annual Conference of the International Society for Computer Assisted Orthopaedic Surgery, CAOS-International, Chicago, IL, Jun. 2004.

Barrera et al., "Freehand Navigation Cutting for Distal Femoral TKR bone for MIS", Annual Symposium of International Society for Technology in Arthroplasty (ISTA), Rome, Italy, Sep. 2004.

Barrera et al., "Intra Operative Graphical Interface for Freehand Navigated Bone Cutting for TKR Without Jigs-Assessment of First Cuts", Poster 246, 5th Combined Meeting of the Orthopaedic Research Societies of Canada, U.S.A., Japan and Europe, Banff, Alberta, Canada, Oct. 2004.

Barrera et al., "Simulation and Navigation for Knee Replacement Surgery", Paper presented at the 16th Annual Nebraska Biomedical Research Workshop, Omaha, NE, Apr. 2003.

Barrera et al.; Towards a standard in assessment of bone cutting for TKR; (presentation poster); 18th Ann. Symposium of the International Society for Technology and Arthroplasty (ISTA); Kyoto, Japan; Sep. 29-Oct. 2, 2005.

Barrera et al.; Towards a standard in assessment of bone cutting for total knee replacement; Proc Inst Mech Eng H; 222(2); pp. 63-74; Jan. 2008.

Bellamy et al.: Validation study of WOMAC: a health status instrument for measuring clinically important patient relevant outcomes to antirheumatic drug therapy in patients with osteoarthritis of the hip or knee. J Rheumatol; 15 (12); pp. 1833-1840; Dec. 1988.

Blue Belt Technologies, Inc.; NavioPFS} (brochure); 4 pgs.; © 2013; downloaded from: http://www.bluebelttech.com; this web address available to applicant(s) at least as of Nov. 2012.

(56) References Cited

OTHER PUBLICATIONS

Bobyn et al.: Osteogenic phenomena across endosteal bone-implant spaces with porous surfaced intramedullary implants. Acta Orthop Scand; 52(2): pp. 145-153, (year of pub. sufficiently earlier than effective US filing date and any foreign priority date) 1981.
Brainlab; Image-Guided Surgery Platforms; 2 pages; printed on Oct. 24, 2013 from http://www.brainlab.com/product/item/image-guided-surgery-platforms (This web address was available to applicant(s) at least as of Jun. 2008).
Brisson et al., Precision Freehand Sculpting of Bone; Lecture Notes in Computer Science; vol. 3217; MICCAI 2004; 7th International Conf. Proceedings, Part II; Saint-Malo, France; pp. 105-112; Sep. 26-29, 2004.
Carlsson et al.; Implant fixation improved by close fit. Cylindrical implant-bone interface studied in rabbits. Acta Orthop Scand; 59 (3): 272-5, Jun. 1988.
Collier et al.; Macroscopic and microscopic evidence of prosthetic fixation with porous-coated materials; Clin Orthop Relat Res; 235; pp. 173-180; Oct. 1988.
Cooke et al.: Universal bone cutting device for precision knee replacement arthroplasty and osteotomy. J Biomed Eng 7(1): pp. 45-50, Jan. 1985.
Davies et al.; Acrobot—using robots and surgeons synergistically in knee surgery; Advanced Robotics; ICAR '97; 8th International Conference; Monterey, CA; Proceedings; pp. 173-178; Jul. 7-9, 1997.
Davies: Rating systems for total knee replacement. Knee; 9(4); pp. 261-266; Dec. 2002.
Dawson et al.; Questionnaire on the perceptions of patients about total knee replacement. J Bone Joint Surg (Br) 80(B): 63-9, Jan. 1998.
Denis et al.: Influence of bone milling parameters on the temperature rise, milling forces and surface flatness in view of robot-assisted total knee arthroplasty. International Congress Series, vol. 1230, pp. 300-306; Jun. 2001.
DiGioia; Computer-Assisted Measurement Tools for Surgeons and Researchers, Presented at the 47th Annual Meeting of the Orthopaedics Research Society (ORS), San Francisco, CA, Feb. 25-28, 2001.
Digioia et al.; Computer Assisted Orthopaedic Surgery Image Guided and Robotic Assistive Technologies; Clinical Orthopaedics and Related Research; No. 354; pp. 8-16; Sep. 1998.
DiGioia et al.; HipNav: Pre-operative planning and intra-operative navigational guidance for acetabular implant placement in total hip replacement surgery; Porc. of the Computer Assisted Orthopaedic Surgery Simposium; Bern, Switzerland; 8 pgs.; Nov. 1995.
Dunbar et al.: Translation and validation of the Oxford-12 Item Knee Score for use in Sweden. Acta Orthopaedica Scandinavica; 71(3); pp. 268-274; Jun. 2000.
Edwards et al.; Design and evaluation of a system microscope-assisted guided interventions (MAGI); MICCAI'99; LNCS 1679; pp. 842-852; Proc. 2nd Int. Conf.; Cambridge, UK; Sep. 19-22, 1999.
Feaver et al.; U.S. Appl. No. 08/431,085 entitled "Energy-emitting attachments and methods for medical instruments," filed Apr. 28, 1995.
Fleute et al.; Incorporating a statistically based shape model into a system for computer-assisted anterior cruciate ligament surgery; Medical Image Analysis; 3(3); pp. 209-222; Sep. 1999.
Forman et al., "Computer-Assisted Freehand Navigation for Knee Replacement Surgery," The Fourth Annual Conference of the International Society for Computer Assisted Orthopaedic Surgery, CAOS-International, Chicago, IL, pp. 192-193; Jun. 2004.
Garvin et al.; Total knee arthroplasty with a computer-navigated saw; Clin Orthop Relat Res.; 471(1); pp. 155-161; Jan. 2013.
Gavaghan et al.; A portable image overlay projection device for computer-aided open liver surgery; IEEE Transactions on Biomedical Engineering; 58(6); pp. 1855-1864; Jun. 2011.
Gibson (Frisken) et al.; Simulating surgery using volumetric object representations, real-time volume rendering and haptic feedback; TR97-02; 21 pgs.; Dec. 1997.
Gibson (Frisken) et al.; Surgical Simulation: A knee arthroscopy system (presentation); SIGGRAPH'99 Course; 43 pgs.; Aug. 1999.
Giraud et al.: Bone cutting. Clin. Phys. Physiol. Meas.; 12(1): pp. 1-19, Feb. 1991.
Grood et al.: A joint coordinate system for the clinical description of threedimensional motions: application to the knee. J. Biomech. Eng.; 105: pp. 136-144, May 1983.
Haider et al., "Computer Simulation of Bone Cutting for Knee Replacement Surgery With Freehand Navigation", SE042, 71st Annual Meeting, American Academy of Orthopaedic Surgeons (AAOS), San Francisco, CA, Mar. 2004.
Haider et al., "Freehand Navigated Bone Cutting for TKR Without Jigs-Assessment of First Cuts", Poster 246, 5th Combined Meeting of the Orthopaedic Research Societies of Canada, U.S.A., Japan and Europe, Banff, Alberta, Canada, Oct. 2004.
Haider et al., "Freehand Navigation Cutting for TKR Surgery Without Jigs: Simulation of Bone Saw Cutting" (abstract), 4th Annual Conference of the International Society for Computer Assisted Orthopaedic Surgery, CAOS-International, Chicago, IL, Jun. 2004.
Haider et al., "Real-Time Simulation of Bone Cutting Minimally Invasive Knee Replacement Surgery", Podium paper No. 1618, International Society for Technology in Arthroplasty (ISTA), San Francisco, CA, Sep. 2003.
Haider et al., Total Knee Replacement Bone Cutting Without Jigs: Is it Time? (podium paper 64, submission 3097); 72nd Annual Meeting of the American Academy of Orthopaedic Surgeons AAOS, Washington, D.C., Feb. 2005.
Haider et al.; A framework and parameters for quantitative assessment of bone cutting for TKR; 5th Annual Meeting fo the International Society for Computer Assisted Orthopaedic Surgery (CAOS); Helsinki, Finland; Jun. 19-22, 2005.
Haider et al.; Quantifying the quality of bone cutting for TKR—a proposed assessment method; (presentation paper); MIS meets CAOS Symposium Series: Less and Minimally Invasive Surgery for Joint Arthroplasty: Facts and Fiction; San Diego, CA, USA; Oct. 20-22, 2005; 5 pgs.
Hall et al.; 2000 National Hospital Discharge Survey; Centers for Disease Control and Prevention (CDC), Advance Data No. 329; 19 pgs., Jun. 19, 2002.
Heilbrun et al.; Stereotactic localization and guidance using a machine vision technique; Stereotact Funct Neurosurg.; 58(1-4); pp. 94-98; 1992; Proc. of American Society for Stereotactic & Functional Neurosurgery; Pittsburgh, PA; Jun. 16-19, 1991.
Imperial College London; Robot Assisted Surgery More Accurate Than Conventional Surgery (press release); 2 pgs.; printed Oct. 24, 2013 from http://www.imperial.ac.uk/college.asp?P=7449; Feb. 2006.
Insall et al.; Rationale of the Knee Society Clinical Rating System, Clin Orthop Relat Res., 248: pp. 13-14, Nov. 1989.
INSALL: Results of Total Knee Arthroplasty. Chap. 34, pp. 975-982. In Insall JN, Windsor RE, Scott WN, Kelly MA, Aglietti P (Eds.), Surgery of the Knee, vol. 2, 2nd ed, Churchill Livingstone Inc., New York, May 1993.
Jakopec et al.; Acrobot: a hands-on robot for total knee replacement surgery; Advanced Motion Control; 7th Intl. Workshop; Piscataway, NJ; pp. 116-120; Jul. 3-5, 2002.
Jakopec et al.; The first clinical application of a "hands-on" robotic knee surgery system; Computer Aided Surgery; 6(6); pp. 329-339; (year of pub. sufficiently earlier than effective US filing date and any foreign priority date) 2001.
Jaramaz et al.; Range of motion after total hip arthroplasty: Experimental verification of the analytical simulator; CVRMed-MRCAS'97; LNCS; vol. 1205; pp. 573-582; Genoble, FR; Mar. 19-22, 1997.
Kazanzides et al.; Force sensing and control for a surgical robot; Proc. of the 1992 IEEE Int. Conf. on Robotics and Automation; Nice, France; pp. 612-617; May 1992.
Kim et al.: An Er: YAG Laser Bone Cutting Manipulator for Precise Rotational Acetabular Osteotomy. Proc. of the 26th Annual International Conference of the IEEE EMBS San Francisco, CA, USA. pp. 2750-2753; Sep. 1-4, 2004.
Kim et al.; Results of the Harris-Galante cementless hip prosthesis; J Bone, Joint Surg Br; 74(1); pp. 83-87; Jan. 1992.

(56) References Cited

OTHER PUBLICATIONS

Knutson et al; Knee revision for aseptic loosening; Surgical Techniques in Orthopaedics and Traumatology; 55-560-C-10; 5 pgs.; (year of pub. sufficiently earlier than effective US filing date and any foreign priority date) 2001.
Leitner et al.; Computer-assisted knee surgical total replacement; CVRMed-MRCAS'97; Lecture Notes in Computer Science; vol. 1205; pp. 629-637; Genoble, FR; Mar. 19-22, 1997.
Levinson et al.; Surgical navigation for THR: A report on clinical trial utilizing HipNav; MICCAI 2000; 3rd Int. Conf.; LNCS; vol. 1935; pp. 1185-1187; Pittsburg, PA; Oct. 11-14, 2000.
Liow et al.: Functional rating for knee arthroplasty: comparison of three scoring systems, Orthopedics, 26(2): pp. 143-149, Feb. 2003.
Liow et al.; The reliability of the American Knee Society Score, Acta Orthopaedica Scandinavica, 71(6): pp. 603-608, Dec. 2000.
Lisien et al.: Mini Bone-Attached Robotic System. Sensor Based Planning Lab, Carnegie Mellon University. Printed Oct. 24, 2013 from http://web.archive.org/web/20041207011420/http://voronoi.sbp.ri.cmu.edu/mbars/; © 2001; Last modified Jun. 1, 2004.
Lotke et al.: Influence of Positioning of Prosthesis in Total Knee Replacement; J Bone Joint Surg Am; 59(1); pp. 77-79; Jan. 1977.
MacDonald: Improved tibial cutting accuracy in knee arthroplasty, Medical Engineering & Physics; 26: pp. 807-812, Nov. 2004.
Michigan Metrology, LLC: Glossary of Surface Texture Parameters, printed Dec. 16, 2013 from internet archive, 9 pgs. (http://web.archive.org/web/20040524202705/http://www.michmet.com/).
Noble et al.; The anatomic basis of femoral component design; Clin Orthop Relat Res; 235; pp. 148-165; Oct. 1988.
O'Toole, III et al.; Towards more capable and less invasive robotic surgery in orthopaedics; CVRMed'95; Nice, France; pp. 123-130; Apr. 3-6, 1995.
Paul et al., A surgical robot for total hip replacement surgery; Proc. of the 1992 IEEE Conf. on Robotics and Automation; Nice, France; pp. 606-611; May 1992.
Piek et al.: Waterjet dissection in neurosurgical procedures: clinical results in 35 patients. J Neurosurg; 96: pp. 690-696, Apr. 2002.
Piltner et al., "Computational Modelling of Novel Implants for Minimally Invasive Knee Replacement Surgery", Poster presented at the 16th Annual Nebraska Biomedical Research Workshop, Omaha, NE, Apr. 2003.
Reaungamornrat et al.; Tracker-on-C: A novel tracker configuration for image-guided therapy using a mobile C-arm; Int J CARS; 6(suppl 1); pp. S134-S137; Jun. 2011.
Richter et al, "Integration of Computer-Based Systems in Foot and Ankle Surgery", Navigation and MIS in Orthopedic Surgery, Ch. 63, pp. 486-495; Dec. 2006.
Rosenberg et al.; Cementless Total Knee Arthroplasty; Chap. 30, pp. 869-890. In Insall et al. (Eds.), Surgery of the Knee, vol. 2, 2nd ed, Churchill Livingstone Inc., New York, Jul. 1993.
Rupprecht et al.; Er: YAG laser osteotomy directed by sensor controlled systems. J Craniomaxillofac Surg, 31(6): pp. 337-342, Dec. 2003.
Sandborn et al.: The effect of surgical fit on bone growth into porous coated implants. 33rd Annual Meeting, Orthopaedic Research Society; San Francisco, CA; pp. 217; Jan. 1987.

Sauer et al.; An augmented reality navigation system with a single-camera tracker: System design and needle biopsy phantom trial; Med. Imaging Computing and Computer-Assisted Intervention—MICCAI 2002; 2489; 5th Int. Conf.; Tokyo, Japan; Proc. Part II; pp. 116-124; Sep. 25-28, 2002.
Schnaider et al.; Implementation and evaluation of an augmented reality system supporting minimal invasive interventions; Virtual and Augmented Reality Status Conference 2004; 10 pgs.; Leipzig; Feb. 19-20, 2004.
Simon et al.; Accuracy validation in image-guided orthopaedic surgery; Proc. of the 2nd International Symp. on Medical Robotics & Computer Assisted Surgery; pp. 185-192; (year of pub. sufficiently earlier than effective US filing date and any foreign priority date) 1995.
Simon et al.; Development and validation of a navigational guidance system for acetabular implant placement; CVRMed-MRCAS'97; Lecture Notes in Computer Science; 1205; pp. 583-592; (year of pub. sufficiently earlier than effective US filed and any foreign priority date) 1997.
Staub et al.; Visual instrument guidance in minimally invasive robot surgery; International Journal on Advances in Life Sciences; 2(3/4); pp. 103-114; 2010 (year of pub. sufficiently earlier than effective US filing date and any foreign priority date).
Tardis et al.; Projector-based augmented reality in surgery without calibration; Engineering in Medicine and Bilogy Society, 2003; Proc of the 25th ann. int, cont. of the IEEE; vol. 1; Sep. 17-21, 2003.
Taylor et al.; An image-directed robotic system for precise orthopaedic surgery; IEEE Trans. on Robotics and Automation; 10(3); pp. 261-275; Jun. 1994.
Toksvig-Larsen et al.; Surface characteristics following tibial preparation during total knee arthroplasty, The Journal of Arthroplasty, 9(1): pp. 63-66, Feb. 1994.
Toksvig-Larsen et al.; Surface flatness after bone cutting. A cadaver study of tibial condyles, Acta Orthopaedica Scandinavica 62(1): pp. 15-18, Feb. 1991.
Troccaz et al.; Computer-augmented surgery; Human Movement Science; 15(3); pp. 445-475; Jun. 1996.
Tsai et al.; An orthopedic virtual reality surgical simulator; JCat 2000; 10th Int. Conf. on Artificial Reality and Tele-existence; Nat. Taiwan Univ.; taipei, Taiwan; 8 pgs.; Oct. 25-27, 2000.
Wapler et al.; Controlling miniature robotic systems in minimally invasive surgery; Intelligent Robots and Systems '94. 'Advanced Robotic Systems and the Real World', IROS '94. Proc. of the IEEE/RSJ/GI Int'l Conf. (vol. 1); Munich, DE; pp. 711-716; Sep. 12-16, 1994.
Wu et al.; The dimensional accuracy of preparation of femoral cavity in cementless total hip arthroplasty; J Zhejiang Univ Sci; 5(10); pp. 1270-1278, Oct. 2004.
Yao et al.; Primary musculoskeletal neoplasms: Effectiveness of core-needle biopsy; radiology; 212; pp. 682-686; Sep. 1999.
Haider et al.; U.S. Appl. No. 14/831,691 entitled "Method and apparatus for computer aided surgery," filed Aug. 20, 2015.
Haider et al.; U.S. Appl. No. 14/831,728 entitled "Method and apparatus for computer aided surgery," filed Aug. 20, 2015.
Haider et al.; U.S. Appl. No. 15/675,345 entitled "Method and apparatus for computer aided surgery," filed Aug. 11, 2017.

* cited by examiner

LID REMOVED

| d | 105 | mm | | |
|---|---|---|---|---|
| a | 94 | deg | | |
| t | MOD/d | MOL/d | MOD | MOL |
| 1 | 13.32 | 28.6 | 1398 | 3001 |
| 2 | 6.65 | 14.3 | 698 | 1502 |
| 3 | 4.42 | 9.5 | 464 | 1002 |
| 4 | 3.31 | 7.2 | 347 | 753 |
| 5 | 2.63 | 5.7 | 277 | 603 |
| 6 | 2.18 | 4.8 | 229 | 504 |
| 7 | 1.86 | 4.1 | 195 | 433 |
| 8 | 1.62 | 3.6 | 170 | 380 |
| 9 | 1.43 | 3.2 | 150 | 339 |
| 10 | 1.27 | 2.9 | 134 | 306 |
| 11 | 1.14 | 2.7 | 120 | 280 |
| 12 | 1.04 | 2.5 | 109 | 258 |
| 13 | 0.95 | 2.3 | 99 | 239 |
| 14 | 0.87 | 2.1 | 91 | 223 |
| 15 | 0.80 | 2.0 | 84 | 209 |
| 16 | 0.73 | 1.9 | 77 | 198 |
| 17 | 0.68 | 1.8 | 71 | 187 |
| 18 | 0.63 | 1.7 | 66 | 178 |
| 19 | 0.58 | 1.6 | 61 | 170 |
| 20 | 0.54 | 1.6 | 57 | 163 |
| 21 | 0.50 | 1.5 | 53 | 157 |
| 22 | 0.47 | 1.4 | 49 | 151 |
| 23 | 0.43 | 1.4 | 46 | 146 |
| 24 | 0.40 | 1.3 | 42 | 141 |

MOD - Minimum Object Distance

MOL - Maximum Object Length (at MOD)

MOD/d = 1/ (tan(a/2+t) - tan(a/2-t))

MOL/d = 1+ 2 (MOD/d)* tan (a/2-t)

FIG. 11B

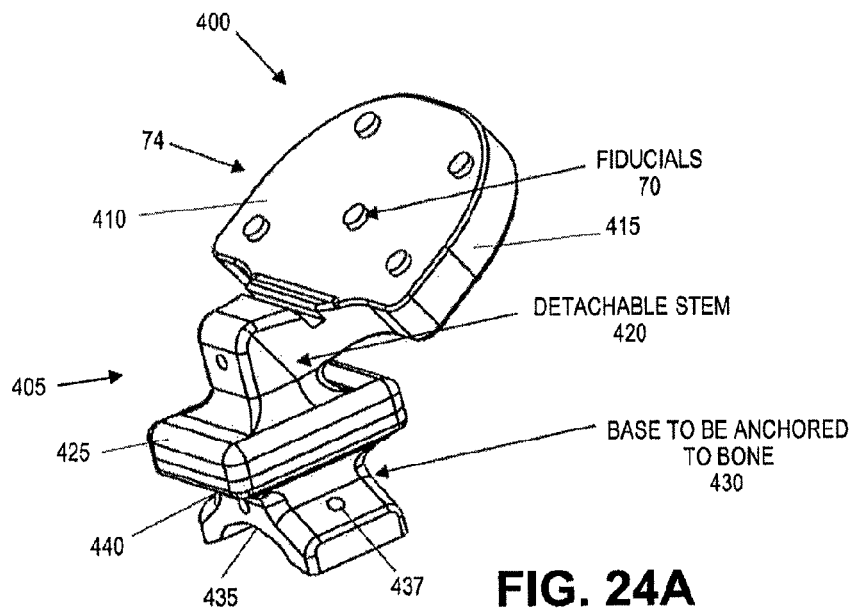
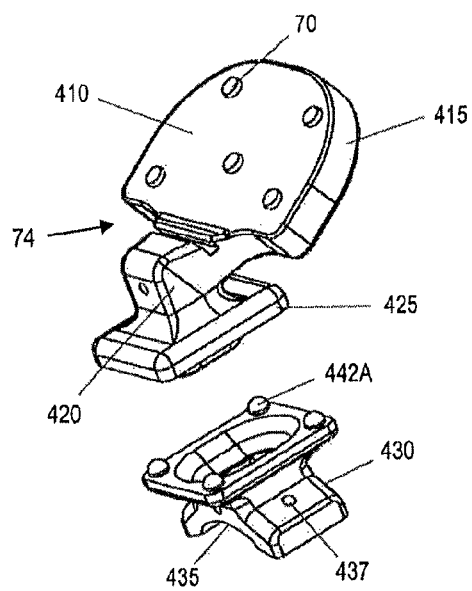
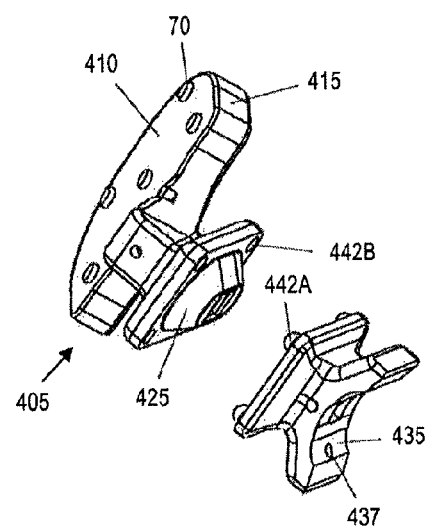
FIG. 24A
FIG. 24B
FIG. 24C

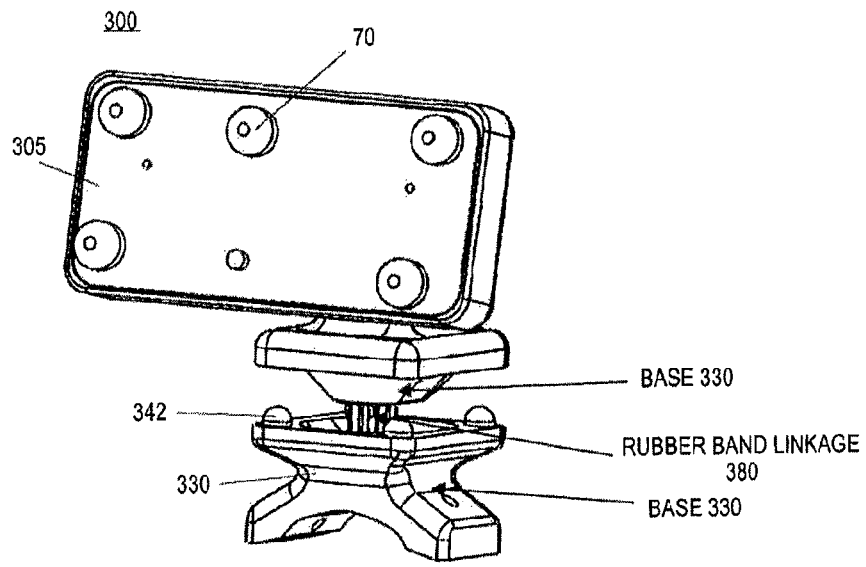
FIG. 26A
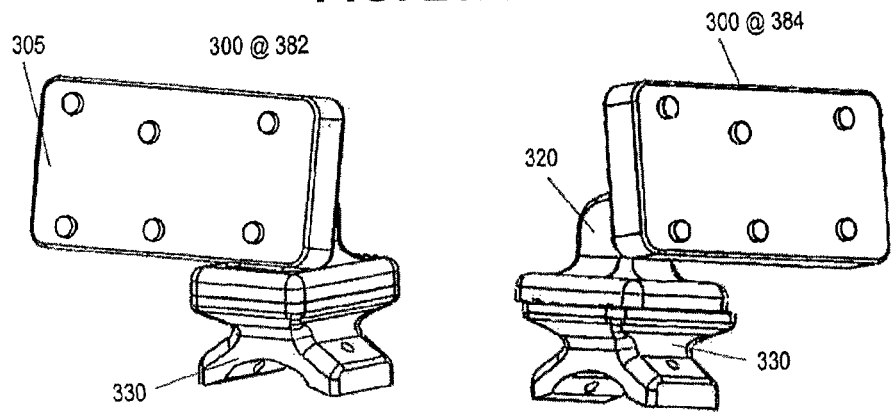
FIG. 26B     FIG. 26C

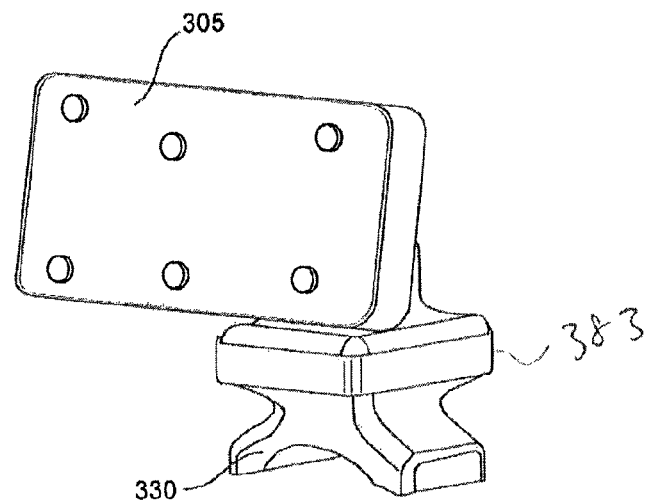
FIG. 26B1a
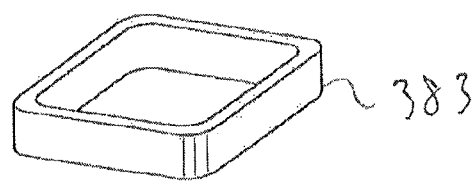
FIG. 26B1b

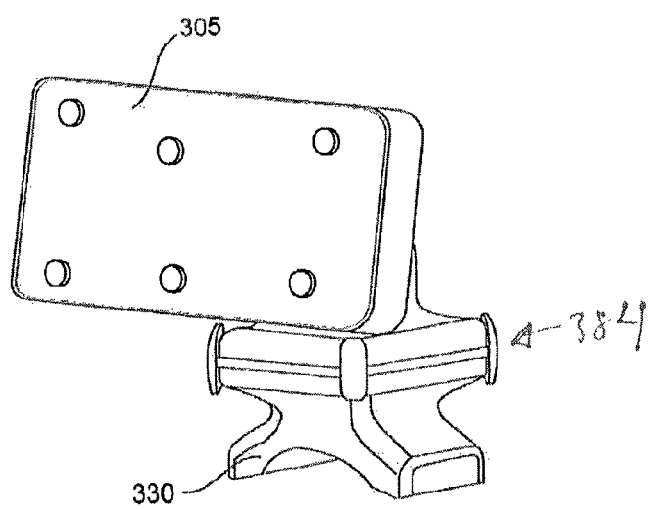
FIG. 26B2a
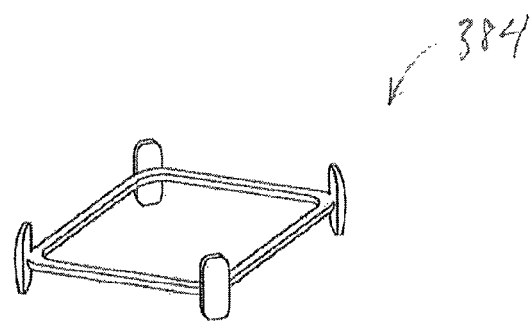
FIG. 26B2b

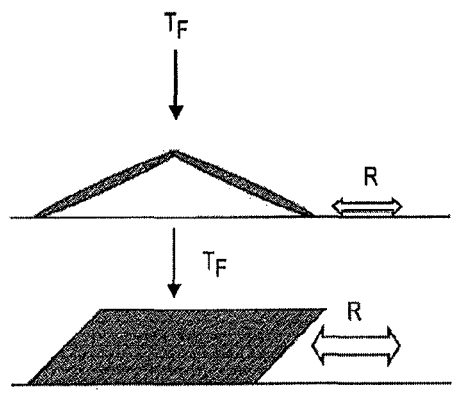
FIG. 37A
FIG. 37B
FIG. 37C
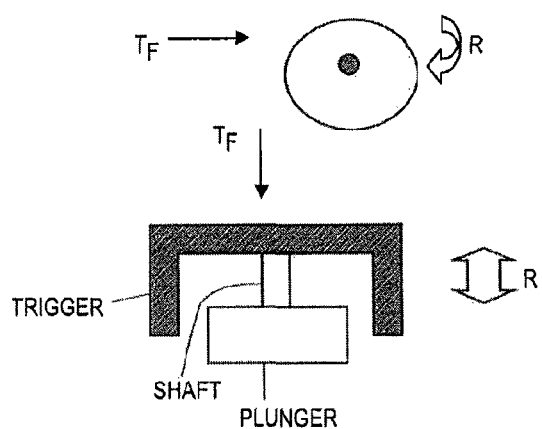
FIG. 37D
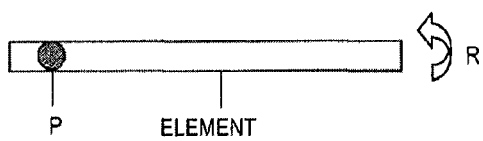
FIG. 37E

FIG. 39A
PUSH-PULL THROUGH A SOLID ACTUATOR
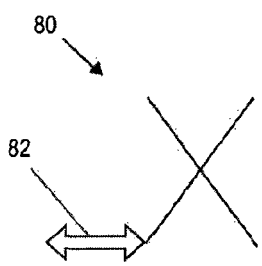
FIG. 39B
PULL / SPRING RETURN - BOWDEN CABLE "NORMALLY OFF"
FIG. 39C
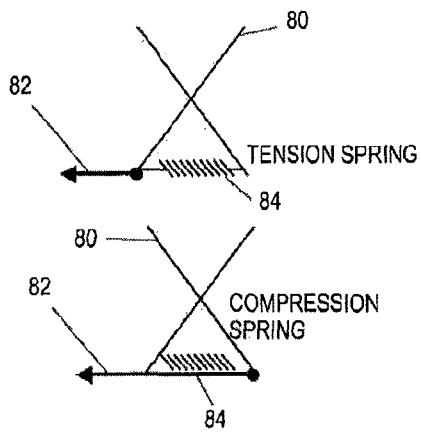
THE MOVEMENT OF THE ACTUATOR SHOWN DETERMINES THE HEIGHT OF THE UPPER END OF THE SCISSOR ARMS THEREFORE THE ELEVATION OF THE SCISSOR MECHANISM. THIS HEIGHT WILL PRESS AGAINST, AND WILL BE FELT BY THE USER PLACING HIS OR HER FINGER ON THE TOOL TRIGGER.

All forces can be determined at all positions

MECHANISM ON TOOL - REPLACES THE TOOL TRIGGER

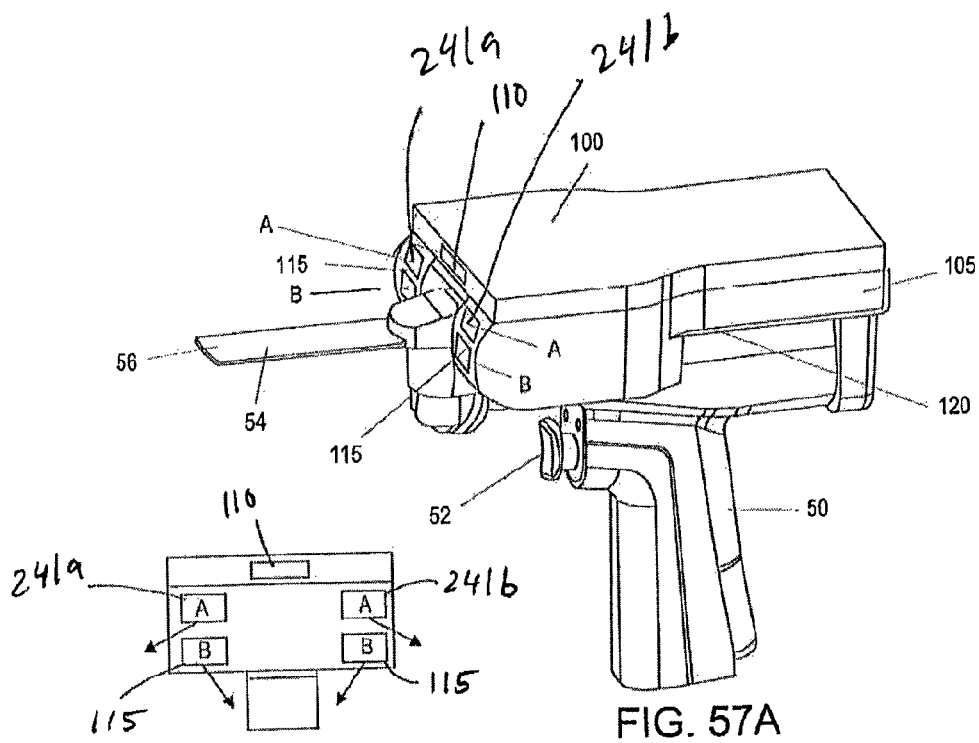
FIG. 57A
FIG. 57B
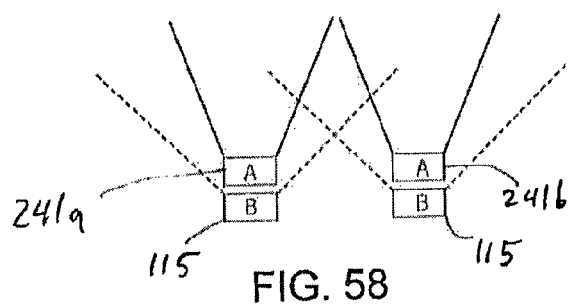
FIG. 58

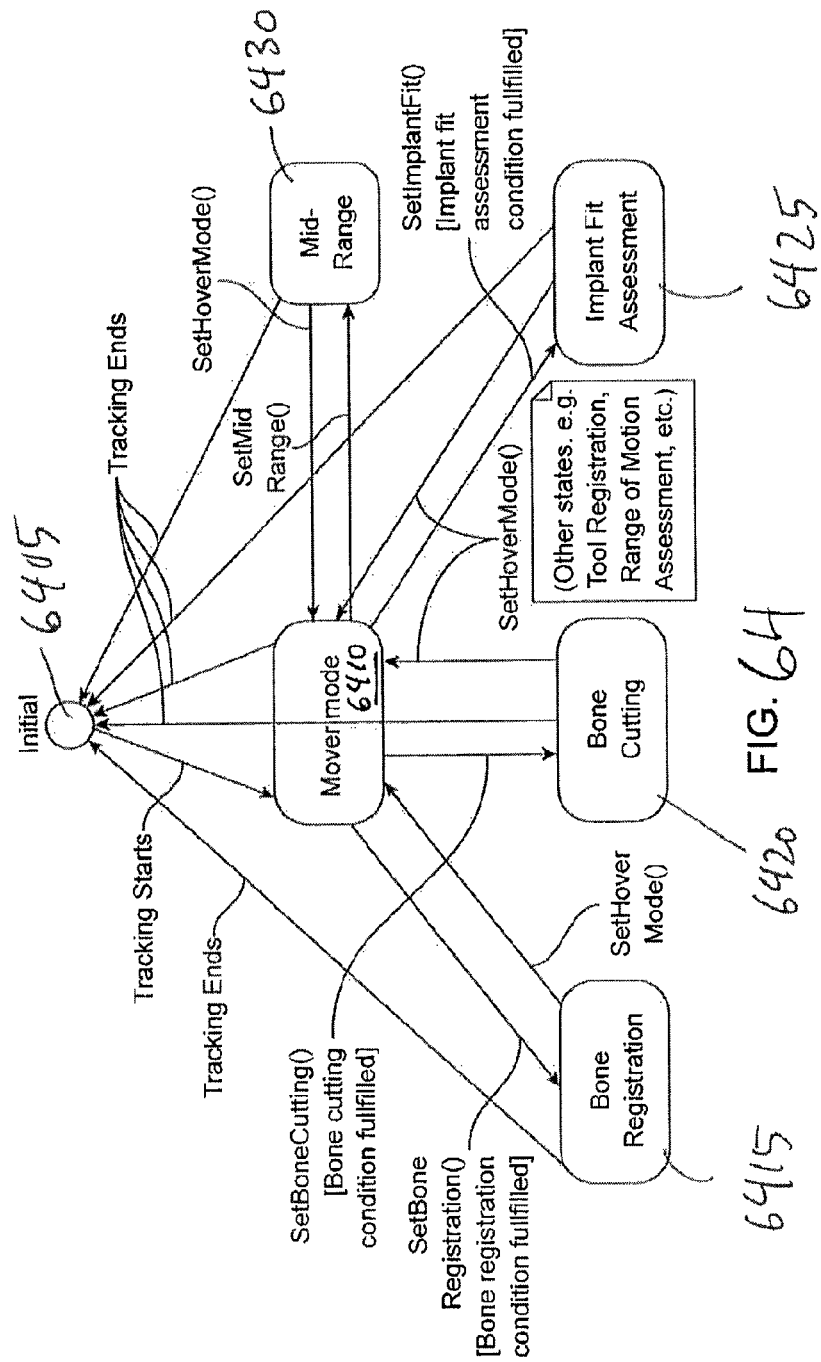

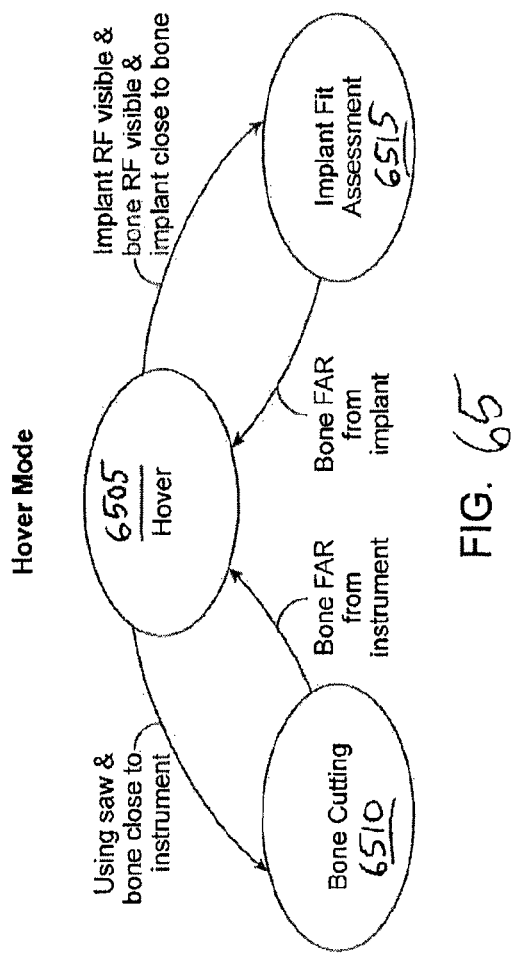

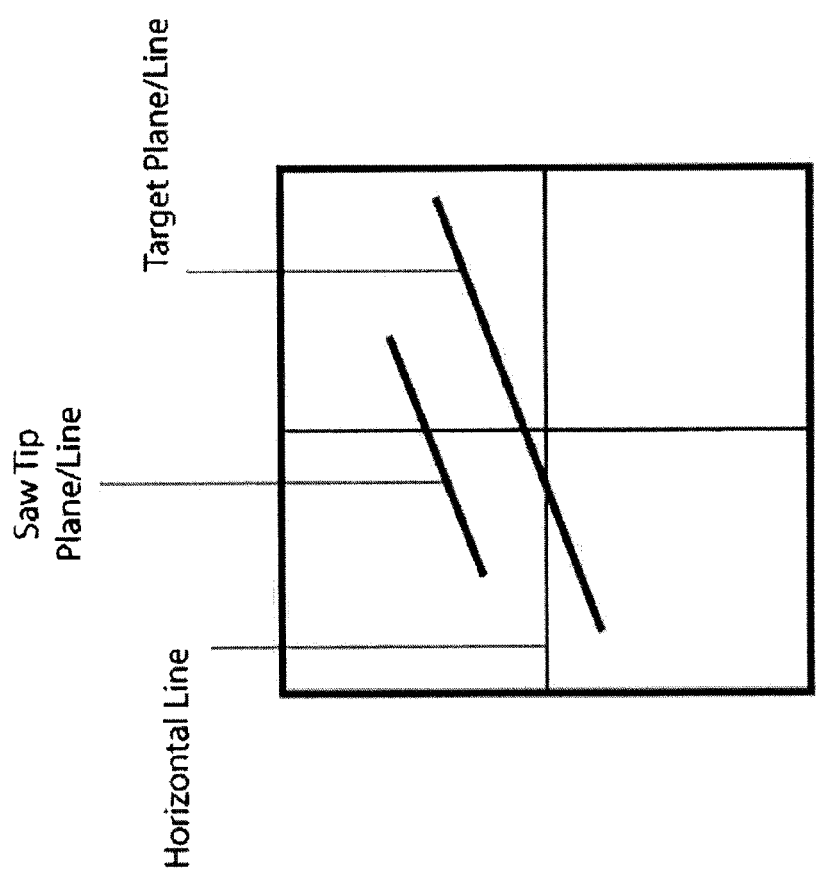

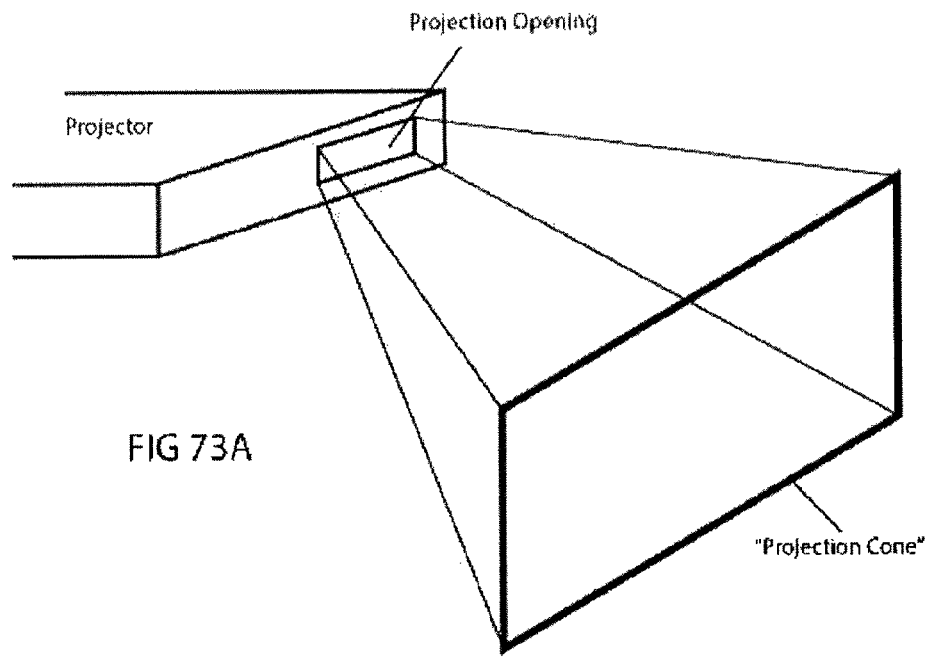
FIG 73A
Frontal view of the projection opening
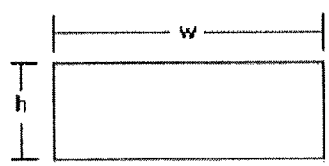
Side view of the projection cone
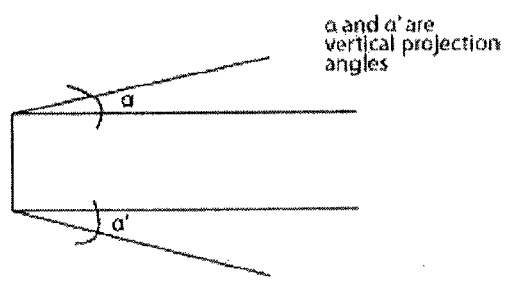
FIG 73B Angles defined in Fig 73B and projector's origin/orientation of Figs 73E and 73F.

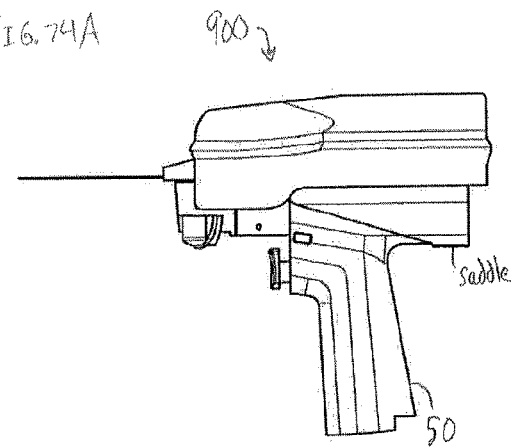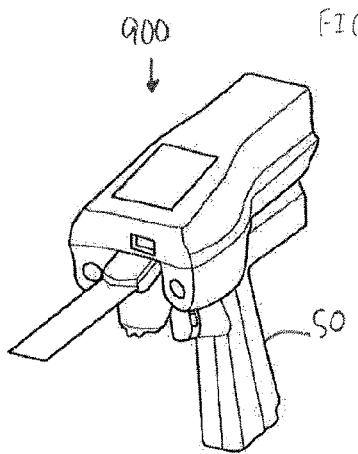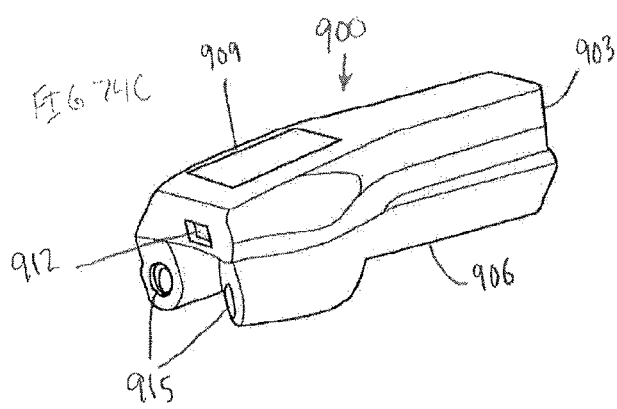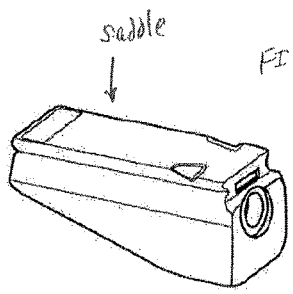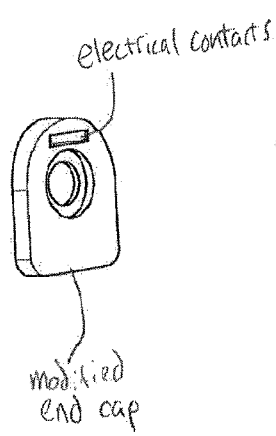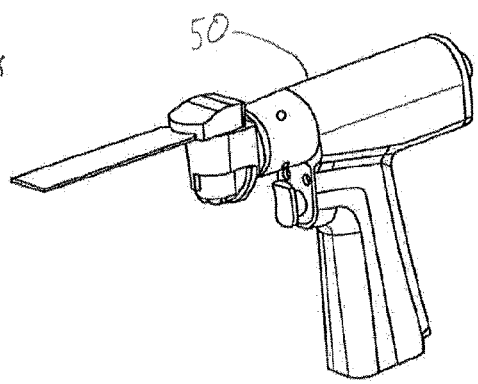

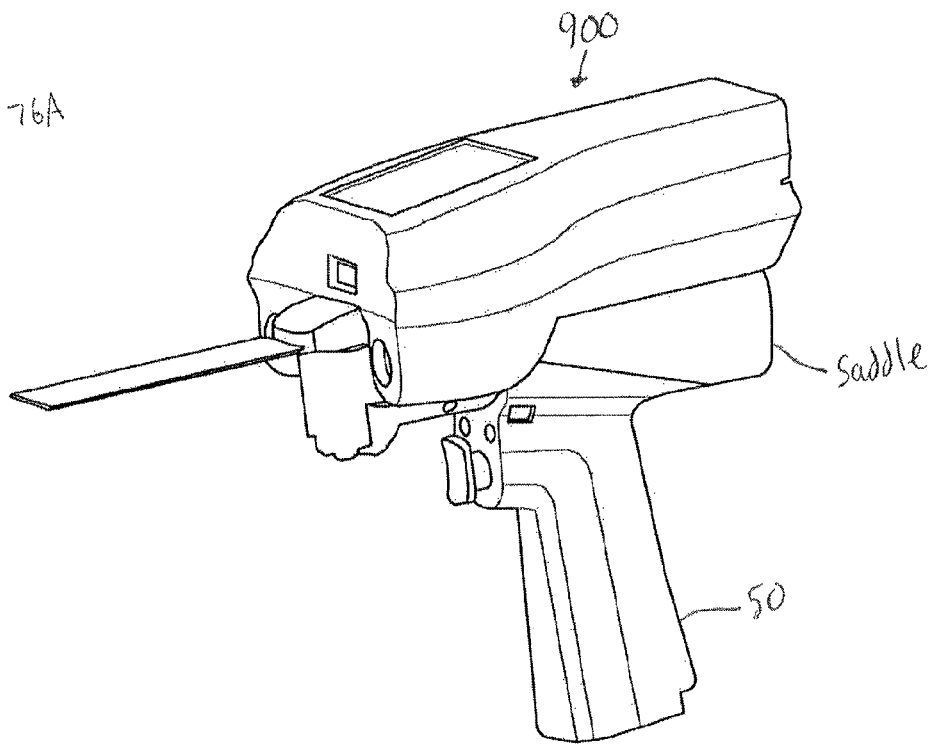
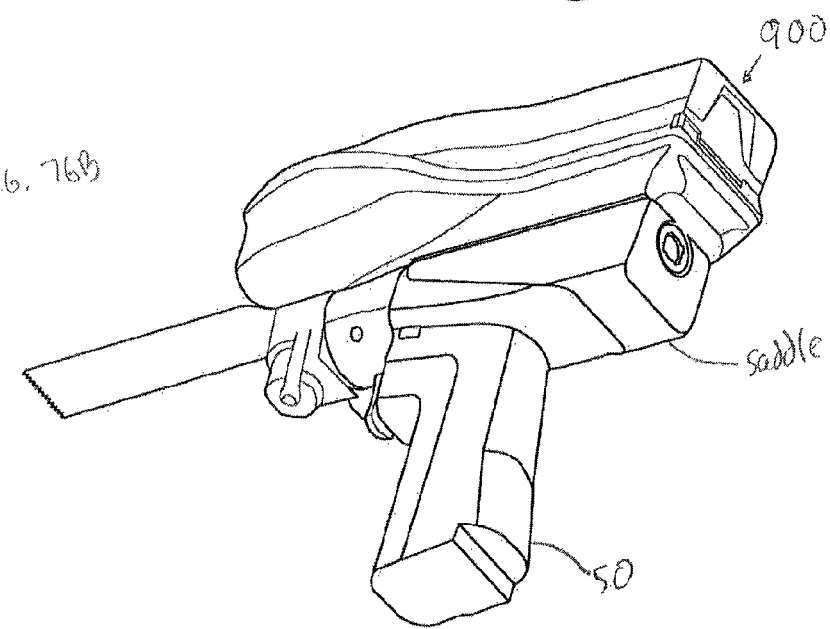

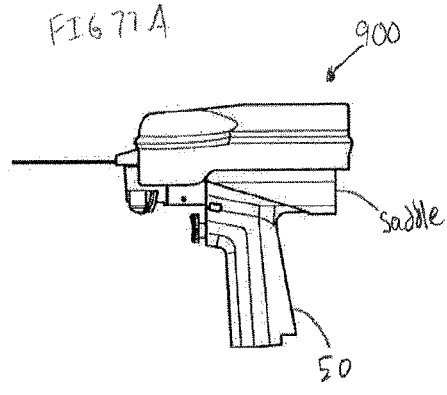
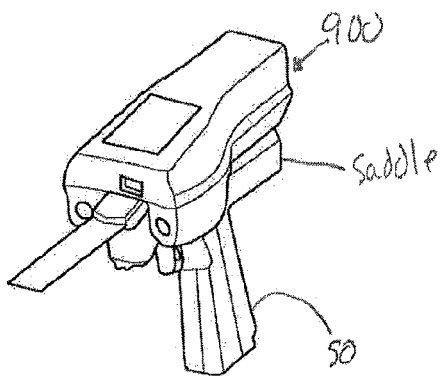
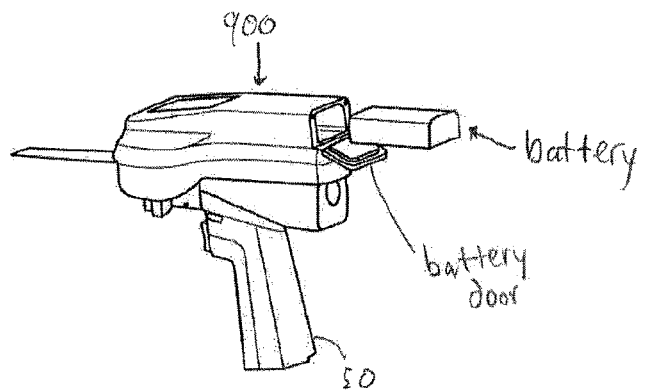
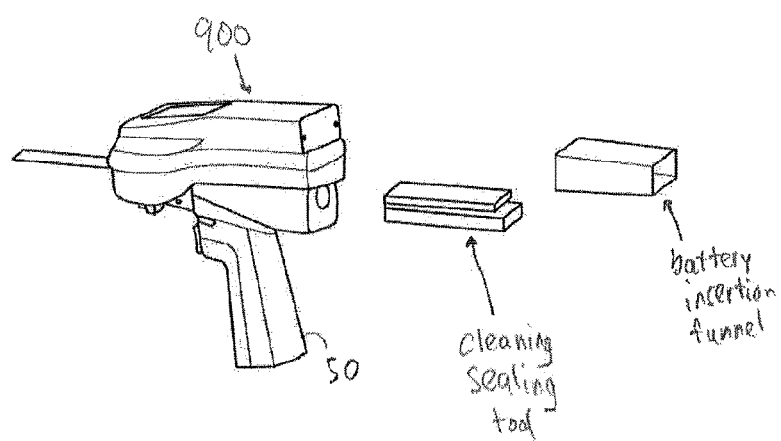

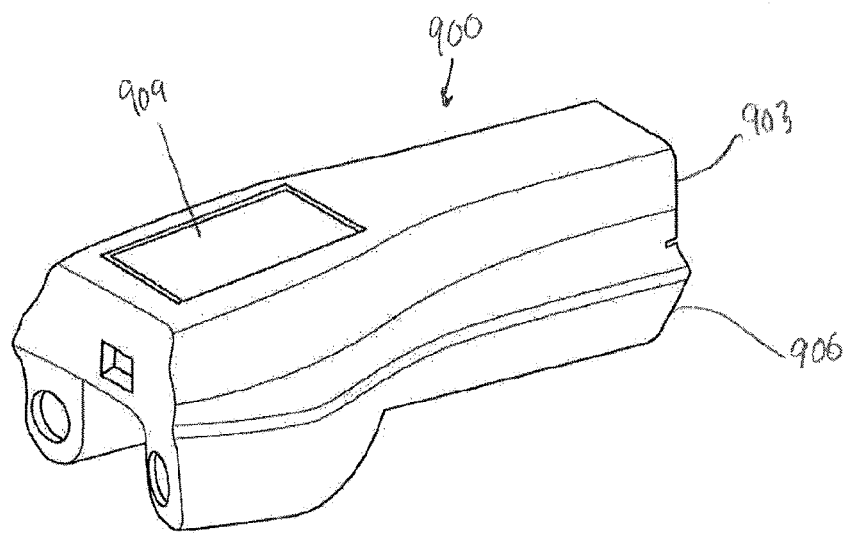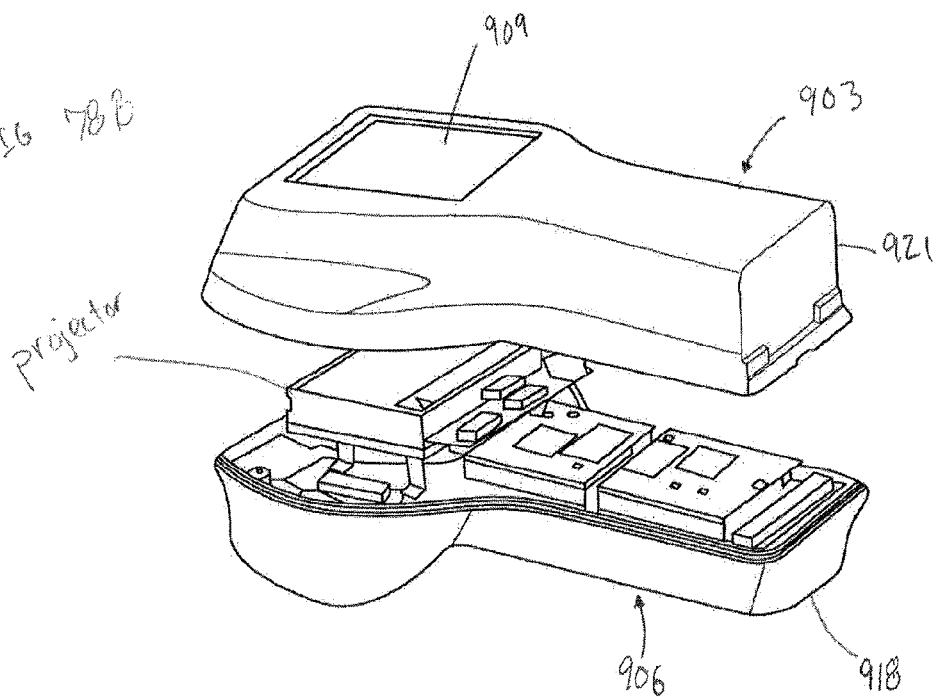

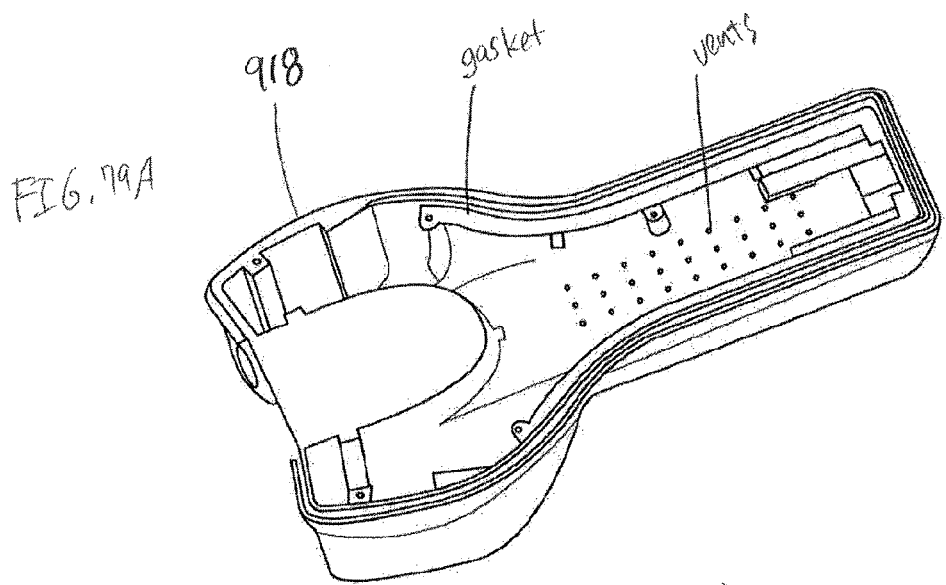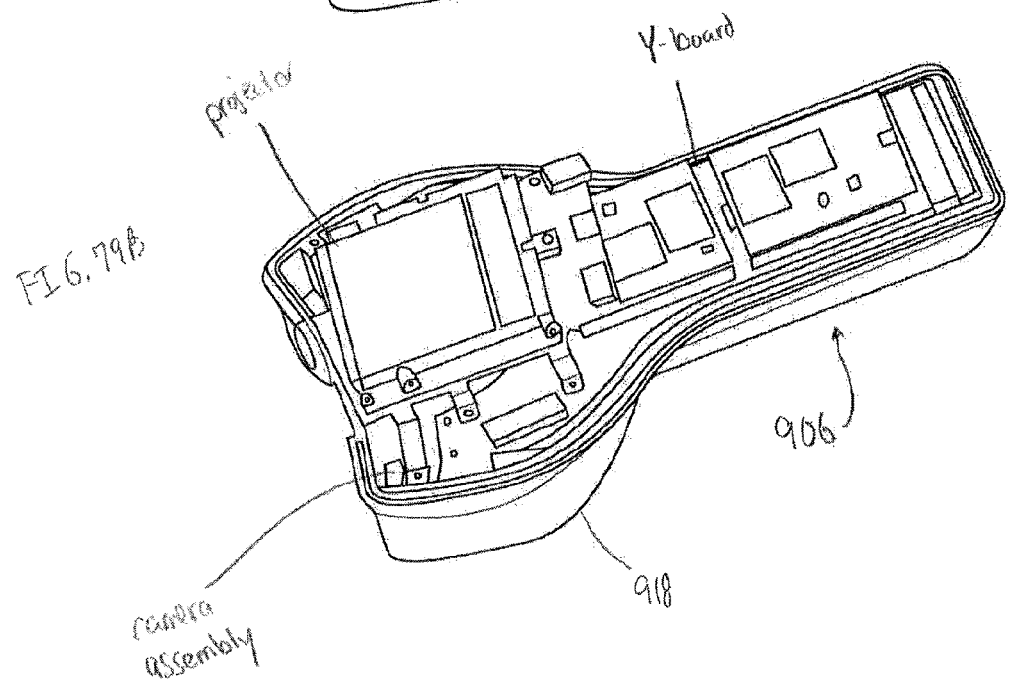

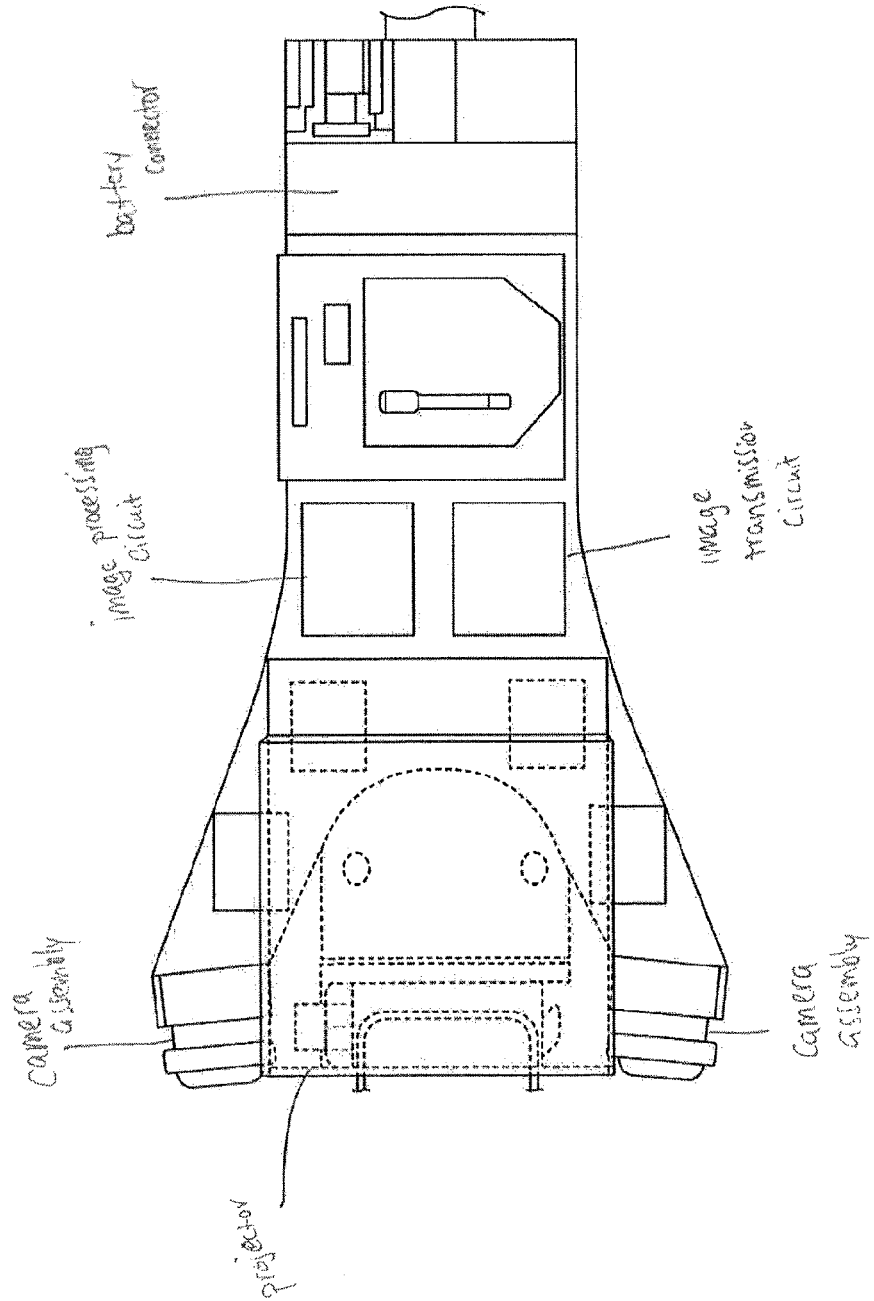

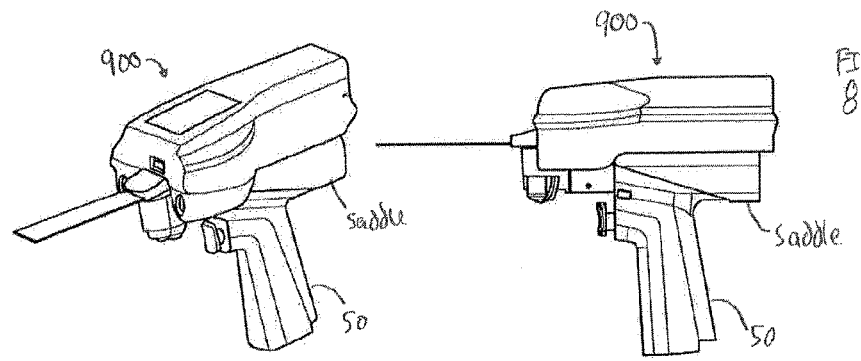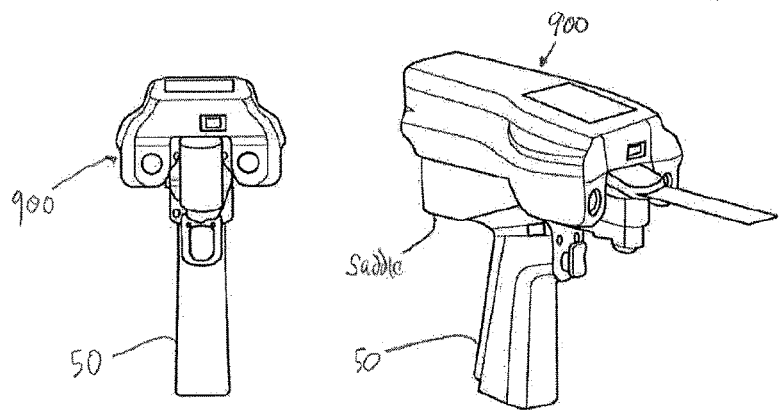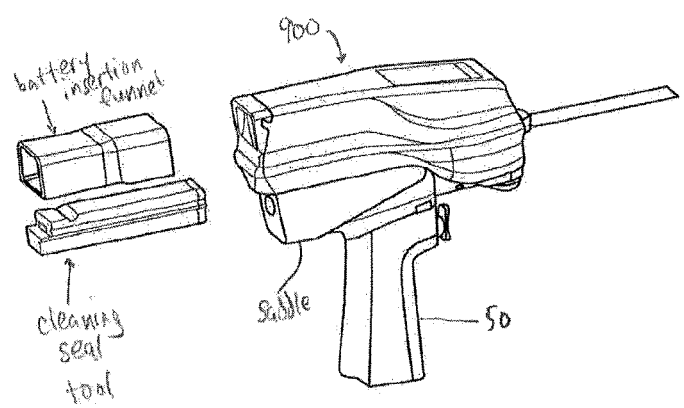

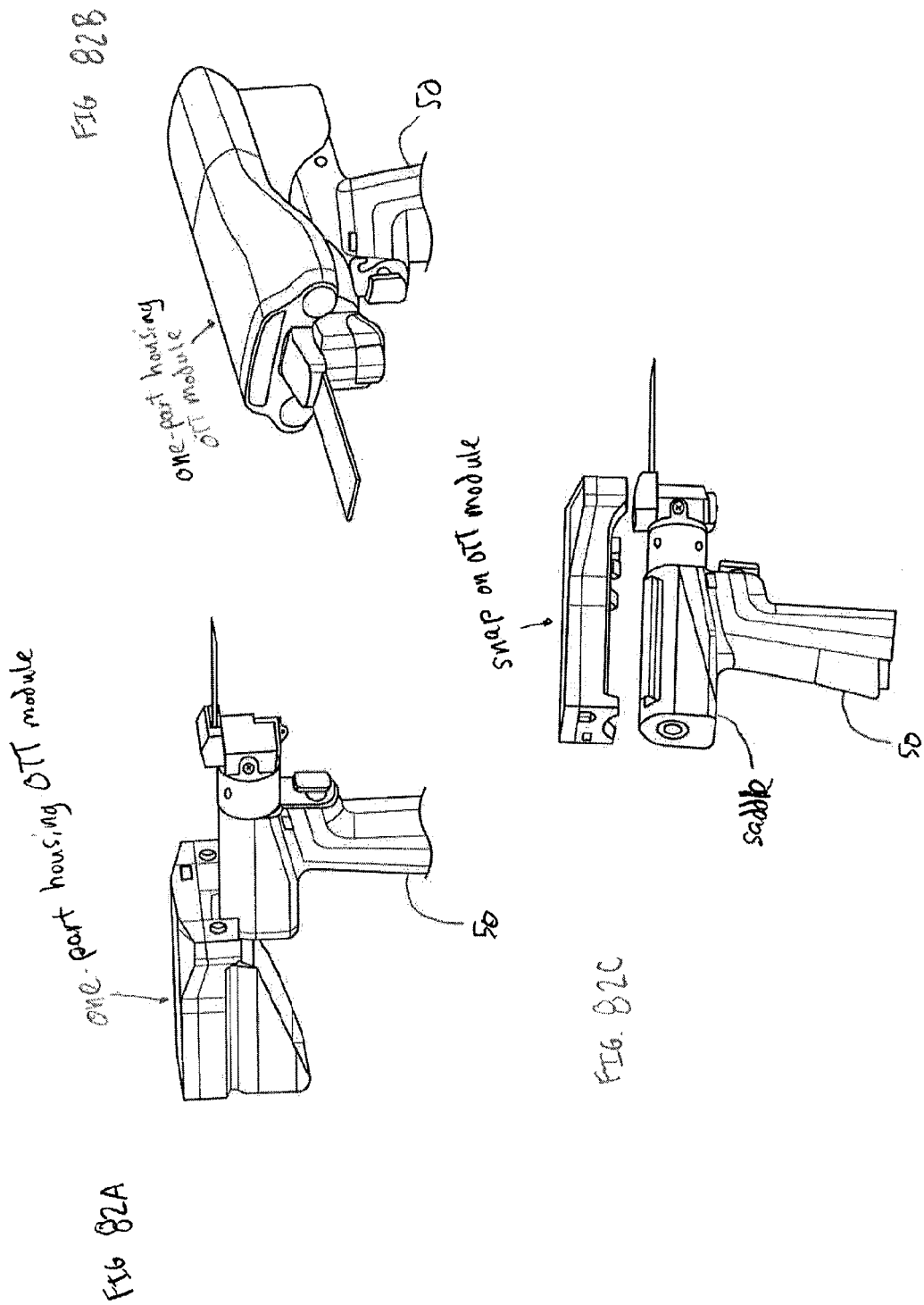

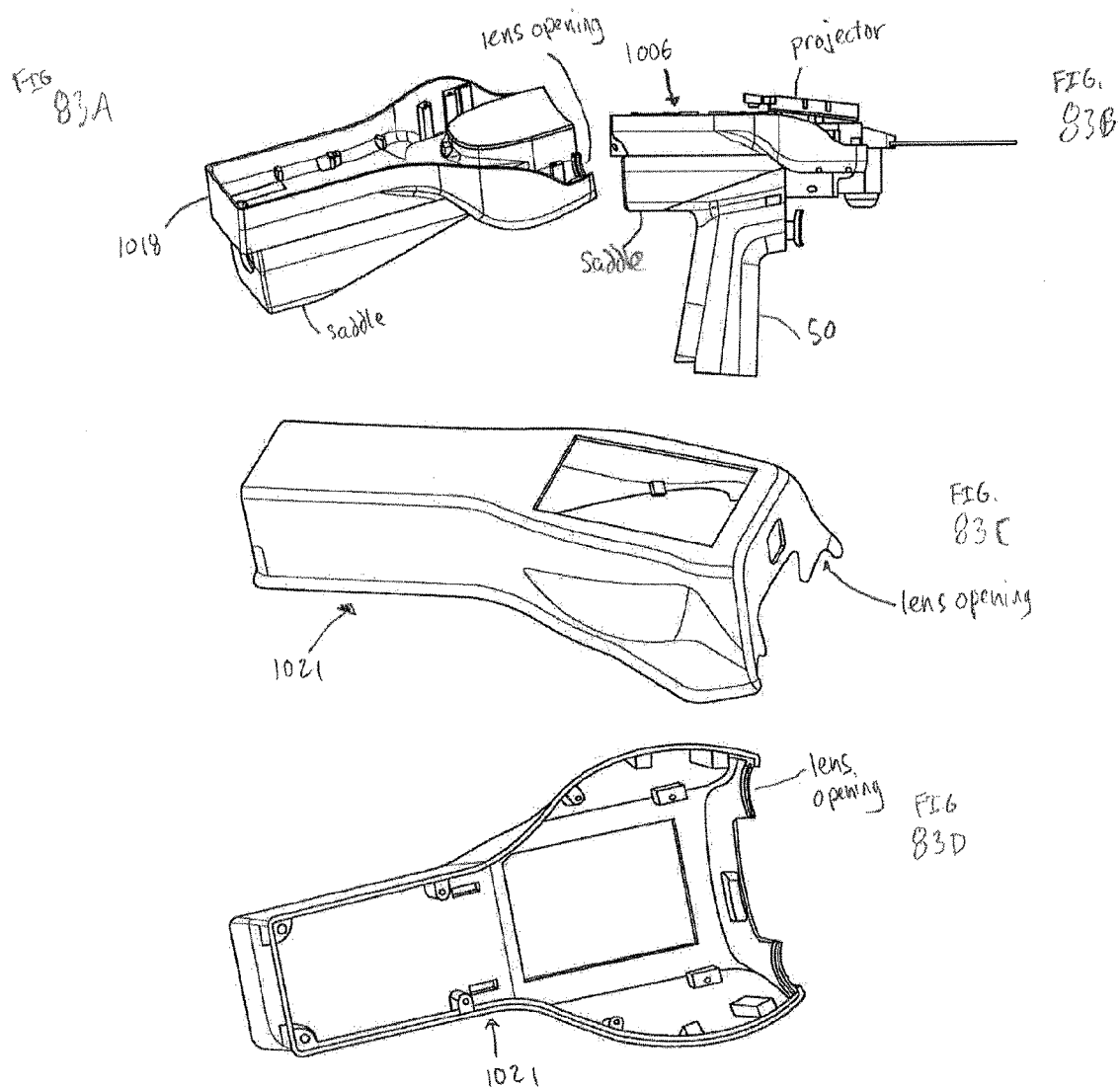

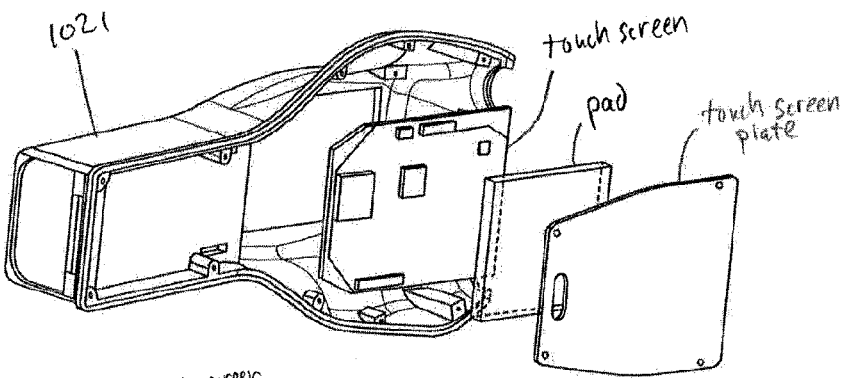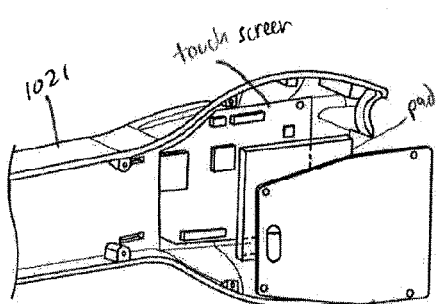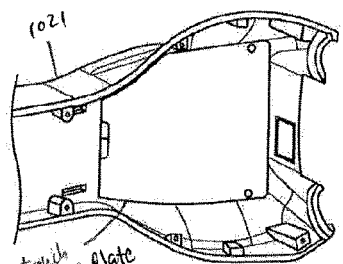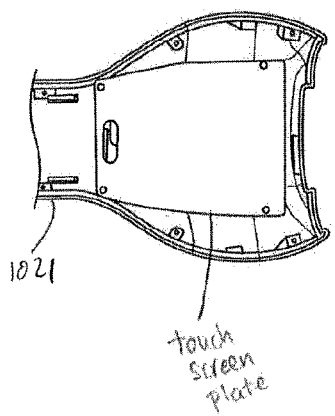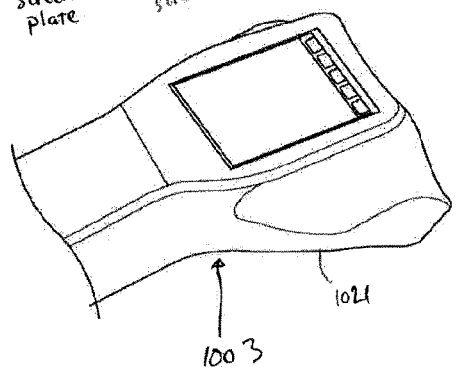

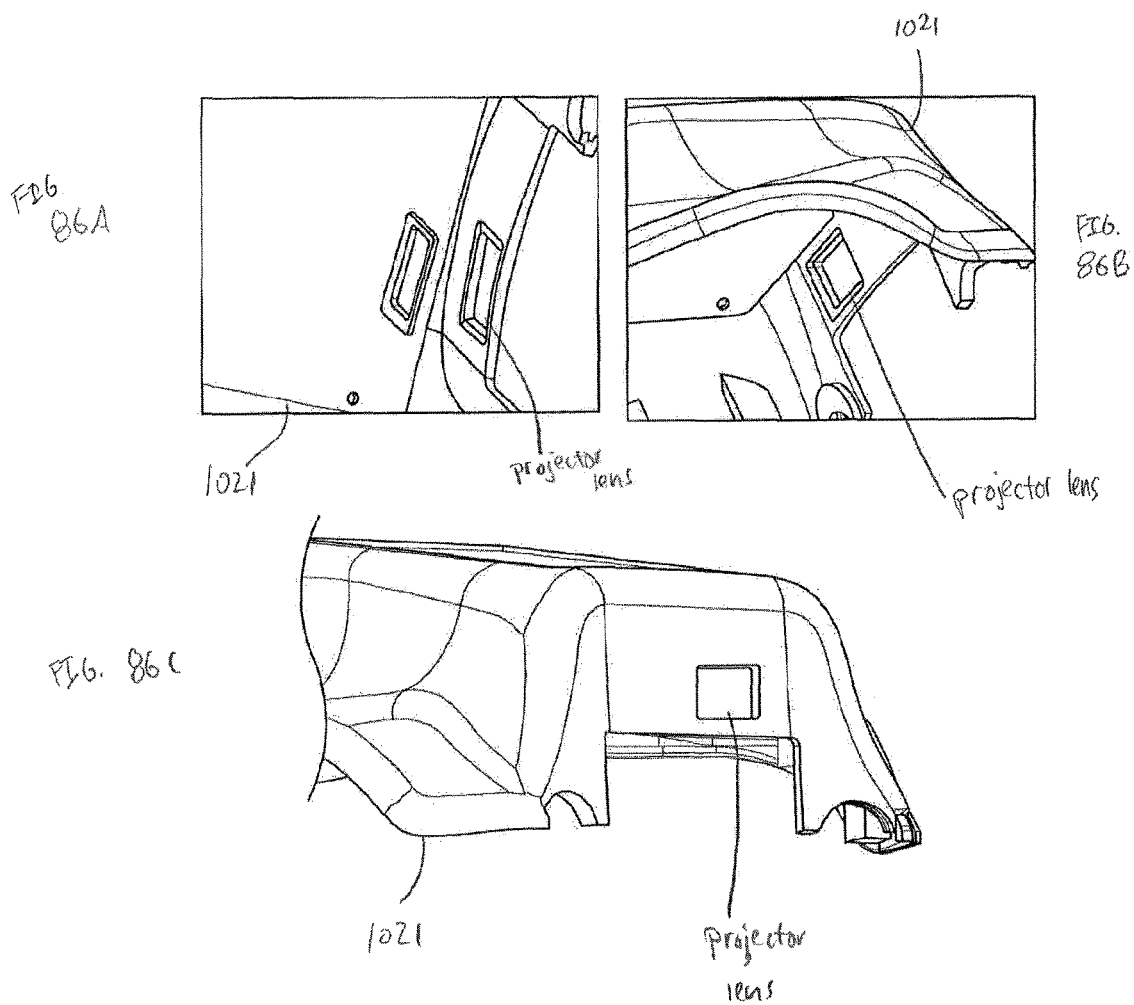

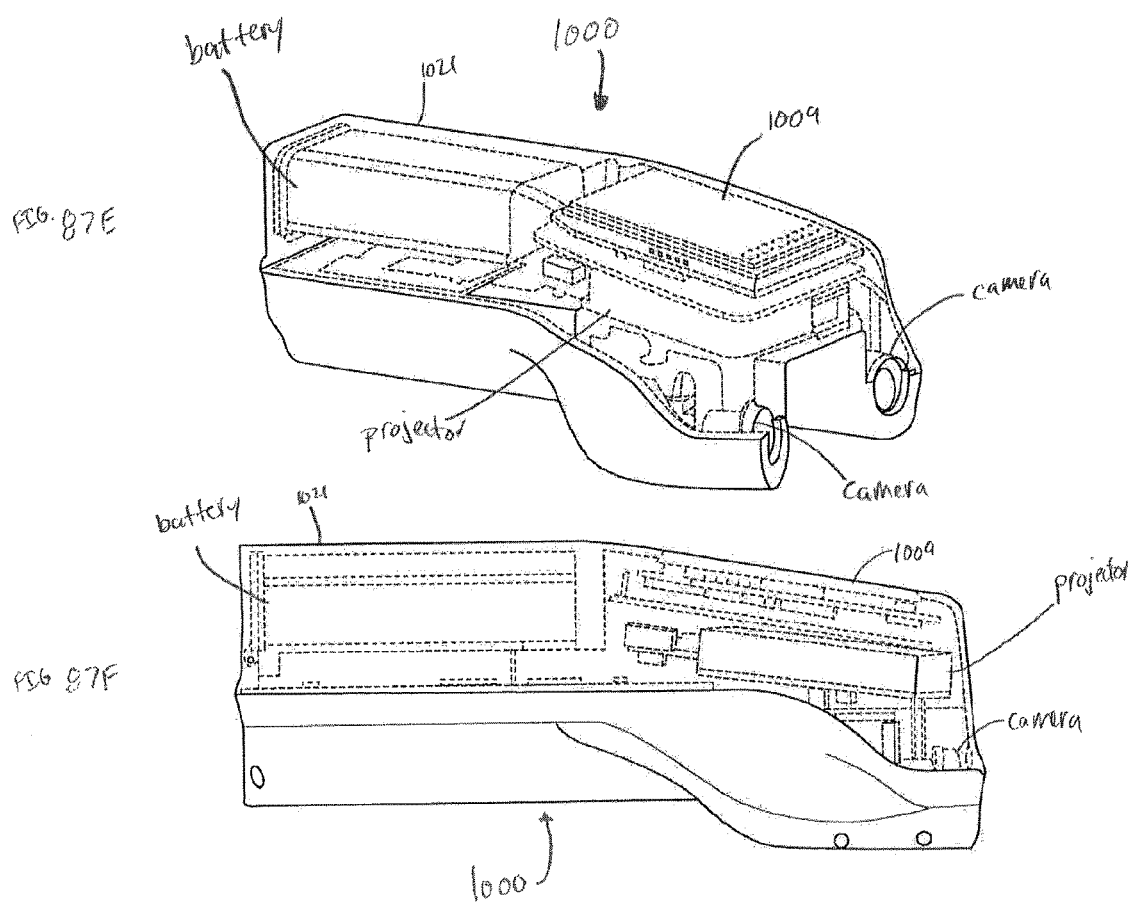

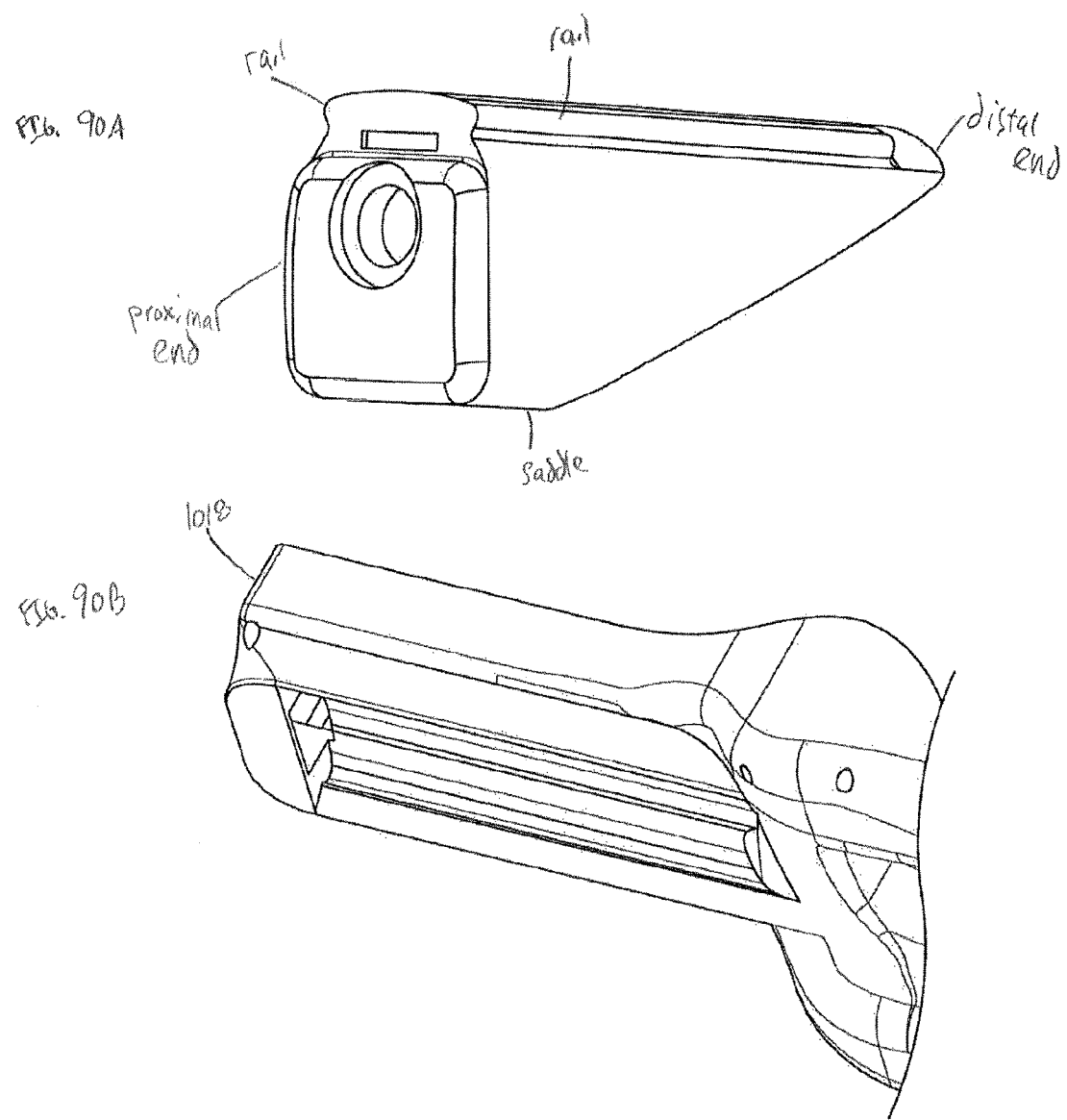

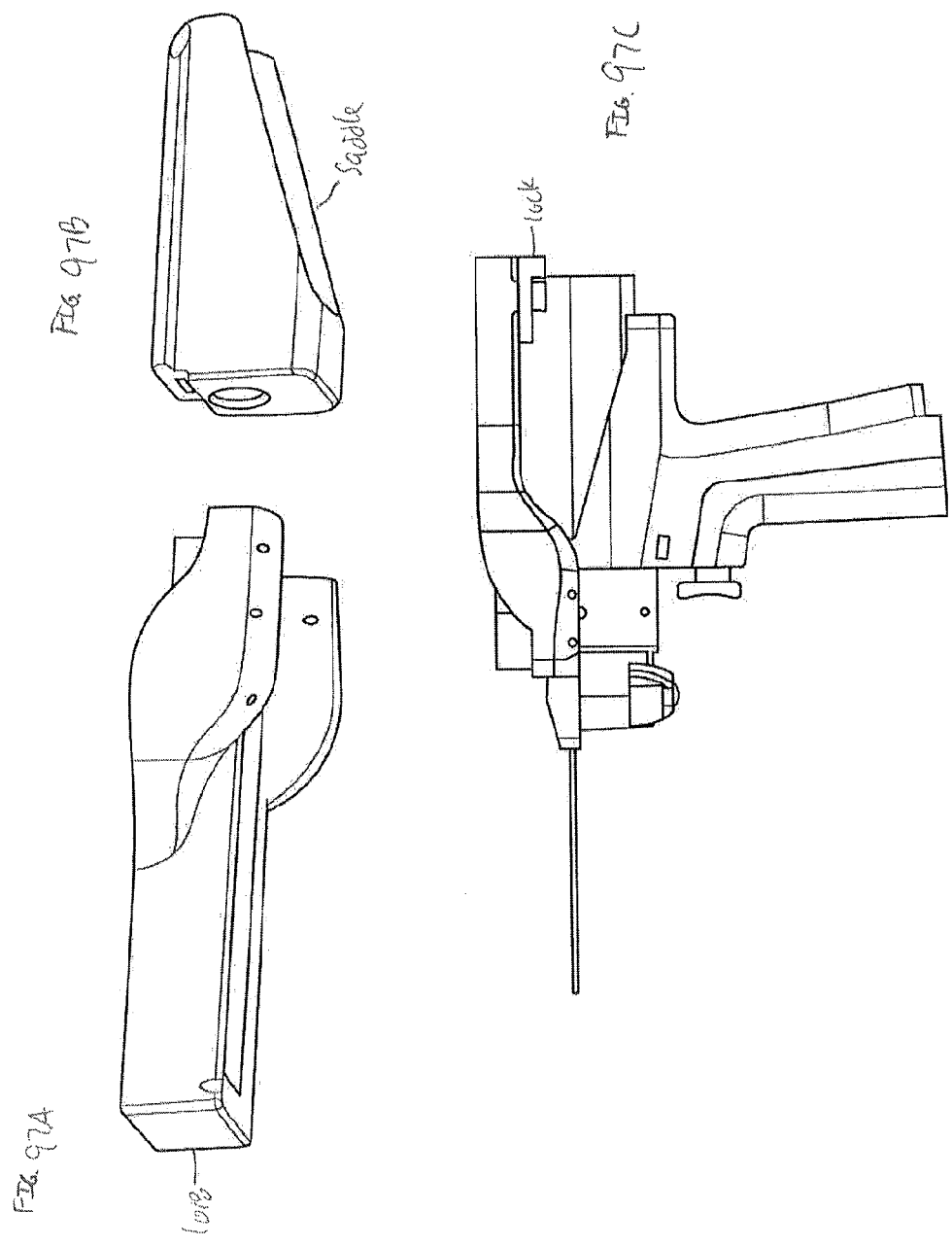

housing housing opening

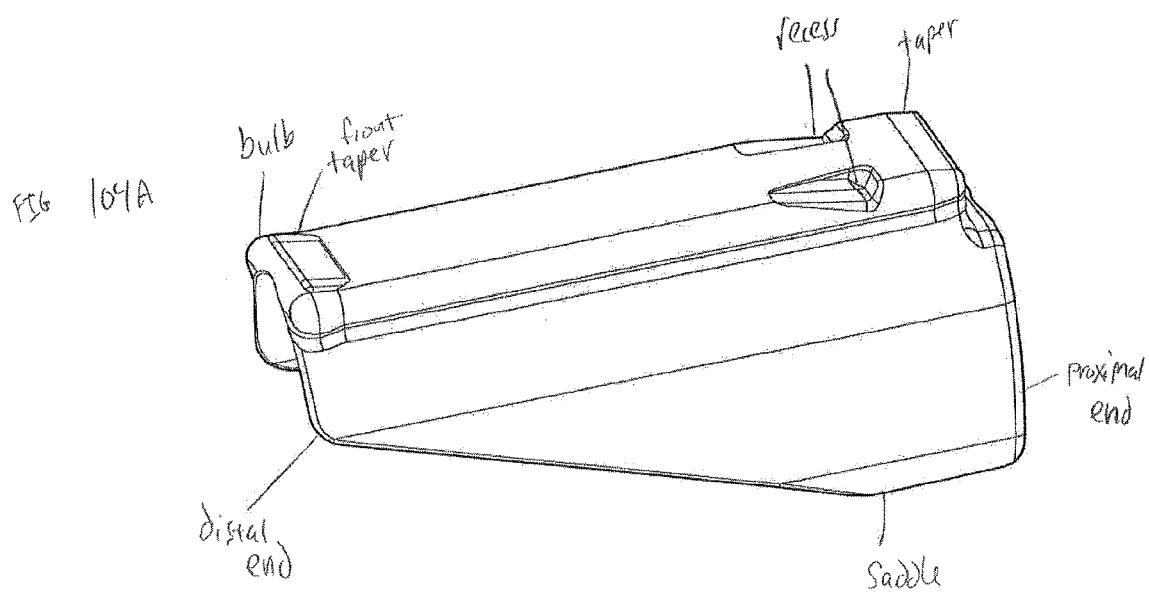

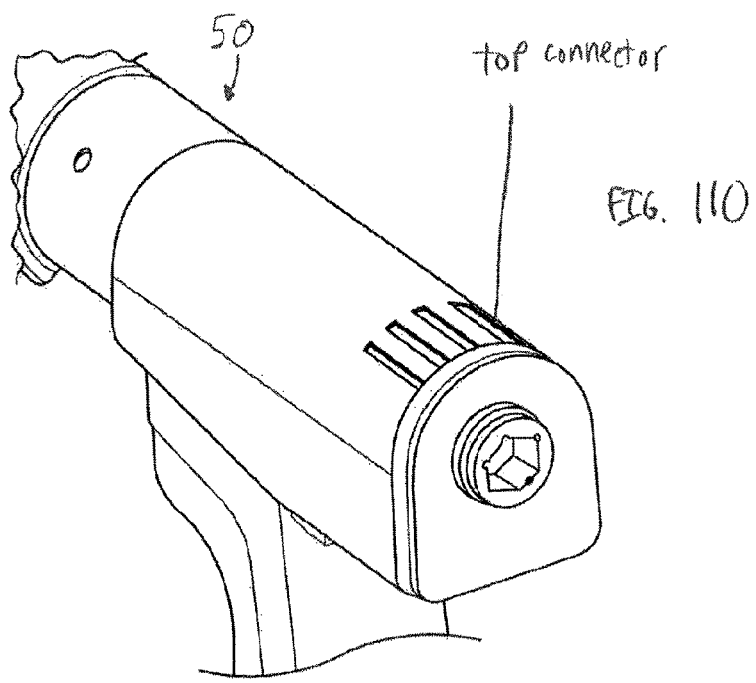

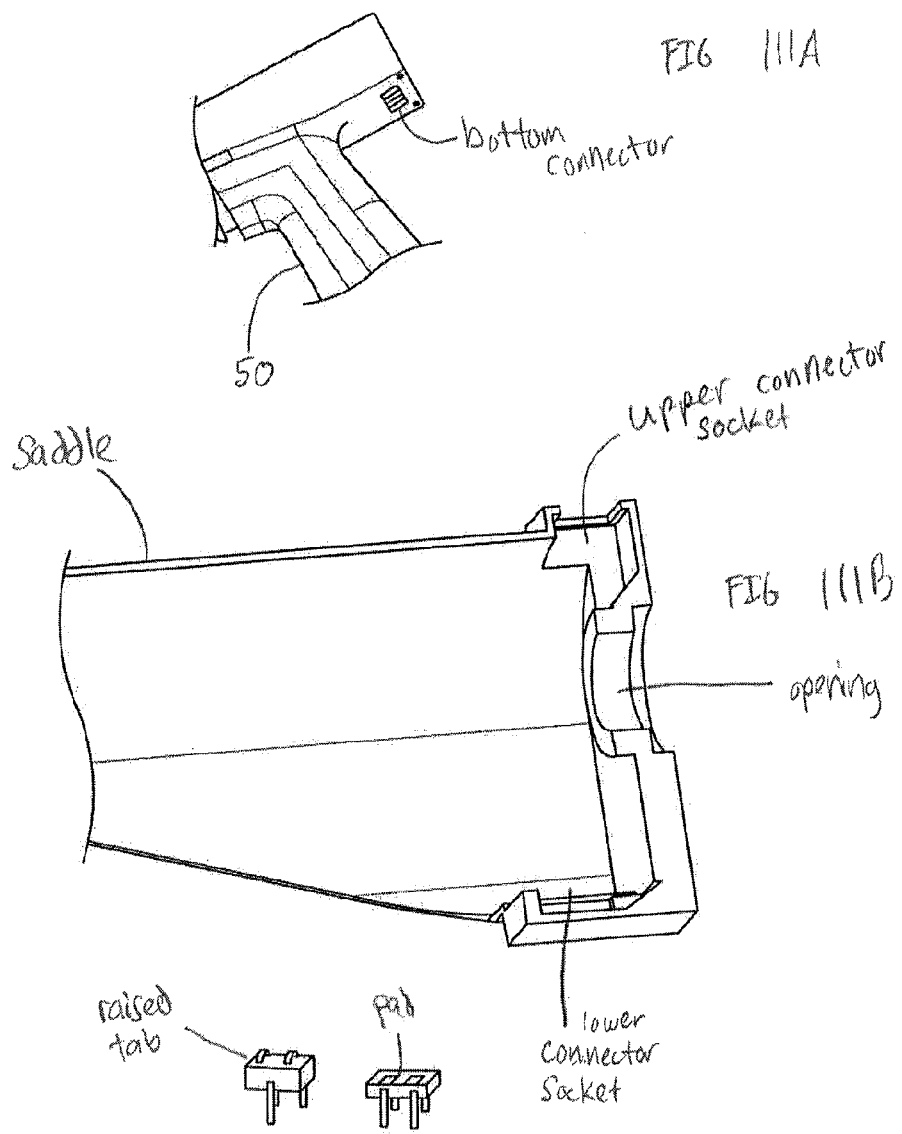

Y-board assembly

Y-board assembly electrical connectors

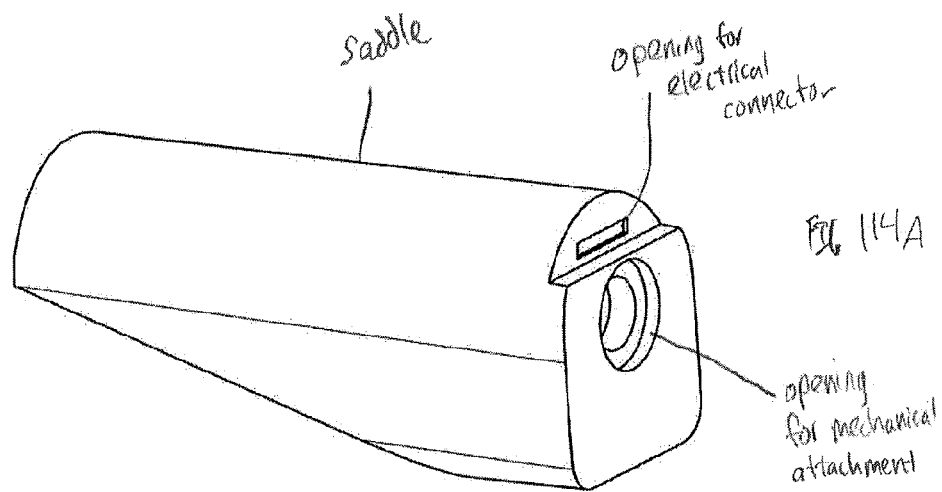
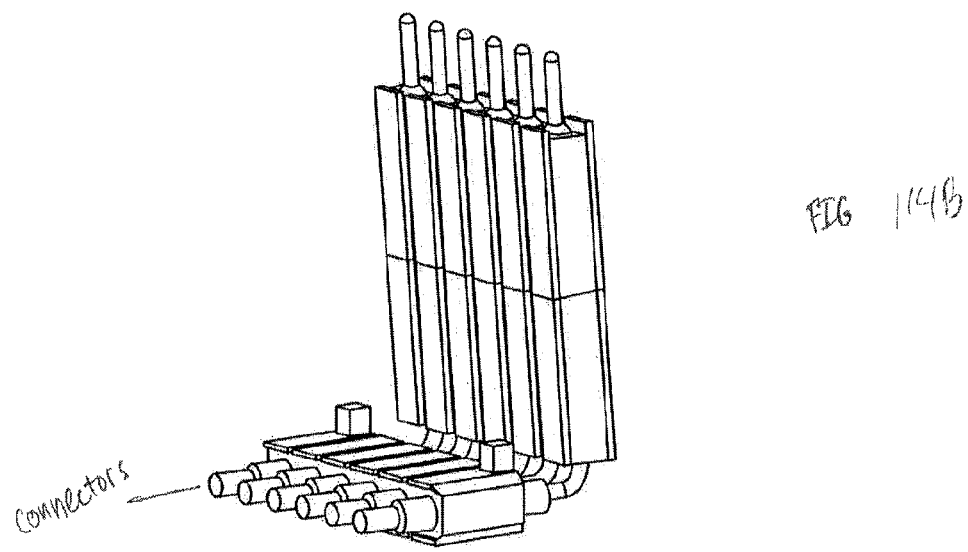

electrical connectors

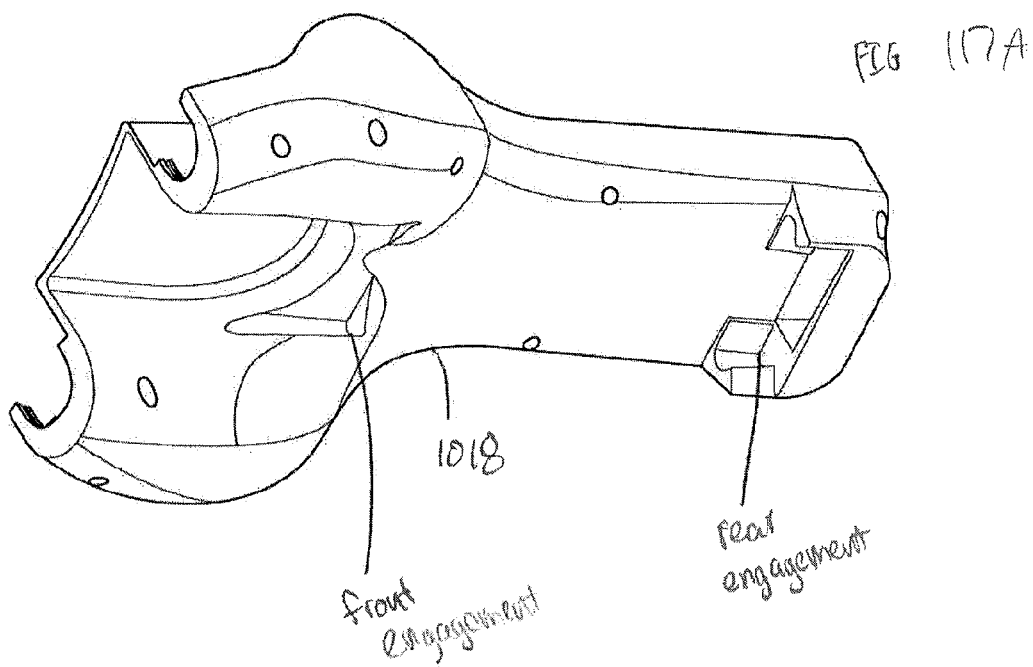

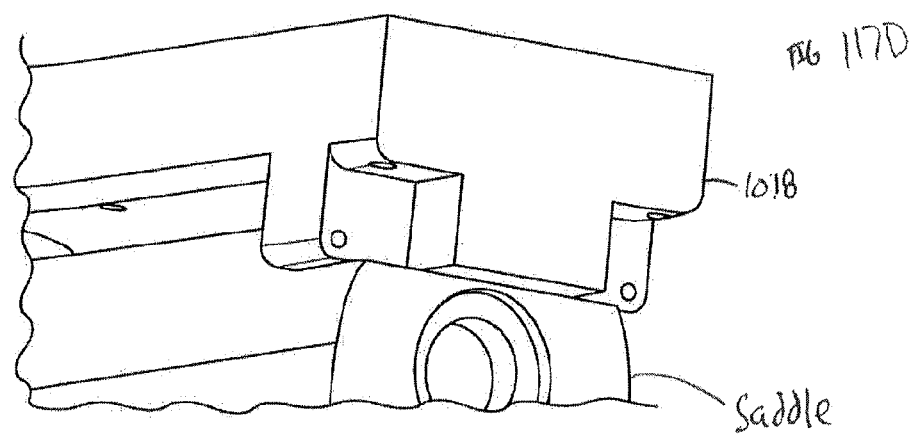

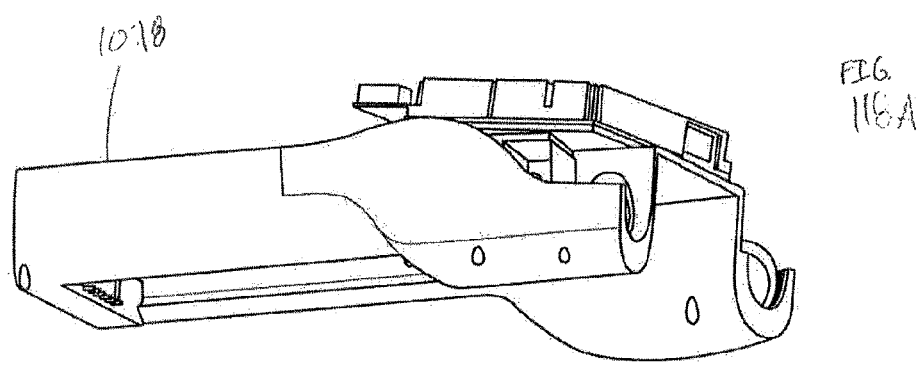
FIG. 118A
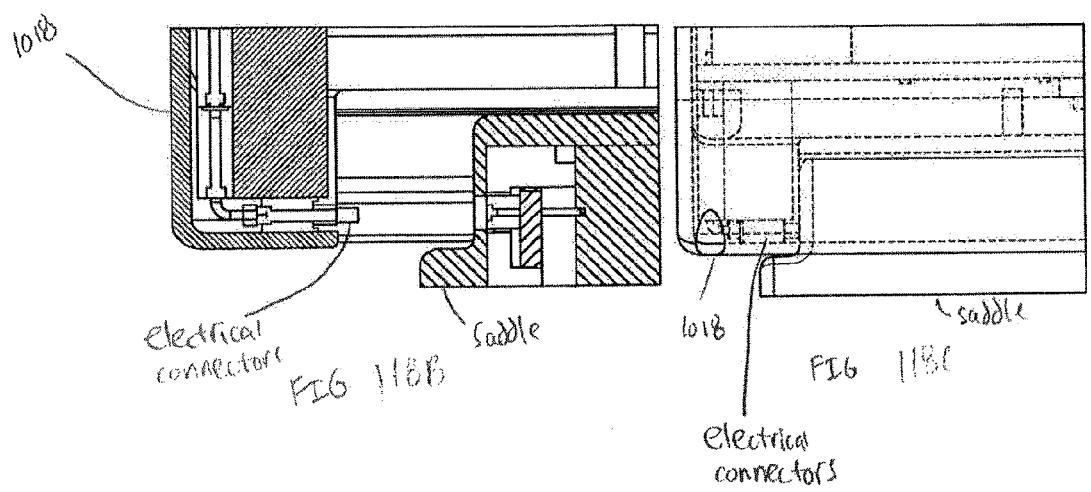
FIG. 118B  electrical connectors  saddle
FIG. 118C  1018  saddle  electrical connectors

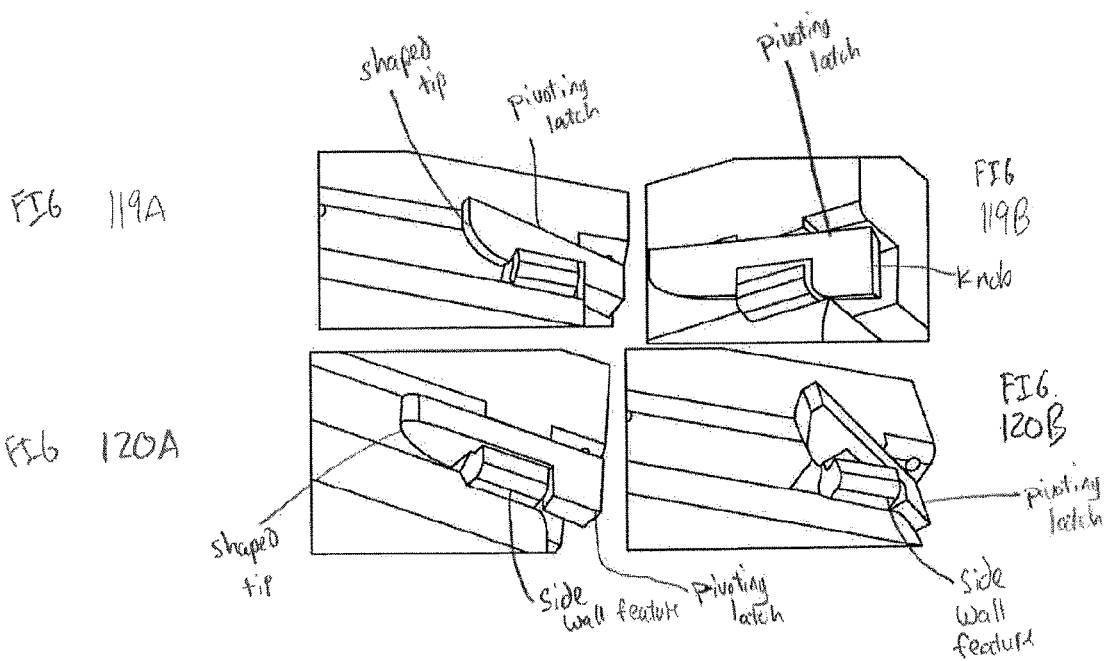
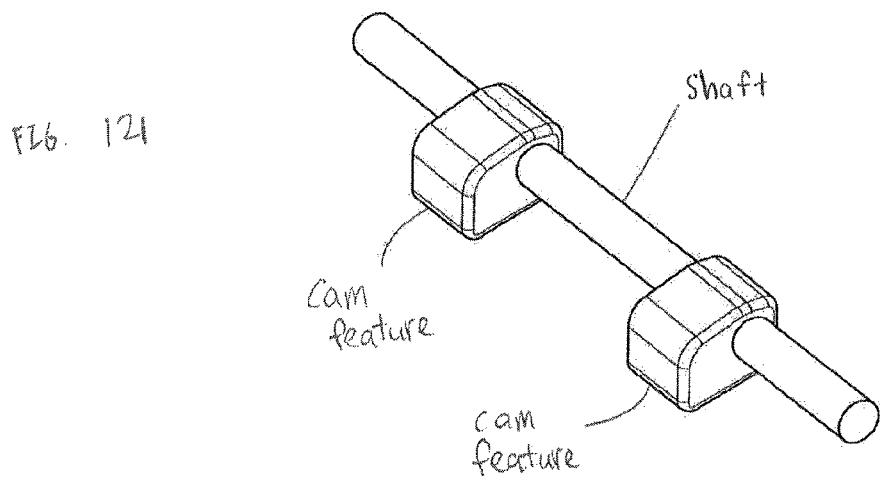

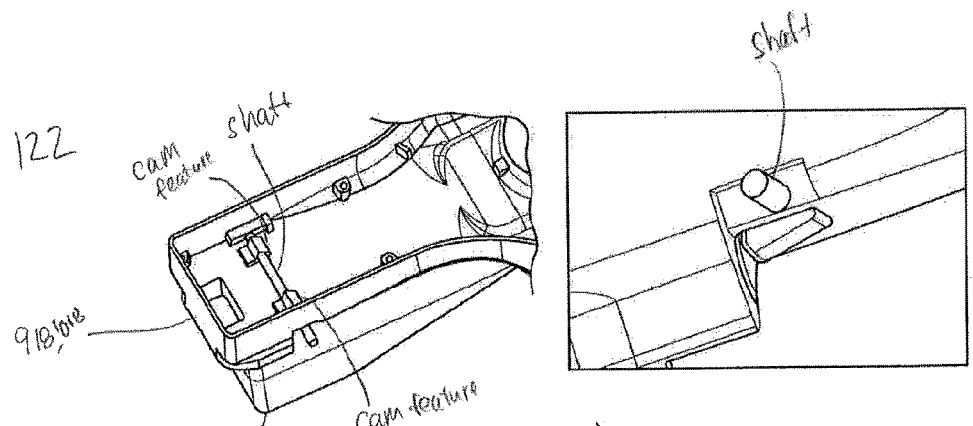
FIG. 122
FIG. 123
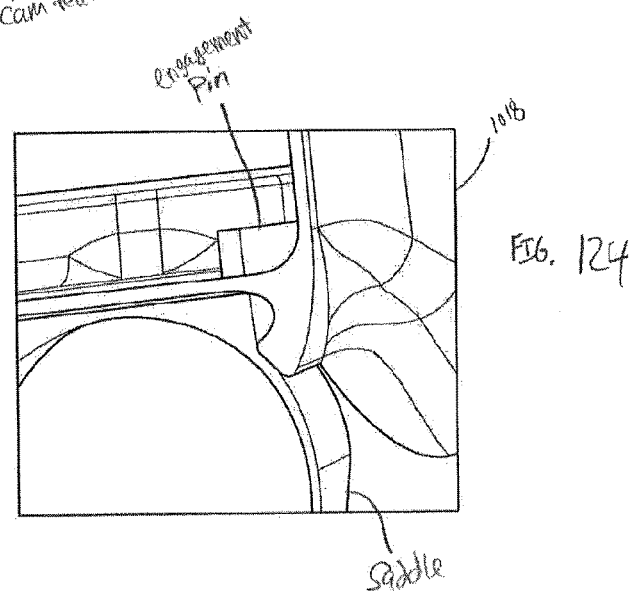
FIG. 124

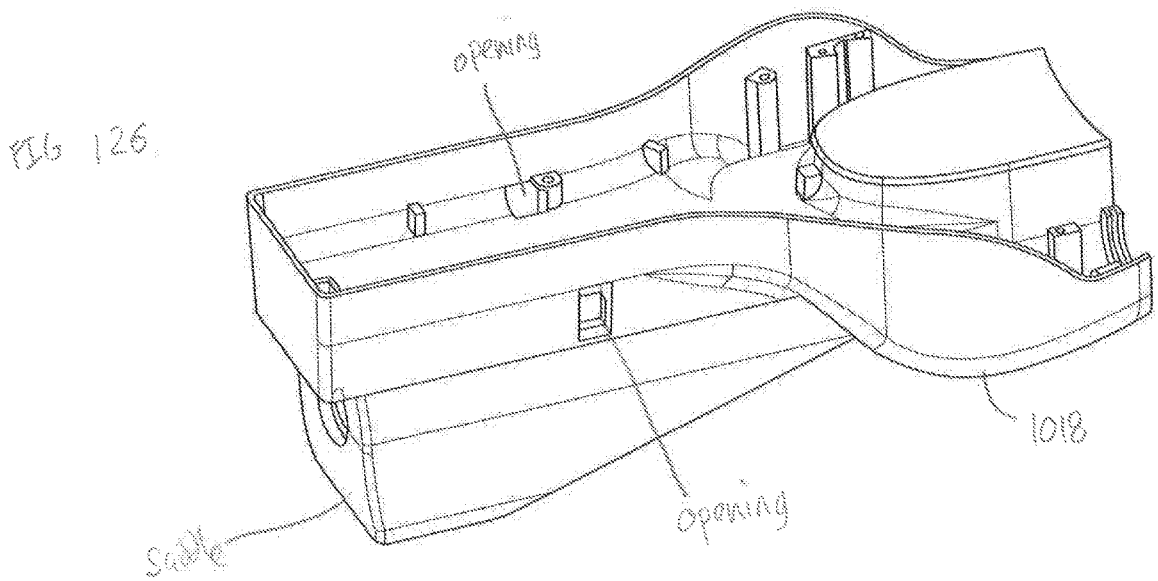
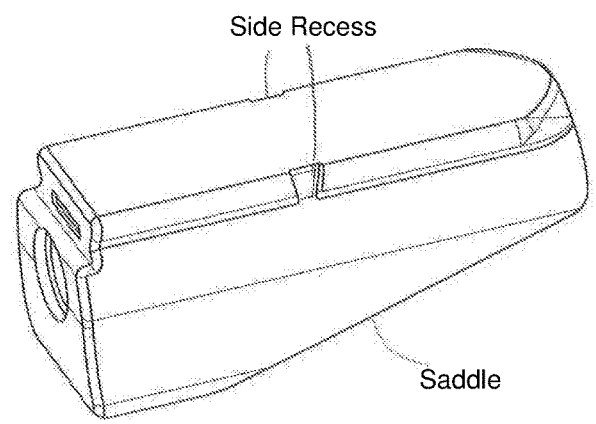
FIG. 125

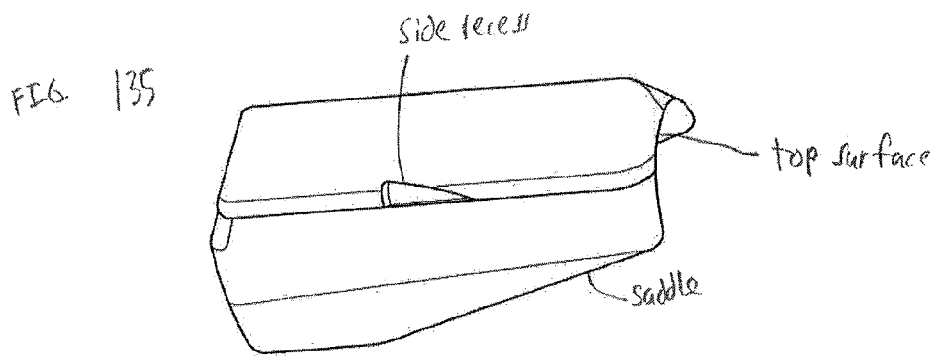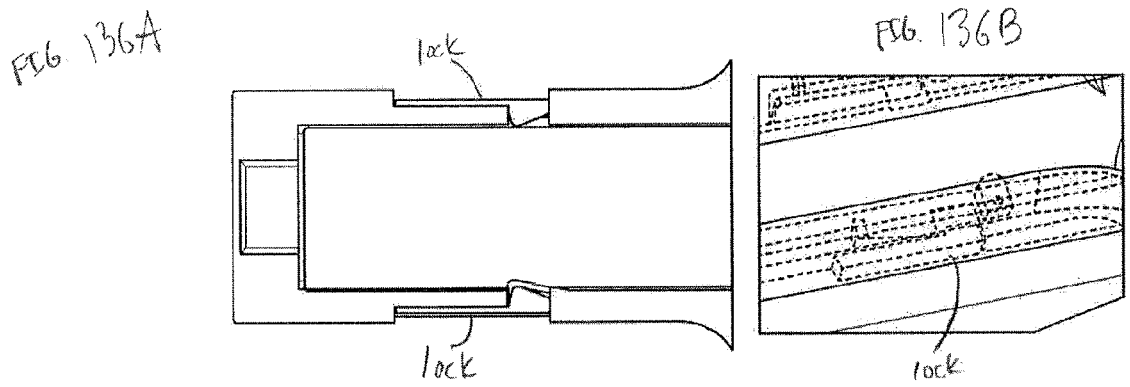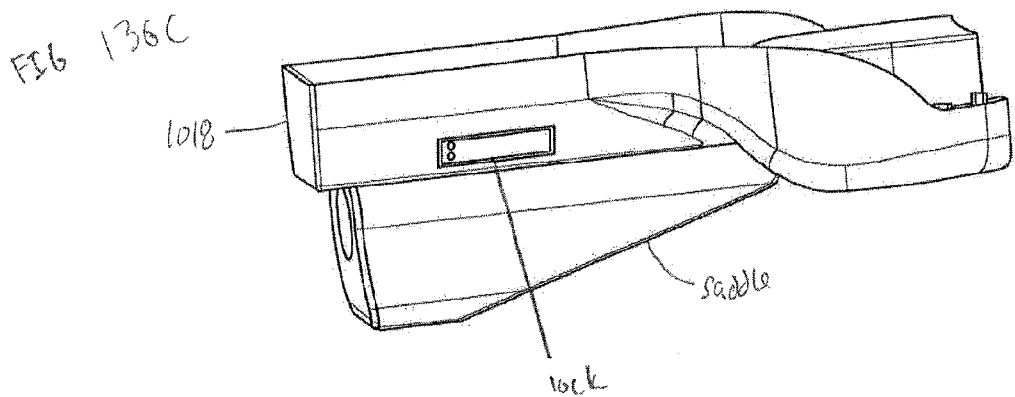

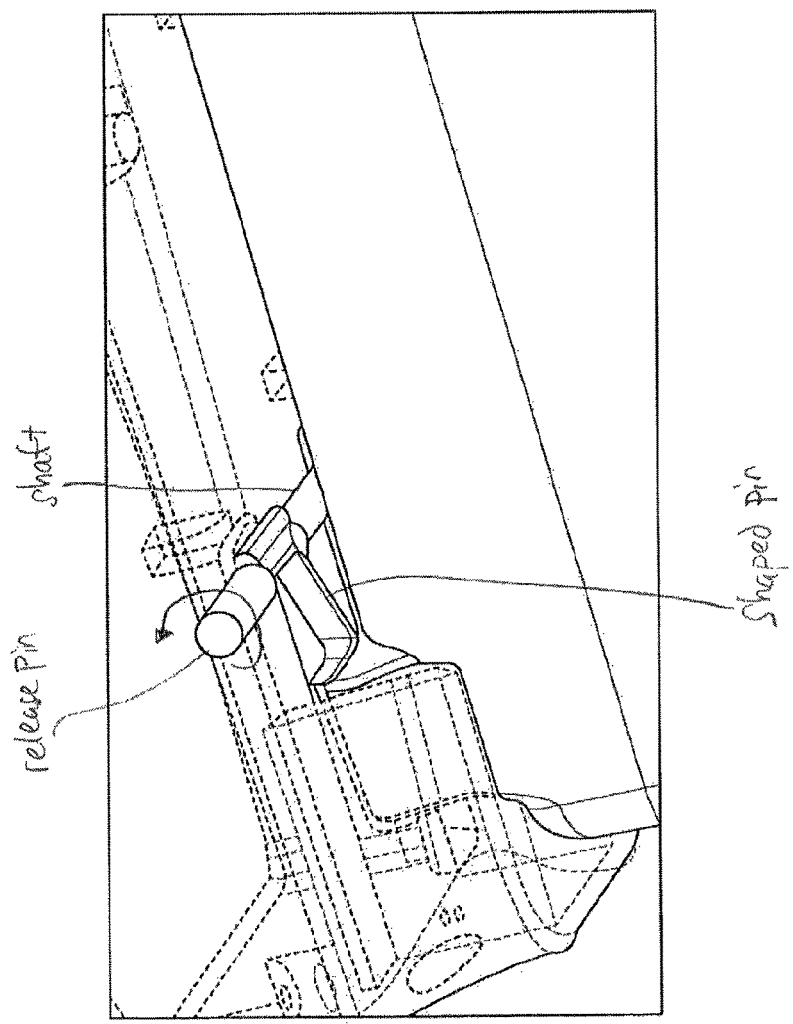

Camera   Camera

Camera

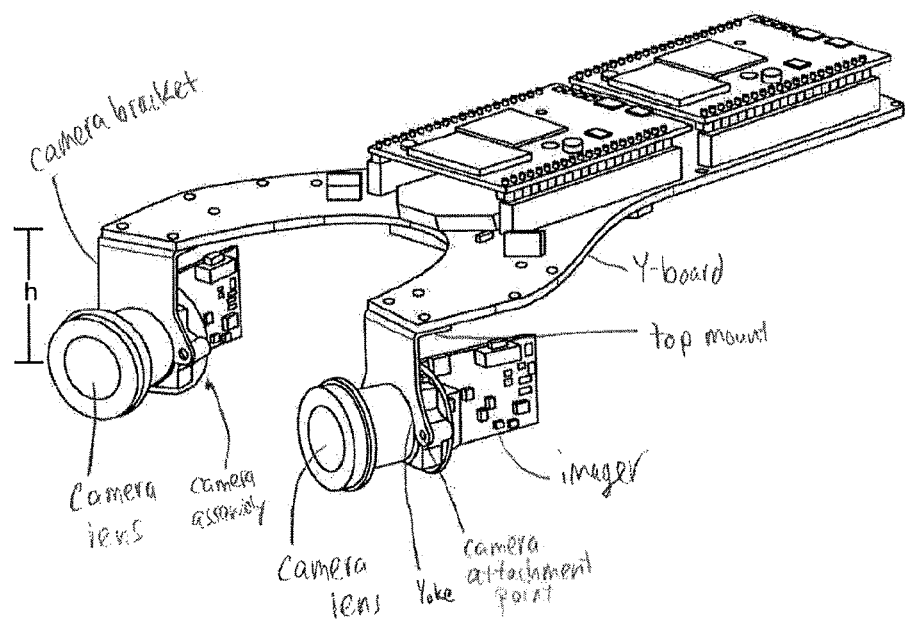
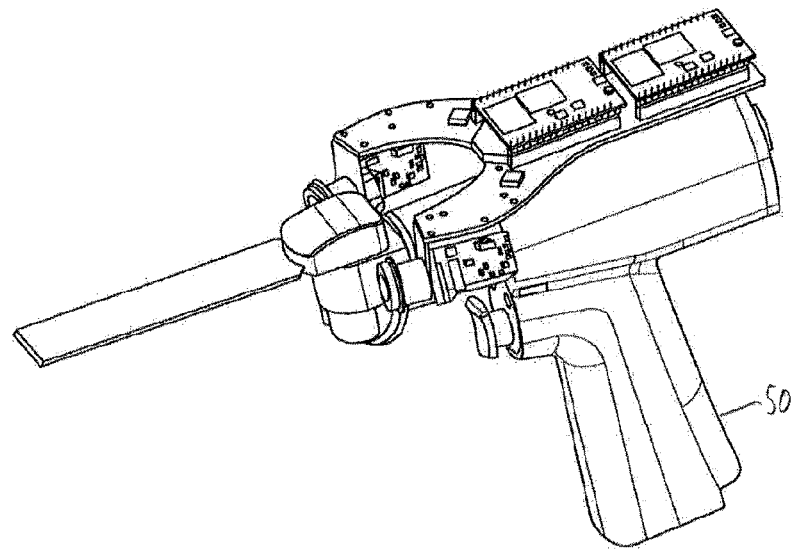

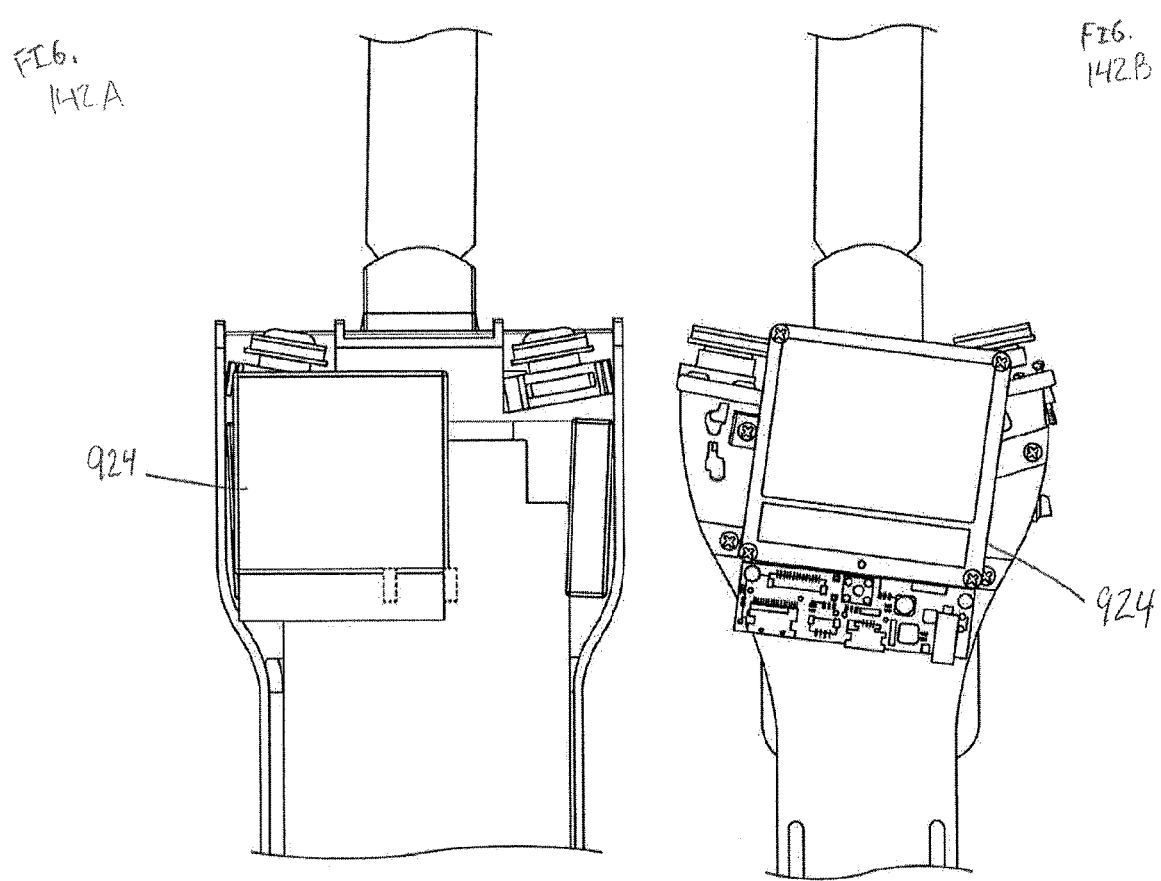

projector bracket projector bracket

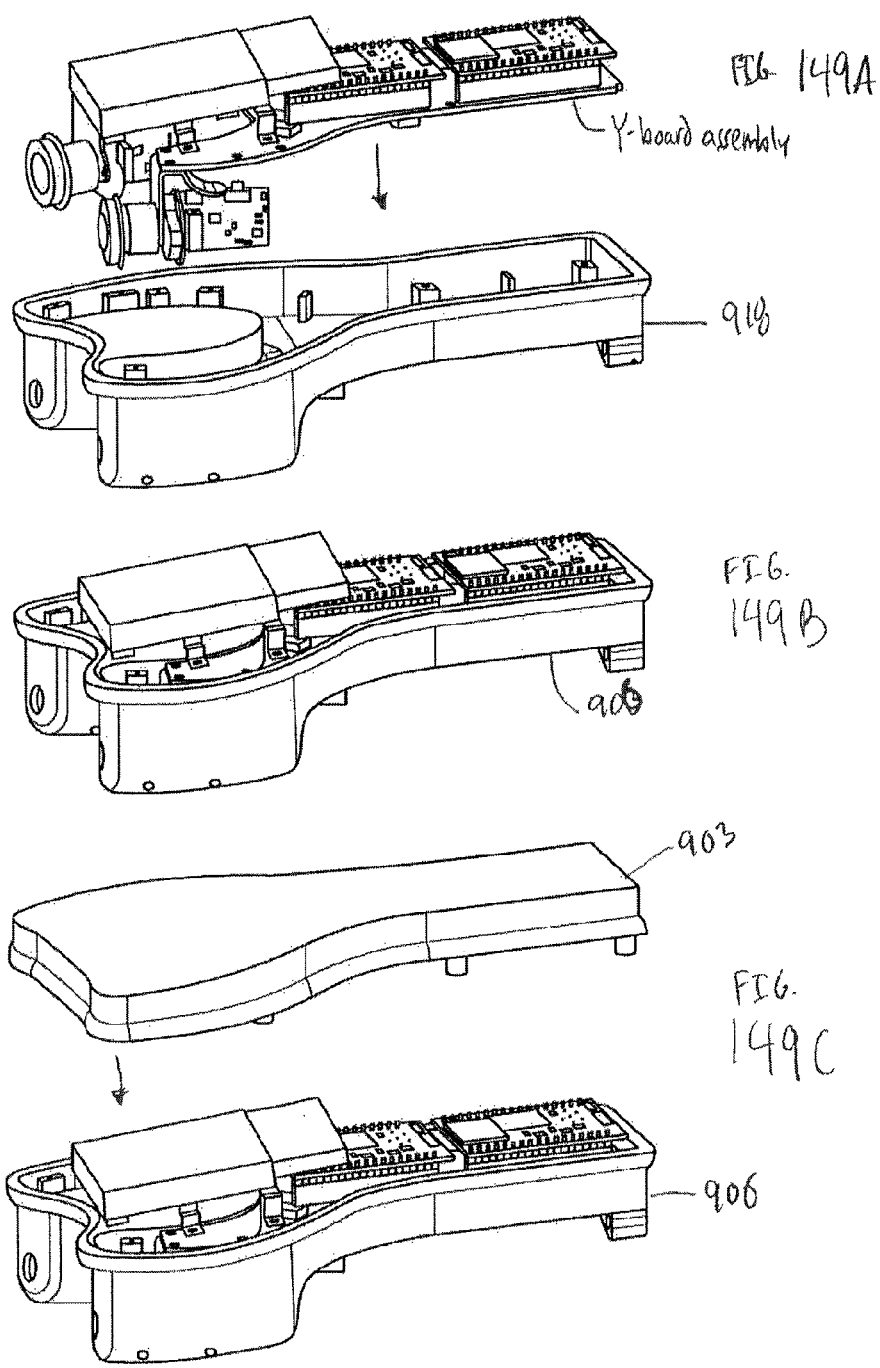

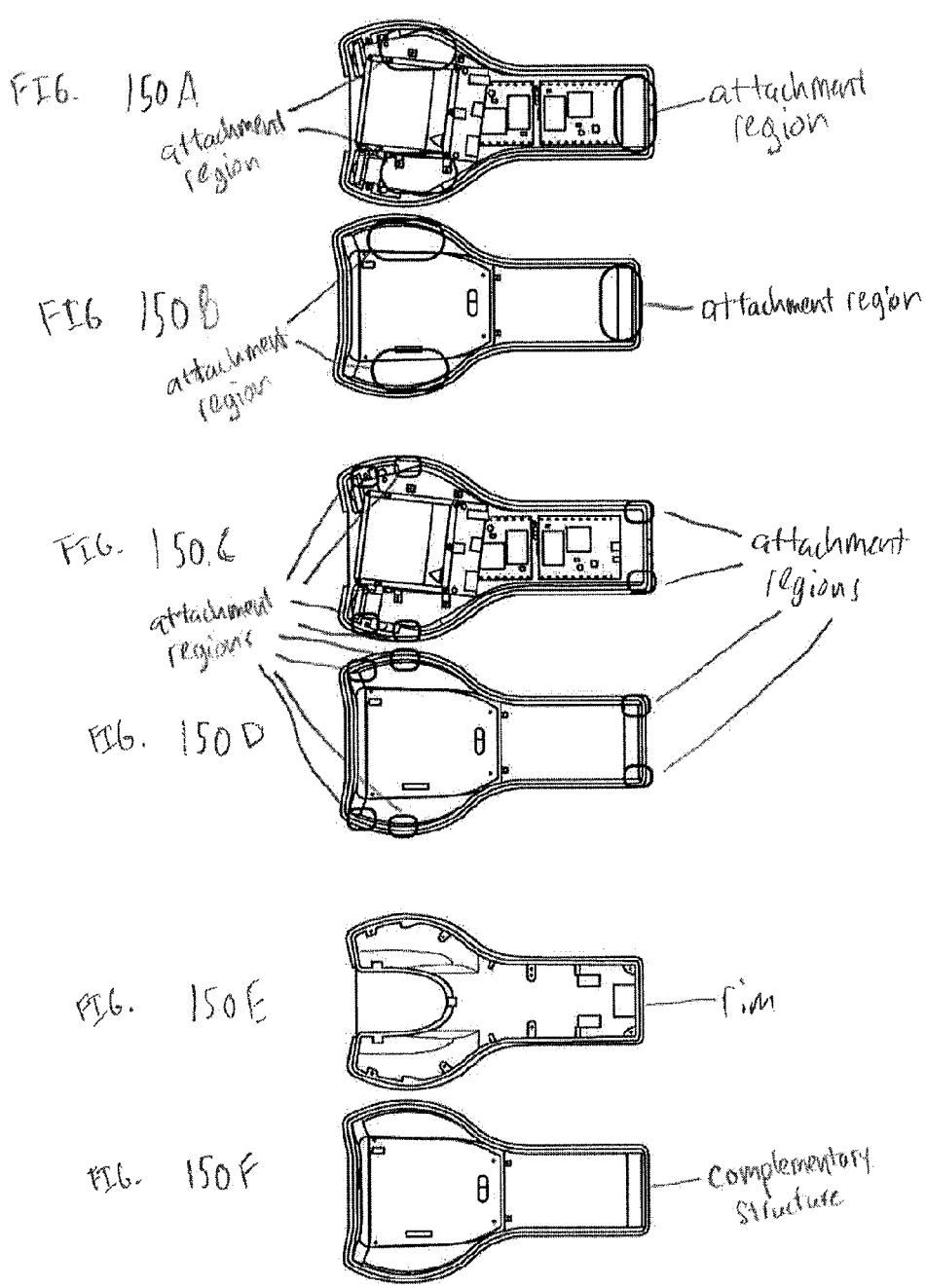

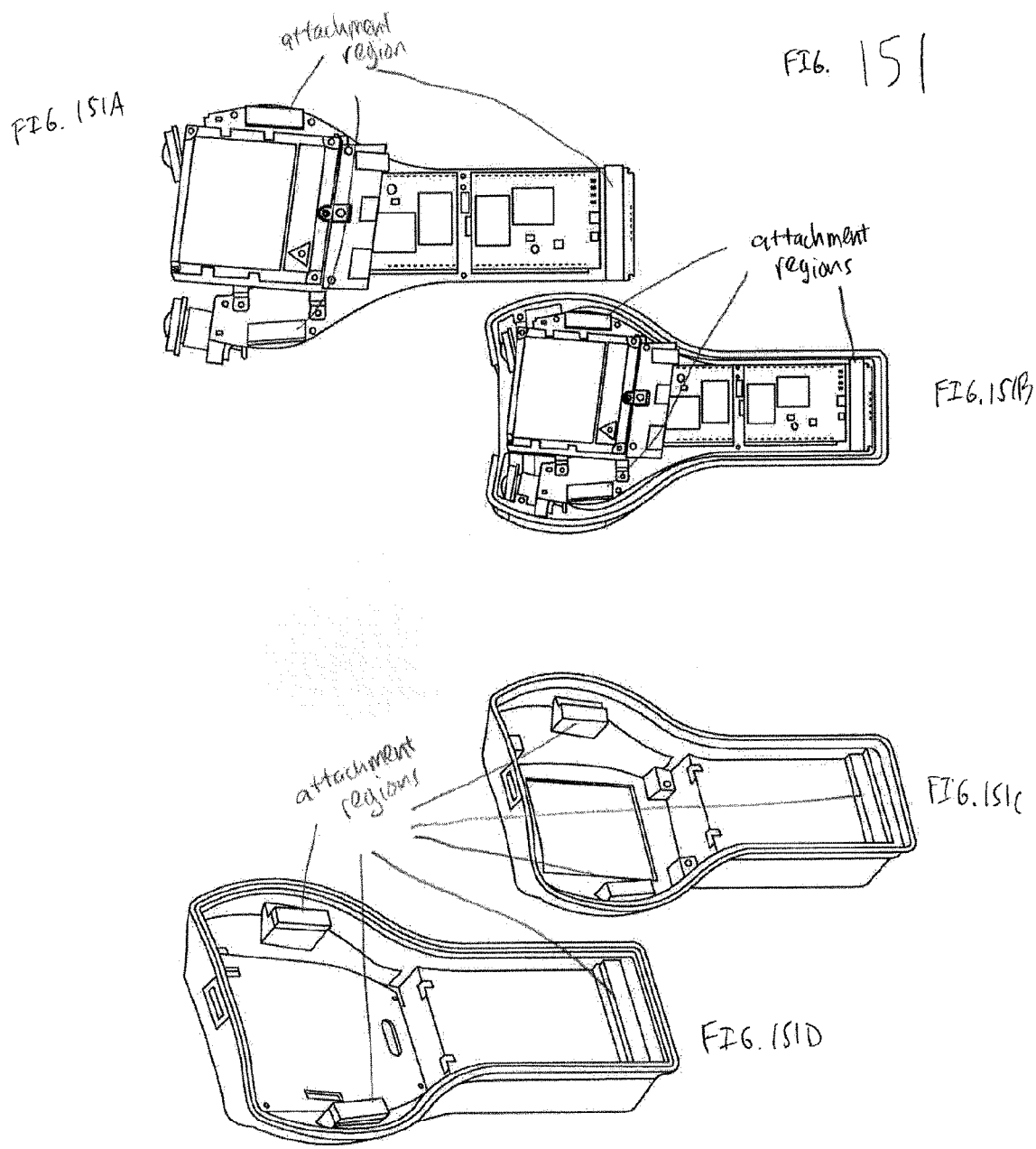

FIG. 151E
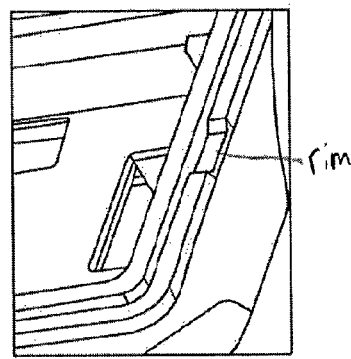
FIG. 151F
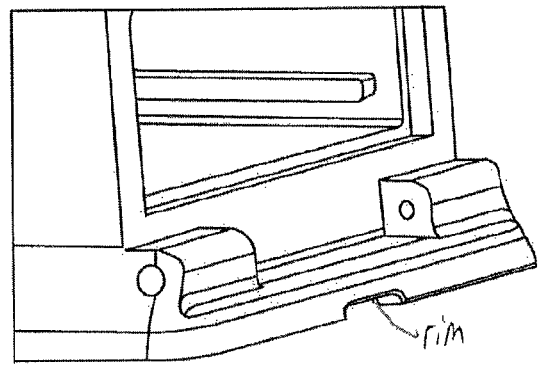
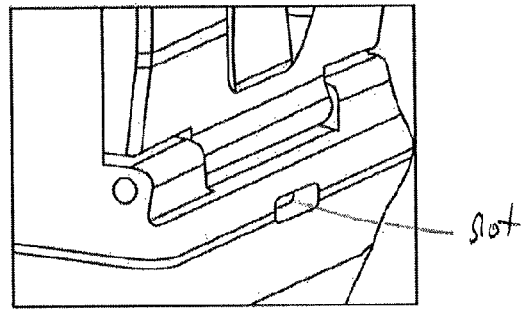
FIG. 151G

— snap fit clip

— Socket

Snap Socket
Snap Stud

Snap Socket
Snap Stud

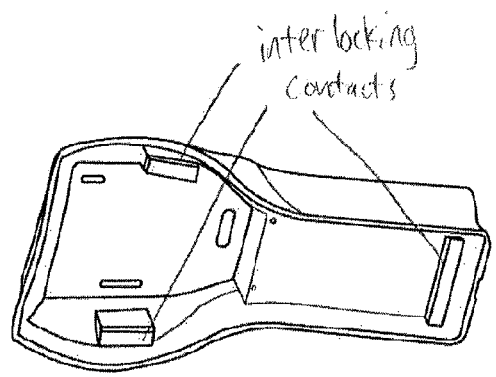

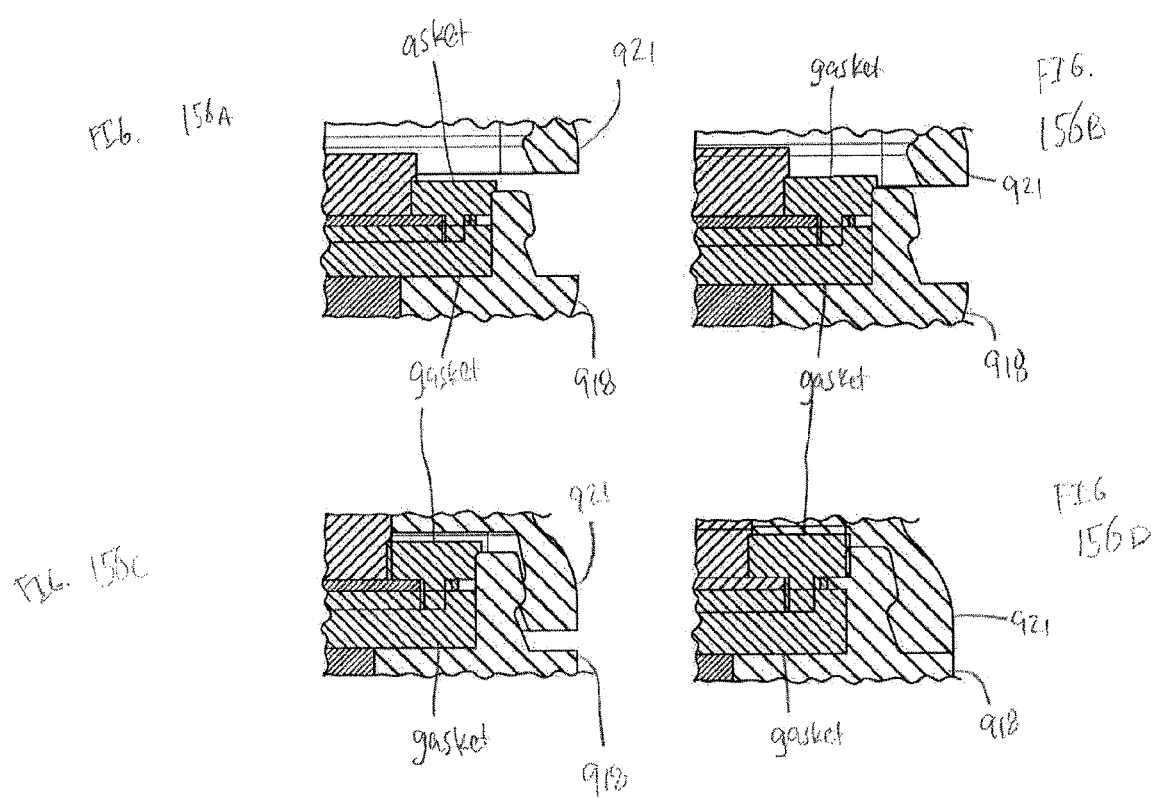

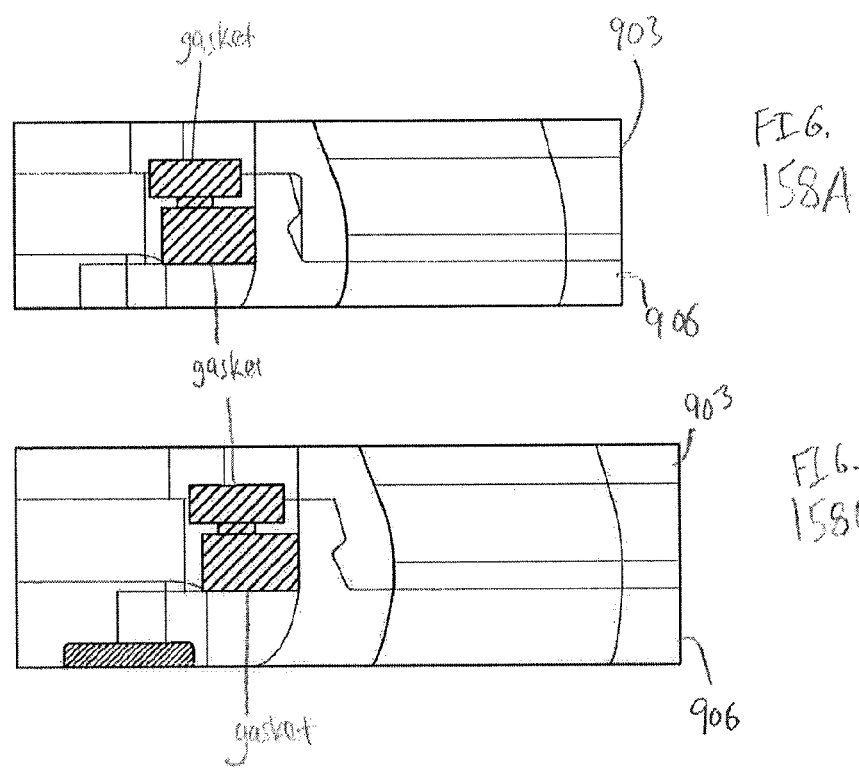

LEDs

Capacitive Switch

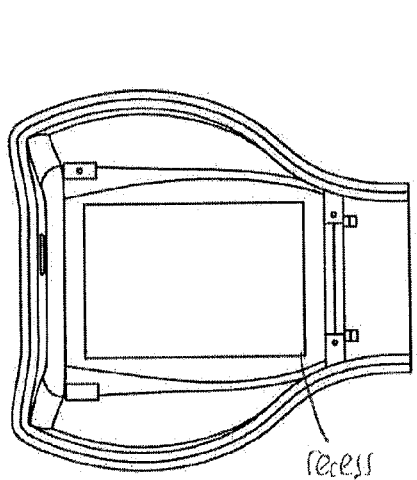
FIG. 162A
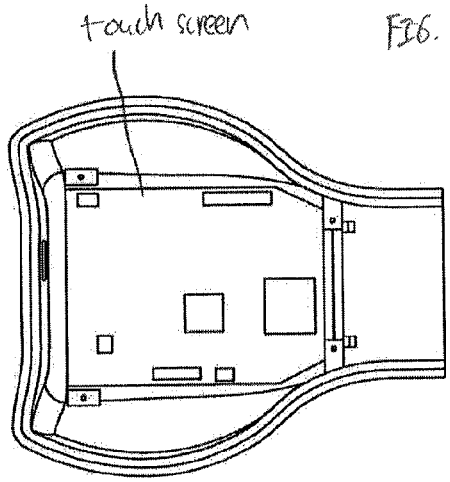
FIG. 162B (touch screen)
recess
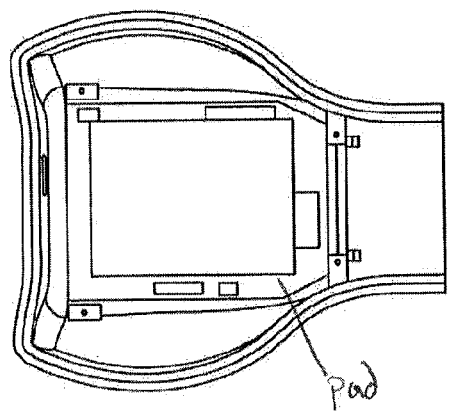
FIG. 162C
pad
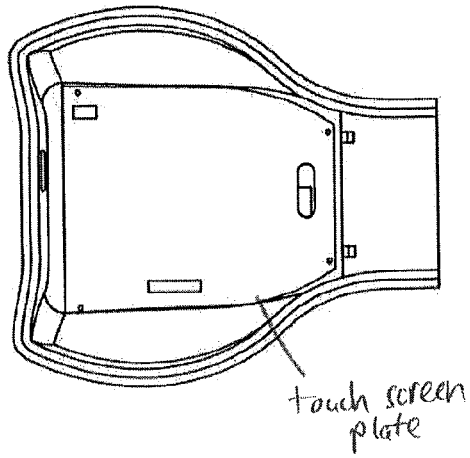
FIG. 162D
touch screen plate

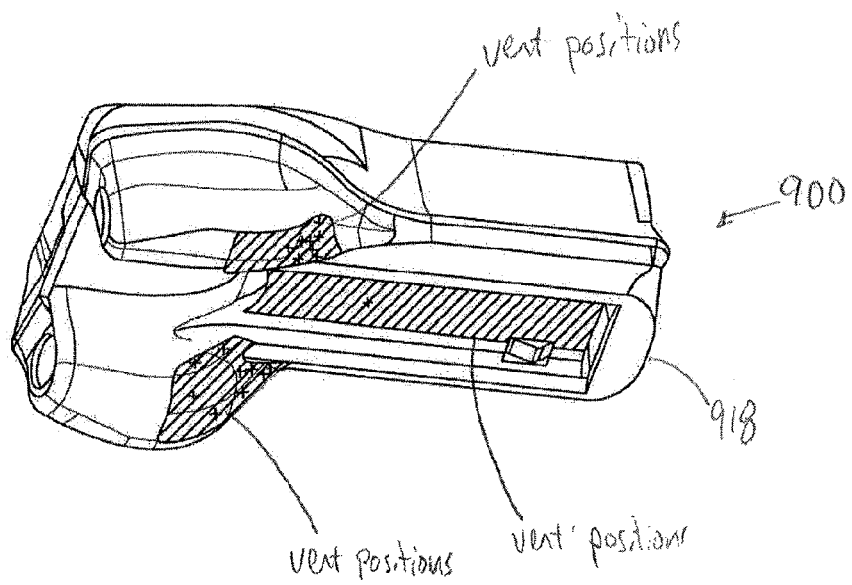

liner liner

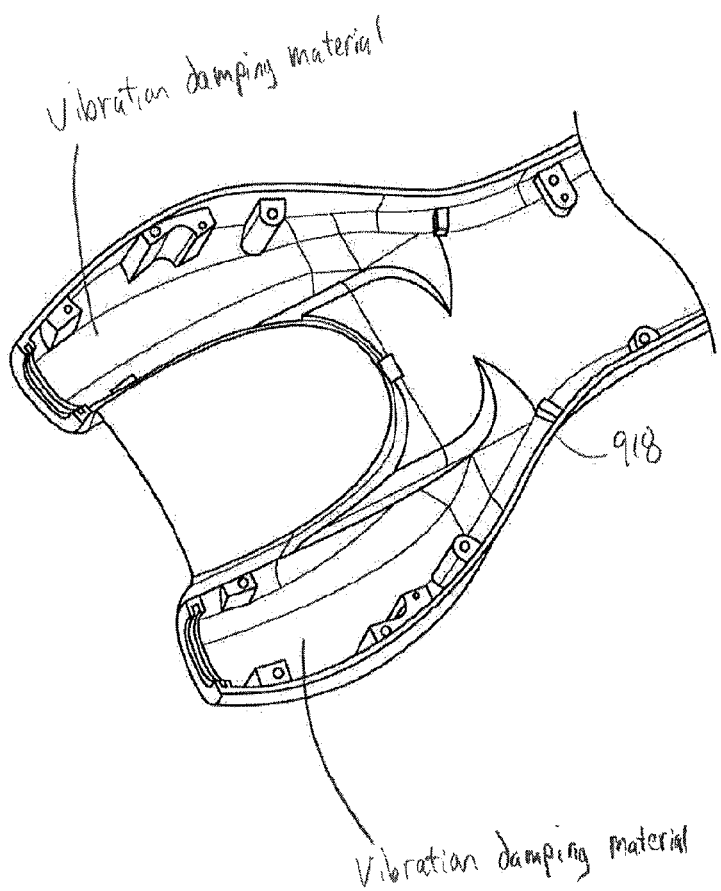

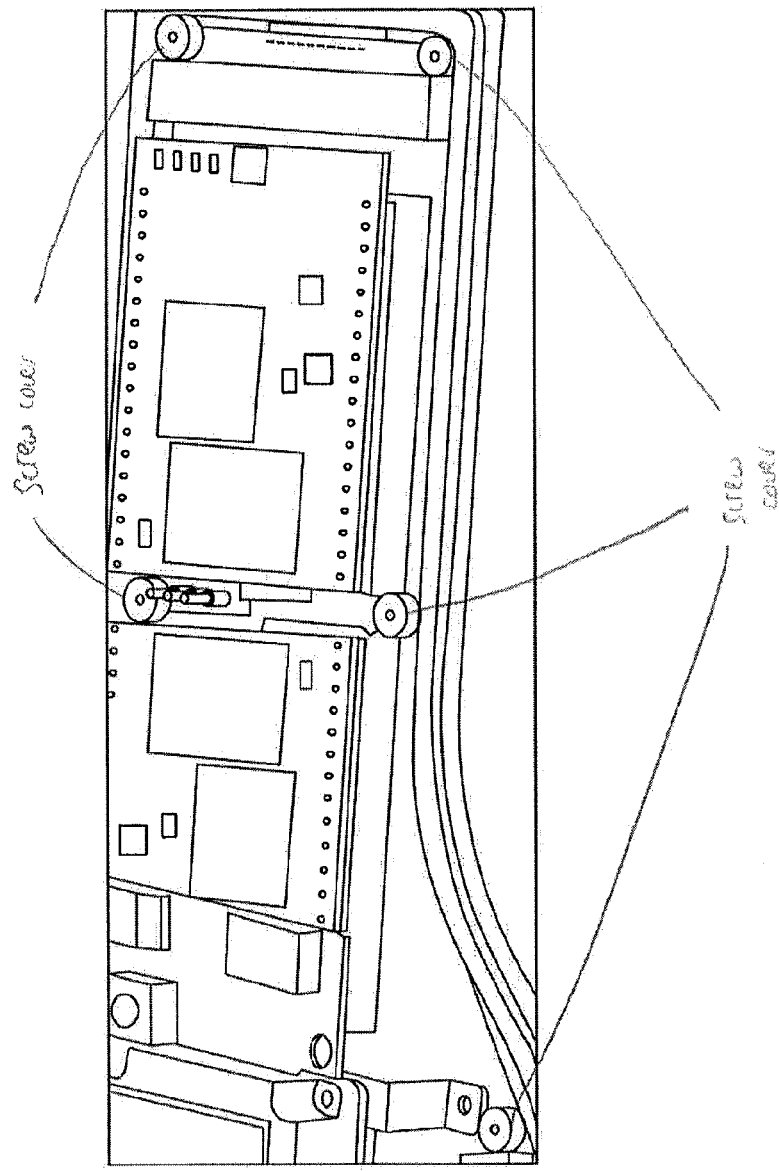

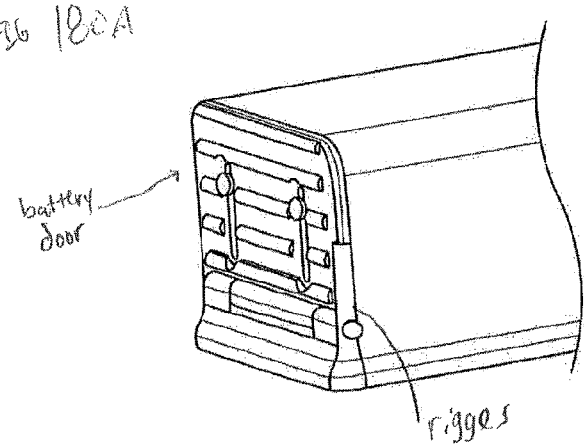
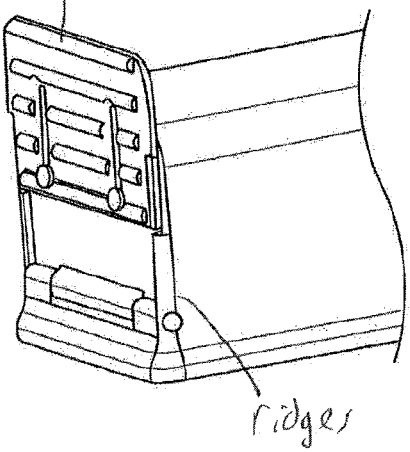
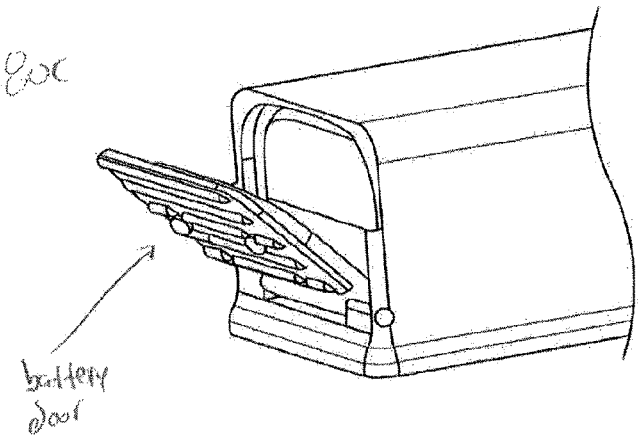

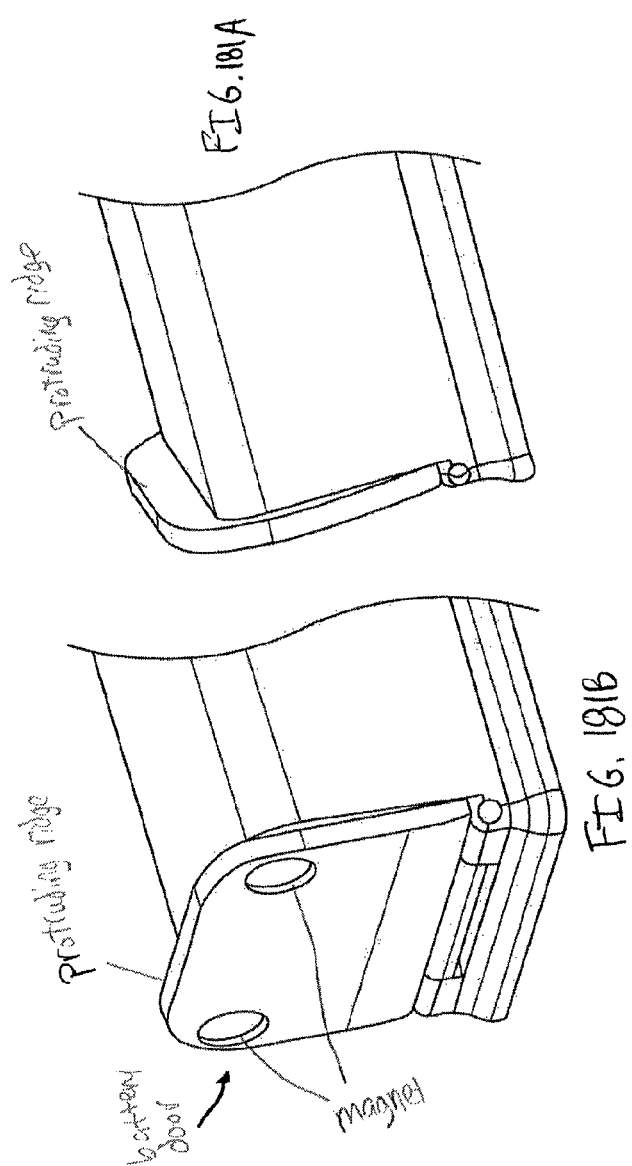

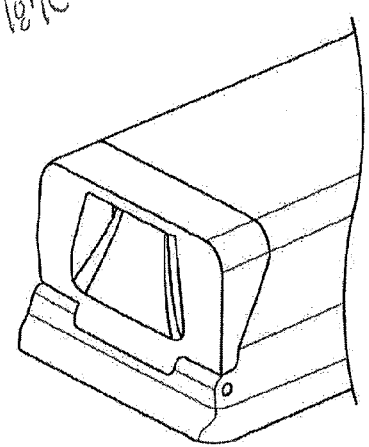
FIG. 187C
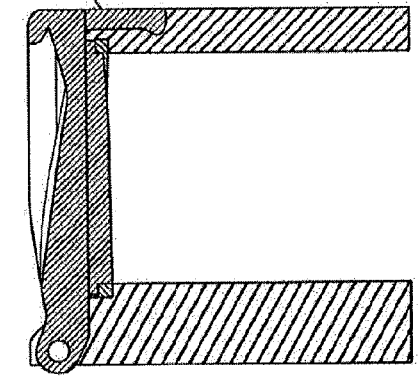
cantilever FIG. 187D

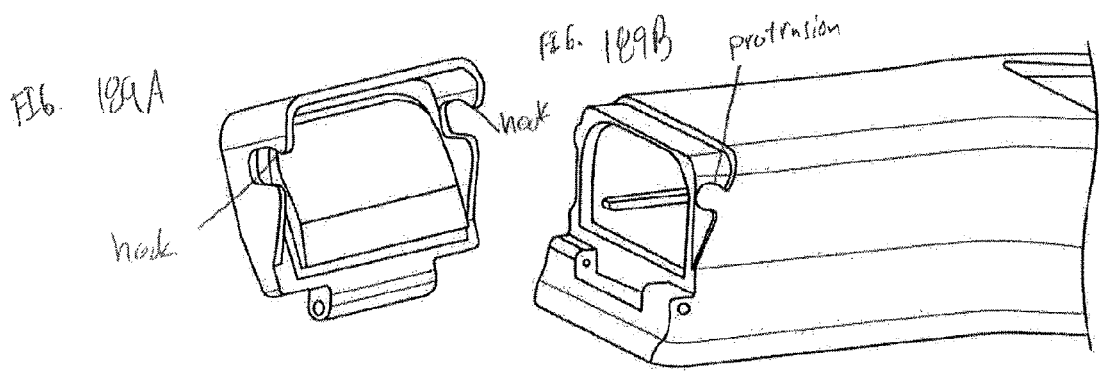
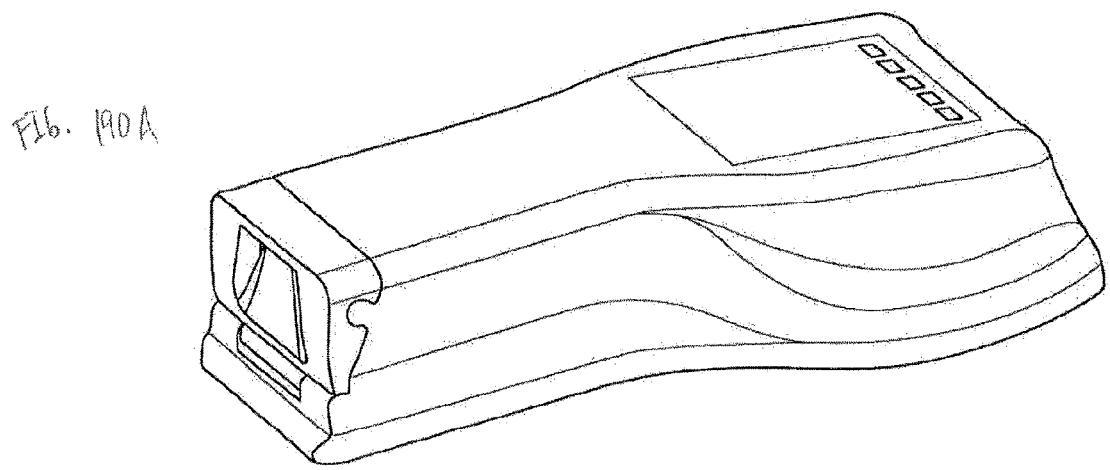
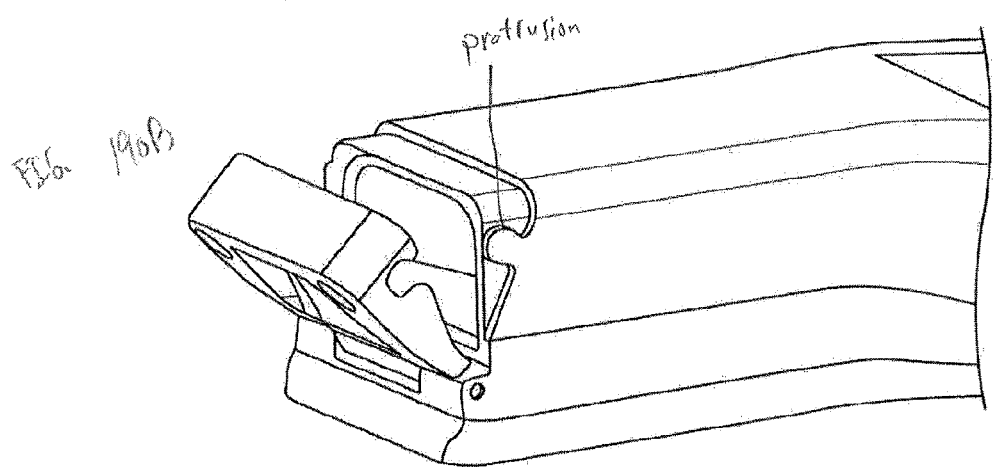

ON-BOARD TOOL TRACKING SYSTEM AND METHODS OF COMPUTER ASSISTED SURGERY

CROSS REFERENCE TO RELATED APPLICATIONS

This application claims priority to provisional application No. 61/799,656 filed Mar. 15, 2013, titled "ON-BOARD TOOL TRACKING SYSTEM AND METHODS OF COMPUTER ASSISTED SURGERY," the full disclosure of which is incorporated by reference herein.

This application is related to International Application Number PCT/US2012/044486 filed Jun. 27, 2012, titled "ON-BOARD TOOL TRACKING SYSTEM AND METHODS OF COMPUTER ASSISTED SURGERY," incorporated by reference in its entirety for all purposes.

This application is also related to U.S. Ser. No. 13/842,526 filed Mar. 15, 2013, titled "ON-BOARD TOOL TRACKING SYSTEM AND METHODS OF COMPUTER ASSISTED SURGERY," incorporated by reference in its entirety for all purposes. This application is also related to International Application Number PCT/US2014/25813 filed Mar. 13, 2014, titled "ON-BOARD TOOL TRACKING SYSTEM AND METHODS OF COMPUTER ASSISTED SURGERY," incorporated by reference in its entirety for all purposes.

STATEMENT AS TO FEDERALLY SPONSORED RESEARCH

This invention was made with Government support under Grant No. 0578104, awarded by the Department of Defense. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to the field of computer assisted surgery. Specifically, the present invention relates to various aspects of a surgical suite in which a tracking system on a tool provides guidance or assistance during a surgical procedure.

BACKGROUND

Many surgical procedures are complex procedures requiring numerous alignment jigs and intricate soft tissue procedures. Preparing and placing the alignment jigs and other preparation is often a significant part of the procedure and involves various errors. For instance, when performing a total knee replacement procedure ("TKR"), the prosthesis must be accurately implanted to ensure that the joint surfaces are properly aligned. If the alignment is inaccurate, the misalignment can compromise the function and eventually lead to failure of the joint, requiring the complex task of replacing one or more portions of the knee prosthesis.

To ensure that the prosthesis is accurately implanted, during a TKR procedure, the surgeon uses a variety of jigs to guide the cutting of the femur, the tibia and sometimes the patella. The jigs are complex and expensive devices that require significant time and skill to locate and attach on the patient during the surgical procedure.

The advent of computer assisted surgery (CAS) provides the promise of simplifying many of the complexities of surgical procedures. To date systems have been developed that utilize separate room based tracking systems designed to monitor the cutting jigs, tools and the patient. In some instances, the computer may be used to guide the surgeon during the process. The placement of the in room camera closer to the tool has been proposed. However, improvements are needed to address the challenges of the line of sight requirements and other real-time and dynamic environment of a surgical procedure.

Although computer assisted surgery holds promise, there are numerous aspects to be addressed to make a system commercially viable and useful to surgeons. There continues to exist numerous aspects of computer assisted surgery that require improvement to improve the efficiency, utility, speed, and/or quality of the procedure for processing of CAS data, and more useful outputs to the user.

SUMMARY OF THE DISCLOSURE

In general, in one embodiment, an on tool tracking and guidance device includes a housing having a surface for engagement with a surface on a saddle, a pair of cameras within or coupled to the housing wherein when the housing is coupled to the saddle the pair of cameras can be in position to provide an image output having a field of view including at least a portion of an active element of a surgical tool coupled to the saddle.

This and other embodiments can include one or more of the following features. The on tool tracking and guidance device includes a projector within or coupled to the housing configured to provide an output at least partially within the field of view of the pair of cameras.

This and other embodiments can include one or more of the following features. The on tool tracking and guidance device can further include a camera within or coupled to the housing above the projector, below the projector, above the pair of cameras, below the pair of cameras, between the pair of cameras, below the active element, or above the active element. The camera can be configured to provide an image output having a field of view including at least a portion of an active element of a surgical tool coupled to the saddle.

This and other embodiments can include one or more of the following features. The on tool tracking and guidance device can further include an electronic image processor within or in communication with the housing configured to receive an output from the pair of cameras and perform an image processing operation using at least a portion of the output from the pair of cameras in furtherance of at least one step of a computer assisted surgery procedure.

This and other embodiments can include one or more of the following features. The computer assisted surgery procedure can be a freehand navigated computer assisted surgery procedure.

This and other embodiments can include one or more of the following features. The on tool tracking and guidance device can further include an electronic image processor within or in communication with the housing configured to receive an output from the pair of cameras, perform an image processing operation using at least a portion of the output from the pair of cameras in furtherance of at least one step of a computer assisted surgery procedure and generate an output to the projector based on the image processing operation, a step related to a computer assisted surgery procedure or a step of a freehand navigated computer assisted surgery procedure.

This and other embodiments can include one or more of the following features. The device can further include a second pair of cameras within or coupled to the housing. The housing can be coupled to the saddle, the pair of cameras or the second pair of cameras can be can be in position to provide an image output having a field of view including at least a portion of an active element of a surgical tool coupled to the saddle.

This and other embodiments can include one or more of the following features. The pair of cameras or the second pair of cameras can include a physical or electronic filter for viewing within the infrared spectrum.

This and other embodiments can include one or more of the following features. The pair of cameras or the second pair of cameras can be positioned to include a physical or electronic filter for viewing within the infrared spectrum.

This and other embodiments can include one or more of the following features. Imaged objects within the field of view of any camera can be from about 70 mm to about 200 mm from the pair of cameras.

This and other embodiments can include one or more of the following features. Imaged objects within the field of view of the first camera and the second camera can be from about 50 mm-250 mm from the first and second cameras.

This and other embodiments can include one or more of the following features. The surface for releasable engagement with a portion of a surgical tool can be shaped to form a complementary curve with the portion of the surgical tool or a modified surgical tool selected for engagement with the housing.

This and other embodiments can include one or more of the following features. The portion of the surgical tool can be modified to accommodate releasable mechanical engagement and/or releasable electrical engagement with the housing surface.

This and other embodiments can include one or more of the following features. The surface for releasable engagement with a portion of a surgical tool can be adapted and configured so that when the surface is coupled to the surgical tool at least a portion of an active segment of the surgical tool lies within the horizontal field of view and the vertical field of view.

This and other embodiments can include one or more of the following features. At least a portion of an active segment of the surgical tool can be substantially all of the surgical tool active element used during the computer assisted surgery procedure.

This and other embodiments can include one or more of the following features. The projector output can be substantially completely within the horizontal field of view and the vertical field of view.

This and other embodiments can include one or more of the following features. The visual axis of the first camera and the visual axis of the second camera can be inclined towards one another relative to lines generally parallel to a longitudinal axis of the housing or of a surgical tool attached to the housing.

This and other embodiments can include one or more of the following features. The visual axis of the first camera and the visual axis of the second camera can be inclined at an angle of between about 0° to about 20° relative to a line generally parallel to a longitudinal axis of the housing.

This and other embodiments can include one or more of the following features. The visual axis of the first camera and the visual axis of the second camera can be inclined at an angle of between about 0° to about 20° relative to a line generally parallel to a longitudinal axis of an instrument associated with a surgical tool coupled to the housing.

This and other embodiments can include one or more of the following features. The projector can be positioned in the housing.

This and other embodiments can include one or more of the following features. The projector can be positioned in the housing and the output from the projector is in a location between the first camera and the second camera.

This and other embodiments can include one or more of the following features. The output from the projector can be closer to one of the first camera or the second camera.

This and other embodiments can include one or more of the following features. The output from the projector can be projected so as to appear in front of an active element associated with a surgical tool attached to the housing.

This and other embodiments can include one or more of the following features. The output from the projector can be projected on or near an active element associated with a surgical tool attached to the housing.

This and other embodiments can include one or more of the following features. The output from the projector can be adapted for projection on a portion of the patient's anatomy, or on or within the surgical field surface in the surgical scene.

This and other embodiments can include one or more of the following features. The portion of the anatomy can be a bone.

This and other embodiments can include one or more of the following features. The adapted output can be adjusted for the curvature, roughness or condition of the anatomy.

This and other embodiments can include one or more of the following features. The output from the projector can include one or more of a projected cut line, text, figures or sprites, a grid, and an axis and navigation lines.

This and other embodiments can include one or more of the following features. The projector can be positioned in the housing above a plane that contains the first camera and the second camera.

This and other embodiments can include one or more of the following features. The projector can be positioned in the housing below a plane that contains the first camera and the second camera.

This and other embodiments can include one or more of the following features. The horizontal field of view passing through the axis of the camera can be generally parallel to or makes an acute angle with the plane defined by the horizontal plane passing through the axis of an active element of a surgical tool when the surgical tool is coupled to the housing.

This and other embodiments can include one or more of the following features. The device can further include a display on the housing.

This and other embodiments can include one or more of the following features. The display can further include a touch screen.

This and other embodiments can include one or more of the following features. The display can be configured to provide a visual output including information from an on tool tracking CAS processing step.

This and other embodiments can include one or more of the following features. The display can be configured to provide guidance to a user of the surgical tool related to a CAS step.

This and other embodiments can include one or more of the following features. The display can be configured to provide guidance to a user of the surgical tool to adjust the speed of the surgical tool.

This and other embodiments can include one or more of the following features. The display can be configured to provide guidance to a user of the surgical tool related to CAS data collected by the on tool tracking device and assessed during the CAS procedure.

This and other embodiments can include one or more of the following features. The projector and display can be configured to provide a visual indication to a user of the surgical tool.

This and other embodiments can include one or more of the following features. The on tool tracking device can be further configured to collect and process computer assisted surgery data. The on tool tracking device or a processing system in communication with the on tool tracking device can be configured to assess the CAS data in real time during the computer assisted surgery procedure. This and other embodiments can include one or more of the following features. Assessing the CAS data can include a comparison of data received from the on tool tracking device and data provided using a computer assisted surgery surgical plan.

This and other embodiments can include one or more of the following features. The on tool tracking device can be configured to process data related to one or more of visual data from the pair of cameras, data from a sensor on the on tool tracking device, and data related to an operational characteristic of the surgical tool.

This and other embodiments can include one or more of the following features. The surgical tool can be configured to receive a control signal from the on tool tracking device to adjust a performance parameter of the surgical tool based on the CAS data.

This and other embodiments can include one or more of the following features. The device can further include an electronic interface between the on tool tracking device and the surgical tool to send the control signal from the on tool tracking device to the surgical tool to control the operation of the surgical tool. The performance parameter can further include modifying a tool cutting speed or stopping a tool operation.

This and other embodiments can include one or more of the following features. The on tool tracking device can be configured to determine a computer aided surgery (CAS) processing mode.

This and other embodiments can include one or more of the following features. Determining the CAS processing mode can be based upon an evaluation of one or more of: a physical parameter within the surgical field such as position or combination of positions of elements tracked in the field through reference frames attached to them a reference frame input, take projected image, a motion detected from a sensor, a motion detection from a calculation, the overall progress of a computer aided surgery procedure, a measured or predicted deviation from a previously prepared computer aided surgery plan.

This and other embodiments can include one or more of the following features. Determining the CAS processing mode can select one of a number of predefined processing modes.

This and other embodiments can include one or more of the following features. The predefined processing modes can be a hover mode, site approach mode, and active step mode.

This and other embodiments can include one or more of the following features. The predefined processing mode can be a hover mode and the on tool tracking device can be configured to receive and process data using a hover mode CAS algorithm.

This and other embodiments can include one or more of the following features. The device can be further configured to provide the user of the surgical tool with an output generated as a result of applying the hover mode CAS algorithm to data received using the on tool tracking device.

This and other embodiments can include one or more of the following features. The predefined processing mode can be a site approach mode and the on tool tracking device can be configured to receive and process data using a site approach mode CAS algorithm.

This and other embodiments can include one or more of the following features. The device can be further configured to provide the user of the surgical tool with an output generated as a result of applying the site approach mode CAS algorithm to data received using the on tool tracking device.

This and other embodiments can include one or more of the following features. The predefined processing mode can be an active step mode and the on tool tracking device can be configured to receive and process data using an active step mode CAS algorithm.

This and other embodiments can include one or more of the following features. The device can be further configured to provide the user of the surgical tool with an output generated as a result of applying the active step mode CAS algorithm to data received using the on tool tracking device.

This and other embodiments can include one or more of the following features. The on tool tracking device can be configured such that each of the predefined processing modes adjusts one or more processing factors employed by a processing system on board the on tool tracking device or a computer assisted surgery computer in communication with the on tool tracking device.

This and other embodiments can include one or more of the following features. The on tool tracking CAS processing mode factors can be selected from one or more of: a camera frame size; an on tool tracking camera orientation; an adjustment to a camera software program or firmware in accordance with the desired adjustment; adjustments to an on tool tracking camera or other camera image outputs to modify a size of a region of interest within a horizontal field of view, the vertical field of view or both the horizontal and the vertical field of view of the camera; drive signals for adjustable camera lens adjustment or positioning; image frame rate; image output quality; refresh rate; frame grabber rate; reference frame two; reference frame one; on reference frame fiducial select; off reference frame fiducial select; visual spectrum processing; IR spectrum processing; reflective spectrum processing; LED or illumination spectrum processing; surgical tool motor/actuator speed and direction, overall CAS procedure progress; specific CAS step progress; image data array modification; an on tool tracking projector refresh rate; an on tool tracking projector accuracy; one or more image segmentation techniques; one or more logic-based extractions of an image portion based on a CAS progress; signal-to-noise ratio adjustment; one or more image amplification process, one or more imaging filtering process; applying weighted averages or other factors for dynamic, real-time enhancement or reduction of image rate, pixel or sub-pixel vision processing; a hand tremor compensation; an instrument-based noise compensation for a saw, a drill or other electrical surgical tool and a vibration compensation process based on information from the on tool tracking each alone or in any combination.

This and other embodiments can include one or more of the following features. The device can be further configured to adjust an output provided to the user based upon the result of the selection of one of the predefined processing modes.

This and other embodiments can include one or more of the following features. The projector can be configured to provide the output to the user.

This and other embodiments can include one or more of the following features. The on tool tracking device can be configured to adjust the projector output based upon a physical characteristic of a surgical site presented during the display of the projector output.

This and other embodiments can include one or more of the following features. The physical characteristic can be one or more of a shape of a portion of a site available for the projector output; a topography in a projector projected field and an orientation of the projector to the portion of the site available for the projector output.

This and other embodiments can include one or more of the following features. The projector can be configured to project an output including information visible to the user of the surgical tool while the surgical tool can be in use in a surgical site.

This and other embodiments can include one or more of the following features. The projector can be configured to project an output including information visible to the user of the surgical tool to indicate the position, relative motion, orientation, or other navigation parameter related to the positioning of an active element of the surgical tool within a surgical field according to a surgical plan.

This and other embodiments can include one or more of the following features. The on tool tracking device can be configured to change the CAS output to the user during a surgical procedure related to a knee.

This and other embodiments can include one or more of the following features. The on tool tracking device can further be configured to display the output on a graphical user interface shown on the display in the on tool tracking device or a mobile device screen.

This and other embodiments can include one or more of the following features. The on tool tracking device can be configured to modify the CAS processing technique or output to the user during a surgical procedure related to a knee.

This and other embodiments can include one or more of the following features. The on tool tracking device can be configured to change a CAS output to the user and change a CAS processing technique based on a user performing one or more steps of a computer assisted surgery procedure on a knee including: making a distal femur cut, making, making a distal femur anterior cut, making a distal femur posterior lateral condyle cut, making a distal femur posterior medial condyle cut, making a distal femur anterior chamfer cut, making a distal femur posterior lateral condyle chamfer cut, making a distal femur posterior medial condyle chamfer cut, and making proximal tibial cut.

This and other embodiments can include one or more of the following features. The on tool tracking device can be configured to change a CAS output to the user and change a CAS processing technique based on a user performing one or more steps of a computer assisted surgery procedure on a knee including: making a distal femur cut, making a distal femur anterior cut, making a distal femur posterior lateral condyle cut, making a distal femur posterior medial condyle cut, making a distal femur anterior chamfer cut, making a distal femur posterior lateral condyle chamfer cut, making a distal femur posterior medial condyle chamfer cut, making the distal femur box cuts (when required), drilling the cavity of a distal femur stabilization post, making a proximal tibial cut, making proximal tibia keel cut, or drilling proximal tibia holes.

This and other embodiments can include one or more of the following features. The on tool tracking device can be configured to change a CAS output to a user during a surgical procedure related to one of a shoulder; a hip; an ankle; a vertebra; or an elbow.

This and other embodiments can include one or more of the following features. The on tool tracking device can be configured to modify the CAS processing technique or output to the user during a surgical procedure related to one of a shoulder; a hip; an ankle; a vertebra; or an elbow.

This and other embodiments can include one or more of the following features. The device can further include a processing system within the on tool tracking device configured to assess data related to a CAS procedure.

This and other embodiments can include one or more of the following features. The device can further include electronic instructions contained within an electronic memory accessible to the processing system relating to the performance of a CAS processing step.

This and other embodiments can include one or more of the following features. The device can further include a processing system in communication with the on tool tracking device configured to assess data related to a CAS procedure.

This and other embodiments can include one or more of the following features. The device can further include electronic instructions contained within an electronic memory accessible to the processing system in communication with the on tool tracking device relating to the performance of a CAS processing step.

This and other embodiments can include one or more of the following features. The display of the device can be configured as an input device for the user of the on tool tracking device.

This and other embodiments can include one or more of the following features. The projector can be positioned within the housing on an inclined base.

This and other embodiments can include one or more of the following features. The projector can be a pico projector.

This and other embodiments can include one or more of the following features. The projector output can be provided in the form of a laser.

This and other embodiments can include one or more of the following features. The portion of the surgical tool can be selected so that, in use with the surgical tool, the cameras and the projector can be positioned above an active element associated with the surgical tool.

This and other embodiments can include one or more of the following features. The portion of the surgical tool can be selected so that, in use with the surgical tool, the cameras can be positioned below an active element associated with the surgical tool.

This and other embodiments can include one or more of the following features. The portion of the surgical tool can be selected so that, in use with the surgical tool, the cameras and the projector can be positioned below or to one side of an active element associated with the surgical tool.

This and other embodiments can include one or more of the following features. The device can further include a communication element within the housing configured to provide information related to the image processing operation to a component separate from the housing.

This and other embodiments can include one or more of the following features. The communication element can provide information wirelessly to and from the component separate from the housing.

This and other embodiments can include one or more of the following features. The communication element can be configured to provide information wirelessly, by Bluetooth, by wifi, or by ultra wideband technology.

This and other embodiments can include one or more of the following features. The communication element can provide information via a wired connection to the component separate from the housing.

This and other embodiments can include one or more of the following features. The component separate from the housing can be a computer containing instructions in computer readable media related to the use of the information for computer assisted surgery using the surgical tool active segment.

This and other embodiments can include one or more of the following features. The communication element within the housing can be configured to provide information related to the image processing operation to a component separate from the housing.

This and other embodiments can include one or more of the following features. The device can further include a communication element within the housing configured to receive and provide instructions to the projector to produce an output at least partially within the field of view of the first camera and the second camera, the output including at least one visually perceptible indication related to a computer assisted surgery processing step performed using an output from the electronic image processor operation.

This and other embodiments can include one or more of the following features. The visually perceptible indication can be perceptible to a user.

This and other embodiments can include one or more of the following features. The visually perceptible indication can be perceptible to the pair of cameras.

This and other embodiments can include one or more of the following features. The device can further include a surgical tool having a trigger and an active element controlled by the operation of the trigger. The housing can be attached in releasable engagement with the surgical tool.

This and other embodiments can include one or more of the following features. The first camera and the second camera arrangement can provide a vertical field of view and a horizontal field of view containing at least a portion of an active element of the surgical tool.

This and other embodiments can include one or more of the following features. The horizontal field of view and the vertical field of view can be selected for viewing a volume that contains substantially all of the active element.

This and other embodiments can include one or more of the following features. The horizontal field of view passing through the axis of the camera can be generally parallel to or makes an acute angle with the plane defined by the horizontal plane passing through the axis of the active element.

This and other embodiments can include one or more of the following features. The surface of the housing for releasable engagement with the surface of the saddle each include part of a two part complementary shaped feature, groove, detent, engagement element, fitting of a mechanical or electrical configuration that when the two surfaces are coupled the housing can be in the proper position on the saddle for use of the various electronic components provided in the housing for use of a surgical tool in a CAS, or on tool tracking CAS, or freehand navigated surgical procedure.

This and other embodiments can include one or more of the following features. One or more electronic features in the housing or the saddle can provide for detection of a certified model of a component or system feature.

This and other embodiments can include one or more of the following features. The electronic feature can provide an irreversible registration of use each time the saddle is connected to the housing.

This and other embodiments can include one or more of the following features. The housing or the saddle can be configured to provide access to the surgical tool coupled to the saddle.

This and other embodiments can include one or more of the following features. The housing or the saddle can be configured to send or receive electrical signals with the surgical tool coupled to the saddle and housing.

This and other embodiments can include one or more of the following features. The housing or the saddle can be configured to send or receive electrical signals between them.

This and other embodiments can include one or more of the following features. The device can be adapted or configured to provide a projector based registration.

This and other embodiments can include one or more of the following features. The device can further include a sensor coupled to or within the housing.

This and other embodiments can include one or more of the following features. The sensor can be selected from the group consisting of an inclinometer, a gyroscope, a two axis gyroscope, a three axis gyroscope or other multiple axis gyroscope, a one-two-three or multiple axis accelerometer, a potentiometer, and a MEMS instrument configured to provide one or more of roll, pitch, yaw, orientation, or vibration information related to the on tool tracking device.

This and other embodiments can include one or more of the following features. The active element of the surgical tool can be a saw blade, burr, or drill.

This and other embodiments can include one or more of the following features. A portion of the surgical tool can be modified to accommodate releasable engagement with the housing surface.

This and other embodiments can include one or more of the following features. The surface for releasable engagement with a portion of the surgical tool can be adapted and configured so that when the surface is coupled to the surgical tool at least a portion of an active element of the surgical tool lies within a horizontal field of view and a vertical field of view of the pair of cameras.

This and other embodiments can include one or more of the following features. The housing can include a lid assembly and a housing assembly, the housing assembly can include the surface for engagement with the surface on the saddle.

This and other embodiments can include one or more of the following features. The lid assembly and housing assembly can have complementary surfaces for releasably engaging together.

This and other embodiments can include one or more of the following features. The lid assembly and housing assembly can be configured to snap together.

This and other embodiments can include one or more of the following features. The lid assembly and housing assembly can snap together over a full perimeter of the lid assembly and a full perimeter of the housing assembly.

This and other embodiments can include one or more of the following features. The lid assembly and housing assembly can snap together over a partial perimeter or at discrete points of the lid assembly and housing assembly.

This and other embodiments can include one or more of the following features. The lid assembly and housing assembly can be configured to engage with each other at multiple discrete locations with a plurality of single elements.

This and other embodiments can include one or more of the following features. The single elements can include screws, pins, and threaded socket and ball.

This and other embodiments can include one or more of the following features. The lid assembly and housing assembly can be configured to engage with each other at multiple discrete locations or multiple arrays of interlocking structures.

This and other embodiments can include one or more of the following features. The interlocking structures can include snap fit clips, a hook and loop structure, or a cap and stem structure.

This and other embodiments can include one or more of the following features. The lid assembly can include the display.

This and other embodiments can include one or more of the following features. The lid assembly can include a battery chamber door and a battery chamber configured to receive a battery, the battery chamber door configured to open to permit a battery to slide into the battery chamber.

This and other embodiments can include one or more of the following features. The device can further include a battery chamber gasket configured to engage with the battery chamber door.

This and other embodiments can include one or more of the following features. The housing assembly can include a Y-shaped board.

This and other embodiments can include one or more of the following features. The Y-shaped board can include image processing and transmission circuits.

This and other embodiments can include one or more of the following features. The first and second cameras of the pair of cameras can be coupled to the Y-shaped board within the housing assembly.

This and other embodiments can include one or more of the following features. The first camera can be coupled to the Y-shaped board by a first camera bracket and the second camera can be coupled to the Y-shaped board by a second camera bracket.

This and other embodiments can include one or more of the following features. The projector can be coupled to the Y-shaped board.

This and other embodiments can include one or more of the following features. The projector can be coupled to the Y-shaped board by a projector bracket.

This and other embodiments can include one or more of the following features. The device can further include an electrical connector configured to provide an electronic control to the surgical tool.

This and other embodiments can include one or more of the following features. The electrical connector can be configured to contact a plurality of electrical contacts on the surgical tool.

This and other embodiments can include one or more of the following features. The electrical connector can be configured to send and receive electrical control signals with the surgical tool. The electrical control signals can modify a speed of the surgical tool.

This and other embodiments can include one or more of the following features. The electrical connector can be coupled to the Y-shaped board.

This and other embodiments can include one or more of the following features. The electrical contacts on the surgical tool can be on a proximal end surface of the surgical tool. An active element can be on a distal end of the surgical tool.

This and other embodiments can include one or more of the following features. The electrical contacts on the surgical tool can be on a top surface of the surgical tool adjacent to the surface for releasable engagement with the saddle.

This and other embodiments can include one or more of the following features. The electrical contacts on the surgical tool can be on a bottom surface of the surgical tool adjacent to a handle of the surgical tool.

This and other embodiments can include one or more of the following features. The surgical tool can be modified to create the electrical contacts.

This and other embodiments can include one or more of the following features. The electrical contacts can be spring loaded or cantilevered.

This and other embodiments can include one or more of the following features. The surgical tool can be designed or modified to position the electrical contacts for engagement with the on tool tacking device.

This and other embodiments can include one or more of the following features. The saddle can include an opening configured to receive the electrical connector therethrough.

This and other embodiments can include one or more of the following features. The electrical connector can be configured to pass through the opening in the saddle to contact the electrical contacts on the surgical tool.

This and other embodiments can include one or more of the following features. The saddle can include a conductive portion configured to contact the electrical connector.

This and other embodiments can include one or more of the following features. The conductive portion of the saddle can be configured to contact the plurality of electrical contacts on the surgical tool.

This and other embodiments can include one or more of the following features. The device can further include a user interface.

This and other embodiments can include one or more of the following features. The user interface can include push buttons and a display.

This and other embodiments can include one or more of the following features. The user interface can include a touch screen.

This and other embodiments can include one or more of the following features. The user interface can include a plurality of LEDs and switches.

This and other embodiments can include one or more of the following features. The housing can include a plurality of vents.

This and other embodiments can include one or more of the following features. The device can further include an antenna configured for wireless data transmission.

This and other embodiments can include one or more of the following features. The antenna can be within the housing.

This and other embodiments can include one or more of the following features. The device can further include an antenna configured for wireless data transmission of the camera signals.

This and other embodiments can include one or more of the following features. The device can further include an antenna configured to receive wireless data corresponding to instructions for the projector.

This and other embodiments can include one or more of the following features. The housing can include a heat sink configured to cool the on tool tracking device during operation of the surgical tool.

This and other embodiments can include one or more of the following features. The heat sink can contact the projector.

This and other embodiments can include one or more of the following features. The device can further include a first wide angle lens on the first camera and a second wide angle lens on the second camera.

This and other embodiments can include one or more of the following features. The device can further include a first infrared filter on the first camera and a second infrared filter on the second camera.

This and other embodiments can include one or more of the following features. The device can further include a gasket.

This and other embodiments can include one or more of the following features. The gasket can be an elastomeric material.

This and other embodiments can include one or more of the following features. The gasket can engage with the Y-board assembly.

This and other embodiments can include one or more of the following features. The gasket can engage with the housing.

This and other embodiments can include one or more of the following features. The gasket can be located on the housing and configured to contact the saddle when the housing is engaged with the saddle.

This and other embodiments can include one or more of the following features. The gasket can be configured to engage with the electrical connector configured to contact the plurality of electrical contacts on the surgical tool.

This and other embodiments can include one or more of the following features. The housing can be configured to releasably engage with a smartphone or tablet computer.

This and other embodiments can include one or more of the following features. The on tool tracking device can be configured to send and receive data to the smartphone or tablet computer.

This and other embodiments can include one or more of the following features. The on tool tracking device can be configured to transmit data to the smartphone or tablet computer to display information relating to a CAS procedure on a screen of the smartphone or tablet computer.

This and other embodiments can include one or more of the following features. The housing surface for engagement with the surface on the saddle can have a complementary shape to engage with a tapered surface on the saddle.

This and other embodiments can include one or more of the following features. The housing surface for engagement with the surface on the saddle can have a complementary shape to engage with two long protrusions on the saddle extending from a proximal end of the saddle to a distal end of the saddle.

This and other embodiments can include one or more of the following features. The housing surface for engagement with the surface on the saddle can have a complementary shape to engage with two rails on the saddle.

This and other embodiments can include one or more of the following features. The housing surface for engagement with the surface on the saddle can have a complementary shape to engage with a front taper and a rear taper on the saddle.

This and other embodiments can include one or more of the following features. The housing can include a rear surface for engagement with a proximal surface of the saddle.

This and other embodiments can include one or more of the following features. The device can further include a lock configured to lock the housing and saddle together.

This and other embodiments can include one or more of the following features. The lock can be spring loaded.

This and other embodiments can include one or more of the following features. The lock can be a cam configured to lock the housing to the saddle through rotary motion of a handle of the cam.

This and other embodiments can include one or more of the following features. The lock can be a locking pin on the housing configured to engage with a corresponding sideway recess in the saddle.

This and other embodiments can include one or more of the following features. The lock can be a cantilevered lock configured to engage with a corresponding recess in the saddle.

This and other embodiments can include one or more of the following features. The cantilevered lock can be configured to releasably snap into the corresponding recess in the saddle.

This and other embodiments can include one or more of the following features. The cantilevered lock can be on the housing surface for engagement with the surface of the saddle.

This and other embodiments can include one or more of the following features. The cantilevered lock can be on a side of the housing.

This and other embodiments can include one or more of the following features. The device can further include a lock release configured to release the lock between the housing and saddle.

This and other embodiments can include one or more of the following features. The device can further include a lining material on a portion of the housing surface for engagement with the surface on the saddle.

This and other embodiments can include one or more of the following features. The cameras can be below the active element of the surgical tool when the surgical tool is coupled to the saddle and the housing is engaged with the saddle.

This and other embodiments can include one or more of the following features. A center of the first camera and a center of the second camera can be below the active element of the surgical tool by about 0 mm to about 5 mm when the surgical tool is coupled to the saddle and the housing is engaged with the saddle.

This and other embodiments can include one or more of the following features. The output from the pair of cameras can include raw image data from the cameras.

This and other embodiments can include one or more of the following features. The output from the pair of cameras can include streaming image data from the cameras.

This and other embodiments can include one or more of the following features. An output from the first camera can be transmitted to the electronic imaging processor external to the on tool tracking device by a first camera signal and an output from the second camera can be transmitted to the electronic imaging processor external to the on tool tracking device by a second camera signal.

This and other embodiments can include one or more of the following features. An output from the first camera and an output from the second camera can be transmitted to the electronic imaging processor external to the on tool tracking device by a combined camera signal.

This and other embodiments can include one or more of the following features. The device can further include an image processor configured to analyze image data from the cameras to identify one or more tracking elements and to convert the image data of the one or more tracking elements to mathematical coordinates relative to the position of the on tool tracking device.

This and other embodiments can include one or more of the following features. The image processor can be within the housing of the on tool tracking device.

This and other embodiments can include one or more of the following features. The image processor can be external to on tool tracking device.

This and other embodiments can include one or more of the following features. The display can be integral with an outer surface of the housing.

This and other embodiments can include one or more of the following features. The display can be configured to be tilted relative to an outer surface of the housing.

This and other embodiments can include one or more of the following features. The projector can be configured to provide an output comprising at least one visually perceptible indication above and below the active element of the surgical tool.

This and other embodiments can include one or more of the following features. The projector can be configured to provide an output based on the image data within 33 ms of taking the image data with the pair of cameras.

This and other embodiments can include one or more of the following features. The device can further include a sterile battery funnel configured to engage with a portion of the housing and adapted to permit a battery to slide through an internal volume of the funnel to a battery chamber of the housing.

This and other embodiments can include one or more of the following features. The housing can be configured to be mechanically connected to the surgical tool.

This and other embodiments can include one or more of the following features. The housing can be configured to be electrically connected to the surgical tool.

This and other embodiments can include one or more of the following features. The housing can be configured to be mechanically and electrically connected to the surgical tool.

This and other embodiments can include one or more of the following features. The device can further include a power management unit configured to receive electrical energy from the battery and distribute the electrical energy to power the pair of cameras, projector, display, and a speed controller for the hand held surgical tool.

This and other embodiments can include one or more of the following features. The device can further include a cleaning attachment configured to releasably engage with the housing surface for engagement with the surface of the saddle.

In general, in one embodiment, an on tool tracking and guidance device includes a housing having a surface for releasable engagement with a saddle. The saddle can be configured to engage with a portion of a surgical tool. A first camera and a second camera in an arrangement where each of the first camera and the second camera provides an image output selected for viewing substantially all of a surgical field selected for a computer assisted surgery procedure. A projector can be configured to provide an output at least partially within the surgical field of view.

This and other embodiments can include one or more of the following features. The device can further include an electronic image processor within the housing configured to receive an output from each of the two cameras and perform an image processing operation using at least a portion of the output from each of the two cameras for use in the computer assisted surgery procedure.

This and other embodiments can include one or more of the following features. Imaged objects within the field of view of the first camera and the second camera can be from about 70 mm to about 200 mm from the first and second cameras.

This and other embodiments can include one or more of the following features. Imaged objects within the field of view of the first camera and the second camera can be from about 50 mm-250 mm from the first and second cameras.

This and other embodiments can include one or more of the following features. The surface for releasable engagement with a portion of a surgical tool can be shaped to form a complementary curve with the portion of the surgical tool or a modified surgical tool selected for engagement with the housing.

This and other embodiments can include one or more of the following features. The portion of the surgical tool can be modified to accommodate releasable mechanical engagement and/or releasable electrical engagement with the housing surface.

This and other embodiments can include one or more of the following features. The surface for releasable engagement with a portion of a surgical tool can be adapted and configured so that when the surface can be coupled to the surgical tool at least a portion of an active segment of the surgical tool lies within the horizontal field of view and the vertical field of view.

This and other embodiments can include one or more of the following features. The at least a portion of an active segment of the surgical tool can be substantially all of the surgical tool active element used during the computer assisted surgery procedure.

This and other embodiments can include one or more of the following features. The projector output can be substantially completely within the horizontal field of view and the vertical field of view.

This and other embodiments can include one or more of the following features. The projector output can include one or more of: a projected cut line, text, figures or sprites, a grid, and an axis and navigation lines.

This and other embodiments can include one or more of the following features. A visual axis of the first camera and a visual axis of the second camera can be inclined towards one another relative to lines generally parallel to a longitudinal axis of the housing or of a surgical tool attached to the housing.

This and other embodiments can include one or more of the following features. The visual axis of the first camera and the visual axis of the second camera can be inclined at an angle of between about 0° to about 20° relative to a line generally parallel to a longitudinal axis of the housing.

This and other embodiments can include one or more of the following features. The visual axis of the first camera and the visual axis of the second camera can be inclined at an angle of between about 0° to about 20° relative to a line generally parallel to a longitudinal axis of an instrument associated with a surgical tool coupled to the housing.

This and other embodiments can include one or more of the following features. The projector can be positioned in the housing.

This and other embodiments can include one or more of the following features. The projector can be positioned in the housing and the output from the projector can be in a location between the first camera and the second camera.

This and other embodiments can include one or more of the following features. The output from the projector can be closer to one of the first camera or the second camera.

This and other embodiments can include one or more of the following features. The output from the projector can be projected so as to appear in front of an active element associated with a surgical tool attached to the housing.

This and other embodiments can include one or more of the following features. The output from the projector can be projected on or near an active element associated with a surgical tool attached to the housing.

This and other embodiments can include one or more of the following features. The output from the projector can be adapted for projection on a portion of the patient's anatomy, or on or within the surgical field surface in the surgical scene.

This and other embodiments can include one or more of the following features. The portion of the anatomy can be a bone.

This and other embodiments can include one or more of the following features. The adapted output can be adjusted for the curvature, roughness, or condition of the anatomy.

This and other embodiments can include one or more of the following features. The projector can be positioned in the housing above a plane that contains the first camera and the second camera.

This and other embodiments can include one or more of the following features. The projector can be positioned in the housing below a plane that contains the first camera and the second camera.

This and other embodiments can include one or more of the following features. A horizontal field of view passing through an axis of the camera can be generally parallel to or makes an acute angle with a plane defined by a horizontal plane passing through an axis of an active element of a surgical tool when the surgical tool is coupled to the housing.

This and other embodiments can include one or more of the following features. The device can further include a display on the housing.

This and other embodiments can include one or more of the following features. The display can include a touch screen.

This and other embodiments can include one or more of the following features. The first camera and second camera can be within the housing.

This and other embodiments can include one or more of the following features. The display can be configured to provide a visual output including information from an on tool tracking CAS processing step.

This and other embodiments can include one or more of the following features. The display can be configured to provide guidance to a user of the surgical tool related to a CAS step.

This and other embodiments can include one or more of the following features. The display can be configured to provide guidance to a user of the surgical tool to adjust the speed of the surgical tool.

This and other embodiments can include one or more of the following features. The display can be configured to provide guidance to a user of the surgical tool related to CAS data collected by the on tool tracking device and assessed during the CAS procedure.

This and other embodiments can include one or more of the following features. The projector and display can be configured to provide a visual indication to a user of the surgical tool.

This and other embodiments can include one or more of the following features. The on tool tracking device can be further configured to collect and process computer assisted surgery data. The on tool tracking device or a processing system in communication with the on tool tracking device can be configured to assess the CAS data in real time during the computer assisted surgery procedure.

This and other embodiments can include one or more of the following features. Assessing the CAS data can include a comparison of data received from the on tool tracking device and data provided using a computer assisted surgery surgical plan.

This and other embodiments can include one or more of the following features. The on tool tracking device can be configured to process data related to one or more of visual data from the pair of cameras, data from a sensor on the on tool tracking device, and data related to an operational characteristic of the surgical tool.

This and other embodiments can include one or more of the following features. The surgical tool can be configured to receive a control signal from the on tool tracking device to adjust a performance parameter of the surgical tool based on the CAS data.

This and other embodiments can include one or more of the following features. The device can further include an electronic interface between the on tool tracking device and the surgical tool to send the control signal from the on tool tracking device to the surgical tool to control the operation of the surgical tool. The performance parameter can include modifying a tool cutting speed or stopping a tool operation.

This and other embodiments can include one or more of the following features. The on tool tracking device can be configured to determine a computer aided surgery (CAS) processing mode.

This and other embodiments can include one or more of the following features. Determining the CAS processing mode can be based upon an evaluation of one or more of: a physical parameter within the surgical field such as position or combination of positions of elements tracked in the field through reference frames attached to them a reference frame input, take projected image, a motion detected from a sensor, a motion detection from a calculation, the overall progress of a computer aided surgery procedure, a measured or predicted deviation from a previously prepared computer aided surgery plan.

This and other embodiments can include one or more of the following features. Determining the CAS processing mode can select one of a number of predefined processing modes.

This and other embodiments can include one or more of the following features. The predefined processing modes can be a hover mode, site approach mode, and active step mode.

This and other embodiments can include one or more of the following features. The predefined processing mode can be a hover mode and the on tool tracking device can be configured to receive and process data using a hover mode CAS algorithm.

This and other embodiments can include one or more of the following features. The device can be further configured to provide the user of the surgical tool with an output generated as a result of applying the hover mode CAS algorithm to data received using the on tool tracking device.

This and other embodiments can include one or more of the following features. The predefined processing mode can be a site approach mode and the on tool tracking device can be configured to receive and process data using a site approach mode CAS algorithm.

This and other embodiments can include one or more of the following features. The device can be further configured to provide the user of the surgical tool with an output generated as a result of applying the site approach mode CAS algorithm to data received using the on tool tracking device.

This and other embodiments can include one or more of the following features. The predefined processing mode can be an active step mode and the on tool tracking device can be configured to receive and process data using an active step mode CAS algorithm.

This and other embodiments can include one or more of the following features. The device can be further configured to provide the user of the surgical tool with an output generated as a result of applying the active step mode CAS algorithm to data received using the on tool tracking device.

This and other embodiments can include one or more of the following features. The on tool tracking device can be configured such that each of the predefined processing modes adjusts one or more processing factors employed by a processing system on board the on tool tracking device or a computer assisted surgery computer in communication with the on tool tracking device.

This and other embodiments can include one or more of the following features. The on tool tracking CAS processing mode factors can be selected from one or more of: a camera frame size; an on tool tracking camera orientation; an adjustment to a camera software program or firmware in accordance with the desired adjustment; adjustments to an on tool tracking camera or other camera image outputs to modify a size of a region of interest within a horizontal field of view, the vertical field of view or both the horizontal and the vertical field of view of the camera; drive signals for adjustable camera lens adjustment or positioning; image frame rate; image output quality; refresh rate; frame grabber rate; reference frame two; reference frame one; on reference frame fiducial select; off reference frame fiducial select; visual spectrum processing; IR spectrum processing; reflective spectrum processing; LED or illumination spectrum processing; surgical tool motor/actuator speed and direction, overall CAS procedure progress; specific CAS step progress; image data array modification; an on tool tracking projector refresh rate; an on tool tracking projector accuracy; one or more image segmentation techniques; one or more logic-based extractions of an image portion based on a CAS progress; signal-to-noise ratio adjustment; one or more image amplification process, one or more imaging filtering process; applying weighted averages or other factors for dynamic, real-time enhancement or reduction of image rate, pixel or sub-pixel vision processing; a hand tremor compensation; an instrument-based noise compensation for a saw, a drill or other electrical surgical tool and a vibration compensation process based on information from the on tool tracking each alone or in any combination.

This and other embodiments can include one or more of the following features. The device can be further configured to adjust an output provided to the user based upon the result of the selection of one of the predefined processing modes.

This and other embodiments can include one or more of the following features. The projector can be configured to provide the output to the user.

This and other embodiments can include one or more of the following features. The on tool tracking device can be configured to adjust the projector output based upon a physical characteristic of a surgical site presented during the display of the projector output.

This and other embodiments can include one or more of the following features. The physical characteristic can be one or more of a shape of a portion of a site available for the projector output; a topography in a projector projected field and an orientation of the projector to the portion of the site available for the projector output.

This and other embodiments can include one or more of the following features. The projector can be configured to project an output including information visible to the user of the surgical tool while the surgical tool is in use in a surgical site.

This and other embodiments can include one or more of the following features. The projector can be configured to project an output including information visible to the user of the surgical tool to indicate the position, relative motion, orientation, or other navigation parameter related to the positioning of an active element of the surgical tool within a surgical field according to a surgical plan.

This and other embodiments can include one or more of the following features. The on tool tracking device can be configured to change the CAS output to the user during a surgical procedure related to a knee.

This and other embodiments can include one or more of the following features. The on tool tracking device can be further configured to display the output on a graphical user interface shown on the display in the on tool tracking device or a mobile device screen.

This and other embodiments can include one or more of the following features. The on tool tracking device can be configured to modify the CAS processing technique or output to the user during a surgical procedure related to a knee.

This and other embodiments can include one or more of the following features. The on tool tracking device can be configured to change a CAS output to the user and change a CAS processing technique based on a user performing one or more steps of a computer assisted surgery procedure on a knee including making a distal femur cut, making, making a distal femur anterior cut, making a distal femur posterior lateral condyle cut, making a distal femur posterior medial condyle cut, making a distal femur anterior chamfer cut, making a distal femur posterior lateral condyle chamfer cut, making a distal femur posterior medial condyle chamfer cut, and making proximal tibial cut.

This and other embodiments can include one or more of the following features. The on tool tracking device can be configured to change a CAS output to the user and change a CAS processing technique based on a user performing one or more steps of a computer assisted surgery procedure on a knee including making a distal femur cut, making a distal femur anterior cut, making a distal femur posterior lateral condyle cut, making a distal femur posterior medial condyle cut, making a distal femur anterior chamfer cut, making a distal femur posterior lateral condyle chamfer cut, making a distal femur posterior medial condyle chamfer cut, making the distal femur box cuts (when required), drilling the cavity of a distal femur stabilization post, making a proximal tibial cut, making proximal tibia keel cut, or drilling proximal tibia holes.

This and other embodiments can include one or more of the following features. The on tool tracking device can be configured to change a CAS output to a user during a surgical procedure related to one of a shoulder; a hip; an ankle; a vertebra; or an elbow.

This and other embodiments can include one or more of the following features. The on tool tracking device can be configured to modify the CAS processing technique or output to the user during a surgical procedure related to one of a shoulder; a hip; an ankle; a vertebra; or an elbow.

This and other embodiments can include one or more of the following features. The device can further include a processing system within the on tool tracking device configured to assess data related to a CAS procedure.

This and other embodiments can include one or more of the following features. The device can further include electronic instructions contained within an electronic memory accessible to the processing system relating to the performance of a CAS processing step.

This and other embodiments can include one or more of the following features. The device can further include a processing system in communication with the on tool tracking device configured to assess data related to a CAS procedure.

This and other embodiments can include one or more of the following features. The device can further include electronic instructions contained within an electronic memory accessible to the processing system in communication with the on tool tracking device relating to the performance of a CAS processing step.

This and other embodiments can include one or more of the following features. The device display can be configured as an input device for the user of the on tool tracking device.

This and other embodiments can include one or more of the following features. The projector can be positioned within the housing on an inclined base.

This and other embodiments can include one or more of the following features. The projector can be a pico projector.

This and other embodiments can include one or more of the following features. The projector output can be provided in the form of a laser.

This and other embodiments can include one or more of the following features. The portion of the surgical tool can be selected so that, in use with the surgical tool, the cameras and the projector can be positioned above an active element associated with the surgical tool.

This and other embodiments can include one or more of the following features. The portion of the surgical tool can be selected so that, in use with the surgical tool, the cameras and the projector can be positioned below or to one side of an active element associated with the surgical tool.

This and other embodiments can include one or more of the following features. The device can further include a communication element within the housing configured to provide information related to the image processing operation to a component separate from the housing.

This and other embodiments can include one or more of the following features. The communications element can provide information wirelessly to and from the component separate from the housing.

This and other embodiments can include one or more of the following features. The communications element can provide information via a wired connection to the component separate from the housing.

This and other embodiments can include one or more of the following features. The component separate from the housing can be a computer containing instructions in computer readable media related to the use of the information for computer assisted surgery using the surgical tool active segment.

This and other embodiments can include one or more of the following features. The communications element within the housing can be configured to provide information related to the image processing operation to a component separate from the housing.

This and other embodiments can include one or more of the following features. The device can further include a communication element within the housing configured to receive and provide instructions to the projector to produce an output at least partially within a field of view of the first camera and the second camera, the output including at least one visually perceptible indication related to a computer assisted surgery processing step performed using an output from the electronic image processor operation.

This and other embodiments can include one or more of the following features. The device can further include a surgical tool having a trigger and an active element controlled by the operation of the trigger. The housing can be attached in releasable engagement with the surgical tool.

This and other embodiments can include one or more of the following features. The first camera and the second camera arrangement can provide a vertical field of view and a horizontal field of view containing at least a portion of the active element.

This and other embodiments can include one or more of the following features. The horizontal field of view and the vertical field of view can be selected for viewing a volume that contains substantially all of the active element.

This and other embodiments can include one or more of the following features. The horizontal field of view passing through the axis of the camera can be generally parallel to or makes an acute angle with the plane defined by the horizontal plane passing through the axis of the active element.

This and other embodiments can include one or more of the following features. The first camera and the second camera can be arranged within the housing to be placed on either side of a longitudinal axis of the active segment.

This and other embodiments can include one or more of the following features. The first camera and the second camera can be inclined towards the longitudinal axis of the active segment.

This and other embodiments can include one or more of the following features. The projector can be positioned in the housing in a substantially horizontal alignment with a longitudinal axis of the active segment.

This and other embodiments can include one or more of the following features. The projector can be positioned in the housing in an angled, converging relationship with respect to a longitudinal axis of the active segment.

This and other embodiments can include one or more of the following features. The device can further include electronics along with communications and software components configured within the device to control the operation of the tool.

This and other embodiments can include one or more of the following features. The device can further include a tactile feedback mechanism configured for cooperation with the trigger.

This and other embodiments can include one or more of the following features. The device can further include a tactile feedback mechanism configured to replace the surgical tool trigger.

This and other embodiments can include one or more of the following features. The tactile feedback mechanism can further include at least one position restoration element coupled to a scissor linkage within the mechanism.

This and other embodiments can include one or more of the following features. The tactile feedback mechanism can further include at least one constraint element coupled to a scissor linkage with the mechanism in order to controllably alter the range of movement or responsiveness of the linkage.

This and other embodiments can include one or more of the following features. The tactile feedback mechanism can be configured for placement alongside the trigger.

This and other embodiments can include one or more of the following features. The tactile feedback mechanism can be configured for placement over the trigger.

This and other embodiments can include one or more of the following features. A characteristic of the motion of the mechanism can be communicated to a component within the housing.

This and other embodiments can include one or more of the following features. The portion of the surgical tool can be selected so that, in use with the surgical tool, the cameras can be positioned below an active element associated with the surgical tool.

This and other embodiments can include one or more of the following features. The portion of the surgical tool can be selected so that, in use with the surgical tool, the cameras and the projector can be positioned below or to one side of an active element associated with the surgical tool.

This and other embodiments can include one or more of the following features. The communication element can be configured to provide information wirelessly, by Bluetooth, by wifi, or by ultra wideband technology.

This and other embodiments can include one or more of the following features. The visually perceptible indication can be perceptible to a user.

This and other embodiments can include one or more of the following features. The visually perceptible indication can be perceptible to the pair of cameras.

This and other embodiments can include one or more of the following features. The device can further include a sensor coupled to or within the housing.

This and other embodiments can include one or more of the following features. The sensor can be selected from the group including an inclinometer, a gyroscope, a two axis gyroscope, a three axis gyroscope or other multiple axis gyroscope, a one-two-three or multiple axis accelerometer, a potentiometer, and a MEMS instrument configured to provide one or more of roll, pitch, yaw, orientation, or vibration information related to the on tool tracking device.

This and other embodiments can include one or more of the following features. The active element of the surgical tool can be a saw blade, burr, or drill.

This and other embodiments can include one or more of the following features. The housing can include a lid assembly and a housing assembly, the housing assembly can include the surface for engagement with the surface on the saddle.

This and other embodiments can include one or more of the following features. The lid assembly and housing assembly can have complementary surfaces for releasably engaging together.

This and other embodiments can include one or more of the following features. The lid assembly and housing assembly can be configured to snap together.

This and other embodiments can include one or more of the following features. The lid assembly and housing assembly can snap together over a full perimeter of the lid assembly and a full perimeter of the housing assembly.

This and other embodiments can include one or more of the following features. The lid assembly and housing assembly can snap together over a partial perimeter or at discrete points of the lid assembly and housing assembly.

This and other embodiments can include one or more of the following features. The lid assembly and housing assembly can be configured to engage with each other at multiple discrete locations with a plurality of single elements.

This and other embodiments can include one or more of the following features. The single elements can include screws, pins, and threaded socket and ball.

This and other embodiments can include one or more of the following features. The lid assembly and housing assembly can be configured to engage with each other at multiple discrete locations or multiple arrays of interlocking structures.

This and other embodiments can include one or more of the following features. The interlocking structures can include snap fit clips, a hook and loop structure, or a cap and stem structure.

This and other embodiments can include one or more of the following features. The lid assembly can include the display.

This and other embodiments can include one or more of the following features. The lid assembly can include a battery chamber door and a battery chamber configured to receive a battery, the battery chamber door configured to open to permit a battery to slide into the battery chamber.

This and other embodiments can include one or more of the following features. The device can further include a battery chamber gasket configured to engage with the battery chamber door.

This and other embodiments can include one or more of the following features. The housing assembly can include a Y-shaped board.

This and other embodiments can include one or more of the following features. The Y-shaped board can include image processing and transmission circuits.

This and other embodiments can include one or more of the following features. The first and second cameras of the pair of cameras can be coupled to the Y-shaped board within the housing assembly.

This and other embodiments can include one or more of the following features. The first camera can be coupled to the Y-shaped board by a first camera bracket and the second camera can be coupled to the Y-shaped board by a second camera bracket.

This and other embodiments can include one or more of the following features. The projector can be coupled to the Y-shaped board.

This and other embodiments can include one or more of the following features. The projector can be coupled to the Y-shaped board by a projector bracket.

This and other embodiments can include one or more of the following features. The device can further include an electrical connector configured to provide an electronic control to the surgical tool.

This and other embodiments can include one or more of the following features. The electrical connector can be configured to contact a plurality of electrical contacts on the surgical tool.

This and other embodiments can include one or more of the following features. The electrical connector can be configured to send and receive electrical control signals with the surgical tool. The electrical control signals can modify a speed of the surgical tool.

This and other embodiments can include one or more of the following features. The electrical connector can be coupled to the Y-shaped board.

This and other embodiments can include one or more of the following features. The electrical contacts on the surgical tool can be on a proximal end surface of the surgical tool. An active element can be on a distal end of the surgical tool.

This and other embodiments can include one or more of the following features. The electrical contacts on the surgical tool can be on a top surface of the surgical tool adjacent to the surface for releasable engagement with the saddle.

This and other embodiments can include one or more of the following features. The electrical contacts on the surgical tool can be on a bottom surface of the surgical tool adjacent to a handle of the surgical tool.

This and other embodiments can include one or more of the following features. The surgical tool can be modified to create the electrical contacts.

This and other embodiments can include one or more of the following features. The electrical contacts can be spring loaded or cantilevered.

This and other embodiments can include one or more of the following features. The surgical tool can be designed or modified to position the electrical contacts for engagement with the on tool tacking device.

This and other embodiments can include one or more of the following features. The saddle can include an opening configured to receive the electrical connector therethrough.

This and other embodiments can include one or more of the following features. The electrical connector can be configured to pass through the opening in the saddle to contact the electrical contacts on the surgical tool.

This and other embodiments can include one or more of the following features. The saddle can include a conductive portion configured to contact the electrical connector.

This and other embodiments can include one or more of the following features. The conductive portion of the saddle can be configured to contact the plurality of electrical contacts on the surgical tool.

This and other embodiments can include one or more of the following features. The device can further include a user interface.

This and other embodiments can include one or more of the following features. The user interface can include push buttons and a display.

This and other embodiments can include one or more of the following features. The user interface can include a touch screen.

This and other embodiments can include one or more of the following features. The user interface can include a plurality of LEDs and switches.

This and other embodiments can include one or more of the following features. The housing can include a plurality of vents.

This and other embodiments can include one or more of the following features. The device can further include an antenna configured for wireless data transmission.

This and other embodiments can include one or more of the following features. The antenna can be within the housing.

This and other embodiments can include one or more of the following features. The device can further include an antenna configured for wireless data transmission of the camera signals.

This and other embodiments can include one or more of the following features. The device can further include an antenna configured to receive wireless data corresponding to instructions for the projector.

This and other embodiments can include one or more of the following features. The housing can include a heat sink configured to cool the on tool tracking device during operation of the surgical tool.

This and other embodiments can include one or more of the following features. The heat sink can contact the projector.

This and other embodiments can include one or more of the following features. The device can further include a first wide angle lens on the first camera and a second wide angle lens on the second camera.

This and other embodiments can include one or more of the following features. The device can further include a first infrared filter on the first camera and a second infrared filter on the second camera.

This and other embodiments can include one or more of the following features. The device can further include a gasket.

This and other embodiments can include one or more of the following features. The gasket can be an elastomeric material.

This and other embodiments can include one or more of the following features. The gasket can engage with the Y-board assembly.

This and other embodiments can include one or more of the following features. The gasket can engage with the housing.

This and other embodiments can include one or more of the following features. The gasket can be located on the housing and configured to contact the saddle when the housing can be engaged with the saddle.

This and other embodiments can include one or more of the following features. The gasket can be configured to engage with the electrical connector configured to contact the plurality of electrical contacts on the surgical tool.

This and other embodiments can include one or more of the following features. The housing can be configured to releasably engage with a smartphone or tablet computer.

This and other embodiments can include one or more of the following features. The on tool tracking device can be configured to send and receive data to the smartphone or tablet computer.

This and other embodiments can include one or more of the following features. The on tool tracking device can be configured to transmit data to the smartphone or tablet computer to display information relating to a CAS procedure on a screen of the smartphone or tablet computer.

This and other embodiments can include one or more of the following features. The housing surface for engagement with the surface on the saddle can have a complementary shape to engage with a tapered surface on the saddle.

This and other embodiments can include one or more of the following features. The housing surface for engagement with the surface on the saddle can have a complementary shape to engage with two long protrusions on the saddle extending from a proximal end of the saddle to a distal end of the saddle.

This and other embodiments can include one or more of the following features. The housing surface for engagement with the surface on the saddle can have a complementary shape to engage with two rails on the saddle.

This and other embodiments can include one or more of the following features. The housing surface for engagement with the surface on the saddle can have a complementary shape to engage with a front taper and a rear taper on the saddle.

This and other embodiments can include one or more of the following features. The housing can include a rear surface for engagement with a proximal surface of the saddle.

This and other embodiments can include one or more of the following features. The device can further include a lock configured to lock the housing and saddle together.

This and other embodiments can include one or more of the following features. The lock can be spring loaded.

This and other embodiments can include one or more of the following features. the lock can be a cam configured to lock the housing to the saddle through rotary motion of a handle of the cam.

This and other embodiments can include one or more of the following features. The lock can be a locking pin on the housing configured to engage with a corresponding sideway recess in the saddle.

This and other embodiments can include one or more of the following features. The lock can be a cantilevered lock configured to engage with a corresponding recess in the saddle.

This and other embodiments can include one or more of the following features. The cantilevered lock can be configured to releasably snap into the corresponding recess in the saddle.

This and other embodiments can include one or more of the following features. The cantilevered lock can be on the housing surface for engagement with the surface of the saddle.

This and other embodiments can include one or more of the following features. The cantilevered lock can be on a side of the housing.

This and other embodiments can include one or more of the following features. The device can further include a lock release configured to release the lock between the housing and saddle.

This and other embodiments can include one or more of the following features. The device can further include a lining material on a portion of the housing surface for engagement with the surface on the saddle.

This and other embodiments can include one or more of the following features. The cameras can be below the active element of the surgical tool when the surgical tool is coupled to the saddle and the housing is engaged with the saddle.

This and other embodiments can include one or more of the following features. A center of the first camera and a center of the second camera can be below the active element of the surgical tool by about 0 mm to about 5 mm when the surgical tool is coupled to the saddle and the housing is engaged with the saddle.

This and other embodiments can include one or more of the following features. The output from the pair of cameras can include raw image data from the cameras.

This and other embodiments can include one or more of the following features. The output from the pair of cameras can include streaming image data from the cameras.

This and other embodiments can include one or more of the following features. An output from the first camera can be transmitted to the electronic imaging processor external to the on tool tracking device by a first camera signal and an output from the second camera can be transmitted to the electronic imaging processor external to the on tool tracking device by a second camera signal.

This and other embodiments can include one or more of the following features. An output from the first camera and an output from the second camera can be transmitted to the electronic imaging processor external to the on tool tracking device by a combined camera signal.

This and other embodiments can include one or more of the following features. The device can further include an image processor configured to analyze image data from the cameras to identify one or more tracking elements and to convert the image data of the one or more tracking elements to mathematical coordinates relative to the position of the on tool tracking device.

This and other embodiments can include one or more of the following features. The image processor can be within the housing of the on tool tracking device.

This and other embodiments can include one or more of the following features. The image processor can be external to on tool tracking device.

This and other embodiments can include one or more of the following features. The display can be integral with an outer surface of the housing.

This and other embodiments can include one or more of the following features. The display can be configured to be tilted relative to an outer surface of the housing.

This and other embodiments can include one or more of the following features. The projector can be configured to provide an output including at least one visually perceptible indication above and below the active element of the surgical tool.

This and other embodiments can include one or more of the following features. The projector can be configured to provide an output based on the image data within 33 ms of taking the image data with the pair of cameras.

This and other embodiments can include one or more of the following features. The device can further include a sterile battery funnel configured to engage with a portion of the housing and adapted to permit a battery to slide through an internal volume of the funnel to a battery chamber of the housing.

This and other embodiments can include one or more of the following features. The housing can be configured to be mechanically connected to the surgical tool.

This and other embodiments can include one or more of the following features. The housing can be configured to be electrically connected to the surgical tool.

This and other embodiments can include one or more of the following features. The housing can be configured to be mechanically and electrically connected to the surgical tool.

This and other embodiments can include one or more of the following features. The device can further include a power management unit configured to receive electrical energy from the battery and distribute the electrical energy to power the pair of cameras, projector, display, and a speed controller for the hand held surgical tool.

This and other embodiments can include one or more of the following features. The device can further include a cleaning attachment configured to releasably engage with the housing surface for engagement with the surface of the saddle.

This and other embodiments can include one or more of the following features. In general, in one embodiment, a method for performing a computer assisted surgery procedure using a hand held surgical tool having an on tool tracking device attached thereto, includes collecting and processing computer assisted surgery data using the on tool tracking device attached to a saddle with the saddle attached to the hand held surgical tool, wherein the data includes data from a pair of cameras within or coupled to the on tool tracking device. Next, assessing the data in real time during the computer assisted surgery procedure. Next, performing CAS related operations using the on tool tracking device selected from at least two of: (1) controlling the operation of the tool, controlling the speed of the tool and providing to the user guidance related to a CAS step; (2) controlling the operation or speed of the tool or providing guidance to the user to adjust the speed of the tool; and (3) providing a user of the surgical tool an output related to the assessing step.

This and other embodiments can include one or more of the following features. The method can further include attaching the saddle to the hand held surgical tool.

This and other embodiments can include one or more of the following features. The method can further include attaching the on tool tracking device to the saddle.

This and other embodiments can include one or more of the following features. Controlling the operation or speed of the tool can include the on tool tracking device sending electronic control signals to the hand held surgical tool.

This and other embodiments can include one or more of the following features. The electronic control signals to the hand held surgical tool can include instructions to stop or slow down the hand held surgical tool.

This and other embodiments can include one or more of the following features. The providing step can further include one or more of displaying, projecting, or indicating an output related to a computer assisted surgery processing step.

This and other embodiments can include one or more of the following features. The providing step substantially can be provided to the user by the on tool tracking device attached to the surgical tool.

This and other embodiments can include one or more of the following features. The output of providing step can further include one or more of a tactile indication, a haptic indication, an audio indication or a visual indication.

This and other embodiments can include one or more of the following features. The tactile indication can include a temperature indication.

This and other embodiments can include one or more of the following features. The haptic indication can include a force indication or a vibration indication.

This and other embodiments can include one or more of the following features. The providing an output step can be performed by a component of the on tool tracking device.

This and other embodiments can include one or more of the following features. The assessing step can further include a comparison of data received from the on tool tracking device and data provided using a computer assisted surgery surgical plan.

This and other embodiments can include one or more of the following features. A data processing step performed during the assessing step can be adapted based upon information received from the on tool tracking device.

This and other embodiments can include one or more of the following features. The information can be related to one or more of visual data from the involved surgical field information, data from a sensor on the on tool tracking device, data obtained related to an operational characteristic of the surgical tool.

This and other embodiments can include one or more of the following features. The output can be the control signal automatically generated to adjust a performance parameter of the surgical tool in response to a result of the assessing step.

This and other embodiments can include one or more of the following features. The performance parameter can include modifying a tool cutting speed or stopping a tool operation the output of providing step can further include electronics to control operation of power tools (modifying cutting speed and/or stopping it).

This and other embodiments can include one or more of the following features. The method can further include determining a computer aided surgery processing mode based on the results of the assessing step.

This and other embodiments can include one or more of the following features. The determining step can be based upon an evaluation of one or more of: a physical parameter within the surgical field such as position or combination of positions of elements tracked in the field through reference frames attached to them a reference frame input, take projected image, a motion detected from a sensor, a motion detection from a calculation, the overall progress of a computer aided surgery procedure, a measured or predicted deviation from a previously prepared computer aided surgery plan.

This and other embodiments can include one or more of the following features. The determining step can select one of a number of predefined processing modes.

This and other embodiments can include one or more of the following features. The predefined processing modes can be hover mode, site approach mode, and active step mode.

This and other embodiments can include one or more of the following features. The predefined processing mode can be a hover mode and data received from the on tool tracking device can be processed using a hover mode CAS algorithm.

This and other embodiments can include one or more of the following features. The providing step can include an output generated as a result of applying the hover mode CAS algorithm to data received using the on tool tracking device.

This and other embodiments can include one or more of the following features. The predefined processing mode can be a site approach mode, and data received from the on tool tracking device can be processed using a site approach mode CAS algorithm.

This and other embodiments can include one or more of the following features. The providing step can include an output generated as a result of applying the site approach mode CAS algorithm to data received using the on tool tracking device.

This and other embodiments can include one or more of the following features. The predefined processing mode can be an active step mode and data received from the on tool tracking device can be processed using an active step mode CAS algorithm.

This and other embodiments can include one or more of the following features. The providing step can include an output generated as a result of applying the active step mode CAS algorithm to data received using the on tool tracking device.

This and other embodiments can include one or more of the following features. Each of the predefined processing modes can adjust one or more processing factors employed by a computer assisted surgery computer or processing system on board the on tool tracking device.

This and other embodiments can include one or more of the following features. The OTT CAS processing mode factors can be selected from one or more of: a camera frame size; an OTT camera orientation; an adjustment to a camera software program or firmware in accordance with the desired adjustment; adjustments to an OTT camera or other camera image outputs to modify a size of a region of interest within a horizontal field of view, the vertical field of view or both the horizontal and the vertical field of view of the camera; drive signals for adjustable camera lens adjustment or positioning; image frame rate; image output quality; refresh rate; frame grabber rate; reference frame two; reference frame one; on reference frame fiducial select; off reference frame fiducial select; visual spectrum processing; IR spectrum processing; reflective spectrum processing; LED or illumination spectrum processing; surgical tool motor/actuator speed and direction, overall CAS procedure progress; specific CAS step progress; image data array modification; an OTT projector refresh rate; an OTT projector accuracy; one or more image segmentation techniques; one or more logic-based extractions of an image portion based on a CAS progress; signal-to-noise ratio adjustment; one or more image amplification process, one or more imaging filtering process; applying weighted averages or other factors for dynamic, real-time enhancement or reduction of image rate, pixel or sub-pixel vision processing; a hand tremor compensation; an instrument-based noise compensation for a saw, a drill or other electrical surgical tool and a vibration compensation process based on information from the OTT each alone or in any combination.

This and other embodiments can include one or more of the following features. The output can be adjusted based upon the result of the selection of one of the predefined processing modes.

This and other embodiments can include one or more of the following features. The output can be provided to the user with a projector in the on tool tracking device.

This and other embodiments can include one or more of the following features. The projector output can be adjusted based upon a physical characteristic the surgical site presented during the display of the projector output.

This and other embodiments can include one or more of the following features. The physical characteristic can be one or more of the shape of the portion of the size available to the projector output; the topography in the projector projected field and the orientation of the projector to the portion of the site available for the projector output.

This and other embodiments can include one or more of the following features. The projector output can include information visible to the user of the surgical tool while the surgical tool can be in use in the surgical site.

This and other embodiments can include one or more of the following features. The projector output can include information visible to the user of the surgical tool to indicate the position, relative motion, orientation, or other navigation parameter related to the positioning of the active element of the surgical tool within the surgical field according to the surgical plan.

This and other embodiments can include one or more of the following features. The step of outputting a CAS output to the user can be changed as a result of one of the above recited steps performed during a surgical procedure related to a knee.

This and other embodiments can include one or more of the following features. The step of providing an output can further include displaying the output on a system screen; on a GUI interface on the OTT or a mobile device screen.

This and other embodiments can include one or more of the following features. An OTT CAS processing technique or output can be modified as a result of one of the above recited steps performed during a surgical procedure related to a knee.

This and other embodiments can include one or more of the following features. The step of outputting a CAS output to the user can be changed and an OTT CAS processing technique or output can be modified as a result of the user performing one or more steps of a computer assisted surgery procedure on a knee including making a distal femur cut, making, making a distal femur anterior cut, making a distal femur posterior lateral condyle cut, making a distal femur posterior medial condyle cut, making a distal femur anterior chamfer cut, making a distal femur posterior lateral condyle chamfer cut, making a distal femur posterior medial condyle chamfer cut, making proximal tibial cut.

This and other embodiments can include one or more of the following features. The step of outputting a CAS output to the user can be changed and an OTT CAS processing technique or output can be modified as a result of the user performing one or more steps of a computer assisted surgery procedure on a knee including making a distal femur cut, making a distal femur anterior cut, making a distal femur posterior lateral condyle cut, making a distal femur posterior medial condyle cut, making a distal femur anterior chamfer cut, making a distal femur posterior lateral condyle chamfer cut, making a distal femur posterior medial condyle chamfer cut, making the distal femur box cuts (when required), drilling the cavity of a distal femur stabilization post, making a proximal tibial cut, making proximal tibia keel cut, or drilling proximal tibia holes.

This and other embodiments can include one or more of the following features. The step of outputting a CAS output to the user can be changed as a result of one of the above recited steps performed during a surgical procedure related to one of a shoulder; a hip; an ankle; a vertebra; or an elbow.

This and other embodiments can include one or more of the following features. An OTT CAS processing technique or output can be modified as a result of one of the above recited steps performed during a surgical procedure related to one of a shoulder; a hip; an ankle; a vertebra; or an elbow.

This and other embodiments can include one or more of the following features. The step of assessing the data can be performed using a processing system within the on tool tracking device.

This and other embodiments can include one or more of the following features. There can be electronic instructions contained within an electronic memory accessible to the processing system relating to the performance of an OTT CAS processing step.

This and other embodiments can include one or more of the following features. The step of assessing the data can be performed using a processing system in communication with the on tool tracking device.

This and other embodiments can include one or more of the following features. There can be electronic instructions contained within an electronic memory accessible to the processing system relating to the performance of an OTT CAS processing step.

This and other embodiments can include one or more of the following features. The method can further include determining a position of a portion of bone or tissue for which the CAS procedure can be to be performed; determining a position of the hand held surgical tool; calculating a distance between the position of the portion of bone or tissue and the position of the hand held surgical tool; setting a mode of the hand held surgical tool to a normal tracking mode if a distance between the portion of bone or tissue and the hand held surgical tool can be greater than a first threshold distance; setting the mode of the hand held surgical tool to an enhanced tracking mode if the distance between the portion of bone or tissue and the hand held surgical tool can be less than the first threshold distance and can be greater than a second threshold distance; and setting the mode of the hand held surgical tool to a cutting mode if the distance between the portion of bone or tissue and the hand held surgical tool can be less than the second threshold distance.

This and other embodiments can include one or more of the following features. The normal tracking mode and enhanced tracking mode allow for secondary tasks selected from the group including calculation of motion between a femur and tibia, recalibration of a reference frame, and determination of the hand held surgical tool proximity to a registration deck. The cutting mode may not allow secondary tasks selected from the group including calculation of motion between a femur and tibia, recalibration of a reference frame, and determination of the hand held surgical tool proximity to a registration deck. The cutting mode may not allow the secondary tasks.

This and other embodiments can include one or more of the following features. Setting the mode to the normal tracking mode and the enhanced tracking mode can include turning off a motor control function of the hand held surgical tool. Setting the mode to the cutting mode can include enabling the motor control function of the hand held surgical tool.

This and other embodiments can include one or more of the following features. Setting the mode to the normal tracking mode can include turning off a two-dimensional guidance graphical interface (GUI) associated with the hand held surgical tool. Setting the mode to the enhanced tracking mode and cutting mode can include turning on the two-dimensional guidance GUI associated with the hand held surgical tool.

This and other embodiments can include one or more of the following features. Setting the mode to the normal tracking mode and enhanced tracking mode can include turning off a projector on the hand held surgical tool. Setting the mode to the cutting mode can include turning on the projector.

This and other embodiments can include one or more of the following features. Setting the mode to the normal tracking mode can include turning off a display on the hand held surgical tool. Setting the mode to the enhanced tracking mode and cutting mode can include turning on the display.

This and other embodiments can include one or more of the following features. Changing the mode from the normal tracking mode to the enhanced tracking mode can include increasing resources appropriated to the navigation and error calculation of the hand held surgical tool.

This and other embodiments can include one or more of the following features. Changing the mode from the enhanced tracking mode to the cutting mode can include increasing resources appropriated to the navigation and error calculation, a tool motor controller, a two-dimensional guidance graphical interface associated with the hand held surgical tool, and a projector or display on the hand held surgical tool.

This and other embodiments can include one or more of the following features. The first threshold distance can be greater than 200 mm and the second threshold distance can be 100 mm to 200 mm.

This and other embodiments can include one or more of the following features. The second threshold distance can be 70 mm to 100 mm.

This and other embodiments can include one or more of the following features. The second threshold distance can be 10 mm to 0 mm.

This and other embodiments can include one or more of the following features. The method can further include setting the first threshold distance and the second threshold distance prior to determining the position of the portion of bone or tissue for which the procedure can be to be performed.

This and other embodiments can include one or more of the following features. The method can further include attaching a reference frame including one or more position markers to the patient at a predetermined spatial orientation to the portion of bone or tissue. determining the position of the portion of bone or tissue can include determining the position of the reference frame.

This and other embodiments can include one or more of the following features. The method can further include using a plurality of cameras to determine the position of the one or more position markers.

This and other embodiments can include one or more of the following features. The plurality of cameras can be within or coupled to the housing.

This and other embodiments can include one or more of the following features. The CAS procedure can be performed on a joint.

This and other embodiments can include one or more of the following features. The joint can be related to one of a knee, a shoulder; a hip; an ankle; a vertebra; or an elbow.

In general, in one embodiment, a method for attaching an on tool tracking device to a surgical tool, the method includes attaching a saddle to the surgical tool, attaching the on tool tracking device to the saddle, and verifying one or more features of the surgical tool, saddle, or on tool tracking device.

This and other embodiments can include one or more of the following features. The method can further include contacting a surface feature on the saddle with a surface feature on the on tool tracking device when the on tool tracking device can be attached to the saddle to complete a circuit in the on tool tracking device.

This and other embodiments can include one or more of the following features. The surface feature can be a bump on the saddle and the surface feature on the on tool tracking device can be a cantilever and contacting the bump on the saddle with the cantilever on the on tool tracking device pushes the cantilever to flip a switch or complete an electrical contact that completes the circuit in the on tool tracking device.

This and other embodiments can include one or more of the following features. The method can further include multiple bumps on the saddle and multiple corresponding cantilevers on the on tool tracking device and contacting the multiple bumps on the saddle with the multiple cantilevers on the on tool tracking device pushes the multiple cantilevers to flip one or more switches or make one or more electrical contacts that complete one or more circuits in the on tool tracking device.

This and other embodiments can include one or more of the following features. The surface feature can be a magnet on the saddle and the surface feature on the on tool tracking device can be a reed switch and contacting the magnet on the saddle with the reed switch on the on tool tracking device completes a circuit in the on tool tracking device.

This and other embodiments can include one or more of the following features. The surface feature can be an exposed contact or surface mounted spring contact on the saddle and the surface feature on the on tool tracking device can be a complementary exposed contact or surface mounted spring contact and contacting the surface feature on the saddle with the surface feature on the on tool tracking device completes an electrical contact that completes the circuit in the on tool tracking device.

This and other embodiments can include one or more of the following features. The method can further include verifying the electrical contacts of the completed circuit with a logic processor in the on tool tracking device.

This and other embodiments can include one or more of the following features. The logic processor can include one or more of nonvolatile memory, a "fusible-link" PROM, or a UV-erasable PROM.

This and other embodiments can include one or more of the following features. The electrical contacts can include one or more of logic processors, RAM, nonvolatile storage, and sensors.

This and other embodiments can include one or more of the following features. The completed circuit can be on the saddle or tool such that the completed circuit interacts with the on tool tracking device.

This and other embodiments can include one or more of the following features. Verifying can include confirming that the on tool tracking device can be authentic.

This and other embodiments can include one or more of the following features. Verifying can include the on tool tracking device transmitting an embedded serial number, an electronic signature or key that authenticates the device for use.

This and other embodiments can include one or more of the following features. Verifying can include confirming that the on tool tracking device can be licensed.

This and other embodiments can include one or more of the following features. Verifying can include confirming that the surgical tool can be the expected surgical tool based on a surgical plan.

This and other embodiments can include one or more of the following features. Verifying can include confirming that the surgical tool can be the expected surgical tool based on user preferences.

This and other embodiments can include one or more of the following features. Verifying can include confirming that the on tool tracking device can be properly mated to the saddle.

This and other embodiments can include one or more of the following features. Verifying can include electronically exchanging data between the on tool tracking device and the surgical tool.

This and other embodiments can include one or more of the following features. Verifying can include providing an irreversible registration each time the saddle can be connected to the on tool tracking device.

This and other embodiments can include one or more of the following features. Verifying can include the on tool tracking device receiving electronic data from the surgical tool or saddle corresponding to information on one or more of: brand, model, and type of surgical tool.

This and other embodiments can include one or more of the following features. The method can further include generating an alert if the brand, model, or type of the surgical tool can be not the brand, model, or type of surgical tool expected in the surgical plan.

This and other embodiments can include one or more of the following features. The method can further include optically determining a type of an active element of the tool using a pair of cameras on the on tool tracking device.

This and other embodiments can include one or more of the following features. The method can further include comparing the active element of the tool with a surgical plan and confirming the active element can be the active element expected in the surgical plan.

This and other embodiments can include one or more of the following features. The method can further include performing a CAS procedure using the hand held surgical tool.

In general, in one embodiment, an on tool tracking device includes a housing having a housing surface for engagement with a surface on a saddle, one or more surface features on the housing surface for engagement with the saddle configured to contact one or more corresponding surface features on the saddle when the housing is coupled to the saddle, and a pair of cameras within or coupled to the housing wherein when the housing is coupled to the saddle the pair of cameras are in position to provide an image output having a field of view including at least a portion of an active element of a surgical tool coupled to the saddle.

This and other embodiments can include one or more of the following features. The surface feature on the housing surface can be configured to complete a circuit when the on tool tracking device can be attached to the saddle and the surface feature on the saddle contacts the surface feature on the housing surface.

This and other embodiments can include one or more of the following features. The saddle surface feature can be a bump on the saddle and the housing surface feature can be a cantilever, wherein the cantilever can be configured such that contacting the bump on the saddle with the cantilever on the on tool tracking device pushes the cantilever to flip a switch or complete an electrical contact that completes a circuit in the on tool tracking device.

This and other embodiments can include one or more of the following features. The device can further include multiple bumps on the saddle and multiple corresponding cantilevers on housing surface. The cantilever can be configured such that contacting the multiple bumps on the saddle with the multiple cantilevers on the on tool tracking device pushes the multiple cantilevers to flip one or more switches or make one or more electrical contacts that complete one or more circuits in the on tool tracking device.

This and other embodiments can include one or more of the following features. The saddle surface feature can be a magnet and the housing surface feature can be a reed switch. The reed switch can be configured such that contacting the magnet on the saddle with the reed switch on the on tool tracking device completes a circuit in the on tool tracking device.

This and other embodiments can include one or more of the following features. The surface feature can be an exposed contact or surface mounted spring contact on the saddle and the surface feature on the housing can be a complementary exposed contact or surface mounted spring contact. The device can be configured such that contacting the surface feature on the saddle with the surface feature on the housing completes an electrical contact that completes the circuit in the on tool tracking device.

This and other embodiments can include one or more of the following features. The device can further include a logic processor in the on tool tracking device configured to verify the electrical contacts of the completed circuit.

This and other embodiments can include one or more of the following features. The logic processor can include one or more of nonvolatile memory, a "fusible-link" PROM, or a UV-erasable PROM.

This and other embodiments can include one or more of the following features. The electrical contacts can include one or more of logic processors, RAM, nonvolatile storage, and sensors.

This and other embodiments can include one or more of the following features. The completed circuit can be on the saddle or tool such that the completed circuit interacts with the on tool tracking device.

In general, in one embodiment, a saddle for a surgical tool includes an inner surface for engagement with an outer casing of the surgical tool, one or more openings to permit access to one or more connectors on the surgical tool, and an outer surface with one or more features or contours adapted and configured for corresponding mating to one or more features or contours on a surface of an on tool tracking housing.

This and other embodiments can include one or more of the following features. The saddle can include plastic.

This and other embodiments can include one or more of the following features. The saddle can include ABS plastic.

This and other embodiments can include one or more of the following features. The saddle can include stainless steel.

This and other embodiments can include one or more of the following features. The one or more connectors on the surgical tool can be mechanical connectors.

This and other embodiments can include one or more of the following features. The one or more connectors on the surgical tool can be electrical connectors.

This and other embodiments can include one or more of the following features. The one or more openings can be covered by the on tool tracking housing when the saddle is coupled to the on tool tracing housing.

This and other embodiments can include one or more of the following features. The one or more features or contours can include a tapered surface on the saddle.

This and other embodiments can include one or more of the following features. The one or more features or contours can include two long protrusions on the saddle extending from a proximal end of the saddle to a distal end of the saddle.

This and other embodiments can include one or more of the following features. The one or more features or contours can include two rails on the saddle.

This and other embodiments can include one or more of the following features. The one or more features or contours can include a front taper and a rear taper on the saddle.

This and other embodiments can include one or more of the following features. The one or more features or contours include a front bulb and front taper and a rear taper.

This and other embodiments can include one or more of the following features. The saddle can further include a lock configured to lock the housing and saddle together.

This and other embodiments can include one or more of the following features. The lock can be spring loaded.

This and other embodiments can include one or more of the following features. The lock can be a cam configured to lock the housing to the saddle through rotary motion of a handle of the cam.

This and other embodiments can include one or more of the following features. The lock can be a locking pin on the housing configured to engage with a corresponding sideway recess in the saddle.

This and other embodiments can include one or more of the following features. The lock can be a cantilevered lock configured to engage with a corresponding recess in the saddle.

This and other embodiments can include one or more of the following features. The cantilevered lock can be configured to releasably snap into the corresponding recess in the saddle.

This and other embodiments can include one or more of the following features. The cantilevered lock can be on the housing surface for engagement with the surface of the saddle.

This and other embodiments can include one or more of the following features. The saddle can include two cantilevered locks on a proximal end of the housing surface for engagement with the surface of the saddle.

This and other embodiments can include one or more of the following features. The saddle can include one cantilevered lock on a proximal end of the housing surface for engagement with the surface of the saddle.

This and other embodiments can include one or more of the following features. The cantilevered lock can be on a side of the housing.

This and other embodiments can include one or more of the following features. The saddle can include two cantilevered locks on side of the housing.

This and other embodiments can include one or more of the following features. The saddle can further include a lock release.

This and other embodiments can include one or more of the following features. The saddle can further include a lining material on a portion of the outer saddle surface for engagement with the housing.

This and other embodiments can include one or more of the following features. The one or more openings can be configured to permit access to a top portion of the surgical tool.

This and other embodiments can include one or more of the following features. The one or more openings can be configured to permit access to an underside of the surgical tool.

This and other embodiments can include one or more of the following features. The one or more openings can be configured to permit access to an endcap of the surgical tool.

This and other embodiments can include one or more of the following features. The outer surface with one or more features or contours can be configured to slidably engage and mate with the corresponding one or more features or contours on the surface of an on tool tracking housing.

This and other embodiments can include one or more of the following features. The outer surface with one or more features or contours can be configured to snap on to mate with the corresponding one or more features or contours on the surface of an on tool tracking housing.

This and other embodiments can include one or more of the following features. The outer surface of the saddle can further include a bump configured to contact a corresponding feature on the on tool tracking device.

This and other embodiments can include one or more of the following features. The outer surface of the saddle can further include multiple bumps configured to contact multiple corresponding features on the on tool tracking device.

This and other embodiments can include one or more of the following features. The outer surface of the saddle can further include a magnet configured to interact with a reed switch on the on tool tracking device when the saddle can be engaged with the on tool tracking device.

This and other embodiments can include one or more of the following features. The outer surface of the saddle can further include an exposed contact or a surface mounted spring contact configured to engage with a complementary exposed contact or surface mounted spring contact on an on tool tracking device when the saddle is engaged with the on tool tracking device.

This and other embodiments can include one or more of the following features. The saddle can further include: a first conductive portion configured to contact an electrical contact on the surgical tool; a second conductive portion configured to contact an electrical contact on the on tool tracking housing; and a conductive material providing electrical communication between the first conductive portion and the second conductive portion.

In general, in one embodiment, a tracker device configured to be coupled to a hand held surgical tool includes a Y-board configured to fit inside of the tracker device having a spacing between the arms of the Y-board is wide enough to accommodate a chuck or active end of the hand held surgical tool, and a first camera mount and a second camera mount coupled to each of the arms of the Y-board.

This and other embodiments can include one or more of the following features. The tracker device can further include: a first camera engaged with the first camera mount and a second camera engaged with the second camera mount, wherein a center of the first camera engaged with the first camera mount and a center of the second camera engaged with the second camera mount can be below the chuck or active end of the hand held surgical tool by about 0 mm to about 5 mm when the hand held surgical tool is coupled to a saddle and the tracker device is engaged with the saddle.

This and other embodiments can include one or more of the following features. The tracker device can further include: a first camera engaged with the first camera mount and a second camera engaged with the second camera mount. A center of the first camera engaged with the first camera mount and a center of the second camera engaged with the second camera mount can be above the chuck or active end of the hand held surgical tool when the hand held surgical tool is coupled to a saddle and the tracker device is engaged with the saddle.

This and other embodiments can include one or more of the following features. The first and second camera mounts can each have a shape and length selected to place the supported camera into a position relative to the tracker device so that when the tracker device can be coupled to the saddle and surgical tool, the first camera and second camera each have a field of vision aligned with a major axis of the tool attached to the tracker device.

This and other embodiments can include one or more of the following features. The active end of the surgical tool can include a drill.

This and other embodiments can include one or more of the following features. The active end of the surgical tool can include a reamer.

This and other embodiments can include one or more of the following features. the active end of the surgical tool can include a sagittal saw.

This and other embodiments can include one or more of the following features. The active end of the surgical tool can include a reciprocating saw.

This and other embodiments can include one or more of the following features. The active end of the surgical tool can include an oscillating saw.

This and other embodiments can include one or more of the following features. The spacing between the arms of the Y-board can be wide enough to accommodate a reciprocating action of the hand held surgical tool.

This and other embodiments can include one or more of the following features. The spacing between the arms of the Y-board can be wide enough to accommodate a circular action of the hand held tool.

This and other embodiments can include one or more of the following features. The spacing between the arms of the Y-board can be wide enough to accommodate an oscillating action of the hand held surgical tool.

This and other embodiments can include one or more of the following features. The tracker device can have a throat configured to receive the chuck or active end of the surgical tool, the throat can be sized to accommodate the arms of the Y-board.

This and other embodiments can include one or more of the following features. The tracker device can further include a first camera engaged with the first camera mount and a second camera engaged with the second camera mount.

This and other embodiments can include one or more of the following features. The tracker device can further include a pico projector in a housing of the tracker device coupled to the Y-board.

This and other embodiments can include one or more of the following features. The tracker device can further include a touch screen on the tracker device.

This and other embodiments can include one or more of the following features. A field of view of the first camera and the second camera can be from about 70 mm to about 200 mm from the first and second cameras.

This and other embodiments can include one or more of the following features. A field of view of the first camera and the second camera can be from about 50 mm-250 mm from the first and second cameras.

In general, in one embodiment, a system for performing a computer assisted surgical procedure, the system including an on tool tracking device with a housing having a surface for engagement with a surface on a saddle and a pair of cameras within or coupled to the housing, wherein when the housing is coupled to the saddle the pair of cameras are in position to provide an image output having a field of view including at least a portion of an active element of a surgical tool coupled to the saddle, the on tool tracking device configured to transmit the image output, and a system computer configured to receive the transmitted image output from the on tool tracking device and perform an image processing function on the image output, the system computer configured to transmit instructions to the on tool tracking device based on the image processing function on the image output.

This and other embodiments can include one or more of the following features. The system of the on tool tracking device can further include a display.

This and other embodiments can include one or more of the following features. The system of the on tool tracking device can further include a projector.

This and other embodiments can include one or more of the following features. The system of the system computer can be configured to run tracking software to determine the position and orientation of the on tool tracking device.

This and other embodiments can include one or more of the following features. The tracking software can determine the position and orientation based on the image output from the pair of cameras.

This and other embodiments can include one or more of the following features. The on tool tracking device can be further configured to receive the instructions from the system computer.

This and other embodiments can include one or more of the following features. The instructions can include one or more of: data for the projector to project an image, data for an image to show on the display, and data corresponding to a control signal for modifying a speed of the surgical tool.

This and other embodiments can include one or more of the following features. The system can be configured to perform a CAS procedure on a joint.

This and other embodiments can include one or more of the following features. The joint can be related to one of a knee; a shoulder; a hip; an ankle; a vertebra; or an elbow.

In general, in one embodiment, a method for performing a computer assisted surgery (CAS) procedure includes performing a step by a user related to the CAS procedure with a surgical tool engaged with an on tool tracking device having a first camera and a second camera, receiving with the on tool tracking device one or more images from either or both of the first and second cameras, transmitting the one or more images from the on tool tracking device to a system computer, performing image processing on the one or more images to determine a significance of the step related to the CAS procedure using the system computer, determining a result for the significance of the step related to the CAS and instructions for the on tool tracking device and user, communicating the instructions to the on tool tracking device, and the on tool tracking device receiving the instructions and displaying the instructions to the user.

This and other embodiments can include one or more of the following features. The method can further include displaying the instructions to the user on a display on the on tool tracking device.

This and other embodiments can include one or more of the following features. The method can further include projecting the instructions to the user using a projector on the on tool tracking device.

This and other embodiments can include one or more of the following features. The instructions can include one or more of: data for the image to be projected; data for the image to be displayed, position and orientation data for the on tool tracker, and a signal with instructions for controlling a speed of tool.

This and other embodiments can include one or more of the following features. The instructions can include one or more of: data for the projector to project an image, data for an image to show on the display, and data corresponding to a control signal for modifying a speed of the surgical tool.

This and other embodiments can include one or more of the following features. The CAS procedure can be performed on a joint.

This and other embodiments can include one or more of the following features. The joint can be related to one of a knee; a shoulder; a hip; an ankle; a vertebra; or an elbow.

This and other embodiments can include one or more of the following features. The on tool tracking device can be configured to display the instructions to the user within 33 ms of the device taking the one or more images from either or both of the first and second cameras.

This and other embodiments can include one or more of the following features. The user interface can include a capacitive switch.

This and other embodiments can include one or more of the following features. The display or touch screen can be configured to be detachable from the housing.

This and other embodiments can include one or more of the following features. The display or touch screen can be separate from the housing.

This and other embodiments can include one or more of the following features. The display or touch screen can be configured to communicate wirelessly with the on tool tracking device and a system computer.

This and other embodiments can include one or more of the following features. The touch screen can be configured to set a processing mode or a user preference for the surgical tool.

This and other embodiments can include one or more of the following features. The touch screen can be configured to control aspects of the on tool tracking device.

This and other embodiments can include one or more of the following features. The control can include starting and stopping the recording of the pair of cameras.

This and other embodiments can include one or more of the following features. The on tool tracking device can be configured to wirelessly communicate with and control the surgical tool.

This and other embodiments can include one or more of the following features. The field of view of the first pair of cameras can be different than the field of view of the second pair of cameras.

This and other embodiments can include one or more of the following features. The field of view of the first pair of cameras can be configured to include substantially all of a reference frame attached to a patient during a surgical procedure.

This and other embodiments can include one or more of the following features. The user interface can include a capacitive switch.

This and other embodiments can include one or more of the following features. The display or touch screen can be configured to be detachable from the housing.

This and other embodiments can include one or more of the following features. The display or touch screen can be separate from the housing.

This and other embodiments can include one or more of the following features. The display or touch screen can be configured to communicate wirelessly with the on tool tracking device and a system computer.

This and other embodiments can include one or more of the following features. The touch screen can be configured to set a processing mode or a user preference for the surgical tool.

This and other embodiments can include one or more of the following features. The touch screen can be configured to control aspects of the on tool tracking device.

This and other embodiments can include one or more of the following features. The control can include starting and stopping the recording of the pair of cameras.

This and other embodiments can include one or more of the following features. The on tool tracking device can be configured to wirelessly communicate with and control the surgical tool.

This and other embodiments can include one or more of the following features. A field of view of the first and second cameras can be configured to include substantially all of a reference frame attached to a patient during a surgical procedure.

This and other embodiments can include one or more of the following features. The position of the tool can be determined relative to one or more position markers attached to a patient; and can further include: using an image processor configured to analyze image data from the cameras to identify the one or more position markers and to convert the image data of the one or more position markers to mathematical coordinates relative to a position of the on tool tracking device and hand held surgical instrument.

This and other embodiments can include one or more of the following features. The image processor can be within the on tool tracking device.

This and other embodiments can include one or more of the following features. The image processor can be external to the on tool tracking device.

In general, in one embodiment, a system for performing computer assisted surgery, including a surgical tool having an active element corresponding to the surgical function of the tool, the on tool tracking device can be coupled to the tool using a housing configured to engage with at least a portion of the surgical tool, and a computer having computer readable instructions stored within electronic memory for performing a computer assisted surgical procedure using data at least partially obtained from the on tool tracking device and to provide an output for use during a step of the surgery.

This and other embodiments can include one or more of the following features. The system of the projector can further include one or more of the following: projection capability to project an output on a portion of the patient's anatomy, a surface within the surgical scene, an electronic device, or other object within the projector output range.

This and other embodiments can include one or more of the following features. The computer can be in the housing.

This and other embodiments can include one or more of the following features. The computer can be separated from the on tool tracking device and connected via a wired or a wireless connection.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 11A, 11B, 11C and 11D provide additional information relating to variations of camera angle.

FIGS. 24A, 24B and 24C illustrate a reference frame and its components.

FIGS. 26A, 26B, and 26C illustrate another reference frame embodiment having a flexible linkage joining the components of the frame.

FIG. 26B1a illustrates a flexible coupling in use about the upper and lower mount as shown in FIG. 26B. FIG. 26B1b is an isometric view of the flexible coupling of FIG. 26B1a.

FIG. 26B2a illustrates a flexible coupling in use about the upper and lower mount of FIG. 26B. FIG. 26B2b is an isometric view of the flexible coupling of FIG. 26B2a.

FIGS. 37A-44 relate to various alternative tactile feedback mechanisms along with related kinematic responses and design criteria.

FIG. 37A illustrates a bent form that deflects to move an actuator in response to trigger force.

FIG. 37B illustrates a sliding trapezoid form that will deform and restore its shape in response to trigger force.

FIG. 37C illustrates a rotating reader or encoder used to provide a rotating response to the trigger force.

FIG. 37 D illustrates a frame moving in response to trigger force to depress a shaft into a base where the movement of the shaft may be registered as an indication of trigger force.

FIG. 37 E illustrates a pinned element that may deflect to indicate an amount of trigger force.

FIGS. 39A, 39B and 39C each illustrate a scissor mechanism without a position restoration element (FIG. 39A), with a tension spring as a position restoration element (FIG. 39B) and a compression spring as a position restoration element (FIG. 39C).

FIG. 41 illustrates an embodiment of a scissor mechanism having a surgeon system override capability.

FIG. 42 illustrates a scissor mechanism similar to the schematic mechanism illustrated in FIG. 41.

FIGS. 43 and 44 illustrate operational characteristics of the mechanism of FIG. 42.

FIG. 47 illustrates the tactile feedback mechanism in an expanded state configured to cover the trigger to prevent or attenuate manual pressing of the trigger and FIG. 48 shows the tactile feedback mechanism collapsed to expose the trigger and allow manual control.

FIGS. 53-59B illustrate various OTT module and multiple camera embodiments.

FIGS. 63, 64, 65, and 65B are various flow charts related to various OTT CAS methods.

FIGS. 66A, 66B and 67 relate to various CAS displays.

FIGS. 73A-73F relate to projector registration.

FIGS. 74A-74F illustrate various views of embodiments of an OTT module, a saddle, a modified end cap for a surgical tool, and a surgical tool in various configurations.

FIGS. 76A-76B illustrate two different views of an OTT module engaged with a surgical tool and saddle.

FIGS. 77A-77D illustrate various views of an OTT module and system engaged with a saddle and surgical tool.

FIGS. 78A-78B illustrate views of an OTT module and the components of the OTT module.

FIGS. 79A-79C illustrate various aspects of a housing and housing assembly of an embodiment of an OTT module.

FIGS. 81A-81E illustrate various views of the OTT module of FIGS. 80A-80E engaged with a surgical tool.

FIG. 82A-82B illustrate additional embodiments of surgical tool modules that are configured to engage with a surgical tool without the use of a separate saddle. FIG. 82C illustrates a two-part housing that can snap on to the saddle engaged to the surgical tool.

FIGS. 83A-83D illustrate various portions of an embodiment of an OTT module having a sloped lid.

FIGS. 85A-85E illustrate various views of a lid of an OTT module in accordance with some embodiments.

FIGS. 86A-86H illustrate various aspects of an OTT module lid in accordance with some embodiments.

FIGS. 87A-87F illustrate various views and portions of an OTT module with a sloped lid configuration.

FIGS. 88A-105D illustrate various embodiments of saddles, surgical tool engagement structures, and OTT modules.

FIGS. 108-111A illustrate various embodiments of electrical contacts on surgical tools. FIG. 111B illustrates an embodiment of a saddle.

FIG. 114A illustrate a saddle in accordance with some embodiments. FIG. 114B illustrates an embodiment of an electrical connector.

FIGS. 117A-117D illustrate various views of a housing of an OTT module engaging with a complementary saddle in accordance with some embodiments.

FIGS. 118A-118C illustrate various views of a housing of an OTT module engaging with a complementary saddle in accordance with some embodiments.

FIGS. 119A-119B and 120A-120B illustrate a pivoting latch with a shaped tip for engagement with the housing in accordance with some embodiments.

FIGS. 121-123 illustrate a cam locking device in accordance with some embodiments.

FIGS. 124-126 illustrate various aspects of a pin lock configuration in accordance with some embodiments.

FIG. 135 illustrates a housing in accordance with some embodiments.

FIGS. 136A-136C illustrate an embodiment of a locking mechanism between a housing and saddle in accordance with some embodiments.

FIG. 137 illustrates a release mechanism for use in conjunction with a housing lock embodiment described herein.

FIGS. 140A-140C illustrate various aspects of camera mounts in accordance with some embodiments.

FIGS. 142A-142B and 143A-143C illustrate various embodiments projector arrangements.

FIGS. 147A-147C, 148A-148D, and 149A-149C illustrate examples of the engagement between the lid and housing in accordance with some embodiments.

FIGS. 150A-150F illustrate various attachment regions between housing and lids in accordance with some embodiments.

FIGS. 151A-151G illustrate various embodiments of attachment structures.

FIG. 154 illustrates an embodiment of interlocking contacts.

FIGS. 155A-155D, 156A-156D, 157A-157E, and 158A-158B illustrate various snap fit engagements between lids and corresponding housings in accordance with some embodiments.

FIGS. 160A, 160B, 161, and 162A-162D illustrate various embodiments of touch screen configurations.

FIGS. 163 and 164A-164B illustrate embodiments of OTT modules including vents.

FIGS. 165A-165C, 166A-166B, and 167A-167C illustrate embodiments of cleaning seal tools that can be used with the OTT devices disclosed herein.

FIGS. 180A-191C illustrate various embodiments of battery doors and battery chambers.

DETAILED DESCRIPTION

Figure 1:
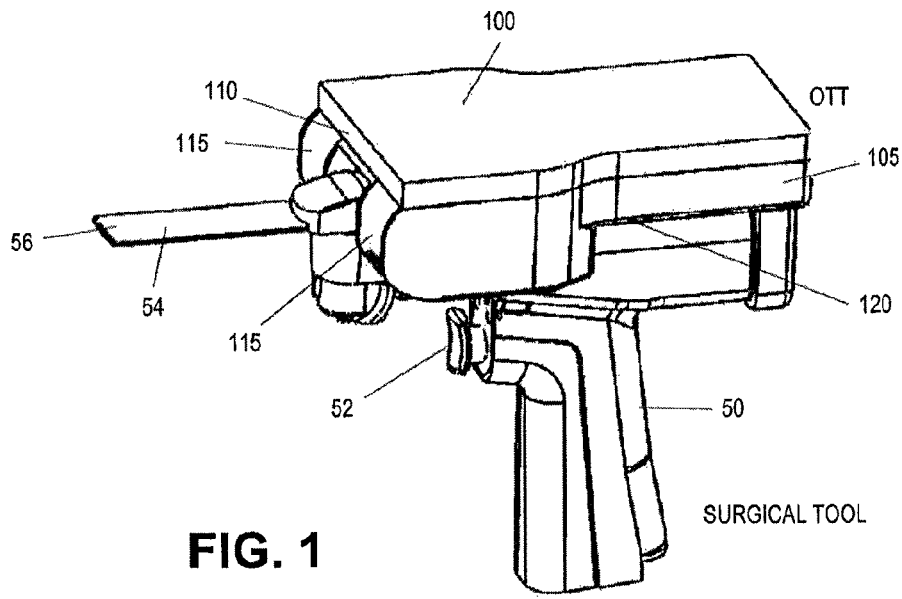
FIG. 1 illustrates an isometric view of an example of an on tool tracking device attached to a surgical instrument.

The present invention is a system for performing computer assisted orthopedic surgery and novel tools for operating that system. The present invention overcomes limitations of current computer assisted surgery systems by optionally combining all elements of computer assisted surgery (tools, displays and tracking) into a single smart instrument. The instrument does not rely on an external navigation system but the tool contains all the tracking equipment on the tool itself in a self-contained assembly. As a result, the overall system is significantly less complicated, less intrusive to the surgeon and easy to integrate into existing practices in orthopedic surgery.

By way of overview, the system is comprised of principal subsystems. The first is the tool itself, which is used to carry a standalone on tool tracking device or modified to contain the subsystems or elements of the subsystems to provide On-Tool Tracking (OTT) functionality. The modifications can be simple, such as an extended chassis to hold the additional components, or complex, such as a modified power system to power the additional subsystems, and/or to stop or control the motor speed or other actuators on the powered tool. The second subsystem is the tracking subsystem, which comprises one or more trackers and one or more tracking elements. The tracker can be a one, two (stereovision) or more cameras that are sensitive to visible light or light from another wavelength. Alternatively, the tracker could be an electromagnetic tracker or other non-camera based system. The tracking element is whatever the tracker tracks. For example, where the tracker is an infrared camera, the tracking element is an infrared LED, or a passive surface reflective of infra-red light emitted from around the camera or elsewhere. Where the tracker is a pair of high-resolution cameras sensitive to visible light, the tracking element could be the specific anatomy of a patient or marks made directly on the anatomy including markers or reference frames. The subsystem can utilize one or more trackers, mounted on the tool in various configurations, to track one or more tracking elements. In one aspect, the tracker(s) (used to track the sensors required to track the tool, the patient and the other relevant objects in order to perform an OTT CAS surgery) are located, at least in part, on-board the surgical tool in a self-contained manner. The navigation system navigates when the tracking subsystem senses and calculates the position (location and orientation/pose) of the tracking element(s) relative to the tool.

The third subsystem is an OTT CAS computer system that contains an appropriate CAS planning software and programming to perform the OTT CAS functions of the implementation of the surgical plan. The surgical plan can be produced and expressed through a variety of means but ultimately contains the locations, orientations, dimensions and other attributes of the resections (e.g. cuts, drill holes, volume of tissue to be removed), intended by the operator, in three-dimensional space. The system can also contain a reference dataset from imaging of the patient's anatomy, such as a computed tomography image (dataset) of a patient's anatomy, and 2D or 3D virtual reconstructed models of the patient's anatomy, or morphed models scaled to fit the patient anatomy as a point of reference. The computer system compiles data from the tracking system and the surgical plan to calculate the relative position of boundaries defining the intended resections by the tool. In some configurations, the computer system can be a wholly separate component, in wireless communication with the other components. In other configurations, the computer system is integrated into the other systems. Together, the tracking system and the computer system can determine if the surgeon's location, orientation and movement of the tool (the surgical path) will produce the desired resection. It is important to note that the computer sub system and the tracking sub system work together to establish the three dimensional space of the surgical site. Elements necessary for the tracking sub-system to function can be located in the computer sub-system or some intermediary mode of transmitting tracking data to the computer sub-system.

The final subsystem is an indicator to provide the surgeon with OTT CAS appropriate outputs related to his position, orientation and movement of the tool, as well as the intended resection, and the deviations (errors) between the two, within a real (or semi real) time OTT CAS step. The indicator can be any variety of means to align/locate the surgical path with the intended resection: a panel of lights that sign directions to correct the surgeon, a speaker with audio instructions, a screen, touchscreen or iPhone or iPad or iPod like device (i.e., a so-called "smartphone") on the OTT equipped tool displaying 3D representation of the tool and the patient with added guidance imagery or a digital projection (e.g., by a pico projector) onto the patient's anatomy of the appropriate location of a resection. The indicator serves to provide an appropriate OTT CAS output to guide the surgeon to make the right resection based on real time (or semi-real time) information.

Looking now to the specific subsystems:

A surgical suite for computer assisted surgery includes a first computer for pre-operative planning use. For example, pre-operative analysis of the patient and selection of various elements and planned alignment of the implant on the modeled anatomy may be performed on the first computer. The suite may also include a second computer, referred to as the OR computer, which is used during a procedure to assist the surgeon and/or control one or more surgical instruments. In addition the suite may include a computer (standalone or collaborating with another computer) mounted on the surgical instrument via an embodiment of an on tool tracking system. Finally, one or more computers are used as dedicated drivers for the communication and medium stage data processing functions interfaced to the cutting instrument tracking system, motor control system, or projection or display system. The first computer is provided in the present instance, but may be omitted in some configurations because the functions of the computer are also implemented on the OR computer, which can be a standalone. Moreover the whole 'pre-surgical planning' may eventually happen instantaneously inside the OR using primarily the OR computer in conjunction with an OTT. Nevertheless, if desired for particular applications, the first computer may be used. The pre-surgical planning and procedure can also be aided by data or active guidance from online web-links. As used herein, the term CAS system or CAS computer refers to those computers or electronic components as provided in any of these combinations to perform CAS function. Furthermore, the micro-processing unit of the system can reside in the on tool tracking instrument. In such a configuration, the computations and user interface can be performed within a computer borne on the surgical tool being used, or in collaboration with the main system computer by wired or wireless communications, and some of which can be done through the sub-system "driver" computers. In collaboration with the main OTT CAS computer by direct wireless communication or indirect through the intermediary driver computers, such system performs error analysis of location of the cutting instrument relative to the ideal cut to be performed, and displays corrective actions and other information on a screen provided as part of the on tool tracker alone or in any combination with an output provided by one or more projectors provided with the OTT for that purpose.

As a result, a surgical suite for OTT CAS may include a tracking/navigation system that allows tracking in real time of the position and orientation in space of several elements, including: (a) the patient's structures, such as the bone or other tissue; (b) the surgical tool, such as the bone saw and/or OTT, which carries the OTT and is controlled by the surgeon based on information from the OR computer or (c) surgeon/assistance specific tools, such as a navigated pointer, registration tools, or other objects as desired. The OR computer or an OTT may also perform some control on the instrument. Based on the location and orientation (pose) of the tool and feedback from an OTT, the system or CAS computer is able to vary the speed of the surgical tool as well as turn the tool off to prevent potential damage. Additionally, the CAS computer may provide variable feedback to a user. The surgical instrument shown in the accompanying description is a surgical saw. It is to be appreciated that many others instruments can be controlled and/or navigated as described herein, such as a drill, reamer, burr, file, broach, scalpel, stylus, or other instrument. Therefore in the following discussion, the OTT enabled CAS system is not limited to the particular tool described, but has application to a wide variety of instruments and procedures.

As discussed further below, one exemplary use of the surgical suite incorporates the use of a virtual model of the portion of the patient upon which a procedure is to be performed. Specifically, prior to a procedure, a three dimensional model of the relevant portion of the patient is reconstructed using CT scans, MRI scans or other techniques. Prior to surgery, the surgeon may view and manipulate the patient model to evaluate the strategy for proceeding with the actual procedure.

One potential methodology uses the patient model as a navigation device during a procedure. For instance, prior to a procedure, the surgeon may analyze the virtual model of a portion of the patient and map out the tissue to be resected during a procedure. The model is then used to guide the surgeon during the actual procedure. Specifically, during the procedure, the on tool tracking device monitors the progress of the procedure. As a result of the OTT CAS processes performed, the progress/results are displayed in real time on the OR computer or on an OTT monitor (e.g. onboard LCD screen) so that the surgeon can see the progress relative to the patient model. Importantly, the surgeon is also provided an OTT projector to provide real type feedback based on OTT CAS processing steps (described in greater detail below).

To provide navigation assistance during an OTT CAS procedure, an on tool tracking device monitors the position of the associated surgical tool within the surgical field. The OTT CAS system may use none, or one or more reference frames including one or more positions sensors or one or more fiducial markers depending upon the requirements of the OTT CAS procedure being undertaken. Any of the above described markers may be utilized in an active or passive configuration. Markers may, optionally, be wired or wireless sensors that are in communication with the system. An active marker emits a signal that is received by the OTT device. In some configurations, the passive markers are (naturally wireless) markers that need not be electrically connected to the OTT CAS system. In general, a passive marker reflects infrared light back to an appropriate sensor on the OTT device. When using passive markers, the surgical field of view is exposed to infrared light that is then reflected back to and received by the OTT, from which the data locations of the passive markers are determined by the OTT CAS, and from such data the location and orientation of the surgical site, and other instruments are computed relative to the OTT and to each other. Some embodiments of an OTT device may be provided with an infrared transmission device and an infrared receiver. The OTT receives emitted light from the active markers and reflected light from the passive markers along with other visual field information reaching the OTT. The OTT CAS system performs calculations and triangulates the three dimensional position and orientation of the tool based on the vision processing of the images including the position of the markers along with other imaging information in the surgical field. Embodiments of the on tool tracking device are operable to detect the position and orientation of the OTT-enabled tool relative to three orthogonal axes. In this way, using information from the OTT device, the OTT CAS system determines the location and orientation of the tool, and then uses that information to determine OTT CAS processing modes and produce appropriate OTT CAS outputs for the user.

As is typical in navigation and other CAS systems, a series of points or surfaces are used to register or correlate the position of the patient's anatomy with the virtual model of the patient. To gather this information, a navigated pointer is used to acquire points at an anatomical landmark or a set of points on a surface within the patient's anatomy. A process referred to as morphing (or kinematic registration) may alternatively be used to register the patient to an approximate (scaled) virtual model of the patient taken from an atlas or database and not originating from actual imaging of that particular patient. During such a process, the surgeon digitizes parts of the patient and some strategic anatomical landmarks. The OTT CAS computer analyzes the data and identifies common anatomical features to thereby identify the location of points on the patient that correspond to particular points on the virtual model.

Accordingly, as set forth above, the on tool tracking device visually monitors the position of several items in real time, including: the position of the associated surgical tool, the position of the patient and the position of items used during a procedure, such as one or more reference frames or one or more markers. Accordingly, the OTT CAS computer processes the OTT CAS data regarding the position of the associated surgical tool, visual field information in OTT image data, the data regarding the position of the patient, and the data regarding the model of the patient. This result of OTT CAS computer processes provide dynamic, real time interactive position and orientation feedback information, which can be viewed by the surgeon on a monitor provided by the OTT device (if provided) or as a displayed output of an OTT projector. Further still, as previously described, prior to a procedure, the surgeon may analyze the patient model and identify the tissue that is to be resected as well as plan for or indicate desired OTT CAS mode for use during an OTT CAS step or during a CAS procedure. This information can then be used during the procedure to guide the surgeon using dynamically adjusted outputs based on the mode of CAS processing and other factors.

The on tool tracking modules described herein can include an OTT module configured to engage with a surgical tool or configured to engage with a saddle that is configured to engage with a surgical tool. The OTT module includes a lid assembly and a housing assembly that can be engaged together to form the OTT module. The housing assembly includes a housing configured to engage with the saddle or the surgical tool along with a Y-board assembly. The Y-board assembly can include a Y-board to support electronics and circuits. A projector can be supported by the Y-board along with a projector support bracket and/or heat sink. The Y-board can include wireless transmission and receiving antennas and circuits. The projector can also include a wireless communication adapter. The Y-board can include a camera bracket to support a camera assembly. The camera assembly can include a camera and imager and optionally a wireless communication circuit. The housing can include a camera lens for each of the two camera assemblies. The housing can include one or more gaskets.

The lid assembly can include a lid/lid housing. The lid can include an opening to support a display or touch screen. The touch screen can be held in place by a cover plate and a placement pad. The lid assembly includes a battery chamber to accommodate a battery. The lid assembly can include a battery door that opens to allow the battery to pass into the battery chamber. A gasket can be used to seal the battery chamber from the external environment. The lid assembly can also include an opening to accommodate the projector output and a projector lens.

The housing can have one or more liners to facilitate engagement with the surgical tool or saddle. The OTT module can also include an electrical connector configured to provide control signals to the surgical tool by contacting electrical contacts on the surgical tool.

The saddle can engage with the surgical tool and include a complementary surface for engagement with the OTT module. The saddle can include an opening to accommodate any electrical connectors on the OTT module.

The surgical tool can have electrical contacts or connectors. The OTT module can have electrical connectors configured to engage with the electrical contacts/connectors on the surgical tool. In some cases the surgical tool can be modified to provide the electrical connectors or to change the location of the electrical connectors to accommodate electrical communication with the OTT module. The end cap of the surgical tool can be modified to have electrical contacts. The end cap assembly can include the modified end cap can, electrical contacts, and a PCB board.

The OTT module can be part of a system including a battery insertion funnel and a cleaning seal tool device. The battery insertion funnel can be used to facilitate putting a non-sterile battery into the OTT module without disrupting the sterile outer surfaces of the OTT module. The cleaning seal tool can have a surface similar to the saddle surface to engage with the OTT module to protect the underside of the OTT housing, and any electrical contacts and vents, from exposure to chemicals during a cleaning process.

FIG. 1 is an isometric view of an on tool tracking device (OTT) 100 arranged for tracking and providing guidance during computer aided surgery using the surgical instrument 50. The OTT 100 has a housing 105 that includes a pair of cameras 115, in an opening for projector output 110. The OTT 100 and also as a housing 105 with a surface 120 adapted and configured to mate with the surgical instrument 50. The surgical instrument 50 includes a trigger 52 for operating a tool 54 having an active element 56. An illustrative embodiment of FIG. 1 the tool 54 is a saw and the active element 56 is the serrated edge of a saw blade at the distal end thereof.

Figure 2:
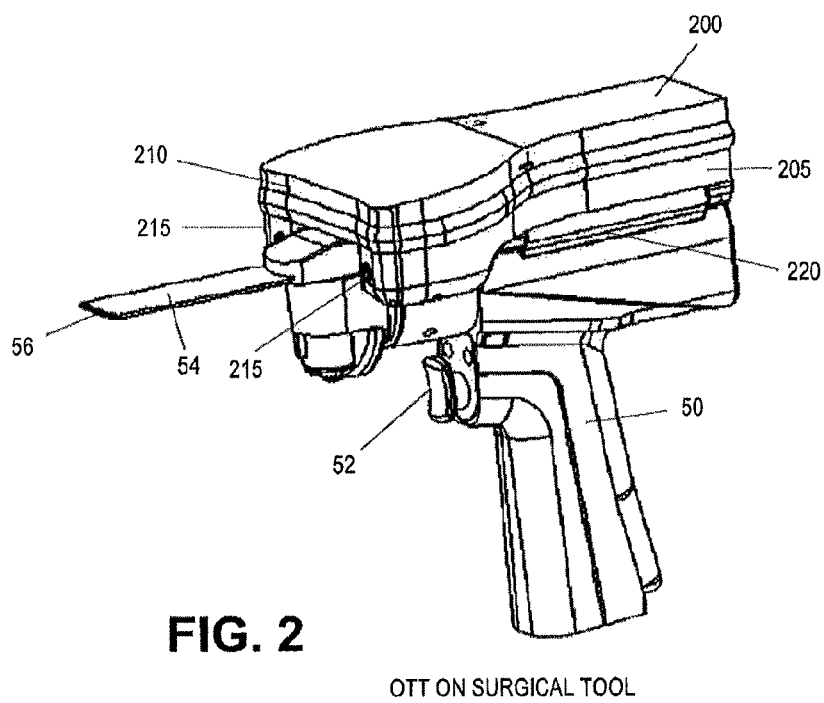
FIG. 2 illustrates an isometric view of an on tool tracking device attached to a surgical instrument.

FIG. 2 is an isometric view of an on tool tracking device (OTT) 200 and arranged for tracking and providing guidance during computer aided surgery using the surgical instrument 50. The OTT 200 has a housing 205 that includes a pair of cameras 215, in an opening for projector output 210. The OTT 200 and also as a housing 205 with a surface 220 adapted and configured to mate with the surgical instrument 50. The surgical instrument 50 includes a trigger 52 for operating a tool 54 having an active element 56. An illustrative embodiment of FIG. 2 the tool 54 is a saw and the active element 56 is the serrated edge of the distal end thereof.

Figure 3:
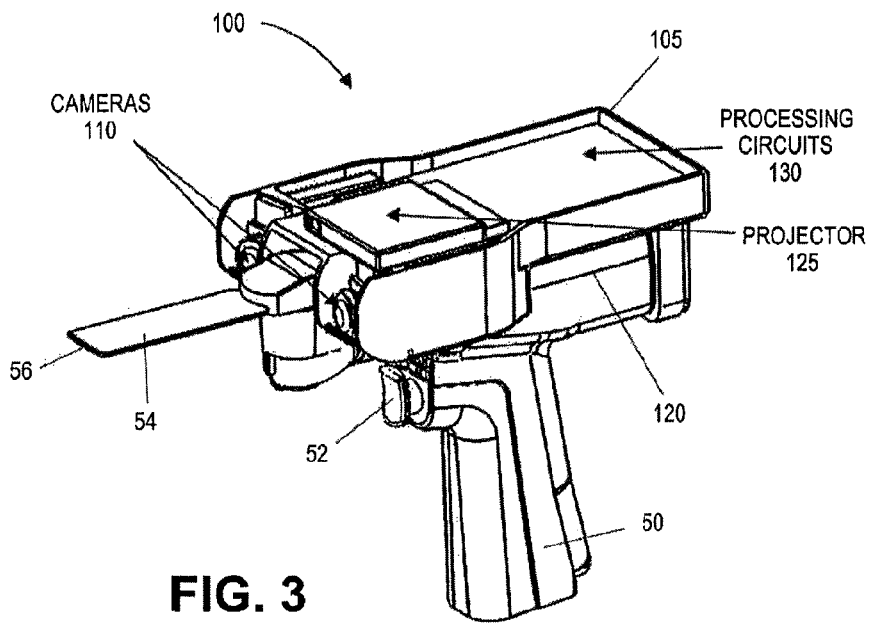
FIG. 3 illustrates an isometric view of the on tool tracking device of FIG. 1 with a cover removed to show internal components.
Figure 4:
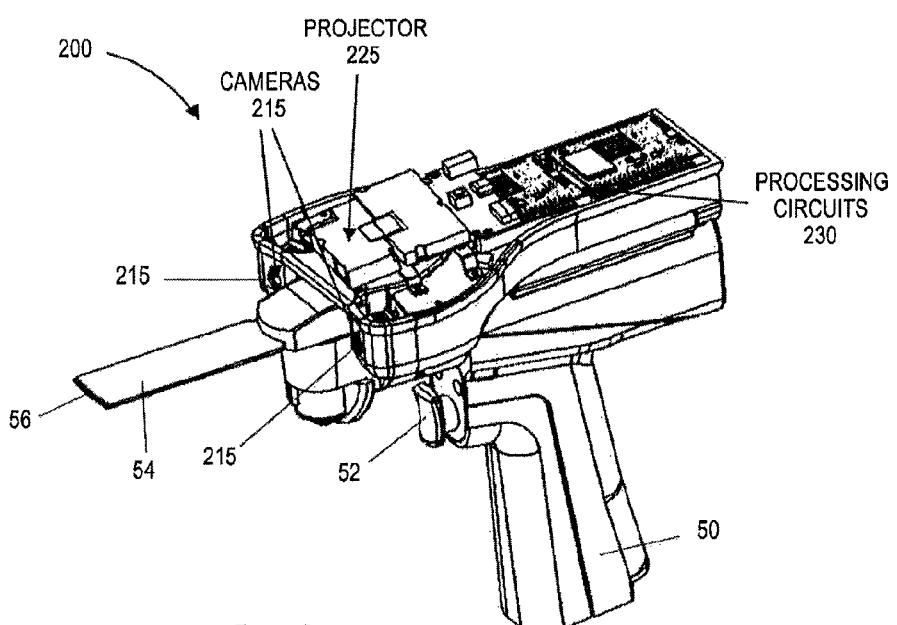
FIG. 4 illustrates an isometric view of the on tool tracking device of FIG. 2 with a cover removed to show internal components.

FIGS. 3 and 4 are isometric views of the on tool tracking devices of FIGS. 1 and 2 with the top cover of the housings removed. In the view of FIG. 3, the interior of the housing 105 exposed in shows the placement of the processing circuits 130, projector 125 and cameras 115. The projector 125 is illustrated in this embodiment in the position above a plane containing the cameras 115, but tilted to make the output of the projector 125 more symmetrically above and below the plane of the cameras 110. The projector can be tilted further or less vertically and some horizontally if needed in special situations, to optimize the image it projects with respects to various criteria such as occlusion (e.g., by the saw blade in FIGS. 3 and 4, or drill bits) or specifics of the nature, shape, reflection and other aspects of the anatomy or surface upon which the image is projected onto. In the view of FIG. 4, the exposed interior of the housing 205 shows the placement of the processing circuits 230, projector 225 and cameras 215. The output 210 of the projector 225 is illustrated in this embodiment in a position above that, and at an acute angle with a plane containing the cameras 215.

Figure 5:
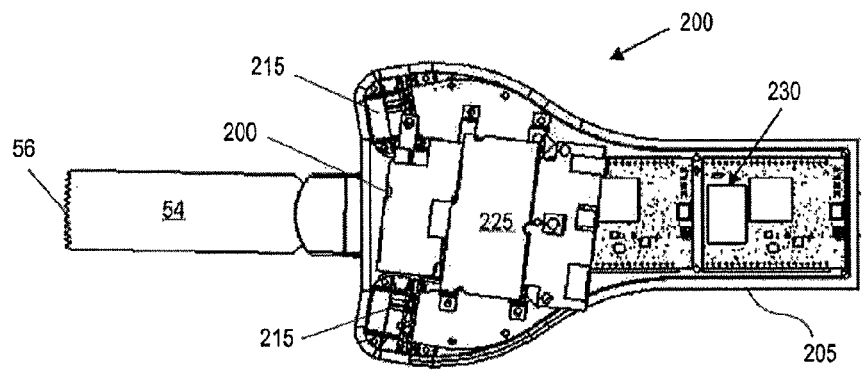
FIG. 5 illustrates a top down view of the on tool tracking device of FIG. 4
Figure 6:
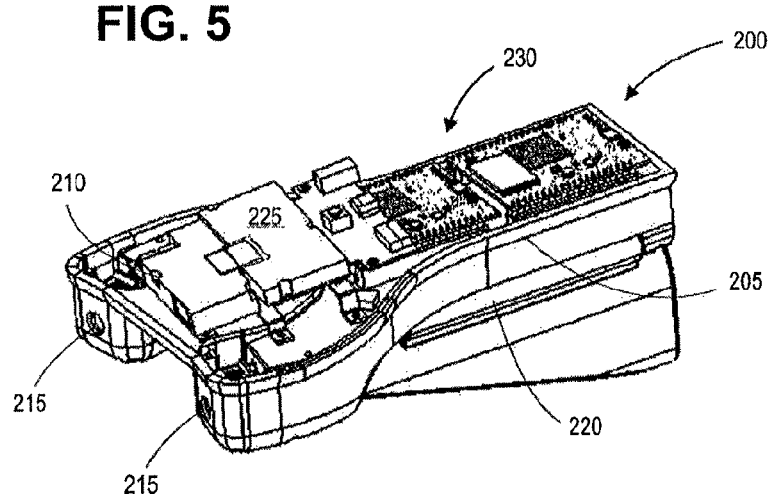
FIG. 6 illustrates an isometric view of the on tool tracking device of FIG. 5 separated from the surgical tool.
Figure 7:
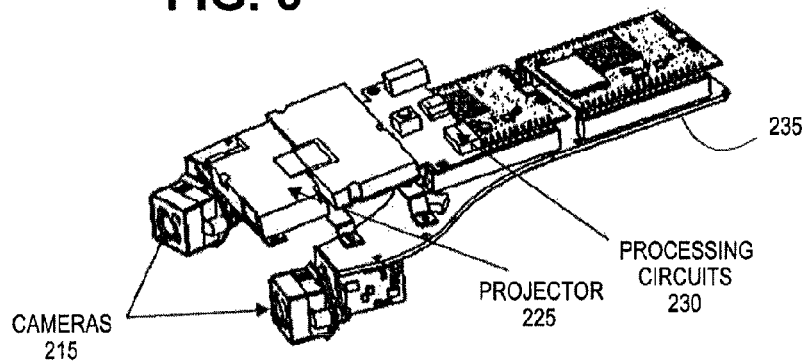
FIG. 7 illustrates electronics package and control circuitry visible in FIGS. 5 and 6 but in this view is removed from the OTT housing.

FIGS. 5, 6, and 7 represent one top down, and two isometric views of the on tool tracker 200. In the top down view of the on tool tracker shown in FIG. 4 the orientation and arrangement of the electronic components is clearly visible. As a result of the type of projector 225 used in this configuration, the projector has been positioned within the housing 205 at an angle and, as shown in FIG. 6 on a slightly inclined surface. In one embodiment, either or both of the cameras or the projector of an on tool tracking device may be positioned in any orientation and the result of that orientation to the operation of the respective device is then compensated for in other ways as described herein. In this way, various different OTT electronic circuits and component designs are possible since the slight physical misalignments may be adjusted for using software techniques as described herein. FIG. 7 illustrates an isometric view of the electronic components of the on tool tracker 200 separated from the housing 205. This figure illustrates one embodiment of a quote one piece" OTT electronics package having cameras 215, projector 225 and associated system and processing electronics 230 on a single board 235 for placement within the housing 205.

Figure 8A:
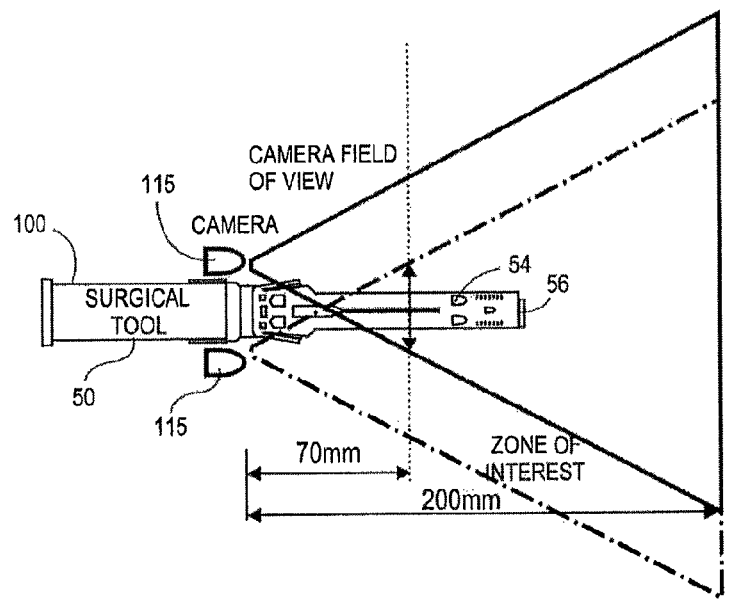
FIGS. 8A, 8B, 9, and 10 provide graphical information relating to the changes in camera field based on camera angle in some OTT device configurations.
Figure 8B:
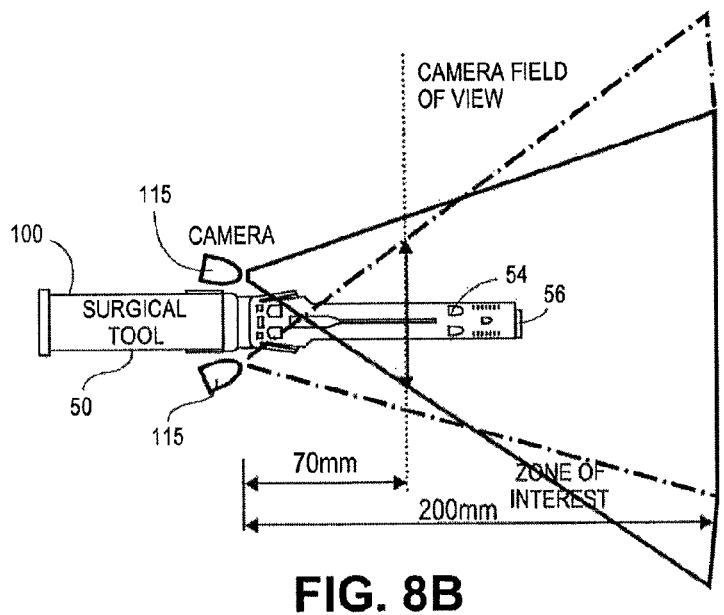
Figure 9:
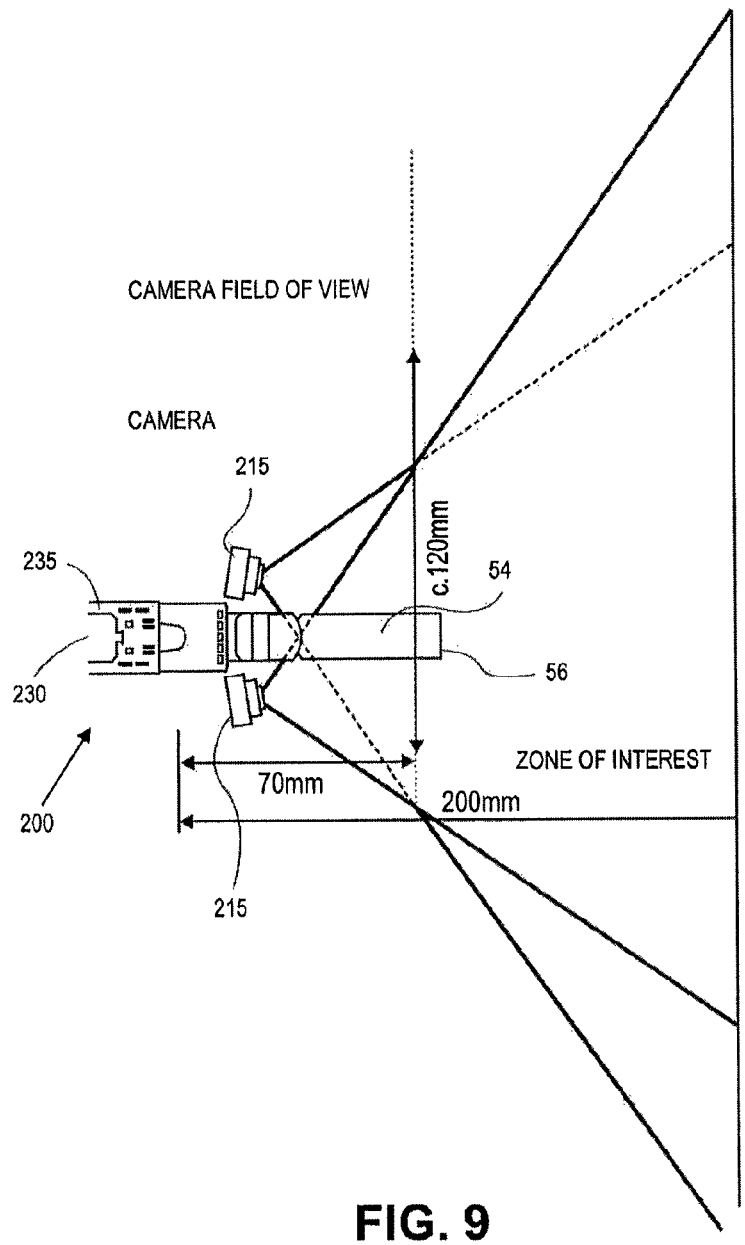
Figure 10:
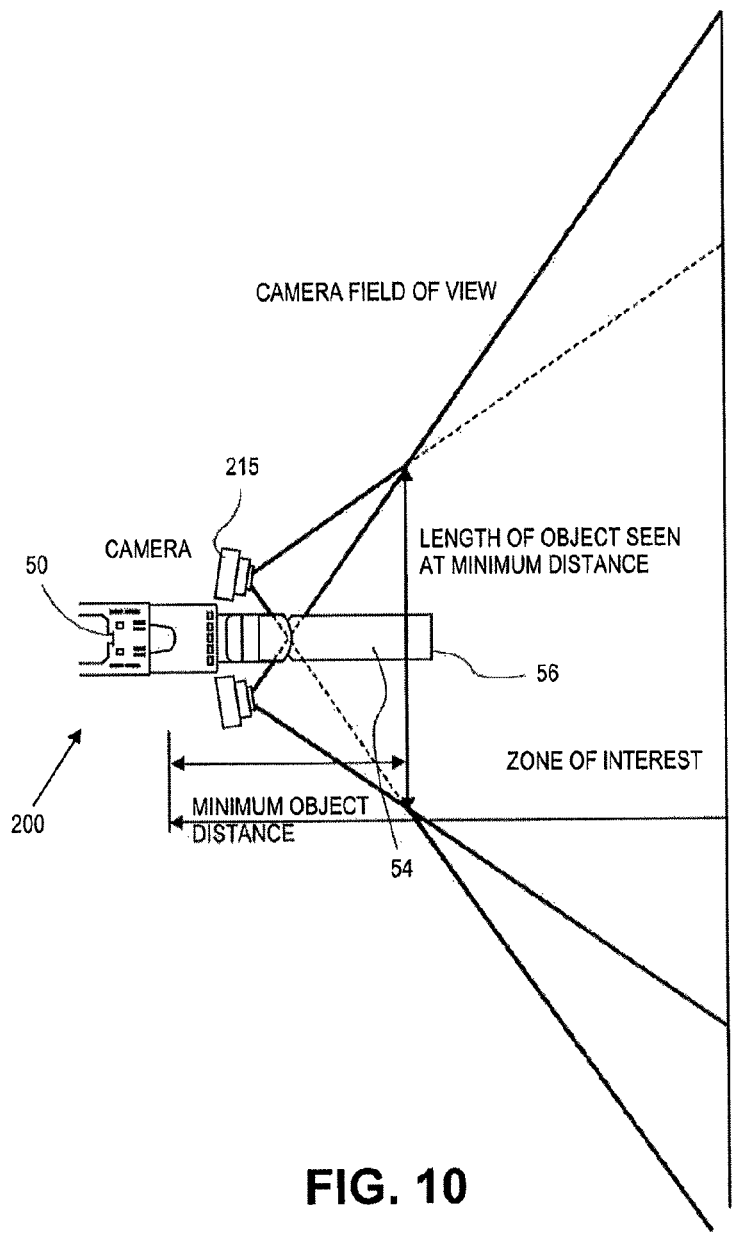

FIGS. 8A, 8B, 9 and 10 all illustrate the result on camera field of view for various angle orientations for the cameras included within an on tool tracking device. The cameras 115 in FIG. 8A are oriented in nearly parallel arrangement with regard to one another and the axis of the surgical tool 54. After accounting for blockage caused by other components, this configuration provides a camera field of view ranging from about 70 mm to about 200 mm. In other embodiments, the camera systems of an exemplary OTT device may operate in a camera field of view ranging from about 50 mm to about 250 mm. It is to be appreciated that the camera field of view may be physically or electronically altered depending upon the desired field of view needed for the particular computer aided surgery procedure that the OTT device will be used to perform.

Figure 11A:
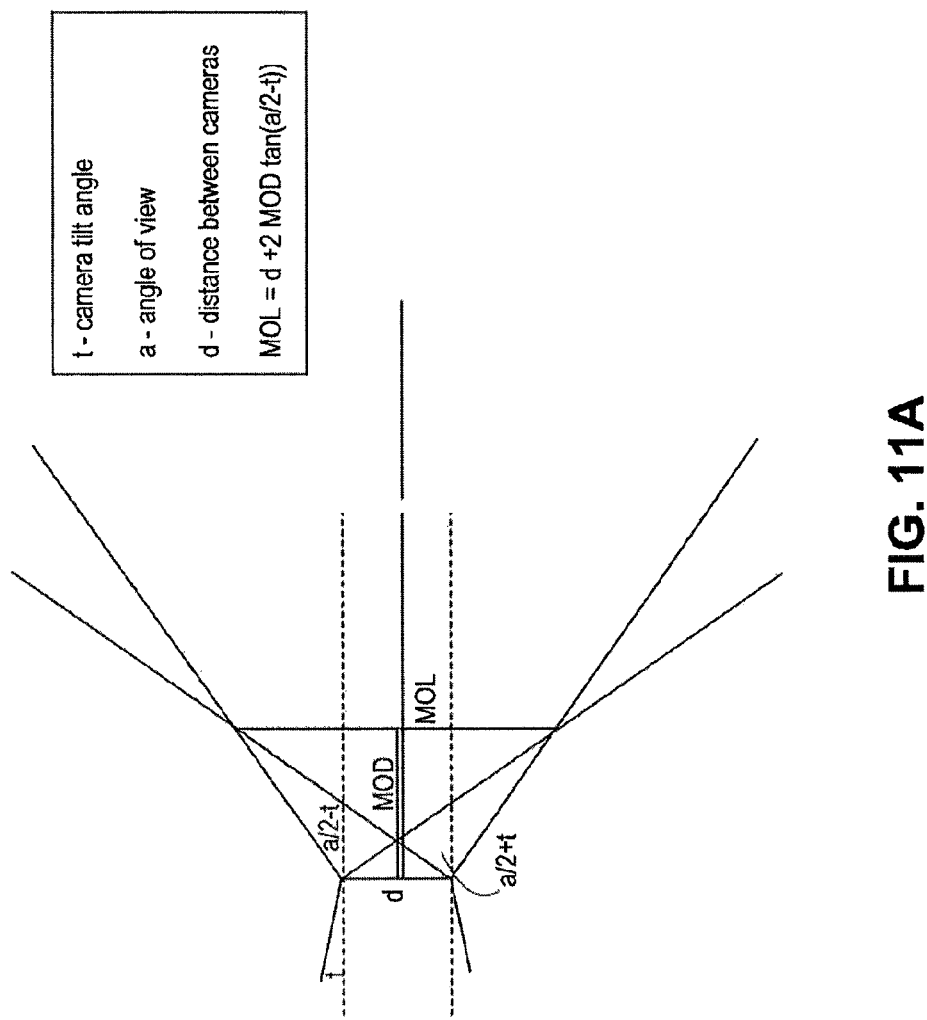
Figure 11C:
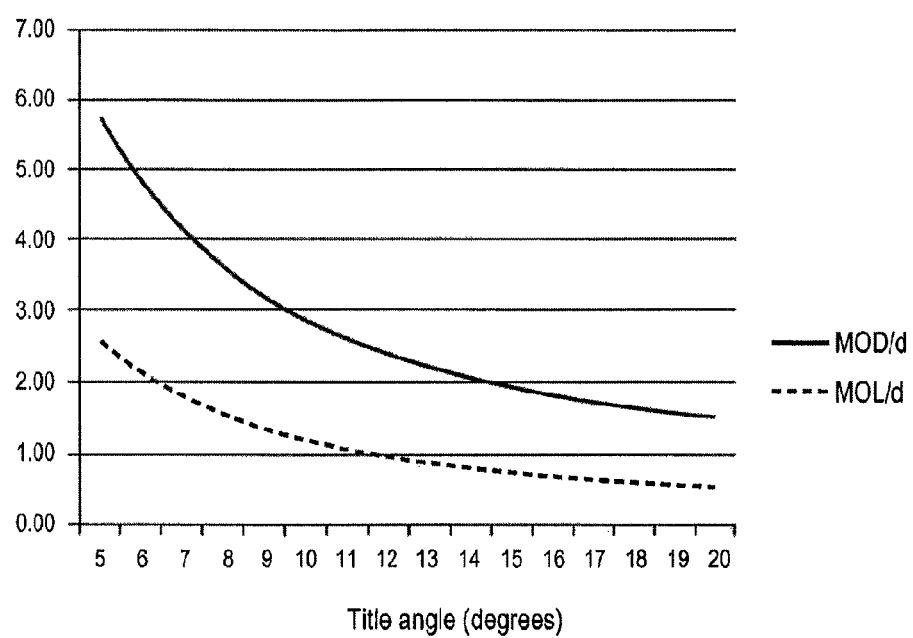
Figure 11D:
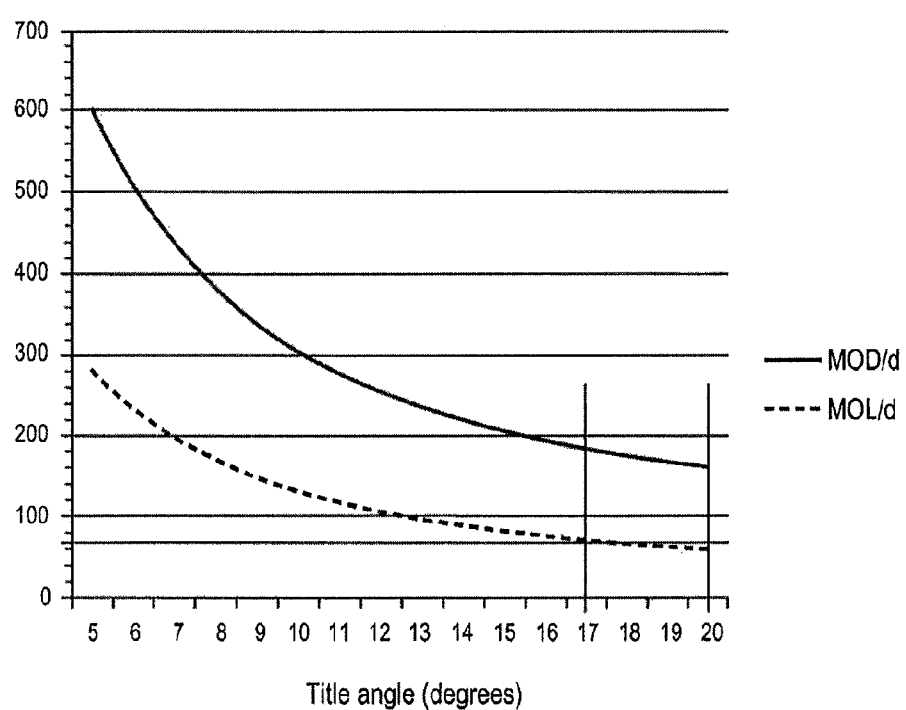

In contrast to the nearly parallel arrangement of the cameras in FIG. 8A, FIGS. 8B, 9 and 10 each demonstrate the result of different camera tilt angles and the resulting alteration of the camera field of view. The relationship of OTT camera positioning and tilt angle and their relationship to the angle of view, minimum object distance and maximum object length are better appreciated with reference to FIGS. 11A, 11B, 11C and 11D. FIG. 11A illustrates the geometric set up and formula for making the calculations used to produce the chart in FIG. 11B that relates tilt angle in degrees to a number of vision field factors. The data from this chart related to tilt angle is reproduced in the graphs shown in FIGS. 11C and 11D. The optical field information presented in these figures is useful in the design and optimization of camera positioning in some of the various embodiments of the OTT devices described herein.

Figure 12A:
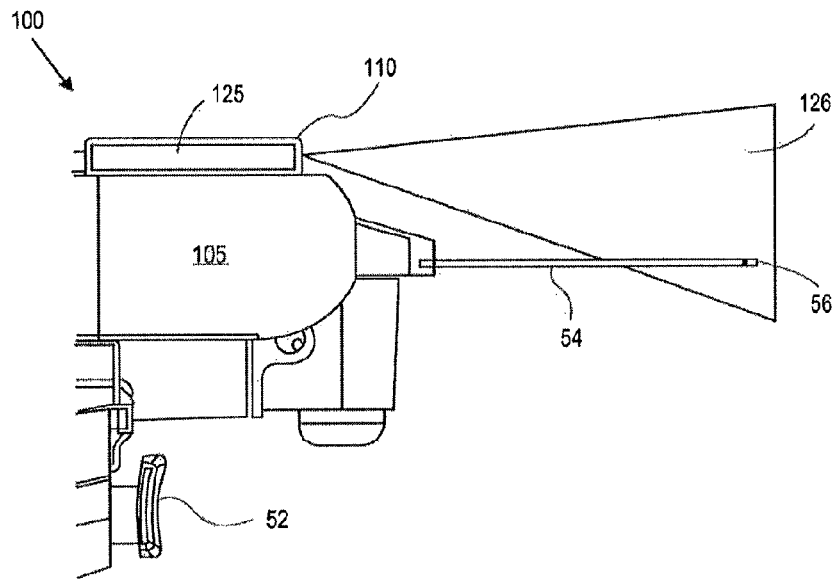
FIGS. 12A and 13A provide side and isometric views respectively of a projector used with an on tool tracking device.
Figure 12B:
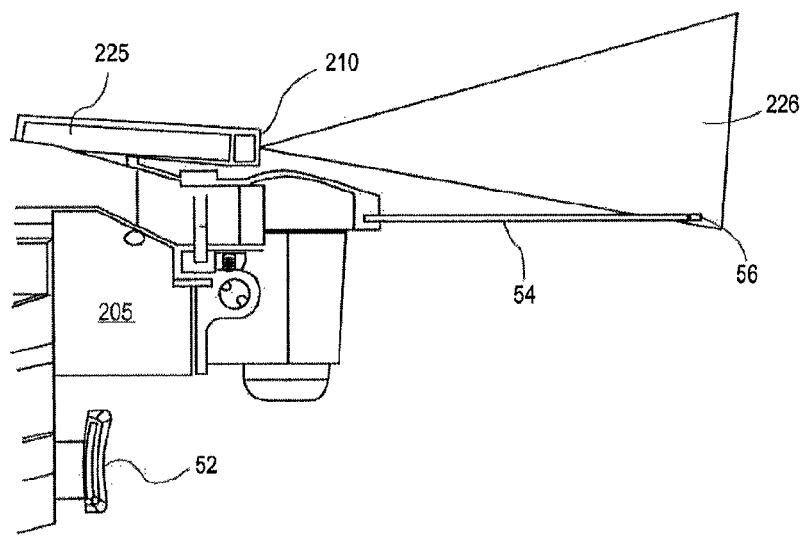
FIGS. 12B, 13B and 13C provide side, isometric and top views respectively of a projector in an angled orientation in use with an on tool tracking device.
Figure 13A:
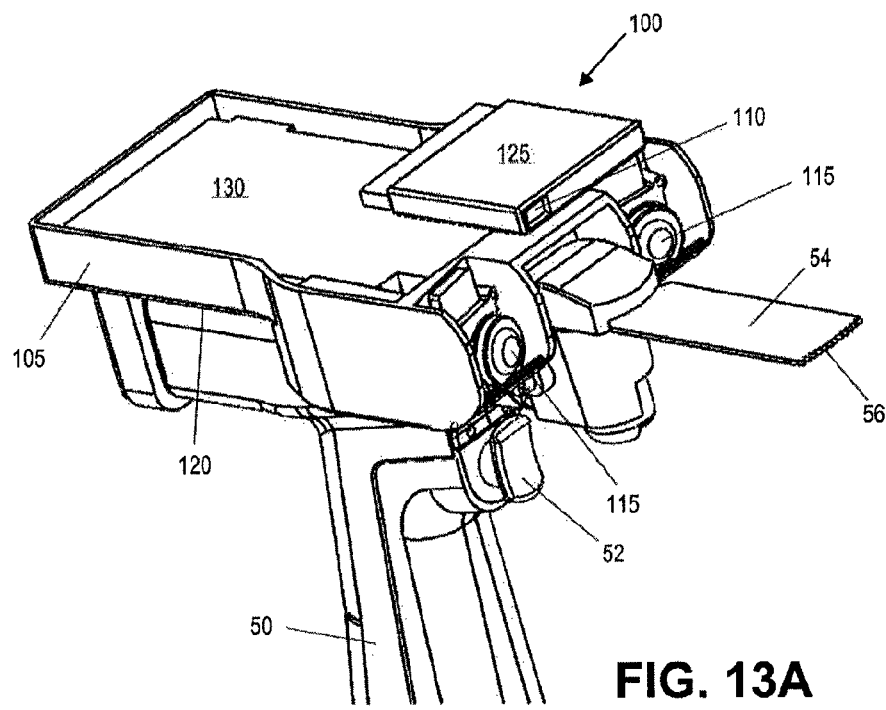
Figure 13B:
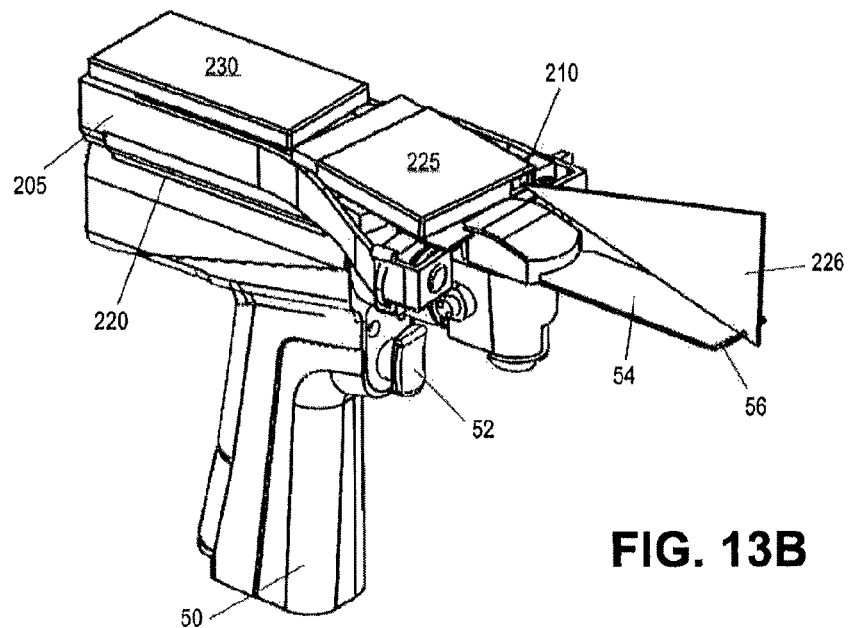
Figure 13C:
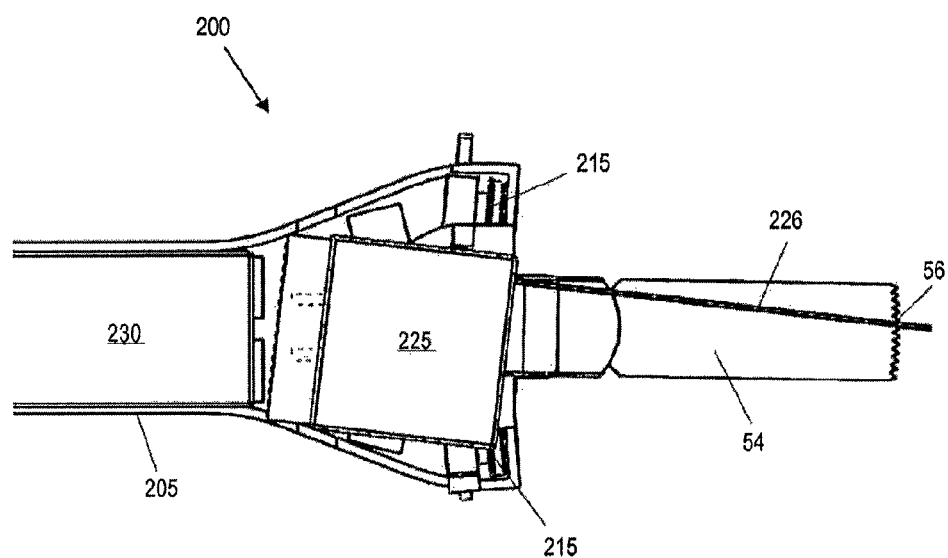

Additional aspects of the projector used with the various OTT embodiments may be appreciated for reference to FIGS. 12A, 12 B, 13A, 13B, and 13C. The impact on projector output based upon projector positioning within the OTT housing is demonstrated by a comparison between FIG. 12A and FIG. 12B. The projector 125 appears to be in a nearly planar relationship relative to the tool 54 as shown in both FIGS. 12A and 13A. However, notice how a portion of the projector output 126 extends beyond and below the tool (in this case saw blade) distal end 56. In contrast, the projector 225 is positioned at an acute angle in relation to the tool 54. Additionally, the projector 210 output is off to one side when compared to its relative position between the cameras 215. However, the projector output 226 is mostly above the blade 54 and crosses only at the distal end 56. Additional aspects of the projector output 226 are apparent upon review of the views in FIGS. 13A and 13B. It is to be appreciated that the projector outputs, projector size and orientations described in these embodiments is not limiting to all OTT device embodiments. A suitable OTT projector may be configured in a number of satisfactory ways and placement within the OTT housing, and may be adjusted based on package size of a desired projector. As is clearly illustrated by the sample outputs of the projector 225, many different projector sizes, orientations and angular relationships may be used and still be effectively operated to meet the projector requirements of the OTT CAS processing system. In other words, a wide variety of projector types, output locations and packaging may be used and still remain within the various embodiments of the OTT devices described herein.

Embodiments of the OTT device of the present invention are provided with a variety of imaging, projector and electronic components depending upon the specific operational characteristics desired for a particular OTT CAS system. The illustrative embodiments that follow are provided in order that the wide variety of characteristics and design factors may be appreciated for this part of the OTT CAS system.

Figure 14A:
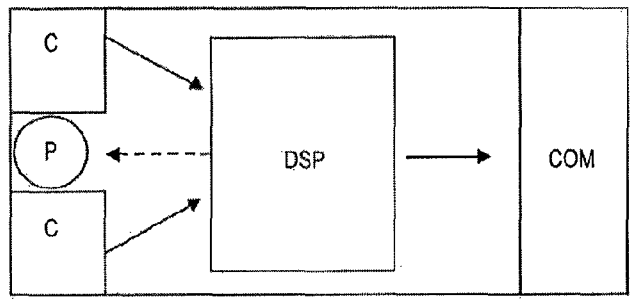
FIGS. 14A, 14B, 15A, and 15B each illustrate schematic views of several different electronic component configurations used by some on tool tracking device embodiments.

FIG. 14A illustrates a schematic of an embodiment of an OTT device. In this illustrated embodiment, there is provided

- Camera/dsp/processing (eg. NaturalPoint Optitrak SL-V120range)
- Computer: PC—Windows 2000/XP/Vista/7; 1.5 GHz Processor; 256 MB of RAM; 5 MB of free hard disk space; USB 2.0 Hi-Speed port (minimum, faster is better)
- COM: Wireless Communication (eg. USB Port Replicator with Wireless USB support)
- Projector: (Laser Pico Projector type)

that are arranged within the OTT housing as shown in the view. This embodiment makes use of what is known as 'smart cameras'—cameras that have the capability of performing localized image processing. This processing can be programmable usually through Field Programmable Gate Arrays (FPGAs). The configuration of the components in this specific embodiment are utilized to provide image processing that occurs both on the OTT devices and on a OTT CAS computer. For example, DSP on the OTT device detects and processes marker data before transferring it to the OTT CAS computer. The configuration greatly reduces processing power required on the host computer while also minimizing the data needed to transmit. It is to be appreciated that the schematic view, while useful primarily to show the type of imaging, data processing and general computer processing capabilities of a particular OTT device or as between an OTT device and a OTT CAS computer, or as between an OTT device and one or more intermediary device driver computers, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an OTT CAS computer (if used) will vary depending upon the specific parameters and considerations of a particular OTT CAS procedure, mode or system utilized.

Figure 14B:
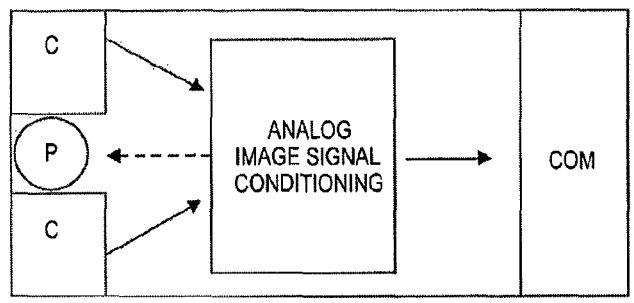

FIG. 14B illustrates a schematic of an embodiment of an OTT device. In this illustrated embodiment, there is provided

- Camera: Analog camera wired or wireless; eg FPV wireless camera
- DSP: uCFG Microcontroller Frame Grabber. This is connected to the PC PCI bus and becomes part of the PC.
- Computer: Computer: PC—Windows 2000/XP/Vista/7; 1.5 GHz Processor; 256 MB of RAM; 5 MB of free hard disk space; USB 2.0 Hi-Speed port (minimum, faster is better)
- COM: Hardwiring or Analog wireless transmitter
- Projector: Microvision's SHOWWX Laser Pico Projector that are arranged within the OTT housing as shown in the view. The configuration of the components in this specific embodiment are utilized to provide use of low cost commodity cameras where no image processing for tracking is performed onboard the OTT and the image signal is captured by a dedicated frame grabber that is part of the PC. The frame grabber accepts the captured image and deposits it into PC memory without any overhead processing by the PC. This embodiment results in a smaller, lighter and lower cost OTT device.

It is to be appreciated that the schematic view, while useful primarily to show the type of imaging, data processing and general computer processing capabilities of a particular OTT device or as between an OTT device and a OTT CAS computer or via one or more intermediary device driver computers, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an OTT CAS computer (if used) will vary depending upon the specific parameters and considerations of a particular OTT CAS procedure, mode or system utilized.

Figure 15A:
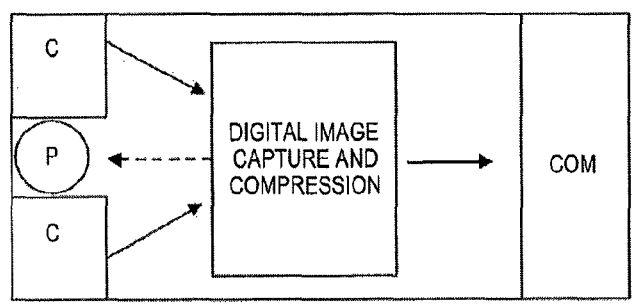

FIG. 15A illustrates a schematic of an embodiment of an OTT device. This embodiment utilizes commodity USB cameras with incorporated electronic circuitry that captures the image from the camera and conditions it to be USB compatible. This output is compressed and then transmitted through wires or wirelessly without further tracking related processing.

In this illustrated embodiment, there is provided

- Camera: (e.g., miniature webcam)
- Computer: (e.g., Dell Precision R5500 Rack Workstation)
- COM: [e.g., Carambola 8 devices Core, or DTW-200D (CDMA2000 1×) and DTW-500D (EVDO Rev A)]
- Miniature Projector: (e.g., Microvision's SHOWWX Laser Pico Projector)

that are arranged as shown in the view. The configuration of the components in this specific embodiment are utilized to provide a modular solution for providing the electronic OTT components. This embodiment uses commodity low cost cameras and allows the cameras to be used in a modular form where they can be changed or upgraded to reflect advances in technology without disrupting the OTT or the ground based systems.

There is no need to use an on-tool DSP if the OTT CAS or intermediary driver computer is optimized for DSP. This embodiment makes it possible to use any of the commercially available image processing libraries. For example, modern image processing software routines from open source or commercial libraries take only about 1 ms to process blobs (bone reference frame LEDs) and compute their centroids. Images can therefore be sent directly from the OTT tool to the OTT CAS Computer to be processed. It is important that the COM will need to be selected to handle higher bandwidth when compared to other embodiments. Similarly, the intermediary driver or OTT CAS Computer will need to be selected to handle more burdensome computation.

It is to be appreciated that the schematic view, while useful primarily to show the type of imaging, data processing and general computer processing capabilities of a particular OTT device or as between an OTT device and an intermediary driver or an OTT CAS computer, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an intermediary driver (if used) or OTT CAS computer (if used) will vary depending upon the specific parameters and considerations of a particular OTT CAS procedure, mode or system utilized.

Figure 15B:
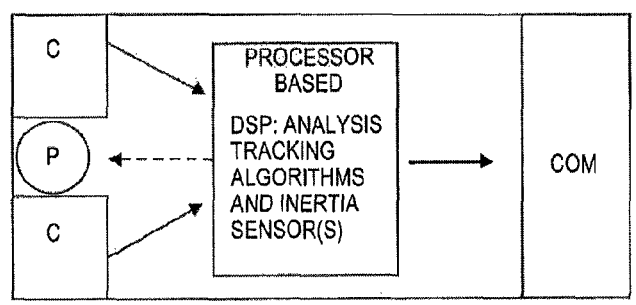

FIG. 15B illustrates a schematic of an embodiment of an OTT device. In this illustrated embodiment, there is provided Camera: Smart camera as in FIG. 15A or USB camera as in FIG. 15C Inertia Sensors: (e.g., Bosch SMB380, Freescale PMMA7660, Kionix KXSD9)

Onboard processor: (e.g., ARM processor)

Computer: [e.g., PC—Windows 2000/XP/Vista/7; 1.5 GHz Processor; 256 MB of RAM; 5 MB of free hard disk space; USB 2.0 or USB 3.0 Hi-Speed port (minimum, faster is better)]

COM: (Standard IEEE 802.11 communications protocol or similar protocol for communication between the OTT borne processor and the ground station intermediary driver PC or OTT CAS PC.

Projector: (e.g., Microvision's SHOWWX Laser Pico Projector)

that are arranged as shown in the view. The configuration of the components in this specific embodiment are utilized to provide an embodiment that performs complex processing onboard the OTT device to accomplish most of the body tracking as needed for purposes of OTT CAS procedures. The device is a complete stand-alone tracking device. The OTT device further contains one or more inertia sensors. DSP involves the use of Inertia sensors to predict the location of the fiducials in the 'next frame'. As a result, the computational burden on the DSP on the OTT device is minimized.

It is to be appreciated that the schematic view, while useful primarily to show the type of imaging, data processing and general computer processing capabilities of a particular OTT device or as between an OTT device and an intermediary driver or OTT CAS computer, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and directly to an OTT CAS computer (if used) or via an intermediary driver computer will vary depending upon the specific parameters and considerations of a particular OTT CAS procedure, mode or system utilized.

In addition to the above described details and specific embodiments, it is to be appreciated that alternative embodiments of an OTT device may have electronic components including components with processing capabilities as well as software and firmware and electronic instructions to provide one or more of the following exemplary types of OTT CAS data in accordance with the OTT CAS processing methods, modes and algorithms described herein:

Receive and process visual and IR spectrum image data

Determining coordinates of the centroid of each of the markers within image frame Determining the sizes of all markers within an image frame Reporting the size and the coordinates of one or more fiducials Sub-pixel analysis to determine the location of the centroid within an image frame, a marker placement or selected marker placements Variable and controllable frame rate from 10 to 60 frames per second based on input from central computer or internal instructions or in response to an OTT CAS processing mode adaptation The inventive on tool tracking devices 100/200 illustrated and described in FIGS. 1-15B and FIGS. 47-52B may also include, for examples, one or more additional cameras, different types of camera functionality, as well as sensors that may be employed by an OTT CAS system as described herein and in FIGS. 31A-36, 63, 64 and 65. Various different OTT configurations will be described with reference to FIGS. 53-63A and 63B.

Figure 53:
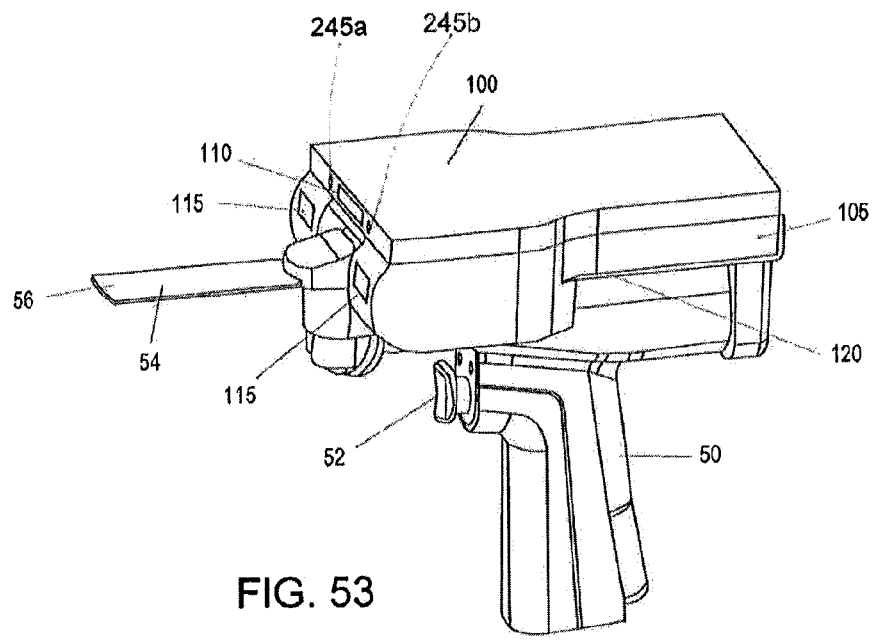

FIG. 53 is an isometric view of the on tool tracking device 100 mounted on the surgical tool 50. The embodiment of the on tool tracking device 100 illustrated in FIG. 53 a modified housing 105 and on-board electronics to include a pair of near field stereoscopic cameras 245a, 245b. In this embodiment the cameras 245a, 245b are mounted adjacent to the projector output or opening 110 near the top of the OTT housing 105. As described herein, the cameras 115 may be used to provide a wide field of view. The cameras 115 are mounted at the midpoint of the housing 105. The wide view stereoscopic cameras 115 are just above the plane that contains the surgical tool 54 that is being tracked by the OTT CAS system. In one aspect, the cameras or wide view cameras 115 are on opposite sides of the tool 54 under OTT CAS guidance. The OTT CAS system operation is similar to that described below in FIGS. 31A to 36 and FIGS. 63, 65 and 65 with the use of the additional camera inputs and data available for OTT CAS methods and techniques. The OTT CAS system and methods of performing freehand OTT CAS may be adapted to receive inputs from one or sets of cameras 115, 245a, 245b or from one or more of cameras 115, 245a, 245b in any combination. Furthermore, any camera of those illustrated may be used for tracking, display, measurement or guidance alone or in combination with the projector 225 in one or modes of operation under control of the OTT CAS system described herein.

Figure 54:
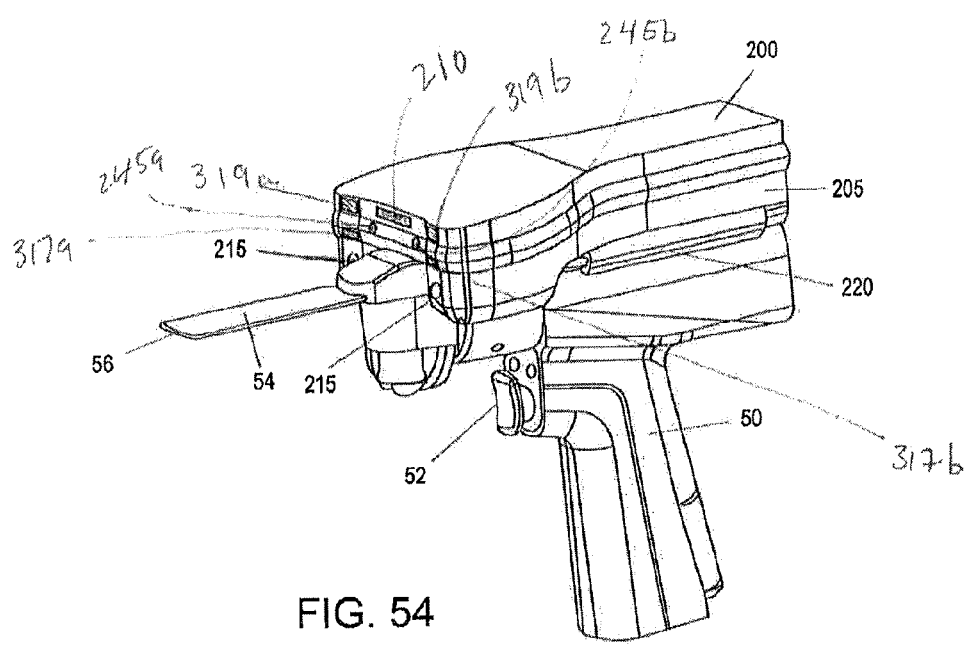

FIG. 54 is an isometric view of the on tool tracking device 200 mounted on the surgical tool 50. As described herein, the cameras 215 are mounted at the midpoint of the housing 205 used to provide a wide field of view. In this alternative embodiment of the on tool tracking device illustrated in FIG. 54, the housing 205 and on-board electronics are modified to include a pair of near field stereoscopic cameras 245a, 245b as in FIG. 53 along with additional cameras 317a, 317b, 319a, and 319b. The additional cameras may provide, for example, an additional wide field view (i.e., wider than that provide by cameras 215) or be configured as IR cameras. As with FIG. 53 the cameras 245a, 245b are mounted adjacent to the projector output or opening 110 near the top of the OTT housing 205. Cameras 319a and 319b are shown mounted adjacent to the projector output or opening 210 near the top of the OTT housing 205. The wide view stereoscopic cameras 215 are just above the plane that contains the surgical tool 54 that is being tracked by the OTT CAS system. Additional cameras 317a, 317b are provided between the cameras 245a, 245b and the cameras 215. In one aspect, the cameras or wide view cameras 215 are on opposite sides of the tool 54 under OTT CAS guidance. The OTT CAS system operation is similar to that described below in FIGS. 31A to 36 and FIGS. 63, 65 and 65 with the use of the additional camera inputs and data available for OTT CAS methods and techniques. The OTT CAS system and methods of performing freehand OTT CAS may be adapted to receive inputs from one or sets of cameras 215, 245a, 245b, 317a, 317b, 319a or 319b or from one or more of cameras 215, 245a, 245b, 317a, 317b, 319a or 319b in any combination. Furthermore, any camera of those illustrated may be used for tracking, display, measurement or guidance alone or in combination with the projector 225 in one or modes of operation under direct or indirect (via intermediary driver computer) control of the OTT CAS system described herein.

Figure 55:
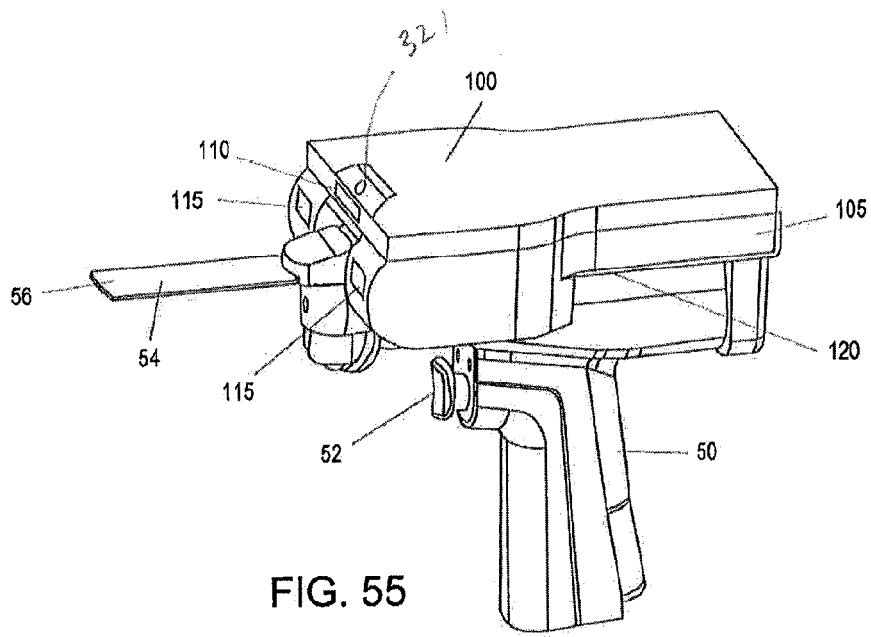

FIG. 55 is an isometric view of the on tool tracking device 100 mounted on the surgical tool 50. The embodiment of the on tool tracking device 100 illustrated in FIG. 55 has a modified housing 105 and on-board electronics to include a single, centrally located camera 321 located above the projector output 110. In this embodiment the camera 321 is mounted adjacent to the projector output or opening 110 build into the top of the OTT housing 105. As described herein, the camera 321 may be used to provide a variety of different fields of view either through mechanical or electronic lens control alone or in combination with software based imaging processing. As illustrated, the camera 321 is mounted at or near the central axis of the tool 54 with a clear view of the active element 56 or other tracking point on the tool 50. The stereoscopic cameras 115 are also shown just above the plane that contains the surgical tool 54 that is being tracked by the OTT CAS system. In one aspect, the cameras 115 are on opposite sides of the tool 54 under OTT CAS guidance. The OTT CAS system operation is similar to that described below in FIGS. 31A to 36 and FIGS. 63, 65 and 65 with the use of the additional camera input and data available for OTT CAS methods and techniques. The OTT CAS system and methods of performing freehand OTT CAS may be adapted to receive inputs from one or sets of cameras 115 or 321 or from one or more of cameras 115 or 321 in any combination. Furthermore, any camera of those illustrated may be used for tracking, display, measurement or guidance alone or in combination with the projector 225 in one or more modes of operation under direct or indirect control of the OTT CAS system described herein.

Figure 56:
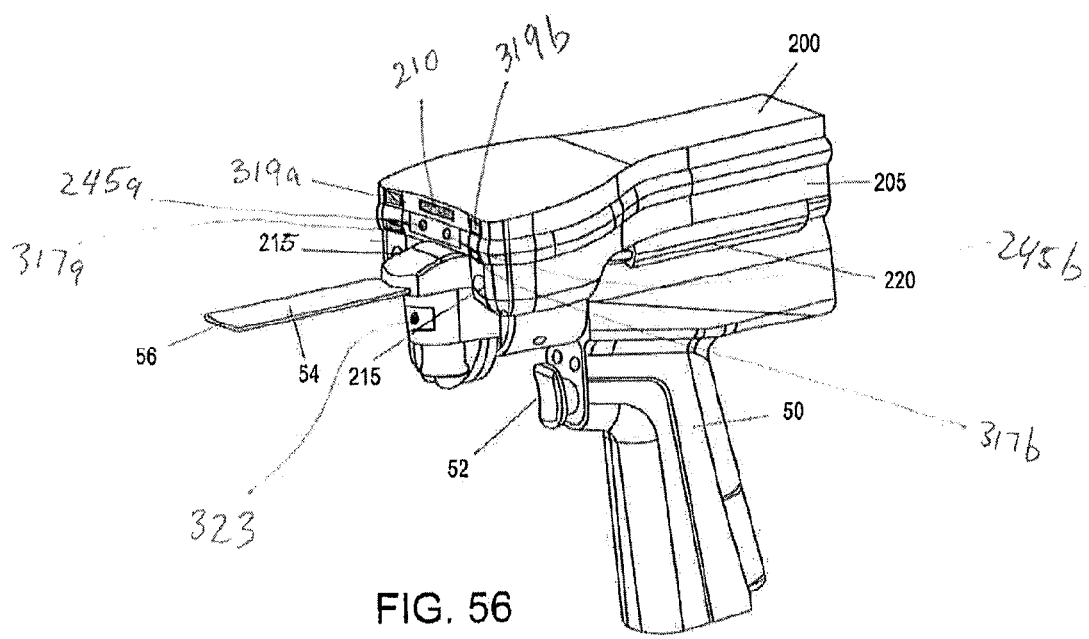

FIG. 56 is an isometric view of the on tool tracking device 200 mounted on the surgical tool 50. This OTT device embodiment is similar to that of FIG. 54 with an addition single camera provided as in FIG. 55. In contrast to FIG. 55, the single camera 323 in FIG. 56 is provided below the tool 53 and active element 56 being tracked under an OTT CAS system. One advantage of the location of camera 323 is that some tools 54—such as the illustrated saw—may block portions of the views available to other camera. In those instances, the input from camera 323 may be used to augment other imaging inputs provided to the OTT CAS system. Additionally, the camera 323 may be particularly useful in monitoring one or more reference frames or markers used as part of the OTT CAS guidance of the attached surgical tool 50. As described herein, the cameras 215 are mounted at the midpoint of the housing 205 used to provide a wide field of view. In this embodiment the camera 323 is mounted in a forward projection of the housing 205 below the tool 54. As described herein, the camera 323 may be used to provide a variety of different fields of view either through mechanical or electronic lens control alone or in combination with software based imaging processing. As illustrated, the camera 323 is mounted at or near the central axis of the tool 54 with a clear view of the underside of the active element 56 or other tracking point on the tool 50. In this alternative embodiment of the on tool tracking device illustrated in FIG. 54, the housing 205 and on-board electronics are modified to include the various cameras of FIG. 54 along with the single camera 323. The OTT CAS system operation is similar to that described above with reference to FIG. 54 as well as below in FIGS. 31A to 36 and FIGS. 63, 65 and 65 with the use of the additional camera inputs and data available for OTT CAS methods and techniques. The OTT CAS system and methods of performing freehand OTT CAS may be adapted to receive inputs from one or sets of cameras 215, 245a, 245b, 317a, 317b, 319a, 319b or 323 or, from one or more of cameras 215, 245a, 245b, 317a, 317b, 319a, 319b or 323 in any combination. Furthermore, any camera of those illustrated may be used for tracking, display, measurement or guidance alone or in combination with the projector 225 in one or modes of operation under control of the OTT CAS system described herein. It is to be appreciated that the single cameras as shown in FIGS. 55 and 56 may be combined into an OTT device as illustrated in FIG. 55 or in combination with other OTT device embodiments.

FIG. 57A is an isometric view of the on tool tracking device 100 mounted on the surgical tool 50. The embodiment of the on tool tracking device 100 illustrated in FIG. 57 has a modified housing 105 and on-board electronics to include an additional pair of cameras 241a, 241b located about the same aspect as cameras 115 and below the projector output 110. In this embodiment the cameras 241a, b are mounted in the OTT housing 105 as with cameras 115. As described herein, the cameras 115, 241a, 241b may be used to provide a variety of different fields of view either through mechanical or electronic lens control alone or in combination with software based imaging processing. As illustrated in FIG. 57B the cameras may by be used to provide different fields of view either by angling the cameras or by having the cameras 115 241a, 241b mounted on a movable stage that provides for altering the direction of camera orientation. FIG. 57B illustrates the embodiment where the cameras 115 are directed inwardly towards the central axis of the tool while the cameras 241a, 241b are directed outward of the central axis. The cameras may obtain the orientations of FIG. 57B by fixed or movable stages. The cameras in FIG. 57A, 57B are also shown just above the plane that contains the surgical tool 54 that is being tracked by the OTT CAS system. In one aspect, one camera of each pair of cameras is provided on opposite sides of the tool 54 under OTT CAS guidance. The OTT CAS system operation is similar to that described below in FIGS. 31A to 36 and FIGS. 63, 65 and 65 with the use of the additional camera input and data available for OTT CAS methods and techniques. The OTT CAS system and methods of performing freehand OTT CAS may be adapted to receive inputs from one or sets of cameras 115 or 241a, 241b or from one or more of cameras 115 or 241a, 241b in any combination. Furthermore, any camera of those illustrated may be used for tracking, display, measurement or guidance alone or in combination with the projector 225 in one or modes of operation under control of the OTT CAS system described herein.

FIG. 58 illustrates another alternative embodiment of camera variation for the configuration illustrated in FIGS. 57A and 57B. In one alternative aspect, the cameras of FIG. 57A may be adjusted—via software or other suitable imaging processes—to provide the view of view illustrated in FIG. 58. In this embodiment, two pairs of cameras are provided as with the embodiment of FIG. 57A. In this embodiment of the camera of the OTT system, the camera angles A do not overlap as shown. The A angles are used to enhance the sides of the tool 54. In the image processing system the various views are synthesized into a unified view by the image processing system of the CAS tracking and guidance system. FIG. 58 illustrates the upper cameras (241a, 241b or A cameras) with a narrow and non-overlapping field of view within the surgical field. The lower cameras (115 or B cameras) have a wider and overlapping field of view. In this embodiment, the image tracking system is able to use the wider overlapping field of view and the narrow focused fields of view in order to provide a variety of different tracking schemes by synthesizing and obtaining information from the various camera views that are provided. The OTT CAS system operation is similar to that described below in FIGS. 31A to 36 and FIGS. 63, 65 and 65 with the use of the additional camera input and data available for OTT CAS methods and techniques. The OTT CAS system and methods of performing freehand OTT CAS may be adapted to receive inputs from one or sets of cameras 115 or 241a, 241b or from one or more of cameras 115 or 241a, 241b in any combination. Furthermore, any camera of those illustrated may be used for tracking, display, measurement or guidance alone or in combination with the projector 225 in one or modes of operation under control of the OTT CAS system described herein.

Figure 59A:
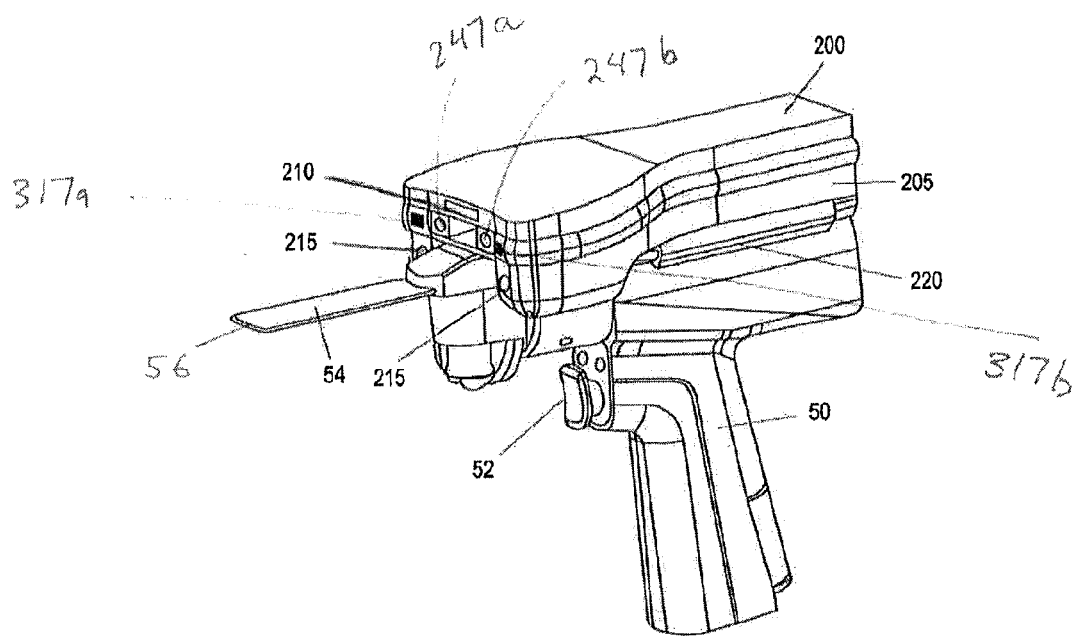
Figure 59B:
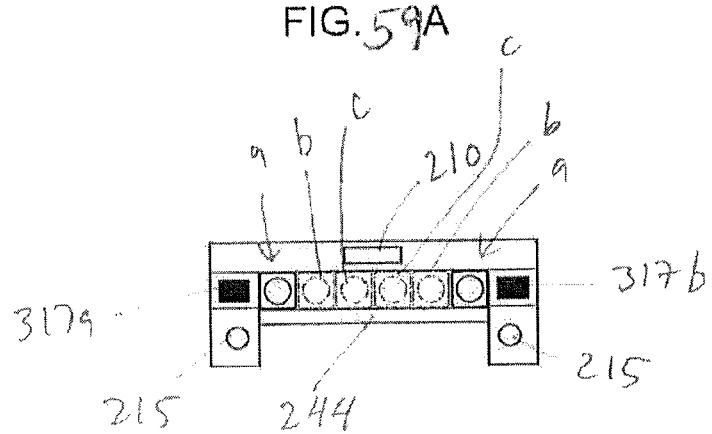

FIG. 59A is an isometric view of the on tool tracking device 200 mounted on the surgical tool 50. This OTT device embodiment is similar to that of FIG. 54 with a moveable camera stage 244 in place of camera pair 315a, 315b and without camera pair 319a, 319b. In this alternative embodiment of the on tool tracking device illustrated in FIG. 59A, the housing 205 and on-board electronics are modified to include a moveable camera stage 244 and included camera pair 247a, 247b. As in FIG. 54, the embodiment of FIG. 59A also includes cameras 215, 317a, and 317b. The additional cameras may provide, for example, an additional field or variable fields of view through OTT CAS system controlled operation of the stage 244. The stage 244 is shown mounted adjacent to the projector output or opening 210 near the top of the OTT housing 205. The stage 244 is provided with motors, a stage or other controlled movement device permitting the spacing between and/or angulation and/or focus of the cameras 247a, 247b to change. As best seen in FIG. 59B the cameras 247a, 247b may move from a wide angle position ("a" positions) a mid-range position ("b" positions) or a narrow range position ("c" position).

In addition or alternatively, the camera motion and selection of view along with the control of the camera motors, stage or other movement device are, in some embodiments, controlled based on user selected inputs such as a pre-set camera view in a smart views system. In still another alternative, the position or orientation of a camera or camera stage or motion device may vary automatically based upon the operations of an embodiment of the CAS hover control system described herein. By utilizing the camera movement capabilities of this embodiment, the image tracking system is also able to use a camera motor controller to obtain wider, mid-range or narrow field imaging as desired based on other CAS hover system parameters and instructions. As such, the moving camera capabilities of this embodiment of an OTT system provides a variety of different tracking schemes by synthesizing and obtaining information from the various camera views that are provided by the camera motion. The OTT CAS system operation is similar to that described below in FIGS. 31A to 36 and FIGS. 63, 65 and 65 with the use of the additional camera inputs and data available for OTT CAS methods and techniques as well as the ability for the OTT CAs system to control the movement of cameras 247a, 247b depending upon OTT CAS techniques and methods described below. The OTT CAS system and methods of performing freehand OTT CAS may be adapted to receive inputs from one or sets of cameras 215, 247a, 247b, 317a, or 317b or from one or more of cameras 215, 247a, 247b, 317a, or 317b in any combination. Furthermore, any camera of those illustrated may be used for tracking, display, measurement or guidance alone or in combination with the projector 225 in one or modes of operation under control of the OTT CAS system described herein.

In still further alternative aspects, it is to be appreciated that any of the OTT device embodiments described herein may, in addition to having multiple cameras or sets of cameras, may provide each camera with filters via hardware and/or software so that each camera may be used in either or both of the visible spectrum and the infrared spectrum. In such case, the two pairs of cameras can be thought as four set of cameras since in one sense the camera operates in the visible field and then those same cameras are operated via filters in the infrared field.

In still further alternative aspects, the OTT device embodiments described herein may, in addition to having multiple cameras or sets of cameras, may utilize any one or more of the onboard cameras to capture images for the purpose of recording and zooming while recording a certain aspect of the procedure for documentation, training or assessment purposes. In still another aspect, there is provided on an OTT module in software or firmware instructions a rolling recording loop of a preset time duration. The time duration could be any length of time as related to a complete OTT CAS procedure, step or portion of a step or planning or registration as related to a OTT CAS procedure or use of an OTT CAS device. There may be storage provided directly on the OTT CAS or on a related computer system. In one aspect, an OTT CAS module or electronics device includes a memory card slot or access to permit recording/storing the camera and/or projector outputs along with all or a portion of a OTT CAS surgical plan or images used in an OTT CAS plan. Still further, the video data and image storage may be on the OTT either a USB or other port or there is just a memory card as is common with handheld video cameras. The feed from the OTT camera(s) is recorded either on command, always on or done in response to a user or system input such as a mouse click, touch screen input, voice command and the like. Imaging data may be stored on the OTT itself or a device or another computer. In one example, the OTT CAS image data referenced here is stored, for example, on an intermediary driver computer. In still another aspect, the recording mentioned herein is started manually from a remotely sent command to the OTT from the master CAS computer, or, optionally from a touch screen command of the LCD screen onboard the OTT device. The commands can be "start video recording", stop video recording", "capture single image" etc. The recorded data or stored images can be stored locally on the OTT, and/or immediately or later relayed to the intermediary driver computer or to the master CAS computer to be associated with the surgical case file.

FIGS. 60, 61, 62A and 62B provide various alternative views of the OTT device electronics package illustrated and described with reference to FIGS. 5, 6 and 7. The various views of FIGS. 60, 61, 62A and 62B illustrate the wide variety of locations and sensor types that optionally may be incorporated into the various embodiments of the OTT device as well as providing further inputs, processing data or enhancements to the various alternative OTT CAS system embodiments and the alternative methods of using the same.

In the exemplary representations of FIGS. 60-62B, a number of different sensor locations are provided. More or different locations are possible as well as the placement of sensors in each of the illustrative locations in different orientations or having multiple types of sensors or of the same type of sensor in one location.

Moreover, for each embodiment of a sensor enabled OTT device, each sensor location utilized has a corresponding modification to the housing 110/210, electronics 130, 230 along with the related specifications and details of FIGS. 5-15B as needed based on the number and type, or numbers and types of sensors employed in that embodiment. In addition, the OTT device is also modified and configured to provide as needed the appropriate number and type of electronic mounts, mechanical or structural supports, electronic or vibration insulation, electrical/data connections, hardware, software, firmware and all related configurations to provide for operation and utilization of each sensor type. The type, number and location of sensors on an OTT device are employed in order to provide enhanced information about the OTT device and/or CAS operating environment in conjunction with other tracking and operating parameters already employed by the OTT CAS system and described herein.

In various alternative operating schemes of utilizing a sensor enhanced OTT device, the OTT CAS system operations, decision making, mode selection and execution of instructions is adapted based upon the addition of data from one or more OTT device sensors to provide one or more of: position, movement, vibration, orientation, acceleration, roll, pitch, and/or yaw, each alone or in any combination as related to the OTT device itself or the surgical tool under OTT tracking and guidance. Still further, multiple sensors or detection or measurement devices of the same type may be placed on the OTT device in different positions and then those same input types from each of the different locations may also be used to provide additional OTT CAS operational inputs, determinations or control factors. Each of the separate sensor outputs or readings may be used individually or the data from the same types of sensors may be collected together and averaged according to the type of sensor and data use. Still further, the collection and use of sensor data (i.e., sampling rate, weighting factors, or other variables applied based upon hover mode state, and/or adjustment of one or more CAS system parameter) may be adjusted according to the various operational schemes described in FIGS. 31A-36 and in particular with regard to adjustments to operating parameters such as slew rate and data collection rates as described in FIG. 63.

Figure 60:
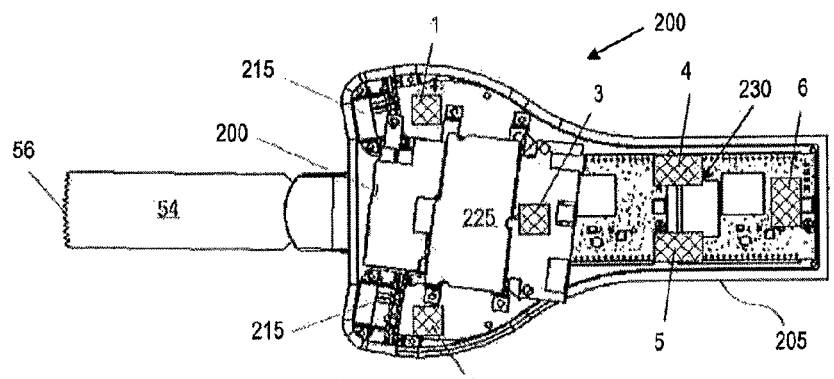
FIGS. 60-62B illustrate various OTT enabled sensor locations.

Turning now to FIG. 60, there is shown a top view of an embodiment of the OTT device 200 with the top of housing 205 removed. Sensor locations 1, 2, 3, 4, 5 and 6 are seen in this view. Sensor locations 1 and 2 are outboard on either side of the OTT device centerline. In this embodiment, the sensor locations 1, 2 are adjacent to the cameras 215. An additional sensor location 3 is illustrated in the central portion of the OTT device. The sensor location 3 may be positioned in, for example, the geometric center of the OTT device, at the center of mass or gravity of the OTT device, or at the center of mass or gravity for the combined OTT device/tool. The location of sensor position 3 may therefore be changed based on the type of tool 50 attached to the OTT device. In addition or alternatively, for OTT device embodiments configured to operate with a variety of different tool types, a corresponding number of appropriately positioned sensors may be placed depending upon the specific type of tool used. In these embodiments, the OTT CAS system is also configured to recognize or receive input as to the type of tool attached to the OTT device and then select or utilize the output from the sensor or sensors in the sensor locations and sensor types associated with that particular tool configuration.

Sensor locations 4 and 5 are positioned towards the rear on the left and right outer edges of the OTT housing 205. Sensor position 6 is on the central portion near the rear of the housing 205. The use of sensor locations 1, 2, 4, 5 and 6 alone or in any combination may be used in obtaining one or more or roll, pitch, or yaw angle data as well and inclination and/or multiple axis movement rates or vibration reading in each of these locations.

Figure 61:
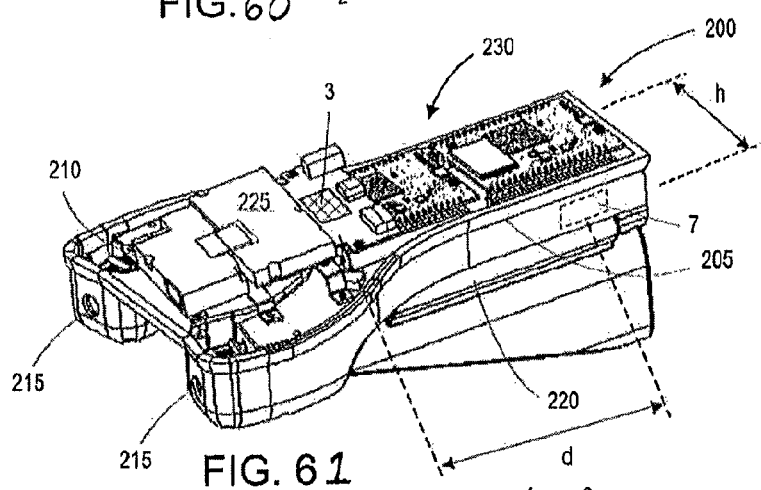

FIG. 61 is a perspective view of the OTT housing 205 of the view of FIG. 60. From this view, the sensor location 3 can be seen in its point near the center of the system. Sensor position 7 that is internal to the housing 205 is shown in phantom along the housing left side. The sensor position 7 is on or within the left wall portion towards the rear of the OTT housing 205. FIG. 61 illustrates the coordinate position of sensor location 7. In this illustrative example, the sensor location 7 is shown relative to a central OTT location, here sensor location 3. Any reference point may be used by the OTT CAS system directly or through a sensor driver intermediary computer for coordination and cross reference of the various sensor inputs. In this example, the sensor location 7 is—relative to the central location 3—spaced rearward by a distance of d. In addition, the sensor location number 7 is spaced by a height h from the elevation of the sensor location 3. The specific location of each one of the sensors may be used to advantage when determining the various parameters of the OTT in use. It is to be appreciated that the OTT CAS system may use absolute x, y, z coordinates, or relative coordinates for the sensor locations employed by an OTT device embodiment.

Figure 62A:
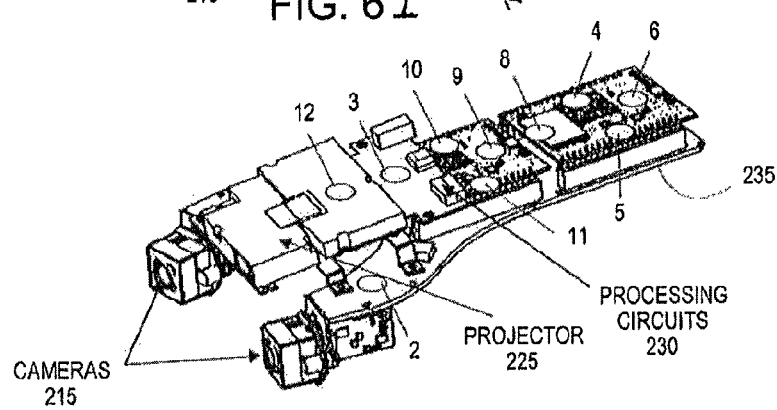
Figure 62:
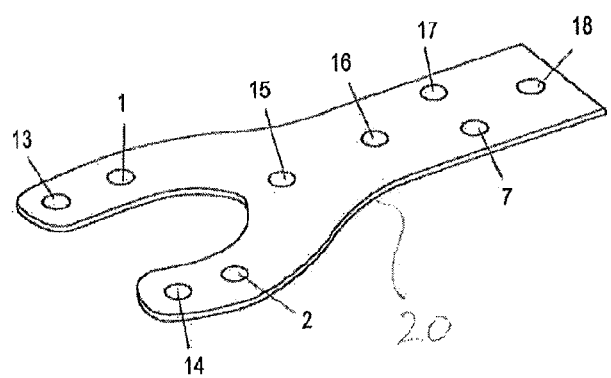

FIG. 62A is a similar isometric view to that of FIG. 61 with the lower OTT housing portion removed. The view of FIG. 62A is used to illustrate several additional optional sensor locations. Sensor locations 8, 9, 10, 11 and 12 are shown in this embodiment. Sensor locations 12, 9 and 8 are shown along the central longitudinal axis of the OTT device fore and aft of the central sensor location 3. Sensor locations 10, 11 provide additional outboard locations similar to positions 4 and 5 but longitudinally separated therefrom. While many of these exemplary locations are shown along or near the longitudinal center line of the OTT device, other sensor locations are possible. For example, sensors may also be located on the underside of the board 235 or other structure within, part of or attached to the OTT device housing. The sensor locations may be placed in, along, above or below the board 235 or in other locations based on design and space requirements for other components and the OTT device electronics package.

In addition to the sensor locations described in FIGS. 60, 61, and 62A, a sensor platform 20 may also be provided within OTT housing 205. A perspective view of an exemplary sensor base 20 is illustrated in FIG. 62B. The sensor base 20 is shown with representative sensor locations 1, 2, 13, 14, 15, 16, 17, 18 and 7. The sensor base 20 illustrates the alternative placement of sensor 7 on the base 20 instead of within or on the wall in FIG. 61. Similarly, sensor positions 1 and 2 are moved from the positions illustrated in FIG. 60 to the base 20. In addition, the location of sensor position 15 is selected to provide the functions of sensor location 3 described above. The various alternative sensor types, numbers and locations may be integrated as described above into an appropriately configured sensor base 20. In various implementations, one sensor base or more than one sensor base may be sized as shown in FIG. 62B where the sensor base mimics the size and shape of the OTT device housing 205. A sensor base may include all the sensors of a particular type, particular orientation, for a particular location or position or function related to the particular OTT device configuration. Given the rate of miniaturization of electronics and sensors, particularly in the field of micro electrical mechanical systems (MEMS), it is to be appreciated that all or substantially all of the sensors employed in an OTT device may be in the form of suitably miniaturized commercially available components.

FIG. 62B shows the sensor locations 13 and 14 corresponding to camera locations and forward of sensor locations 1, 2. Sensor positions 13, 14, 1 and 2 are provided in proximity to the camera locations. Sensor locations 15, 16 and 18 are near the center line of the OTT device module when the sensor board 20 is in place. Sensor locations 15 or 16 may be positioned above a specific location of interest in the OTT guided tool such as a vertical central axis of the tool, trigger location or other feature of interest to facilitate tracking of that tool. In one aspect, a sensor location is positioned to indicate the trigger of the surgical tool being used in the CAS system. In one embodiment, sensor locations 17 and 7 are positioned to the left and right outboard positions behind the center of mass for the tool. Sensor location 18 is the rearward sensor location furthest to the rear of the OTT module when the sensor board 20 is installed into the OTT housing 205.

Each one of the sensor locations illustrated and described with reference to FIGS. 60-62B and elsewhere in this specification, may be used to provide a variety of different sensor or instrumentation types to be used by the position and tracking systems described herein. By way of example and not limitation, the various instruments or sensors used in conjunction with an OTT device include: an inclinometer, a gyroscope, a two axis gyroscope, a three axis gyroscope or other multiple axis gyroscope, an one-two-three or multiple axis accelerometer, a potentiometer, a MEMS sensor or micro-sensor or MEMS instrument configured to provide one or more of roll, pitch, yaw, orientation, or vibration information related to the OTT device, or the operation of an OTT device/surgical tool combination or the operation, use or status of a tool attached to an OTT device and being used under an OTT CAS system as provided herein or as otherwise used in an operating environment of the OTT system for tool or prosthetic registration, fit assessment or surgical planning, surgical plan revision and the like.

Figure 16A:
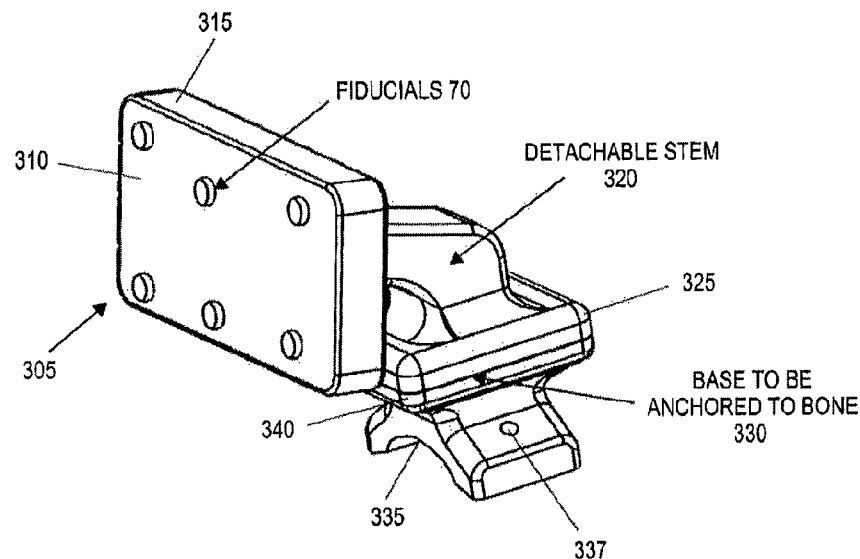
FIGS. 16A, 16B and 16C illustrate various views of a reference frame.
Figures 16B, 16C:
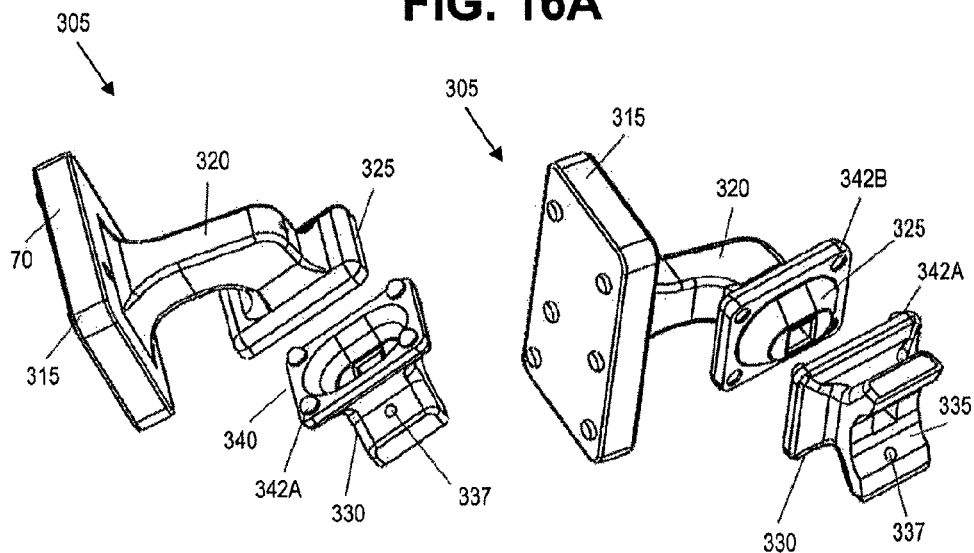

FIGS. 16A, 16B and 16C provide various views of a reference frame 300 for use in a computer assisted surgery procedure. There is a 305 frame having a planar or general 3D surface 310 bounded by perimeter 315. One or more active or passive fiducial marker 70 are arranged in a pattern 72 across the surface 310 or carried individually through some frame structure. There is a stem 320 extending from the frame 305 and a coupling 325 on the stem. The coupling 325 is used to join the frame 305 to a base 330. The base 330 has a first surface 335 configured to engage a portion of the anatomy within a surgical field related to the procedure. The base 330 has a second surface 340 to engage with the coupling 325. The coupling 325 and the second surface 340 are engaged in FIG. 16A but are separated in FIGS. 16B and 16C. In the views of FIGS. 16C and 16C at least one registration element is visible on the coupling and at least one registration element is visible on the second surface. In the illustrated embodiment, the registration element 342*b* is a female feature on the coupling 325 while the coupling element 325*a* on the second surface 340 is a male feature. The registration elements are sized and positioned to mating cooperation when the coupling 325 and the second surface 340 are engaged. It is to be appreciated that a variety of different registration element types and positions may be adapted and configured for providing mating cooperation when the coupling is engaged to the second surface.

The base 330 includes a second surface 335 used to engage the anatomy. All or a portion of the surface may include a serrated edge to assist in engaging with anatomy, particularly bony anatomy about the joint. The base first surface 335 comprises a curvature that is complementary to the anatomical site upon which the base first surface is to be affixed during the surgical procedure. In one aspect, the curvature is complementary to an anatomical site comprising a skin portion of the anatomy, where the bone may not be exposed but the reference frame is attached to it through the skin with screws or other fastening device mentioned below. In one additional embodiment, the bony portion of the anatomy is adjacent to a joint that is the subject of the surgical procedure. The joint may be selected from a knee, a shoulder, a wrist, an ankle, a hip, a vertebrae or any other surgical site where a bone osteotomy is to be performed. The base 330 includes at least one aperture 337 adapted and configured for a fixation element used to affix the base to a site on the body. The fixation element may be selected from one or more of a pin, a screw, a nail, surgical staple or any form of glue or cement to be applied to the element or to be exposed (e.g., peeling of a double sided tape).

Figure 17:
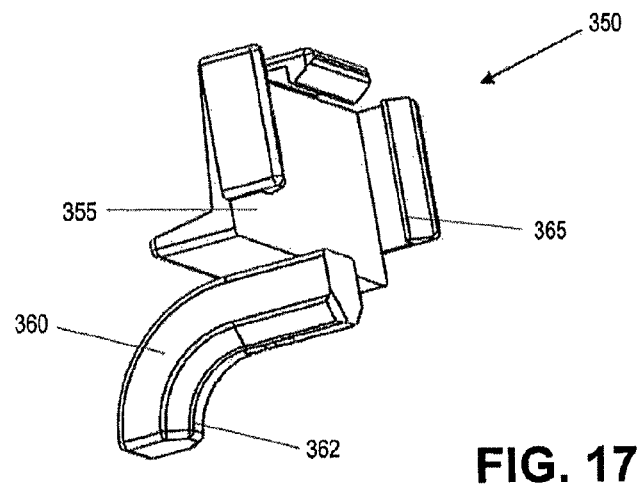
FIG. 17 illustrates an isometric view of a reference frame guide and FIG. 18 illustrates the guide of FIG. 17 attached to the reference frame of FIG. 16A.
Figure 18:
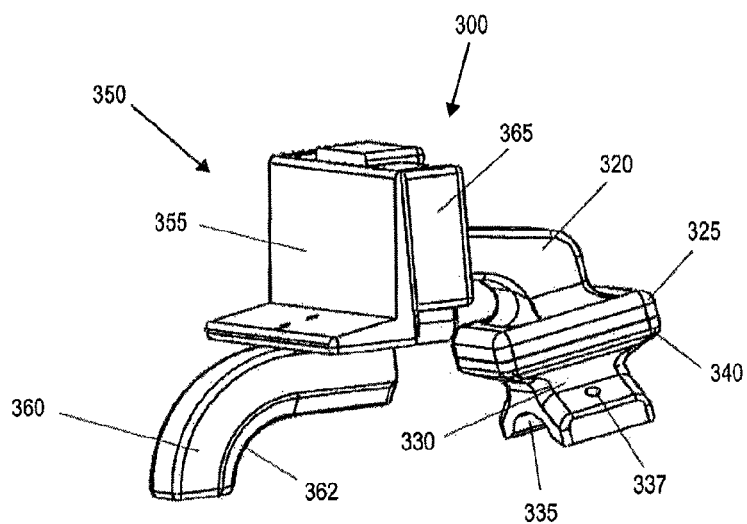

FIG. 17 illustrates an isometric view of the reference frame guide 350. The reference frame guide 350 has a frame 355 and a stem 360 extending from the frame 355. The stem 360 has a curvature or shape configured to engage with an anatomical feature to assist, when the frame guide is attached to the frame 305, the reference frame 300 is placed in a desired position and orientation within the surgical field. The reference frame guide 350 also includes one or more engagement elements 365 along the frame 355 for temporary engagement with the perimeter 315 or a portion of the reference frame 305 to permit proper positioning and adjustment of a base 330 associated with a reference frame 300 attached using the elements 365. FIG. 18 illustrates a reference frame guide attached to the frame 305 of a reference frame 300. In use, the engagement elements 365 may be broken off in order to remove the reference frame from the guide frame during surgical procedure. While illustrated in mating cooperation with reference frame 300, reference frame guide 350 may be adapted and configured to form a mating engagement with reference frames of different shapes and sizes, such as the reference frame 400 in FIG. 24.

Figure 19:
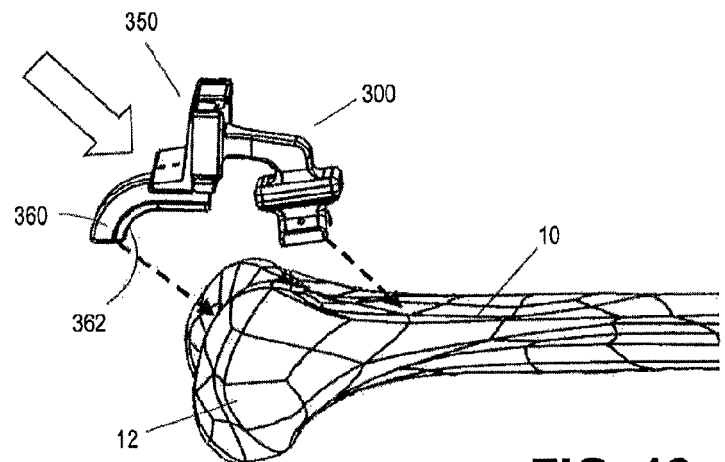
FIG. 19 illustrates the components of FIG. 18 being moved and position for attachment to the anatomy and FIG. 20 is an isometric view illustrating said attachment.
Figure 20:
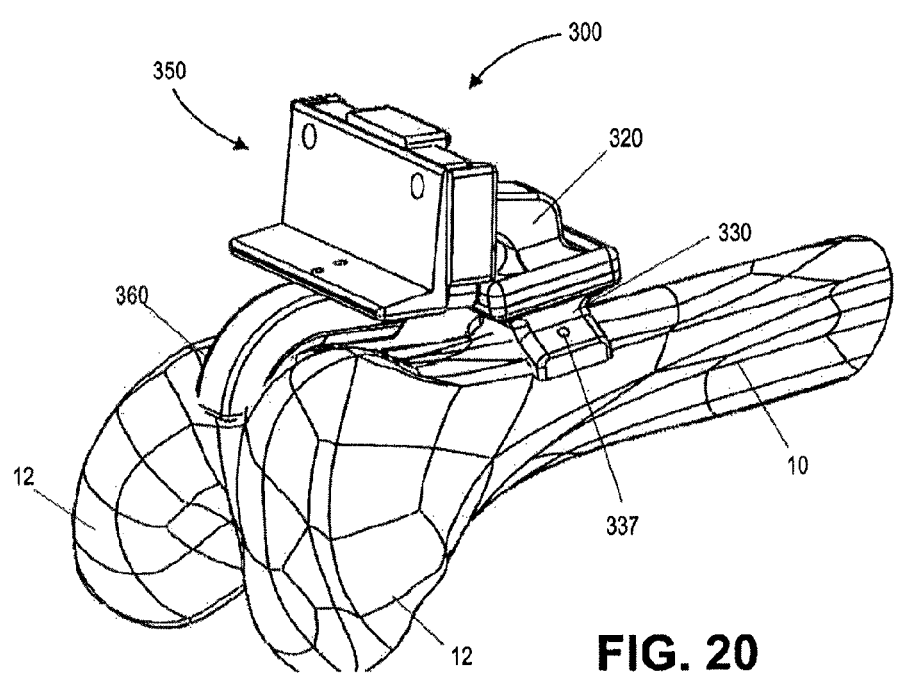
Figure 21:
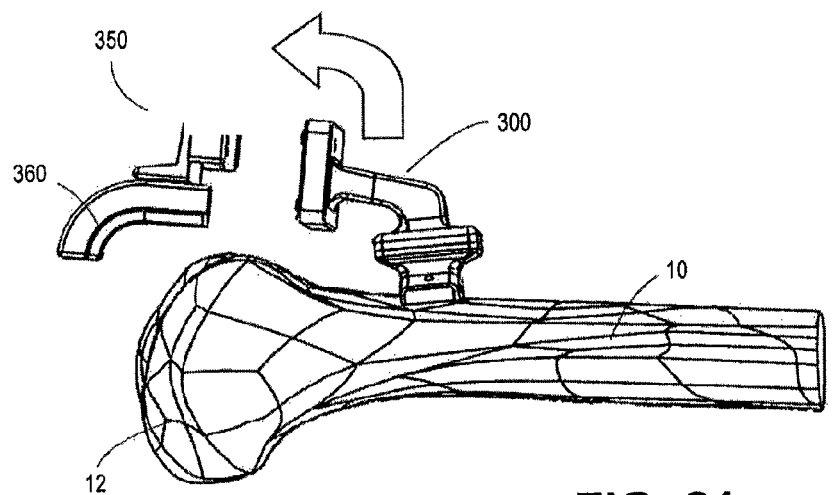
FIG. 21 illustrates the removal of the guide frame and FIG. 22 illustrates the remaining frame in position on the anatomy.
Figure 22:
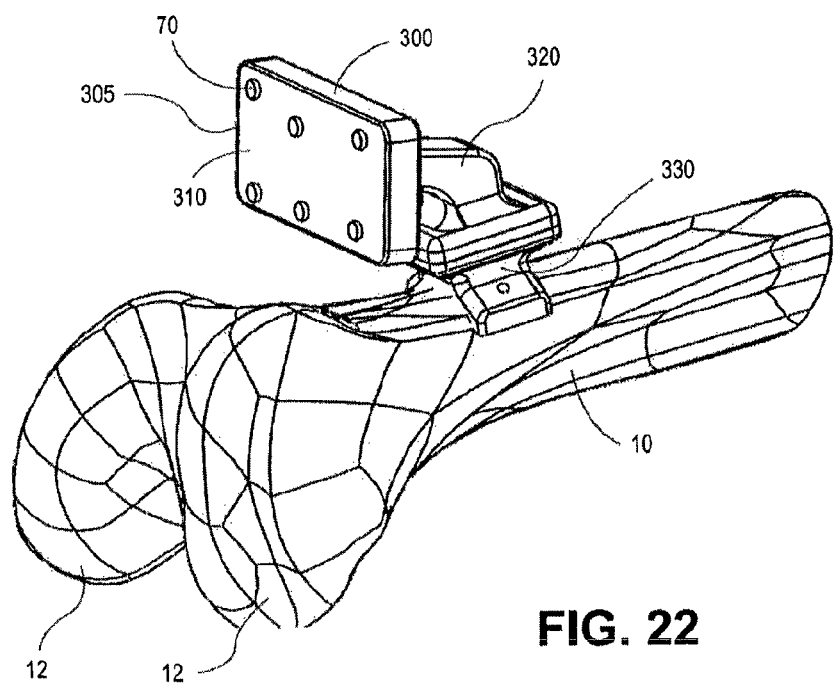

In one particular embodiment, the curvature or shape 362 of the stem 360 is configured for placement of the stem in relation to the condyles in order to provide alignment within the surgical field for the reference frame 300 along the femur. Positioning of the base 330 along the femur 10 is shown in FIGS. 19 and 20. The joint reference frame guide and reference frame structure (see FIG. 18) are positioned (following the arrow in FIG. 19) so as to align the curvature 362 of the stem 360 between the condyles 12 of the femur 10 in order to place the base 330 in proper orientation on the femur as shown in FIG. 20. Thereafter the reference frame 300 is attached to the femur 10 by joining the base first surface 335 using one or more methods such as and screws or nails applied the aperture 337 or the use of a biocompatible bone cement. Once the reference frame 300 is confirmed in the proper position, the reference frame guide 350 is removed (FIG. 21) leaving only the reference frame in the desired location along the femur 10 in the desired relation to the condyles 12 according to a surgical plan to be implemented (FIG. 22).

Figure 23:
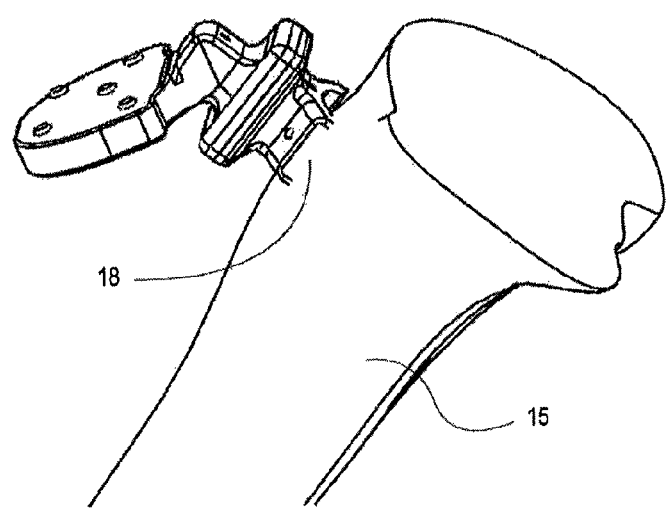
FIG. 23 illustrates another reference frame in position on the tibia.
Figure 25:
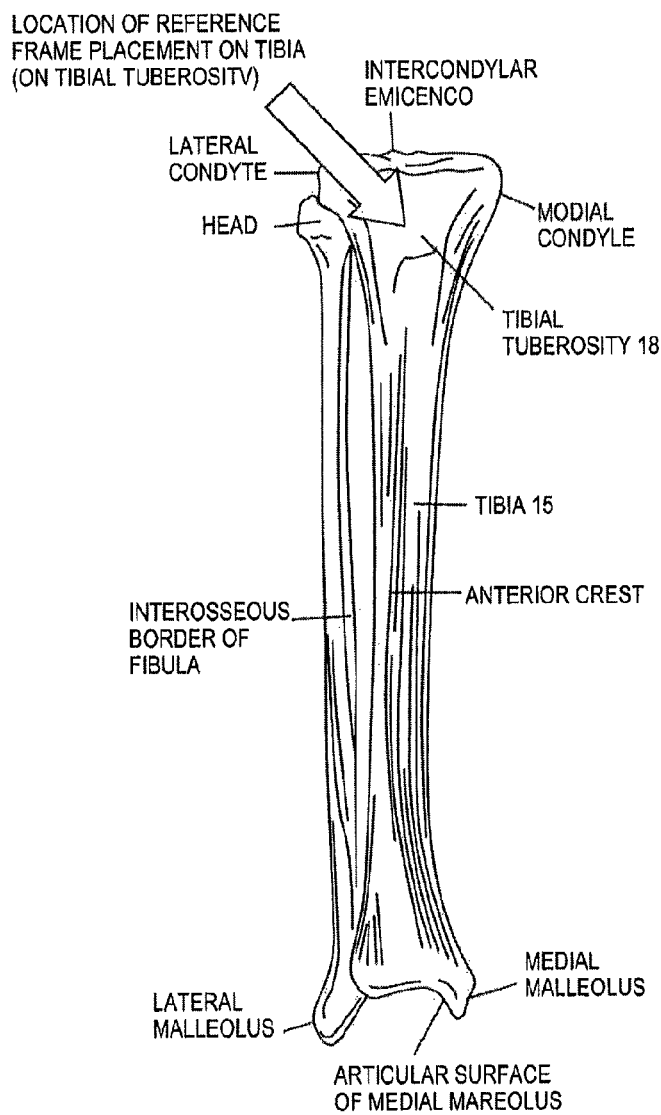
FIG. 25 illustrates an implantation site on the tibia.

FIG. 23 illustrates an embodiment of the reference frame 400 and position along the tibia 15. In this illustrated embodiment the reference frame 400 is attached on or about the tibial tuberosity (shown more clearly in FIG. 25) and secured to the bone using any one of the several fixing methods described above with regard to the reference frame 300. Additional details of the reference frame 400 may be provided upon review of FIGS. 24A, 24B and 24C. These figures provide various views of a reference frame 400 for use in a computer assisted surgery procedure. There is a 405 frame having a surface 410 bounded by perimeter 415. One or more active or passive fiducial markers 70 are arranged in a pattern 74 across the surface 410. There is a stem 420 extending from the frame 405 and a coupling 425 on the stem. The coupling 425 is used to join the frame 405 to a base 430. The base 430 has a first surface 435 configured to engage a portion of the anatomy within a surgical field related to the procedure. The base 430 has a second surface 440 to engage with the coupling 425. The coupling 425 and the second surface 440 are engaged in FIG. 24A but are separated in FIGS. 24B and 24C. In the views of FIGS. 24C and 24C at least one registration element is visible on the coupling and at least one registration element is visible on the second surface. In the illustrated embodiment, the registration element 442b is a female feature on the coupling 425 while the coupling element 425a on the second surface 440 is a male feature. The registration elements are sized and positioned to mating cooperation when the coupling 425 and the second surface 440 are engages. It is to be appreciated that a variety of different registration element types and positions may be adapted and configured for providing mating cooperation when the coupling is engaged to the second surface.

The base 430 includes a second surface 435 used to engage the anatomy. All or a portion of the surface may include a serrated edge to assist in engaging with anatomy, particularly bony anatomy about the joint. The base first surface 435 comprises a curvature that is complementary to the anatomical site upon which the base first surface is to be affixed during the surgical procedure. In one embodiment, the bony portion of the anatomy is adjacent to a joint that is the subject of the surgical procedure. The joint may be selected from a knee, a shoulder, a wrist, an ankle, a hip, or a vertebrae. The base 430 includes at least one aperture 437 adapted and configured for a fixation element used to affix the base to a site on the body. The fixation element may be selected from one or more of a pin, a screw, a nail, a surgical staple or a glue or adhesive based fixation.

Turning now to FIGS. 26A, 26B and 26C, additional aspects of the reference frame designed to be described. With reference to FIG. 26A, the orientation between the frame 305 and the base 300 may be adjusted between a number of preset orientations. Altering the relationship between these two components is accomplished by altering which of a plurality of registration elements available to the joint as components are engaged. In one aspect, there are a plurality of registration elements on the coupling and a plurality of registration elements on the second surface. The orientation of the reference frame may be adjusted between a first orientation 382 and a second different orientation 384 based on which grouping of registration elements is used for joining the base 330 to the frame 305. In one embodiment, wherein a portion of the registration elements on the coupling are engaged with a portion of the registration elements on the second surface the result will orient the frame in a first orientation within the surgical field. In another aspect, the mating different registration elements on the coupling with different registration elements on the second surface, the result is that the frame 305 will present in a second, different orientation within the surgical field. In one aspect, the first orientation is a known position used in surgical preplanning. In still another aspect, the second orientation is another known position used in surgical preplanning. Either or both of the first orientation and the second orientation may be used in furtherance of the OTT CAS techniques described herein. Both can be used in sequence without new software registration each time. The registration for each configuration or only one is done first and once, and the software registration for the other is computed from the geometry or measured separately and its data stored and accessible whenever needed.

FIG. 26A also illustrates one embodiment of a mount coupling adapted and configured to maintain the relative position and orientation of the coupling and the second surface. In this embodiment a flexible linkage 380 is shown between the two components and is sized shaped and oriented within the reference frame to maintain the orientation of the frame 305 within the surgical field. In other words, the mount coupling is sufficiently rigid that if the frame 305 is bumped during a procedure, its components can be temporarily displaced relative to each other through deformation of the elastic element in the coupling, but then can return back or be returned back by the user to the original alignment, and so it will not lose its alignment due to the registration elements within it. If the bump of the reference frame was sufficiently strong, the registration elements would disengage and not return automatically, but the use can return them and the original software registered alignment is still not lost. In the illustrative embodiment, the flexible linkage 380 is disposed completely within the structure in use, here the base 330. As best seen in FIG. 26A, one portion of the linkage 380 attaches to the upper base 330 and another portion to the lower base 330. In another alternative aspect, a mount coupling is provided in so that when the mount coupling is attached to the reference frame the mount coupling substantially or completely surrounds the area of mating contact between the coupling and the second surface. FIG. 26B1a illustrates a perspective view of a flexible mount coupling 383 that completely surrounds the interface between the upper and lower base 330. FIG. 26B1b illustrates a perspective view of the flexible mount coupling 383. FIG. 26B2a illustrates a perspective view of a flexible mount coupling 384 that substantially surrounds the interface between the upper and lower base 330. The coupling 384 includes four corner mounts connected by linkages. The corner mounts and linkages are—like coupling 383—designed for a snug fit around the interface between the upper and lower mounts. FIG. 26B2b illustrates a perspective view of the flexible mount coupling 383.

Figure 27A:
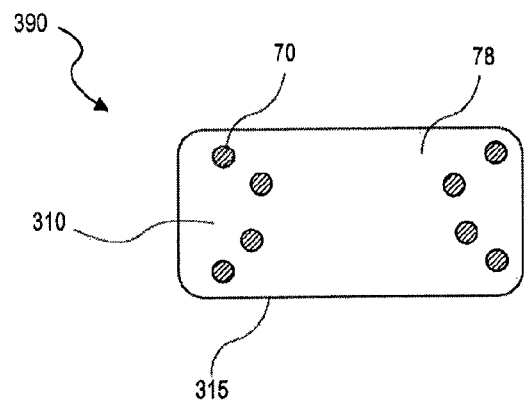
FIGS. 27A and 27B illustrate two alternative reference frame surfaces.
Figure 27B:
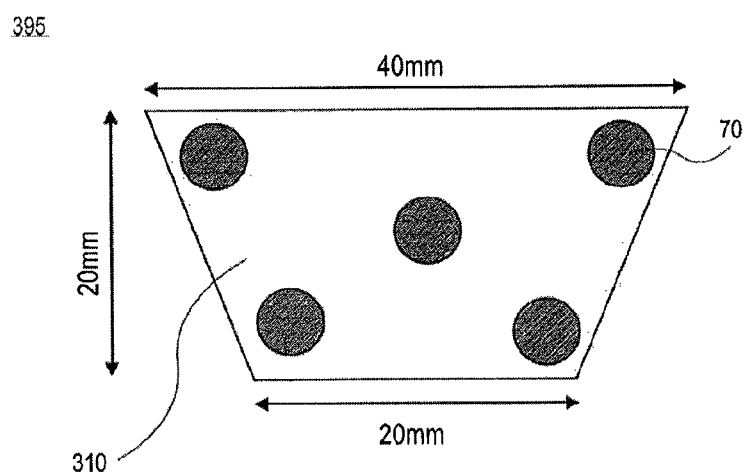

FIGS. 27A and 27B provide alternative reference frame surface shapes as well as alternative height to show marker patterns. FIG. 27A illustrates a generally rectangular frame 390 of a reference frame having a plurality of fiducial markers 70 arranged in a pattern 78. FIG. 27B illustrates a generally trapezoidal surface shape 310 on the frame 395. A plurality of fiducial markers 70 arranged in a pattern on the surface 305.

Figure 28:
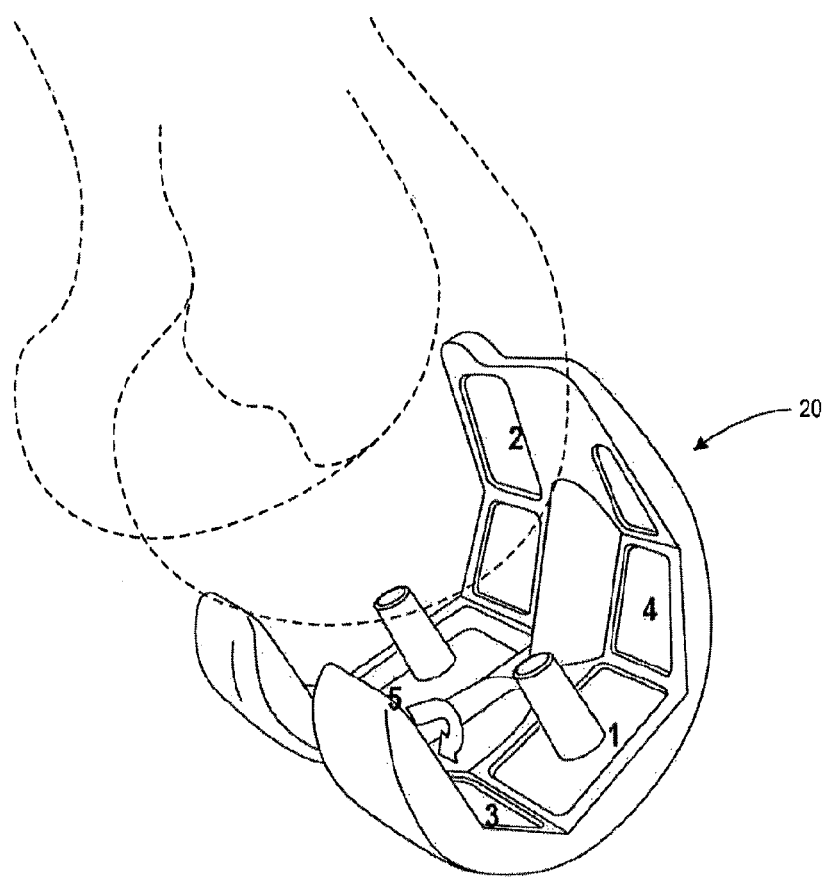
FIG. 28 is an isometric view of an exemplary knee prosthesis near a schematically outlined distal femoral bone.

FIG. 28 illustrates an isometric view of a representative of prosthesis 20 for use in a total knee replacement procedure. The numbers indicated on the prosthesis 20 are representative of the types of cuts undertaken during knee surgery. FIGS. 29A-29I and 30 illustrate one of the unique combinations of the OTT CAS system described herein. While each of the reference frames described above may be used independently or in conjunction with other anatomical sites or surgical equipment, the reference frames 300 and 400 have particular advantage for the on tool tracking devices and OTT CAS procedures described herein. One challenge of using on tool tracking devices for handheld precut surgery is obtaining relevant tracking information and maintaining a tracking frame of reference during the procedure. By the unique design and placement the reference frames 300 and 400 may be used to provide just this type of dynamic reference frame tracking using the OTT tracking techniques described herein. As shown in the figures that follow in each one of the representative cuts used for implanting the prosthetic 20, the vision system carried onboard the OTT 100 is able to visually identify and register with all or a portion of the reference frame 300 and the reference frame 400. While these particular configurations are illustrative of the capabilities of the OTT CAS system and tools for knee surgery, it is to be appreciated that the reference frames and vision guidance techniques described herein may be adapted to other joints in the body and to other procedures.

FIGS. 29A-29I and 30 each illustrate a representative surgical set up for the placement of a reference frame 300 on the femur 10 and the reference frame 400 along the tibia 15, in particular on or about the tibial tuberosity 18. Is to be appreciated that the illustrated OTT CAS procedure that follows utilizes the reference frames 300, 400—they are not moved but remain in the same position during all of the following OTT CAS process steps. An on tool tracking device 100 is coupled to a surgical tool 50 for the positioning and use of a tool 54 having an active element 56.

Figure 29A:
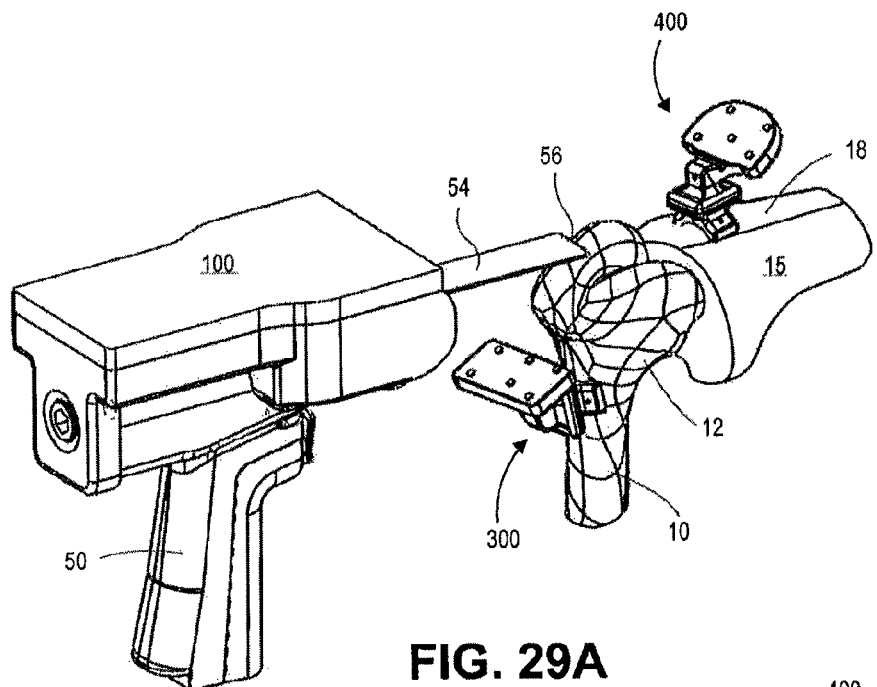
FIGS. 29A-29I and 30 illustrate the various views of an on tool tracking system and associated surgical tool in position for performance of a total knee replacement OTT CAS procedure.

In the illustrative embodiment of FIG. 29A, the OTT 100 is providing guidance for the use an active element 56 for making a distal lateral condyle cut. During this cut, the cameras carried onboard OTT 100 are capturing, imaging, and providing relative navigation and positioning information based on information received from both reference frames 300 and 400 during all or a substantial portion of the illustrated cut.

Figure 29B:
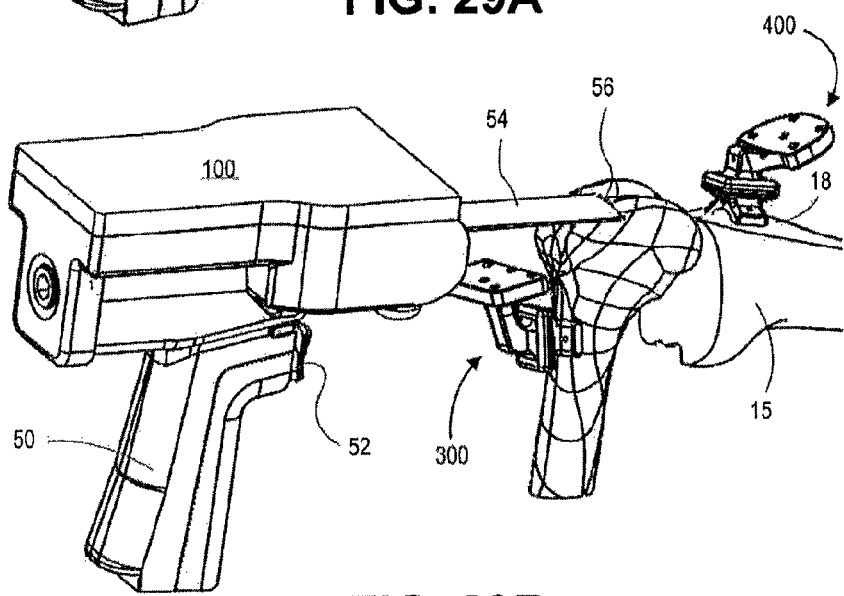

In the illustrative embodiment of FIG. 29B, the OTT 100 is providing guidance for the use an active element 56 for making a distal medial condyle cut. During this cut, the cameras carried onboard OTT 100 are capturing, imaging, and providing relative navigation and positioning information based on information received from both reference frames 300 and 400 during all or a substantial portion of the illustrated cut.

Figure 29C:
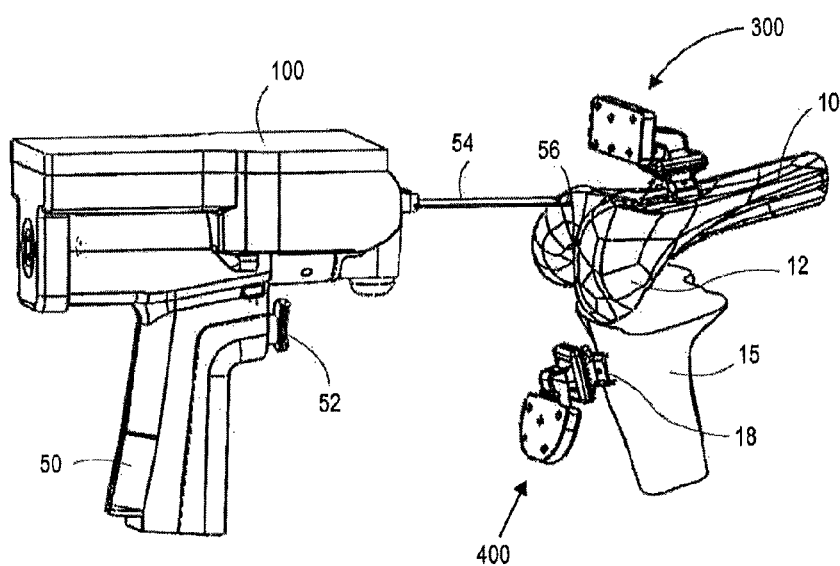

In the illustrative embodiment of FIG. 29C, the OTT 100 is providing guidance for the use an active element 56 for making an anterior cut. During this cut, the cameras carried onboard OTT 100 are capturing, imaging, and providing relative navigation and positioning information based on information received from both reference frames 300 and 400 during all or a substantial portion of the illustrated cut.

Figure 29D:
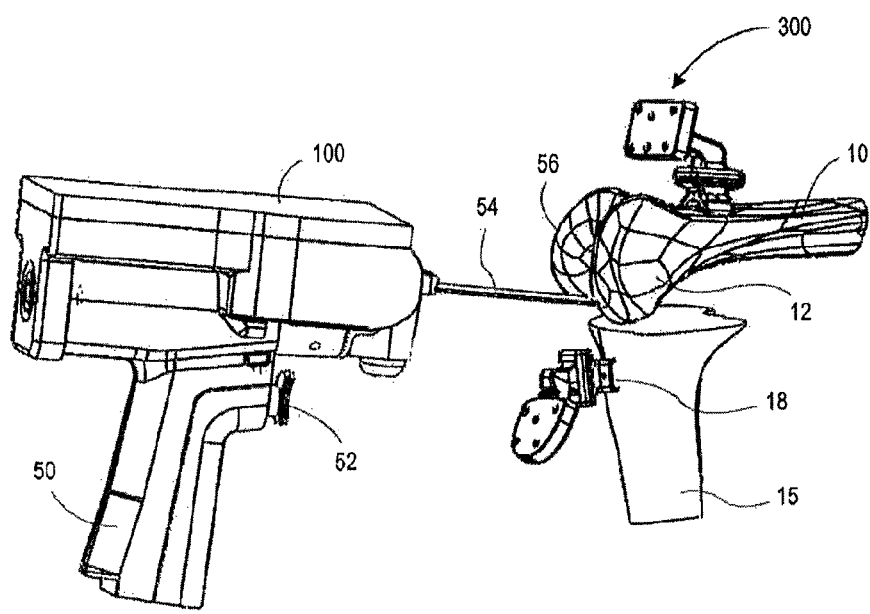

In the illustrative embodiment of FIG. 29D, the OTT 100 is providing guidance for the use an active element 56 for making a posterior lateral condyle cut. During this cut, the cameras carried onboard OTT 100 are capturing, imaging, and providing relative navigation and positioning information based on information received from both reference frames 300 and 400 during all or a substantial portion of the illustrated cut.

Figure 29E:
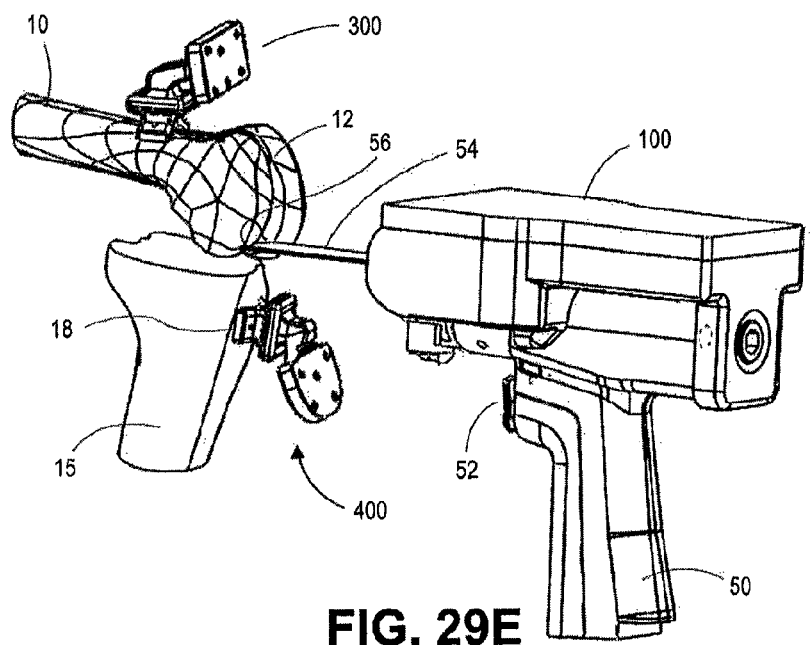

In the illustrative embodiment of FIG. 29E, the OTT 100 is providing guidance for the use an active element 56 for making a posterior medial condyle cut. During this cut, the cameras carried onboard OTT 100 are capturing, imaging, and providing relative navigation and positioning information based on information received from both reference frames 300 and 400 during all or a substantial portion of the illustrated cut.

Figure 29F:
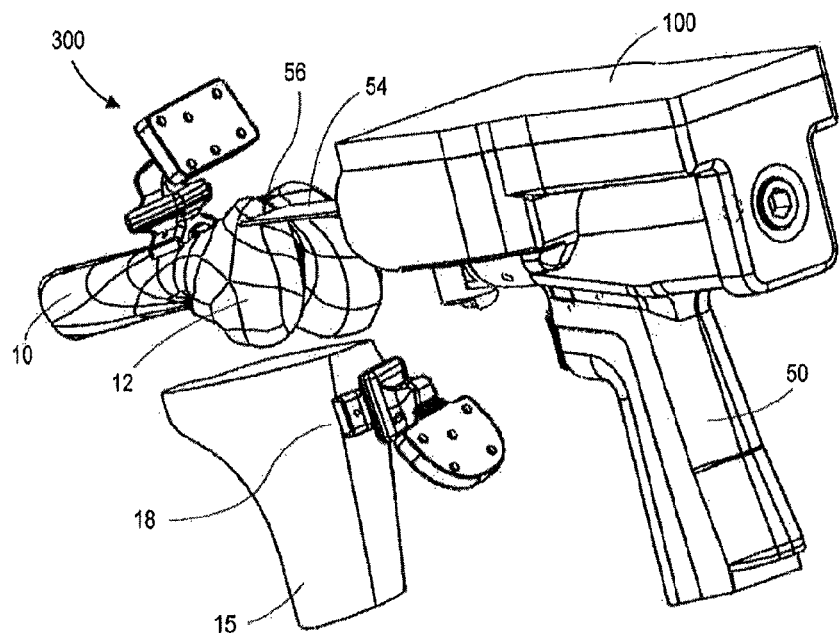

In the illustrative embodiment of FIG. 29F, the OTT 100 is providing guidance for the use an active element 56 for making an anterior chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29G:
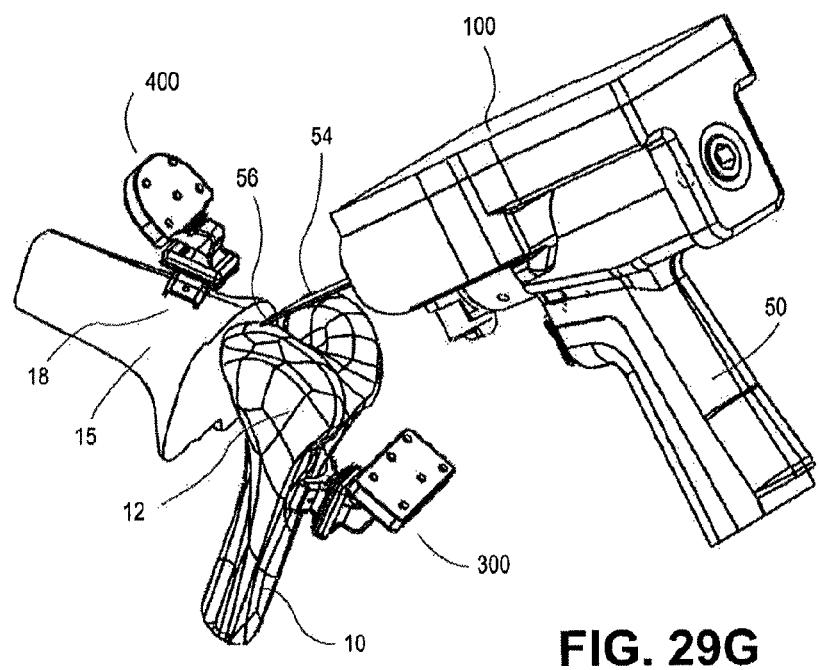

In the illustrative embodiment of FIG. 29G, the OTT 100 is providing guidance for the use an active element 56 making a posterior lateral condyle chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29H:
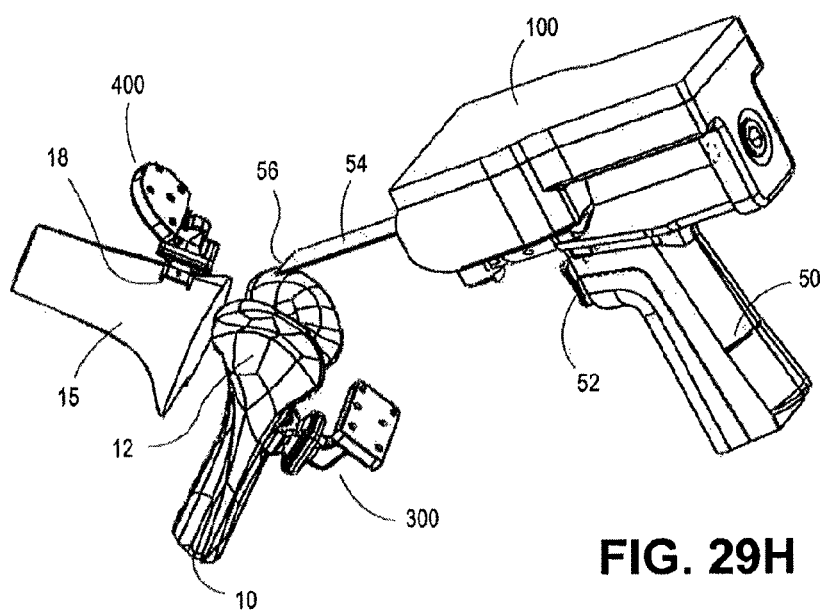

In the illustrative embodiment of FIG. 29H, the OTT 100 is providing guidance for the use an active element 56 making a posterior medial condyle chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29I:
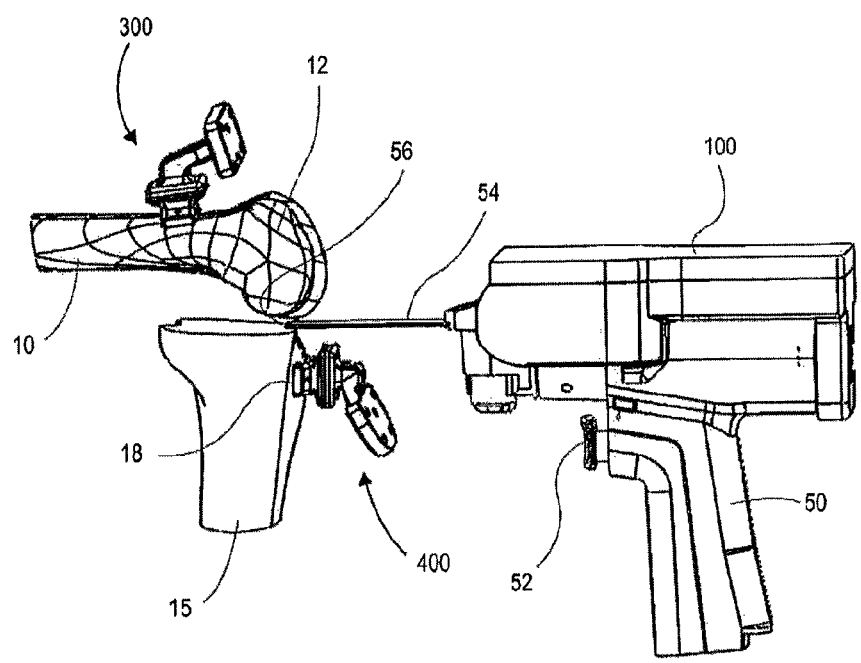

In the illustrative embodiment of FIG. 29I, the OTT 100 is providing guidance for the use an active element 56 making a tibial cut. During this cut, the cameras carried onboard OTT 100 are capturing, imaging, and providing relative navigation and positioning information based on information received from both reference frames 300 and 400 during all or a substantial portion of the illustrated cut.

Figure 30:
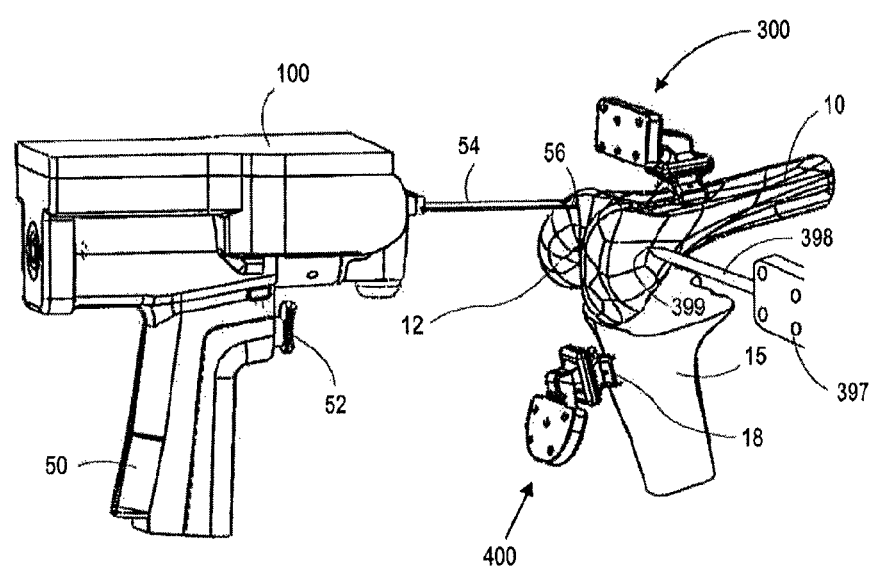

FIG. 30 illustrates an OTT 100 coupled to a surgical instrument 50 having a tool 54 and an active element 56. Reference frames 300, 400 are also shown in relation to an OTT CAS surgical site about the knee. An additional reference frame 397 having a stem 398 and tip 399 is being used for further registration or notation of the surgical field. The registration of the reference frame 397 is being provided by the imaging system of the OTT 100m with a tool. The registration frame 397 is being registered along with one or both of the registration frames 300, 400. While embodiments of the OTT CAS methods described herein by utilize both the reference frames 300, 400, it is to be appreciated that the, because of the improved image based tracking capabilities of the OTT and OTT CAS processing the OTT CAS system have both reference frames available but elect during processing to only use tracking information from one reference frame.

When considering the use of the unique reference frame embodiments described herein, consider the manner by which a view may be preferred by an OTT CAS system user. The OTT CAS system is pre-programmed so that certain views are shown by default for certain cuts. For instance, in the example of resecting a femur in preparation for a femoral prosthetic for a TKR procedure, several surfaces are to be cut, as shown in FIGS. 29 and 30. Each surface may be best viewed from a different perspective during the procedure. When cutting the anterior surface of the medial condyle a first view may be desirable, whereas when cutting the anterior surface of the lateral condyle a second view may be desirable. Accordingly, the system sets a pre-defined first view for viewing the virtual model when the anterior surface of a medial condyle is resected. Similarly, default visual views can be defined for a number of common resection procedures. When the OTT CAS system determines the cut to be performed, the system determines the best match for the cut and displays the default automatically without the intervention of the surgeon. In much the same way the vision based processes performed by the OTT CAS computer may be preselected to use all or a portion of the available tracking information from one or both reference frames, automatically, depending upon the circumstances. In addition, the OTT CAS may guide a user in adjusting orientation of a reference frame within a surgical field to improve guidance information from that frame. The adjustable orientation of the frame while maintaining the registration position of the base is described herein.

In another alternative aspect, there is a divot or other feature present on one or more of the reference frames described with reference to FIGS. 16A-30. In one aspect, contact is made with the divot using the surgical tool, touch screen, or navigated pointer and produces a result in the system indicating the initiation or completion of a step. In one example, contact with the reference frame (e.g., touching with a navigated pointer) the OTT CAS system registers the initiation of an operation or alternatively the completion of an operation. In one specific embodiment, the act of touching the reference frame indicates the start of an operation involving that particular reference frame. One exemplary operation conducted with a reference frame is bone registration. In an additional aspect, this input and/or interaction with a particular reference frame is also an input to or part of a selection criteria for a CAS Hover mode, smart view, display or other function.

It is to be appreciated that any of a number and variety of powered or non-powered tools can be utilized with the OTT CAS systems described herein. For example, in the orthopedic surgery field, the system can be built upon a single orthopedic power saw such as a Stryker System 6 Precision Oscillating saw. Similarly the system can be used with other power tools commonly used in orthopedic surgery, such as a burr or a drill. In such application, the system could be integrated within the design of the surgical tool, or added as a retrofit. In addition, the system could utilize a tool that does not require any external power source—such as a pointer, a marker or a scalpel. Ideally, the system could accommodate multiple smart tools to be used at different phases of a surgical procedure and make the system robust enough to perform a wide variety of surgical procedures. It is to be appreciated that the OTT 100 may be adapted to fit the housing of a wide variety of surgical tools, free hand tools as discussed above and elsewhere in this application. Alternatively, the OTT may be built (fully integrated) into the design of freehand tools or hand-held power instruments and its housing manufactured together with such tools. Additional OTT housing configurations such as various two part housings are illustrated and described below with reference to FIGS. 68*a*-72.

The system could be used in other applications outside of orthopedic surgery. For example, it could be used in simulations and simulators for teaching and training surgeons for orthopedic surgery. Alternatively the system could be used for other medical procedures that require precise orientation and manipulation of rigid tissue. The present techniques computer assisted surgery could readily facilitate such dental procedures. The system can also be used in non-medical applications, for example in carpentry, sheet metal work and all other engineering marking and machining processes to guide the user to make a certain pattern of cutting or drilling of materials.

Embodiments of the OTT CAS system described herein eliminates the need for external tracking devices by placing one or more trackers on board the tool. The present invention can completely eliminate the need for an external tracking system or utilize the tracking sub-system to add new tracking data. In either configuration, the tool itself tracks the patient's anatomy, or tracks itself relative to a patient anatomy, as opposed to an external tracker that tracks both to determine the relative position of one to the other. Furthermore, because the components providing input to the tracking system are located on the tool itself, all tracked elements of the system are tracked relative to the tool. As a result, the tracking data produced by the on-tool trackers is very different. The position of the tool, for example, need not be independently tracked because all other tracked objects are tracked from the tool's vantage. The on board tracking system alleviates concerns faced by externally tracked systems, where all components of the system including the surgical instrument are tracked by an external device. Logistically, the present invention allows the operating room to eliminate or at least minimize the need for a separate piece of equipment in the operating room by placing the tracking or the components providing input to the processing part of the tracking system on the tool itself. With the sensors for the tracking on board the tool, this brings another advantage of being closer to the tracked target, and thus higher resolution and accuracy may result as well as less stringent requirements for "line of sight" access between the tracker and the tracked element of other systems.

The tracker-tracking subsystem further comprises one or more tracking elements that are detectable to the trackers on board the surgical instrument. There are a wide variety of tracking elements that can be utilized in the system. For example, reference frames that contain one or more reflective surfaces can reflect infrared or visible light back to the surgical tool. Light emitting diodes can similarly indicate the position of tracked objects back to the surgical tool. Other approaches, such as fiducial points or image recognition, could eliminate the need for external reference frames to be placed on the objects, such as the patient's tissue, that needs to be tracked. In further embodiments, the specific image of the patient's anatomy can serve as the tracking element without the aid of any other reference points.

The surgical instrument tracks the position of the tracked element by means of one or more trackers. In one embodiment, the system utilizes stereoscopic placement of two cameras as the tracker. In some embodiments the cameras are stereotactic vision cameras. The cameras are side by side, tilted at a range of angles suitable for stereo-vision, on either side of the saw's blade/drill-bit/burr, etc. For other tools, such as a drill, the cameras can similarly be placed stereoscopically, side by side, on either side of the drill bit or any other tool's end effector.

The placement of the cameras, relative to the end effector of the tool, impacts the operation of the tracker-tracking element subsystem. For example, placement of the camera or cameras far back from the end effector expands the field of view. For applications like joint replacement, or when the tool is in close proximity to the patient's anatomy, a wide field of view is helpful. With an expanded field of view, the tool can find the tracking element more easily. Placing the camera or cameras closer to the tool's end effector constricts the field of view, but adds magnification and resolution useful for applications such as dental surgery. In addition, placement of the camera must take into account the relative position of the other elements of the subsystem. Placing the cameras so their axes are in the plane of the end effector of the tool would minimize the extent to which the end effector blocks the view of the cameras. It is contemplated, however, that the cameras may be placed in any configuration that is deemed appropriate for tracking one or more tracking elements in a surgical procedure. As technology advances, configurations beyond those currently described may be more favorable in regards to particular tools and surgical environments.

The sub system can utilize a wide variety of cameras or systems of cameras. Generally, the system utilizes digital cameras. In addition, the system utilizes at least two cameras to provide stereoscopic/stereotactic vision. It is possible to use analog cameras, provided there was effective means of digital conversion such as the established technology of image format conversion which are sometimes known as 'frame grabbers' or 'capture cards'. Stereoscopic vision, and the ability to gain further information based on the differences in the images from the two cameras, helps the system to better locate the tracking element in three dimensions in terms of position and orientation or pose. Systems could utilize more than two cameras utilizing what is known as "redundancy" to improve the ability to navigate, such as in the cases when some of the tracked elements are not visible to one or more of the cameras and thus two cameras would not suffice in those instances. Additionally, a system could utilize a single camera but would need additional image processing to navigate as accurately as a stereoscopic system.

Alternatively, the subsystem could utilize a different system of trackers and tracking elements. In one alternative, the tracker is a high-resolution camera optimized for image recognition under the visible light spectrum present in standard Operating Room conditions. The tracking element is the patient's anatomy, based on the medical image stored in the surgical plan. In addition, a narrower field of view may also benefit the efficient recognition of the patient's anatomy. Finally, the surgical plan itself may need to incorporate or identify particular anatomical landmarks of the patient to establish functional tracking elements.

Regardless of configuration, the cameras need to have sufficient resolution to accurately track the tracking element to a certain predetermined level of accuracy. For example, a system with a tracking element that is a reference frame with infrared LED's, cameras with 640×480 resolution have sufficient resolution to track the tracking element with surgical accuracy. Systems can utilize additional elements, such as infrared filters, and isolate the tracking element for the cameras. A lower resolution camera, in such a system, can be sufficient to produce highly accurate tracking.

Resolution is not the only characteristic of the cameras that influences the operation of the system. The frame rate is an important consideration, depending upon the particular configuration of the system. For example, a very high frame rate of around 100 Hz (frames per second) would produce minimal latency but would be very burdensome on the image processor. The system would require a powerful processor in order to extract the tracking element from so many captured images in a given unit of time. Alternatively, if frame rate is too low then the system will produce too much latency. If the operator were to move the tool too quickly then the system would not be able to continuously track the tool. The minimally acceptable frame rate should be utilized in the system. For a system that utilizes infrared LED's in the reference frame along with an array of VGA cameras, a frame rate of 30 Hz would produce a system suited to freehand orthopedic surgery.

Together, these examples illustrate a variety of configurations for the tracking element and the cameras that comprise the exemplary camera-tracking embodiments of the tracker-tracking element subsystem. In addition to the accurate placement of the tracking element, the tracking element's location must be extracted from the images captured by the camera. An image signal received from the cameras must undergo digital signal processing (DSP) to convert the image of the tracking element to mathematical coordinates, relative to the tool. The mathematical coordinates are then sent to a computer system and compared against the surgical plan, allowing the computer system to determine if the surgical path is following the intended resection.

Consider that there are several steps to process the raw data from the cameras into the mathematical coordinates. Initially, the system must acquire the image. For the camera detecting the markers (e.g. infrared LED's, reflecting bodies, fiducials, etc.), the system must: determine the coordinates of the centroid of each of each individual marker used in the overall tracking element, determine the sizes of each element, and report the size and shape and the coordinates of each LED to the computer system. Additional operations to process the captured image, such as sub-pixel analysis to determine the location of the centroid can improve accuracy.

For systems that operate at 30 Hz, steps must be completed in approximately 33 ms, and the computer will need to determine the relationship between the individual LED's and calculate the position and orientation of the tracking element. From that data, the computer will have to determine the orientation of the model and the relative positions between the bone and the surgical tool. The signal processing only has the amount of time between two successive frames to perform any needed operations. (For example, for a frame rate of 30 Hz, the processing system has the above mentioned 33 ms period to perform these operations) In one embodiment, the majority of the forgoing steps can be accomplished on the tool itself often by integrated CPU's on the cameras (or other trackers) themselves.

For example, additional processing of images captured by the cameras can be accomplished via a CPU that is integrated into the camera, or on the computer system or some combination of the two. For example, many small cameras have integrated CPU's capable of running digital signal processing algorithms prior to exporting the data signal. The DSP can comprise a simple step, like converting color images to grayscale or complex operations, like cropping the video image to a small box that surrounds the identified LED's. The initial processing makes the final extraction of the tracking element from the images captured on the camera less computationally burdensome and the overall tracking process more efficient. In some embodiments the camera subsystem transmits raw image data. Additional details on the characteristics of the cameras are also described in the camera section below.

The camera-tracking element subsystem can either utilize digital cameras with digital image transmission, or with wireless transmission. There is a wide variety of cameras with digital image transmission which are generally termed "IP" or "Wifi" cameras. Many small, low cost solutions can be used, streaming images (which can be synchronized between two cameras) in any format (e.g. Mpeg) and fed to the processing electronics through one of many known digital streaming protocols. Alternatively, analogue Image transmission can used as has been in model airplanes with what is known as First Person View (FPV) technology. This facilitates readily available commodity cameras, with minimal weight and size, small wireless transmission and low cost. After image processing and extraction of the coordinates for the tracked elements, additional processing is necessary to create tracking data sufficient to inform the computer system. The coordinates of the tracked elements are combined with information about the cameras (such as the specifications and calibration data) to further refine the location space of each tracked element. Based on the refined location of each tracked element, the sub system utilizes user-defined definition of clusters for the particular tracking element (sometimes called a reference frame) to detect valid clusters for the tracking element and their position and orientation in space. The data determining position and orientation in space is the formatted for use. For example, the system can place the special coordinates into a matrix that is compatible with the overall definition of the space used in a surgical plan.

The forgoing processing is different from the processing that can occur on the tool and is not image conditioning and spatial extraction. It can be processed through dedicated software that could be in the same computer system where the surgical plan and planned resection is computed or it could happen on an intermediary computer that could be on the tool or separate from both the tool and the computer system.

Additional navigation data can augment the camera-tracking element system. The tool can further contain one or more accelerometers or inertia sensors to determine the orientation and movement of the tool along the surgical path. The accelerometers can provide additional data to the computer system, in addition to the tracking data from the camera or cameras. Alternatively, an external tracking system can augment the on-board tracking of the tool. No such application is required but can serve to augment the tracking capability of the system mainly by 'anticipating' the movement of the user. Systems could further include multiple tracker-tracking element modalities. For example, the system could include an infrared camera and a tracking element with an infrared LED as well as a visible light camera for optical resolution. Tracking information from both could be processed to establish the coordinates of the tool in three dimensions.

As is typical in computer aided surgery, a surgical plan is determined before commencing the desired surgical procedure or prior to performing a step in the desired surgical procedure. The surgical plan is based on intended resections designated by the surgeon on a computer rendition of a patient's anatomy. A computer rendition of a patient's anatomy may be procured through a variety of medical imaging techniques, such as CT or MRI scanning. In addition, a computer rendition of a saw, drill, burr, implant, or any surgical instrument or part thereof may be procured by design specifications (or models) programmed into the computer system. Once a computer rendition of patient's anatomy is accessible through a computer interface such as a display, mouse, keyboard, touch display, or any other device for interfacing with a computer system, the surgeon may manually designate resections for the surgical plan by entering one or more cuts to be performed, a region to be drilled, or a volume of tissue to be removed into the computer system. Alternatively the computer system may be configured to generate the surgical plan based on a set of specified parameters selected by the surgeon. The specified parameters may correspond, for instance, to the shape, size, and/or location of an implant that the surgeon wishes to attach to the patient's anatomy. The computer may accordingly generate a surgical plan comprising the resections necessary to fit the implant to the patient's anatomy. Once the surgical plan is designated by the surgeon, the computer system translates the surgical plan into one or more mathematically defined surfaces defining the boundaries of the intended resections that comprise the surgical plan. Data acquired by the previously described tracker-tracking element subsystem can then be used to compare the instrument's surgical path with the surgical plan in order to determine the deviation of the surgical path.

Next, the surgical plan is delineated as one or more surfaces mathematically defined in an acceptable three dimensional coordinate system such as Cartesian, spherical, or cylindrical coordinates, or other anatomically based coordinate systems. For example, in a surgical plan that uses Cartesian coordinates, a cut may be defined as a specified distance along each of the X, Y, and Z axes from an XYZ coordinate defining the origin. The specified distances along each axis need not be linear. For example, a cylinder representing a region to be drilled in the patient's anatomy may be defined in Cartesian coordinates as a circular surface having a specified diameter located around an origin and protruding for a specified distance from the origin in a direction that is perpendicular to the circular surface. Any cut, series of cuts, or volume of tissue to be removed may be mathematically defined through a similar approach of defining surfaces that delineate the boundaries of the surgical plan that the surgical instrument must follow to complete the designated resections.

As previously noted, the surgeon may manually designate the resections of the surgical plan on a computer rendition of the patient's anatomy. In one embodiment the surgeon can use the computer interface to view and manipulate a three dimensional rendition of the patient's anatomy and make marks representing cuts. The marks made on the three dimensional rendition are then translated into the mathematical surfaces delineating the surgical plan that the surgeon must follow with the surgical instrument.

In surgical procedures utilizing implants such as a total knee replacement surgery, it is advantageous to use the physical specifications of the implant when delineating the surgical plan for better assurance that the implant will fit onto the patient's anatomy correctly. In such an embodiment, the surgeon can use the computer interface to view and manipulate a three dimensional rendition of the patient's anatomy as well as one or more specified implants. For example, the surgeon may be able to choose from a catalog of implants having different physical characteristics such as size, shape, etc. The surgeon may choose the appropriate implant and manipulate the three dimensional rendition of the implant to fit over the three dimensional rendition of the patient's anatomy in the desired alignment. The surgeon can then select an option for the computer system to generate the surgical plan comprising the planned resections required to prepare the patient's anatomy to receive the implant. Accordingly, the computer system may be configured to generate the appropriate mathematical surfaces to delineate the surgical plan by calculating the surfaces at each intersection between the computer renditions of the implant and the patient's anatomy as they have been aligned by the surgeon.

In order to guide the surgeon to follow the surgical plan with the surgical instrument there must be a means for comparing the path of the surgical instrument with the planned resection. The tracker-tracking element subsystem may accordingly track the three dimensional location and orientation of the mathematically defined surfaces of the surgical plan relative to the tool. In one embodiment, the mathematical surfaces are referenced by the tracking element located at a fixed position on the patient's anatomy. For better accuracy the tracking element may be fixed to rigid tissue at an easily identifiable location. Doing so will simplify registration of the patient's anatomy with the tracking system and will avoid unwanted error that may be caused by unpredictable movement of soft tissue. Once the patient's anatomy is registered with the tracking system, the mathematical surfaces defined in the computer system can be tracked based on their coordinates relative to coordinates of the tracking element's fixed position. Since the tracking system is located on the surgical instrument, tracking data collected by the tracking system regarding the location and orientation of the patient's anatomy and the corresponding mathematical surfaces of the surgical plan are relative to a defined reference point on the surgical instrument. Accordingly, during the surgery, the computer system may use the tracking data to make iterative calculations of the deviation between the surgical path followed by the surgical instrument and the surfaces of the surgical plan. Errors in alignment between the surgical path and the surgical plan as well as corrective actions may be communicated to the surgeon by an indicator such as a graphical notification on a computer screen, LCD, or projected display, a flashing light, an audible alarm, a tactile feedback mechanism, or any other means for indicating deviation error.

In one aspect, an indicator is a system to provide guidance to the surgeon on how to align the surgical path to achieve the intended resection of the surgical plan. In one embodiment, the indicator is an element of the computer system used to provide information to the surgeon in the operating room. U.S. patent application Ser. No. 11/927,429, at paragraph [0212] teaches the use of an operating room computer to guide the surgeons operation of a surgical tool. One means of indication taught in the '429 patent is the actuation of the surgical instrument. As the surgeon's surgical path deviates from the intended resection, as detected by the on-board camera-tracking element subsystem, the computer system will communicate with the surgical tool to slow or even stop the tool from operating. In such a system, the actuation of the surgical tool is the means by which the surgeon receives indication from the computer assisted surgery system as further taught in the '429 application at paragraph [0123].

In another embodiment, the computer system could indicate when the surgical path deviates from the intended resection via an external display. The computer system can display a three dimensional rendition of the surgical tool and the patient's anatomy. Overlaid onto that image is a three dimensional rendition of the surgical plan. The computer system updates the relative position of the surgical tool and the patient's anatomy, as determined by the camera-tracking element sub system, and overlays the intended resections. The surgeon can then utilize the display to align the surgical path with the intended resection. Similarly, the relative position of the surgical tool and the patient's anatomy can be displayed on other screens, such as a personal eyewear display, a large projected display in the operating room, a smartphone or a screen attached to the tool. The combination of an external screen, such as the one on the computer system, and other screens, such as a screen on the tool itself, may provide the surgeon with an optimal amount of information. For example, the screen on the computer system can provide the surgeon with a global overview of the procedure whereas the screen on the tool can provide particular guidance for a specific resection or step in the procedure.

A screen on board the surgical tool is taught in the '429 application at paragraph [0215]. The on board screen could display the same kind of image as described above on external display. An exemplary implantation in the context of an OTT device is shown and described in FIGS. 52A and 52B. The on board screen could display a simplified depiction of the alignment of the surgical path and the intended resection. In one embodiment, the simplified display is comprised of three lines. The surgical path is depicted by two lines, one small and one large. The small line depicts the distal end of the surgical path while the wider line depicts the proximal end of the surgical path. The third line depicts the intended resection. The first two lines are calculated from the navigated position (location and orientation) of the surgical tool. The computer system compiles all three to display on the screen on the surgical tool. The display shows both the proximal and distal parts of the surgical path, indicating to the surgeon its relative position in three dimensions. When the surgical path is aligned with the intended resection, all three lines are aligned. The indicator shows the surgeon how to correct the position of the tool in three dimensions.

In one embodiment, the display is optimized to provide guidance for navigating a saw. The surgical path is depicted by lines, which roughly correspond to the shape of the cut that a saw makes. In another embodiment, the simplified depiction could be depicted by two circles: a small circle depicting the distal end of the surgical path and the larger depicting the proximal end. A second shape that is roughly equivalent in size, such as a cross or diamond, depicts the intended resection. As previously described, the surgeon can align the surgical path to the intended resection by lining up the shapes. The circles depict the surgical path of a different tool, like a drill. In this manner, the system can provide guidance for a wide variety of surgical tools. In one embodiment, the position of all of the elements described in the indicator should be updated, by the computer and tracking sub systems, at a rate that is faster than human reaction time.

One limitation of surgical displays is that they divert the surgeon's attention away from the patient. One solution is to project the indication information directly onto the part of the patient's body where the procedure is taking place. Any variety of projectors could be placed onto the tool and display any of the indication methods onto the patient. In one embodiment, an on board Pico projector could display the three line simplified approach described above. In many respects, the third line would be enormously helpful as it would depict, precisely onto the patient, where the intended resection would start relative to the rest of the patient's anatomy. In addition, the indicator can provide more direct guidance as to how to correct the surgical path for alignment with the intended resection and project the guidance information directly onto the patient. For example, the projector can depict an arrow that points in the direction the surgeon needs to move to correct the surgical path.

There are several challenges to accurately project the indication information onto the patient anatomy. Foremost, for an onboard, on-the-tool approach, the projection platform would be constantly in motion. In addition, the surface that the projector is projecting on is not flat. To resolve the second question the system utilizes information obtained during the surgical planning. First, the system knows the geometry of the surface of the patient's anatomy. The surgical plan contains a medical image of the patient, such as a CT scan, from which it can extract the geometry of the surface that the indicator will project on. The system accordingly projects guidance information so that it is properly seen by the surgeon viewing the projected information on the surface of the patient's anatomy For example, if the system is to indicate where the surgeon should cut with a saw, by utilizing a straight line, then the system can bend and curve the line so that, when projected onto the patient's anatomy, it will appear to be straight. Utilizing that approach, the indicator can project the three line simplified depiction of alignment taught above.

Similarly, the system also calculates the relative position of the tool by means of the tracking system. With that information, the system can continuously modify the angle of projection to ensure that the indicator projects to the proper position of the intended resection on the patient's anatomy. The indicator can use a wide variety of projectors such as a mini standard-LED projector or a laser-scanning pico projector system. Notwithstanding, nothing in the forgoing prevents the utilization of a projector that is not on board the tool or used in any other form of computer-assisted surgery. For example, an externally tracked system could include a separate projection system that would similarly project indication information onto the patient's anatomy.

In addition to a screen or a projector on board the saw, the system can utilize a smartphone or tablet computer, such as an Apple IPhone 4G, to provide indication to the surgeon. An indicator that uses a smartphone or tablet computer has the further advantage of a removable screen. Additionally, just as the on board screen, the smartphone can display renditions of both the tool and the patient or a simplified image, such as the two line embodiment. A different simplified display could provide indication when the surgical path and the intended resection are aligned and direction when they are misaligned. For example, if the surgeon is approaching the resection too low, then the screen can depict an arrow pointing up. The arrow can be rendered in three dimensions, providing further indication to the surgeon.

For simplified indicators, the display need not be as robust as a smartphone or other high-resolution screen. A bank of LED's, for example, could display either the three line or arrow indication previously described. The Indication method need not be visual. The system could audibly indicate to the user when the surgical path deviates from the intended resection, as further described in the '429 application at paragraph [0122].

As detailed above, computer assisted surgery proceeds from a computer-based anatomical model such as those based on images and reconstruction obtained using any known medical imaging modality, or from anatomical models generated through morphing or other known processes for rendering anatomical or bone models for use in computer aided surgery with the aid of computer-based anatomical models, a surgical plan is developed to be implemented for a specific patient and procedure. Surgical preplanning includes a number of steps such as obtaining pre-surgery image data, surgical planning for the specific procedure to be undertaken, adaptations of the plan for patient specific anatomy or condition and, if appropriate, to any specific prosthesis, devices, implants, or other structures to be placed in, joined to or used at a chosen 3D alignment during the CAS procedure. With this general pre-surgical planning information in hand the surgeon moves to the patient specific intraoperative planning to be implemented at the surgical site. The patient specific intraoperative surgical plan will be adapted to address the specific site or specific procedure such as any orthopedic procedure or minimally invasive procedure that may be enhanced through the use of computer assisted surgery. For example a specific joint may be aligned for some form of repair, for partial replacement or for full replacement. It is to be appreciated that the techniques described herein may be applied to other joints such as the ankle, hip, elbow, shoulder or for other portions of the skeletal anatomy (e.g. osteotomies or spine surgery procedures) that would benefit from the improvements to computer aided surgery described herein. Examples of skeletal anatomy that may benefit from these techniques include, without limitation, vertebrae of the spine, the shoulder girdle, bones in the arm, bones in the leg, and bones in the feet or hands.

By way of a non-limiting example a total knee arthroplasty will be used as a specific example. For purposes of discussion the total knee arthroplasty will normally include five surgical cuts for the femur (on a CR or PCL retaining and eight cuts on a PS or PCL sacrificing) and one or more cuts for the tibia each of them described below in greater detail. It is to be appreciated that these cuts may be modified to emphasize a particular aspect or aspects of a portion of a surgical procedure or step. For example, the specific geometry, orientation, or feature of a prosthetic device for a particular procedure may lead to modifications in certain aspects of the surgical plan. In another example, a particular procedure or prosthesis may benefit from a specific type of cut, tool, or surgical approach. Any of these factors may also be used to adjust the way that the computer aided surgery proceeds according to the embodiments described herein. By way of a non-limiting example, the computer aided surgery system may select the surface (e.g. plane) of cut as the most important information to be presented to the surgeon immediately prior to or during a computer aided surgery step. In still further aspect, and OTT CAS will permit the user to select or base surgical step decisions using 2-D, 3-D or other output information related to a representation of either the surgical tool being used or the resulting use of that tool on the anatomy. For example, if the surgical tool is a saw then the user may select from rectangular shapes generally sized to correspond to the profile of the saw, or to one or more surfaces (in this specific example a plane) that correspond to the resulting cuts formed in the anatomy by the saw. In an additional example, the surgical tool includes a drill and the user is provided with or the system basis processing decisions using circles corresponding to the size of the drill, cylinders related to the anatomical impact of the use of the drill, as well as other factors that might represent the engagement of the drill cutting tip to the anatomy. In still another example, the surgical tool includes a reamer or other spherically shaped tool. In this example, the system or the user is provided with circular, cylindrical, hemispherical, or spherical representations that are likewise used for display and feedback to the user or as part of processing decisions used within the OTT CAS system. In a final example, the surgical tool includes a flat filing blade, whereby the representation will again be a flat surface (or thin rectangular block) depicting a certain thickness of filing action which would result upon contact to the anatomical surface.

In the embodiments that follow, an on-tool tracking system (OTT) embodiment is used to acquire, perform some data-processing on board, and provide real-time data regarding the surgical procedure to the computer-aided surgery computer, and to receive commands from the latter to set its own motor speed, attenuate speed or even stop to prevent unintended cutting. The on tool tracking system is used to provide a variety of data for use by the computer aided surgery system. One form of data is imaging data from imaging sensors provided by the on-tool tracker. The data provided by these imaging sensors include for example stereoscopic images, which once processed, can be used for tracking and information to be projected onto the surgical field by a standalone or an embodied projector or any type of projector provided for use with the on tool tracking system. Other data provided by the imaging sensors includes, reference frame location, orientation, alignment or other physical attribute of a reference frame used for defining the surgical field. One or more reference frames that may be positioned around the field, around the joint, around the knee, or sized and shaped in relation to a surgical field where the reference frame is visible during at least a portion of all or substantially steps of a surgical procedure. (See, for example, reference frame embodiments described with regard to FIGS. 16-30. Still further, data may be selected only from a relevant reference frame or portion thereof based upon the dynamic, real time assessment of a CAS procedure or CAS step.

For example, in a CAS procedure where two frames are present, both may be used at the beginning of a cut and then the system shifts to using only one reference frame used during the cut. In a similar way, the system may use less than all the fiducial markers available on a specific reference frame during a procedure in furtherance of the mode adjustments described below. Fewer fiducials to process may permit faster updates or reduced image processing computer cycle time. As shown and described herein, the reference frames may have the same shape or different shapes and may contain any of a variety of fiducial markers in any of a variety of suitable arrangement for detection by a visual or an infrared tracking system in the OTT. Still further data available from the imaging sensors includes scene information such as anatomical configurations of real or artificial anatomy or structures, markers positioned on the patient, additional targets positioned around the surgical field such as pointers, markers or the instrument being used in the field such as a saw, drill, burr, file, scene information refers to image capture, image processing or camera adjustments to select and process a portion of a frame, adjust a camera to zero in on or focus or zoom to a portion of interest in the surgical field based on real-time dynamic CAS procedures and consideration of a CAS surgical plan, reamer or any other surgical tool to which the on tool tracking system is mounted.

When resecting the various portions it may be desirable to modify the view of the virtual model displayed on the OTT monitor. For instance, when cutting along a first plane it may be desirable to view the virtual model from a first perspective, and when cutting along a second plane it may be desirable to view the virtual model from a second perspective. Accordingly, the OTT CAS system tracks various data regarding the status of a procedure, including, but not limited to the following: the position of the surgical tool relative to the tissue to be resected and the orientation of the surgical tool relative to the tissue to be resected. Based on the position and orientation of both the tissue and the surgical tool, the system calculates which surface is about to be cut during the procedure and update the OTT monitor accordingly.

Further, the OTT CAS system can be configured to account for the preference of each user as well as the characteristics of the instrument using the OTT device. Specifically, a surgeon may desire a different view than the default view for a particular resection step or cutting plane. The system allows the surgeon to override the default selection and specify the view for a particular cut. The system stores the information regarding the desired view for the particular cut for the particular surgeon and uses the view as the default view in the future when the system determines that a similar cut is to be made. The system tracks the user preference based on the user logged into the OTT CAS system.

In addition to the types of data described above, the on tool tracking system may also provide other kinds of data such as output from one or more sensors on the on tool tracker. Exemplary sensors include position sensors, inclinometers, accelerometers, vibration sensors and other sensors that may be useful for monitoring, determining or compensating for movements of the tool that is carrying the on tool tracking system. For example, there may be sensors provided within the on tool tracking system to compensate for noises or vibrations generated by the tool so that the noise and vibration may be compensated for i.e. cancel out of the imaging data or other OTT data being transmitted to the computer aided surgery system computer. In still another example, an accelerometer or motion sensor may be provided to produce an output to the computer aided surgery system used in predicting the next frame or estimating where relevant information in an imaging frame may be located based on the movement of the tool and a tracking system. In still another aspect, sensors carried on board the on tool tracking system may be used to detect, measure and aid in canceling unwanted movement that may interfere with, impair the quality of or complicate CAS or OTT image processing. Specific examples of this type of feedback include sensors to detect and aid in the cancellation of hand shaking or movement by the user. In still another example sensors may be provided to detect and aid in the cancellation or compensation of unwanted movements or other interference generated during active surgical steps.

In other variations, image capture, processing and camera adjustment may also be used in or become the subject of compensation techniques, including to dynamically optimize the field-of-view and volume-of-interest. In one example, a camera provided on the OTT contains an auto focus capability that, under instructions from the CAS computer and the various factors described herein, will dynamically adjust the camera and view to zoom, track, pan or focus on a frame, a portion of a frame or a natural or artificial feature. In another aspect, the imaging portion of a camera on the OTT is provided with a suitable on board movement system to tilt or adjust the lens to direct the lens to one or more features under the direction of the CAS computer. This tilting lens may be used in conjunction with the dynamic lens above or with a lens having fixed (i.e., not adjustable characteristics). In one aspect, a micro mechanical base supporting the camera lens is adjusted according to the instructions from the CAS computer. It is to be appreciated that while the lens/camera adjustment may be done internally with a MEMS structure, it may be done external to as well. For example, a camera in a housing may be carried by a dynamic stage (x-y-z or x-y motion for example) where the state receiver instructions from the CAS computer to adjust the camera position in accord with the OTT CAS processes described herein. Still another form of compensation provides for image processing or other adjustments for OTT-tool orientation such as top mounted OTT, left side mounted OTT or right side mounted OTT. Still further, the various aspects described above for controlling the field of view (including either or both of the horizontal and vertical field of view alone or in any combination) along with adjustments to a volume of interest within the surgical field may be accomplished dynamically and optimized in real time utilizing the instructions contained within the OTT CAS system, the CAS mode select processing sequences and/or any of the specific CAS mode algorithms including vision based algorithms or specific mode algorithms.

Another example of settings and compensation techniques include the implementation and switching on/off of infrared filters placed in front of the camera lens so that the imaging can be of infrared only or emitted or reflected by the reference frame markers to cut-out white light noise and to ease image processing and marker detection.

It is to be appreciated that these aspects of compensation may be implemented mechanical components, electrical components or with software, each alone or in any combination.

For purposes of discussion and not limitation the data from the on tool tracking system will be categorized as imaging data and sensor data to capture the broad categories described above. Using system resources provided either on the on tool tracking system itself or provided by the computer-aided surgery computer, the data is processed to provide an output for use by the computer aided surgery system. The desired output of data processing comes in a number of different forms depending upon the specific processes being evaluated and as described in greater detail below. For purposes of this overview, one may consider that the data output obtained from the on tool tracking system may include such things as the orientation of the on tool trackers in the surgical field, the position of the tools or the on tool trackers in relation to the surgical field, information regarding the surgical field such as physical changes to the anatomy undergoing surgery, movement of the OTT tracked tool within the surgical field, displacement of the tool within the surgical field, apparent progress of the surgical step being tracked and other information related to the initiation, progress or completion of a surgical step or a computer aided surgical procedure.

The output of the on tool tracker, in whatever form suited to the particular computer aided surgical procedure undertaken, is next compared to the step, or procedure undertaken according to the surgical plan. The result of this comparison produces an output back to the on tool tracker that gives information related to the plan, step, or progress with in a step of the surgical plan. In general, this output is manifested for the user as the result of a projected image from a projector on board the on tool tracker, but it can also include audio feedback, changes/messages in a computer screen if available, actions on the cutting tools (e.g. changes of cutting speed, direction and stopping), etc. It is to be appreciated that the output from this projector (as example) may be adapted based on a number of considerations such as the available surgical field upon which an image may be projected, the likely position and orientation of the on tool tracker and its tool to the surgical field, and the likely challenges of making the projected image visible to the user. As a result, the onboard projector is capable of projecting images in a variety of configurations based upon the dynamic, real-time circumstances presented during the surgical procedure. Moreover, the on tool tracking system may be provided with additional illumination sources to enable the system or the user to obtain image data in the visible spectrum, infrared spectrum, or in any other spectrum suited to image processing using the on tool tracking system. In still further aspects, one or more of the CAS mode processing methods described herein may be modified to incorporate the use of any of a variety of pattern recognition, computer vision, or other computer-based tracking algorithms in order to track the location and orientation of the OTT instrument in space relative to the surgical site, or relative to other instruments near the surgical site, and progress of an OTT CAS surgical step, without or substantially without the use of reference frame-based tracking information. In other words, the embodiments of an OTT CAS method include the use of visual information obtained from the trackers or cameras on board the OTT for the purpose of identifying, assessing, tracking, and otherwise providing the CAS data sufficient for the purposes of providing appropriate CAS outputs for the user to complete one or more CAS processing steps. In one aspect, a portion of the anatomy within the surgical field is marked or painted for the purpose of enhancing vision based tracking and vision based algorithm processes. As a result of being provided information from the projector of the on board tracking system, the user may respond to that information by making no change to his actions or by adjusting, as warranted under the circumstances for the step or procedure, one or more of the operation, placement, orientation, speed, or position of the tool in the surgical field. The information from the projector may be provided alone or in combination with other OTT components or feedback or indications such as tactile or haptic feedback.

Next, the continued action or change of action by the user is detected by the on tool tracking system and the process of providing data processing data and providing it for comparison and evaluation by the computer aided surgical system continues.

Against this general overview is to be appreciated how, in use, embodiments of the on tool tracking enabled computer aided surgery system described in herein monitors and evaluates one or more of the position, movement, use, predicted movement of an instrument using the on tool tracker against the planned computer aided surgery procedure and produces appropriate computer aided surgery outputs to the user based at least in part on a real-time computer aided surgery assessment by the computer aided surgery system.

Figure 31A:
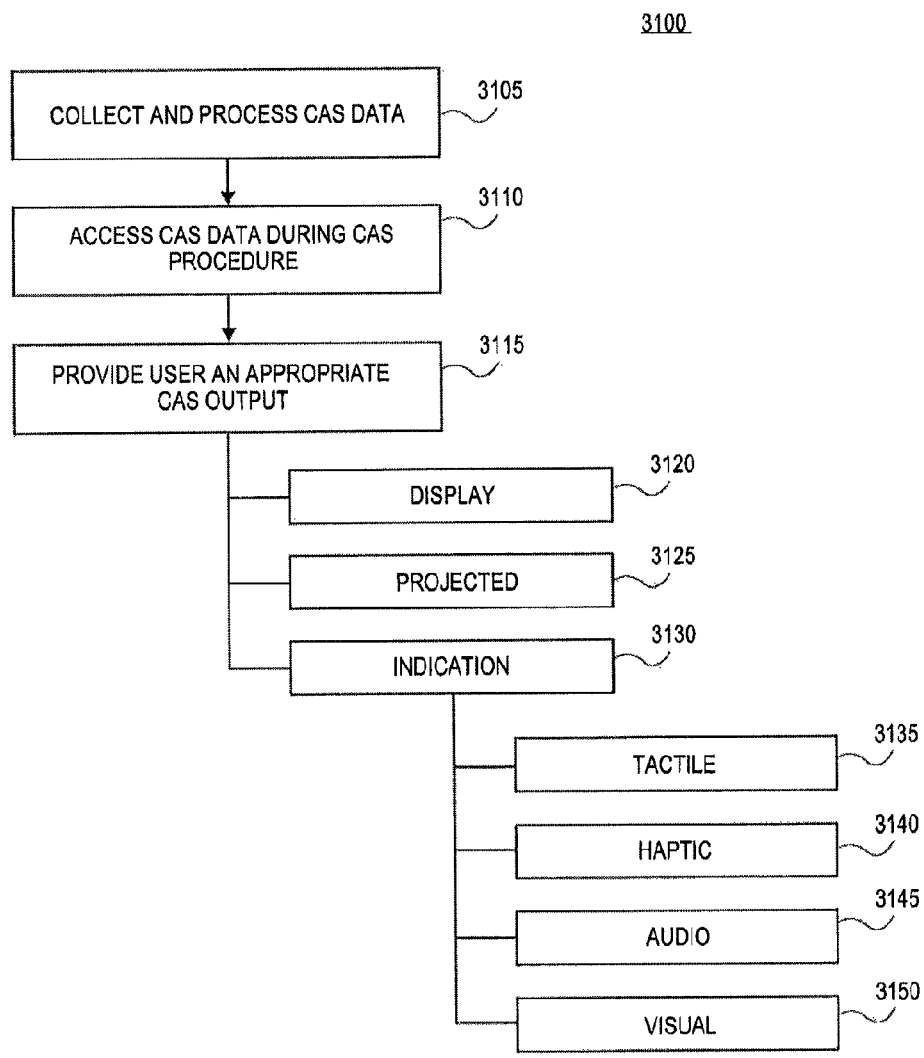
FIG. 31A is a flowchart representing an exemplary loop of a cyclic OTT CAS method (i.e. looped or repeated in time).
Figure 31B:
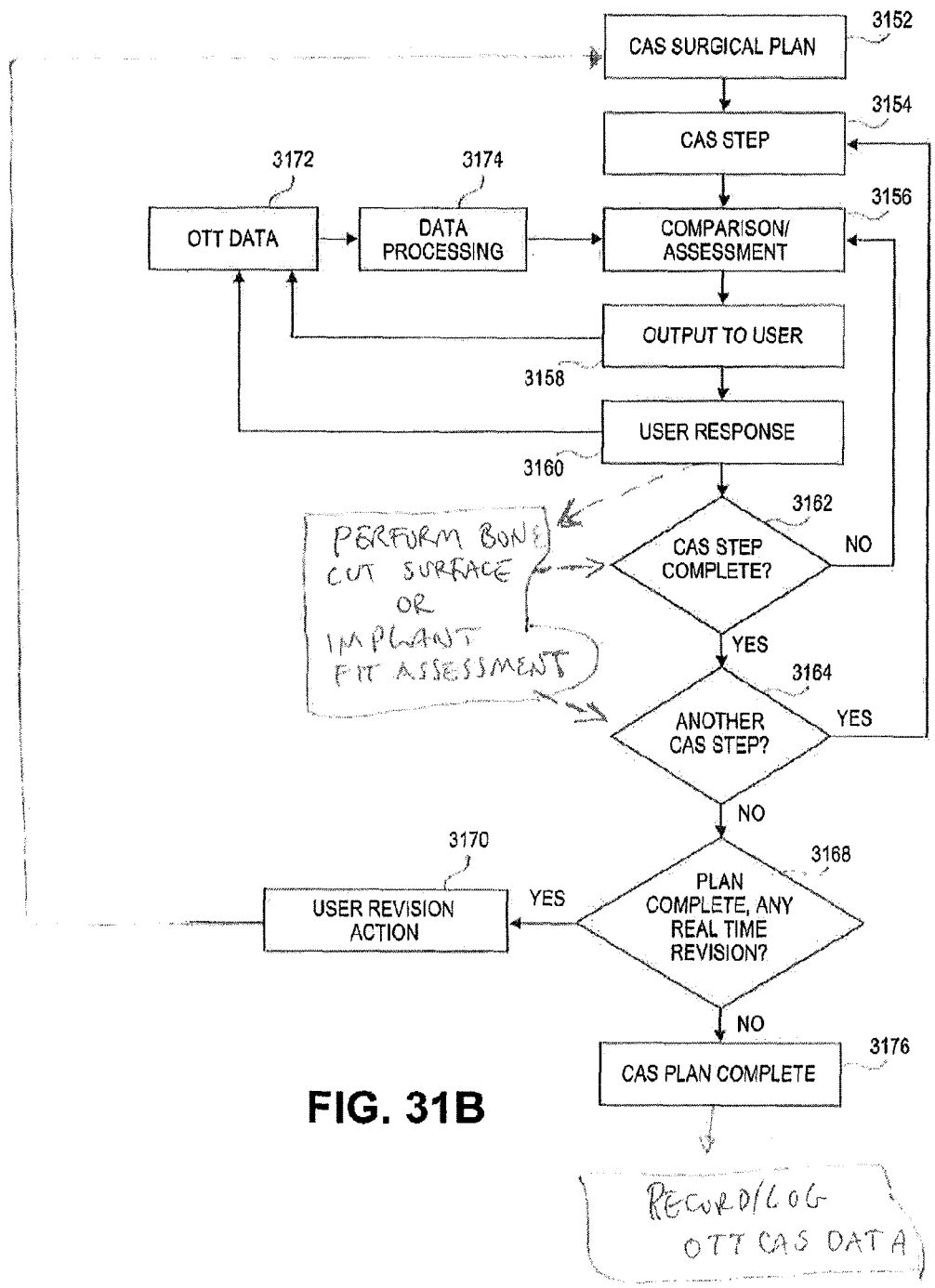
FIG. 31B be is a flowchart providing additional details of the exemplary processing steps performed using the method described in FIG. 31A.

Turning now from the general overview to more specific discussions of how computer aided surgery is modified by the use of the on tool tracking system described herein. FIG. 31A illustrates a general process flow of information for computer assisted surgery. FIG. 31B similarly represents the general step wise approach used during the actual delivery of the computer assisted surgical plan. These two flow charts will be used to provide a general frame work for the improvement to computer assisted surgery according to embodiments described herein.

With reference to FIG. 31A, information obtained by the system is processed. This can include information from a variety of sources located within the surgical field or from instruments used during surgical procedure in a continuously running feedback loop. Next, the information that has been obtained and processed is assessed using an appropriate computer assisted surgery algorithm. Finally, an output is produced from the assessment to aid the user in performance of the surgical procedure. The output produced may include one or more of the display, a projected image, or an indication. Indications may include, for example, a tactile feedback signal including for example temperature variations, a haptic feedback signal with forces or vibration of different frequency and/or amplitude, remote or onboard control of the instrument's motors or actuators with regards to their speed, direction, brake and stopping, an audio signal or visual signal provided to the user in a manner appropriate to the circumstances and use of the on tool tracking system and the instrument attached thereto.

While similar to the conventional computer aided surgery in some respects, the systems and techniques described herein are different and provide unique advantages over conventional computer assisted surgery systems and methods.

The on tool image and projection module is adapted and configured with a number of different characteristics based upon the type of computer assisted surgery being undertaken. OTT position in relation to surgical field during expected use for a CAS procedure, orientation of projector to the tool being guided, shape and surface condition (i.e., rough presence of blood or surgical debris) of the surface in the surgical field being projected on, horizontal field of view accommodation, vertical field of view accommodation are just a number of the considerations employed in the embodiments described herein.

Still other embodiments of the computer aided surgery system described herein compensate for variations and alternatives to the component selection and configurations resulting from the above described features. One exemplary compensation relates to camera adjustment or image adjustment (discussed above) for the surgical step or field adjustment based on a particular computer aided surgery technique. Another exemplary compensation relates to the actual projector position on a particular embodiment. The projector position of a particular embodiment may not be on the centerline of the device or in an optimum position based on horizontal or vertical field of view or may be tilted in order to address other design considerations such as making a device smaller or to accommodate other device components. One form of compensation for this aspect is for the projector output to be adjusted based on the actual projector location. This type of compensation is similar to keystone adjustments for a projector output. The projector provided on board the on tool tracking system may have its output compensated for the expected or actual portion of the surgical field where the projector output will display. During the surgical procedure the surgical site is likely not to be flat and so would not faithfully reflect the intended image from the projector. However, since the geometry of the target anatomy (e.g. bone surface) is known, the image to be projected by the projector can be changed by software to compensate such that when projected on the non-flat surface, it would appear clearer as intended to the user. The target anatomy surface for projection may vary in shape, orientation, curvature or presence of debris, blood and still further, the output of the OTT projector may be adjusted based on real time factors such as these detected by the OTT vision system and object detection techniques. When the cutting has started, there would be a new source of 'unflatness', namely, the interface between the original native surface of the bone, and the new surface introduced by the cut. This can be calculated (and compensated for) during cutting by logging where the cut was made, or assumed to be the desired ideal/planned surface, or digitized (e.g. with the pointer) after each cut.

Still further differences between the OTT surgical technique and conventional computer assisted surgical techniques include the types and manner of providing outputs or receiving inputs from the on tool tracking system or the user. Sensors and systems to provide tactile, haptic or motion feedback may be used as well as a variety of indicators such as alarms, visual indicators or other user inputs specific to the capabilities of a specific OTT system.

FIG. 31B relates the general OTT enabled CAS process with added details to call of additional aspects of the OTT CAS system. When the procedure begins, the user has a selected surgical tool with the on tool tracking system mounted thereto in either top mount, right side mount, left side mount or bottom mount as determined by the user and the OTT CAS plan. The tool with attached OTT is identified to the system through a tool registration procedure such as the tool transmitting an identification signal or a self-registration process or other suitable registration process. The pre-surgical planning steps, as needed, are completed according to the procedure to be undertaken. Beginning with the computer aided surgery surgical plan, the user initiates a computer aided surgery step. As a result of the use of the on tool tracking system, on tool tracking data is generated. The on tool tracking data is processed and then provided to the computer system that compares and assesses the planned surgical step information to that received from the on tool tracking data. As a result of this comparison and assessment of the on tool tracking data, an appropriate output is provided to the user or to the OTT's on board motor control circuitry as a motor or actuator control signal to slow, stop or reverse the instrument or let it continue at the speed desired by the user through the manual onboard hand trigger. This output is detected and acted upon by the on tool tracking system which provides additional data that is again provided to the tracking computer. Next the user responds to the output provided and either continues the current action, or changes the use of the tool being tracked by the on tool tracking system. The users response, whether involving action or not, is detected by the on tool tracking and becomes additional data input to the surgical computer. These processes continue as the computer system processes the progress of the step against the surgical plan. If the answer to step completion is no, comparison of data and output to the user continues. If the answer to step completion if yes, then the user may initiate the next surgical step or the surgical planning computer may provide an output to the user to notify him that one step is completed and any one of other remaining other steps can be undertaken. The sequence of CAS steps to be performed are totally up to the user, except in situations where one step cannot be performed without a prerequisite other step(s) identified in the set surgical plan. The control is totally in the hands of the user, with the computer being only (optionally) suggestive of what steps can be done, or (optionally) prohibitive of what steps cannot be done. These processes continue in accordance with computer aided surgery procedures until the plan is delivered. If the plan is complete, the use may determine whether any real-time revision of the surgical area is to be undertaken. The revision process may also be tracked and monitored to provide information to the user. If no revision is required or the CAS plan is completed, then the CAS plan is completed.

Figure 32:
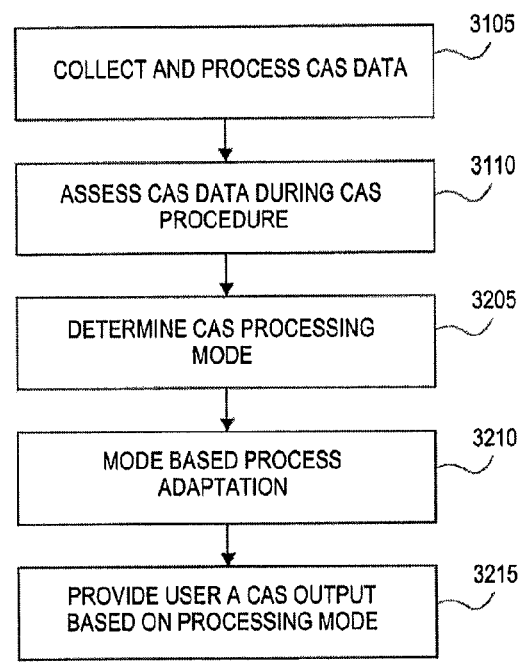
FIG. 32 is a flow chart providing exemplary additional details of the processing steps used for determining a CAS processing mode.

FIG. 32 provides a flowchart that will be used to describe still another improvement to computer aided surgery provided by embodiments of the on tool tracking system described herein. As before, the system will collect and process computer aided surgery data. Next, the computer aided surgery system will assess the CAS data during the CAS procedure. As a result of this assessment, the CAS computer will determine the CAS processing mode. Thereafter, mode based processed adaptation will be applied to the data used in the CAS process. Finally, the OTT CAS system provides a user or the instrument motor/actuator a CAS output (or speed and motor direction set-point) based on the processing mode.

Figure 33:
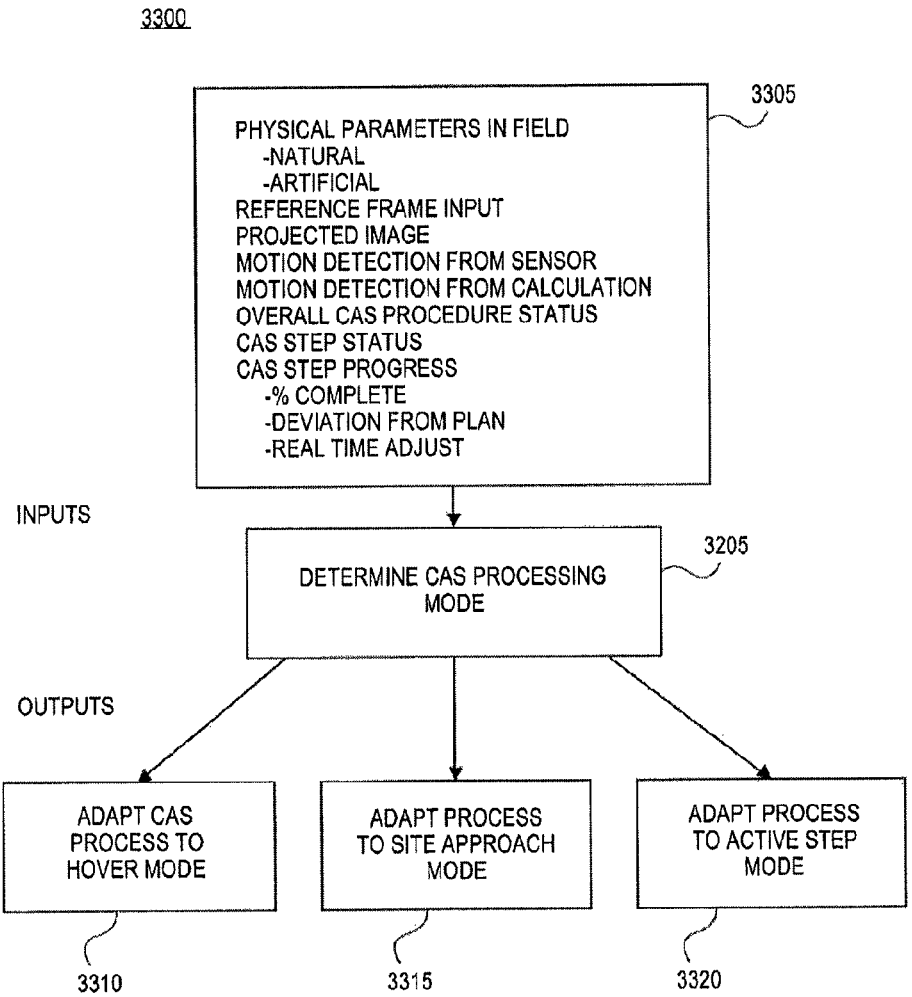
FIG. 33 is a flowchart diagramming a number of factors considered as inputs for determining a CAS processing mode as well as a representative outputs.

Mode selection relates to the OTT CAS system ability for a dynamic, real time assessment and trade off of a number of aspects of the CAS operation including the need to update the user, processing rates, cutting instrument motor control/ actuation instantaneous speed and prospective response times and requirements to obtain improved or different data, relative importance of portions of data based upon CAS step progress or interaction with the patient or other factors relating to the overall responsiveness of the OTT CAS system. Additional aspects of the step of determining the CAS processing mode described above in FIG. 32 may be appreciated with reference to FIG. 33. FIG. 33 relates to the inputs considered by the system to determine the processing mode and the result of that determination. Exemplary inputs used by the OTT CAS system for determining processing mode include, by way of example and not limitation, one or more of the following: speed or motion of the tool or its motor/actuator speed, input or indication from a tool monitoring device, voice input or indication from user, physical parameters in the surgical field, including natural or artificial parameters; reference frame input; projected image; motion detection from sensors; motion detection from calculations; overall CAS procedure status; CAS step status; user input (e.g. CAS screen, OTT touch screen, touch screen, motions sensor, gesture recognition, GUI interface, etc.); CAS step progress including, for example, percentage complete, deviations from plan, real-time adjustments. As a result of the determination step performed by the OTT CAS computer a processing mode will be selected based on the real-time circumstances and evaluation of the surgical procedure as made by the algorithms of the CAS for OTT computer. Criteria used by the OTT CAS computer for determining mode include such factors as the physical proximity of the surgical tool to the patient anatomy, actions being undertaken by the user, sensor inputs of tool motion, predicted tool motion, speed of tool motion, speed of the tool's motor or cutting actuator and other factors related to the placement, orientation, or use of a surgical tool within the OTT image field. By way of non-limiting example, CAS processing modes may include a hover mode, a site approach mode, and an active step mode. In general terms, hover mode refers to those circumstances during an OTT CAS procedure when the on tool tracker and tool is near or within the surgical field without contact between the tool and the patient. In general terms, site approach mode refers to those circumstances during an OTT CAS procedure when the on tool tracker and tool is within the surgical field and in contact with patient, but without the tool actively engaging the patient anatomy to perform a surgical step such as sawing, cutting, reaming, drilling, burring, shaving, filing and the like. In general terms, active step mode refers to those circumstances during an OTT CAS procedure when the on tool tracker and tool is engaged with the patient anatomy to perform a surgical step such as sawing, cutting, reaming, drilling, burring, shaving, filing and the like. As a result of the determine CAS processing mode decision, the OTT CAS computer will adapt the CAS processing mode to or between: hover mode, site approach mode, or active step mode as is appropriate under the circumstances.

Figure 34:
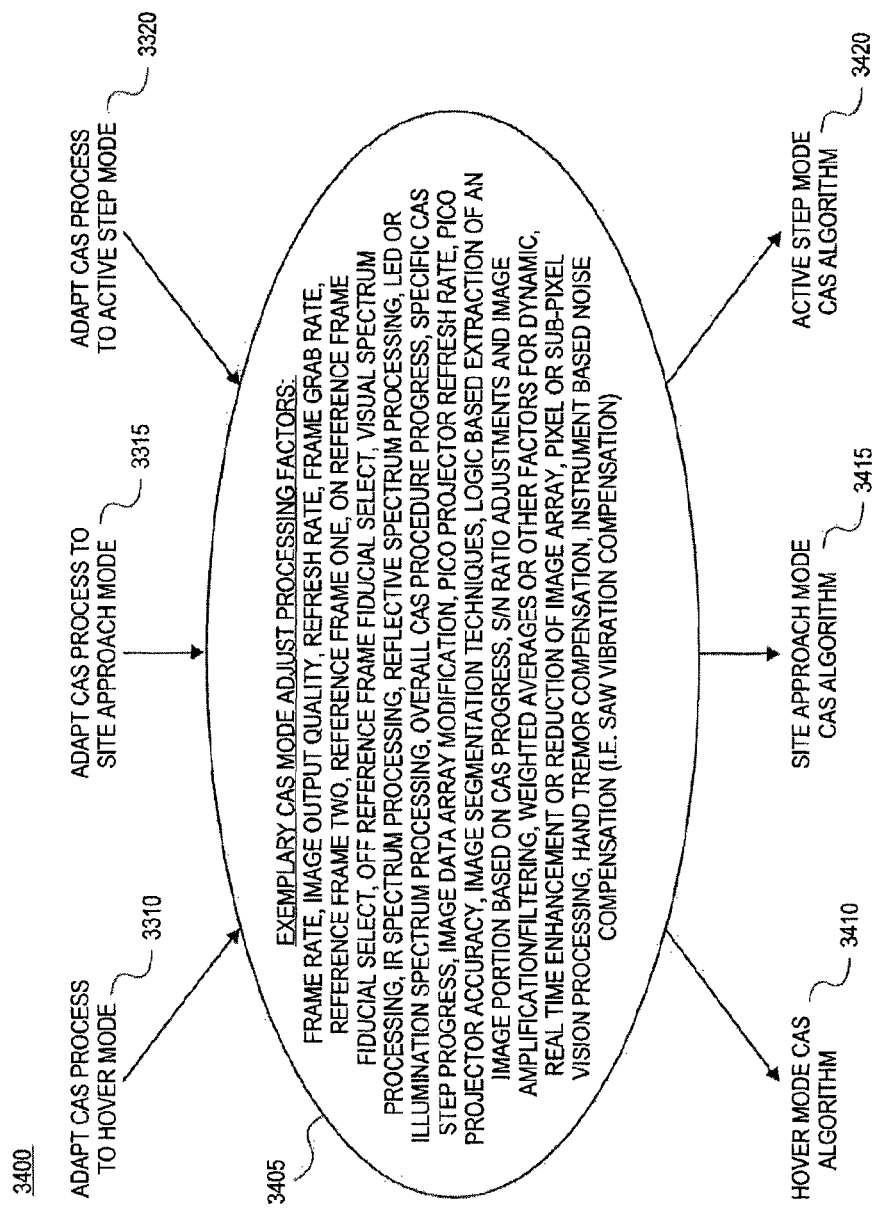
FIG. 34 is a flowchart representing the exemplary OTT CAS mode adjust processing factors used to determine the process loads for a hover mode, a site approach mode and an active step mode.

Step of adapting the CAS process to a particular mode as described above with regard to FIG. 33 is further described with reference to FIG. 34. In general terms, the OTT CAS computer is adapted and configured to adapt the CAS process mode based on adjustment factors to produce a particular mode processing algorithms. By way of example, the various mode adjust processing factors are shown in FIG. 34. Based on the processing inputs as detailed in the flowcharts above, the OTT CAS computer will adjust the processing steps undertaken for OTT CAS based on one or more of or combinations of or variations of the following CAS mode processing adjustment factors: camera frame size and/or camera orientation (if camera software or firmware provides for such adjustment); adjustments to camera image outputs to modify a size of a region of interest within a horizontal field of view, the vertical field of view or both the horizontal and the vertical field of view of the camera; drive signals for adjustable camera lens adjustment or positioning; image frame rate; image output quality; refresh rate; frame grabber rate; reference frame two; reference frame one; on reference frame fiducial select; off reference frame fiducial select; visual spectrum processing; IR spectrum processing; reflective spectrum processing; LED or illumination spectrum processing; surgical tool motor/actuator speed and direction, overall CAS procedure progress; specific CAS step progress; image data array modification; projector refresh rate; projector accuracy; set projector or other OTT electronics "OFF" or in sleep mode or power save mode; image segmentation techniques; logic-based extraction of an image portion based on a CAS progress; signal-to-noise ratio adjustment; image amplification and filtering; weighted averages or other factors for dynamic, real-time enhancement or reduction of imager rate, pixel or sub-pixel vision processing; hand tremor compensation; instrument-based noise compensation (i.e. saw vibration compensation). Put another way, the various factors listed above may be grouped into the various ways of providing adjustments of the camera based on those adjustments that can take place within the camera such as in the software or firmware or operating modalities provided by the camera electronics themselves on the one hand. And on the other hand, on a broader scale, the overall adjustment of the camera in its housing in relation to the OTT housing. In this way camera movement speaks of a more general shifting of the entire camera body or the camera lens itself rather than internal electronic modifications or adaptations of camera output based on electronic processing of camera image information. For within camera variations these are such things as focal point, zoom, exposure, aperture and other camera based modifications that will adjust the cameras output as part of an imaging adjustment. In one specific example, one or more of the above features are used to produce a hover mode CAS algorithm that is used during hover mode processing adaptation. In one specific example, one or more of the above features are used to produce an approach mode CAS algorithm that is used during approach mode processing adaptation. In one specific example, one or more of the above features are used to produce an active step mode CAS algorithm that is used during active step mode processing adaptation.

Figure 35:
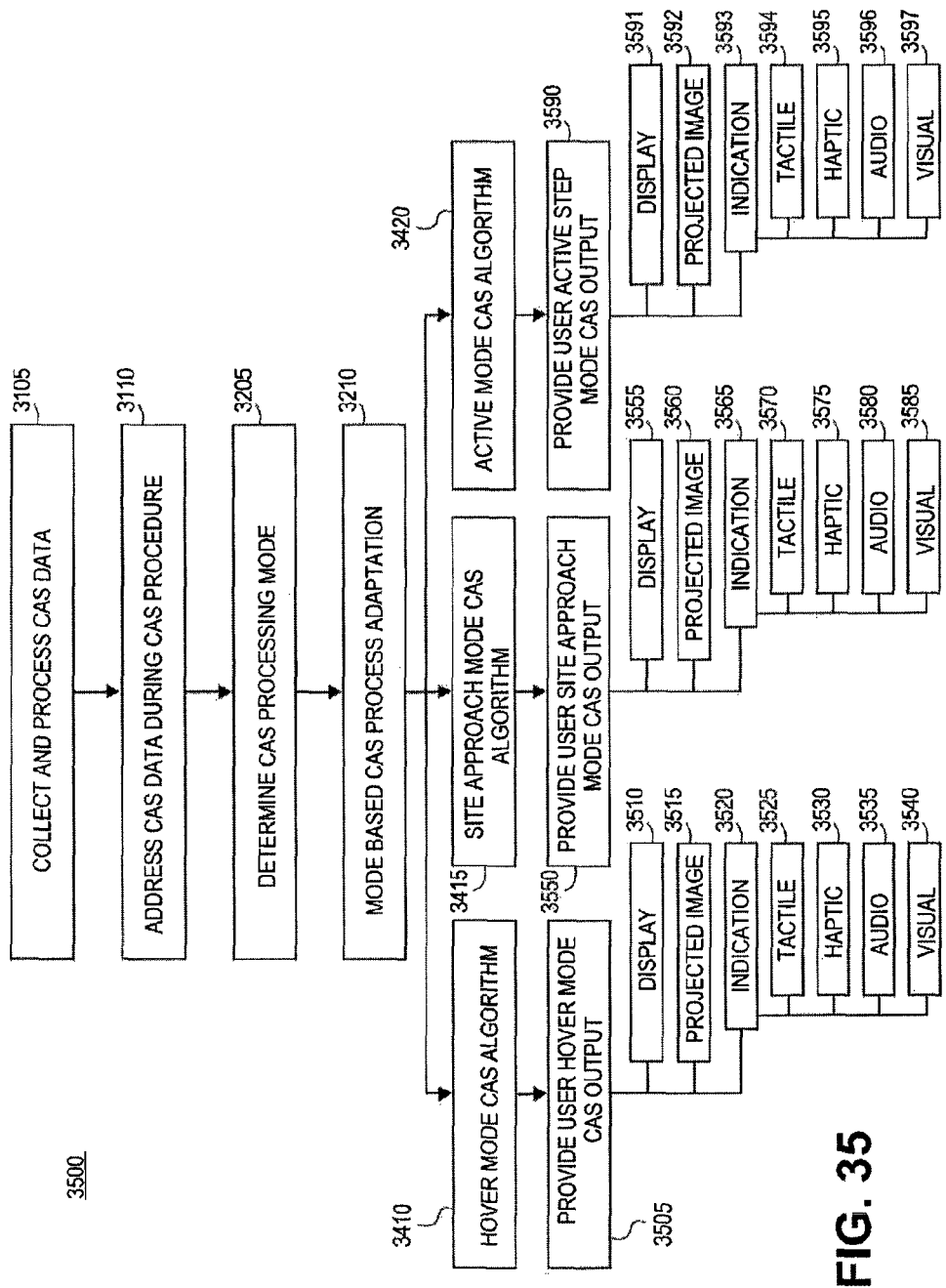
FIG. 35 is a flowchart representing an exemplary OTT CAS process including the result of an OTT CAS process adaptation and the resultant mode algorithm and modified outputs thereof.

FIG. 35 illustrates a flowchart of an exemplary OTT CAS process building upon the steps described above. Collect and process CAS data. Assess CAS data during a CAS procedure. Determine CAS processing mode. Undertake mode based CAS assess adaptation. Based on the result of the mode based determination, if hover mode, apply hover mode CAS algorithm to processing. Provide the user with hover mode CAS outputs, or provide the OTT motor control circuitry with speed control commands/signals. Exemplary user outputs include hover mode display outputs, hover mode projected image outputs, hover mode indications such as tactile, haptic, audio and visual indications adapted to the processing steps used in the hover mode. Based on the result of the mode based determination, if site approach mode, apply site approach mode CAS algorithm to processing. Provide the user with site approach mode CAS outputs. Exemplary outputs include approach mode display outputs, approach mode projected image outputs, approach mode indications such as tactile, haptic, audio and visual indications adapted to the processing steps used in the approach site mode.

Based on the result of the mode based determination, if active step mode, apply active step mode CAS algorithm to processing. Provide the user with active step mode CAS outputs. Exemplary outputs include active step mode display outputs, active step mode projected image outputs, active step mode indications such as tactile, haptic, audio and visual indications adapted to the processing steps used in the active step mode.

Figure 36:
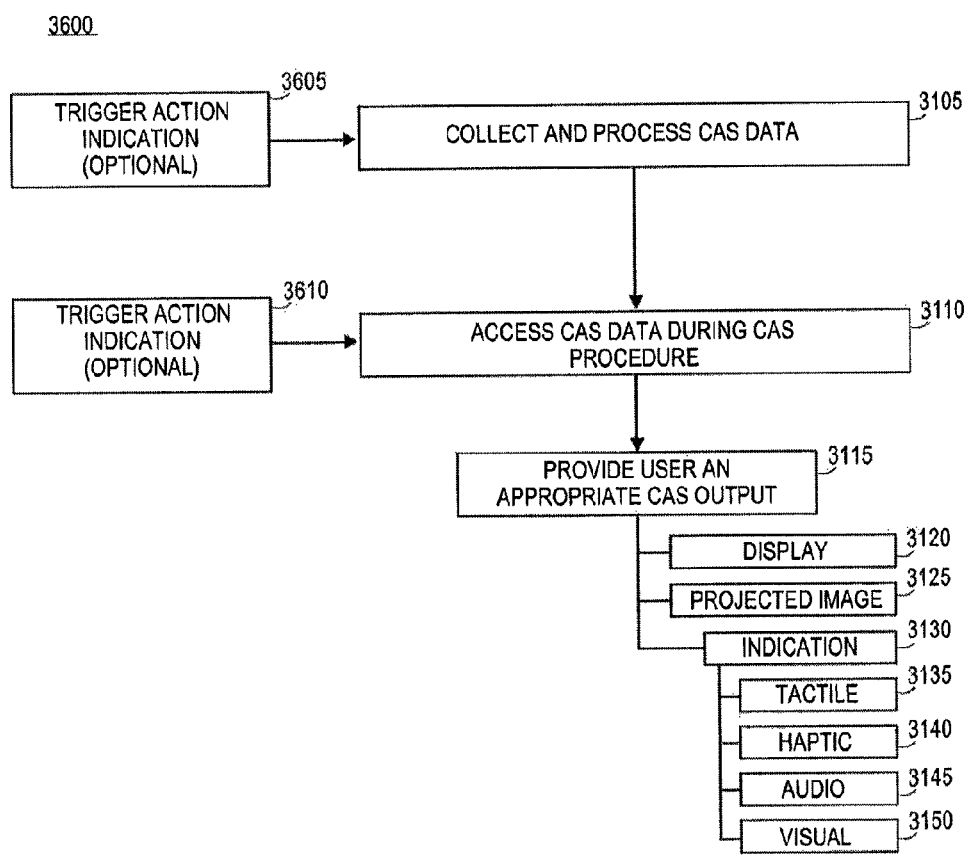
FIG. 36 is a flowchart representing an exemplary OTT CAS process including modification of any of the above described OTT CAS processes to include associated surgical tool operational characteristics, parameters or other data related to the use of an active element in any OTT CAS process or procedure.

FIG. 36 illustrates a flowchart amid exemplary OTT CAS process based upon those described above but using a unique trigger action indicator tool monitor or tactile or haptic feedback to further provide benefits to users of an OTT CAS system. Various alternative embodiments of the trigger action indicator are provided below with regard to FIGS. 37A-52B. As before, the OTT CAS process proceeds by collecting and processing CAS data. In one alternative aspect, the collection and processing may also include an indication from the trigger action. Next, following the processes described above, the OTT CAS system will assess CAS data during a CAS procedure. Here again, a trigger action indication may also be applied to this step and assessed along with other CAS data. Thereafter, the user will be provided with an appropriate CAS output based upon the use of one or more trigger action indicators as described above. The appropriate CAS outputs may include a display, a projected image, or any of a number of indications such as tactile indications, haptic indications, audio indications or visual indications as described above or as are typical in CAS procedures.

Against this backdrop of the various aspects of OTT CAS processes, the following examples are provided.

It is to be appreciated that OTT CAS mode may be detected and determined by many factors (e.g., reference frame(s), positions, relative motion, etc.). Additionally, in the context of a surgical procedure, there is also benefit in relating the defining attributes of an OTT CAS mode based on tool/target proximity or use. Consider the following examples of: A) Hover: both tool and target within surgical field, but no contact; B) Approach: Both tool and target within surgical field AND they are in contact; and C) Active step mode: Both tool and target within surgical field AND they are in contact AND there is active engagement of tool with tissue. In one aspect, the OTT device electronics incorporates this mode selection functionality in a 'smart views' module. This module is provided within the main CAS system computer or within the OTT device where electronics including software and firmware implement all or a substantial part of the modes detection algorithms, and triggers the different events of the OTT CAS mode selection functionality.

In some additional aspects of OTT CAS mode control, one or more of the following variations or alternatives may be incorporated:

1. Due to the temporal/special resolution on an OTT CAS system and CAS system generally, some embodiments of the Approach mode may be considered appropriate when tool and target are within a given user-pre-selected (settable) distance envelope. The distance envelope may be designated in a measurement range. One exemplary range may be between 10 mm to 0 mm as determined by the OTT CAS system. In other aspects, the Approach mode may be delineated by the OTT CAS system determining that there is likely contact between an active element of a surgical tool and the anatomy within the OTT CAS surgical field.

2. In some aspects, an OTT CAS mode is provided with a 'hysteresis' factor. This OTT CAS hysteresis factor is selected to include the types of circumstances or CAS conditions that, if satisfied such as continuously for a pre-determined time period, will result in that CAS mode being maintained. In other words, the parameters of the OTT CAS mode hysteresis must be met continuously during a period of time to 'lock into the mode' or maintain that OTT CAS mode. As used herein, continuously is meant to be within the context of the time domains of OTT processing times and sample rates and is not intended to denote the absolute non-interruption of the conditions monitored. By way of similar example, the hysteresis or some of the hysteresis conditions have to NOT be met continuously during a period of time to 'unlock' or permit adjustment of the OTT CAS mode. The use of OTT CAS mode hysteresis factors improves the system response to transients, avoids or reduces the likelihood of the system to jump from one OTT CAS mode to another inappropriately and improves usability of the system since the user is likely to see more stable OTT CAS outputs as the system will be providing those outputs from a single OTT CAS mode.

3. During some OTT CAS steps, there are activities performed by the user that may not require use of the projector, may require different input-output (IO) devices (e.g. during implant location assessment it may not be possible to project information on the bone), and/or may not have a defined target-tool relationship (e.g. knee range of motion assessment only requires seeing tibial and femoral reference frames). It is to be appreciated that the OTT CAS system may also receive inputs from other sources and there are OTT CAS outputs where no projector output is provided or utilized.

4. In general, the processing algorithms and OTT CAS mode factors are selected based on the probability or likelihood that, as for such things as the relative motion for bones, instruments, implants, etc. will be decreasing as the OTT CAS mode progresses from Hover to Active. The one exception to this general process assumption is when the OTT CAS device or system is used for the process of an assessment of a range of motion for an involved joint within the surgical field or for that joint that is the objective of the OTT CAS procedure or step.

OTT CAS Mode Examples

Bone Registration:

Objective: Finding out the geometrical relation between the origin of the reference frame and the origin of the bone model.

Procedure: Digitization of points on the surface of the bone with a tool (e.g. navigated pointer), and processing of these points against pre-determined geometry data of the bone model How the OTT CAS System Identifies this Task:
Pointer's AND bone's (either tibia or femur) reference frames (RFs) are visible to OTT.

Initiation of the Task:
The OTT CAS system recognizes both reference frames coexisting in the scene (for at least a minimum period of time suited for this registration)
An additional 'guess' factor is the stage of the procedure because for example, cutting cannot be done until the bones are registered.) In this case, the trigger for this event may be the OTT device is maintained in position to keep two reference frames within the field of view until a bone registration process is completed. This trigger can optionally be confirmed by the system computer prompting the user to confirm and they respond.

The information obtained during OTT device bone registration may be annotated or overwritten if needed by user's input (touch screen, voice command, touching with the pointer on a specific divot on the bone's reference frame, etc.)

The latter (divot) is a specified point (position) on the reference frame that when touched by a navigated pointer, would tell the system that the user is intending to perform a task (or one of the dedicated tasks) which involve that reference frame itself. For example, this could be a registration of the bone attached to that reference frame, and this may also invoke a change of mode from e.g. from Hovering/smart-views to registration screen etc.

OTT CAS Modes

Hovering:

Range Condition: OTT device is too far away from the RFs, or the 2 RFs are too far apart. The range to trigger this condition is settable during the calibration/tuning of the system, or by user preferences, and is specified as a distance threshold between the cameras to the target anatomy reference frame beyond the optimum FOV (in our embodied case greater than 200 mm).

Tracker: Lower refreshing rate

Projector: May not project any image on the bone (as the bone location is not yet defined), but can project elementary helpful information such as confirming this mode/status etc. on any reflective surface which happens to be in the way. Low refreshing rate, limited by the trackers.

System: Monitors the pointer's tip and the bone's RF location in 'world' coordinates. Drives tracker, projector, and other 10 devices.

Approach:

Range Condition: Medium OTT/RFs and RF/RF distances. The range to trigger this condition is settable during the calibration/tuning of the system, or by user preferences, and is specified as a distance range from the target anatomy reference frame such as 100-200 mm.

Tracker: High refreshing rate, optimizing pointer and bone RFs readings (e.g. ignoring or disregarding other RF's)

Projector: As above, may not project any defined image (as the bone location is not yet defined), but can project a solid screen that changes colors (e.g. red, yellow and green) based on 'readiness' to start collecting registration points.

System: Monitors the pointer's tip and the bone's RF location in 'world' coordinates. Drives tracker, projector, and other IO devices.

Active:

Smaller OTT/RFs and RF/RF distances. For example, less than 70-100 mm distance from the target reference frame, again settable by user preferences as above.

Tracker: High refreshing rate, optimizing pointer and bone RFs readings

Projector: As above.

System: Monitors the pointer's tip and the bone's RF location in 'world' coordinates. Records pointer's tip location for each digitized bone. Drives tracker, projector, and other IO devices. Monitors progress of the registration process, and when finished it calculates the final registration matrix.

May or may not require additional IO device (e.g. touch screen)

OTT CAS Considerations for Transitions Between Modes:

Mode shift is based on distance thresholds.

If there is no bone registration information then it is not possible to determine bone-pointer 'contact' or 'closeness'. The system alternatively looks at a nominal distance between the pointer (which IS registered) and the bone's reference frame (instead of the bone itself). The resulting nominal distance may then be used to estimate or assume approximate registration based on the nominal position in which that (bone) reference frame is usually recommended to be placed (see picture sheet 18-23). Another alternative is to (optionally) simply use any old registration information by the system (of another default bone or one from a previous patient or surgery) to make the approximate registration for the purposes of determining what "mode" the system should be in. The availability of this option is also settable/selectable by the user.

Or by user's input.

End of the Task:

All registration landmarks have been visited and pointed (registration process is fully completed).

OR the system ceases to see the pointer's RFs (for at least a minimum period of time)

Alternatively, the process could be complemented or overwritten by user's input (touch screen, voice command, touching with the pointer on a specific divot on the bone's reference frame, etc.)

Bone Cutting/Drilling:

Objective: Re-shaping the bone with a tool (usually a powered, smart instrument such as a saw, drill, burr, file, etc.) to allocate and implant.

Procedure: Following the system's direction, the user cuts/drills (usually) one surface at a time. This particular activity applies to different individual 'target surfaces' on each bone, one per cut/hole to be performed, so the system will maintain such reference when using or processing locational or orientational errors of the tool relative to the bone. Different tools have different active elements (e.g. cutting tips), and so the different active elements of each tool shapes result in different 2D and 3D modification of the anatomy when the tool or tool active element interacts with the anatomy in the surgical field. As such, the guidance for each tool will vary with the type of tool and active elements in use during an OTT CAS process step.

How the system OTT CAS system identifies this task:

OTT detects at least one bone's reference frame (RFs).

The named bone is registered.

The reference frame of the bone being cut is within a user selectable maximum distance (say, for example only, less than 200 mm).

Initiation of the Task:

The system recognizes both RFs coexisting in the scene (for at least a minimum period of time)

This could be complemented or overwritten by user's input (touch screen, voice command, touching with the pointer or the cutting instrument on a specific divot or mark on the bone's reference frame or the bone itself, etc.)

Modes

Hovering:

OTT is too far away from the bone. For example, more than 200 mm (values settable by the user).
  Tracker: Lower refreshing rate
  Projector: May not project any image (the bone could be out of the projector's sight) or may just display rough shapes (e.g. arrows to indicate in what direction to move the instrument—e.g. saw, drill, etc.—to align it with the bone). Optionally, the projector output is modified to simply show different colors as in the previous example. Low refreshing rate, limited by the tracker's refresh settings.
  System: Monitors the tool location and orientation relative to the bone (i.e. in bone's coordinates). Drives tracker, projector, and other IO devices. Communicates bi-directionally and drives smart instruments.

Approach:

OTT is at medium distance to the bone. For example, between 100 mm and 200 mm.
  Tracker: High refreshing rate, optimizing pointer and bone RFs readings.
  Projector: Shows alignment aids (colored text, lines, circles, arrows, etc.) corrected for bone geometry at medium refreshing rate.
  System: Monitors the tool location relative to the bone (i.e. in bone's coordinates) and calculates roll, pitch, yaw, and distances deviations. Drives tracker, projector, and other IO devices. Communicates bi-directionally and drives smart instruments.

Active:

OTT is close to the bone. For example, between 70 mm and 100 mm.
  Tracker: High refreshing rate, optimizing pointer and bone RFs readings.
  Projector: Shows alignment aids (colored text, lines, circles, arrows, etc.) corrected for bone geometry at high refreshing rate.
  System: Monitors the tool location relative to the bone (i.e. in bone's coordinates) and calculates roll, pitch, yaw, and distances deviations. Drives tracker, projector, and other IO devices. Communicates bi-directionally and drives smart instruments at higher speed.

Transition Between Modes:

Transition may be based on distance thresholds.

Transition based on user input.

End of the Task:

User moves on to another task

All cuts and refinements are fully completed.

In one alternative, the OTT CAS system ceases to see the bone's RFs (for at least a minimum period of time)

This step could be amended, complemented or overwritten by user's input (touch screen, voice command, touching with the pointer on a specific divot on the bone's reference frame, etc.)

Assessment of Bone Cut:

Objective: Evaluating a new surface (e.g. plane, cylindrical hole, etc.) orientation, surface roughness, depth, etc.

Procedure: Total or partial digitization of the surface (e.g. touching/traversing it with a navigated pointer), assessing a cut location and orientation with a 'surface monitor' (a navigated tool with a flat surface that sits on the flat cut), gauging the depth of a hole with a navigated pointer, etc.

How the OTT CAS System Identifies this Task:

OTT sees at least one bone's reference frame (RFs) as well as the assessing instrument's (surface monitor or pointer) RF.

The named bone and the instrument have been registered.

At least a cut has been performed.

The bone being cut is within a maximum distance 'D'.

Initiation of the Task:

The system recognizes both RFs (bone and instrument) coexisting in the scene (for at least a minimum period of time), while the conditions above are fulfilled.

This could be complemented or overwritten by user's input (touch screen, voice command, touching with the pointer or the cutting instrument on a specific divot or mark on the bone's reference frame or the bone itself, etc.)

Modes

Hovering:

OTT is too far away from the RFs, or the 2 RFs are too far apart.
  Tracker: Lower refreshing rate.
  Projector: May not project any defined image (as the bone can be out of projector's sight), or it can project a solid screen that changes colors (e.g. red, yellow and green) based on 'readiness' to start the process. Low refreshing rate, limited by the tracker.
  System: Monitors the tool location relative to the bone (i.e. in bone's coordinates). Drives tracker, projector, and other IO devices.

Approach:

OTT is at medium distance to both RFs AND medium bone-tool distance.
  Tracker: High refreshing rate, optimized for instrument and bone RFs readings.
  Projector: May not project any defined image (as the bone can be out of projector's sight), or it can project a solid screen that changes based on 'readiness' to start the process. Medium refreshing rate.
  System: Monitors the tool location relative to the bone (i.e. in bone's coordinates). Drives tracker, projector, and other IO devices.

Active:

OTT is at medium/close distance to both RFs AND small bone-tool distance.
  Tracker: High refreshing rate, optimized for instrument and bone RFs readings.
  Projector: May not project any defined image (as the bone can be out of projector's sight), or it can project a solid screen that changes based on process status (start to end of data collection). High refreshing rate.
  System: Monitors the tool location relative to the bone (i.e. in bone's coordinates). Records pointer's tip location for each digitized point or surface monitor location and orientation. Drives tracker, projector, and other IO devices. Monitors progress of the assessment process, and when finished it calculates, records and displays the calculated parameters.
  May or may not require additional IO device (e.g. touch screen)

Transition Between Modes:

Simply based on distance thresholds.

Or by user's input

End of the Task:

Assessment process is fully completed.

Optionally, the OTT CAS system ceases to see the instrument's RFs (for at least a minimum period of time)
This could be complemented or overwritten by user's input (touch screen, voice command, touching with the pointer on a specific divot on the bone's reference frame, etc.)

Assessment of Implant Fit and Alignment
Objective: Comparing the actual location of the implant (or trial) on a bone, relative to where it was expected to be according to plan. This can happen during trial, and before/during/after implant cementing or locking.
Procedure: An implant (e.g. femoral component, tibial tray, etc.) gets a RF attached, and is tracked in 'bone' coordinate system. At any given time the system can display/record its position (relative to the bone), and instant errors (if any) compared to where it was supposed to be.
How the System Identify this Task:
OTT sees at least one bone's reference frame (RFs) as well as the corresponding implant's RF.
The named bone and the implant have been registered.
All cuts have been performed.
The bone being and implant are within a maximum distance 'D'.
Initiation of the Task:
The system recognizes both RFs (bone and implant) coexisting in the scene (for at least a minimum period of time), while the conditions above are fulfilled.
This could be complemented or overwritten by user's input (touch screen, voice command, touching with the pointer or the cutting instrument on a specific divot or mark on the bone's reference frame or the bone itself, etc.)
Modes
Hovering:
OTT is too far away from the RFs, or the 2 RFs are too far apart.
  Tracker: Lower refreshing rate.
  Projector: May not project any defined image (as the bone can be out of projector's sight), or it can project a solid screen that changes colors (e.g. red, yellow and green) based on 'readiness' to start the process. Low refreshing rate, limited by the tracker's.
  System: Monitors the implant/trial location relative to the bone (i.e. in bone's coordinates). Drives tracker, projector, and other IO devices.
Approach:
Medium OTT/RFs distance AND implant/trial relatively close to the bone.
  Tracker: High refreshing rate, optimized for implant/trial and bone RFs readings.
  Projector: May not project any defined image (as the bone can be out of projector's sight), or it can project a solid screen that changes based on 'readiness' to start the process. Medium refreshing rate.
  System: Monitors the implant location relative to the bone (i.e. in bone's coordinates). Drives tracker, projector, and other IO devices.
Active:
Smaller OTT/RFs distance AND implant/trial is close/touching to the bone.
  Tracker: High refreshing rate, optimized for implant and bone RFs readings.
  Projector: May not project any defined image (as the bone can be out of projector's sight), or it can project a solid screen that changes based on process status (start to end of data collection). High refreshing rate.
  System: Monitors the implant/trial location relative to the bone (i.e. in bone's coordinates). Calculates and displays (and record when needed) the errors defined by the actual location/orientation of the navigated implant relative to where it is supposed to be according to plan. Drives tracker, projector, and other IO devices. Monitors progress of the assessment process, and when finished it calculates, records and displays the calculated parameters.
  May or may not require additional IO device (e.g. touch screen)
Transition Between Modes:
Simply based on distance thresholds.
Or by user's input
End of the Task:
Assessment process is fully completed.
(or) The system ceases to see the instrument's RFs (for at least a minimum period of time)
This could be complemented or overwritten by user's input (touch screen, voice command, touching with the pointer on a specific divot on the bone's reference frame, etc.)

Range of Motion:
Objective: Assess the range of motion and biomechanics of the joint after implantation. It can be done with trials or final implants on.
Procedure: After placing the trial (or actual implant) on, before removing the bones' RFs and closing the wound, the surgeon flexes the knee and performs handles the joint, reaching limit positions like maximum flexion and hyper extension). This maneuvering is performed while pointing OTT to the tibial and femoral RFs. Dynamic measurements (tibia relative to femur) are expressed in anatomical terms.
How the System Identify this Task:
OTT sees both tibia's and femur's reference frames (RFs).
Both bones have been cut. (Bone cutting and implant location could have or could have not been performed.)
Initiation of the Task:
The system recognizes both RFs coexisting in the scene (for at least a minimum period of time), while the conditions above are fulfilled.
This could be complemented or overwritten by user's input (touch screen, voice command, touching with the pointer or the cutting instrument on a specific divot or mark on the bone's reference frame or the bone itself, etc.)
Modes
Hovering:
OTT is too far away from the RFs.
  Tracker: Lower refreshing rate.
  Projector: May not project any defined image (as the bone can be out of projector's sight), or it can project a solid screen that changes colors (e.g. red, yellow and green) based on 'readiness' to start the process. Low refreshing rate, limited by the tracker's.
  System: Monitors the tibia location relative to the femur. Drives tracker, projector, and other IO devices.
Approach:
Medium OTT/RFs distance.
  Tracker: High refreshing rate, optimized for bones' RFs readings.
  Projector: May not project any defined image (as the bone can be out of projector's sight), or it can project a solid screen that changes based on 'readiness' to start the process. Medium refreshing rate.

System: Monitors the implant location relative to the bone (i.e. in bone's coordinates). Drives tracker, projector, and other IO devices.

Active:

Smaller OTT/RFs distance AND implant/trial is close/ touching to the bone.

Tracker: High refreshing rate, optimized for implant and bone RFs readings.

Projector: May not project any defined image (as the bone can be out of projector's sight), or it can project a solid screen that changes based on process status (start to end of data collection). High refreshing rate.

System: Monitors the tibia location relative to the femur. Calculates and displays (and record when needed) the dynamic motion (flexion/extension, varus/valgus, internal/external rotation, AP motion, etc.). Drives tracker, projector, and other IO devices. Monitors progress of the assessment process, and when finished it saves all parameter recorded and notifies the user.

May or may not require additional IO device (e.g. touch screen)

Transition Between Modes:

Simply based on distance thresholds.

Or by user's input

End of the Task:

Assessment process is fully completed.

(or) The system ceases to see the bones' RFs (for at least a minimum period of time)

This could be complemented or overwritten by user's input (touch screen, voice command, touching with the pointer on a specific divot on the bone's reference frame, etc.)

Other activities (e.g. registration verification, bone cut refinement, etc.) can be considered sub-cases of the above.

In one aspect in any of the above described examples, lower refreshing rate refers to changes in refresh rate from about 30-100 Hz to as low as 1-10 Hz.

When resecting a portion of a bone a surgeon may cut more rapidly and aggressively when the cutting tool is relatively far from the boundary of the area to be resected. As the OTT CAS detects the surgeon approaching the boundary of the resection area, the surgeon may receive appropriate OTT CAS outputs to slow the pace of cutting to ensure that the resection remains within the desired boundaries. To help the surgeon readily assess the proximity to the resection boundary, the OTT CAS system may provide a number of appropriate OTT CAS outputs to the surgeon as the surgeon approaches the boundary. Further still, the OTT CAS system may be configured to provide feedback related to the control the operation of the OTT equipped surgical tool in response to the proximity of the tool to the resection boundary and the corresponding OTT CAS data processing response and resulting CAS outputs.

As described above, the OTT CAS system provides for the pre-operative analysis of a patient model and the identification of the tissue to be resected. After the portion of the tissue to be resected is determined, the OTT CAS system may analyze the data for the model and identify the boundary for the resection. The tissue to be resected may then be identified in the OTT projector output using a plurality of colors based on the relation to the resection boundary.

For instance, the OTT projector output may be adapted based on OTT CAS processing factors to project onto a portion of the tissue that is not to be removed in red. Optionally, the OTT projector output may indicate a portion of the tissue that is to be resected that is relatively close to the resection boundary in yellow. In still another alternative, the OTT CAS processes may produce an OTT projector output whereby the remainder of the tissue to be resected may be eliminated in green. In this way, as the surgeon views the surgical field during a procedure the surgeon may cut rapidly and aggressively while the OTT projector output indicates the tool is operating on tissue in the green zone. As the surgeon approaches the resection boundary, the OTT-based projector output indicates the tool is operating on tissue in the yellow zone. These OTT CAS determined projector outputs serve as indications to the surgeon to proceed more slowly as the tool approaches the resection boundary. In this way, the OTT CAS system provides a readily identifiable visual and graphical display directly onto the surgical field that informs the surgeon of the proximity of the current surgical action to a resection boundary. Similarly, the OTT CAS system can be used to visually recognize and use an OTT-based projector output to identify the proximity of the surgical tool to sensitive anatomical structures, such as nerves, vessels, ligaments etc. OTT CAS output to the projector may include distinctive color schemes to identify the structures within the surgical field as part of OTT CAS output for the user.

FIGS. 37A-44 relate to various alternative tactile feedback mechanisms along with related kinematic responses and design criteria.

FIG. 37A illustrates a bent form that deflects to move an actuator in response to trigger force. FIG. 37B illustrates a sliding trapezoid form that will deform and restore its shape in response to trigger force. FIG. 37C illustrates a rotating reader or encoder used to provide a rotating response to the trigger force. FIG. 37D illustrates a frame moving in response to trigger force to depress a shaft into a base where the movement of the shaft may be registered as an indication of trigger force. FIG. 37E illustrates a pinned element that may deflect to indicate an amount of trigger force.

Figure 38A:
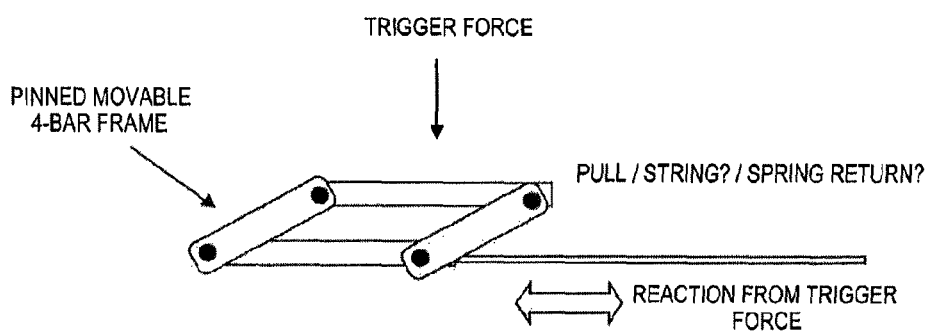
FIGS. 38A and 38B illustrate a simple four bar mechanism, in a raised and lowered, positions respectively that may be used to register trigger force and displace a shaft.
Figure 38B:
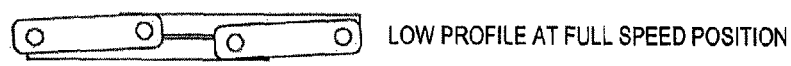

FIGS. 38A and 38B illustrate a simple four bar mechanism, in a raised and lowered, positions respectively that may be used to register trigger force and displace a shaft.

FIGS. 39A, 39B 39C each illustrate a scissor mechanism 80 without a position restoration element (39A) and driving an actuator 80, with a tension spring as a position restoration element 84 (39B) and a compression spring as a position restoration element 84 (39C). The movement of the actuator shown determines the height of the upper end of the scissor arms therefore the elevation of the scissor mechanism. This height will press against, and will be felt by the user placing his or her finger on the tool trigger.

Figure 40A:
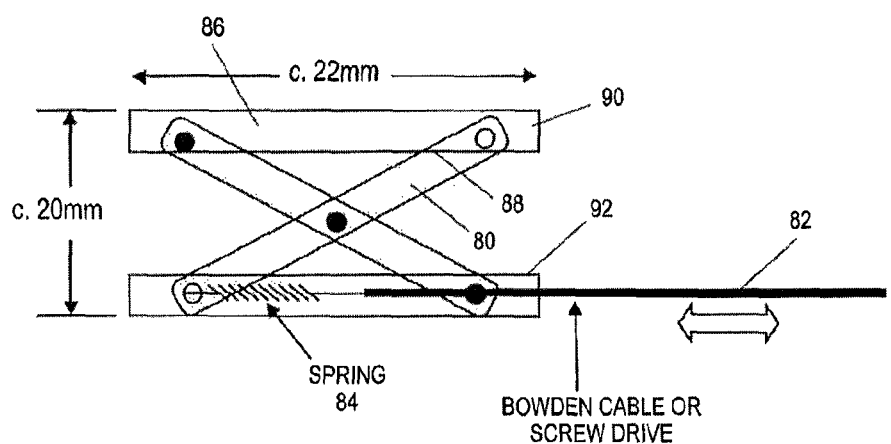
FIGS. 40A and 40B illustrate a side view of a scissor mechanism in a raised and lowered configuration, respectively in accordance with some embodiments.
Figure 40B:
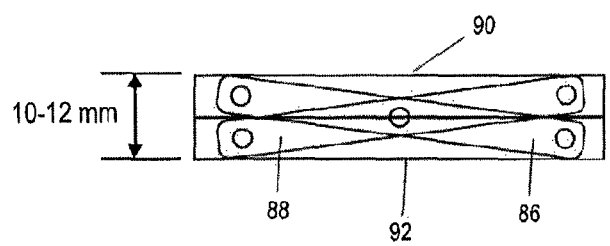

FIGS. 40A and 40B illustrate a side view of a scissor mechanism in a raised and lowered configuration, respectively. The scissor mechanism 80 includes a first link 86 and a second link 88 coupled at a pivot point whereby movement of the scissor raises and lowers the first and second platforms 90, 92. A position restoration element 84, here shown as a spring, is coupled to one end of the second link and to an actuator 82. The platforms have a length of about 22 mm and a maximum rise of about 20 mm in the elevated condition shown in FIG. 40.

Figure 40C:
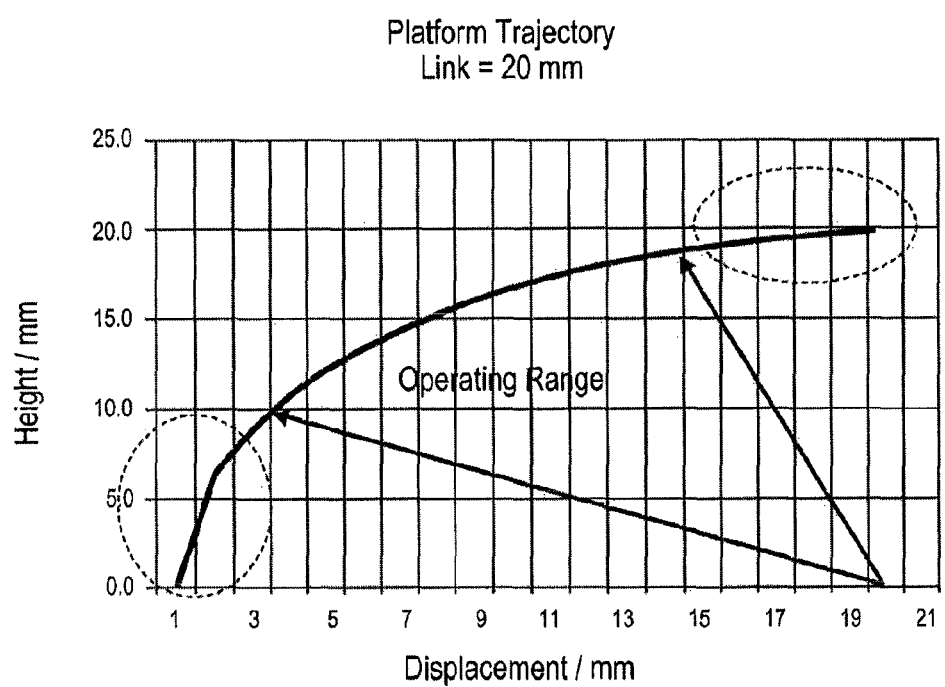
FIGS. 40C and 40D are charts relating to the displacement characteristics of the scissor mechanism of FIGS. 40A and 40B.
Figure 40D:
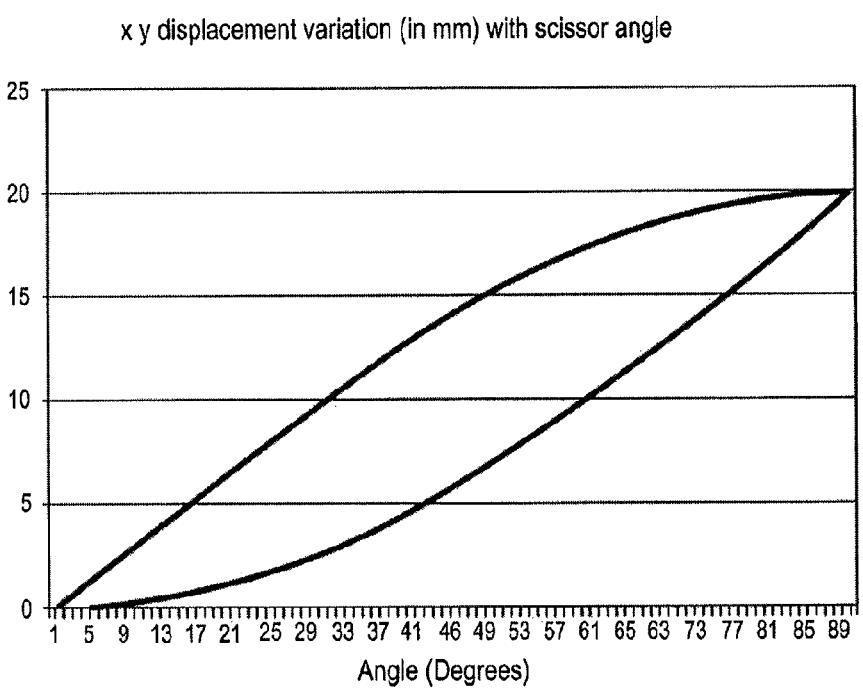

FIGS. 40C and 40D are charts relating to the displacement characteristics of the scissor mechanism 80 of FIGS. 40A and 40B. FIG. 40C relates a platform trajectory with a height of the device. FIG. 40D relates to the scissor angle with the displacement variation of the device.

Figure 41:
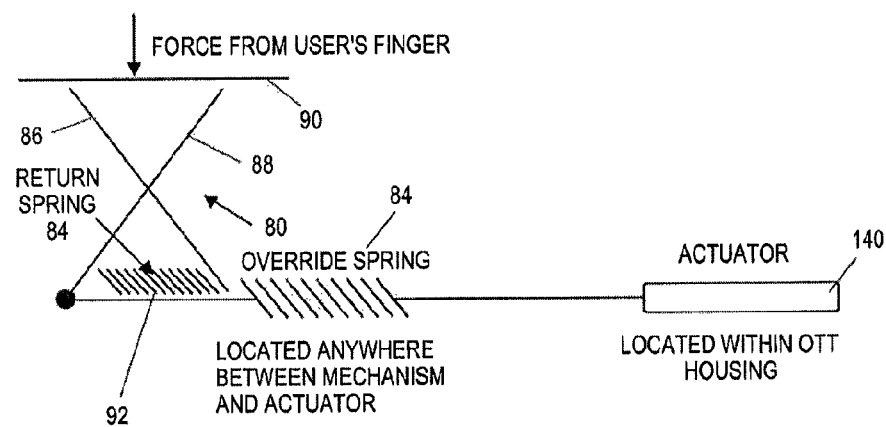

FIG. 41 illustrates another scissor mechanism 80 having a surgeon system override capability. The override capability is provided via the inclusion of a spring in line with the force application through the actuator. The actuator may be a component 140 is used for providing or receiving OTT CAS data during computer assisted surgery procedures. In this aspect, the on tool tracking device includes a component 140 adapted and configured to translate a movement received from a feedback mechanism, such as from the shaft 80 relative movement into a signal used in a computer assisted surgery procedure. The component 140 may be provided in a number of different configurations such as an encoder, an actuator or a motion transducer. In one aspect, the signal relates to the operation of the surgical tool operated by the trigger. In still a further embodiment, the component is or is adapted to include an actuator to impart movement to the shaft to influence the relative movement between the first platform and the second platform. In a further aspect, the actuator is configured to impart movement to the shaft in response to a signal related to controlling the operation of the surgical tool during a computer assisted surgery procedure.

The illustrated scissor mechanism embodiment shows the relationship of the first platform 90 and the second platform 92 borne by the links 86, 88 of the scissor mechanism 80. In addition, this embodiment shows a scissor mechanism having a pair of position restoration elements used in conjunction with the scissor mechanism 80. One position restoration element is the return spring positioned within the scissor mechanism 80. Another position restoration element is the override spring positioned between the scissor mechanism and the actuator or component 140.

Figure 42:
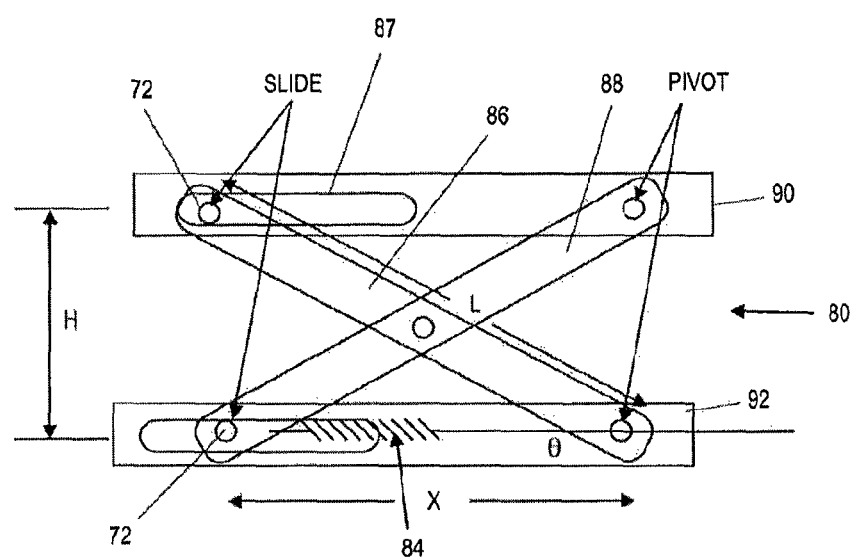
Figure 43:
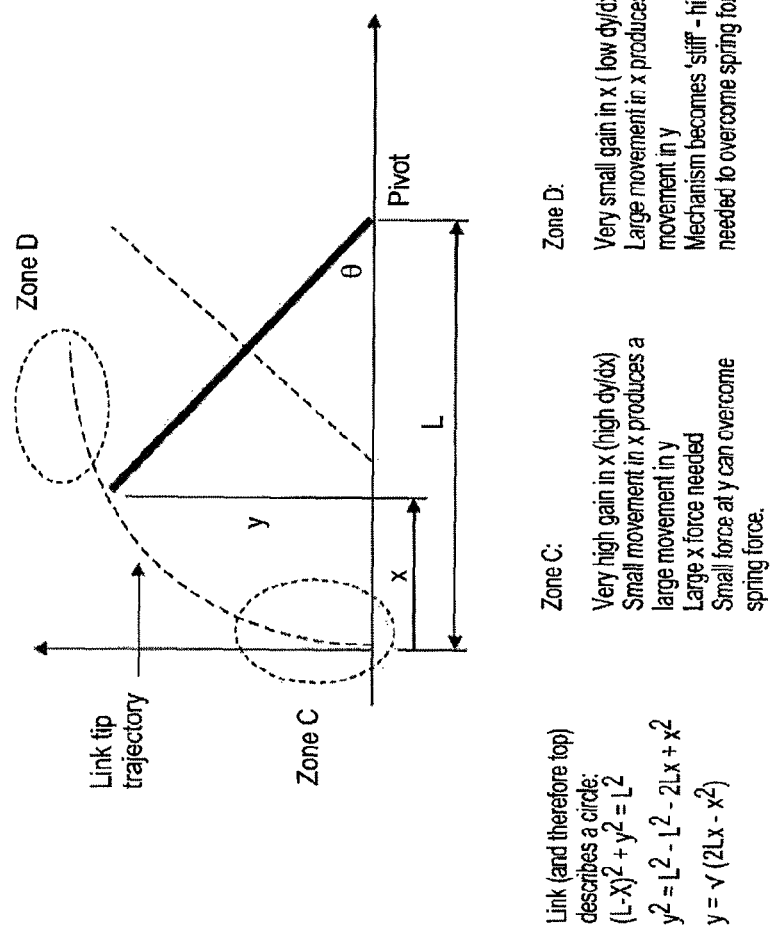
Figure 44:
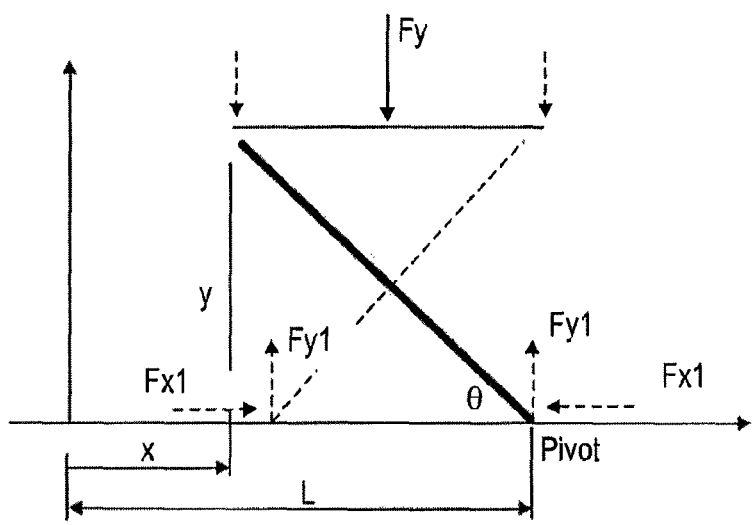

FIG. 42 illustrates a scissor mechanism similar to the schematic mechanism illustrated in FIG. 41. The scissor mechanism 80 includes a first platform 90 and the second platform 92 connected at one end of the links 80, and 86 in the pivoting relation to the first and second platform and sliding relation with the other end of the links 88, 86. A position restoration element, here a spring, is placed between the actuator or cable and a sliding and of a scissor link 88. This embodiment also includes the details of the elongate slots the first and of the platforms to permit sliding movement of the link first end relative to the first and second platform. The second end of the links 88, 86 are coupled in pivoting relation to the first platform and the second platform 90, 92. Here the motion of the first and second platforms is adjusted to the use of the spring or under the influence of the actuator. The operational characteristics of the mechanism of FIG. 42 are better appreciated with reference to the charts and FIGS. 43 and 44.

Figure 45:
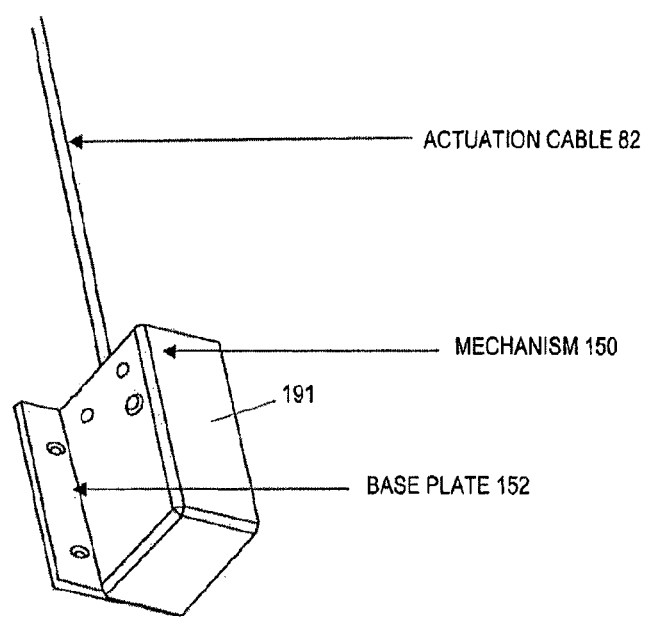
FIG. 45 is an isometric view of a tactile feedback mechanism.
Figure 46A:
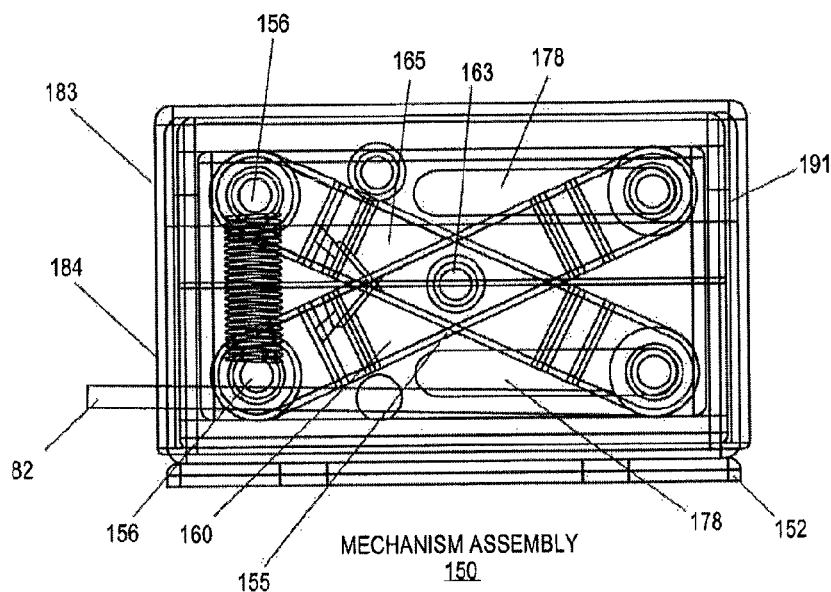
FIGS. 46A-46F illustrate various views of the components and operation of the mechanism of FIG. 45.

FIG. 45 is an isometric view of a tactile feedback mechanism. FIGS. 45 and 46A illustrate isometric and side views of a tactile feedback mechanism 150, respectively. The view of FIG. 45 shows the base plate 152 use for attachment to a surgical tool 50 adjacent a trigger 52. The scissor mechanism (best seen in FIG. 46A) is covered by a cover 191 that is borne by the first platform 183 and moves along with the platform. An actuation cable 82 is coupled to the scissor mechanism and moves in response to movement of the scissor mechanism.

Figure 46B:
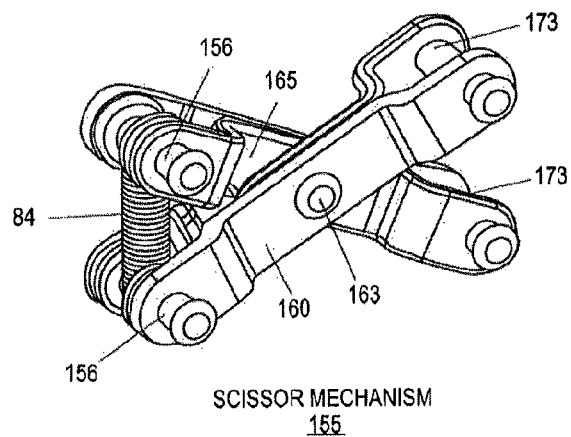

FIG. 46B illustrates an isometric view of the scissor mechanism 155 of FIG. 46A without the cover 191 or the platforms 183, 184. The Y-shaped linkage 160 and 165 are pinned 163 to form a scissor mechanism 155. A position restoration element 84 is positioned between the first ends of the first link and the second link. Also visible in this view is the shaft 173 used to slide along the slots 178 in the platforms.

Figure 46C:
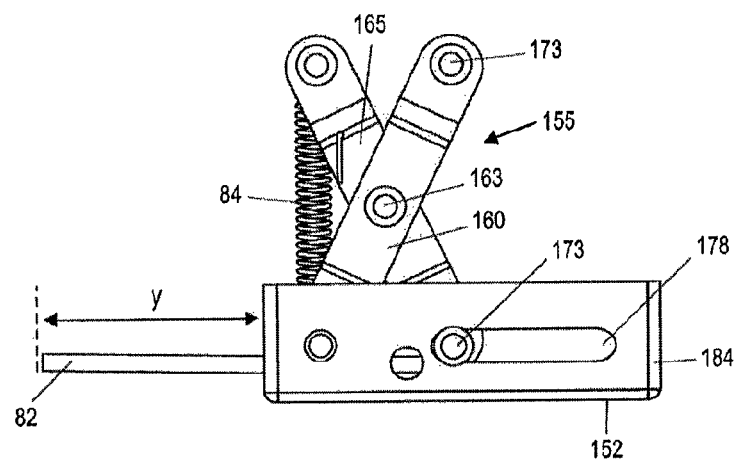
Figure 46D:
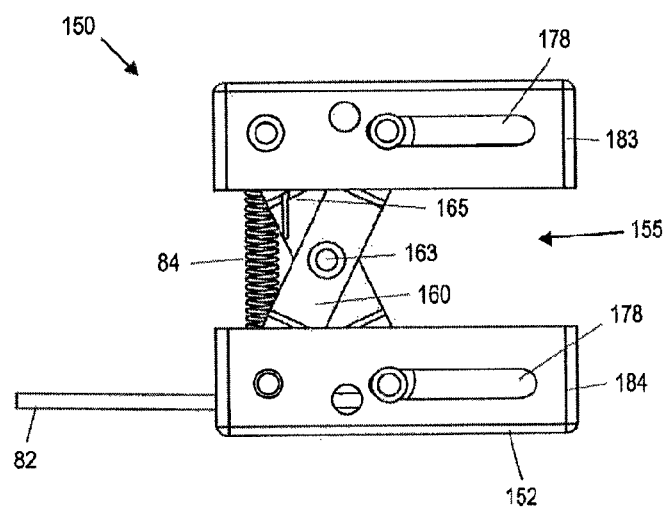

FIGS. 46A-46F illustrate various views of the components and operation of the mechanism of FIG. 45. FIGS. 46C and 46D show the TFM 150 of FIGS. 45 and 46A in an extended condition with (FIG. 46D) and without (FIG. 46C) the top platform 183. The cable 82 is moved a displacement +y from the lower platform 184 in relation to the length of movement of the links along the slots 178.

Figure 46E:
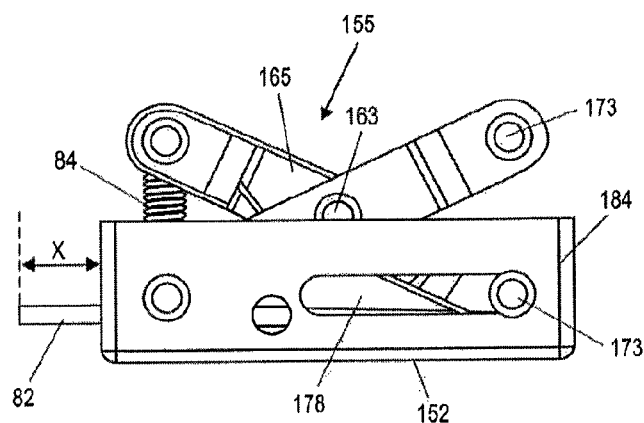
Figure 46F:
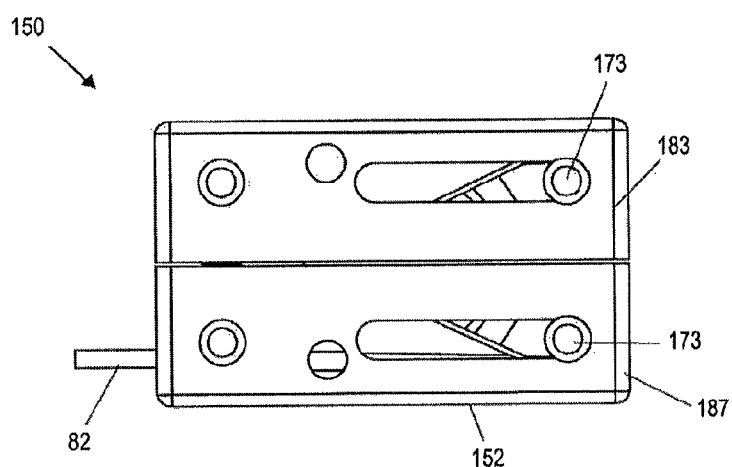

FIGS. 46E and 46F show the TFM 150 of FIGS. 45 and 46A in an closed or retracted condition with (FIG. 46F) and without (FIG. 46E) the top platform 183. The cable 82 is moved a displacement +x from the lower platform 184 in relation to the length of movement of the links along the slots 178.

Figure 47:
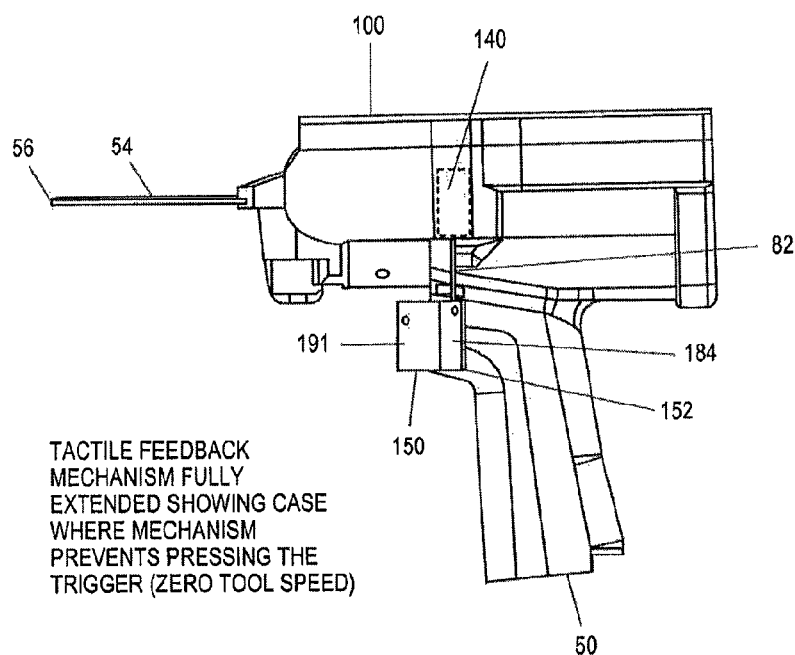
FIGS. 47 and 48 illustrate a side view of an on tool tracking device mounted on a surgical instrument having a tool (here a saw) with the tactile feedback mechanism of FIG. 45 in position to interact with the trigger of the surgical instrument.
Figure 48:
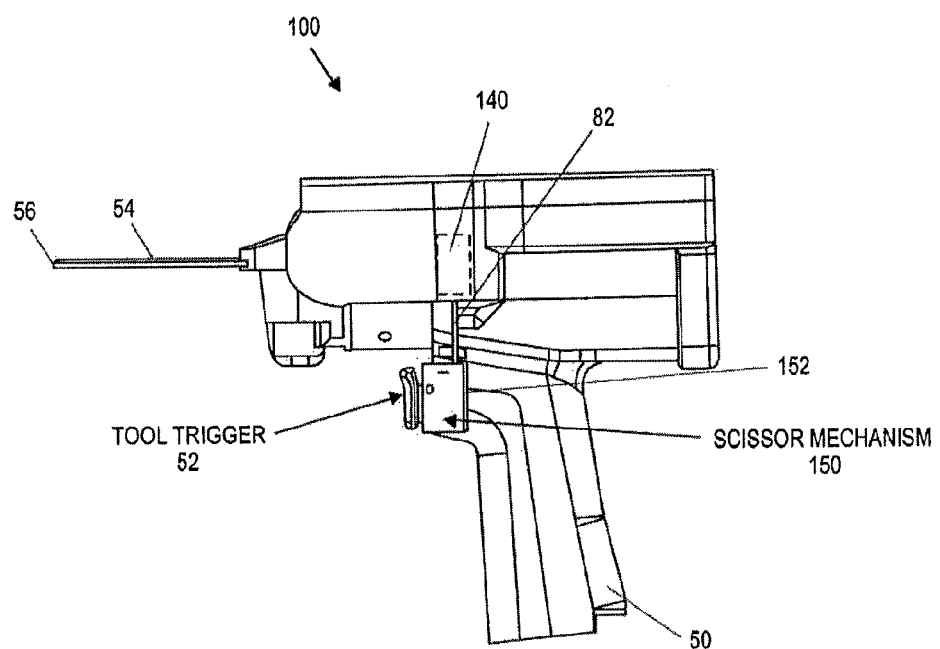

FIGS. 47 and 48 are side views of an OTT 100 on a surgical tool 50 having a TFM 150 positioned adjacent the trigger of the surgical tool. The actuator 82 extends from the TFM into the OTT 100. A component 140 within the OTT is configured to receive and provide output to or receive from the TFM. In this embodiment, the cover 191 is expended away from the base 152 exposing a portion of the base 184.

When the TFM moves the cover 191 into the position show, the trigger function on the surgical tool is impaired by the cover 191 that blocks access to the trigger 152. FIG. 48 illustrates the cover 191 in a loosened configuration where the trigger 52 is accessible.

FIGS. 47 and 48 illustrate a side view of an on tool tracking device mounted on a surgical instrument having a tool (here a saw) with the tactile feedback mechanism of FIG. 45 in position to interact with the trigger of the surgical instrument. FIG. 47 illustrates the tactile feedback mechanism in an expanded configured that covers the trigger and FIG. 48 shows the tactile feedback mechanism collapsed to expose the trigger.

Figure 49A:
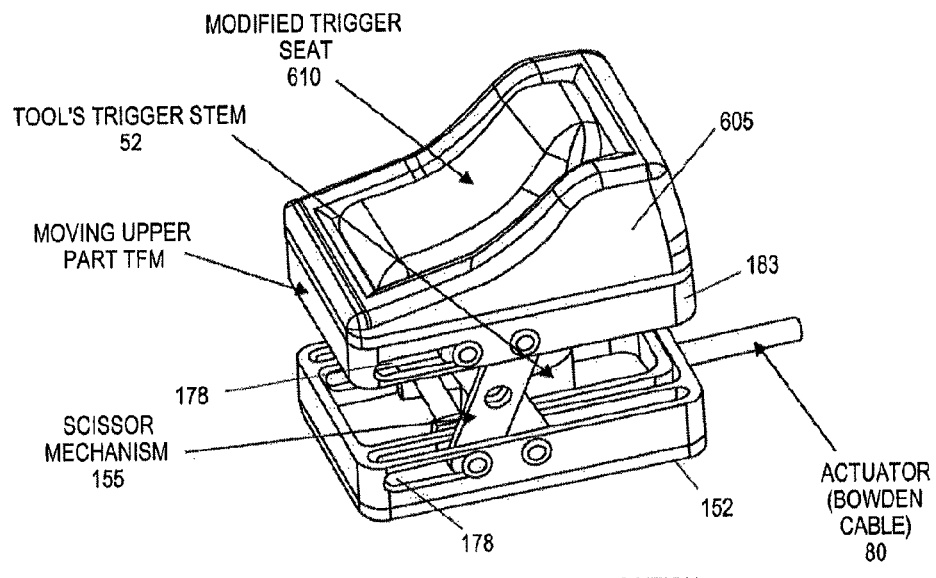
FIGS. 49A-49B illustrate another alternative of a tactile feedback mechanism in an open or expanded state (FIG. 49A) and a closed state (FIG. 49B).
Figure 49B:
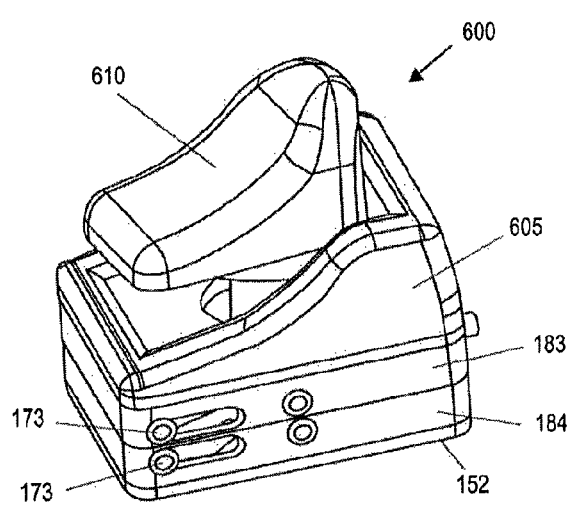
Figure 49C:
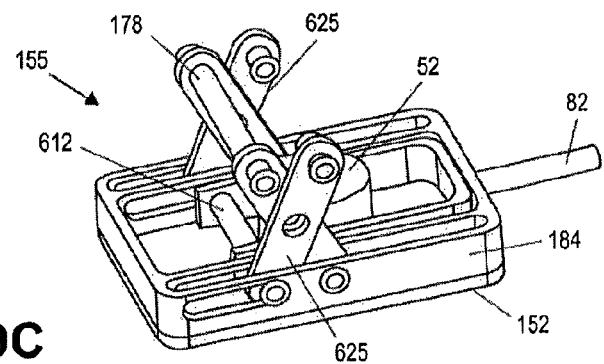
FIGS. 49C-49E illustrate the various views of the internal mechanisms of the devices in FIGS. 49A and 49B.
Figure 49D:
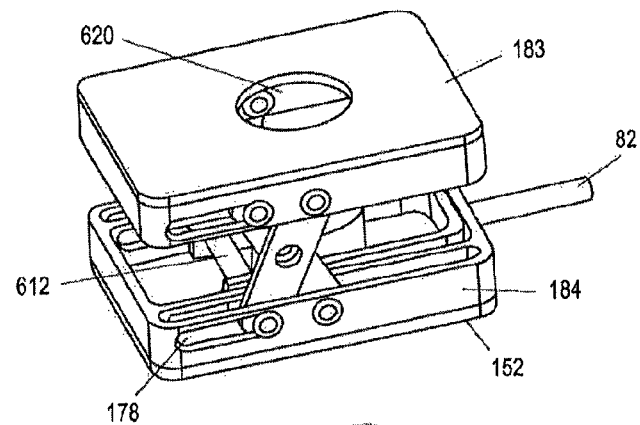
Figure 49E:
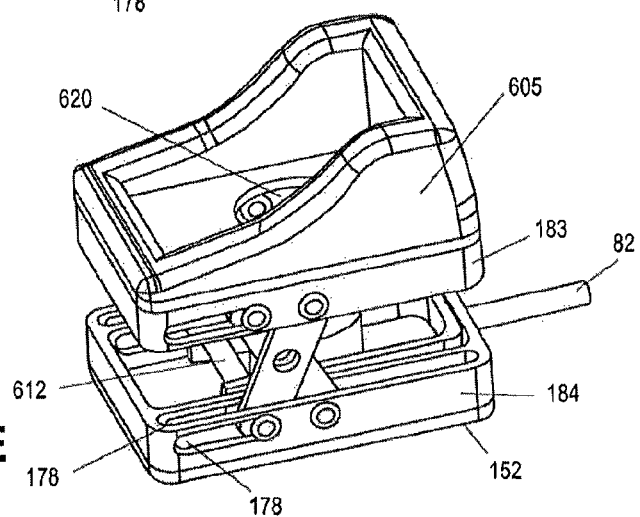

FIGS. 49A-49B illustrate another alternative of a tactile feedback mechanism in an open or expanded state (FIG. 49A) and a closed state (FIG. 49B). FIGS. 49C-49E illustrate the various views of the internal mechanisms of the devices in FIGS. 49A and 49B.

The FIGS. 49A and 49B illustrate isometric views of an over the trigger tactile feedback mechanism 600 in a raised and lowered condition, respectively. The over trigger tactile feedback mechanism 600 has a trigger adapter 605 attached to the first platform 183. A modified trigger seed text and is adapted to engage with the trigger 52. The modified trigger seed fits within and is movable relative to the trigger adapter 605. A scissor mechanism 155 is provided as before to move the first platform and the second platform.

The relative positions of the platforms in views illustrate how in the collapsed condition the modified trigger seat 610 is raised above the trigger adapter 605. In contrast, in the raised condition the modified trigger seat 610 is withdrawn within and below the upper surfaces of the trigger adapter 605.

FIG. 49C is an isometric view of the scissor mechanism 155 in a raised condition with the upper platform and the trigger adapter removed. FIG. 40 9D is similar to the view of FIG. 40 9C with the upper platform 183 attached to the scissor mechanism 155. An aperture 620 is provided in the upper platform 183. The aperture 620 used to provide coupling between the modified trigger seat 610 and the trigger 52.

Figure 50:
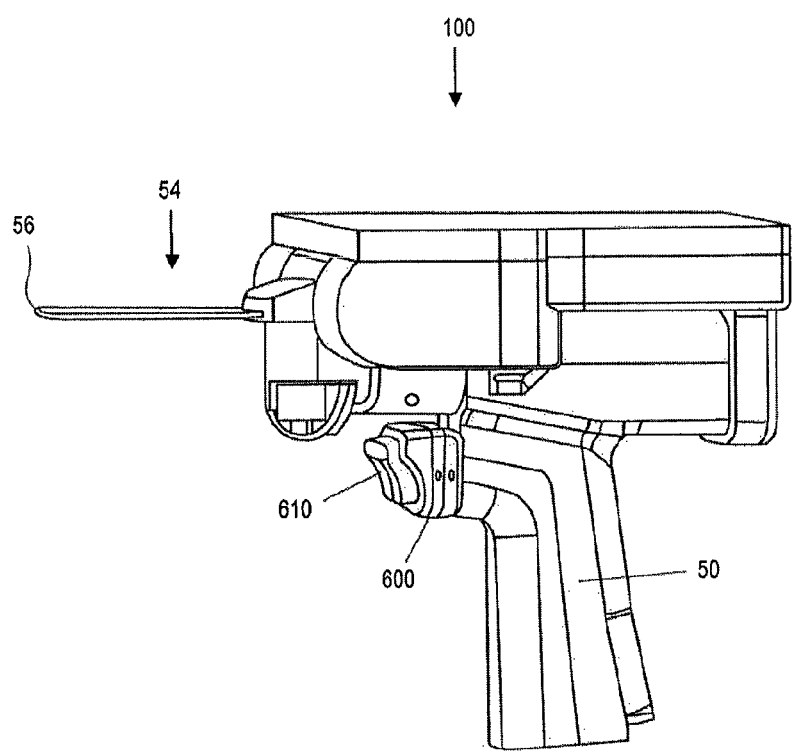
FIG. 50 illustrates an embodiment of an OTT coupled for use with a surgical tool having an embodiment of the mechanism of FIGS. 49A and 49B mounted for cooperation with the trigger of the surgical tool and configured to send and to receive trigger related signals with a component in the OTT.

FIG. 49E is similar to the other embodiments with the addition of the trigger adapter 605 in position on top of the first platform 183. FIG. 50 illustrates an embodiment of an OTT 100 coupled to a surgical tool 50 where the trigger 52 of the tool 50 is covered by the tactile feedback mechanism 600.

In the configuration of FIG. 50, a user's ability to manipulate the trigger 52 is covered by the operation of the tactile feedback mechanism 600.

FIG. 50 illustrates an embodiment of an OTT coupled for use with a surgical tool having an embodiment of the mechanism of FIGS. 49A and 49B mounted for cooperation with the trigger of the surgical tool and configured to send and to receive trigger related with a component in the OTT.

Figure 51:
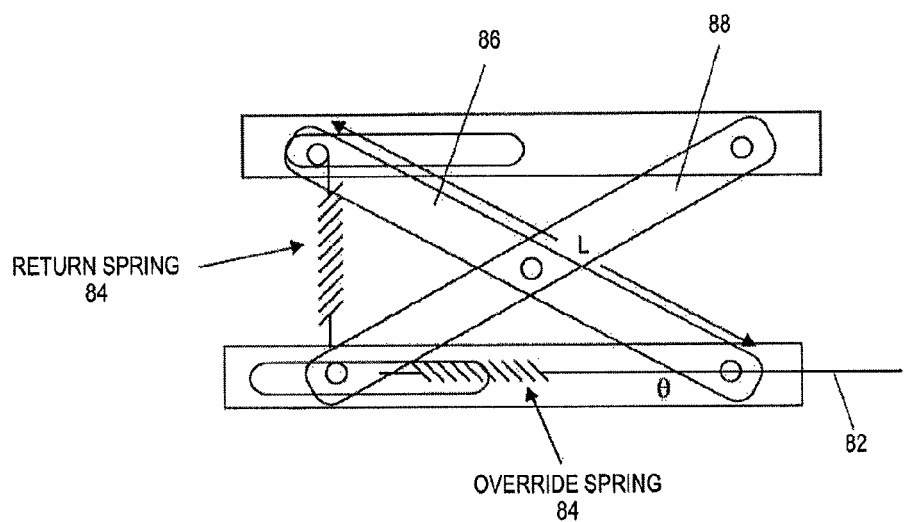
FIG. 51 is a cut away view of an alternative embodiment of a scissor mechanism utilizing two position restoration elements.
Figure 52:
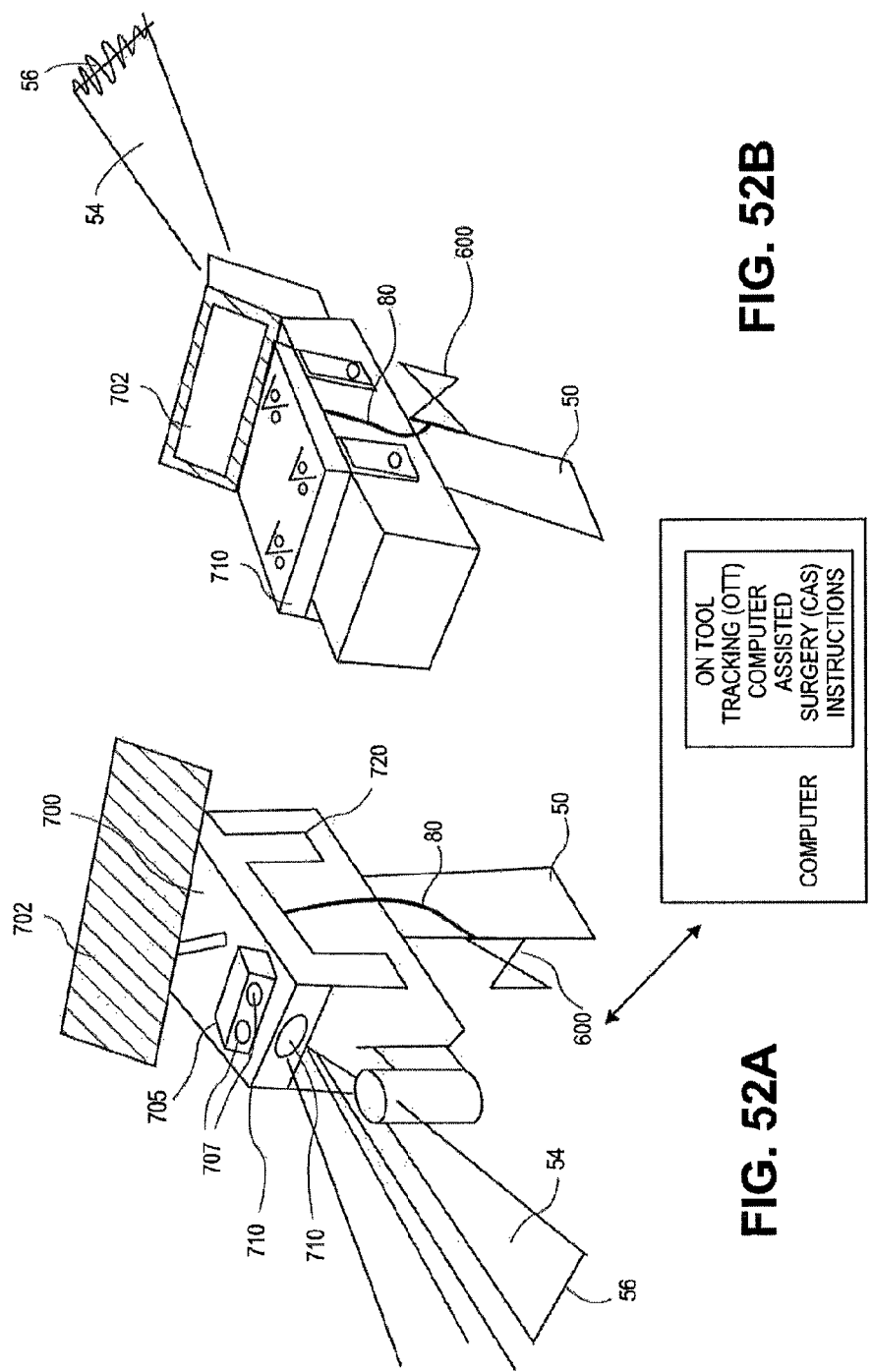
FIGS. 52A and 52B are front and rear isometric views respectively of an on tool tracking and navigation device (OTT) that includes a display with OTT housing coupled to a surgical tool having a trigger based feedback mechanism coupled to the OTT. The view also shows an exemplary computer system in communication with the OTT.

FIG. 51 is an alternative embodiment of a scissor mechanism utilizing two position restoration elements. FIG. 51 illustrates a scissor mechanism similar to FIG. 42. In contrast to the scissor mechanism of FIG. 42, the illustrated scissor mechanism in this embodiment includes a pair of position restoration elements. One position restoration element 84 is a return spring extended between the first and second platforms and coupled to the first ends of the links 86, 88. The return spring is used to modify the movement platforms and hence control trigger responsiveness. The other position restoration element is the override spring extending along the second platform. The override spring is coupled to a sliding and of the link 88 and the cable 82. The return spring in the override spring work in concert to provide a variety of different responsive features to the tactile feedback mechanism as schematically represented by FIG. 51. As a result the use of more than one in different types of position restoration element provides a wide variety of response characteristics for the tactile feedback mechanisms described herein.

FIGS. 52A and 52B illustrate front isometric and rear isometric views, respectively, of another OTT embodiment coupled to a surgical tool 50. OTT 700 includes a housing 710 having a camera mount 705 and projector 710. In this embodiment, the camera mounts 705 is on the upper surface of the housing 710. The mount 705 contains a pair of cameras 707 directed towards the tool 74 for imaging the active element 56. In addition, this embodiment includes a TFM hundred over the trigger of the tool 50. The cable 80 provides an interface between the TFM 600 and the OTT 700 for the various purposes of tactile feedback as described herein. The OTT 700 also includes a display 702 on the upper surface of the housing 710. The display 702 may be used to provide OTT CAS output information for the user. Additionally or alternatively, display 702 is used as a user interface for user inputs. The display 702 may be configured as a graphical user interface (GUI) or other type of computer input device. Also shown is a computer in communication with the OTT 700 for the purpose of utilizing the information obtained from the use of the OTT during a CAS procedure in furtherance of the completion of a computer aided surgery. The computer includes within an electronic memory accessible to the processing unit instructions for on tool tracking computer assisted surgery. In one embodiment, computer is included within the OTT 700 as part of the electronics package within the housing. In another embodiment, the computer is an external component configured for receiving and transmitting data related to OTT CAS processes either wirelessly or via a wired connection to and from the OTT 700.

As the above examples in the illustrative embodiments make clear, embodiments of the TFM mechanisms of the present invention may be adapted or configured to provide outputs related to trigger movement or position or for further processing by the OTT CAS computer. The various TFM mechanisms provided herein may be used to provide in a minimally intrusive manner an indication of tool operation, characteristics or parameters (speed, position, rotation, setting, power level and the like) for use by the OTT CAS system. An output from a tactile feedback mechanism may be provided via an encoder/reader in the mechanism, in the OTT device, or mounted on the surgical tool itself. Still further, feedback mechanism embodiments may include wireless communications for transmitting tactile feedback mechanism information or trigger information for further processing in the OTT device or the OTT CAS computer. In a still further aspect, one or more components of the tactile feedback mechanism may be driven under instructions received based on OTT CAS processes, modes or algorithms. In some embodiments, tactile feedback mechanism indications and data are used to provide a dynamic real-time feedback loop from the OTT CAS system. Indications from the tactile feedback mechanism may also be used to provide the automatic control of one or more surgical tool control features such as: the tools motor, actuator attenuating its motor/cutting/drilling action speed or stopping it as part of an appropriate OTT CAS processing output. In one aspect, the feedback loop control is provided based on a determination of the OTT CAS system that automatic intervention of surgical tool functionality is needed to prevent an improper cut, or harm to an anatomical structure within the OTT CAS surgical field.

In still further aspects, embodiments of the tactile feedback mechanism or other feedback mechanisms configured to utilize the outputs from the systems and methods described herein may be used to automatically or semi-automatically control one or more operating characteristics of an active element of a surgical tool utilizing an on tool tracking device. Still further an embodiment of the OTT CAS system may also be configured to control the operation of the surgical tool in response to a determination of the position of the surgical tool relative to the desired boundary. Specifically, if the system determines that the tool is positioned within the tissue to be resected that is not proximate the boundary (i.e. in the green zone), the system may allow the surgical tool to controlled as desired by the surgeon. If the system determines that the tool is positioned within the tissue to be resected that is proximate the boundary (i.e. the yellow zone), the system may reduce or attenuate the operation of the surgical tool. For instance, if the tool is a saw, and it enters the yellow zone, the system may slow down the reciprocation or revolution of the saw as it moves proximate the resection boundary. Further still, if the system detects that the tool is positioned at the boundary or on tissue that is not to be resected or operated on, the system may control the surgical tool by completely stopping the tool. Although the system may automatically control the operation of the surgical tool, the system includes an override function that allows the surgeon to override the control of the tool. In this way, if the surgeon determines that a portion of tissue should be resected that was not identified for resection during the pre-operative analysis; the surgeon can override the system and resect the tissue during the procedure.

Embodiments of the tactile feedback mechanism include a wide variety of tactile stimulus. For example, the stimulus could be as simple as enhanced vibration to indicate deviation of the surgical path from the intended resection. Tactile stimulus provides the opportunity for more sophisticated indications in accordance with the various modifications and outputs provided by the OTT CAS methods described herein.

In general, powered surgical tools are activated by means of a trigger and embodiments of the feedback based mechanisms described herein provide detectable and variable (increases and decreases under control of the OTT CAS computer) resistance on the trigger or pressure on the surgeon's finger actuating the tool in a manner to indicate to the surgeon when the surgical path or current use of the active element deviates from the intended resection or other action according to the OTT CAS surgical plan. It is to be appreciated that the variety of different configurations for providing tactile feedback may be used with an unmodified, modified or replaced trigger for actuating the surgical tool used with an OTT device. In some various alternative embodiments, a trigger based feedback assembly includes a dynamic member coupled to a scissor mechanism that is in turn coupled to a stationary base (usually mounted on the handle of the surgical tool. The position or stiffness of the assembly, typically as a result of interaction with a transmission shaft or cable is dictated by a control unit within the OTT. The control unit may be configured to provide a wide variety of OTT related feedback functions including, by way of example, an actuator to operate the transmission shaft which in turn changes the force to close the scissor mechanism, moves the trigger mechanism to a full extended position, move the trigger mechanism to a full contracted position, move to a position to impair operation of the trigger, or, optionally to stop operation of the active element of the tool. In one aspect, the transmission shaft or cable or element is Bowden cable. In still other embodiments, the transmission shaft that couples the scissor mechanism to the associated component in the OTT may be any suitable element such as a rod, spring, solenoid, chain, gear, or a mini pneumatic or hydraulic actuated system. Still further, it is to be appreciated that the actuator used for the controls described above may also be included within the feedback mechanism in proximity to the trigger. In one alternative of this aspect, the actuator may be connected to the OTT device via a wired or wireless connection to provide the appropriate OTT CAS process control signals to the actuator in furtherance of the above described OTT CAS techniques.

The control unit is also capable of receiving data from the computer system. When the system determines a deviation in excess of a specified threshold level exists between the surgical path and the surgical plan by comparing the position of the tool to the intended resection of the surgical plan, the control unit actuates the transmission, increasing the resistance required to pull the trigger. Indication can be provided in the form of preventing the depression of the trigger so that the surgeon cannot activate the tool. Alternatively, indication can take the form of increased resistance, which the surgeon can overcome by the application of more force.

The trigger and other tool control embodiments described with regard to FIGS. 37A-51 may also be utilized with an externally tracked tool such as those described in co-pending and commonly assigned applications Ser. No. 11/764,505 filed on Jun. 18, 2007 and Ser. No. 11/927,429 filed on Oct. 29, 2007, each of these applications are incorporated herein by reference in its entirety.

FIGS. 52A and 52B are front and rear isometric views respectively of an on tool tracking and navigation device (OTT) that includes a display with OTT housing coupled to a surgical tool having a trigger based feedback mechanism coupled to the OTT. The view also shows an exemplary computer system in communication with the OTT.

FIG. 36 is a flowchart representing an exemplary OTT CAS process including modification of any of the above described OTT CAS processes to include associated surgical tool operational characteristics, parameters or other data related to the use of an active element in any OTT CAS process or procedure. The OTT CAS process 3600 includes many of the same processing steps described above with regard to OTT CAS process 3100 in FIG. 31A.

Figure 63:
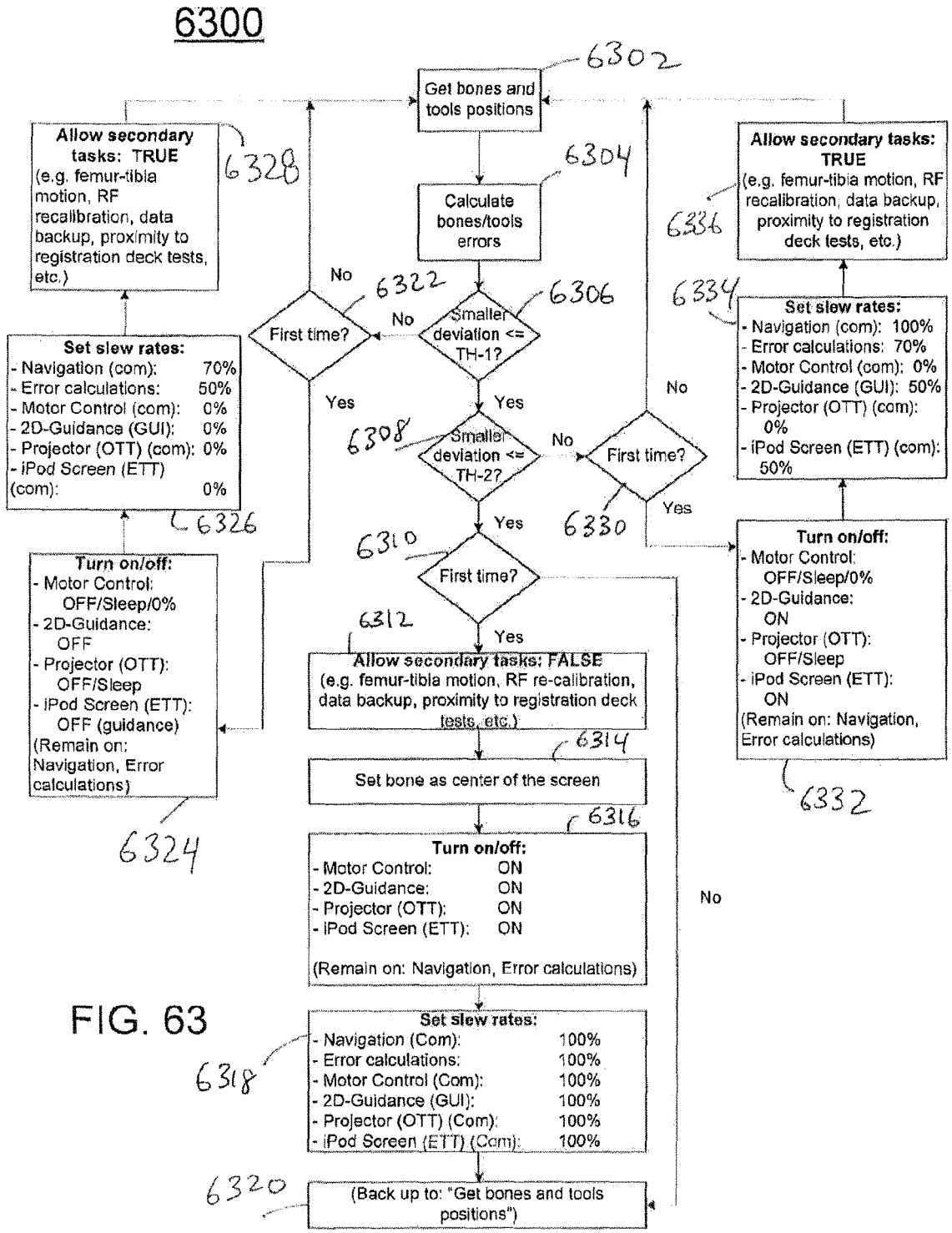

FIG. 63 illustrates a flowchart 6300 illustrating the various steps performed by the CAS guidance system when operating in hover mode. The steps start by getting bones and tool positions in registration at step 6302. Next, at step 6304 calculate deviations (i.e. bones and tools errors relative to the plan). Next at step 6306, determine whether the deviations calculated are less than or equal to TH-1. TH-1 is the outer threshold spacing. In this context, the outer threshold spacing is used to determine when the tool is at a distance spaced sufficiently far away from the point of surgery that certain aspects or secondary operations may be utilized with system resources, or that high tolerance tracking or control is not critical. If the answer at step 6306 is yes then the process proceeds to step 6308. At step 6308, the calculated errors are compared against a smaller deviation which is threshold TH-2. The threshold TH-2 is used as an inner threshold value to trigger when the system is close in to the surgical field. If the answer to step 6308 is yes then the method proceeds to step 6310 to determine whether this is the first time that the threshold TH-2 has been triggered. If the answer at 6310 is yes then the method proceeds to step 6312 where all secondary tasks are not permitted to operate, and FIG. 63 shows examples of those in box 6312. In step 6312 the system is essentially overriding all other operations so that maximum resources are made available for the tracking mode since the comparisons at step 6306 and step 6308 have determined that the system is near or is within cutting mode. Examples of secondary tasks that would not operate during this time include, for example, RF recalibration, data backup, proximity to registration and various data tests performed by the system. After step 6312, the next step 6314 sets the bone as the center of the screen on the display used by the OTT, unless overridden by the user or the user has preferences set to the contrary. Next at step 6316, additional control signals are sent within the system. In the illustrative steps of 6316, motor control is turned on, 2-D guidance is turned on, projector is turned on in the OTT embodiment. Again, here and from this point onwards, the description assumes that the user has not set options to the contrary of what is described here. If an ETT system is being used, the iPod screen is also turned on and a suitable user selectable default initial view shown. In addition, the navigation and error calculations functions remain in operation. Next at step 6318, various slew rates are set to 100%. In the illustrative step of 6318, navigation, error calculations, motor control and communications, 2-D guidance, projector, and iPod screen are all set to 100%. Next at step 6320, this mode of operational loop is repeated and the system continues to get bones and tool positions at step 6302.

Continuing on from 6302 to calculate bones and tools errors at 6304, next at step 6306, if the response at step 6306 is "no" then the system proceeds to step 6322 to determine whether or not this is the first time that the system has registered an error that is greater than the near threshold TH-1. If the answer is yes to step 6322 the method proceeds to step 6324 which permits some aspects of the system to be placed into different states. Next at step 6326, the slew rates are set to a variety of different levels in contrast to the slew rate settings found in step 6316. Next at step 6328, secondary tasks may be performed by the system. At step 6328, secondary tasks are allowed and system resources may be devoted to other activities since the system is likely not in cutting mode. Thereafter, the system returns to the base step of 6302 to get bone and tool position information. Returning down the method from 6302 to the calculation steps 6304 and the smaller deviation comparison for near threshold TH-1, if the answer at step 6306 is yes and the answer at the near field deviation TH-2 (step 6308) is no, the method then proceeds to decision step 6330. If the answer to the question first time at 6330 is no, indicating that this is not the first time that the near threshold error has been greater than the error threshold TH-2 then the method returns back to step 6302 to get bone and tool information. If, the answer to first time query at step 6330 is "yes", then the system proceeds to step 6332. In step 6332, various control functions are set to different values based upon the computer's determination of the tool position. Next at step 6334, various slew rates are set for navigation, error calculations and 2-D guidance. Thereafter, at step 6336 secondary tasks are also allowed to operate similar to step 6328. The secondary tasks are permitted because the system has determined that system resources may be used for other than critical navigation with motor control functions simultaneously. In each of the first time blocks, 6322 and 6330 and 6310, this is a simplification for a validation and latching process to prevent repeated switching of states when not necessary and adding some hysteresis to prevent toggling back and forth from one state to another based on random fulfillment of a condition. By setting the thresholds TH-1 and TH-2 to appropriate levels then the system may determine whether or not a user's movement of the OTT is intentional and directed away from the field of surgery or intentional towards the field of surgery or continuing on a step of cutting with only a minor adjustment, for example. Such intended hysteresis of course reduces the effect of digital noise and random errors especially near the boundaries of different states of the system.

In general, in the method 6300, the left hand steps (6328, 6326, and 6324) indicate a normal hover mode where the system liberates resources for secondary tasks when time sensitive tasks are not required. On the right hand side of the method 6300 (steps 6332, 6334 and 6336) are used when the system indicates that it is within a volume of interest relative to the target bone but still not in a position to cut the target bone (like a standby when the sensors and resources would be available to switch motor control on at short notice). Secondary tasks are still allowed in this condition, but time sensitive aspects are more closely monitored than in the previous case described above on the left hand side. In the bottom portion of the method 6300, these indicate the time-sensitive tasks are in action during active cutting. Method steps 6312, 6314, 6316, and 6318 are all used to insure that full slew rates are applied to all cut-related processes. During this time, system resources are not directed towards secondary resources or secondary activities are neglected all together.

In general, in the method 6300, the left hand steps (6328, 6326, and 6324) indicate a normal hover mode where the system primarily saves electric battery power and reduce heat generation and dissipation and liberates resources for secondary tasks when time sensitive tasks are not required. On the right hand side of the method 6300 (steps 6332, 6334 and 6336) are used when the system indicates that it is within a volume of interest relative to the target bone but still not in a position to cut the target bone (like a standby when the sensors and resources would be available to switch motor control on at short notice). In still another aspect, an additional factor or consideration in steps 6326, 6324, 6332, or 6334 is that one or more electronic devices may be shut down, placed in standby mode or otherwise adjusted to save power. As a result of this type of determination by the OTT CAS system, it is believed that battery life in an OTT module may be extended because high energy consuming devices like the projector, for example, may be placed in an energy conservation mode if the OTT CAS mode deems that a practical step.

FIG. 64 illustrates a simplified hover mode state diagram. The mode state diagram begins at initiation at step 6405. Next, the system may enter into hover mode at step 6410. Thereafter, if system parameters indicate that bone registration is being performed the system will move into a bone registration mode at step 6415. At the completion of bone registration, the system may either end tracking or return to the initiation step 6405. Alternatively, at the conclusion of bone registration the system may set hover mode and return to the hover mode step 6410. In addition, from the hover mode step 6410, the system may detect bone cutting steps. In this case, the system will go into bone cutting mode as shown at step 6420. At the conclusion of the bone cutting step, the system may return to hover mode at step 6410, or cease tracking and return to initial mode 6405. Another option from hover mode 6410 is to move into a bone implant fit assessment at step 6425. At the conclusion of any implant fit assessment, the system may return to hover mode at 6410, or cease tracking and return to initial mode state 6405. One example of assessment (that is not shown in the diagram to avoid clutter) is to assess the quality of the cut with a navigated surface tester, with which a cut surface location and orientation are tested to assess their quality and suggest further cutting refinements if needed. Still another alternative path from hover mode 6410, is to go into mid-range tracking at step 6430. From the mid-range tracking step 6430, the system may cease tracking and return to the initial state 6405. Alternatively, the mid-range tracking step 6430 may conclude and return to the hover mode tracking step 6410.

Figure 66A:
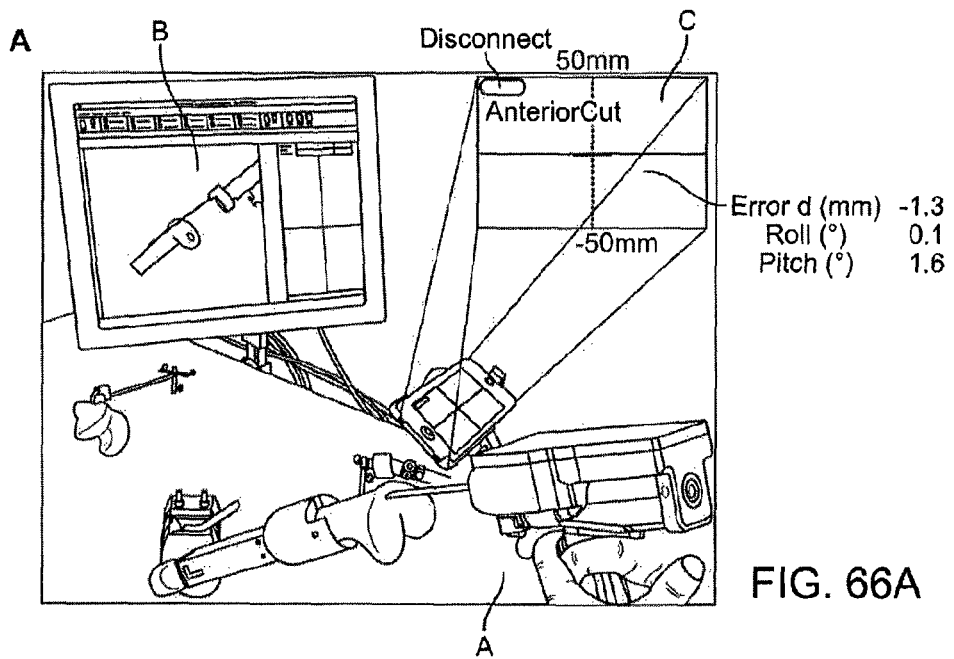
Figure 67:
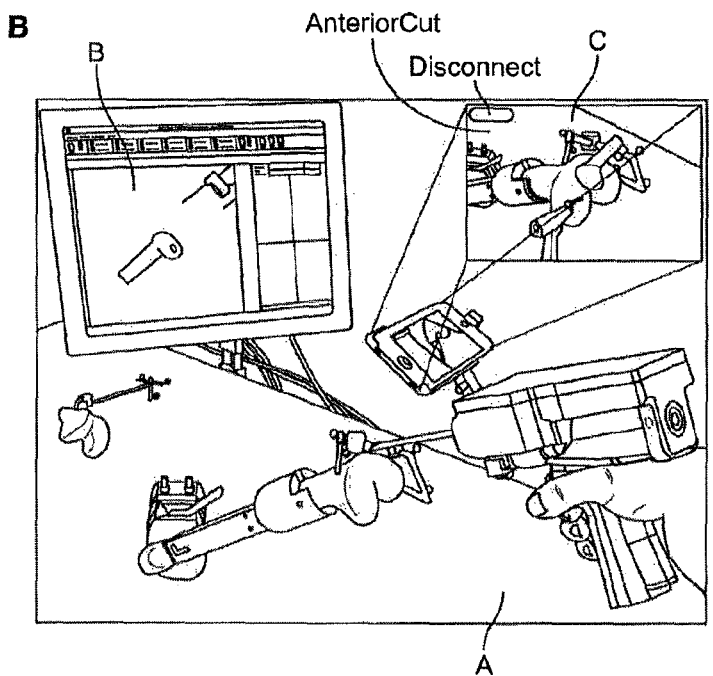

FIG. 65 illustrates another alternative view of the hover mode operation. In the sequence illustrated by FIG. 65, the system is shown moving between three modes; hover mode 6505, a bone cutting mode 6510 or in implant or cut fit assessment mode 6515. When in the hover mode 6505, using a saw and with the bone being close to an instrument will move the system into a bone cutting tracking mode 6510. Alternatively, as the bone is moved further away from the instrument, or vice versa, the saw away from the bone, the system will detect such movement and move from the bone cutting mode 6510 and back into a remote 6505 hover mode. Alternatively, if the system detects a navigated implant trial or navigated bone (cut) surface assessment tool are visible or implant trial or such tool is close to the bone, then the system will shift from hover mode 6505 into the implant fit or bone surface assessment step 6515. At the conclusion of the assessment above, as when the bone is now far from the trial implant or assessment tool, the system will return to hover mode 6505. FIGS. 66A, 66B and 67 illustrate various in-room display and on tool display or projector views depending on the operation of the OTT. Turning now to FIG. 66A, the in-room scene (A) illustrates an active cutting step. Since an active cutting step is involved, the on tool display (portion B of the view of FIG. 66A) is indicating the angular error (orientational deviation around two axes) or other cutting information about error rate or location of the blade relative to a surgical plan (offset) as described herein. In the view of FIG. 66B, the in-room display is showing the side view of the tool and blade in contact with the bone according to the surgical plan.

Determining Orientation for the 2D Guidance Display

In various places of our graphical user interface (GUI) on the main CAS computer, we sometimes use our flight simulator like (2D) graphical guidance system 66B. This display guides the user to move the instrument so the plane (labeled) merges with the target surface plane (labeled) by tipping, or changing the pitch of, the saw downwards, and rolling, to make the two lines coincide with each other (hence saw pitch is correct) AND both lie along the horizon line (hence saw roll is correct). Whether the guidance lines should go up or down depends on whether the navigated saw was held normally or upside down—and latter is possible.

To determine if the guidance to go up or down, depending on whether the saw is upside down or normal, is for the computer which logs positions to store recent history (eg. a few ms or seconds) and examine the moving average. If upon reviewing the last one hundred or ten or say one second of tracking, the computer notes that it is telling the user to go up and yet we are going down, then it must be that we are holding the saw upside down. So if it finds that the user is getting further away while we they are trying to move towards the target, it switches the guidance by 180 degrees and tells you so verbally (by voice). If you want to oppose that function and override it, you can optionally stop that.

Also, the computer can tell if you are almost aligned (near the target in 3D) and within a few degrees. Then it knows that you are in the right orientation. But if you are almost 180 degree upside down to the target (i.e. parallel to the target but within almost 180 degrees) then it means that you are holding the saw upside down so it automatically switches its coordinate system to adjust. If it sees you persistently holding the saw at 180 degrees towards the target plane, (you are close to the target plane but you are holding it at about 180 degrees plus or minus a certain threshold, say plus or minus say 10 degrees) then it automatically switches the guidance to be the other way round so the guidance is effectively going in the correct direction.

The concept relies on a knowledge based system and the following proviso: The user almost knows what they are doing and they are almost right, but the system suffered a reversal of coordinate system sign due to the user flipping the device upside down. We can make this detect and correct automatically within a few milliseconds or much less than a second.

Figure 65B:
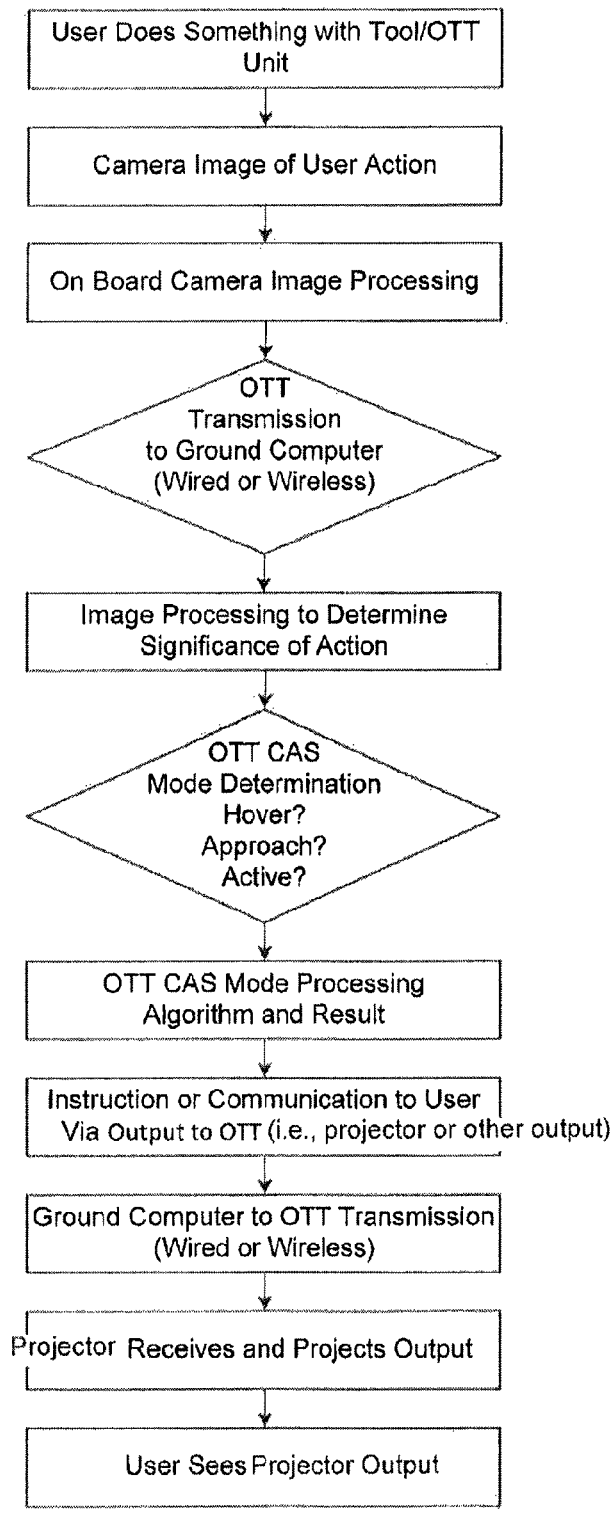

FIG. 65B illustrates a flow chart of an embodiment of a representative information/action flow of an OTT CAS process. In a first step the user does something with the tool or OTT unit. The OTT cameras then capture an image or images of the user action followed by on board camera image processing. The image processing can include simple transmission of the raw image data or additional image processing steps as described elsewhere herein with respect to FIGS. 14A, 14B, 15A, and 15B. In some OTT configurations, the OTT transmits the image data to a ground computer. The transmission can be wired or wireless. The ground computer can perform additional image processing on the image data to determine the significance of the user action. The ground computer and/or OTT module can then perform the OTT CAS mode determination as described herein. For example the processing mode can be determined between a hover mode, approach mode, and active mode. The OTT CAS can apply the mode processing algorithm to achieve a result. An instruction or communication is prepared for an output on the OTT module. The ground computer sends a transmission with the instruction to the OTT. The projector receives the instruction and projects the output so that the user can see the projector output.

FIG. 67 shows the location of an OTT system relative to a bone on an approach or an evaluation step. In the view of FIG. 67A, the in-room view, the tool is shown approaching the surgical field. The in-room display B also shows the approach of the tool to the bone within a surgical field. The view of FIG. 67C shows the display on the on tool system which indicates the alignment of the tool relative to the bone. The view shown in FIG. 67C is adjustable using the smart views command as described herein and elsewhere.

Examples of Module and Tool Combinations Including Two Part OTT Housing Modules

Various alternative OTT CAS modules and related details of their design and operation in an OTT CAS system have been illustrated and described with regard to FIGS. 1-15B and FIGS. 53-62B. Additional alternative embodiments of the OTT devices are set out in FIGS. 68a-69b, 70b-72, 74A-C, 75C-G, 76A-B, 77A-D, 78A-78B, 79A-B, 80A-80E, 81A-81E, 83A-83D, 84A-84C, 85A-85E, 86A-86H, 87A-87F, 90C-E, 91B, 92B, 93B, 95A, 95B, 96A-C, 97A, 97C, 98A, 99B, 100A, 100B, 101B, 102A-C, 103A-B, 104C-E, 112A, 112D, 116A-116C, 117A-D, 118A-C, 119A-B, 120A-120B, 122, 123, 124, 126, 128-130, 132, 133A-B, 134, 136A-136C, 137, 146A-146E, 147A-C, 148A-148D, 149A-149C, 150A-F, 151B-G, 154, 155A-D, 156A-156D, 157A-157E, 158A-B, 159A-B, 160B, 161, 162A-D, 163, 164A-B, 165A, 166B, 167B, 167C, 168A-C, 169A-B, 170B, 173A-173B, 174A-174B, 174C, 175A, 176B-C, 177B, 178A, 178B, 179C, 179D, 190A, and 190B. In these additional alternatives, the OTT CAS module is divided into two parts, generally a lower housing that attaches to a surgical tool and an upper housing that attaches to the lower housing. The lower housing is generally referred to as the saddle and is shaped for attachment to the surgical tool 50. The upper housing or the other part of the OTT CAS module attaches to the saddle. In general, the projector, cameras and associated electronics are located in the upper housing or the module that attaches to the saddle. In the various alternative embodiments that follow, a number of alternative upper housing—lower housing or saddle-electronics module configurations will be described.

Various alternative embodiments of a two part OTT device are illustrated in FIGS. 68a-69b, 70b-72, 74A-C, 75C-G, 76A-B, 77A-D, 78A-78B, 79A-B, 80A-80E, 81A-81E, 83A-83D, 84A-84C, 85A-85E, 86A-86H, 87A-87F, 90C-E, 91B, 92B, 93B, 95A, 95B, 96A-C, 97A, 97C, 98A, 99B, 100A, 100B, 101B, 102A-C, 103A-B, 104C-E, 112A, 112D, 116A-116C, 117A-D, 118A-C, 119A-B, 120A-120B, 122, 123, 124, 126, 128-130, 132, 133A-B, 134, 136A-136C, 137, 146A-146E, 147A-C, 148A-148D, 149A-149C, 150A-F, 151B-G, 154, 155A-D, 156A-156D, 157A-157E, 158A-B, 159A-B, 160B, 161, 162A-D, 163, 164A-B, 165A, 166B, 167B, 167C, 168A-C, 169A-B, 170B, 173A-173B, 174A-174B, 174C, 175A, 176B-C, 177B, 178A, 178B, 179C, 179D, 190A, and 190B. In general, the saddle is the component that has at least one surface for coupling to the tool to be guided by the OTT device. The saddle also includes at least one surface for mating to an OTT electronics module. The OTT electronics module includes the cameras, projector, sensors and other electronics as described herein in FIGS. 1-15B and 53-62B. In the examples that follow a number of alternative mechanical, electrical, and mechanical and electrical connections between the two OTT housing components. As will become apparent in the description that follows, a wide variety of different functions can be provided by the mating of these two OTT device components. In some embodiments, the functions relate to the use of the OTT device and the surgical tool 50. In other embodiments, the functions relate to the overall OTT CAS system operation. These and other details will be appreciated in the description and figures that follow.

Figure 68A:
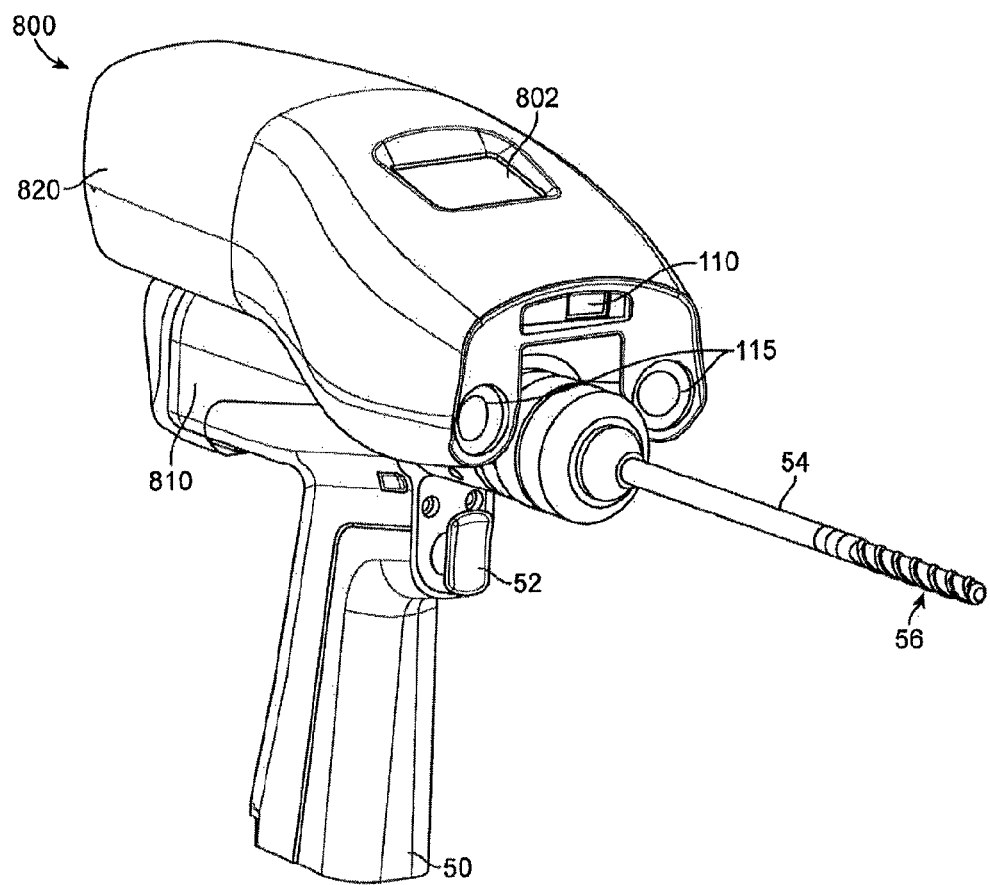
FIGS. 68A-72 relate to various embodiments of a two part OTT housing.

FIG. 68a is an isometric view of a two part OTT device 800 coupled to a surgical tool 50. In this exemplary embodiment, the two part OTT device 800 includes a saddle 810 and an OTT electronics module 820 coupled to the saddle 810. The module includes a sloped lid. The module 820 includes a display 802, cameras 115, and projector 110. In this example, the tool 54 is a drill and the active element 56 is the tip of the drill bit. The two part OTT device can be embodied in a number of examples, as illustrated in FIGS. 68a-69b, 70b-72, 74A-C, 75C-G, 76A-B, 77A-D, 78A-78B, 79A-B, 80A-80E, 81A-81E, 83A-83D, 84A-84C, 85A-85E, 86A-86H, 87A-87F, 90C-E, 91B, 92B, 93B, 95A, 95B, 96A-C, 97A, 97C, 98A, 99B, 100A, 100B, 101B, 102A-C, 103A-B, 104C-E, 112A, 112D, 116A-116C, 117A-D, 118A-C, 119A-B, 120A-120B, 122, 123, 124, 126, 128-130, 132, 133A-B, 134, 136A-136C, 137, 146A-146E, 147A-C, 148A-148D, 149A-149C, 150A-F, 151B-G, 154, 155A-D, 156A-156D, 157A-157E, 158A-B, 159A-B, 160B, 161, 162A-D, 163, 164A-B, 165A, 166B, 167B, 167C, 168A-C, 169A-B, 170B, 173A-173B, 174A-174B, 174C, 175A, 176B-C, 177B, 178A, 178B, 179C, 179D, 190A, and 190B.

Figure 68B:
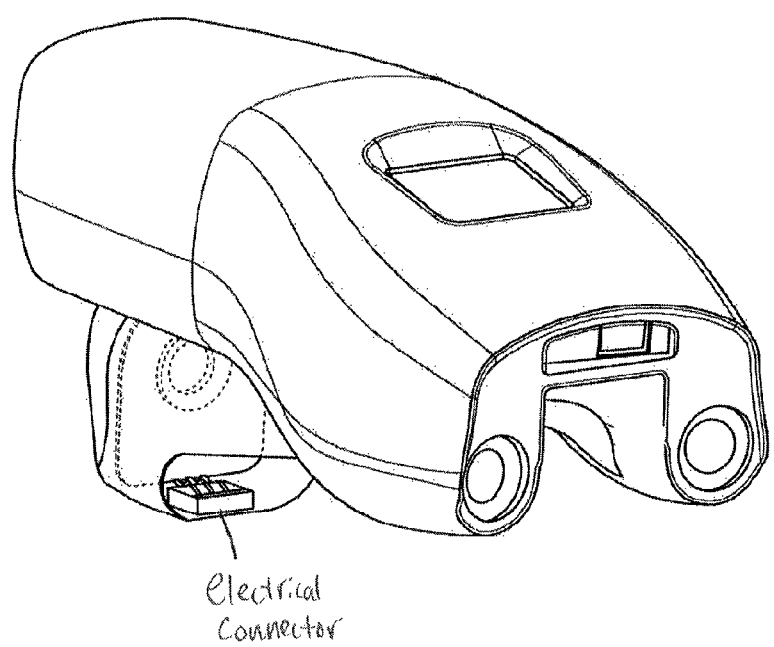

FIG. 68B illustrates the upper housing 820 separated from an optional saddle. The upper housing 820 includes electrical connectors to control the speed of the tool. The device illustrated in FIG. 68B can be a one-part housing or could optionally be used with a saddle for a two-part housing. The loop structure has a closed back area and may optionally have another connector. The device illustrated in FIG. 68B includes electrical connectors. In contrast to the closed rear area illustrated in FIG. 68B, both FIGS. 68E and 70 have open backs. FIG. 68B also does not include the slots for the saddle pegs used in the device illustrated in FIG. 68A.

Figure 68C:
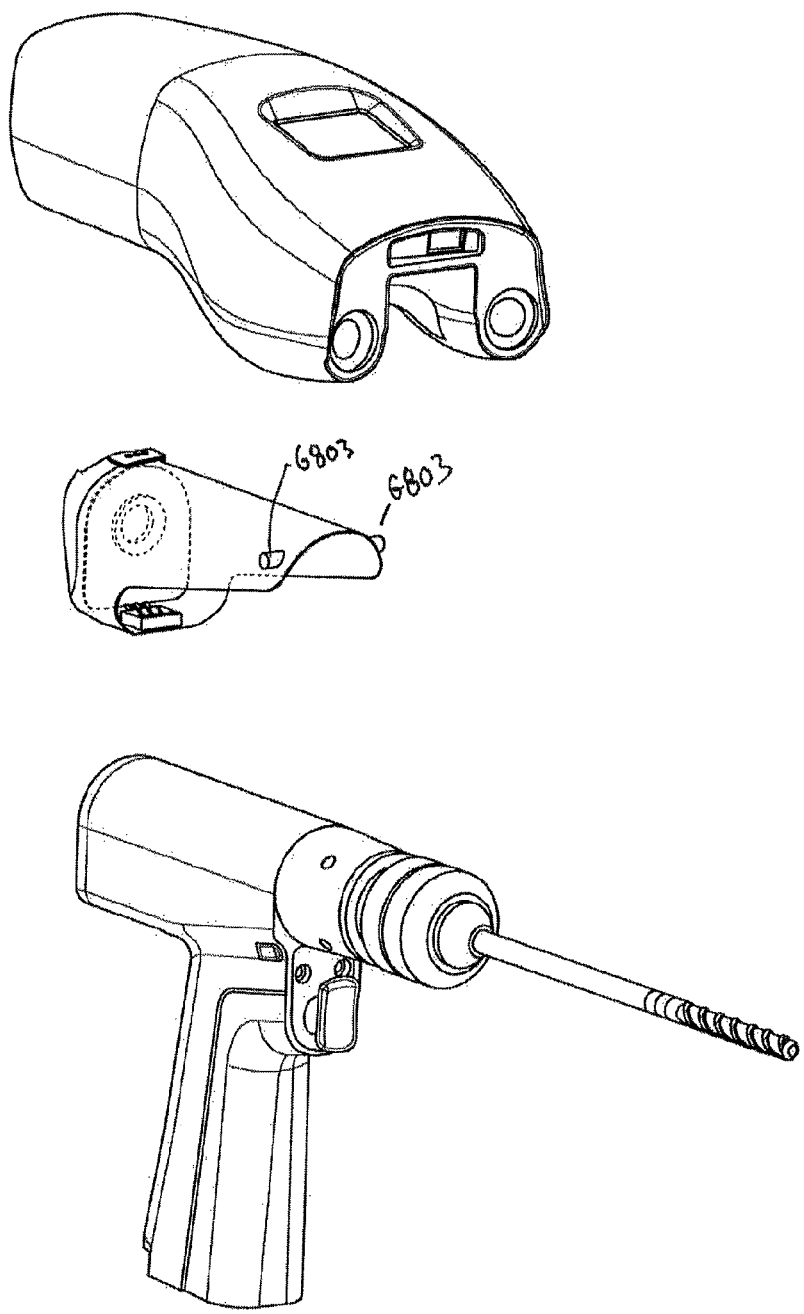
Figure 68D:
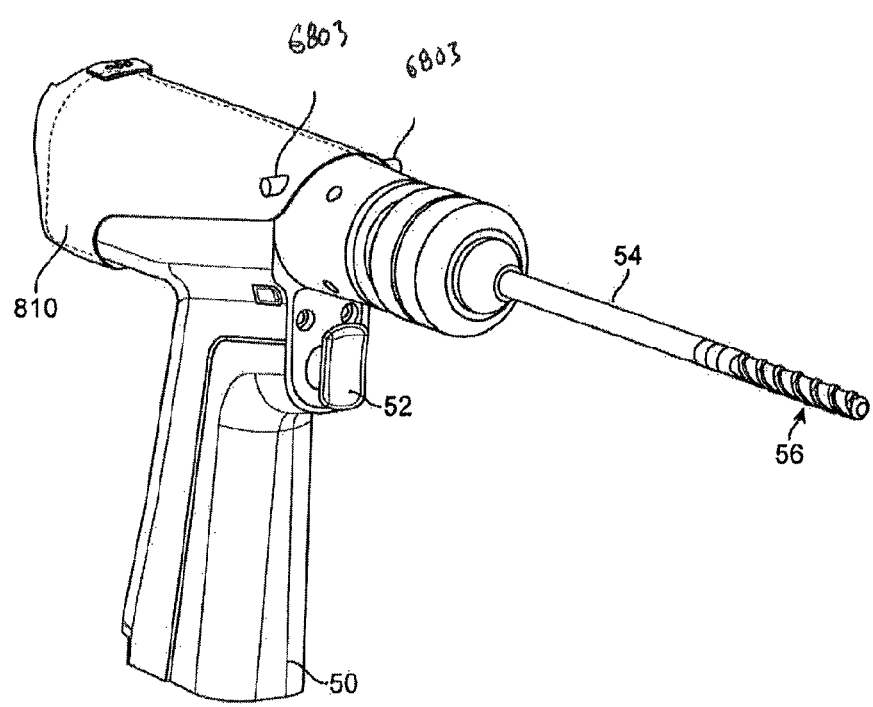

As best seen in the exploded view of FIG. 68C, there are three major components available in the illustrated assembly of FIG. 68A: the handheld surgical tool, instrument, or device 50; a mating attachment, which is also referred to as a saddle 810; and the removable OTT electronics module 820, which contains the tracking electronics and sensors to guide the tool in CAS. The tool 50 is typically a handheld cutting instrument intended for the cutting of bone in orthopedic surgery, including but not limited to, a saw, drill or reamer. The saddle has an inner mating surface (6800), which is optimized, by shape, to fit the surface contours of the tool 50, and an outer mating surface (6801), which is optimized and contoured to fit the inner surface (6802) of the removable OTT electronics module 820. A pair of optional guide posts (6803) are positioned on the distal end in position to receive the corresponding guide slots (6804) in the upper housing 820. It is expected that the saddle 810, when used in an embodiment, is attached to the tool 50 in a permanent manner. The saddle 810 may also be attached using a removable mechanism as long as the saddle is firmly attached to the tool and free from movement or vibration. The saddle 810 is shown attached to the instrument 50 in FIG. 68D.

Once the cooperative attachment between the lower and upper OTT housings is completed, the assembly (see FIG. 68A) is simply two working pieces used by the operator; the tool 50 and the assembled OTT module 800.

The OTT electronics module is attached to the tool by cooperative fitting of the lower surface of the upper housing to the matting surface (generally the upper surface) of the saddle.

In the embodiment of FIG. 68C, the upper housing 820 is oriented above and in front of the lower housing 810 so that the pins on the saddle may engage with the groove on the interior surface of the upper housing 820. The upper housing 820 then slides along the pins until seated in position. The groove may have friction fit, curved shapes, ratchet features, stops or other such locking devices to ensure that the upper housing moves the full length of travel to a secure, seated position engaged with the saddle 810.

With the saddle in place and the upper and lower housing coupled together, the overall OTT device 800 looks similar to the OTT devices of the earlier embodiments.

The saddle and the OTT electronics module have matching surface contours to guide the attachment of the OTT electronics module to the tool, ensuring a stable fit. Various alternative mating or complementary surfaces may be provided for this purpose. A number of different mating or complementary surfaces are illustrated, for example, in FIGS. 68b, 68c, 68g, 68h, 69a, 69b, 70b, 70c, 70d, 70e, 70f, 70g, 71c, 71d, 74d, 75A-G, 76A-76B, 77A-77D, 80A-E, 81A-81E, 82C, 83A-83B, 84B, 88A-88B, 89A-B, 90A-90E, 91A-B, 92A-B, 93A-B, 94A-C, 95A-B, 96A-C, 97A-97C, 98A-98B, 99A-B, 100A-100B, 101A-B, 102A-C, 103A-103B, 104A-E, 105A-105D, 111B, 112A-D, 114A, 116B-C, 117A-D, 118A-118C, 122, 124, 125, 126, 128, 129, 130, 131, 132, 133A-B, 134, 135, 136A-C, 137, and 147C. In addition, there may also be friction fit features, detents, dimples, spring ball and socket fittings, tongue and groove, dovetail and other similar two part joints provide to ensure secure yet releasable engagement between the upper and lower housing.

Figure 68E:
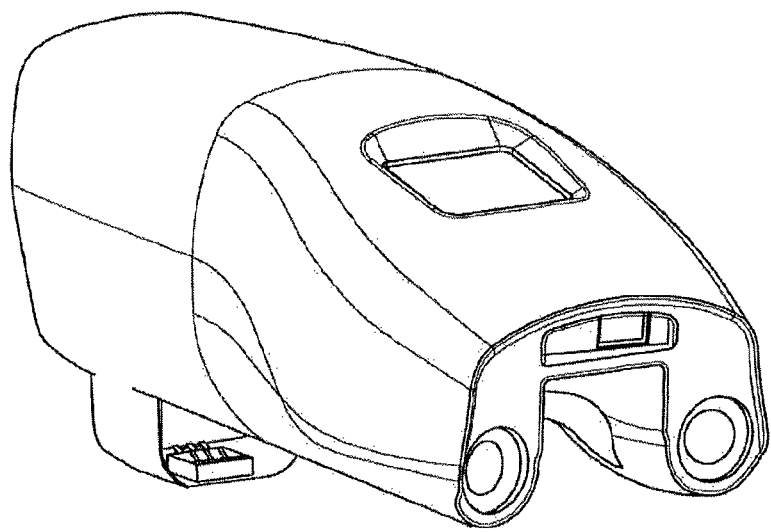
Figure 68F:
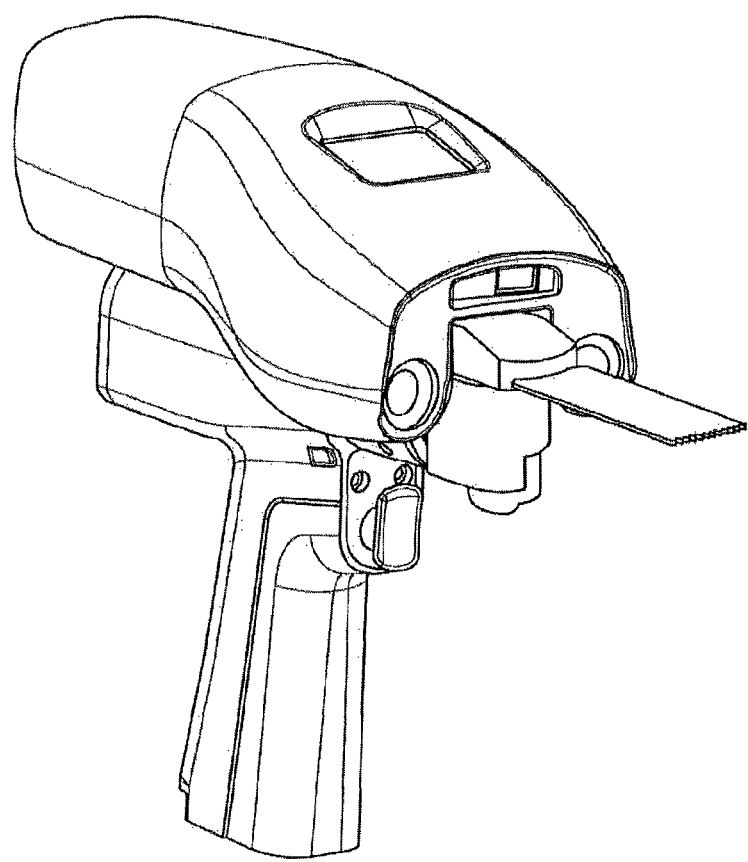
Figure 68G:
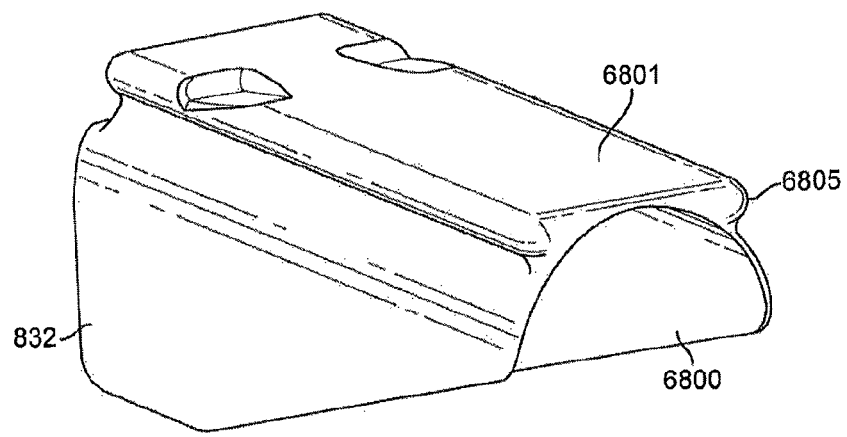
Figure 68H:
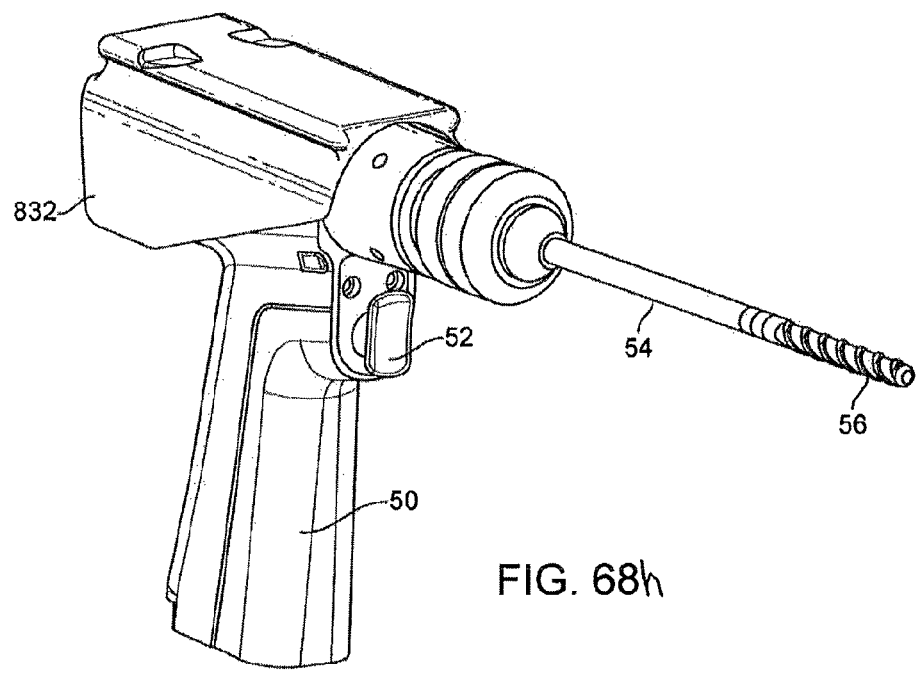

FIG. 68G is an isometric view of a saddle 832 having a surface (6801) for mating with the upper housing. In this illustrative embodiment, there is a rounded edge feature used to mate with the upper housing. In addition, a pair of mating features are positioned along the surface (6805). The lower surface of the upper housing will have a corresponding rounded edge and flat surface as well as features to mate with the pair of detents. FIG. 68H illustrates the saddle 832 shown in FIG. 68G engaged with the tool 50.

FIG. 68F is an isometric view of the two part OTT housing 800 having a sloped lid in place on a surgical tool 50. In the illustrative embodiment of FIG. 68F the surgical tool 50 is a surgical saw. It is to be appreciated that the saddle 810 is configured to be positioned on different surgical tools according to the tracking requirements of the active element of that particular surgical tool. As such, the alignment and position of a saddle relative to the surgical tool 50 and the active element 56 is selected by design such that when the OTT electronics module is coupled to the saddle, the camera, sensors, projector, display and other functionality of the OTT device are in proper alignment, orientation and/or spatial relationship to the tool 54, tool handle and active element 56.

FIG. 74A illustrates a side view of an OTT device/module 900 engaged with a saddle and a surgical tool 50. FIG. 74B is an isometric view of the OTT module 900 engaged with the saddle and surgical tool 50. FIG. 74C is an isometric view of the OTT module 900 having a lid assembly 903, a housing assembly 906, display 909, projector lens 912, and camera lenses 915. FIG. 74D illustrates an example of saddle configured to engage with a surgical tool and provide a complementary surface to engage with the housing of the OTT module 900. FIG. 74E illustrates a modified end cap assembly including a modified end cap of the tool that has been modified to add electrical contacts. FIG. 74F illustrates a surgical tool 50.

Figure 75A:
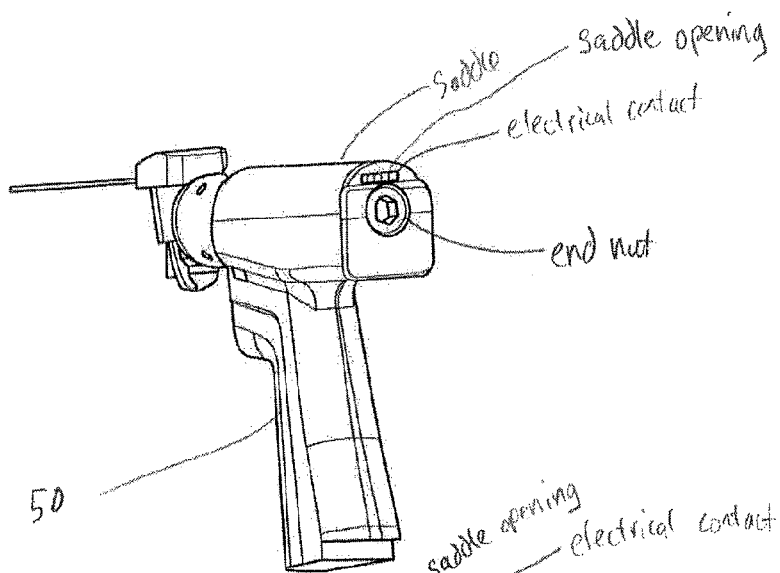
FIGS. 75A-75B illustrate embodiments of saddles engaged with a surgical tool.
Figure 75B:
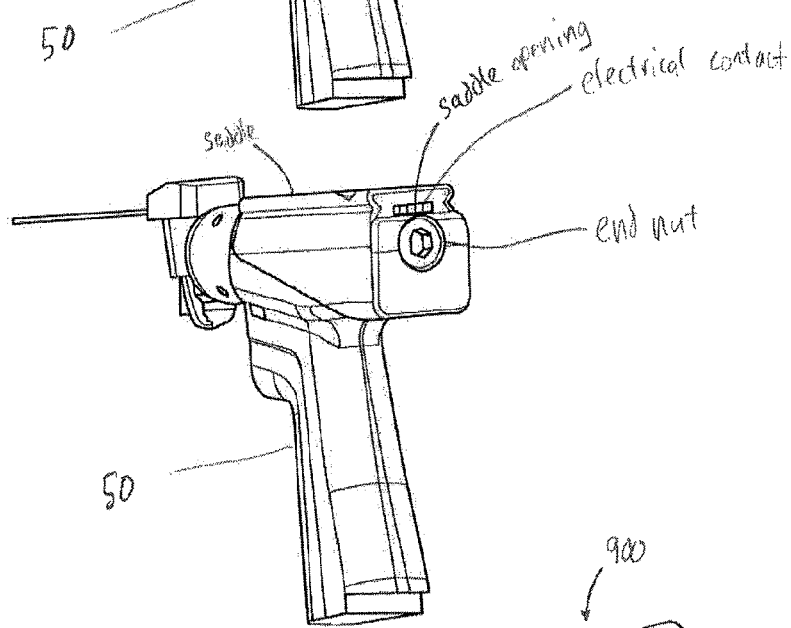
Figure 75C:
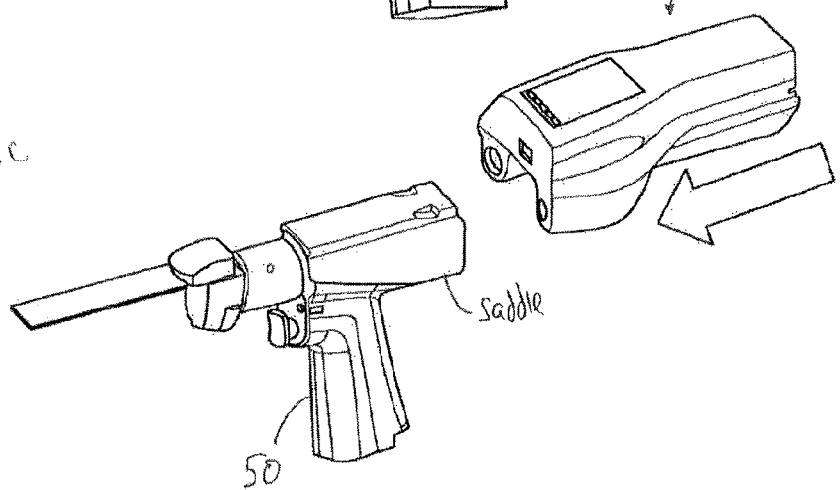
FIGS. 75C-75G illustrate embodiments of an OTT module sliding into engagement with a surgical tool and saddle.
Figure 75D:
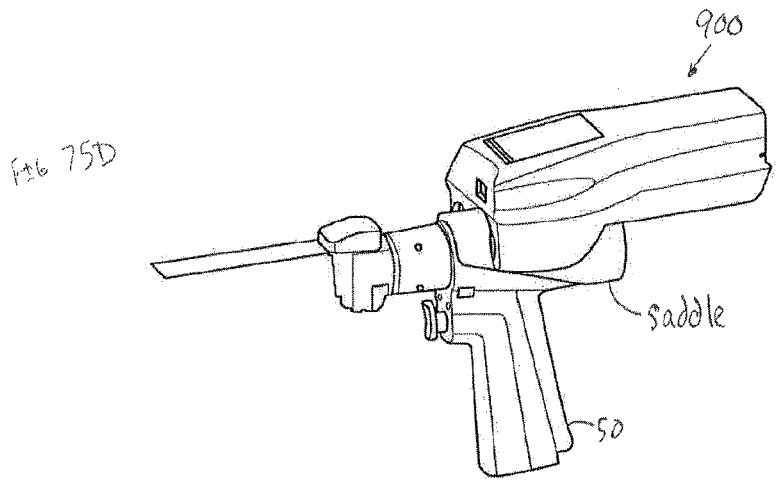

FIGS. 75A-75B illustrate two different embodiments of saddles engaged with a surgical tool having an end cap modified to include electrical contacts. The saddles are attached to the surgical tool and secured in position using the end nut. FIGS. 75C-75D illustrates an OTT module sliding into engagement with the tool 50 and saddle illustrated in FIG. 75B.

FIG. 75D illustrates an OTT module 900 sliding onto the saddle and tool 50 illustrated in FIG. 75A.

Figure 75E:
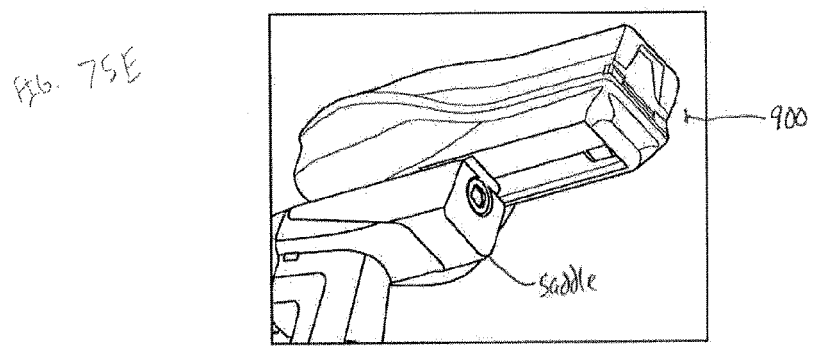
Figure 75F:
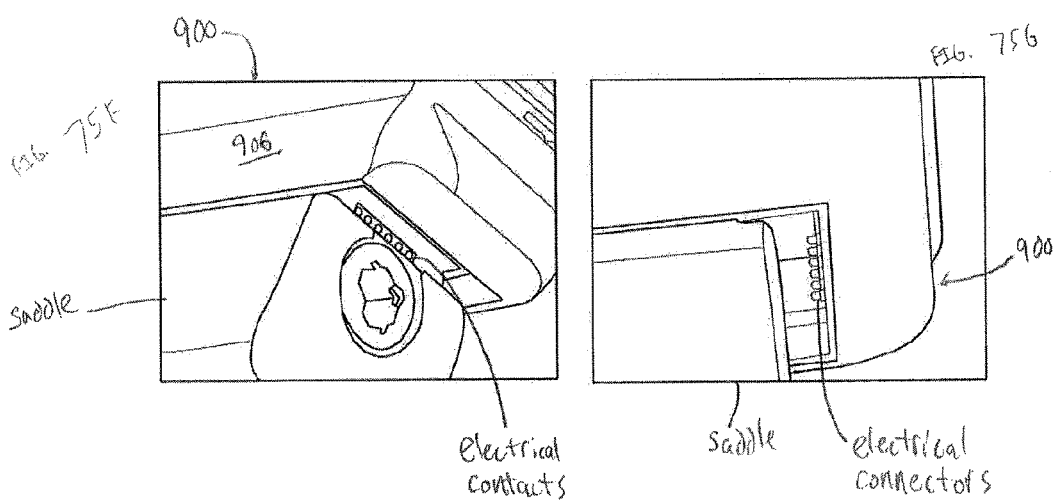
Figure 75G:
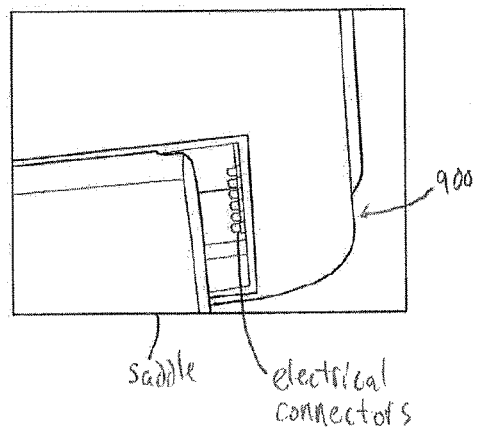

FIGS. 75E-75G illustrate bottom views of the OTT module 900 sliding onto the saddle. FIG. 75F illustrates the electrical contacts on the modified end cap of the surgical tool through the opening in the saddle. FIG. 75G illustrates a bottom view of electrical connectors on the OTT module right before the connectors pass through the opening in the saddle to engage with the electrical contacts on the modified end cap of the surgical tool.

FIGS. 76A-76B illustrate two different views of an OTT module 900 engaged with a surgical tool 50 and saddle.

FIGS. 77A-77B illustrate a side view and isometric view, respectively of an OTT module 900 engaged with a surgical tool 50 and saddle. FIG. 77C illustrates the OTT module 900 with a battery door open to receive a battery to power the OTT module. FIG. 77D illustrates a surgical system including an OTT module 900 attached to a surgical tool 50 and saddle along with a battery insertion funnel and cleaning seal tool.

FIG. 78A illustrates an isometric view of an OTT module 900 and FIG. 78B illustrates separate components of the OTT module 900 of FIG. 78A. The OTT module 900 includes a lid assembly 903 configured to accommodate a battery and a display/user interface (e.g. touchscreen) 909. A housing 918 is configured to accommodate a Y-board, which can be a printed circuit board. The printed circuit board can accommodate electronic components including two camera assemblies and a projector. The housing assembly 906 includes the housing 918 and the contents supported within the housing 918, such as the Y-board, projector, and camera assemblies. The lid assembly includes the lid 921 shell and the items supported by or within the lid shell such as the battery, display, etc. The lid assembly 903 is configured to be secured to the housing 918.

FIG. 79A illustrates a housing 918 with a gasket configured to contact a Y-board assembly. FIG. 79B illustrates the housing of FIG. 79A with a Y-board assembly inside the internal volume of the housing. The Y-board assembly includes a projector, camera assembly, projector bracket and electronics, including image processing and transmission circuits.

FIG. 79C has a top view of a Y-board with image processing and transmission circuits in accordance with some embodiments. In some embodiments the image processing and transmission circuits can be used for data transmission of a bit map stream from the cameras. In some embodiments image processing on the camera stream can be done on the Y-board to identify a constellation, determine a relative position and orientation between the OTT module and the constellation, and to send the relative position coordinates to a ground or system computer. In some embodiments the image processing and transmission circuit is configured to identify the constellation and send only constellation data to the ground computer.

Figure 80A:
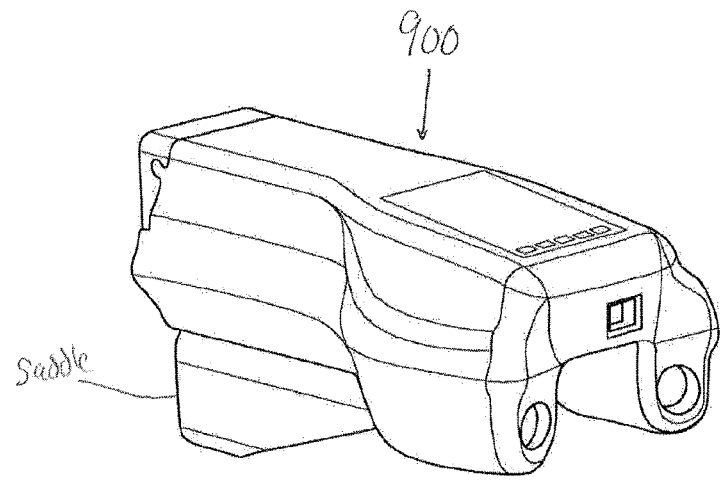
FIGS. 80A-80E illustrate various views of an embodiment of an OTT module engaged with a saddle in accordance with some embodiments.
Figure 80B:
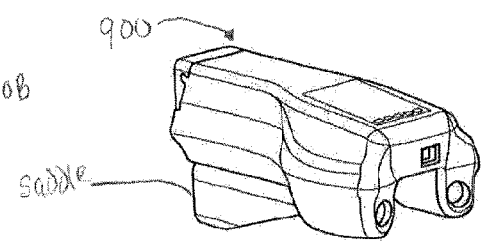
Figure 80C:
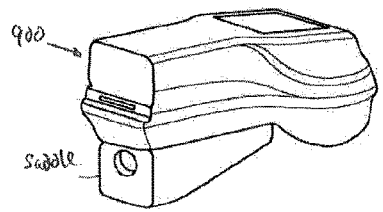
Figure 80D:
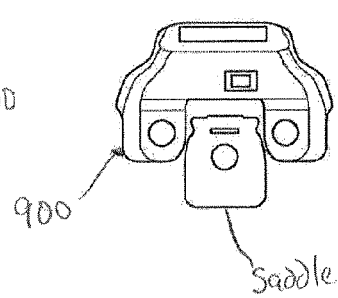
Figure 80E:
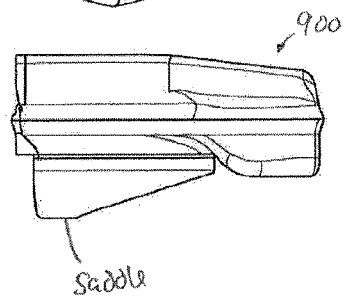

FIGS. 80A-80E illustrate various views of an embodiment of an OTT module 900 engaged with a saddle. FIGS. 80A and 80B are isometric top views of the OTT module 900 engaged with the saddle. FIG. 80C is an isometric back view of the OTT module 900 engaged with the saddle. FIG. 80D is a front view of the OTT module 900 engaged with the saddle. FIG. 80E is a side view of the saddle and module 900.

FIGS. 81A-81E illustrate various views of the OTT module of FIGS. 80A-80E engaged with a surgical tool, which is illustrated as a saw. FIG. 81A is a top isometric view of the OTT module 900 and saddle engaged with the surgical tool 50. FIG. 81B is a side view of the OTT module 900 engaged with the saddle and the surgical tool 50. FIG. 81C is a front view of the OTT module 900 engaged with the surgical tool 50 and saddle. The projector and cameras are configured to observe and project along the area in front of the active element of the surgical tool 50. FIG. 81D is a different isometric view of the OTT module 900 engaged with the saddle and surgical tool 50. FIG. 81E is a back view of the OTT module 900 attached to the saddle and tool 50. FIG. 81E also includes additional components that can be included with the surgical systems disclosed herein, such as a battery insertion funnel and cleaning seal tool.

Any of the OTT devices disclosed herein may be adapted and configured to work alone or with complementary saddles with any handheld surgical tool for use in an OTT CAS system including, for example, a saw, a sagittal saw, a reciprocating saw, a precision saw, a drill, a reamer or other hand held surgical tool.

FIG. 82A-82B illustrate additional embodiments of surgical tool modules that are configured to directly engage with the tool without the use of a separate saddle. These embodiments can be referred to as one-part housing devices. The one-part housing devices can be either reusable or disposable. The lower part of the one-part housing is designed to engage with the surgical tool as described herein.

FIG. 82C illustrates a two-part housing that can snap on to the saddle engaged to the surgical tool. The saddle illustrated in FIG. 82C could be designed to accommodate the OTT module in a snap on fashion. The saddle could be permanently attached to the tool in some embodiments.

Figure 105A:
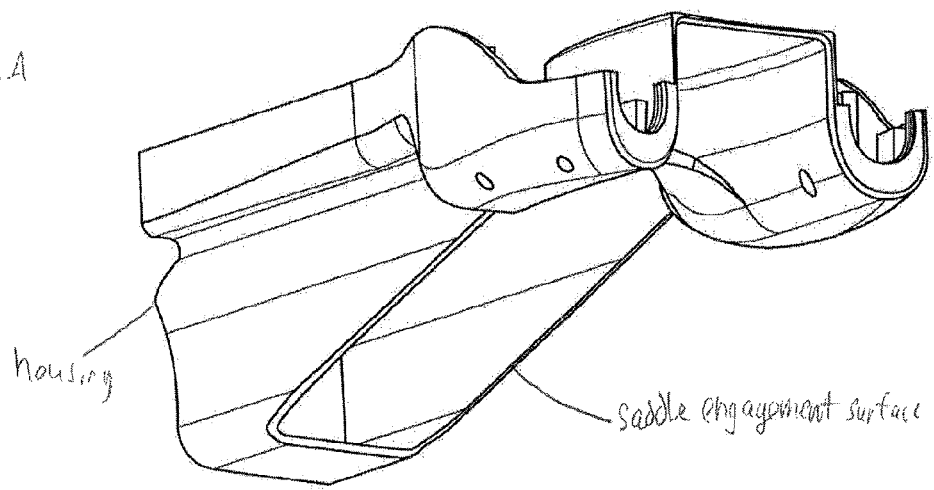
Figure 105B:
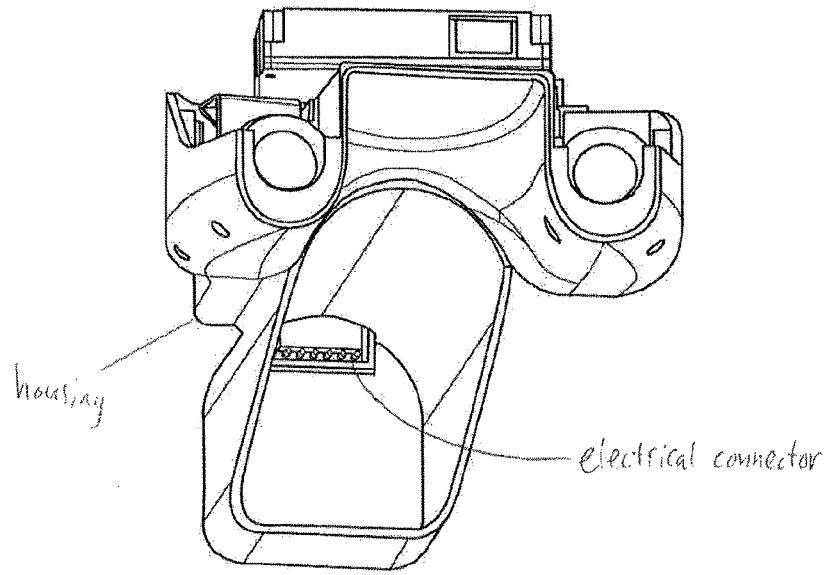
Figure 105C:
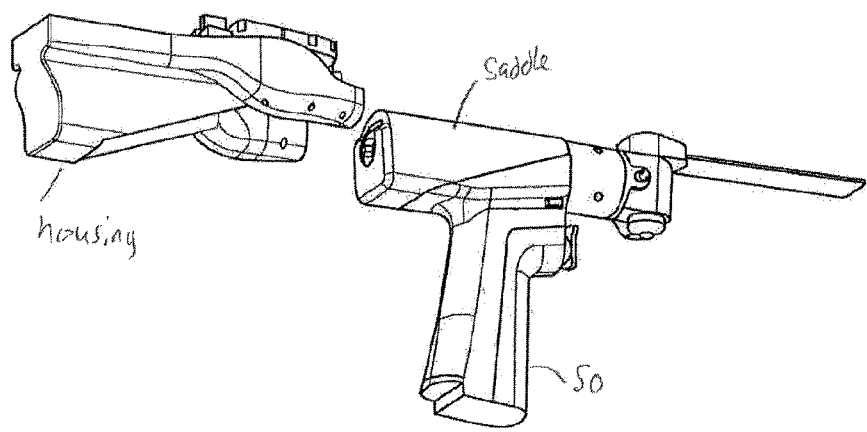
Figure 105D:
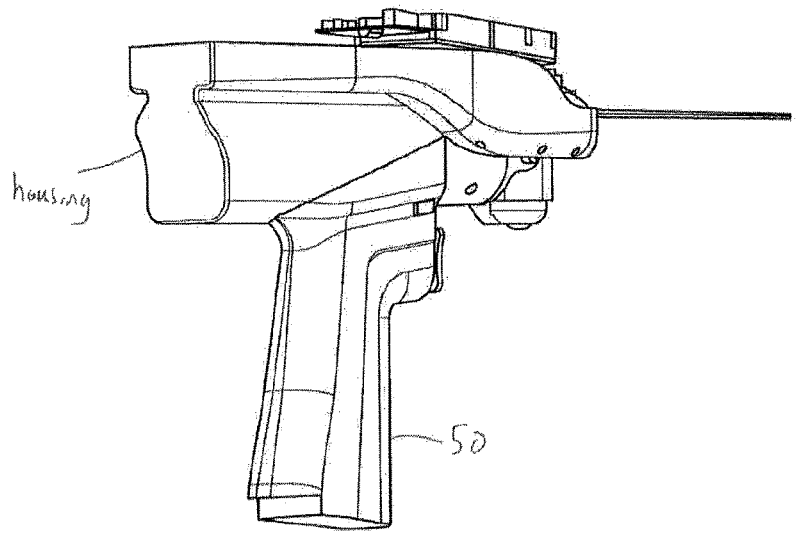

FIGS. 105A-105D illustrate various views of an OTT having a flat bottom to accommodate a more boxy surgical tool for use in OTT CAS systems. These views also illustrate how some one piece OTT designs may—optionally by adjusting the OTT saddle engagement surface—be modified to be used with a saddle. In addition, these views show both open rear panels (FIG. 105B) or closed rear panels (FIGS. 105A, 105C, and 105D). In contrast to the embodiment of FIG. 68E, the illustrated OTT housing has an electrical connector positioned for a rear face or upper rear portion of the surgical tool 50. Here, the loop base is configured to mate by encircling an outer housing of the tool 50. The OTT modules illustrated in FIGS. 105A-105D are configured to mate with a tool having a body outer housing that may be more boxy or a square bottom with a rounded top (see interior curve detail best seen in FIG. 105B). The strap of the OTT may be shaped to conform to any outer surface of the tool or tool saddle combination presented on a handheld surgical tool being tracking using an OTT and the OTT CAS methods described herein. FIG. 105C shows the OTT approaching the saddle/tool from the rear for sliding engagement to a seated position as shown in FIG. 105D.

FIGS. 83A-83D, 84A-84C, 85A-85D, 86A-86H, and 87A-87F illustrate embodiments of OTT modules that have a sloped lid and housing engagement structure. In contrast to the OTT module illustrated in FIG. 147A-C, which illustrates a lid and housing that engage together with a generally planar or flat arrangement, the sloped lid OTT modules have complementary structures that are non-planar. It should be appreciated that any of the features illustrated FIGS. 83A-

83D, 84A-84C, 85A-85D, 86A-86H, and 87A-87F can be used in the other embodiments of OTT modules described herein.

FIGS. 83A-83D illustrate an embodiment of an OTT module 1000 having a sloped lid 1018. FIG. 83A is top isometric view of the OTT housing 1018 engaged with a saddle and FIG. 83B is a side view of the OTT housing assembly 1006 and saddle engaged with a surgical tool 50. The OTT housing 1018 has a planar upper housing surface at the proximal end and a sloped, non-planar surface at the proximal end adjacent to the cameras. The proximal end of the housing has a semi-circular opening to accommodate a lens for the camera. FIGS. 83C-83D are views of the complementary lid 1021 for the OTT housing 1018 illustrated in FIGS. 83A-83B. FIG. 83C shows a top view of the lid 1021 with an opening for a display or touchscreen. FIG. 83D shows a bottom view of the lid 1021. The lid has a proximal end with a partial circular opening to accommodate a portion of a lens for the camera.

Figure 84A:
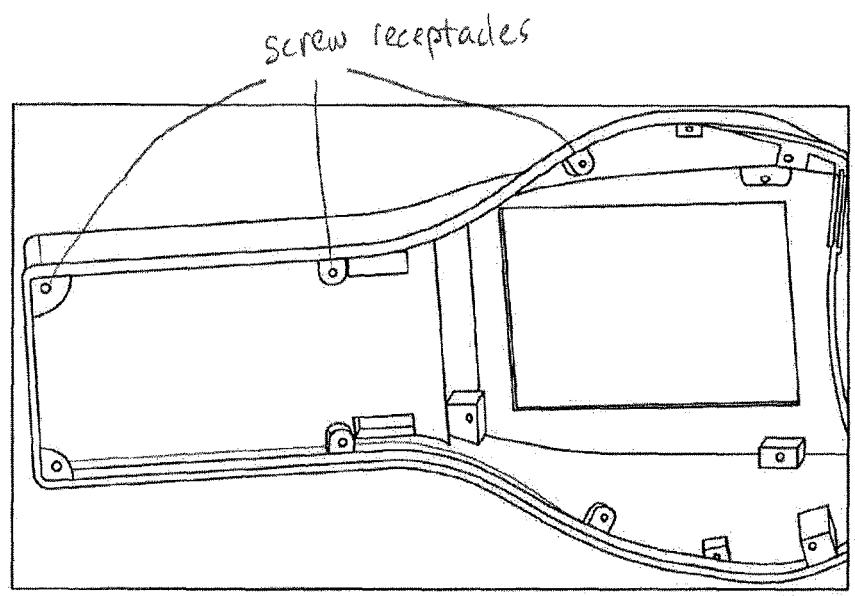
FIGS. 84A-84C illustrate various views of an embodiment of an OTT module having a sloped lid.
Figure 84B:
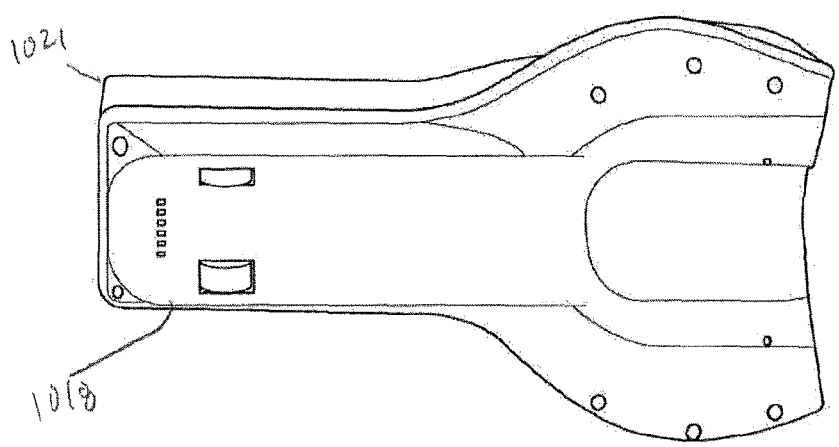
Figure 84C:
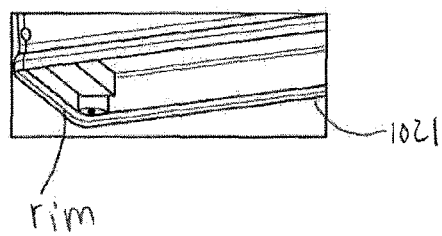

FIGS. 84A-84C illustrate an embodiment of an OTT module 1000 having a sloped lid 1021. FIG. 84A illustrates a bottom view of the lid 1021 with a number of screw receptacles to facilitate engagement with the housing 1018. FIG. 84B illustrates the lid 1021 attached to the housing 1018. FIG. 84C shows a portion of the lid 1021 with a rim to facilitate engagement with the housing 1018.

FIGS. 85A-85D illustrate various views of a lid 1021 of an OTT module 1000 in accordance with some embodiments. FIG. 85A illustrates a bottom view of the lid 1021 with a touch screen, pad, and touch screen plate. FIG. 85B illustrates the touch screen engaged with the lid 1021. FIG. 85C illustrates the touch screen plate in place to hold the touch screen and pad in place. FIG. 85D is a top view of the touch screen in the lid 1021 to form the lid assembly 1003. FIG. 85E is a bottom view of the touch screen plate engaged with the lid 1021 using screws. A gasket can be optionally added to hold the touch screen in place.

Figure 86D:
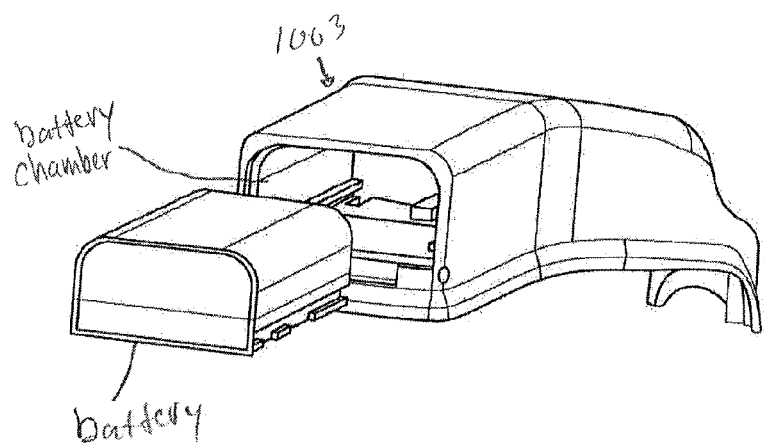
Figure 86E:
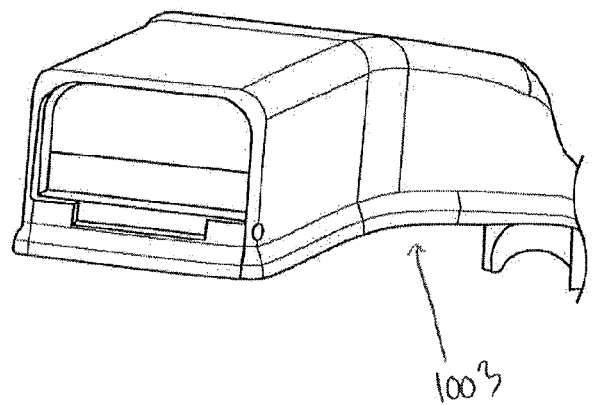
Figure 86F:
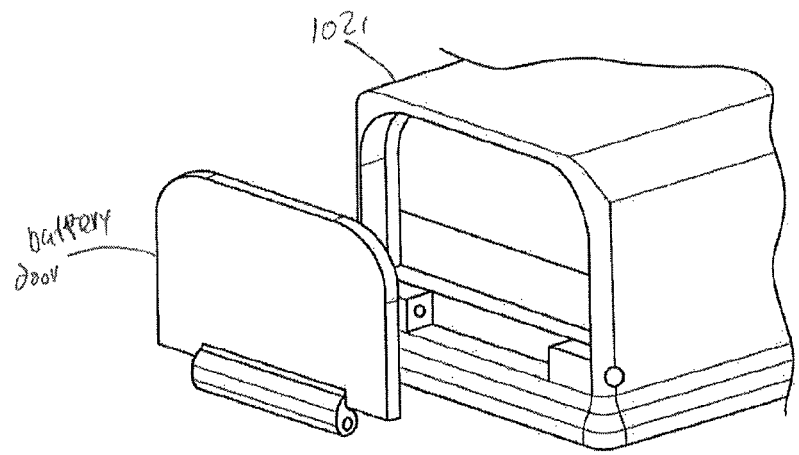
Figure 86G:
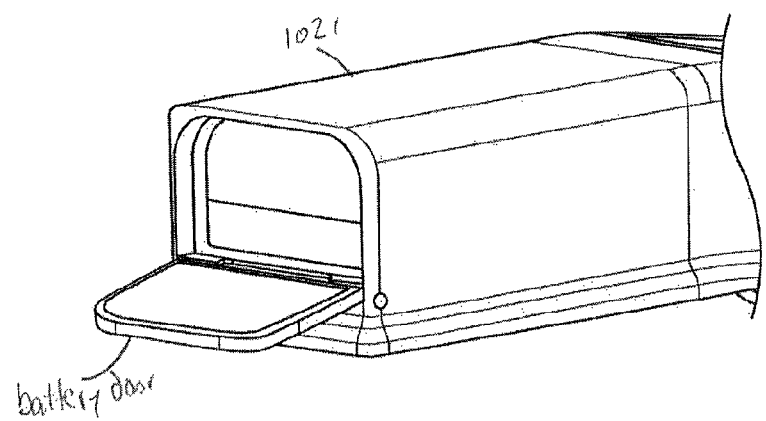
Figure 86H:
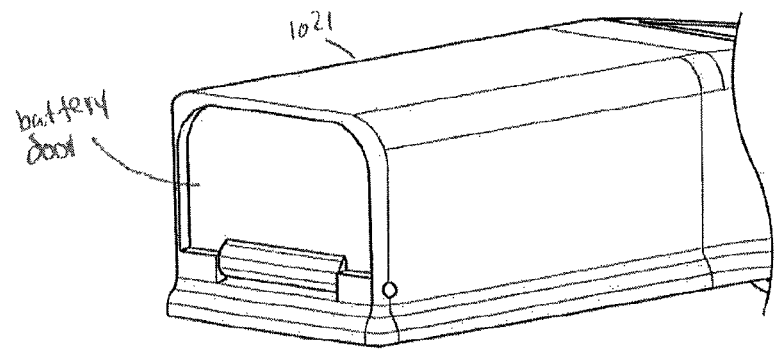

FIGS. 86A-86H illustrate various aspects of an OTT module lid 1021. FIGS. 86A-86C illustrate various views of a projector lens engaged with a hole in the lid 1021 configured to accommodate the output of the projector. FIGS. 86D and 86E illustrate a battery prior to sliding into a battery chamber within the lid assembly 1003. FIGS. 86F-86H illustrate a battery door in separate, open, and closed arrangements relative to the lid 1021, respectively.

Figure 87A:
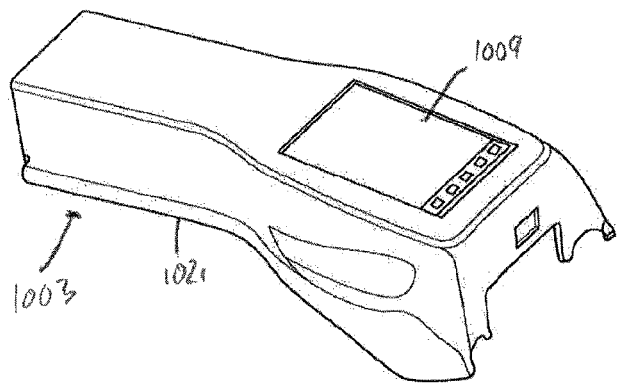
Figure 87B:
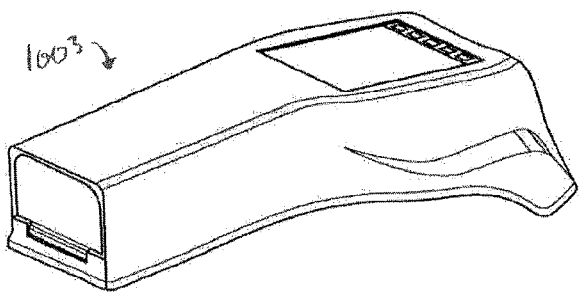
Figure 87C:
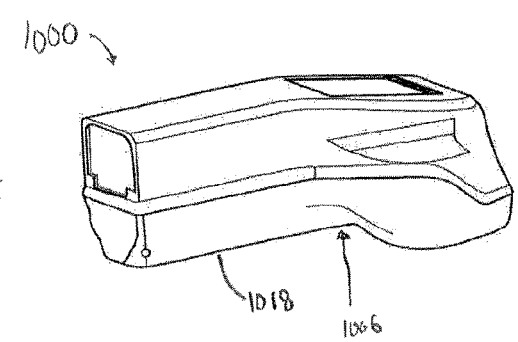
Figure 87D:
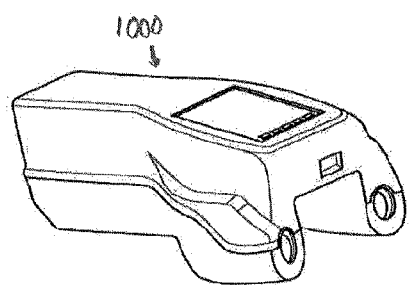

FIGS. 87A-87F illustrate various views and portions of an OTT module 1000 with a sloped lid configuration. FIGS. 87A-B illustrate two different isometric views of the lid assembly 1003. FIGS. 87C-D illustrate two different views of the assembled OTT module 1000. FIGS. 87E-F illustrate an isometric and side view, respectively, of an OTT module 1000 with a see through lid 1021 to show the interior arrangement of the battery, touch screen 1009, and cameras.

Directly Mating the OTT Electronics Module to the Tool

Figure 70A:
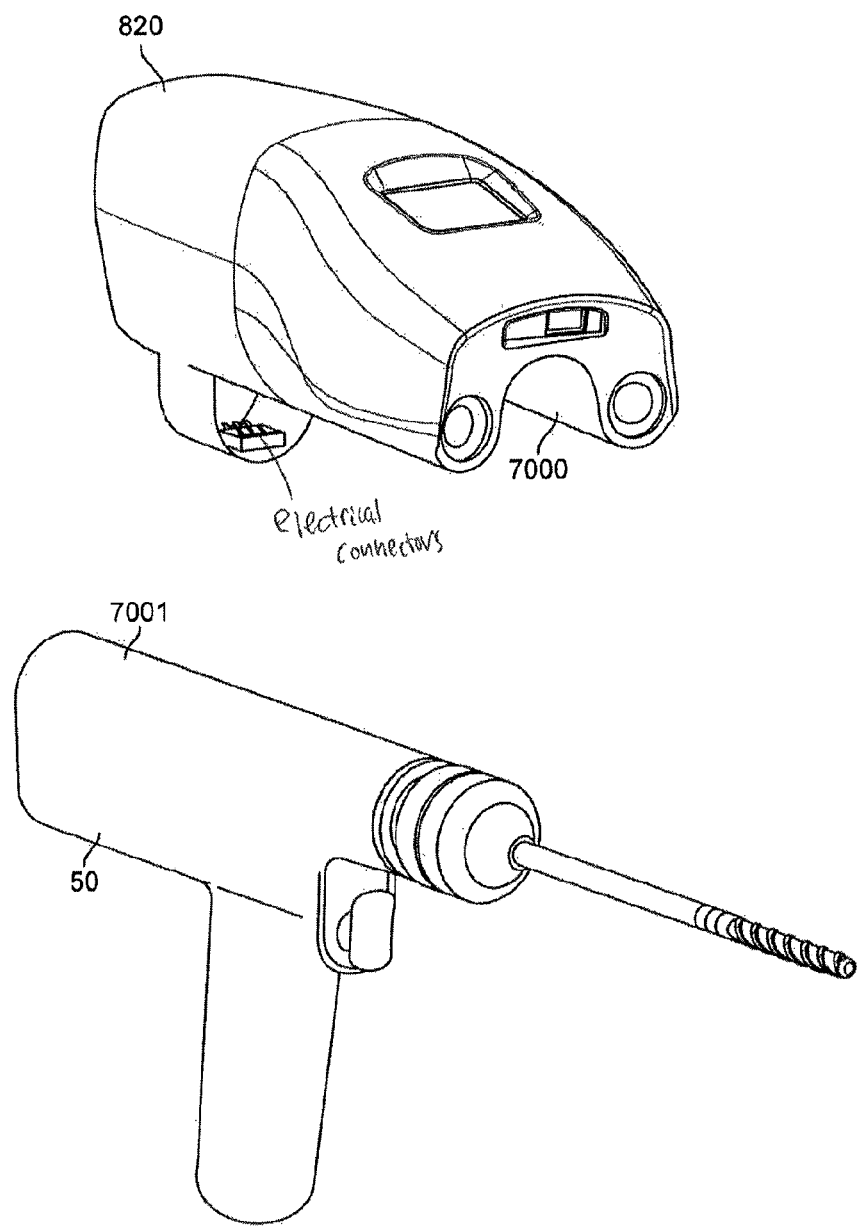

In one example FIG. 70A, the inner mating surface (7000) of the OTT electronics module (820) is contoured to provide an inner mating surface that conforms to the outer surface (7001) of the body of an existing tool (50) and does not require the use of the saddle (810) to provide the mating surfaces between the tool and the OTT electronics module. In such an example, the underside of the module is contoured to fit directly onto the instrument body and hold snuggly either through surface contact or through some additional means of securing and fastening the module to the tool, including but not limited to, screws, holding straps, or a tensioning device to squeeze the OTT electronics module so as to firmly hold onto the tool. The illustrated contour has a looped bottom with an open back and electrical connectors to mate with the electrical contacts on the surgical tool.

To provide governing control, defined by the example of allowing the module to regulate the motor function of the tool, by shutting it off or slowing it, retrofitting the tool is necessary. Such retrofitting adds electrical connection points that mate with connection points on the module.

Figure 69A:
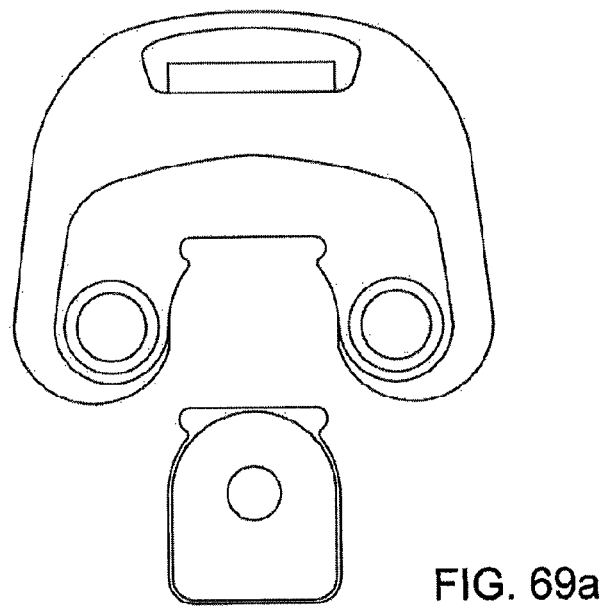
Figure 69B:
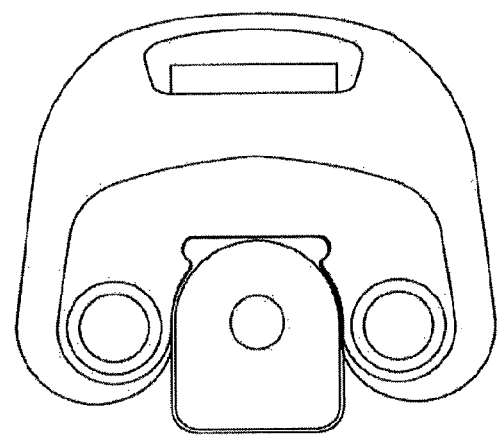

Mating the OTT Electronics Module to the Tool with an Intermediary Saddle Fitting In another example, illustrated in the embodiment of FIG. 68G, a saddle is used to provide mating surfaces optimized for the tool and the module. The saddle is designed with a contoured inner mating surface, which is designed to provide an optimum fit to the surface of the tool when attached (see, e.g., FIG. 68H). FIG. 68H illustrates the saddle of FIG. 68G in position on a hand held surgical tool. In this illustrative embodiment, the handheld surgical tool is a drill. The contoured outer mating surface is designed to provide optimal fit and contact with the inner surface of the module. FIGS. 69A and 69B illustrate, in cross section views separately and engaged, respectively, the correspondence between the saddle and tool module shapes.

In addition to the contoured mating surface, FIG. 68G also illustrates two recesses formed in the top saddle surface in proximity to the distal end of the saddle. The profile of the recesses is adapted and configured for engagement with a correspondingly shaped locking feature as described in greater detail below. It is to be appreciated that the size, number, shape, orientation and position of a locking recess may vary as described herein in the various alternative embodiments. Still further, the engagement between the saddle and the housing surfaces may be further modified to engage other complementary shaped aspects/features, or to facilitate other design aspects such as, for example, sealing, fit or vibration attenuation as described elsewhere herein.

Figure 70B:
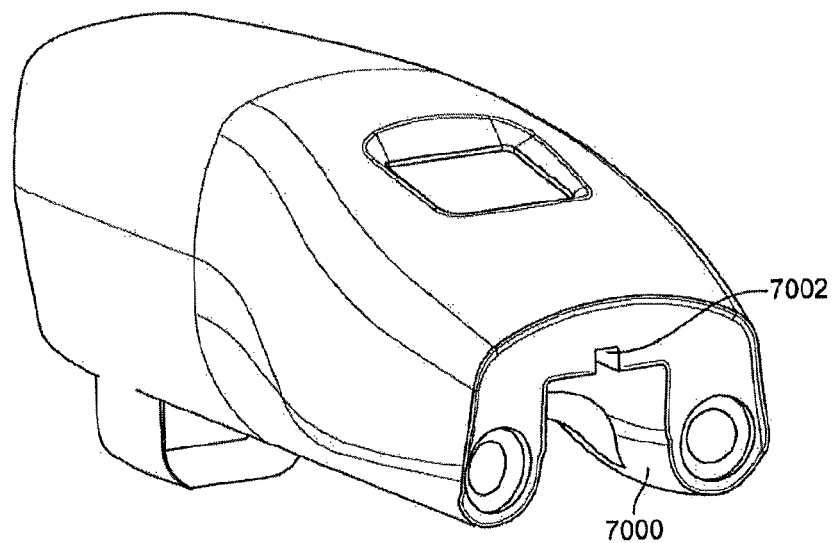
Figure 70C:
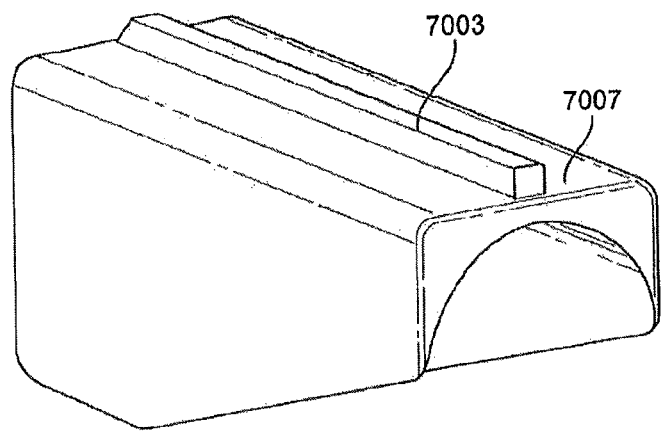
Figure 70D:
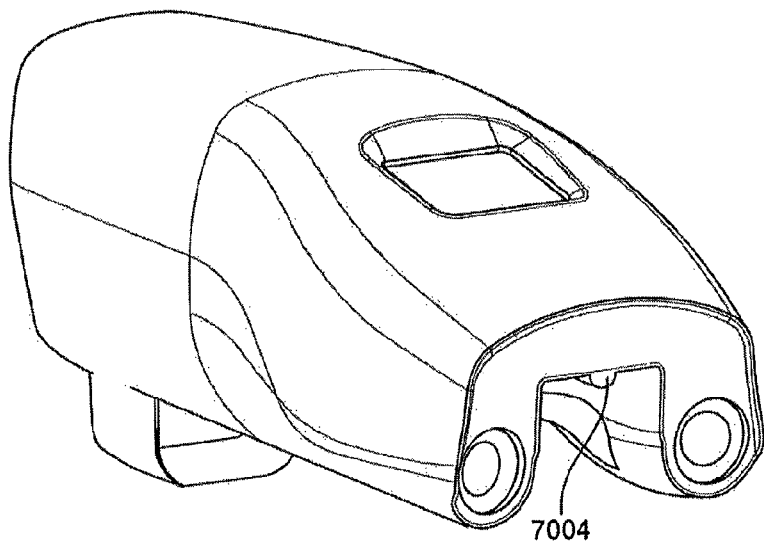
Figure 70E:
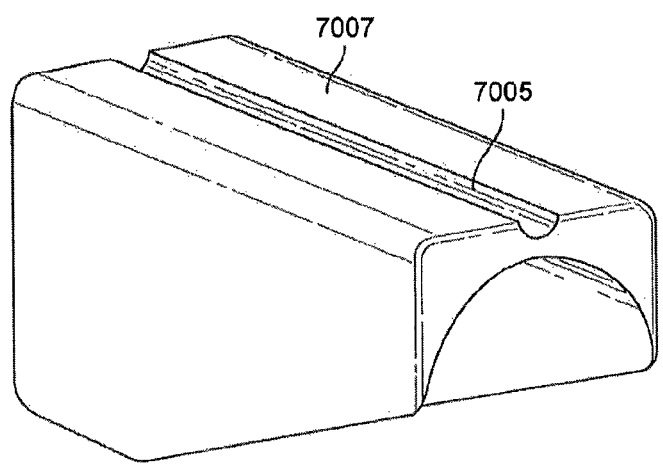
Figure 70F:
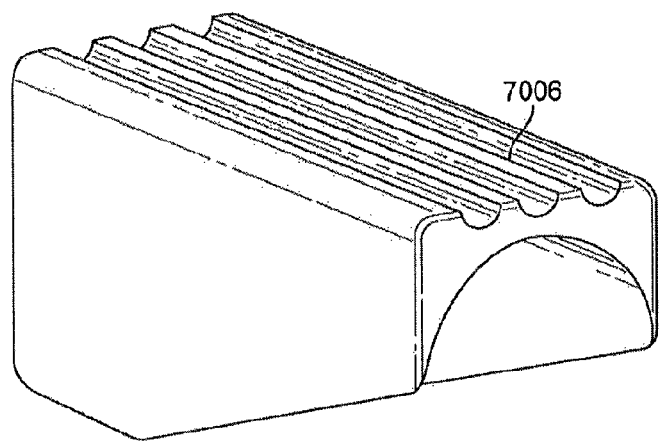
Figure 70G:
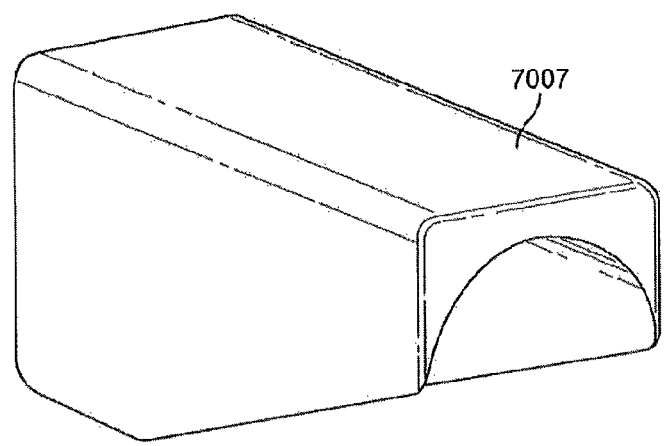
Figure 89A:
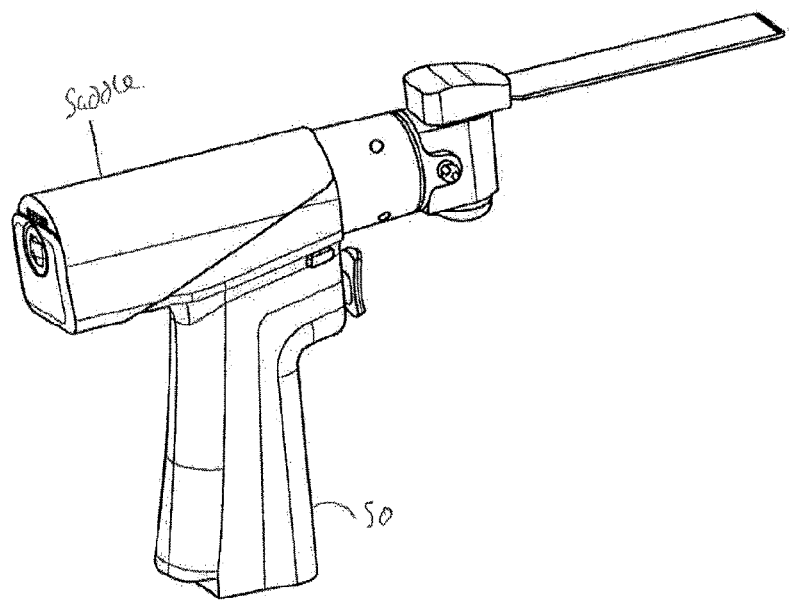
Figure 89B:
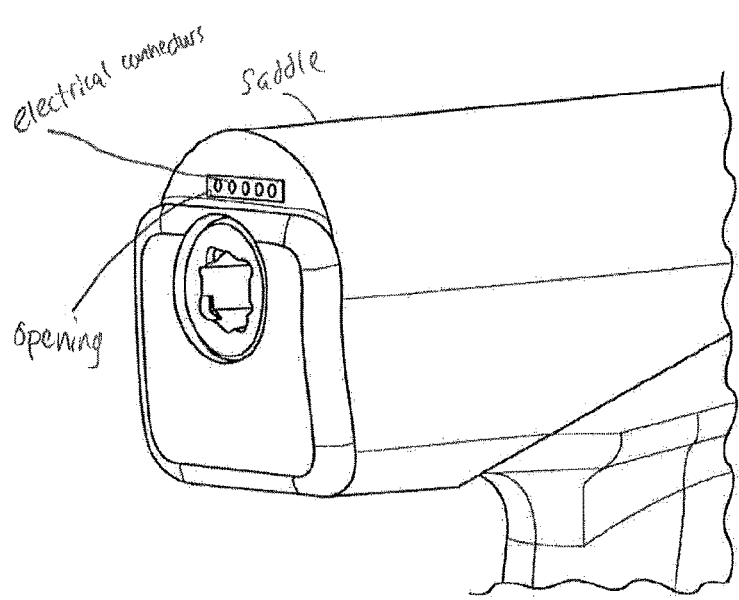
Figure 90D:
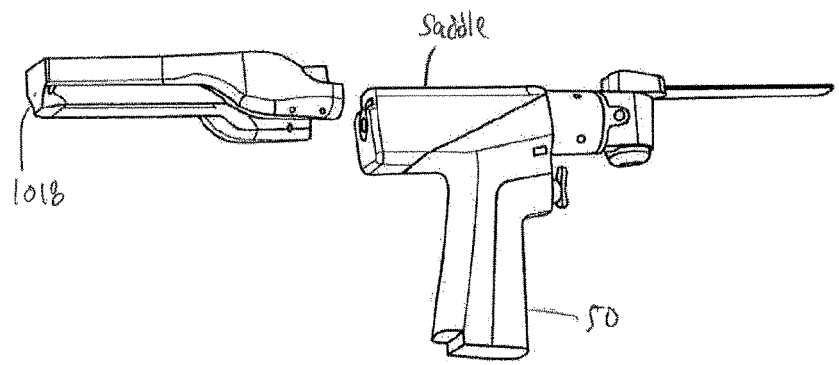
Figure 90E:
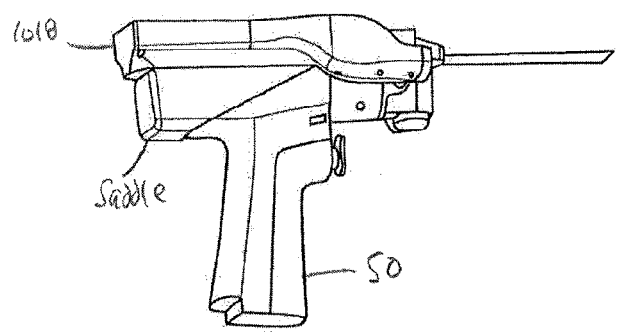
Figure 92A:
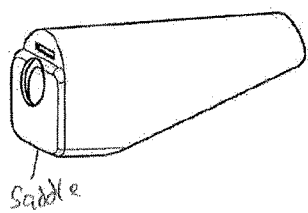
Figure 94A:
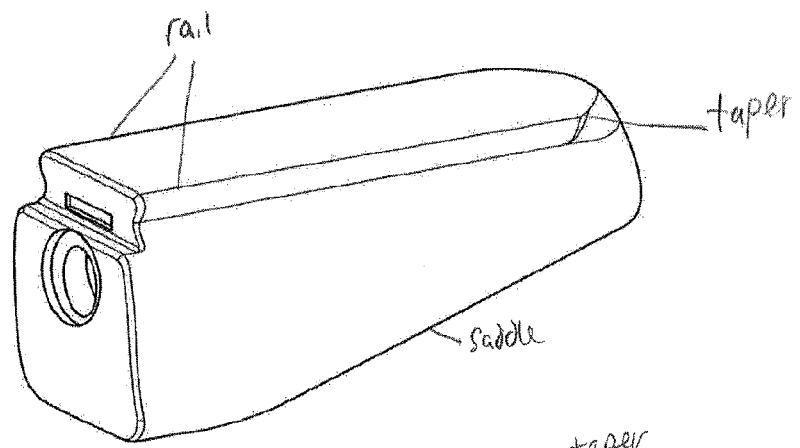
Figure 94B:
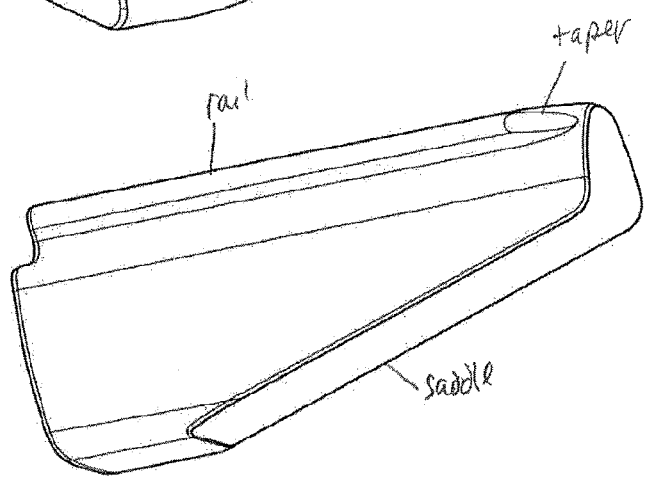
Figure 94C:
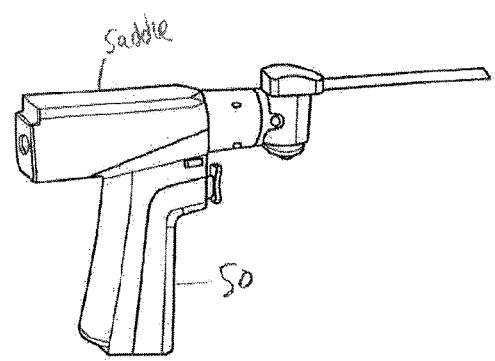

There could also be more than one complementary feature between the OTT housing assembly and the saddle as shown in FIG. 70F or no features (FIG. 70G) where some other mode of connection maintains the saddle-OTT housing position. FIG. 70G shows a block shape overall that may be used to couple to the OTT housing assembly. Other overall shapes, including complex shapes may similarly be employed. Consider for example the curved saddle shape illustrated in FIG. 92A having a sloped sidewall and rear mounted electronics interface as shown in the views of FIGS. 89A-89B. FIG. 89A shows the saddle of FIG. 92A on a hand held surgical tool 50 adapted for CAS OTT operations. In this embodiment, the surgical tool is a saw. The view illustrated in FIG. 89B is enlarged to show how one or more openings in the saddle may be provided to ensure that impairment of the tool is minimized through the use of the OTT saddle. In the illustrated embodiment, there is provided as best seen in FIG. 92A there is an elongate opening to allow for engagement to an electrical connector on the tool and a circular opening to permit mechanical access and engagement to the tool An additional variation of complementary surfaces is illustrated in the FIG. 90A and the corresponding surface in housing FIG. 90B. Attachment is shown by sliding as best seen in FIGS. 90D-90E. FIG. 90A illustrates a saddle with two rails as the guide surface. The rails extend along substantially all of the distance between the proximal end and distal end of the saddle. The guide surfaces may be adjusted in other embodiments. The distal end is tapered in the views of the saddle alternative shown in FIGS. 94A-94B and shown on a hand held surgical tool 50 as shown in the view of FIG. 94C. In this embodiment the handheld surgical tool is a saw.

Figure 88A:
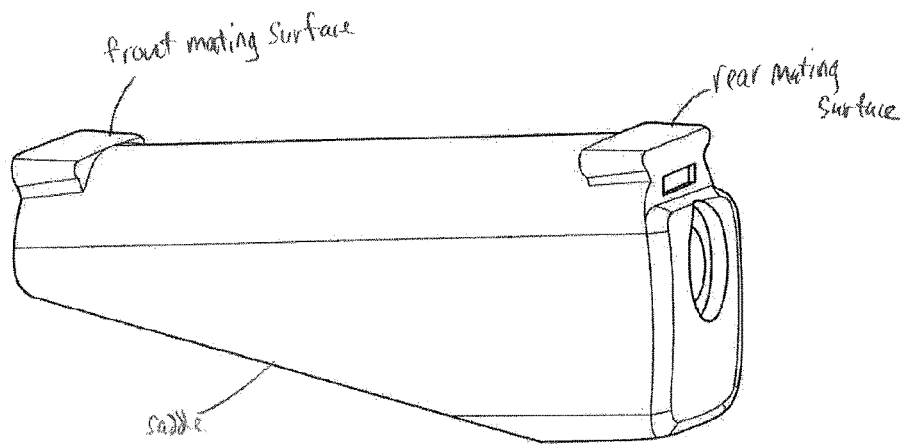
Figure 88B:
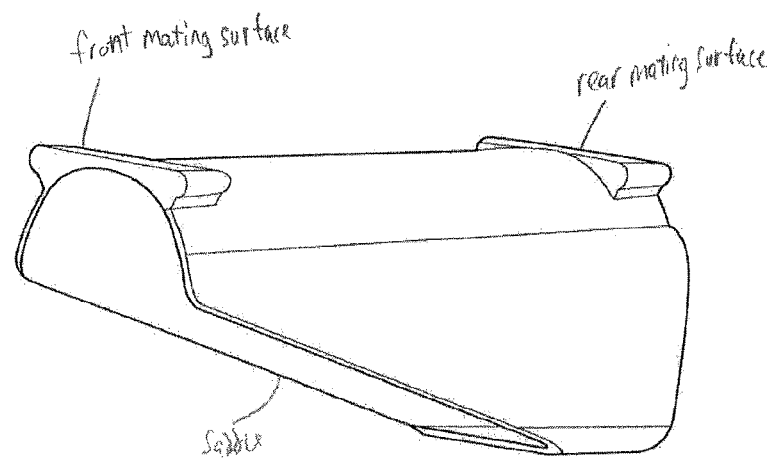
Figures 116A, 116B, 116C:
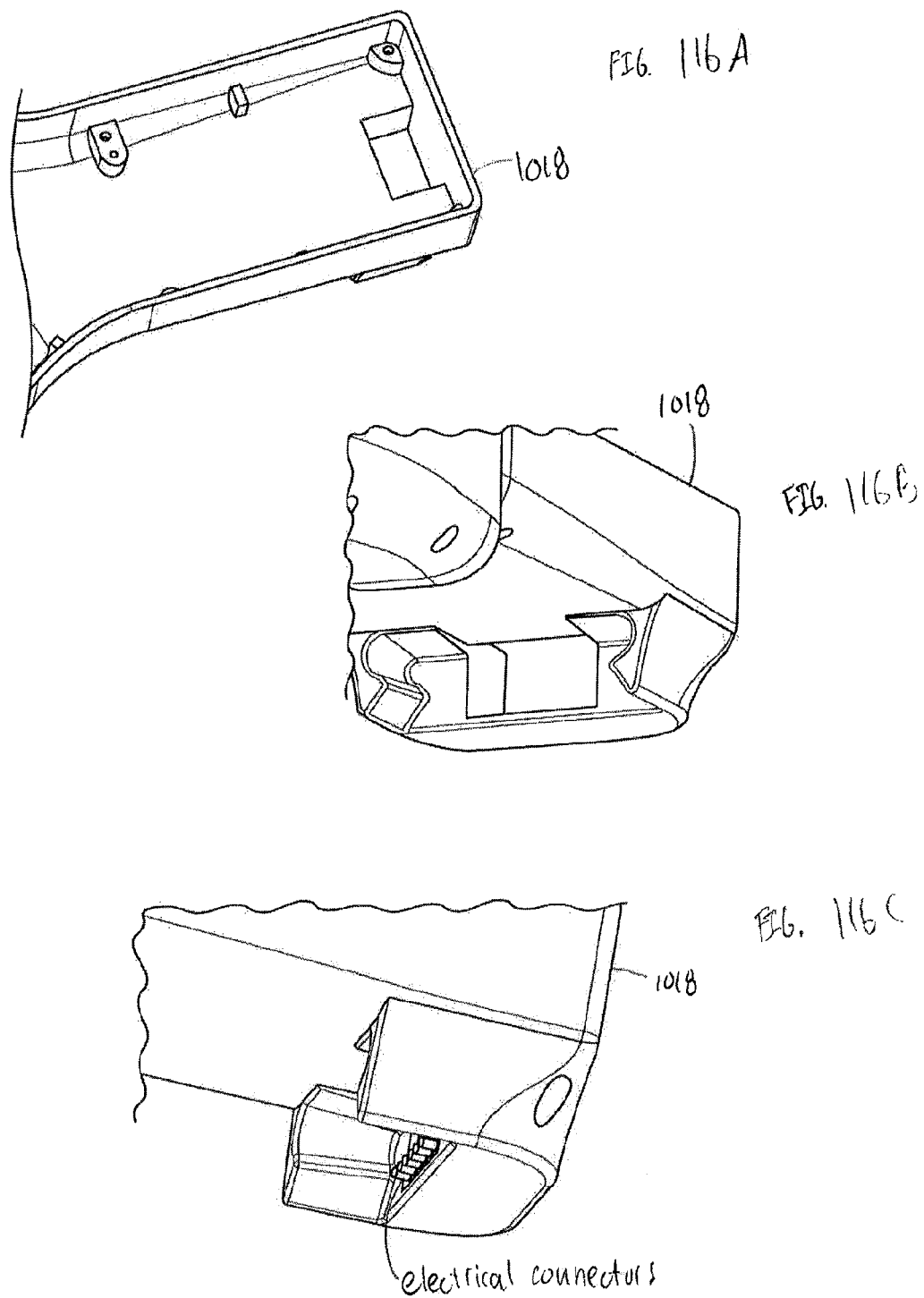
FIGS. 116A-116C illustrate various views of a housing of an OTT module in accordance with some embodiments.
Figure 117B:
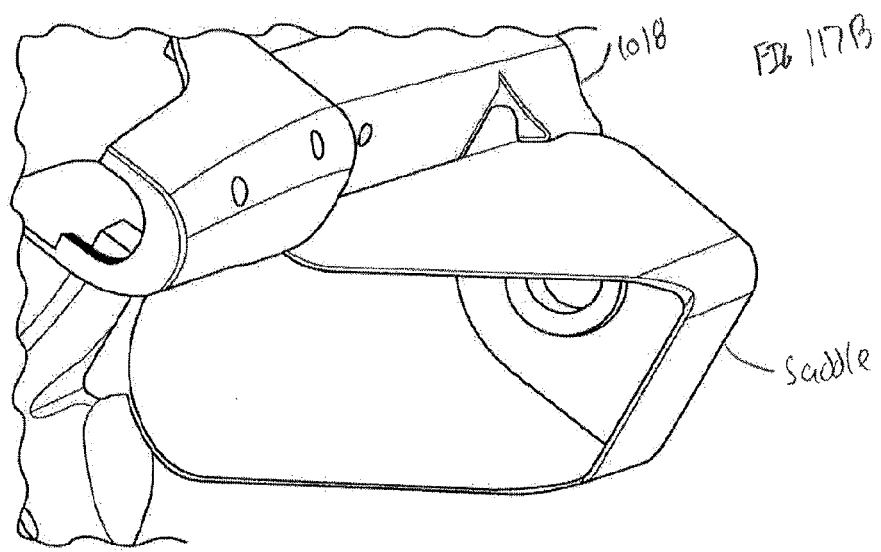
Figure 117C:
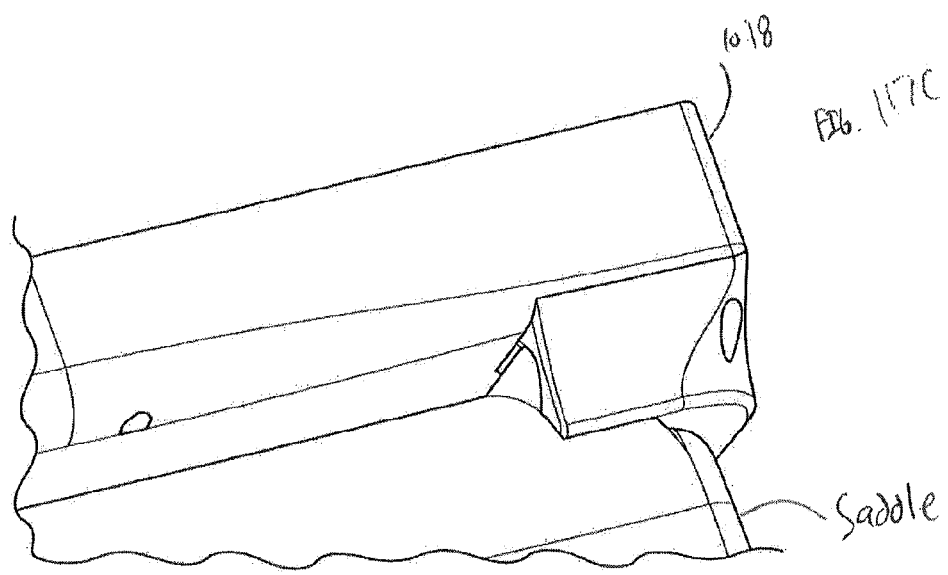

An additional variation of complementary surfaces is illustrated in the separate first and the second saddle mating surfaces seen in FIGS. 88A-88B. There are corresponding surfaces in the OTT housing 1018 as seen in the bottom up view of FIG. 117A and the enlarged view of the rear section seen in FIG. 116A. The engagement of the first and second saddle mating surfaces with the housing 1018 are best seen in the bottom isometric view of FIG. 117B. A side view of the engagement of the rear portion is shown in FIG. 117C. The corresponding housing 1018 surface for engagement with the saddle is shown in FIG. 116B. Attachment is achieved by sliding the OTT relative to the saddle. One advantage of the shorter saddle engagement features is that the OTT may be positioned above and forward of the mating surfaces and then engaged by sliding the OTT back until seated. As best seen in FIG. 116B this movement will engage the OTT and saddle mechanically while also ensuring the electrical connectors are appropriately coupled to the corresponding electrical connectors n the tool designated for OTT CAS operation. The shortened saddle guide or mating surfaces may be further modified or adjusted to incorporate design aspects of other saddle and OTT housing embodiments.

FIG. 118A illustrates a view of an OTT housing with FIGS. 118B and 118C showing cross-sectional side views the engagement of the housing with the saddle and tool. FIG. 118B shows the electrical connectors prior to passing through an opening to contact the electrical contacts on the tool. FIG. 118C illustrates the electrical connectors in contact with the electrical contacts on the modified end cap of the tool.

Figure 90C:
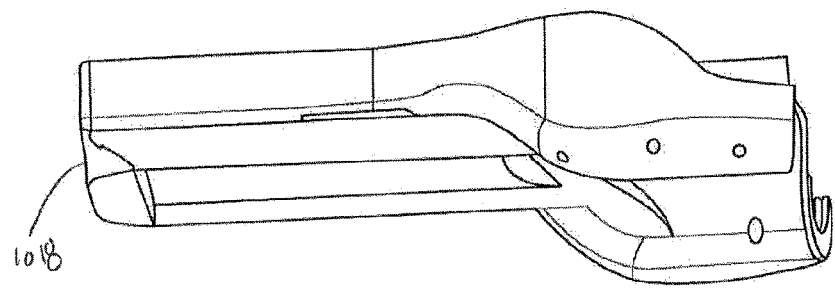
Figure 95A:
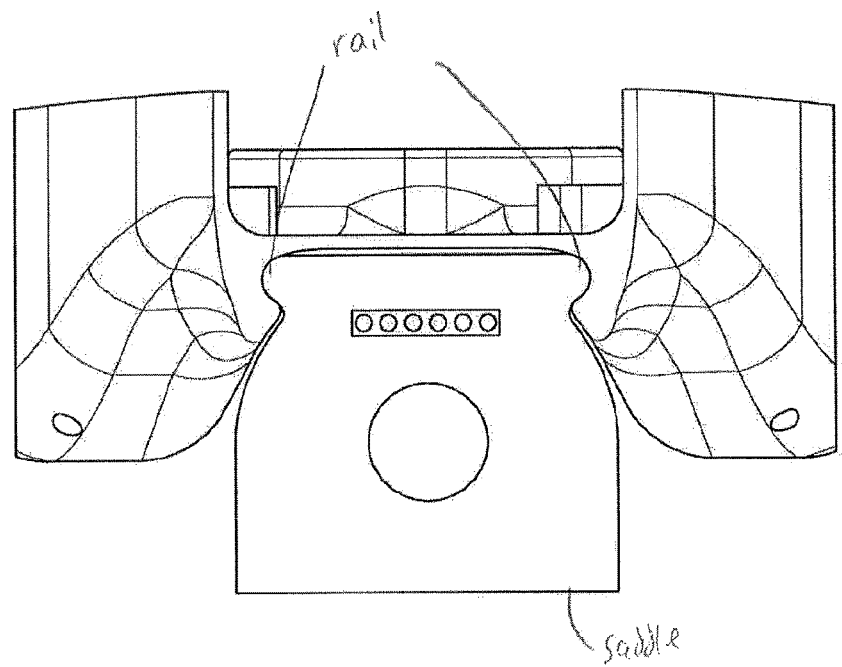
Figure 95B:
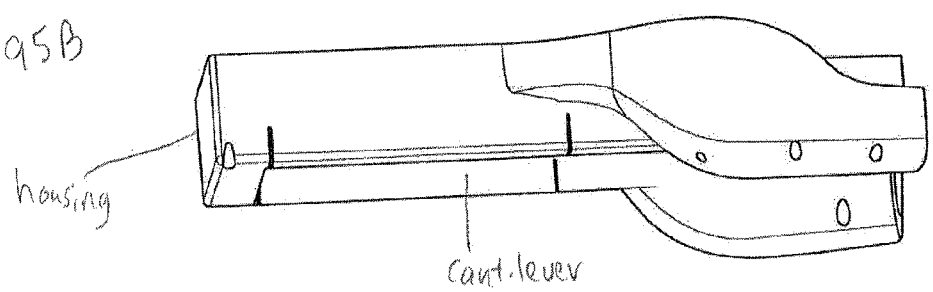

The OTT and saddle may engage in a number of ways such as by horizontal or sliding motion only or in combination with other motion or actions depending upon the attributes of the engagement features. For example, the engagement of the OTT to the saddle may include vertical or downward motion to bring the OTT into alignment or position with the saddle from a position over or above the saddle. Thereafter, this movement will engage the saddle with the OTT or by additional movement the OTT and saddle will engage. FIG. 82C shows a saddle on a tool. A pair of engagement surfaces or features are shown near the upper portion of a curved top saddle embodiment. The features here are positioned in the mid portion of the saddle such that there are no features at the proximal and distal most portions of the saddle surface in contrast to the saddle embodiments illustrated in FIGS. 88A and 89A described above. An OTT housing with a corresponding surface is also shown in FIG. 82C. The various movements used to engage the OTT and the saddle may lead to changes in configuration, size, or shape of one or both components or, optionally or additionally, the inclusion of one or more of additional materials (e.g., seal, gasket or material changes) or other modifications to one or both as described herein. FIG. 82C illustrates a further view of the OTT above in position before snap fit engagement with the saddle. FIG. 90C illustrates the modification of a portion of the OTT lid assembly mating surface to permit the two ribs carrying the guide grooves to form undersized spring loaded cantilever. One aspect of such a design would permit the housing assembly mating surface to flex around and lock onto the raised surfaces shown in the saddle shown in, for example, FIG. 82C. Additional details of one type of side modification are best seen in the view of FIG. 95B. The cantilever shape in the housing of FIG. 95B and relation to the saddle rail shape may be appreciated in the end on cross section view of FIG. 95A.

Figure 91A:
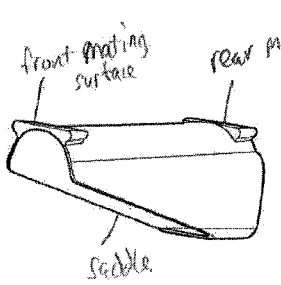
Figure 91B:
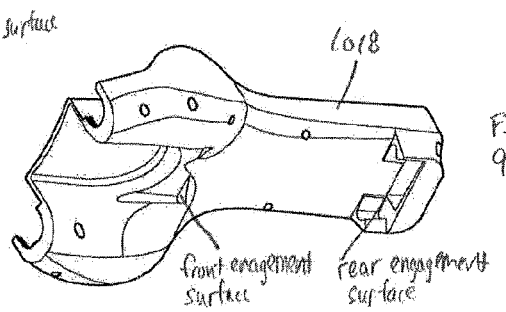
Figure 92B:
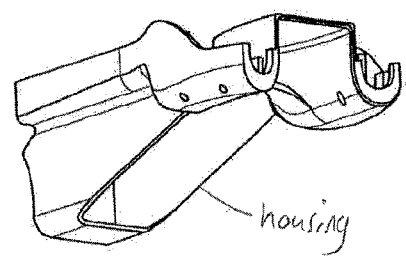
Figure 93A:
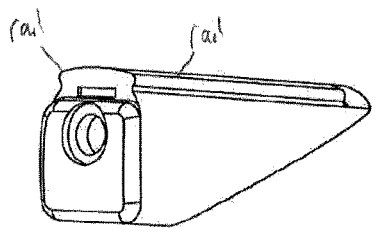
Figure 93B:
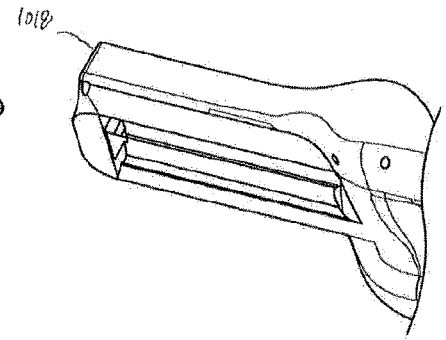

FIGS. 91A and 91B illustrate an embodiment of a saddle and a housing 1018 with a complementary structure. The saddle in FIG. 91A includes a front mating surface and a rear mating surface with the housing 1018 of FIG. 91B having complementary front engagement structure and rear engagement structure. FIGS. 92A and 92B illustrate an embodiment of a saddle and a housing with a complementary structure with the saddle having a smooth outer surface and the housing having a rectangular structure to receive the outer surface of the saddle. FIGS. 93A and 93B illustrate an embodiment of a saddle with two rails and a housing with a complementary structure.

Figure 96A:
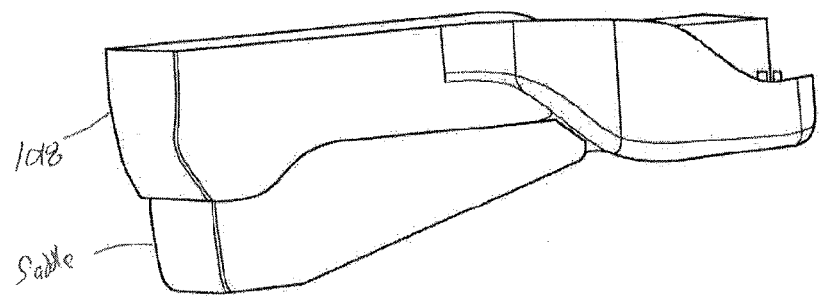
Figure 96B:
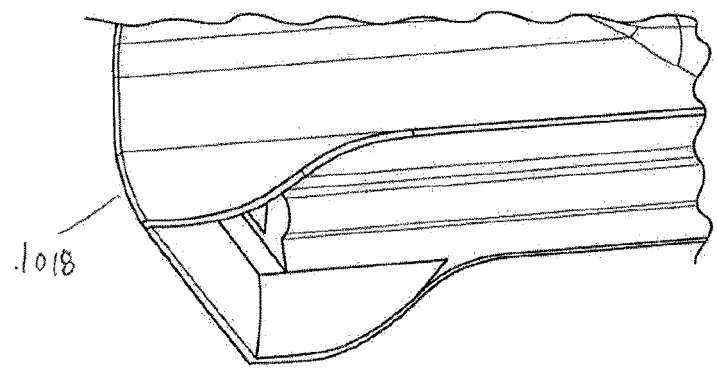
Figure 96C:
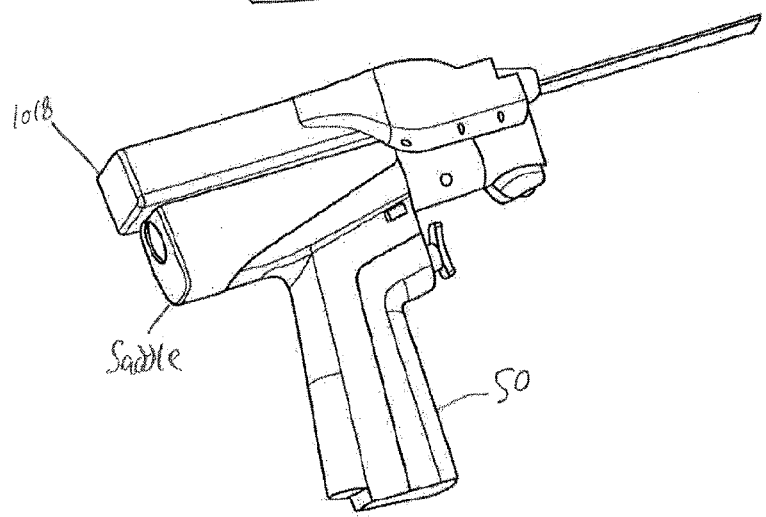

FIG. 96A is a side view of a housing 1018 engaged with a saddle. FIG. 96B shows the bottom surface of the housing 1018 configured to engage with the saddle and FIG. 96C shows the saddle and housing 1018 engaged with a surgical tool 50.

FIG. 97A illustrates a housing 1018 having a complementary surface to slidably engage with a saddle illustrated in FIG. 97B. FIG. 97C illustrates the housing 1018 and saddle engaged with the surgical tool 50 with the housing locked to the saddle by the lock. Additional details on locking structures are discussed in the locking section below.

Figure 98A:
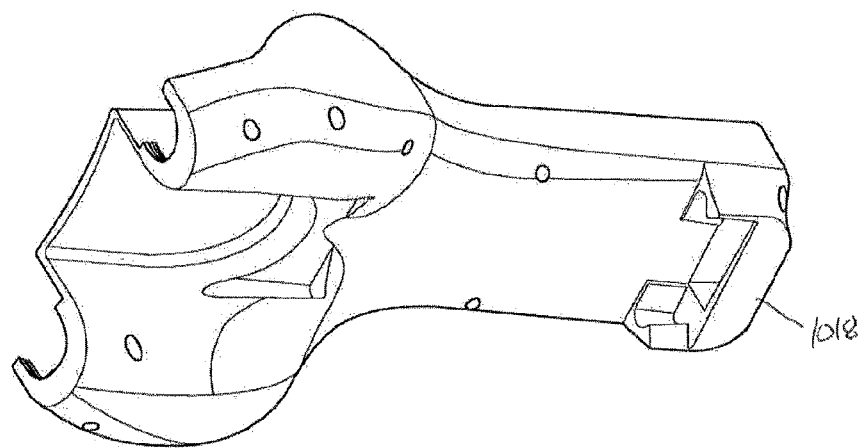
Figure 98B:
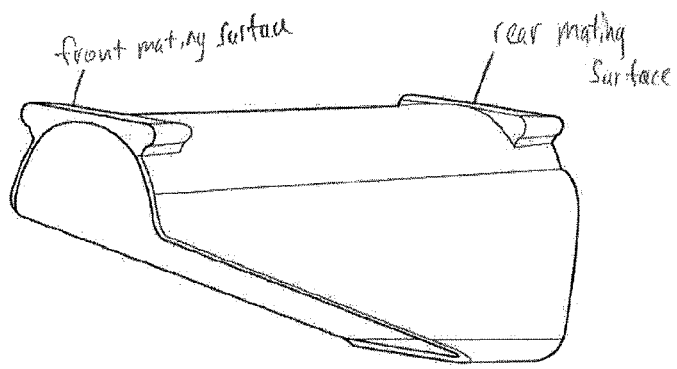

FIGS. 98A and 98B illustrate an embodiment of a saddle and a housing 1018 for a sloped lid having a complementary structure configured to slidably engage with the saddle of FIG. 98B.

Raised forms can take different shape as shown in the isometric view of the saddle in FIG. 68g and positioned on the hand held tool (here a drill) in FIG. 68h. The OTT housing would also have a corresponding shape along the length of the surface that would be coupled to the saddle engagement surface. As shown in FIG. 69a the end view of the saddle/tool and OTT make clear the complementary shapes. The complementary shapes of the saddle and OTT are shown coupled together in the end view of FIG. 69b.

It is to be appreciated that the OTT housing saddle engagement surface or portion of the saddle engagement surface may also include one or more features for further engagement between the OTT housing and the saddle. The engagement or locking features are complementary and may engage using any of a number of different modes such as by relative movement between the OTT and the saddle, operation of a latch or locking mechanism or activation of a locking device. In the view of FIG. 68E a pair of recesses are shown along the edges of the saddle top surface, just distal to the distal most end of the saddle top surface. The size, shape, position, orientation and other features of the recess may be adjusted based on the specific type of engagement device and engagement mode implemented. Consider for example the alternative saddle embodiment illustrated in the views of FIGS. 104A and 104B. In this illustrative embodiment, the pair of engagement features have a longer engagement surface and different slope than that of FIG. 68E. In addition, there is a sloped portion and raised profile (looks like a slope and a bulbous or more rounded distal end than in FIG. 68g) at the distal end of the saddle embodiment of (FIGS. 104A-104B). In this specific embodiment, the shape of the sloped recesses may be used to further engage with a corresponding feature provided on, along or within a portion of the OTT housing saddle engagement surface. Additional details and various alternatives for engagement and/or locking the relative position of the saddle and OTT are further described herein and with reference to FIGS. 68b, 68c, 68g, 68*h*, 69*a*, 69*b*, 70*c*, 70*e*, 70*f*, 70*g*, 71*c*, 71*d*, 74*d*, 75A-G, 76A-76B, 77A-77D, 80A-E, 81A-81E, 82C, 88A-88B, 89A-B, 90A, 90D, 90E, 91A, 92A, 93A, 94A-C, 95A, 96A-C, 97B, 98B, 99A, 101A, 102A-C, 104A-B, 105C, 111B, 112A-D, 114A, 117B-D, 118B-118C, 122, 124, 125, 126, 128, 131, 132, 133A-B, 135, 136A-C, 137, and 147C, along with FIGS. 97C, 103A, 103B, 104D-E, 119A-B, 120A-120*b*, 121-132, 133A-133B, 134, 135, 136A-C, 137, 167C, 168A-C, 169C, and 170B. Next are the variations in the saddle shown in FIGS. 99A, 99B, 100A, 100B, 101A, 101B, 102A-102C, 103A, and 103B about locking designs. It is to be appreciated that these additional aspects of saddle/OTT housing engagement may be applied to any of the saddle and OTT embodiments described herein.

Figure 99A:
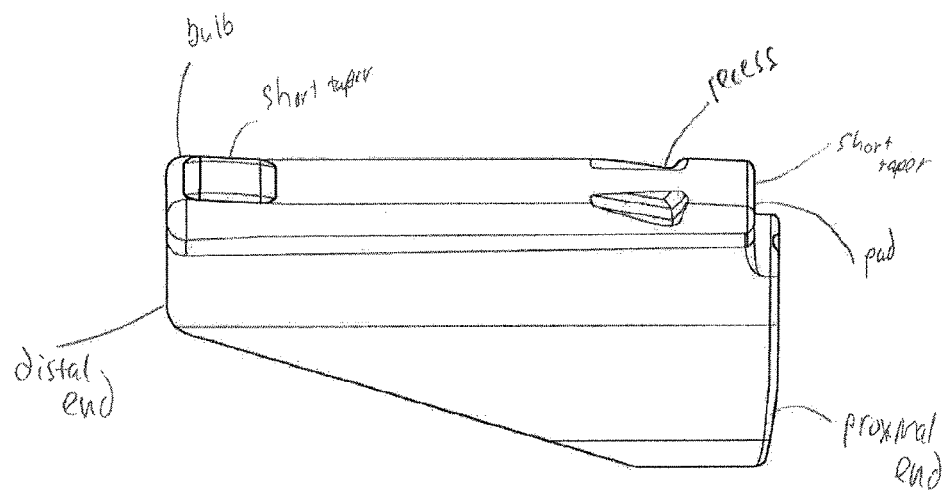
Figure 99B:
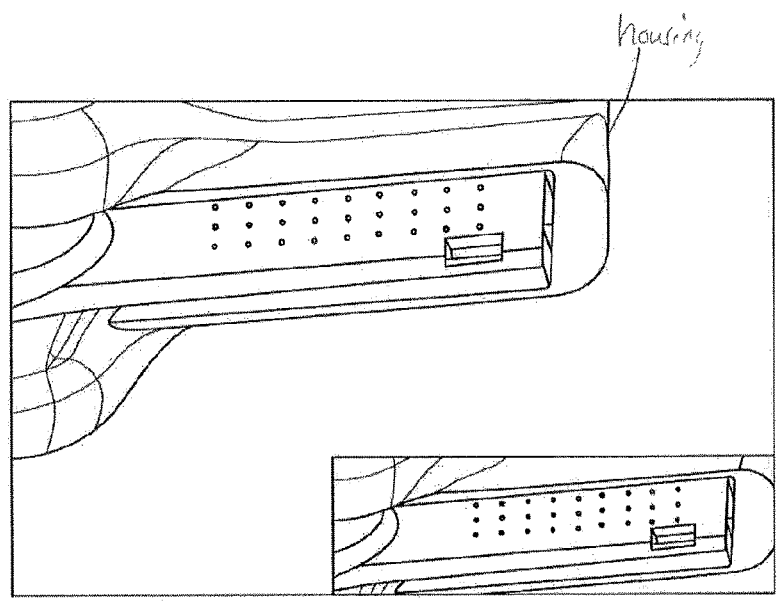

FIGS. 99A and 99B illustrate an embodiment of a saddle and a housing having a complementary structure configured to slidably engage with the saddle of FIG. 98B. FIG. 99A illustrate an alternative saddle configuration to that illustrated and described in FIG. 68G. In this embodiment, the ends of the engagement surface are tapered. The front end is tapered to increase from a proximal to a distal direction. The distal most end has a bulbous shape. The increasing taper indicates that the thickness of the upper saddle surface is increasing. A raised portion may optionally be added or changed in size/shape to further enhance fit between the saddle and housing. The rear portion of the saddle surface is also modified. The portion of the saddle surface proximal or rearward of the two recessed features also has been tapered. The rear taper decreases towards the rear surface form the recessed features. The recesses are configured to engage with a locking structure on the housing (see FIGS. 103A-103B). The proximal end is also illustrated as having a short taper and a pad. The OTT housing surface is adjusted according to the features provided by the saddle FIG. 99B is a bottom up isometric view of a housing with complementary features to the pad tapered from and rear ends and overall size and shape of the saddle top surface in FIG. 99A. There is a front taper recessed portion and a rear taper recessed portion. A section between the front tapered portions is adapted and configured to correspond to the size, shape and/or contours of the saddle (see FIG. 99A). The bottom up view of FIG. 99B provides an additional view of the housing lower surface shaped to accommodate the rear taper. Also visible in this view is an opening positioned to provide access to the recess features. An engagement feature (not shown) such as a latch or cantilevered leg is provided access to the recesses on the saddle via one or more appropriately sized and spaced openings. Exemplary latches or pins are described below. Also shown in this view are several vent holes formed in the housing.

Figure 100A:
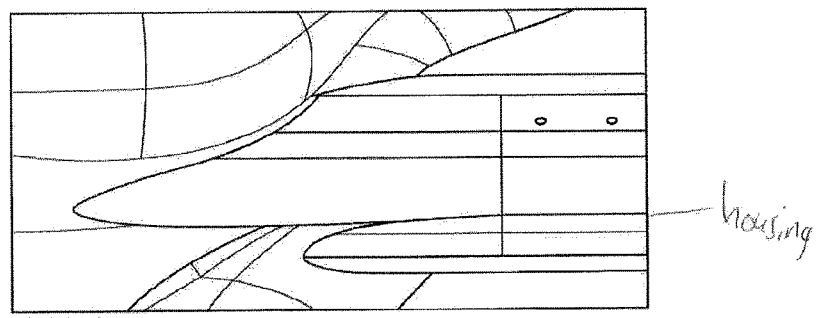
Figure 100B:
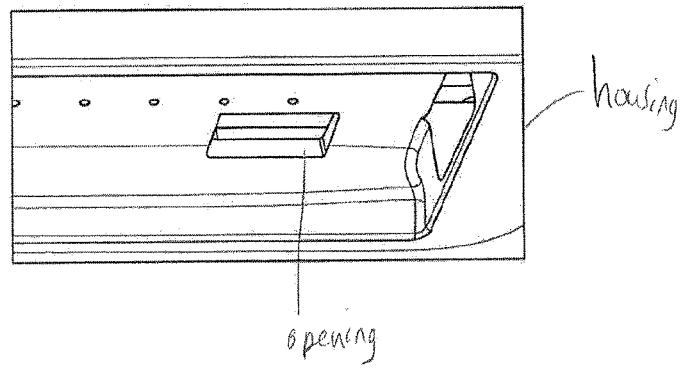

FIGS. 100A-B illustrate additional views of a mating surface of an OTT housing configured to engage with the saddle illustrated in FIG. 99A.

Figure 101A:
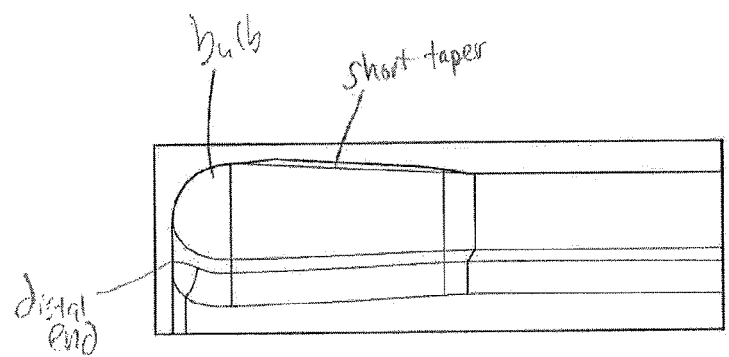
Figure 101B:
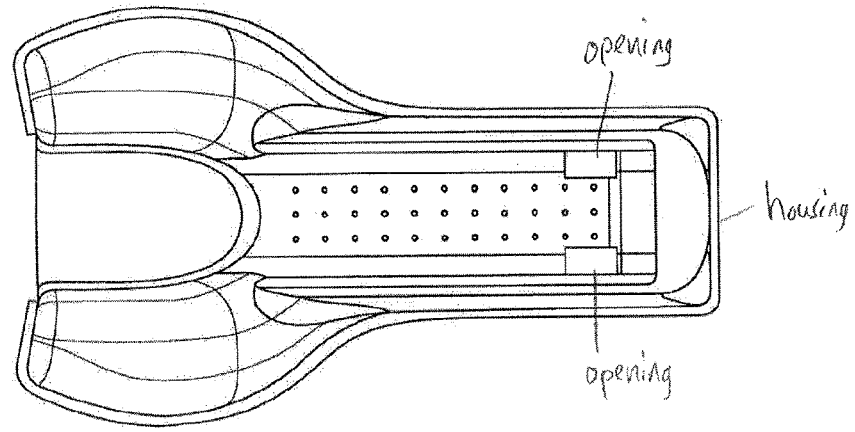

FIG. 101A is a side view of the distal end of saddle of FIG. 99A. This view provides additional details of the increased front taper surface, and the bulb at the distal end. FIG. 101B is a bottom view of a housing assembly configured to engage with the saddle of FIGS. 99A and 101A. FIG. 101B illustrates a bottom view of the housing configured to engage with the saddle of FIG. 99A with openings to accommodate a locking structure.

Figure 102A:
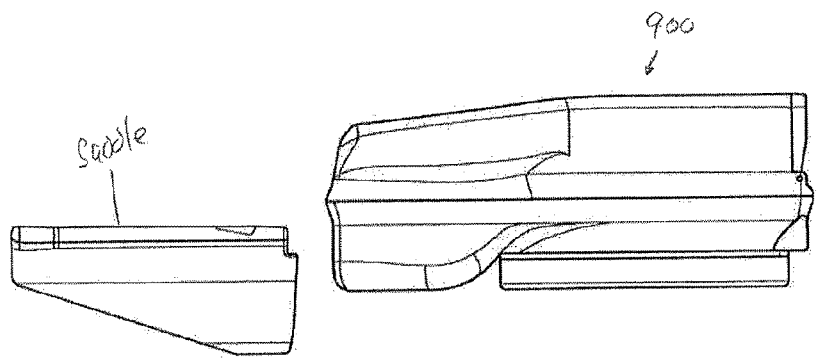
Figure 102B:
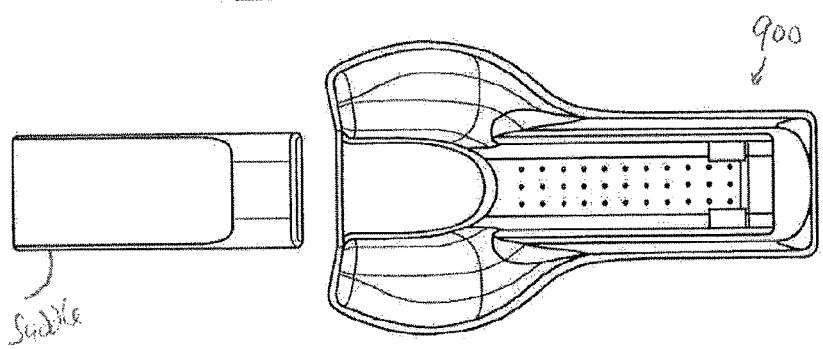
Figure 102C:
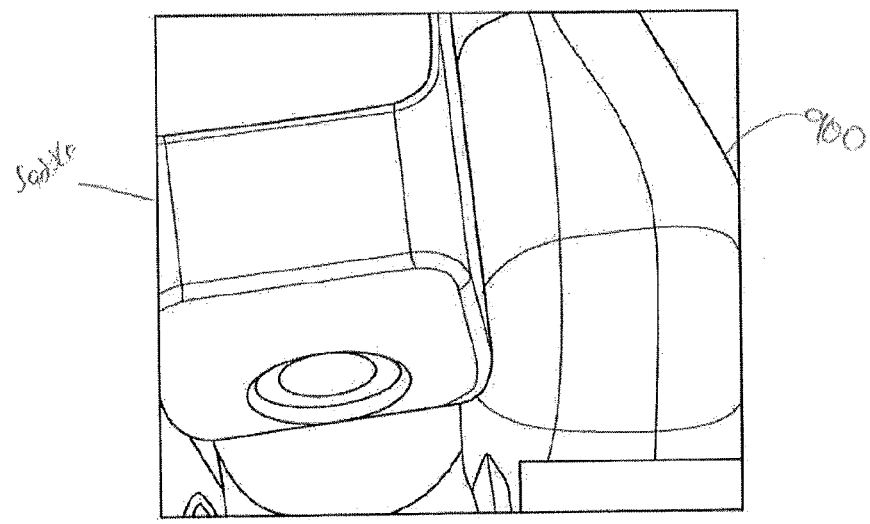

FIGS. 102A-102C illustrate different views of the saddle and housing prior to engagement and after engagement. FIG. 102A illustrates a side view of embodiments of a saddle having a recess to accommodate a lock and a housing with a surface configured for slidable engagement with the saddle. FIG. 102B is a bottom up view of FIG. 102A. FIG. 102C illustrates a close up view of the saddle engaged with the housing from FIGS. 102A-B.

Figure 103A:
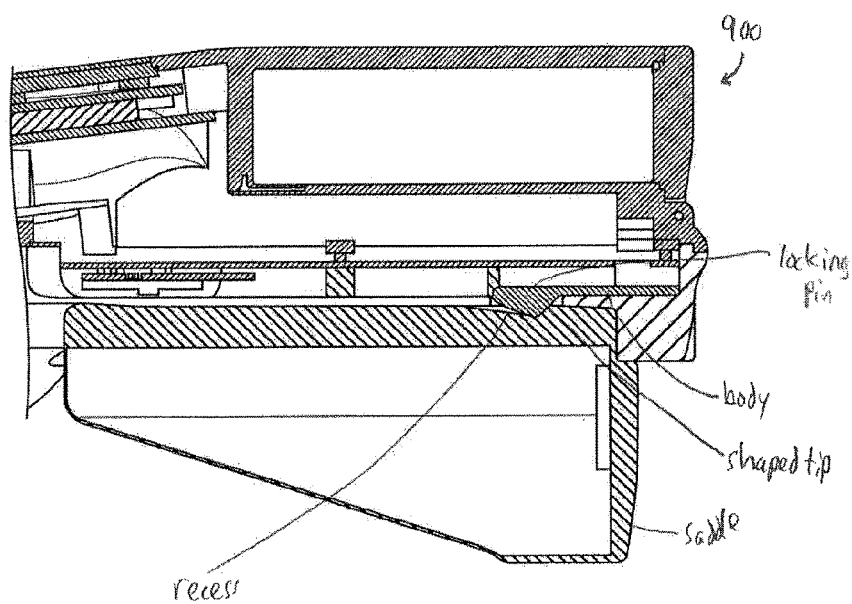
Figure 103B:
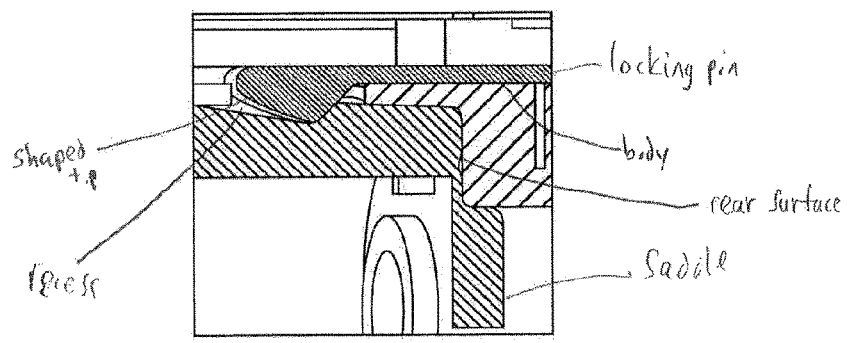

FIGS. 103-103B illustrate side views of an OTT module coupled to a saddle as illustrated in FIG. 68G. As shown in FIG. 103A and better seen in the enlarged view of FIG. 103B an engagement member attached to the housing extends from the bottom surface of the housing when the housing and the saddle are properly positioned then the engagement feature rests within the recesses in the saddle top surface. In this specific embodiment, the locking pin has a body and a shaped tip. The shaped tip is contoured to engage with the recesses in the saddle top surface (see FIG. 68G). In addition, the housing engagement surface may include a rear surface positioned to act as a stop during coupling of the housing to the saddle. As best seen in the enlarged views of FIG. 103B when the saddle/housing are correctly engaged the locking pin tip is seated in the recess and the saddle rear wall is against the housing rear wall or stop.

Figure 104C:
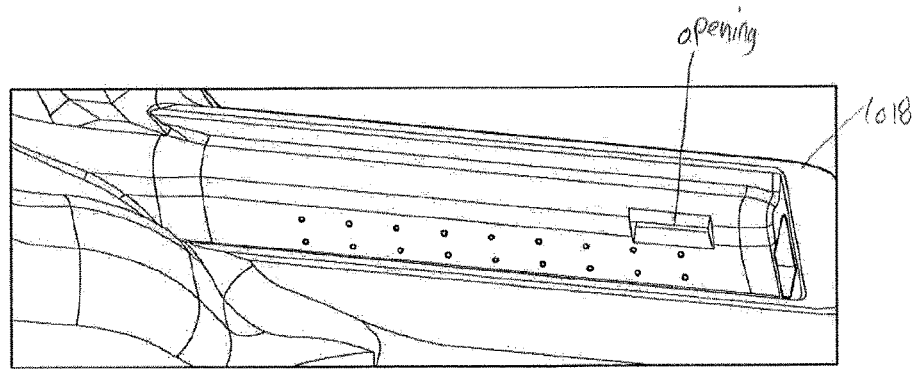
Figure 104D:
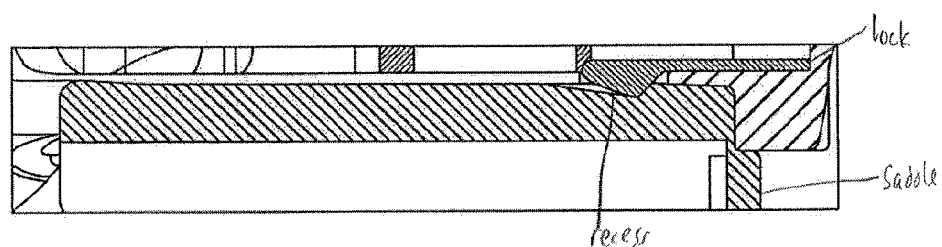

FIGS. 104A-104B are front and rear isometric views, respectively, of an alternative tapered saddle design. The front (distal) end of the saddle surface is modified to have a slot increasing taper (increasing towards the front). A rear tapered portion is also provided at a proximal end. The saddle also includes two recesses. The rear taper decreases in size towards the rear. FIG. 104C illustrates the corresponding surface of a housing having regions adapted to conform to the front and rear taper. Also shown in this view is the opening for an engagement feature or pin (not shown) shaped to interlock with the saddle surface recesses. FIG. 104D is a cross section view of the housing-saddle engagement of the current embodiment. Note that the housing has a complementary surface for engagement with the taper regions and top surface. Also shown is a lock carried by the housing and locked within the saddle recesses.

Figure 104E:
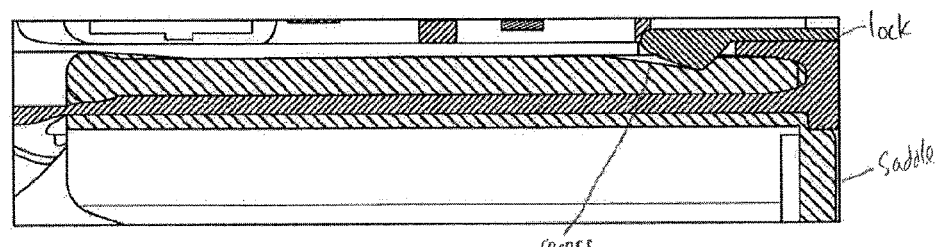
Figure 101B:
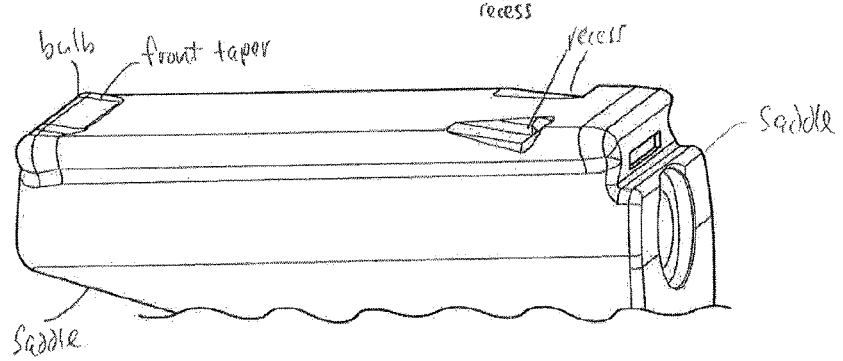

FIG. 104E illustrates a section view of another saddle embodiment with tapered ends and lock.

In some aspects, a locking mechanism is provided to fix the relative position of the OTT housing/module to the tool or tool/saddle combination once the OTT module is in the proper position.

FIGS. 97C, 119A-B, and 120A-B illustrate a pivoting latch with a shaped tip for engagement with the side wall feature/tab. To disengage, the knob is pressed raising the distal end of the tip clear of the side wall feature tab whereby the assemblies are released for relative movement.

FIGS. 121 and 122 illustrate a cam locking device. The cam locking component is shown in the isometric view of FIG. 121 having a shaft and two cam features. The isometric top view of a housing 918, 1018 coupled to a saddle shows the position correspondence between the location of the cams and the openings in the housing permitting engagement with the recessed slots on the saddle top surface. The cam locks are released by rotating the shaft. FIG. 123 is an external side view showing the shaft of the cam locking device.

In contrast to earlier top surface recesses, saddle-tool engagement may be provided via connection at different locations. FIG. 125 illustrates another saddle embodiment having a pair of side recesses. The housing assembly has corresponding sidewall openings to permit locking engagement with the side recesses. FIG. 124 illustrates a section view through the opening shown in FIG. 126 with an engagement pin engaged to lock the housing to the lid.

Figure 127:
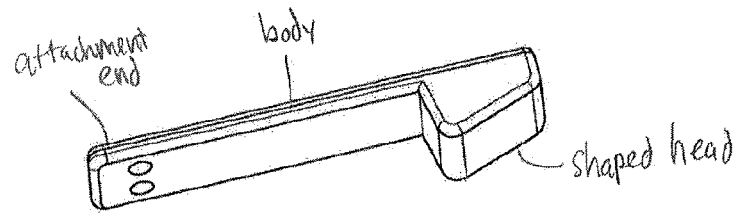
FIGS. 127-130 illustrate various aspects of locking mechanisms in accordance with some embodiments.
Figure 128:
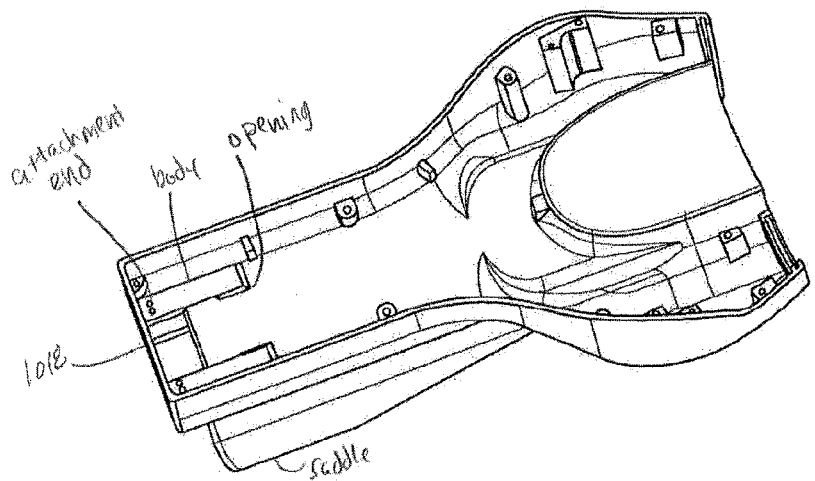
Figure 130:
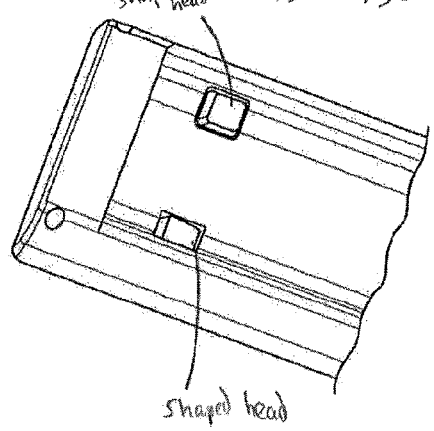
Figure 131:
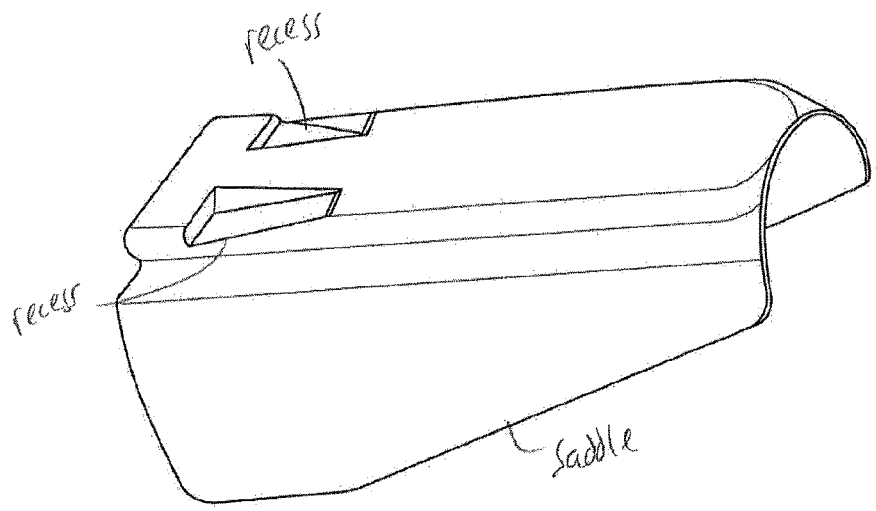
FIG. 131 illustrates a housing in accordance with some embodiments.

FIGS. 127, 128, and 130 provide additional views of the locking pin of FIGS. 103A, 103B, 104D, and 104E. FIG. 127 is a view of a housing lock of a leaf spring design. The leaf spring design has a body with a shaped head and an attachment end. As best seen in FIG. 128 the attachment end is coupled to an interior surface of the housing assembly. An opening is positioned to permit access of the sloped head through the housing assembly for engagement with a complementary surface on the saddle. The shaped end protrudes from the lower housing assembly surface as seen in FIG. 130. FIG. 131 illustrates an embodiment of a saddle with two recesses configured to engage with the housing illustrated in FIGS. 128 and 130.

Figure 129:
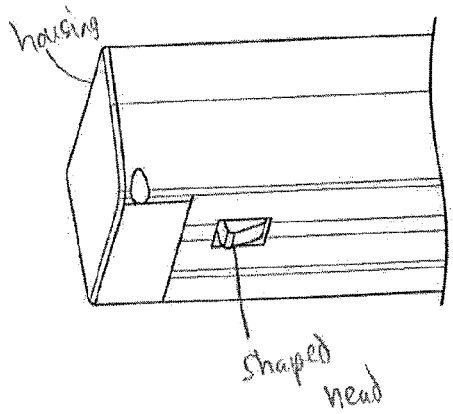
Figure 132:
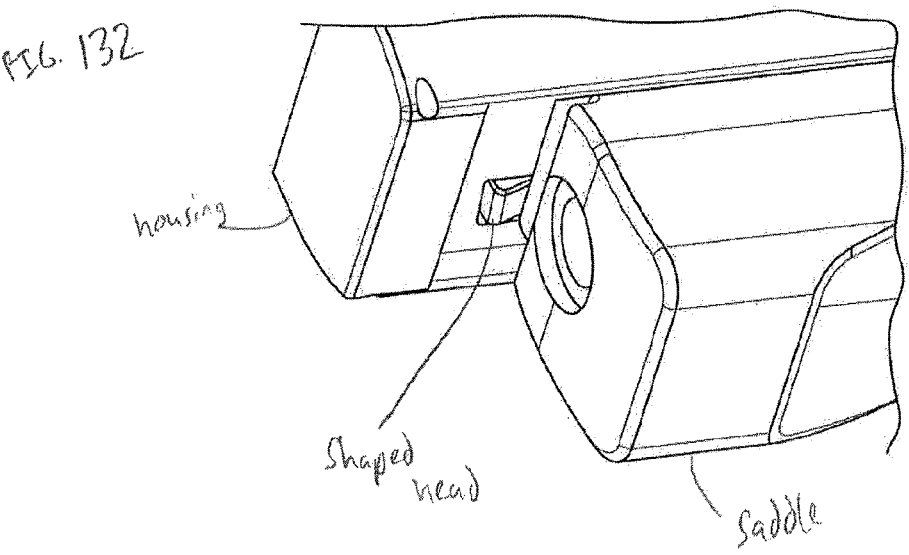
FIG. 132 illustrate a locking mechanisms for a housing engaged with a saddle in accordance with some embodiments.

While embodiments of FIGS. 128 and 130 illustrate two housing locks on the side of the housing, other configurations are possible such as more or fewer locks or locks in different orientations. FIG. 129 illustrates a bottom up isometric view of an OTT housing having only a single centrally located housing lock. The shaped head is shown protruding from the housing assembly. FIG. 132 illustrates a bottom up isometric view of the single centrally located shaped head housing lock just prior to engagement with a compatibly shaped saddle configured to engage with a central housing lock.

Figure 133A:
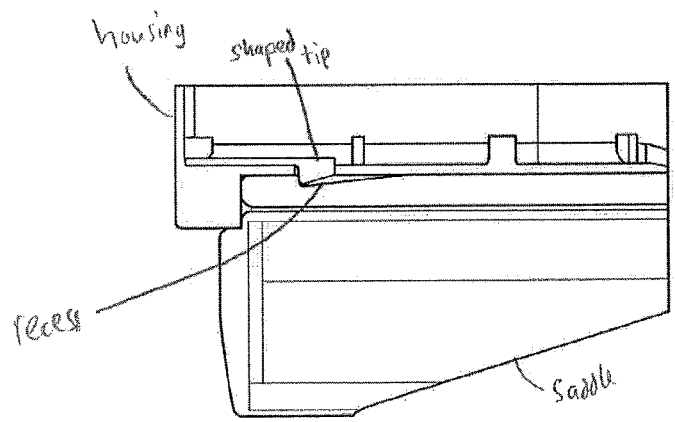
FIGS. 133A-133B illustrate an embodiment of a locking mechanism between a housing and saddle in accordance with some embodiments.
Figure 133B:
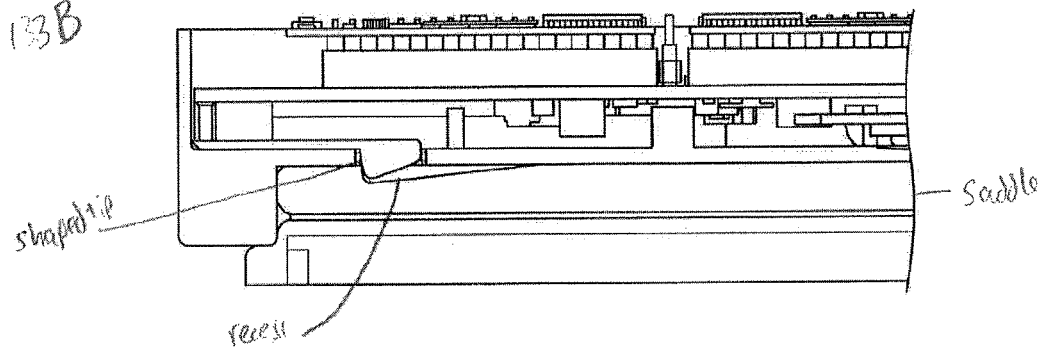
Figure 134:
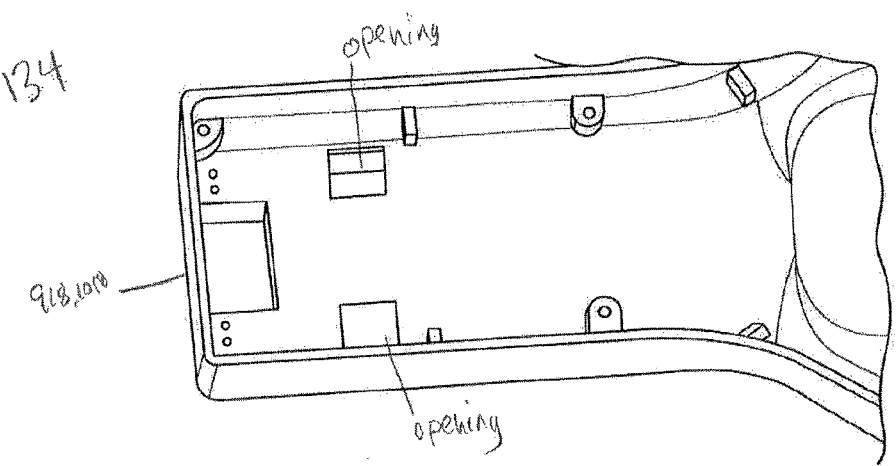
FIG. 134 illustrates a housing in accordance with some embodiments.

The size, shape, length and degree of engagement of the one or more housing locks may vary depending upon the specific designs of a housing lock and saddle taper. FIG. 133A is a section view of a housing-saddle combination where the view is through a housing lock. As seen in this view the edge of the shaped tip is shaped to engage with the saddle tapered recess. FIG. 133B is an alternative sectional view of FIG. 133A including the electronics supported on the Y-board assembly. FIG. 134 is a top view of the housing 918, 1018 with openings that can be used in FIGS. 133A-B in some embodiments.

In still a further embodiment, the one or more saddle housing locks are provided along the sides of the saddle. FIG. 135 is an embodiment of a saddle having a top engagement surface with one or more side recess attachment points. FIG. 136C is a side view of a housing assembly with a housing lock in the side wall positioned to engage with the saddle side recesses when positioned as shown in FIG. 136A. FIG. 136B illustrates the internal view of the engagement of the lock with the housing and saddle. It is to be appreciated that while the housing lock in the various embodiments have been illustrated and described as separate attached components, this aspect of the invention is not so limited. In some embodiments, the housing lock is integrally formed with the housing assembly rather as a separate component that is appropriately attached to the housing assembly.

FIG. 137 illustrates a release mechanism for use in conjunction with a housing lock embodiment described herein. In the illustrative embodiment, a release pin includes a shaft, having a feature positioned and shaped to engage with and sufficiently displace an adjacent housing lock to release the involved housing-saddle combination. In the illustrated embodiment, the housing lock has an extended tip in contact with the shaft. Rotation of the shaft causes the feature to engage with and displace the shaped tip of the housing lock. Once the shaped tip have been moved out of engagement the saddle-housing are unlocked. The size, shape, position and amount of rotation of the release mechanism may vary depending upon the size and shape of the feature in relation to the position, size and shape of the shaped tip or other aspects of the housing lock embodiment being unlocked by the release mechanism.

As a further example of saddle variants, FIG. 70C, FIG. 70E, FIG. 70F and FIG. 70G, the outer mating surface could also contain grooves, channels and other surface features to provide a better fit and/or to ensure that only a specific OTT electronics module can be mated to a tool using a specific saddle. The upper housing has a corresponding feature to mate with the saddle. The upper housing of FIG. 70B has a rectangular slot to correspond to the ridge/same feature in the saddle of FIG. 70C. The upper housing of FIG. 70D has a protruding rounded or semicircular guide to correspond to the same shaped groove feature in the saddle of FIG. 70E. In the same way, the saddle of FIG. 70F includes a number of rounded grooves that would find similar features in an upper housing. FIG. 70G illustrates a housing that may have a generally flat surface that may join by friction fit or other mechanically locking joining operation to maintain a fit to an upper housing.

The outer mating surface of the saddle itself could be further customized with features, including but not limited to, channels, cantilevers with raised notches, rails and corresponding features on the mating surface of the module to ensure a reliable fit as well as a positive user experience during the mating process. Such features would provide the user with a secure feeling that the OTT electronics module has been properly mated with the tool and is in the correct position. In one example, using cantilevers with raised bumps on the OTT electronics module and corresponding recessed notches on the saddle, the user would feel a 'click' when the OTT electronics module is slid fully into its correct position along the saddle (see e.g., FIGS. 122, 124, 126, 128-130, 132, 133A-133B, and 136A-136C).

The on tool tracking module houses one or more cameras, a projector, a user interface and associated electronics for their operation in accordance with an OTT CAS process, technique or system as described herein. Additional functionally may also be provided. One additional functionality referenced in earlier sections relates to the OTT module exerting control over an OTT enabled surgical tool. Referred in a general way as speed control, an OTT module may be configured to exert OTT CAS surgical tool control in at least three configurations: (1) no speed control; (2) tactile feedback or (3) electronic speed control.

The no speed control configuration of an OTT module has the above mentioned functionality and components except the speed control functions. This OTT configuration displays visual indications for guidance and/or gives visual or audio warnings if a surgeon using the OTT tool deviates from a pre-determined OTT CAS procedures or plan.

The tactile feedback configuration has the same components and functionality above but additionally includes a tactile feedback mechanism which gently presses against the user's finger pressing against the tool's trigger to warn the user to reduce speed or stop the tool. The speed of the tool is not controlled by the OTT software but instead remains under the full control of the user with the software only giving tangible signals. In one way of thinking, this configuration is intended for users who do not like to use tools that 'have a mind of their own'. The mechanism is tailored to the particular make of the tool used but with no need to access inside of tool. FIGS. 37A-51 above provide additional details and alternative embodiments for the OTT module configuration.

The electronic speed control configuration also includes appropriate Electronic Speed Control Model electronic circuits that control the speed of the surgical instrument along with other OTT module functionality instrument are controlled by the main system wirelessly. As a result, the instruments cutting or drilling speed is reduced (or stopped) if the user deviates from the established OTT CAS plan. The sensitivity envelope can be set and adjusted per user. The trigger signals of the surgical tool are now also passed to the OTT system electronics circuitry, where they are taken into consideration together with the computer tracking system to govern the surgical tool motor status. The surgical tool motor control circuitry is located in the tool housing in some embodiments or in an OTT module in a others, for example. In one aspect, motor control is achieved through a hardware module that fits inside the surgical tool. In one aspect, this module is powered by the battery of the tool, its function is to drive the motor, controlling on/off, direction, speed and braking (speed of stopping) functions based on the manual trigger status. OTT hardware modules for tool control may take a variety of forms, for example by: modification of an existing power tool to accept a new controller hardware module to provide the above described functionality and cooperation with an OTT module, a newly designed power tool designed from the beginning for OTT enabled operations. In this aspect a surgical tool manufacturer or other designer may modify an existing or new surgical tool design to incorporate appropriate electronics and/or hardware to enable the OTT CAS enabled control functions described herein.

Figure 106:
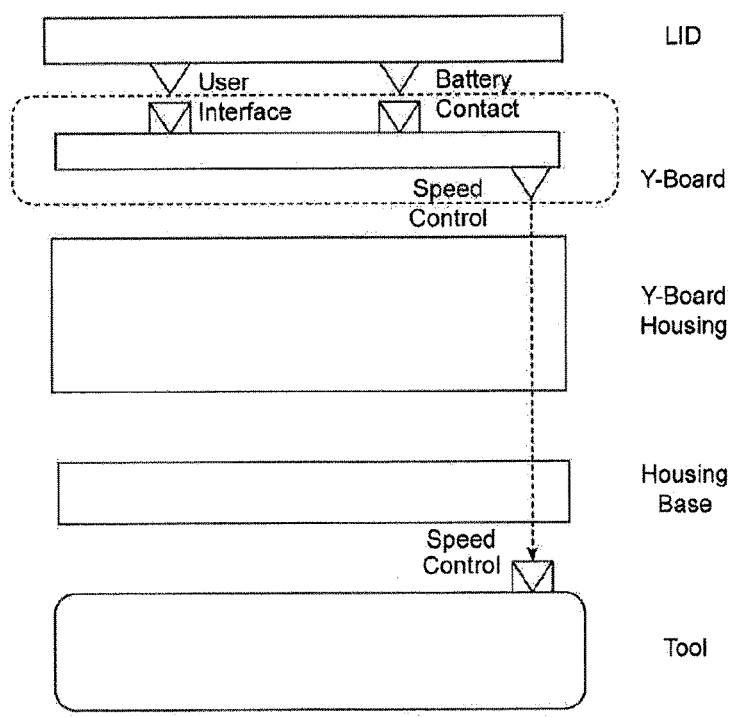
FIG. 106 is a schematic illustration of electrical contacts and circuits formed during the operation of the OTT module in accordance with some embodiments.
Figure 108:
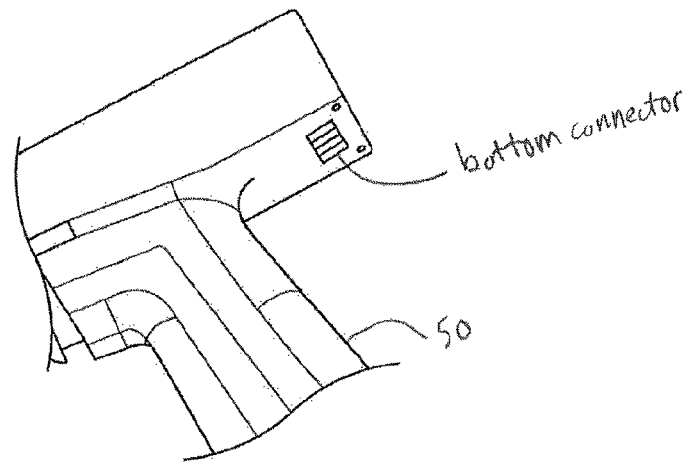

As with the previous example, providing governing control, defined by the example of allowing the OTT module to regulate the motor function of the OTT CAS enabled surgical tool, retrofitting the tool may not be necessary if existing contacts are available as in, for example, a bottom connector as shown in FIG. 108, or a top connector as shown in FIG. 110. Optionally, OTT speed control may be initiated or connected by OTT-tool/saddle engagement or by engagement of the lid assembly as shown in FIG. 106, which is a schematic illustration of electrical contacts and circuits formed during the operation of the OTT module. FIG. 106 illustrates electrical contacts between the user interface (e.g. touch screen) and battery between the lid assembly and the Y-board assembly. The speed control circuit can be part of the Y-board assembly and can provide electrical signals to the tool to control the speed of the tool as schematically depicted in FIG. 106.

If existing surgical tool connectors are available, then appropriate OTT-tool or OTT-saddle/tool connections are made. If existing contacts are available or provided on a surgical tool, then an OTT module may be provided that is adapted and configured for operation via those connections. In one aspect, an OTT saddle is provided that contains the appropriate OTT-saddle and saddle to tool electrical connections. With reference to exemplary tool with bottom connectors (see FIGS. 108 and 111A), an exemplary saddle is illustrated in the section view of FIG. 111B. This saddle includes appropriately shaped interior and exterior contours as described herein for coupling to both the selected surgical tool and OTT module. A pair of connector sockets are shown. The upper connector socket is provided to house the connector for electrical connection of the saddle to the OTT module. The lower connector socket is provided to house the connector for electrical connection of the saddle to the tool. The saddle also includes appropriate electrical connections or electronics as needed to provide electrical communications between OTT module tool. In this way one will appreciate how various saddle embodiments may advantageously provide for both electrical and mechanical coupling between a wide variety of both OTT module and surgical tool embodiments.

Any of a wide variety of connectors may be used to provide appropriate electrical contacts between OTT-tool. So long as connections maintain contact under the conditions of surgical tool operation. In some cases, this means that the connector should be adapted and configured to remain in contact during vibrations caused by surgical tool operations during OTT CAS procedures. One exemplary connector is a raised-flat connector. Another exemplary connector is a pin-socket connector. Still another exemplary connector is a raised contact style connector illustrated in. In yet another exemplary connector, a pogo type or spring loaded pin connector is provided. This type of connector comes in various lengths and configurations. This type of connector may be used to engage with a contact pad or surface or, optionally, with an appropriately sized receiver or female socket. In some cases the female socket can be spring loaded. It is to be appreciated as from these exemplary embodiments that the number and arrangement of the connectors may vary depending upon the OTT-Tool embodiment.

Figure 112A:
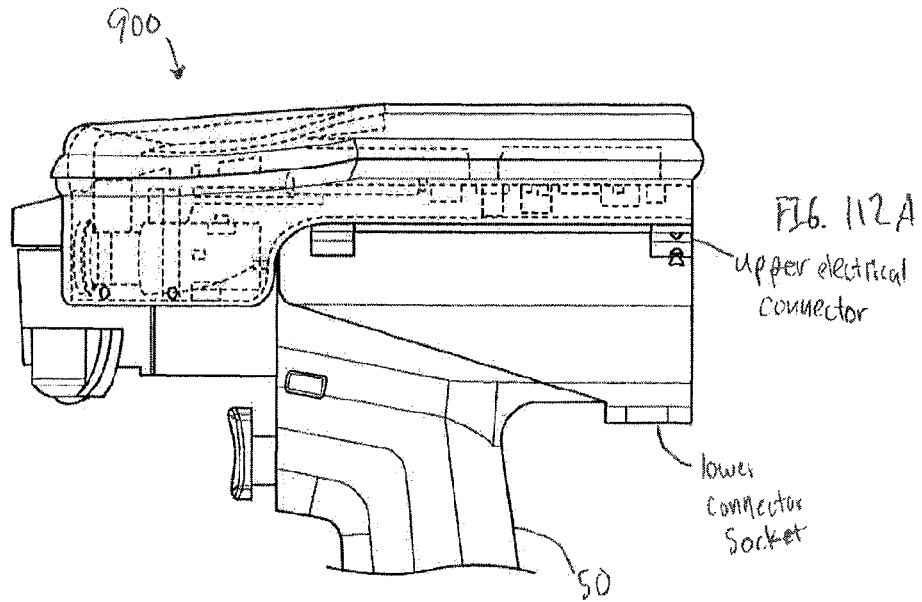
FIGS. 112A, 112B, 112C, and 112D illustrate various views of one embodiment of a speed control enabled OTT tool, saddle, and module combination.
Figure 112B:
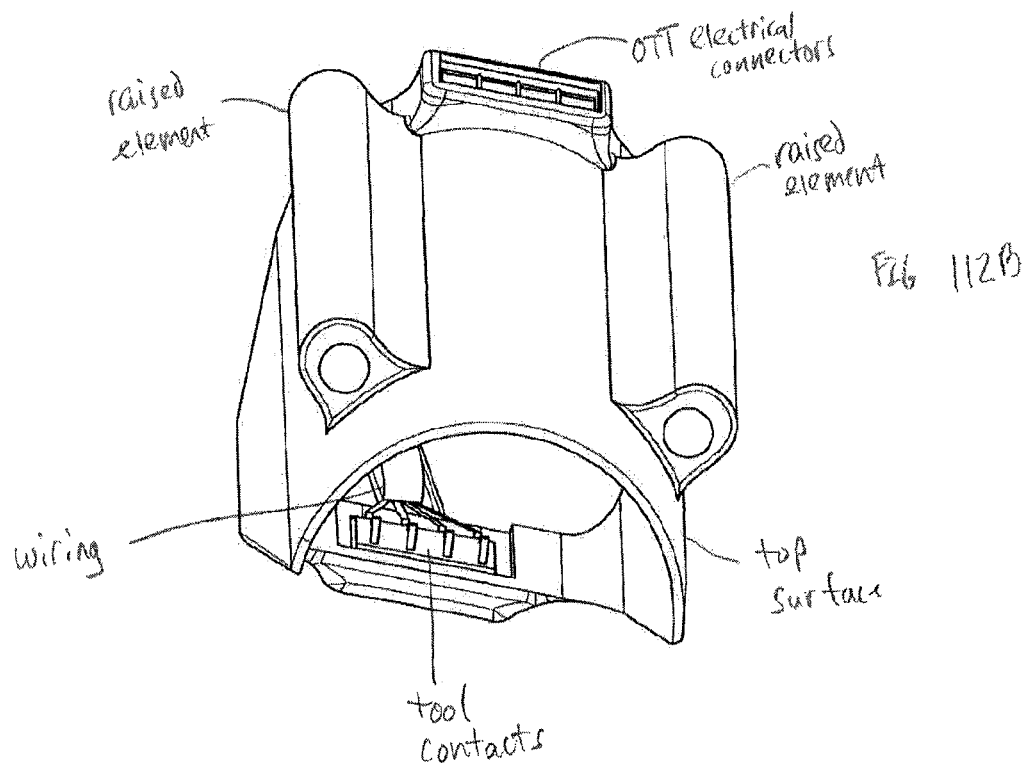
Figure 112C:
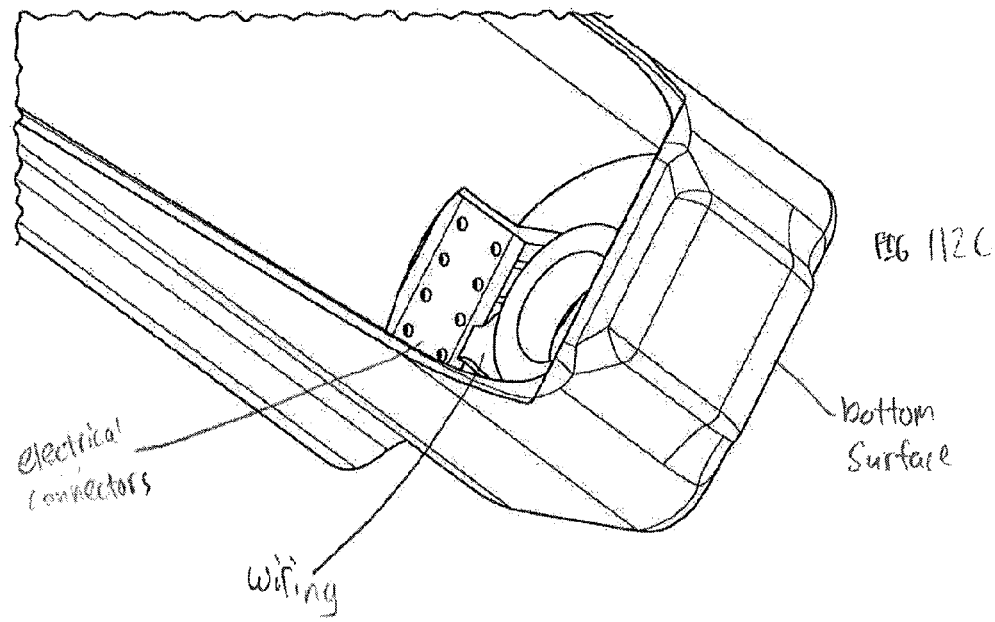
Figure 112D:
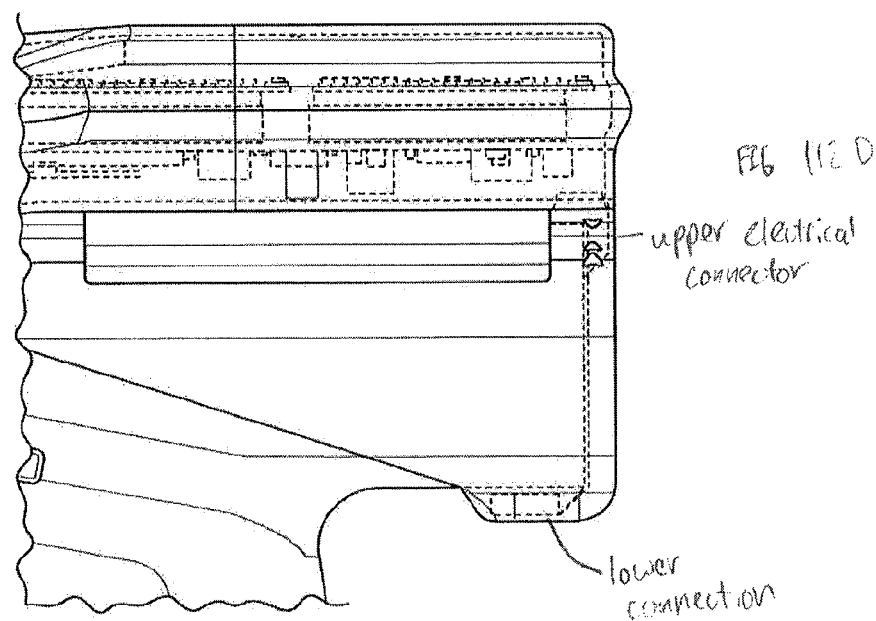
Figure 113A:
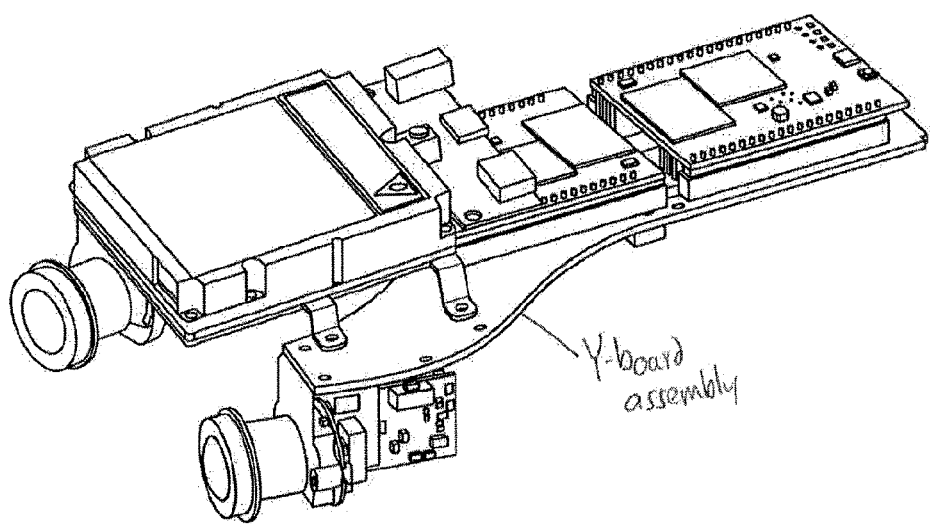
FIGS. 113A-113B illustrate a Y-board assembly in accordance with some embodiments.
Figure 113B:
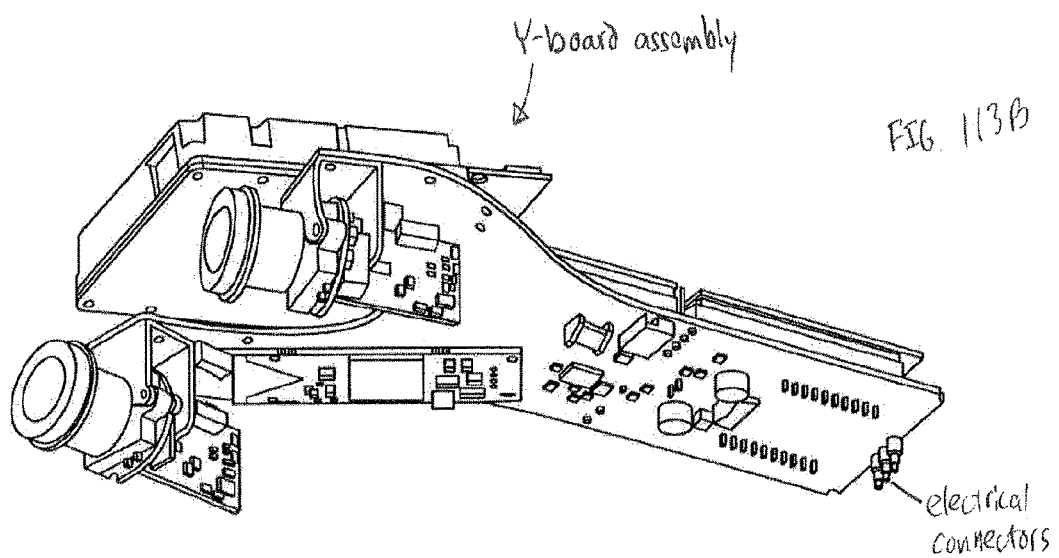
Figure 115A:
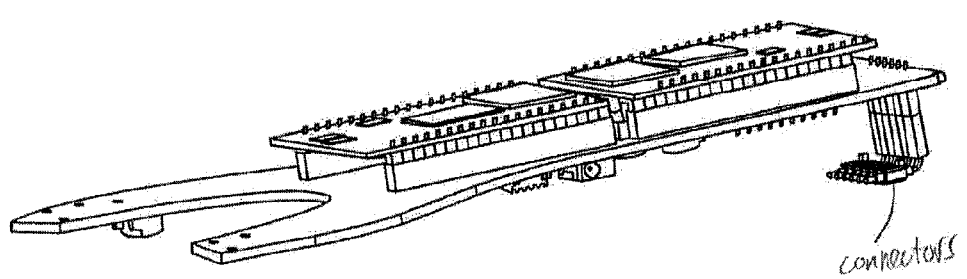
FIGS. 115A-115C illustrate a Y-board assembly in accordance with some embodiments.
Figure 115B:
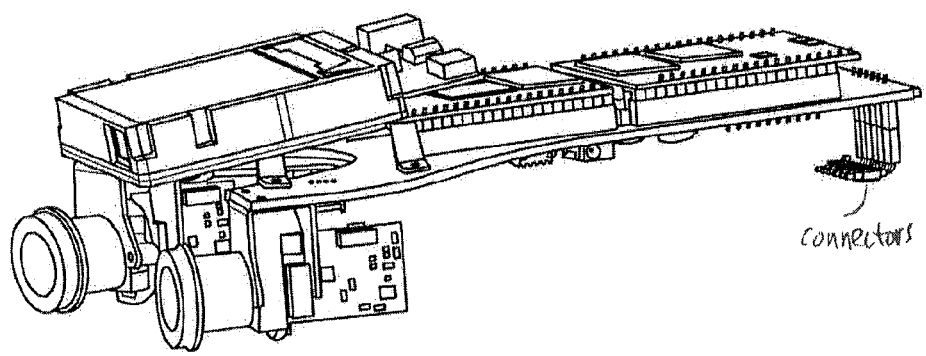
Figure 115C:
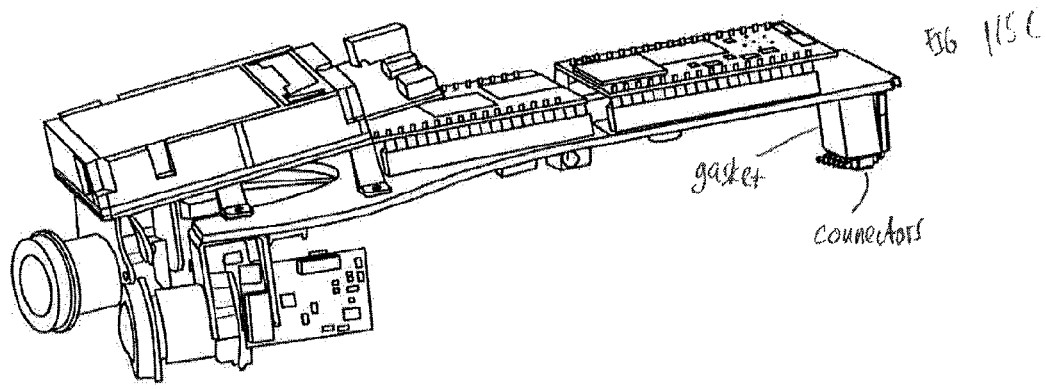

FIGS. 112A, 112B, 112C, and 112D illustrate various views of one embodiment of a speed control enabled OTT tool, saddle, and module combination. FIGS. 112B and 112C provide top down and bottom up views, respectively, of a saddle having electrical connectors for both an OTT module 900 and a surgical tool 50 configured for OTT tool control functionality. FIG. 112B shows the position of orientation of a four raised style tool contacts positioned to engage the bottom connectors on a tool (when the saddle is coupled to the tool). The OTT connectors (here, four pad contacts) are shown at the upper rear portion of the saddle to engage with compatible connectors of the OTT when the saddle is coupled to the OTT module. This view also shows a pair of axially aligned raised elements/features used for mechanical coupling of OTT to the saddle as detailed elsewhere herein. Wiring or other conductive material connects the OTT electrical connector to the tool contacts. FIG. 112D illustrates the underside of the saddle-OTT connector as well as a portion of the intra-saddle electronics or electrical connectors provided, as appropriate to the particular OTT and tool connectors of a given configuration.

FIGS. 112A and 112D illustrate various section views of an OTT module saddle-tool embodiment using the saddle of FIGS. 112B-112C to connect an appropriately configured OTT module to a surgical tool having bottom mounted electrical connectors as shown in FIG. 108. As appreciated by these various views the mechanical engagement of the OTT onto the saddle (previously attached to the tool result in the appropriate mechanical coupling as well as appropriate electrical connectivity between the OTT module of the surgical tool.

If needed, appropriate electronic and mechanical connections are provided to connect the OTT module to the tool. In one embodiment, a retrofit of a surgical tool includes replacement of the tool's end cap. An end cap would be fitted to the surgical tool at the time the tool is modified. In one aspect, the end cap incorporates the motor control circuitry for the tool. FIG. 74E illustrates a rear views of an illustrative tool end cap for electronic speed control functionality. The overall shape and size of the end cap is adapted and configured to engage with the tool housing as appropriate. A circuit board contained within the housing (not shown) contains appropriate electronic components and electrical connections to enable OTT-tool connectivity and control as described herein. An OTT connector with six terminals is also illustrated although various other connection types are possible and described herein.

Advantageously, incorporation of the appropriate tool control connections and electronics into a modified tool cap may in some embodiments, reduce or eliminate the need for electrical or electronic components in the saddle (i.e., as illustrated in FIG. 112B as such, incorporation of electronic speed controls into the tool would then enable the use of a so called "circuit-less" saddle used to provide appropriate mechanical coupling of the OTT-tool as described elsewhere herein.

Figure 109:
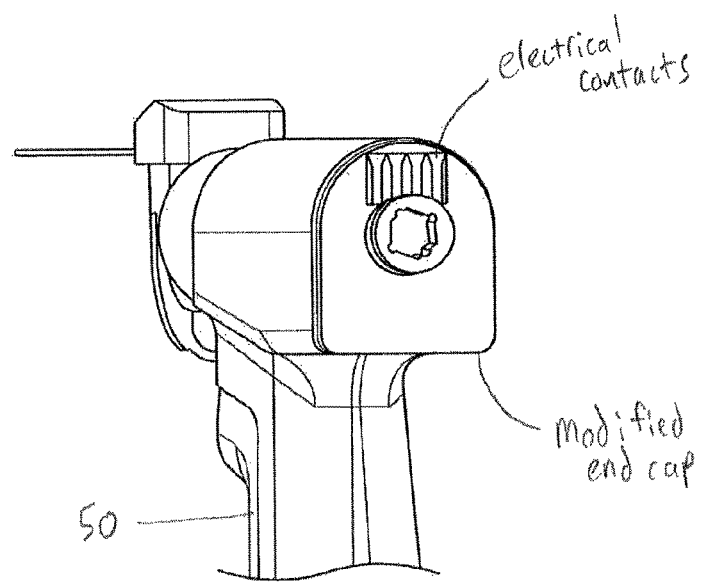

FIG. 109 illustrates an embodiment of a surgical tool modified to provide built in electronics to enable OTT CAS tool control as described herein. In this illustrative embodiment, an OTT enabled end cap electronics module is shown on a handheld surgical tool 50. The modified end cap provides a bank of electrical contacts for connection to an appropriately configured OTT module. In this illustrative embodiment, four horizontally arrayed contact points are provided for OTT connection.

As appreciated through reference to the views of FIG. 74E and FIG. 114A both the replacement end cap and saddle have one or more openings as needed to accommodate other tool access points or connectors used in tool operation. In these exemplary illustrations a circular opening is provided in both the replacement end cap and the saddle to accommodate a tool connector positioned on the rear wall of the tool. The end cap or other tool modified component and saddle may be modified in other ways depending upon the specific tool configuration being modified for OTT CAS operations.

Figure 179A:
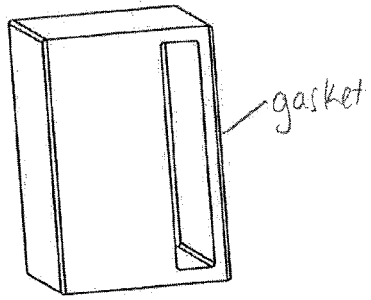
Figure 179B:
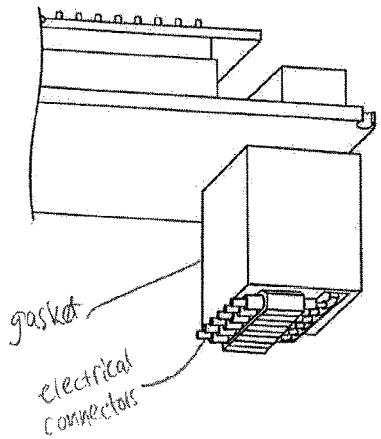
Figure 179C:
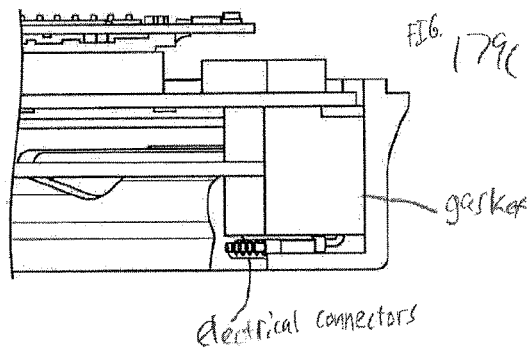
Figure 179D:
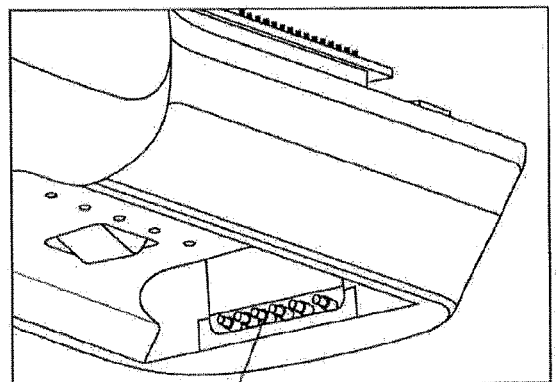

It is to be appreciated that the OTT module may also be modified, as needed, to accommodate any connectors added to an OTT enable surgical tool. Consider for example a surgical tool modified for OTT operations by installation of a modified end cap modified to include electrical contacts as illustrated in FIG. 74E. An appropriate saddle design is shown in FIG. 114A having an appropriately sized opening positioned to provide access to the electrical contacts on the back of the surgical tool when the saddle is mechanically engaged with the surgical tool. An opening for mechanical attachment on the saddle can be used to attach the saddle to the surgical tool and/or OTT module. The OTT module may then be modified as appropriate to engage mechanically and electrically with the saddle or described in the various embodiments of the application. Given the connector type illustrated in FIG. 74E then one appropriate OTT connector would include a horizontal arrangement of six connectors as shown in the illustrative connector of FIG. 114B. The connector of FIG. 114B is shown integrated into a Y-board assembly in FIGS. 113A-B and 115A-C. Note how the connector is appropriately positioned and sized to span the distance from the Y-board electrical connection location to the end cap electrical location on the saddle. Optionally, the connector may be provided with an insulation gasket seen best in FIG. 179A. The connector with insulation block installed may be appreciated by reference to FIG. 179B. The final position of the connectors relative to the housing assembly are best seen in the side section and bottom up views, respectively of FIGS. 179C and 179D. Also seen in these views are the positions of a housing lock a plurality of vent holes and a gasket described elsewhere herein.

FIGS. 118B-C illustrate the relative position of the OTT saddle tool illustrated and described above just prior to electrical engagement in FIG. 118B. At this point, the OTT module and saddle engagement surfaces are aligned and joined. Next, the OTT housing and saddle tool components are moved together such that the OTT connector makes appropriate electrical contact with the tool connector via the saddle as best seen in the section view of FIG. 118C.

In still other aspects, the surgical tool could also be devised to contain a wireless control module with which the module communicates in order to provide the same governing functions.

Additional OTT Camera Details

FIG. 140B illustrates a side view of an embodiment of a camera attached to a Y-board. The camera includes a lens and a lens holder that are positioned, sized, adapted and configured for use with an imager. An appropriately configured electronics package, such as the illustrated image sensor board, is provided for processing the image sensor signals and providing an appropriate output for other OTT CAS camera signal processing, depending upon OTT module configuration. A camera mount is also coupled to the lens/housing/imager electronics assembly to facilitate attachment of the camera lens in the appropriate position according to the design requirement s of a particular OTT module. In this aspect the distance between the lenses can be about 52 mm.

Figure 138A:
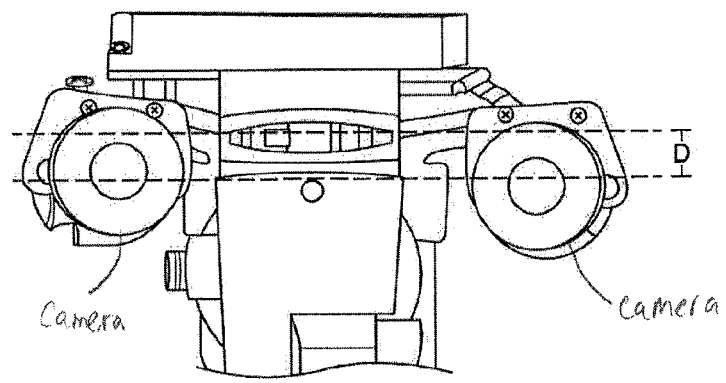
FIGS. 138A-138B and 139 illustrate the orientation between an active element of a surgical tool and a pair of cameras.
Figure 138B:
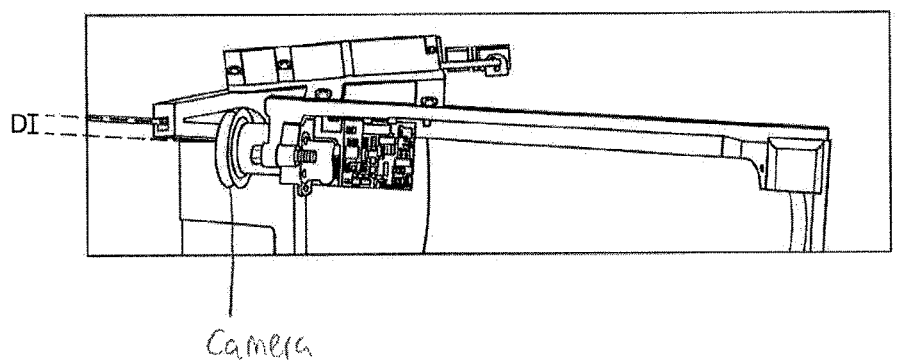
Figure 139:
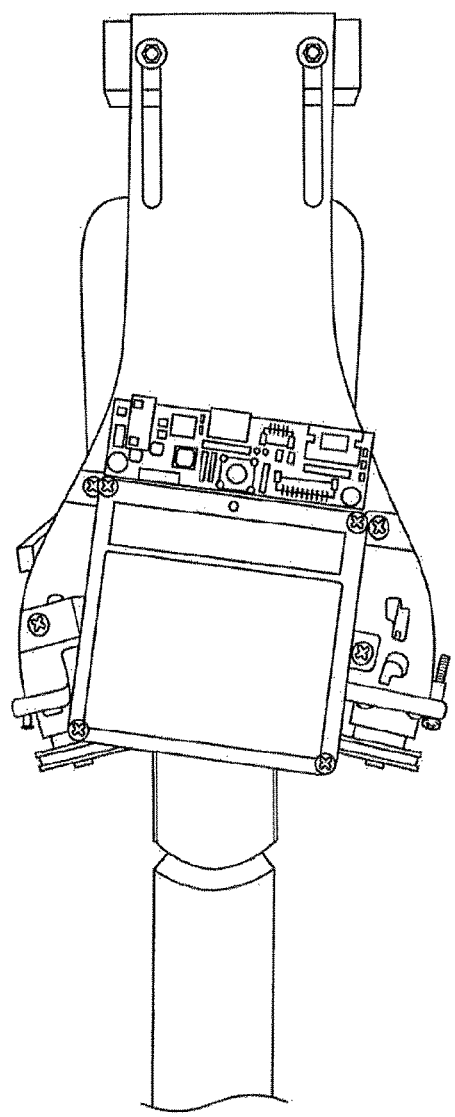

In one aspect, a pair of cameras is positioned in an OTT module such that all reference frames in an OTT CAS procedure are within the camera field of view during all cuts of an OTT CAS procedure. FIGS. 138A-138B illustrate end on and side views of one example of OTT camera spacing and orientation for this purpose. In the embodiment illustrated in FIGS. 138A-138B the cameras are located a distance of 5 mm below a plane containing the illustrated saw blade (illustrated as "D" in FIGS. 138A-138B). A line joining the two lens centers is located 19 mm behind the base of the saw blade and the camera lens visual axes are parallel to the saw blade axis. In this aspect the distance between the lens centers is 58-59 mm in the embodiment illustrated in FIG. 139.

In still another embodiment, an OTT camera has a low profile mega pixel lens with no IR cert of filter adapted for a ⅓" image sensor and a focal length of 3 mm. In still another aspect, the OTT camera has a focal length of 1.50 mm and is adapted to provide a 138° HFOV, a 103° VFOV and a 175° DFOV for an ¼" image sensor. In still another aspect, an OTT camera has a wide angle lens with a focal length of 1.7 mm is adapted to provide a 123° HFOV, a 92° VFOV and a 155° DFOV for a ¼" image sensor.

In one embodiment, a pair of OTT cameras are positioned within an OTT module so that the optical axes of each camera is spaced apart by about 60 mm. In an additional aspect, the cameras are tilted inwards (i.e., towards one another and a central longitudinal axes of an OTT toll within a range of about 10°-15°. The camera spacing and tilt angle is selected to optimize the measurement volume and accuracy of tracking depending upon the camera lens field of view (i.e., see FIG. 11A).

In one aspect, an OTT camera pair is selected to have a lens and an imager with an angle of view that enables viewing of the reference frames used in an OTT CAS procedure during all cuts to be performed in that procedure. In one aspect, the OTT camera pair is selected to also maintain a saw blade with a length of 95-100 mm with the view along with the reference frames during all cuts in an OTT CAS procedure.

In one aspect, an OTT camera has a CMOS ¼" format sensor. In another aspect, an OTT camera has a CMOS WXGA HD sensor. In one aspect, the OTT camera has a 1 megapixel HD sensor.

In one aspect, an OTT camera uses a standard M8x0.35 mm lens, or optionally, a wide angle lens.

In still another aspect an OTT camera includes an infrared filter.

In still another aspect, the cameras on an OTT module are selected to provide field of view that enables successful viewing of the reference frames throughout all cuts of an OTT CAS procedure as described herein.

In one aspect, an OTT camera has a wide angle lens, an ¼" imaging sensor or an ⅓" imaging sensor, optionally utilizes distortion dewarping software, optionally has no IR cut-off coating, optionally has an integrated IR cut-off filter, optionally has a mega pixel miniature fish eye lens.

In still further aspects, an OTT camera has a HFOV of 123°, a VFOV of 92°, and a DFOV of 155°. In still further aspects, an OTT camera has a HFOV of 102°, a VFOV of 77°, and a DFOV of 126°. In still further aspects, an OTT camera has a HFOV of 94°, a VFOV of 70°, and a DFOV of 117°. In still further aspects, an OTT camera has a HFOV of 74°, a VFOV of 53°, and a DFOV of 97°. In still further aspects, an OTT camera has a HFOV of 107°, a VFOV of 79°, and a DFOV of 136°.

In still further aspects, an OTT camera has a focal length of 1.67, 1.7, 1.97, 2, 2.2, or 3 mm.

In one aspect, an OTT camera has a ¼" sensor size with a 4.5 mm sensor diagonal, a 4×3 sensor format, a 94° HFOV, a 78° VFOV, and a 107° DFOV.

In one aspect, an OTT camera has a ⅓" sensor size with a 6.0 mm diagonal, a 4.3 sensor format, a 110° HVOV, a 94° VFOV and a 122° DFOV.

In one aspect, an OTT camera has a 1/2.5" sensor size with a 7.2 mm sensor diagonal, a 4×3 sensor format, a 120° HFOV, a 104° VFOV and a 130° DFOV.

In some embodiments a camera mounting bracket is provided for attaching the camera, holder, imager and associated electronics to the OTT Y-board. The specific configuration of a camera bracket may be modified in order to position the OTT cameras in the desired position relative to other OTT components and the desired OTT FOV. Camera brackets may be formed from any suitable material, such as, plastic, metal or stainless steel.

Figure 140A:
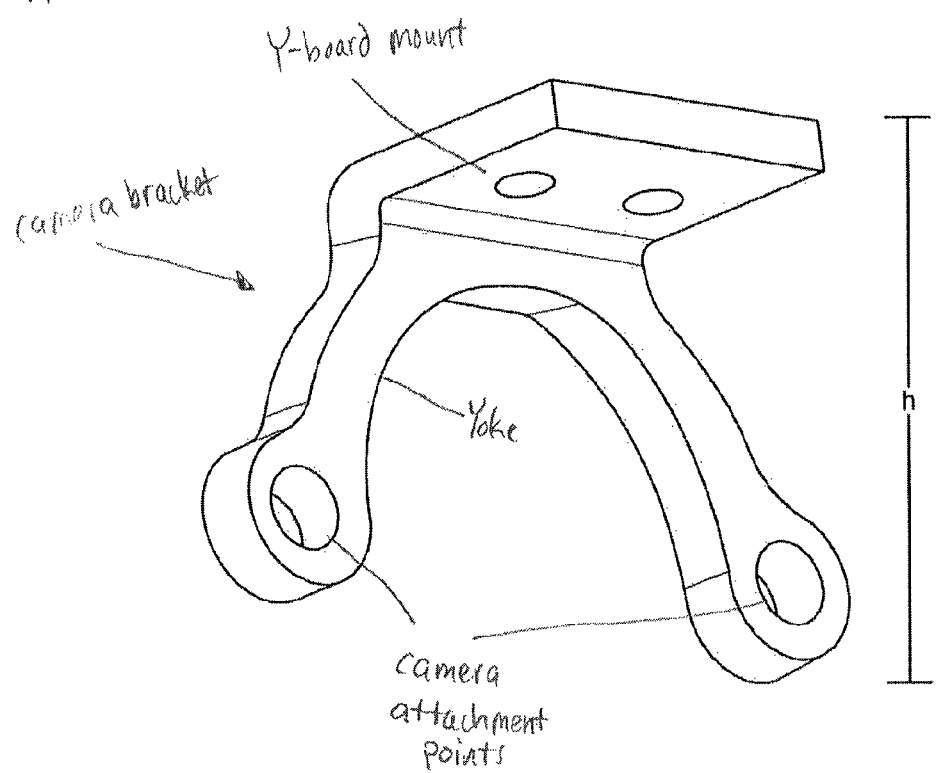

FIG. 140B illustrates one embodiment of a camera bracket. In this embodiment the bracket has a top mount for attachment to a Y-board and a semi-circular yoke with attachment points to a camera assembly. The yoke shape is selected to confirm approximately to the exterior shape and size of the lens housing. As appreciated by reference to the alternative bracket configurations that follow, the height of the bracket (i.e., distance from Y-board to camera mount) may be adjusted in order to provide the desired resulting camera axis/FOV in a specific OTT enabled module/surgical tool embodiment as described herein. FIG. 140C illustrates the Y-board of FIG. 140A on a surgical tool.

An alternative camera bracket is illustrated in FIG. 140A. There is a Y-board mount as well as a camera housing yoke and camera attachment points as in the previous example. Camera bracket illustrated in FIG. 140A has a short height between the Y-board mount and the camera attachment points.

Figure 141A:
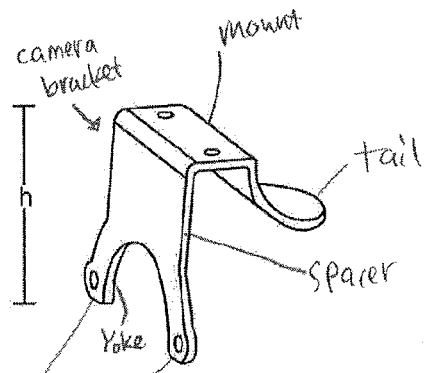
FIGS. 141A-141C illustrate various aspects of camera mounts in accordance with some embodiments.
Figure 141B:
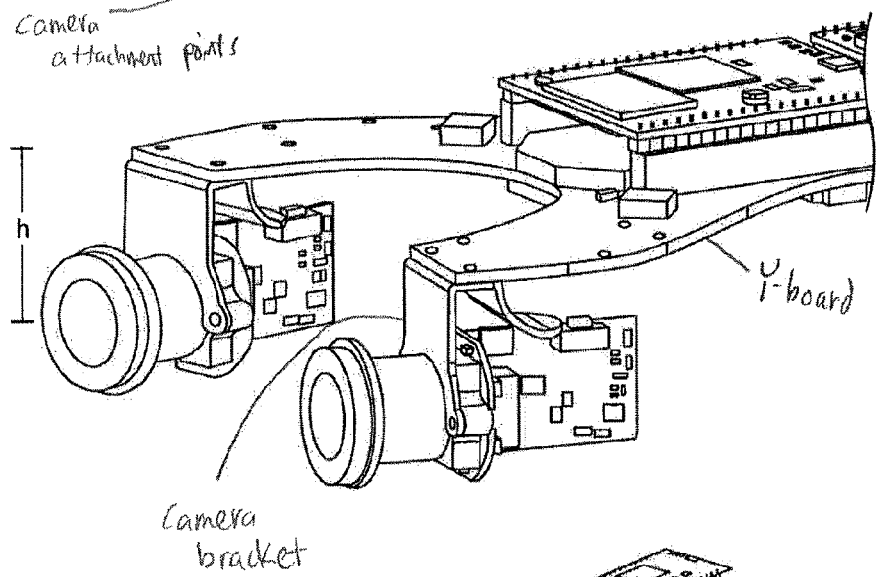
Figure 141C:
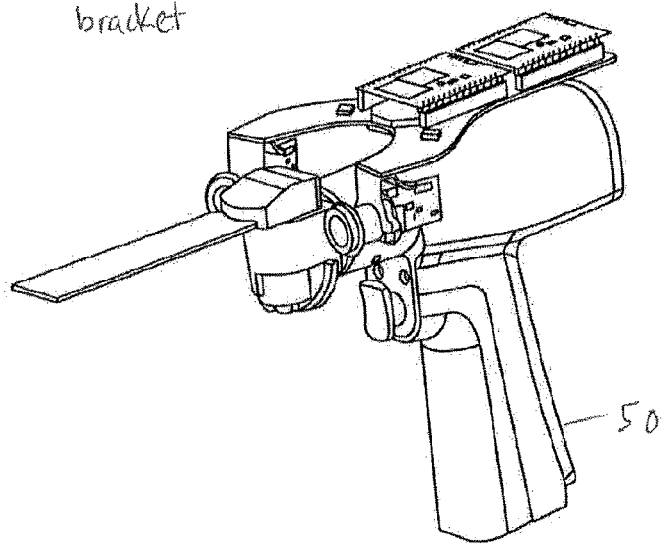

In an additional aspect, a camera mount may be provided with additional features to provide stability, vibration attenuation or otherwise support an OTT camera module or assembly, depending upon the specific camera configuration. FIG. 141A illustrates a camera bracket having a strut/tail extending from the Y-board mount to a part of the camera assembly. The camera bracket includes a spacer between the mount and yoke along with camera attachment points. In this specific embodiment, the strut is curved and shaped to contract the camera assembly electronics, as best seen in FIG. 141B. FIG. 141C illustrates the Y-board and camera mounts of FIG. 141B on top of a surgical tool.

Figure 148A:
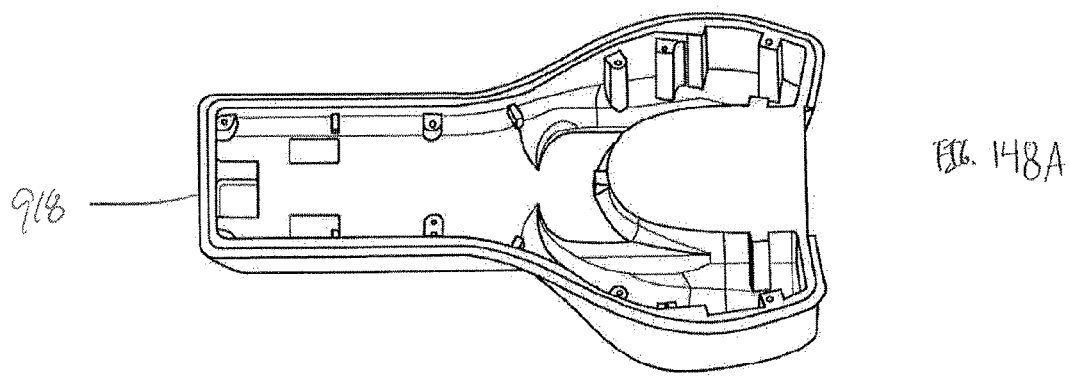
Figure 148C:
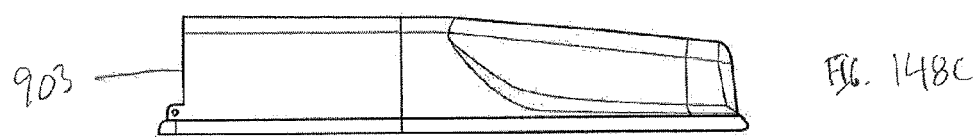
Figure 148D:
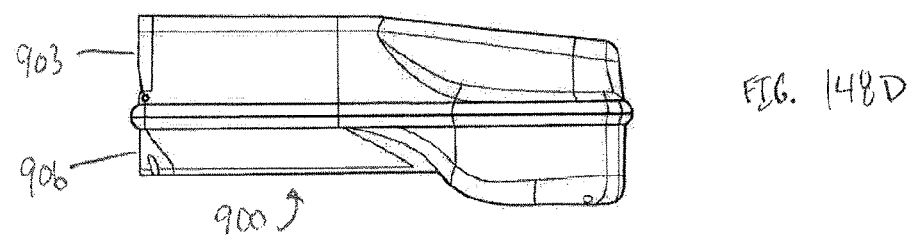

In some embodiments, a protective lens is provided in the OTT module for each OTT camera and the projector. The lens may be of any suitable transparent material such as glass or plastic. In one embodiment of the camera protective lens, there is a contoured opening in an OTT housing as shown in FIG. 148D. An appropriately shaped lens for the opening is then secured into the contoured recess. An exemplary camera protective lens is shown in the housing illustrated in FIGS. 149A-149C. The contoured edges of the lens is adapted to conform with the corresponding portions of the contoured recess shown in FIG. 148D. An embodiment of a camera protective lens is shown installed in the exterior view of FIG. 149A-C. The protective lens can be suitably aligned to the camera lens, lens holder and imager.

Figure 146A:
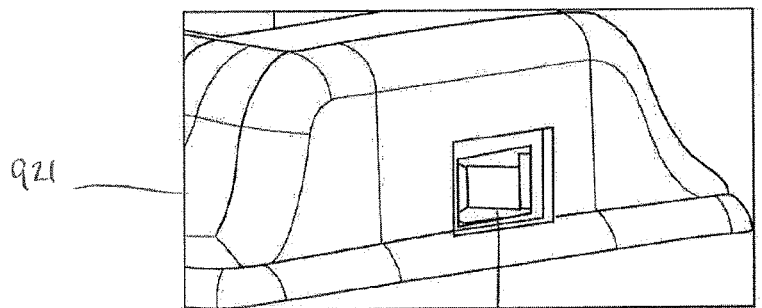
FIGS. 146A-146E illustrate various configurations of housing lids and projector lenses in accordance with some embodiments.
Figures 146B, 146C:
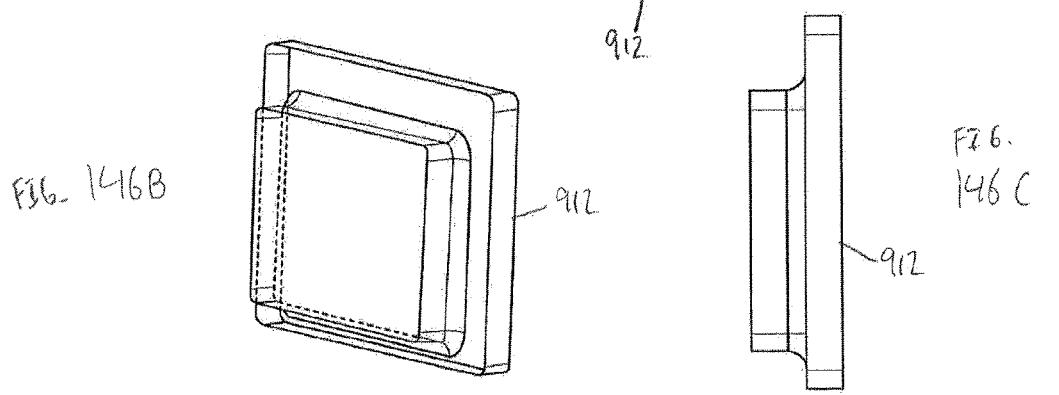
Figures 146D, 146E:
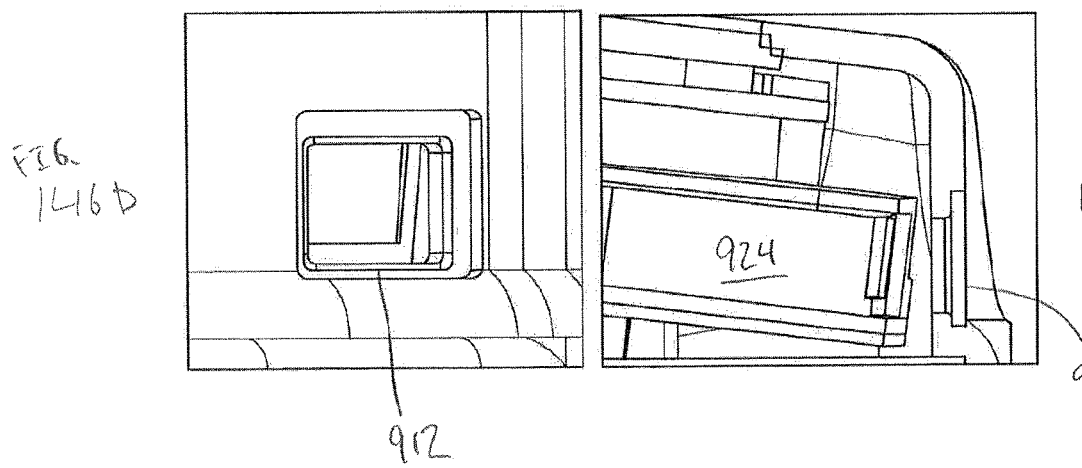

Similarly, in some embodiments, a projector protective lens is provided in the OTT module. In one embodiment there is a contoured opening formed in an OTT module to accommodate a projector protective lens 912. FIG. 146A illustrates one embodiment of a contoured opening to receive a projector protective lens 912. FIGS. 146B and 146C illustrate rear isometric and side views, respectively of a projector protective lens 912. As seen in these views the overall perimeter shape and edge width is selected to correspond to the OTT module opening as needed by the specific position of the projector 924 within the OTT module. FIG. 146D is an enlarged view of the lid 921 and projector lens 912. FIG. 146E is a cross-section side view of a lid 921, projector 924 and projector lens 912. FIG. 86B is a bottom up view of an OTT lid 912 with a projector protective lens 912 installed.

The projector protective lens and the corresponding opening in the lid assembly are adapted and configured to ensure that the projector protection lens is normal to or nearly so to the projector front lens. Put another way, the lens and opening are selected so that the projector lens and protections lens are nearly parallel. These general design attributes are adapted to each specific projector lid orientation (see e.g., FIGS. 3, 4, 13A, 13B, 13C, 74A-C, 75C-G, 76A-B, 77A-D, 78A-78B, 79A-B, 80A-80E, 81A-81E, 82A-82C, 83A-83D, 84A-84C, 85A-85E, 86A-86H, 87A-87F, 90C-E, 91B, 92B, 93B, 95A, 95B, 96A-C, 97A, 97C, 98A, 99B, 100A, 100B, 101B, 102A-C, 103A-B, 104C-E, 105A-D, 112A, 112D, 116A-116C, 117A-D, 118A-C, 119A-B, 120A-120B, 122, 123, 124, 126, 128-130, 132, 133A-B, 134, 136A-136C, 137, 146A-146E, 147A-C, 148A-148D, 149A-149C, 150A-F, 151B-G, 154, 155A-D, 156A-156D, 157A-157E, 158A-B, 159A-B, 160B, 161, 162A-D, 163, 164A-B, 165A, 166B, 167B, 167C, 168A-C, 169A-B, 170B, 173A-173B, 174A-174B, 174C, 175A, 176B-C, 177B, 178A, 178B, 179C, 179D, 190A, and 190B).

A bone registration process may be performed according to a method using a pair of OTT cameras and a projector output. In one aspect, the cameras used for this process are provided without IR pass filters (i.e., the cameras are not filtered with IR pass filters).

Additional OTT Projector Details

As described above, the OTT module also includes a projector for displaying a user or system output from an OTT CAS process. In one aspect, the projector is a pico projector similar to such a pico projector as is adapted and configured for use in a smart phone. In one aspect, the projector is a pico projector such as a DLP pico projector available from Texas Instruments. In still another aspect, the projection is sized with a form factor so as to fit within an OTT enclosure, such as within an OTT lid assembly or an OTT housing. In some embodiments a heat sink is provided for the projector. In one configuration, the OTT CAS ground computer communicates OTT CAS process outputs via wires or wirelessly to the projector using suitable connections and an interim wired or wireless electronic communication board.

It is to be appreciated that appropriate electronics and auxiliary components are provided in the OTT for operation of the projector and communication with the ground computer. In one aspect a microcontroller or microprocessor with build in or stand alone image processing may be provided. Moreover, it is to be appreciated that wireless OTT embodiments may include components for wireless communication having internal antennas or, optionally, also external antennas used in combination. Antennas, if used, may be in appropriate locations in an OTT module. Exemplary wireless antenna locations include, for example, towards the front of the OTT module near one or both cameras or towards the rear of the OTT module or on the inner side of the housing or underneath the battery cavity.

Figure 143A:
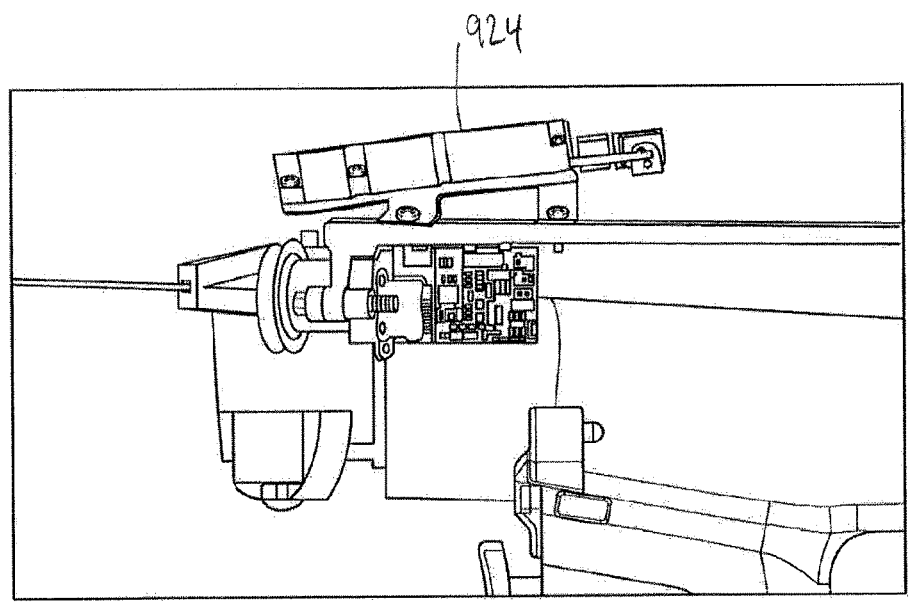
Figure 143B:
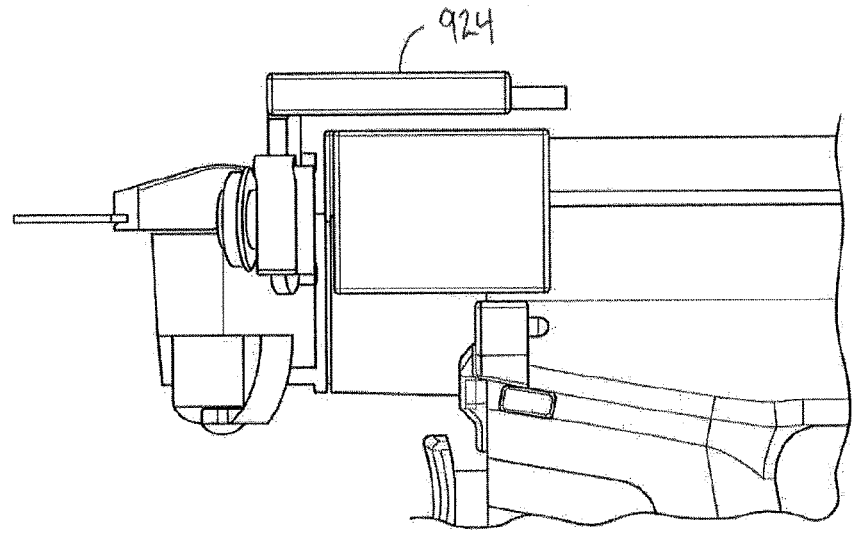
Figure 143C:
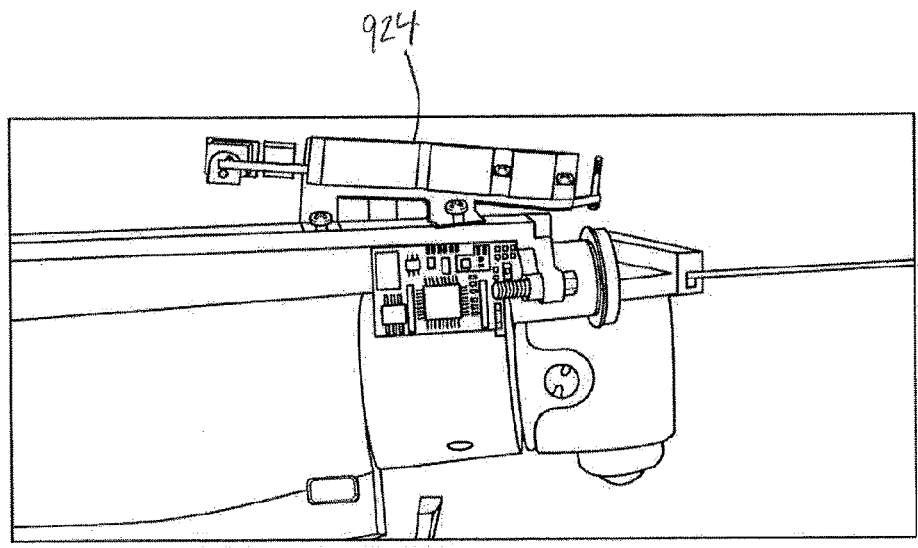

FIG. 142A illustrates a projector 924 on an OTT housing assembly that is offset from the center of the OTT housing in accordance with some embodiments. FIG. 142B illustrates a projector 924 on an OTT housing is tilted relative to an axis of the active element of the tool. FIG. 143A illustrates a projector 924 that is angled down towards the active element of the tool. FIGS. 143B-C illustrates a projector 924 that is parallel to the Y-board and active element of the tool.

Figure 144A:
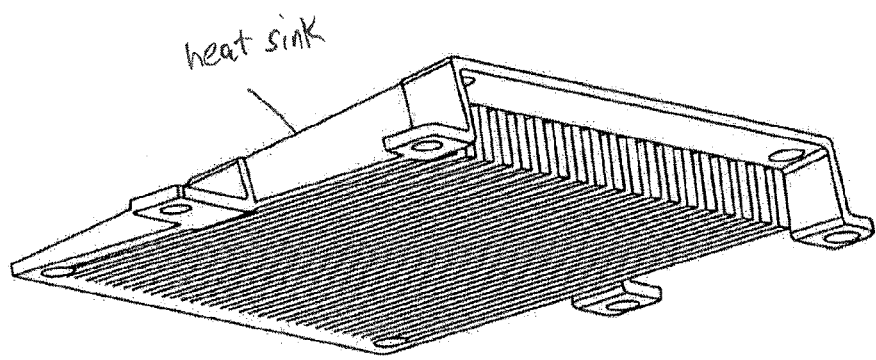
FIGS. 144A-144C illustrate various projector configurations in accordance with some embodiments.
Figure 144B:
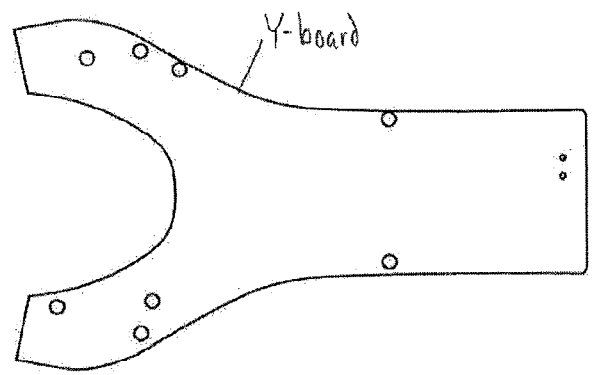
Figure 144C:
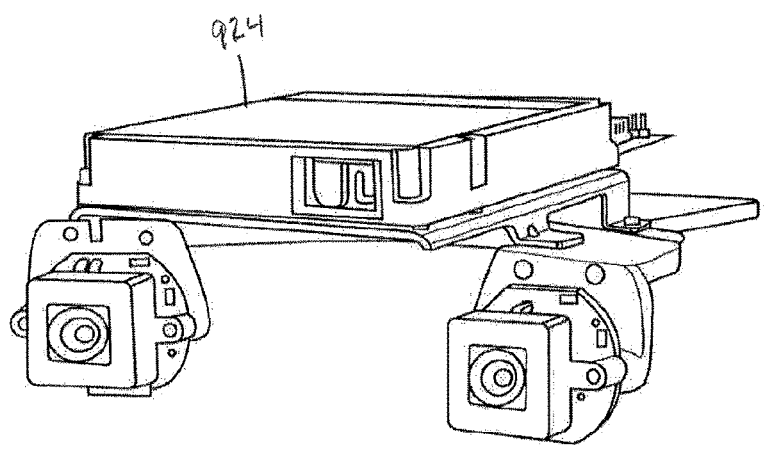
Figure 145A:
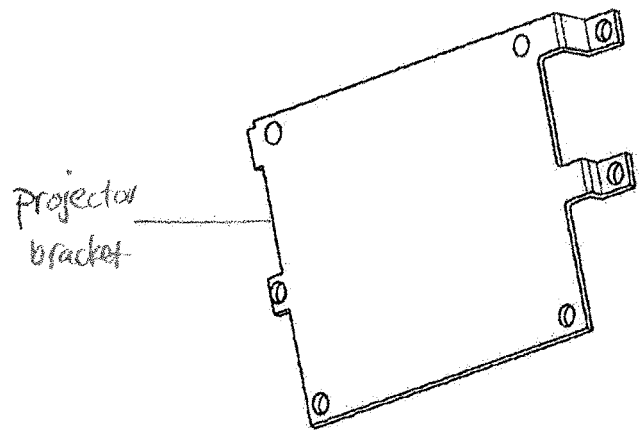
FIGS. 145A-145B illustrate embodiments of projector mounting brackets.
Figure 145B:
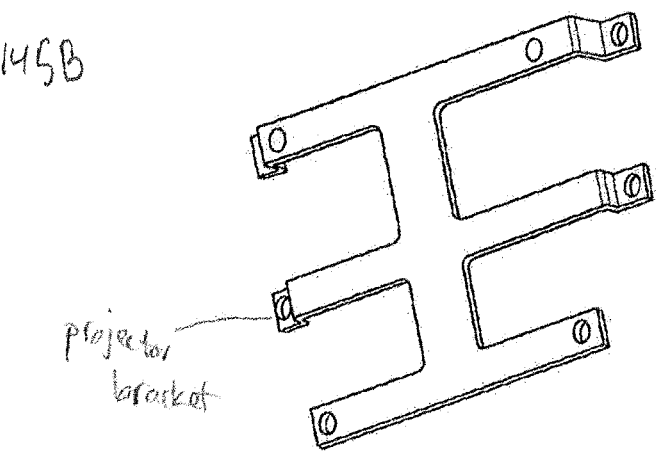

An appropriate projector attachment bracket sized for the specific projector and elevated, as needed, for projector position may be included within an OTT module as needed by the OTT design and projector configuration. A projector bracket may include an elevated slotted base as shown in FIG. 145B where the elevation provides the designated angulation of the projector output based on the projector position on the Y-board, OTT design, projector output and other factors. The projector bracket may also be solid rather than slotted as shown in FIG. 145A. Additionally or alternatively the projector bracket may include or have an added heat sink (FIG. 144A). FIG. 144C illustrates a heat sink underneath a projector bracket. The heat sink or projector bracket can support the projector 924 and engage with the Y-board from FIG. 144B as shown in FIG. 144C.

In one embodiment, there is provided in the OTT CAS system a wireless module with a small footprint to establish communication between the projector and the ground station PC. In one specific embodiment, there is a wireless module having a small footprint, low power consumption and programmability to enable transmission of the minimum amount of data wirelessly from the ground PC to the projector for minimum use of bandwidth and PC processing time.

One of the features of an OTT CAS system is the capability to present visual information to the user. In another aspect, the projector on the tool already has a pico projector that can be used to 'inform' the user of the progress of the cut, etc. Including use of flashing lights and sounds for example. In one aspect, the projector functions as an image generator having appropriate hardware and software components.

An OTT CAS system produces a wide range of visual items to be output by the projector. In one configuration, the basic types of output information to display includes: projected cutting line, text, figures (sprites), grid and axis plus navigation lines.

Within each of these outputs are a wide range of parameters that may also be included in the display such as: colors, size, font, style, grid size, thickness, and location (x,y). Appropriate information such as parameters defining an image are provided by the OTT CAS system to the projector based on specific OTT CAS processing outputs or results of OTT CAS processes. The OTT CAS system may operate the projector to display an image that contains all or part of the information that is described herein as well as to generate a video image of the following information: image, compress image and spline.

In one configuration, the OTT CAS system uses a toll plus bone plus target location (wireframe technique, vertex plus edges) to generate a curve for display.

An electronic memory associated with the project may include appropriate information for displaying OTT CAS output information, such as, for example, background color, character graphics, sprites in numeric order, character graphics, and/or character graphics.

In another alternative embodiment wireless communication is provided by an Ultra Wide Band Technology for connectivity between the ground PC and the OTT. A system may consist of two dongles a wireless USB PC adapter and a wireless USB device adapter. The Wireless A/V Adapter set provides same room coverage, up to 30 feet range between PC and OTT.

Ultra Wide Band Technology (UWB) is a wireless radio technology, suited for transmitting data between consumer electronics (CE), PC peripherals, and mobile devices within short range at very high speeds while consuming little power. UWB technology for OTT handles the very high bandwidths required to transport multiple audio and video streams as needed. The selected UWB does not cause interference to other radios such as cell phones, cordless phones, broadcast television sets, Bluetooth devices and WIFI. The UWB may have a same room range of up to 30 feet. The wireless communication may be provided with appropriate security.

OTT Housing and Lid Details

Some on tool tracking and display modules have a two piece assembly as variously described and illustrated herein. In general, these two parts when attached form an OTT module suited for use with an OTT CAS system. The joint or seam between these two assemblies may take on any of a number of various configurations based on the specific contours of each of the assemblies particularly along the seam. In one aspect, the sealing surfaces and resulting seam formed between a lid assembly and a housing assembly is flat. A flat configuration is illustrated in, for example, the assemblies illustrated in FIGS. 74A-74C, 75A-75E, 76A-76B, 77A-77D, 78A, 78B, 79A, 79B, 80A-80E, 81A-81E, and 147A-147C, 148A-148E, 149A-C and other figures.

Figure 147A:
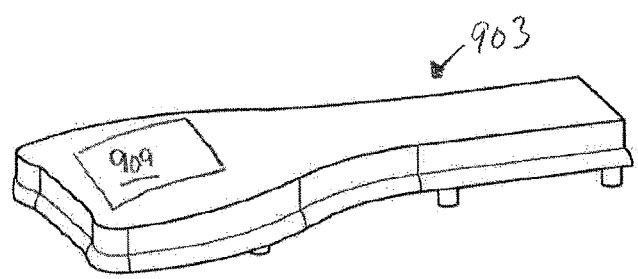
Figure 147B:
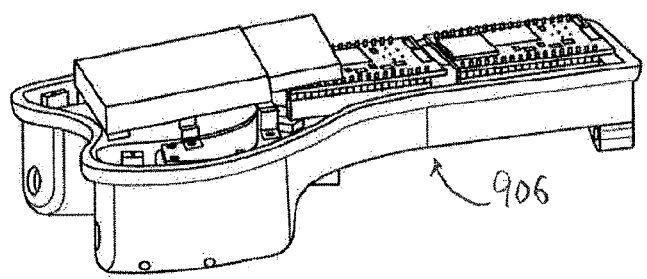
Figure 147C:
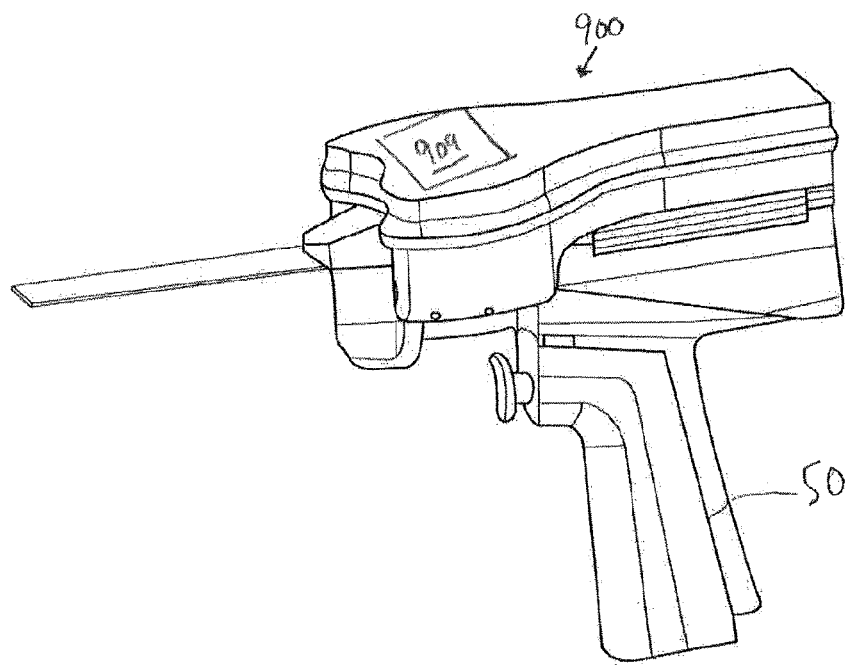
Figure 148B:
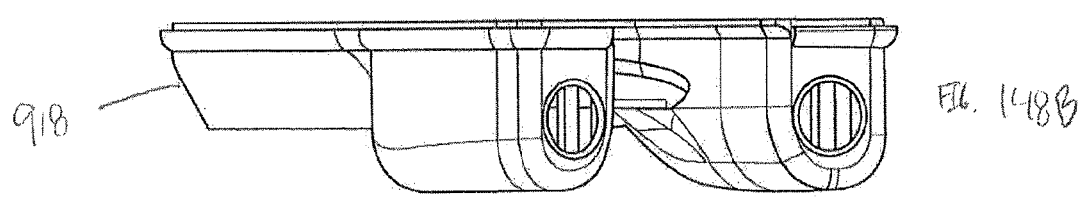

FIG. 147A-147 illustrate a lid assembly 903 and a housing assembly 906 prior to engagement and after engagement to form the OTT module 900. FIGS. 148A and 148B illustrate top and side views of a housing 918. FIG. 148C illustrates a side view of a lid assembly 903. FIG. 148D shows the OTT module 900 after engaging the lid assembly 903 and housing assembly 906 together. FIG. 149A illustrates a Y-board assembly prior to engage with a housing 918. FIG. 149B illustrates the housing assembly 906, which is a combination of the Y-board assembly and housing 918. FIG. 149C illustrates a lid assembly 903 engaging with a housing assembly 906.

In an alternative aspect, the sealing surfaces and resulting seam formed between a lid assembly and a housing assembly is curved or sloped. A curved or sloped configuration is illustrated, for example, in FIGS. 83A-83D, 85A-85D, 86A-86E, and 87A-87F. Irrespective of the type of configuration the lid assembly and housing assembly are attached to form a suitable enclosure for the various components within each assembly.

A wide variety of attachment techniques may be employed to attach a lid assembly to a housing assembly. A wide variety of attachment locations may be provided in one or both assemblies.

A number of different attachment locations may be used for positioning the selected interlocking contacts for a particular lid assembly-housing assembly pair.

Figure 177A:
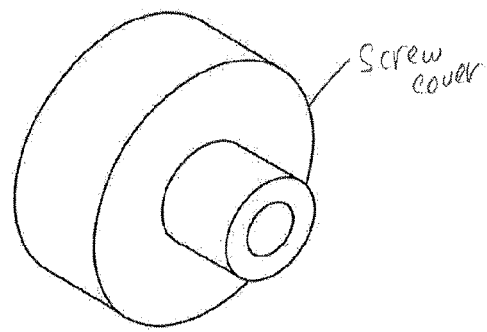
Figure 177B:
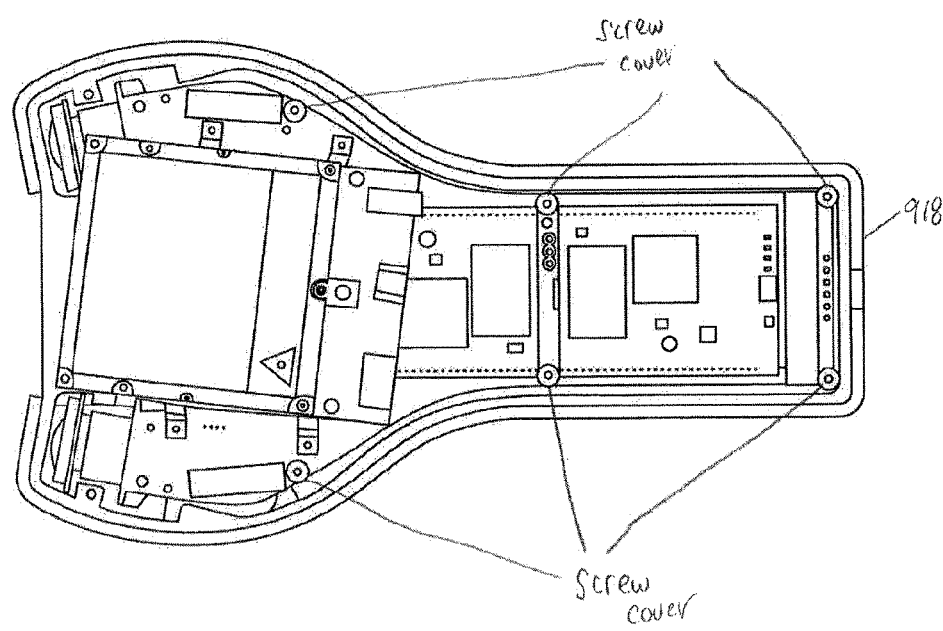

FIG. 177B-C illustrate a top down view of a housing assembly with installed Y-board. Six attachment locations are indicated—two just distal to the cameras (only one of these shown in the view in FIG. 177C), two in the mid portion of the housing and two at the rear corners. More or fewer may be used as well as in different locations. In one specific embodiment, a screw used secure the Y-board to the housing is in the form of a snap stud at the indicated locations. The lid assembly accommodates the corresponding snap socket positioned to mate when the lid assembly is brought into contact with the housing assembly.

FIGS. 150A-150B illustrate general regions for the placement of interlocking connectors described herein. In this embodiment, FIG. 150A is a view of the mating surface of the housing assembly with attachment regions adjacent the cameras and an additional attachment region at the rear. In this embodiment, the attached regions are positioned on the Y-board. FIG. 150B illustrates a top down view of the mating surface of the lid assembly. The attachment regions in the lid assembly correspond to those in the housing assembly of FIG. 150A.

FIGS. 150C-D illustrate more specific attachment regions than those in FIGS. 150A-B. FIG. 150C-D is a top down view of the mating surface of a housing assembly. Two pairs of attachment regions are indicated adjacent to the cameras and projector and another pair is indicated in the rear. The indicated attachment regions are shown for the use of a portion of the housing assembly outside of the Y-board. This design is in contrast to the use of a portion of the Y-board for attachment in the illustrative embodiment of FIGS. 150A-B.

FIGS. 151A-D illustrate an embodiment where specific platforms are included within the housing assembly and the lid assembly for use as attachment regions. FIG. 151B illustrates three attachment region locations—two adjacent the cameras and projector and a transverse region at the rear of the housing. FIGS. 151C-D illustrate top isometric views of lid assemblies with corresponding platforms located in a lid assembly.

FIGS. 150E-F illustrate the use of the rim or edge region and a complementary structure of the assembly as yet another location interlocking connectors.

FIGS. 151E-G illustrate one exemplary release slot to facilitate separation of the lid assembly from the housing assembly. FIG. 151E illustrates a top isometric view of a rear portion of the housing assembly. A slot is indicated adjacent to the rim. FIG. 151F is a rear view of a corresponding slot formed in the lid assembly. FIG. 151G illustrates the assembled lid and housing assembly and the resulting slot formed between the assemblies. To separate the lid assembly from the housing assembly, a suitable tool is inserted into the slot and twisted to begin the process of disengaging the one or more interlocking contacts used to releasably secure the lid assembly to the housing assembly.

In one embodiment, the assembly is separated by inserting a tool into the slot then rotation of the tool begins to separate the assemblies. In one specific embodiment, a pair of reverse action forceps with tips shaped for a corresponding slot shape are used to initiate separation of a housing-lid assembly. While only one slot is illustrated, it is to be appreciated that more than one slot may be provided. The slot location is indicated in the rear adjacent a rear position attachment region as described elsewhere herein. Alternative embodiments may have more than one slot positioned in other locations depending upon the number and type of interlocking contacts and regions employed in a specific embodiment. In one aspect, the slot is a split oval recess.

In still other embodiments, the junction between the lid assembly and the housing assembly includes a raised rim and corresponding recess that may be used for a sealing or gasket material. In still other aspects, this feature may be used as still another attachment region for placement of the interlocking connectors. A recess in the lid assembly can engage with a corresponding rim in the housing assembly. The edge sized for engagement with the corresponding rim can be around a full perimeter of the housing or around a partial perimeter of the lid. In a specific embodiment, a gasket is positioned also by this edge in furtherance of the sealing and/or vibration absorption or attenuation techniques as described elsewhere herein.

In one aspect, interlocking contacts are provided in one or more suitable locations in each housing to join the assemblies together. It is to be appreciated that the two part interlocking contacts may be variously employed such that one part is borne by the lid assembly and the other by the housing assembly such as a male connector on the lid assembly and socket or female connectors on the housing assembly or vice versa. One example of an interlocking contact is a screw passing through one assembly and into an appropriate receiver (i.e., a threaded socket in the case of simple machine screws or an area of engagement in the case of the soft tapping screws). Other exemplary interlocking contacts include snap fit connections. Any attachment technique may be further modified to include the use of magnets. Single point discrete connections and multiple point connections or connector arrays. Examples of each type will be described in turn.

Figure 152A:
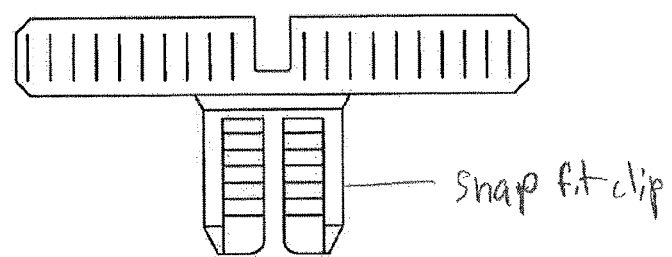
FIGS. 152A-152B and 153A-153B illustrate various snap fit assemblies in accordance with some embodiments.

In one aspect, a snap fit connector refers to one or more mating joints, typically male-female or snap stud-snap socket. When brought into contact, FIG. 152A illustrate an embodiment of a snap fit clip where the snap stud includes a finned or segmented prong and a corresponding socket (See FIG. 152B).

Figure 152B:
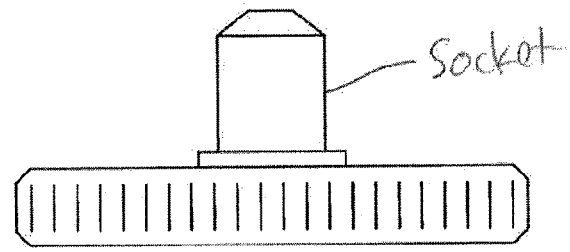

In another aspect, a snap fit connector embodiment includes a shaped clip snap stud as illustrated in FIG. 152B. A corresponding snap socket would be provided in the corresponding assembly in an appropriate location.

Figure 153A:
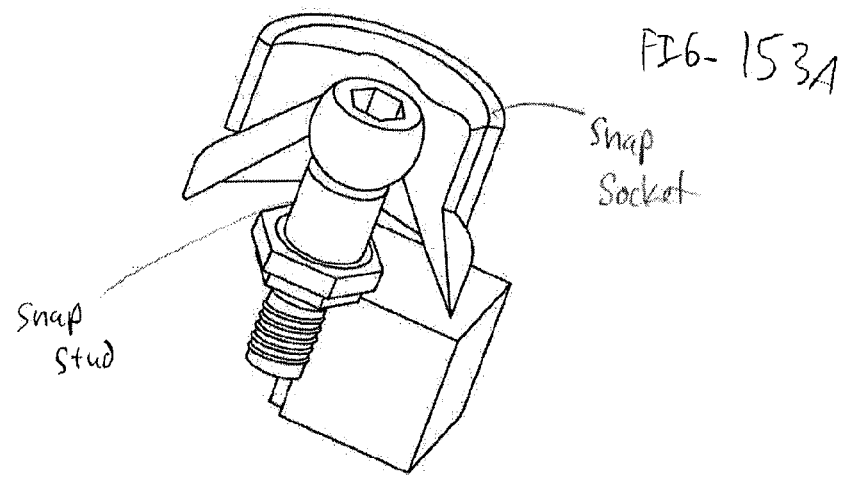

In another embodiment, a snap fit connector pair is illustrated in FIG. 153A. In this embodiment the snap stud has a rounded or bulbous tip. The snap socket has a shape that corresponds to the snap stud to provide a snap fit when engaged.

Figure 153B:
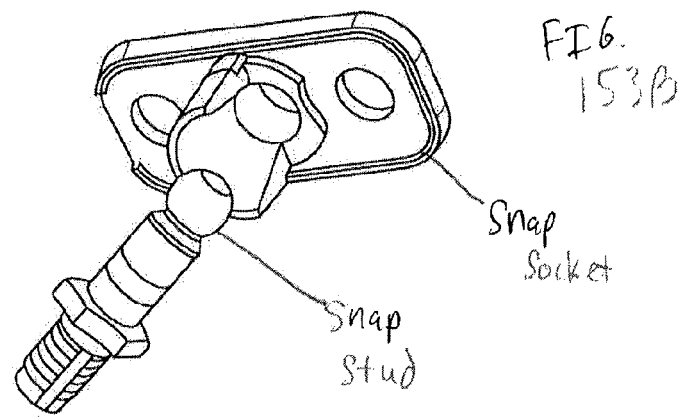

In another embodiment, a snap fit connector includes a ball and socket arrangement as illustrated in FIG. 153B. In this type of snap fit arrangement, the snap stud includes a thread position for attachment to an assembly and a rounded tip at the end of a shaft. The snap socket includes a shaped receiver and socket sized for cooperation with the tip and shaft. In one aspect, the materials or design of the ball and socket snap fit are selected to provide vibration isolation or to act as shock joints in addition to joining together lid-housing assemblies. In one aspect, the snap socket is a blind rivet joint. In a still further aspect, a snap socket includes a characteristic of vibration and noise-decoupling functionality. In still further aspects in contrast to the discrete connectors about some embodiments join assemblies using multiple array interlocking contacts.

In one embodiment, a multiple array of interlocking contacts refers to the use of interlocking hook and loop elements. FIG. 154 illustrates a plurality of interlocking contacts as part of a lid assembly. In one aspect, a hook array is attached to the lid assembly and a loop array is attached to the housing assembly, or vice versa. In still another embodiment, the multiple array of interlocking contacts refers to the use of mushroom cap or stem features used to form interlocking stems. Multiple array interlocking contacts are widely available commercially under the trade name "Velcro", "3M Dual Lock" recloseable fasteners, or Velcro brand extreme strength fasteners.

In still another further embodiment, an interlocking connector refers to a snap fit joint provided around a portion of the perimeter or the full perimeter of the lid assembly housing assembly joint.

Figure 155A:
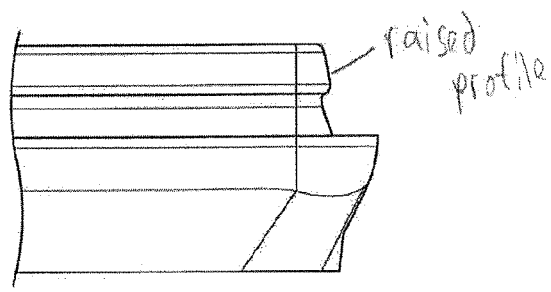
Figure 155B:
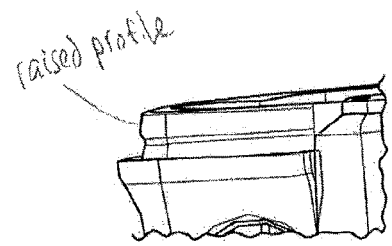
Figures 155C, 155D:
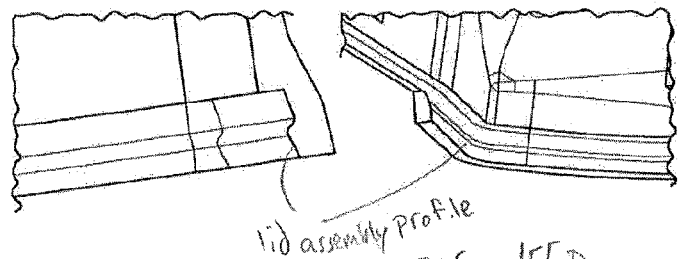

FIG. 155A illustrates a side view of an embodiment of a housing assembly having a raised profile shaped for snap fit engagement with a corresponding profile in a matching lid assembly. In this illustrative embodiment, the raised profile is provided around the entire housing assembly perimeter. One exemplary raised profile is shown in the enlarged partial views of FIGS. 155A-155B show the side and isometric views respectively. The corresponding lid assembly profile is appreciated with reference to FIGS. 155C-D.

The corresponding nature of the snap fit profile is appreciated through reference to FIGS. 156A-156D. These figures are partial cross section views of a corresponding housing-lid assembly with a snap fit closure. FIGS. 156A-156B illustrate the lid above but not engaged to the housing. FIGS. 156C-156D illustrate the lid-housing engaged using the snap fit profile. Also shown in these figures is a gasket, vibration mount, or dampener. The dampener is formed from a suitable absorber material and positioned to absorb or attenuate vibration from operation of the surgical tool attached to an OTT (shown elsewhere in the figure) from adversely impacting operation of OTT electronics or components. In addition, such vibration dampener or shock absorber may be useful in providing a more stable platform for the projector operation. These and other details of vibration absorption or attenuation are described further herein.

Figure 157A:
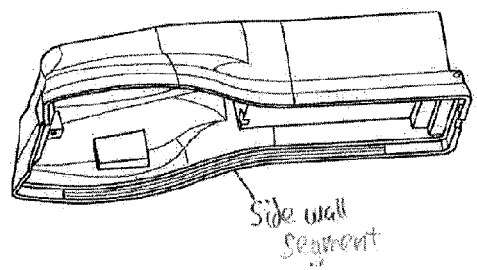

FIGS. 157A-E illustrate various view of a partial perimeter snap fit profiles in a lid assembly. FIG. 157A is a bottom up isometric view of a lid assembly having a number of snap fit profiles in discrete or continuous arrangement around the sealing perimeter. A number of snap fit profile segments are shown along the side.

Figure 157B:
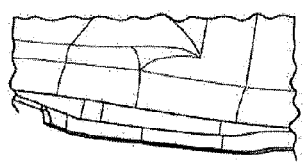
Figure 157C:
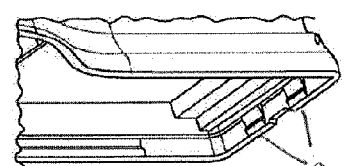
Figure 157D:
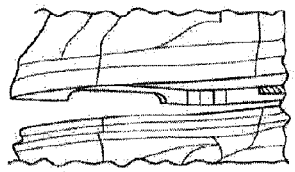
Figure 157E:
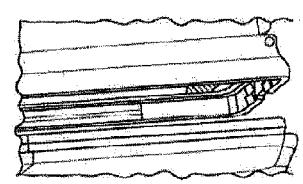

Two additional snap fit profile segments are seen in the rear wall of the housing. FIG. 157B is an enlarged view of the front of FIG. 157A. In this view, a snap fit profile section is shown on the front wall. In addition, another view of the side wall segments are also visible. FIG. 157C is an enlarged view of FIG. 157A showing the two snap fit profile segments on the rear wall as well as another view of a sidewall segment. FIGS. 95A-95B is an exterior side view of the housing assembly showing the location of the sidewall profile segments. FIGS. 157D-E illustrates the partial snap fit segments shown in view of FIGS. 157B-C in position for snap fit engagement with a corresponding profile on a housing assembly. In the illustrative embodiments of FIGS. 157D-E the corresponding profile on the housing assembly is a full perimeter profile. In one aspect, the spaces between the profiled segments in the lid are adapted and configured to act as an indirect vent for the assembled lid-housing OTT module. In another aspect, instead of a full perimeter profile segment, the housing may have corresponding profile segments that correspond to the those in the lid assembly (i.e., as in FIGS. 157A-C).

FIGS. 158A-158B illustrate another embodiment of a snap fit profile for the lid assembly 903 and housing assembly 906. FIGS. 158A-B illustrate gaskets on the lid assembly 903 and the housing assembly 906 in contact when the housing and lid snap together.

It is to be appreciated that these additional aspects of saddle and OTT housing engagement may be applied to any of the saddle and OTT embodiments described herein.

OTT User Interface Details

The user interface for the system optionally includes a display device (e.g., an iPad) dedicated to user interface, a large screen located some distance from the operating table with a remote pointing and selection device and using one of the surgical tools with OTT for this interface.

In one aspect, the user interface provides graphical image manipulation and pointing for a variety of purposes including image orientation and view display, alignment settings and adjustments, implants, etc.

In one aspect, the user-system interface is positioned on the back of the tool being used in an OTT CAS system.

In an additional aspect, the user holds an OTT enabled tool in one hand and interfacing and image manipulation is done with the other hand.

In still another aspect, there is a stand designed and provided to hold the tool during access to the user interface.

Figure 159A:
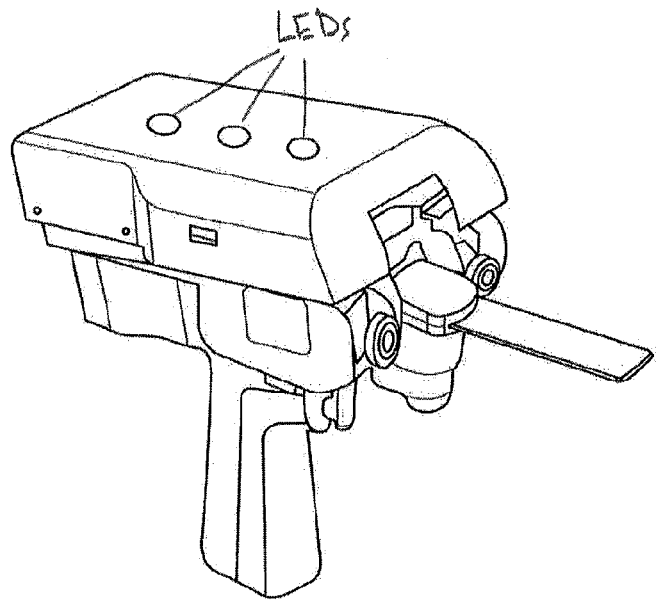
FIGS. 159A-159B illustrate various embodiments of user interfaces for the OTT module.

In one aspect, there are simple LEDs for state indication and a few switches for user input as illustrated in FIG. 159A.

Figure 159B:
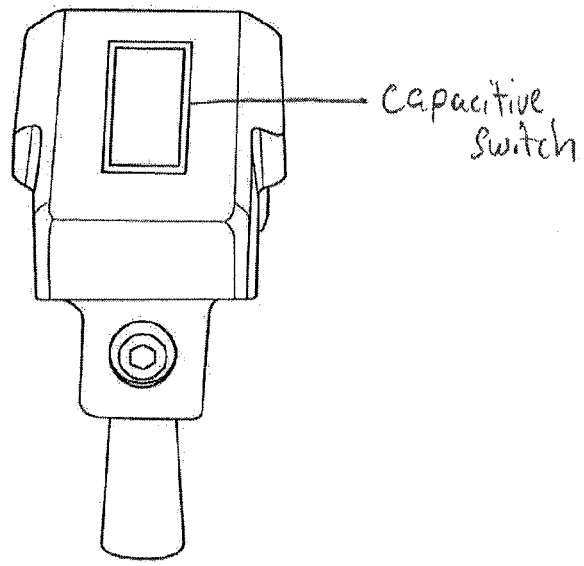

In another aspect, there is one or more membrane or capacitive switches (flexible, thin about 1 mm), e.g., a Molex for user input as illustrated in FIG. 159B.

The OTT system has two main output channels. One output is from the tool borne projector displaying images on the patient's body mainly to indicate location of cut and directions to the user to adjust the pitch, yaw and tilt of the surgical tool during the cut. In addition, warnings can be displayed visually in the form of arrows, warning colors or green screens for example to indicate various states of the procedure. Another output can be a large monitor as close as possible to the surgeon's line of sight to display various views to assist the surgeon with the procedure. However, other indicators may be needed during the operation for example to indicate the state of charge of the tool, state of communication links, etc.

In addition, input buttons may also be needed to allow for user selections and commands. Perhaps the best location for these interfaces would be on the upper face of the OTT module or a location easily seen by the user during most of an OTT CAS procedure.

One interface may include a small display for more complex communication with the user. Another alternative is a touch screen to combine information output and input.

In one aspect the OTT circuit module for speed control and other functions may incorporate these functions within that module.

In a still further aspect, one or more indicators/switches on the lid can be part of a single pcb (attached to the housing lid for example) that is connected to the main Y-board via a suitable electrical connector.

In one aspect, the lid is provided with one or more visual indicators or switches to provide status indicators and facilitate user input.

In still another aspect, a touch screen is placed on the back of the tool housing. This would yield a much higher flexibility for the interface with the possibility of adding programmability and simpler modifiability.

A touchscreen has the advantage of one device for both user input to the OTT CAS system and displaying OTT CAS system output information to the user.

In one embodiment, the OTT module is a device that is attached to or clipped onto a base that is securely attached to the surgical tool. The OTT module can be sterilized using conventional sterilization techniques such as with Ethylene oxide (ETo). Thereafter, a sterile OTT module attached to the surgical tool enabling use in an OTT CAS enabled surgical operation.

In one aspect, the user interface system is on the lid using dedicated electronics. Such a configuration would advantageously reduce the processing load on the housing assembly electronics (i.e., "Y-board") I/O system.

The associated electronics for the OTT system may all be on the Y-board or the housing circuitry depending on configurations. In one alternative, the speed control circuitry is provided by the Y-board or housing electronics package while the lid assembly contains the user input and associated electronics/circuitry.

In one alternative, the user interface is made part of the lid having electronics independent of the Y-board electronics. In one aspect, the Y-board lid electronics connection is provided when the lid assembly is engaged to the housing assembly.

The OTT CAS system provides several user interface configurations. The user interface may include one or more of, in any combination, visual indicators, LEDs, flexible, thin membrane or capacitive switches, a display and/or a touchscreen.

The electronics provided for the user interface are selected based on the type of user input selected. In one aspect, the user input circuitry includes capabilities to operate LEDs. In another aspect the user input circuitry includes capabilities to operate capacitive or membrane switches.

In still another aspect, the user interface electronics includes capabilities for a touch screen driver circuit, or a processor for operating the user interface.

In one aspect, the touch screen electronics includes a graphics processor unit adapted and configured for use with a touch color LCD and touch controller.

In still another aspect, there is a small touch screen with functionality provided by dedicated electronics, such as a driver circuit for the screen and/or a processor to drive the interface.

In one embodiment, the user interface is a touch screen accommodated in a recess in the lid shaped to accept a touch screen. An example of a touch screen accommodated in a recess in the lid assembly is illustrated in FIGS. 161 and 162A-162D. Optionally, a sealing gasket is added. FIG. 162A illustrates a recess in the lid assembly housing. The touch screen can be accommodated in the recess as shown in FIG. 16213. A sealant or gasket can be used between the touch screen and the lid body. As shown in FIG. 162C a pad can be added underneath the touch screen. The pad can be added to force the touch screen against the lid body to improve sealing as well decrease heat transfer from the projector to the touch screen. A touch screen plate can be secured to the lid body to further hold the touch screen in place as illustrated in FIG. 162D.

Figure 160A:
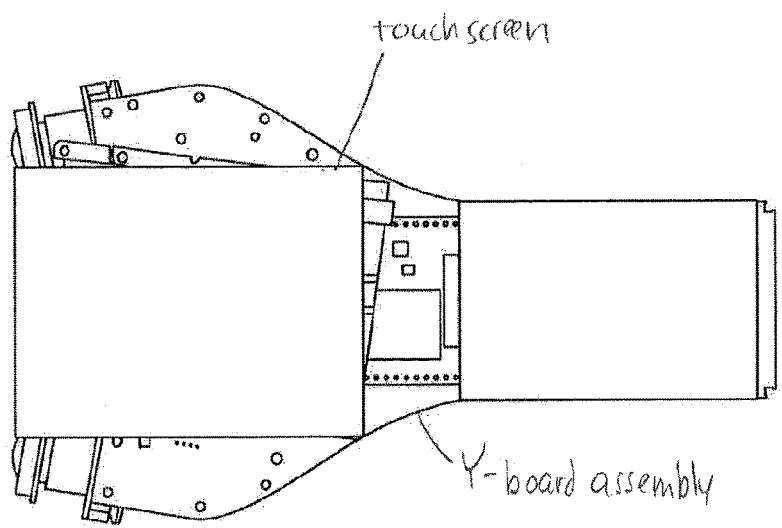
Figure 160B:
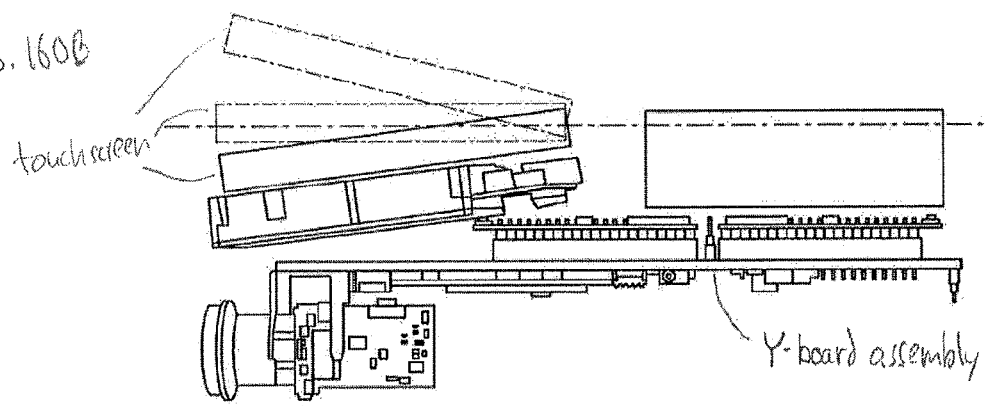
Figure 161:
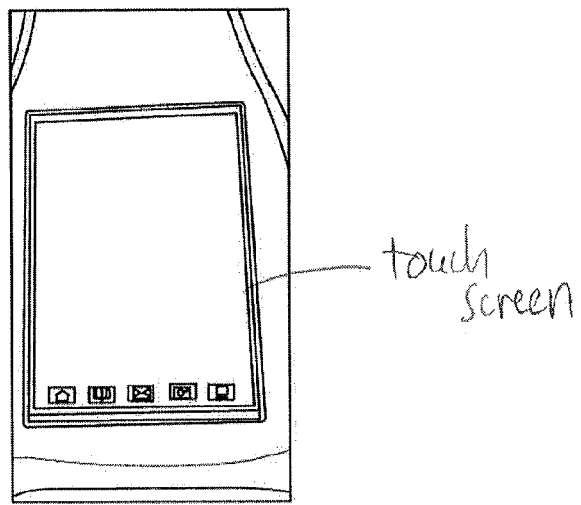

In some embodiments the touch screen can be tilted relative to the housing surface and/or Y-board as illustrated in FIG. 160B. FIG. 160A is a top view of the assembly having the touch screen illustrated in FIG. 160B. FIG. 160B illustrates the touch screen display with three different orientations relative to the Y-board/housing. The touch screen can be arranged parallel to the Y-board assembly as illustrated by dashed line. The touch screen can have a negative slope relative to the Y-board illustrated by touch screen. The touch screen can have a positive slope relative to the Y-board illustrated by touch screen.

OTT Module Vents

Figure 164A:
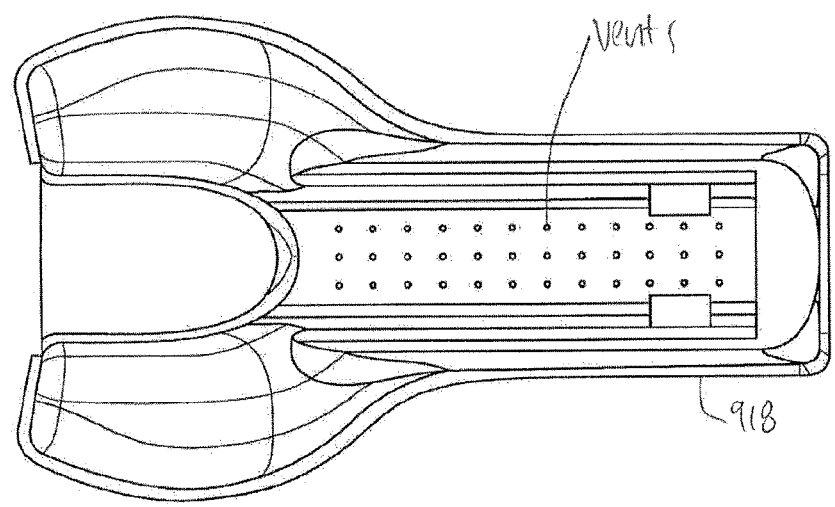
Figure 164B:
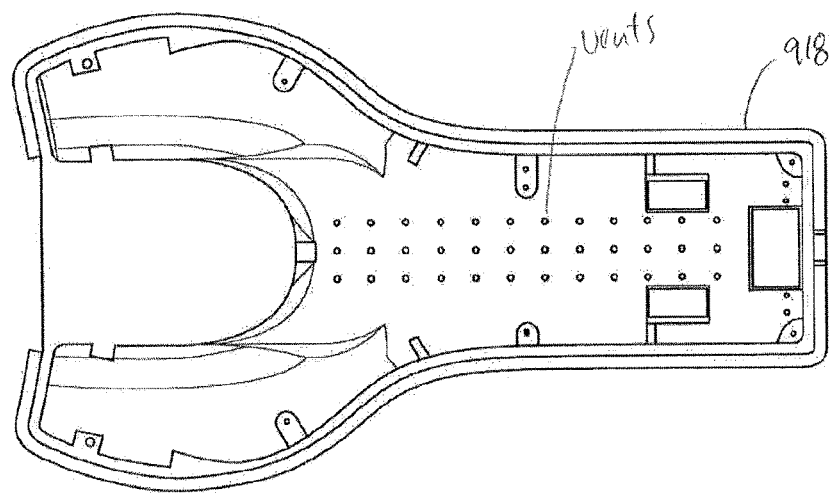

In some embodiments vents can be incorporated into the housing of the on tool tracking device. The vents can provide additional heat transfer to cool the components inside of the housing. The vents can also allow for ingress of ethylene oxide or other sterilization gas to sterilize the components inside the housing. In some embodiments the vents can be located on the housing surface for releasable engage with the saddle as illustrated in FIGS. 163 and 164A-B. The vents can provide some additional heat transfer to cool the components inside the housing during operation of the tool. Locating the vents on the underside of the on housing of the on tool tracking device can also shield the vents from contact with fluid during the surgical procedure. FIG. 163 illustrates vent positions as shaded areas on the underside of the housing 918 of the on tool tracking device 900. The saddle can also provide shielding to prevent fluid from entering the vents during the surgical procedure. FIG. 164A-B illustrates vents on the underside of the housing 918 on tool tracking device that are blocked or covered up when the saddle is engaged with the on tool tracking device.

After the surgical procedure the on tool tracking device can be removed from engagement with the saddle thereby exposing the vents. The on tool tracking device can be exposed to a sterilization gas during the sterilization procedure with the gas entering the internal volume of the housing through the plurality of vents.

OTT Module Sealing Tools

A sealing tool can be used with the on tool tracking device to protect the inside parts of the on tool tracking device and the exposed position locks and electrical connectors from the cleaning environment. The cleaning seal tool is configured to slide onto the housing in a manner similar to the saddle. The cleaning seal tool can be made from a soft plastic material, such as silicone, PTFE, butyl rubber, natural rubber, etc. The sealing tool can be configured with any of the complementary saddle structures disclosed herein.

Figure 165A:
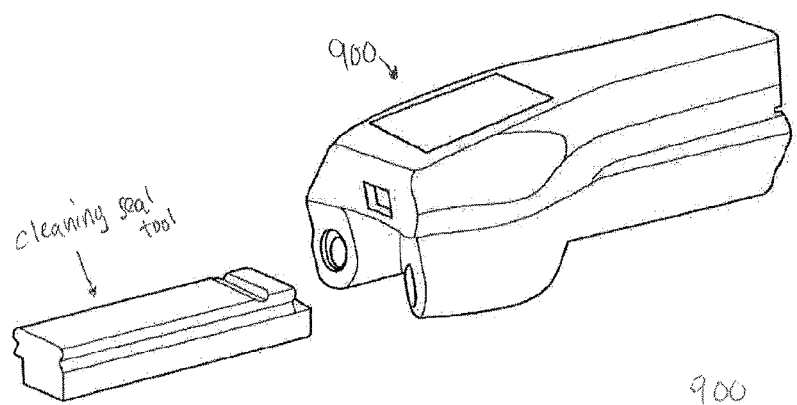
Figure 165B:
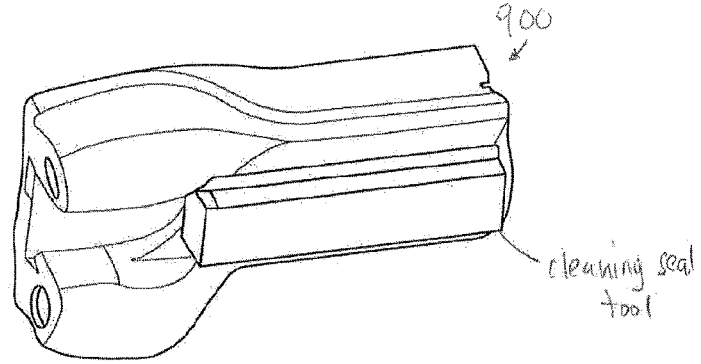
Figure 165C:
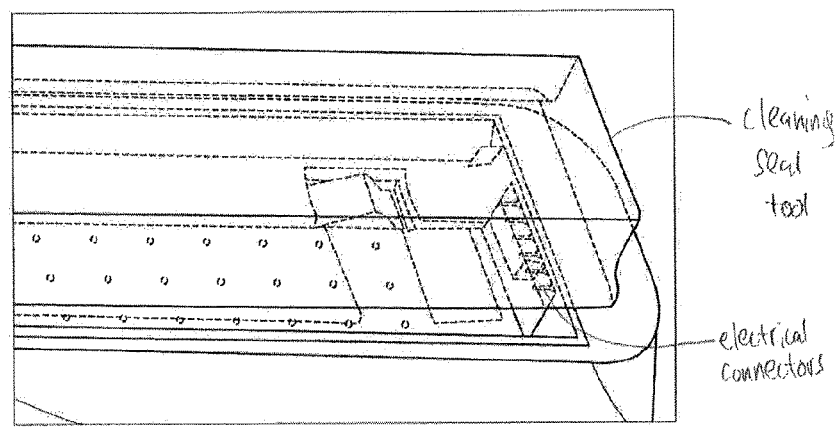
Figure 16A:
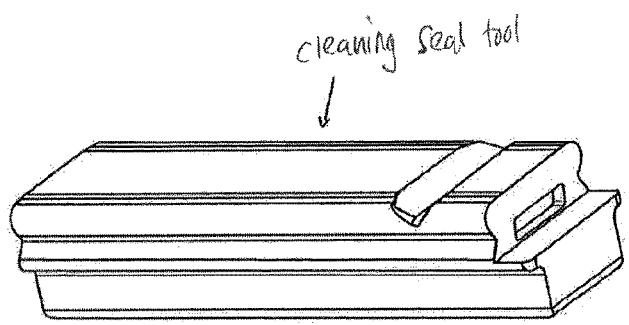
Figure 16B:
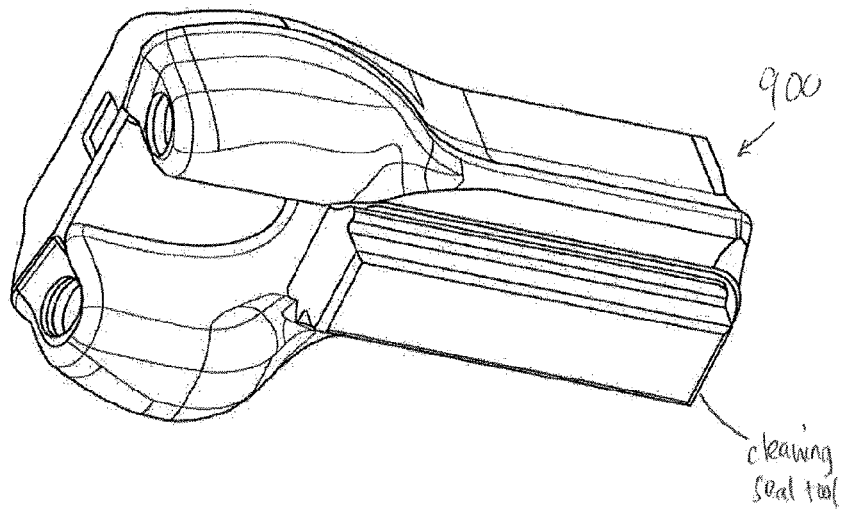

FIG. 165A illustrates an embodiment of a cleaning seal tool configured to engage with the housing of an on tool tracking device 900. FIG. 165B illustrates the cleaning seal tool engaged with the on tool tracking device 900. FIG. 165C illustrates the cleaning seal tool engagement with the electrical contacts of the on tool tracking device 900 to protect the electrical contacts from the external environment. FIGS. 166A-B illustrates another embodiment of a cleaning seal tool with a different configuration than the device illustrated in FIG. 165A along with the cleaning seal tool engaged with the on tool tracking device 900. The cleaning seal tool can be locked to the on tool tracking device as shown in FIG. 166B using any of the structures described herein with respect to securing the on tool tracking device to the saddle.

Figure 167A:
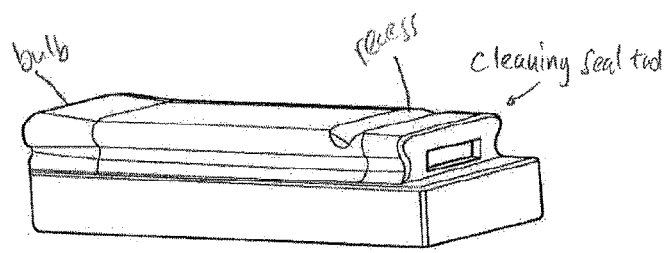
Figure 167B:
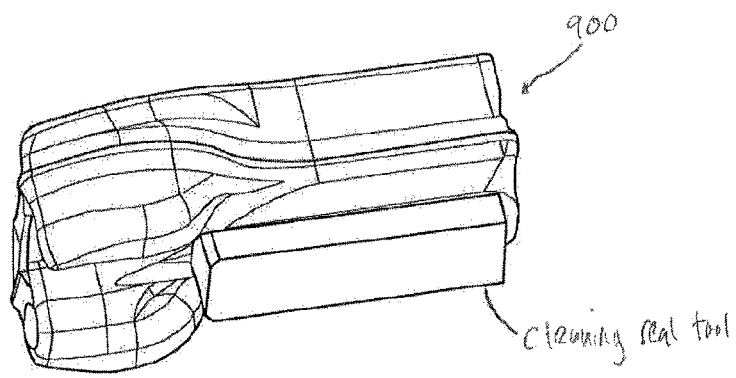
Figure 167C:
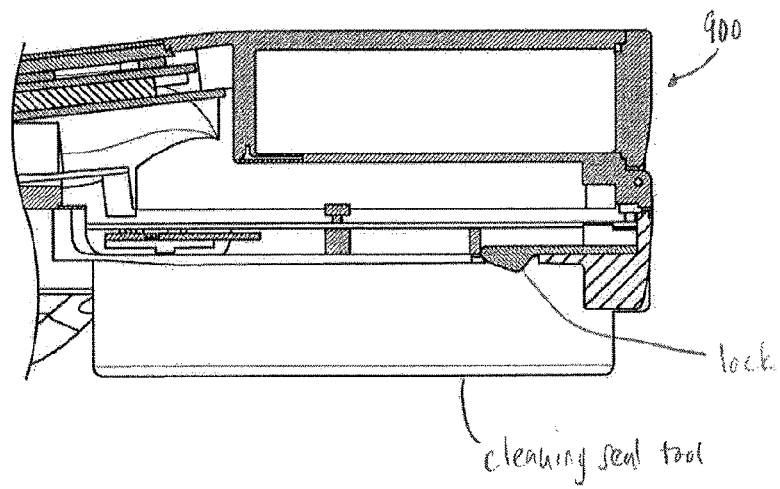

FIGS. 167A-167C illustrate an embodiment of a cleaning seal tool having a recess configured to engage with a lock on the housing. The cleaning seal tool has a bulb on one end and a recess on a back end as shown in FIG. 167A. The sealing tool slides on to the housing as shown in FIG. 167B. A lock on the housing clicks into the recess on the sealing tool as illustrated in FIG. 167C.

A sealing tool can have any of the analogous saddle structures illustrated in FIGS. 68b, 68c, 68g, 68h, 69a, 69b,

70c, 70e, 70f, 70g, 71c, 71d, 74d, 75A-G, 76A-76B, 77A-77D, 80A-E, 81A-81E, 82C, 88A-88B, 89A-B, 90A, 90D, 90E, 91A, 92A, 93A, 94A-C, 95A, 96A-C, 97B, 98B, 99A, 101A, 102A-C, 104A-B, 105C, 111B, 112A-D, 114A, 117B-D, 118B-118C, 122, 124, 125, 126, 128, 131, 132, 133A-B, 135, 136A-C, 137, and 147C.

OTT Module Liners

In some embodiments a liner can be used on an external surface of the housing. The liner can improve the engagement with the saddle surface. The lining can be made by an elastomeric material such as a compressible plastic or rubber. The lining can be incorporated along a portion of the surface of the housing that is complementary to the saddle design. The lining can increase the engagement between the housing and the saddle, dampen vibration along with simplify the housing and saddle designs. Examples of elastomeric materials that can be used include rubber, butyl/rubber, PTFE, silicone, polyurethane foam, neoprene, and nitrile.

Figure 168A:
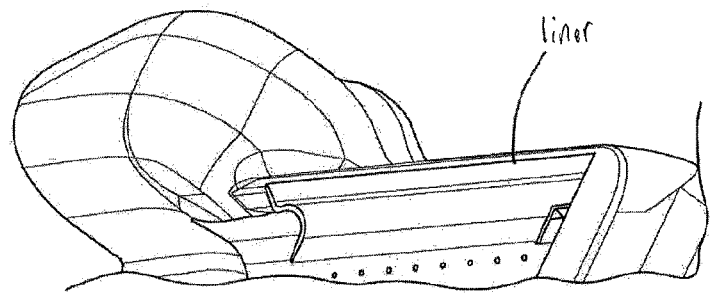
FIGS. 168A-173B illustrate various embodiments of lining materials.
Figure 168B:
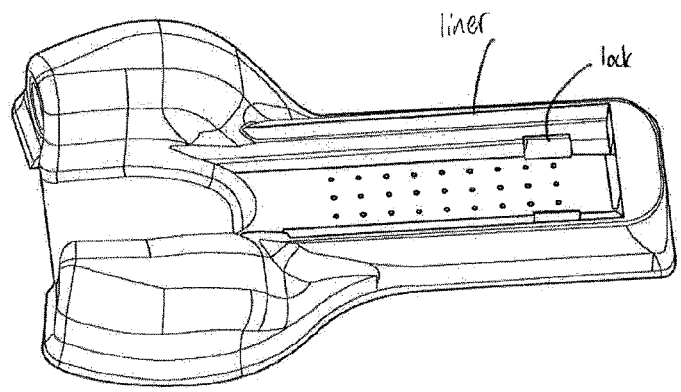
Figure 168C:
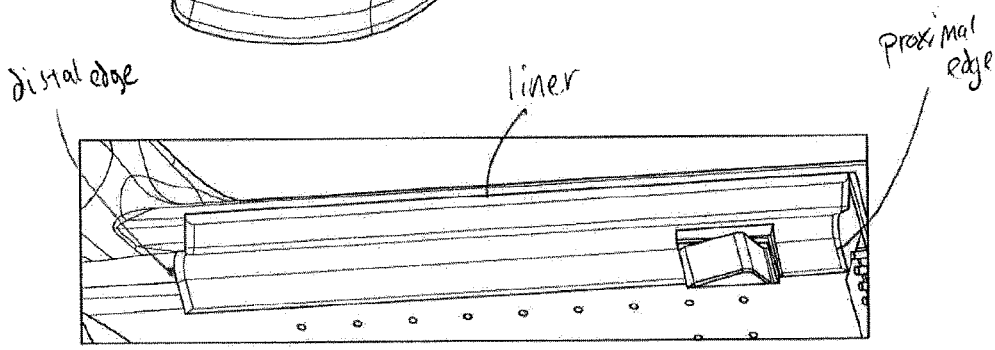
Figure 169A:
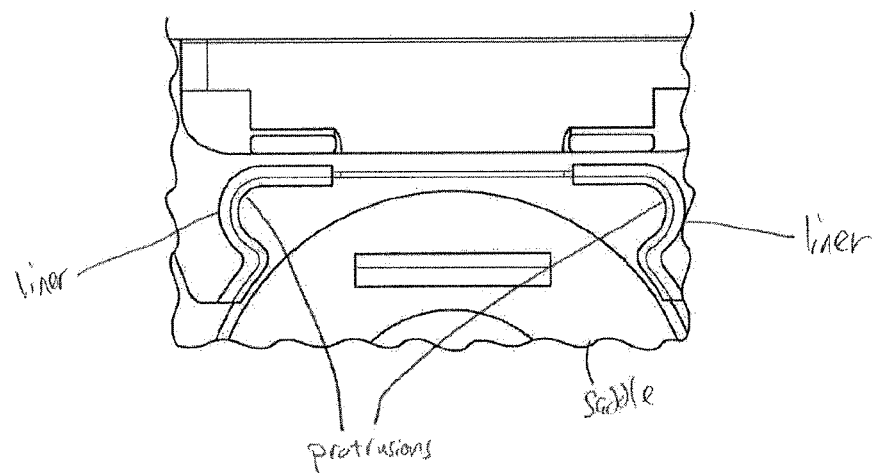
Figure 169B:
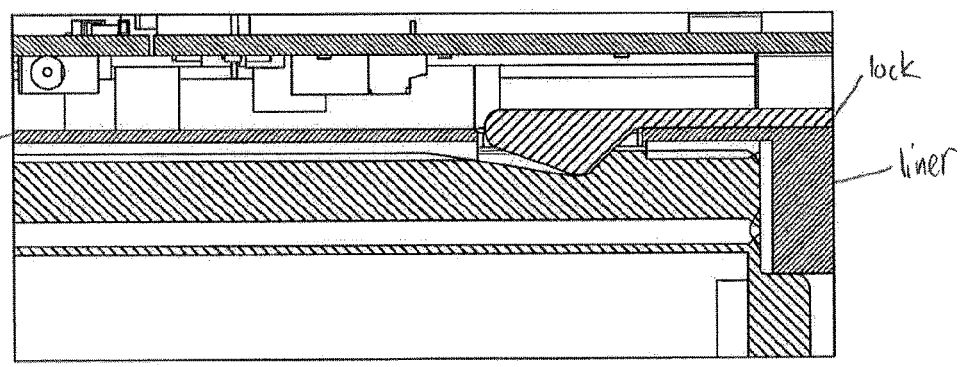

A variety of lining material configurations are illustrated in FIGS. 168A-173B. FIGS. 168A-C illustrate embodiments of a lining material within a recess formed in the housing surface configured for releasable engagement with the saddle. The use of the recess is optional. The lining material extends along the housing surface walls to improve engagement with the saddle guides. The lining material includes a cut out to accommodate a lock in the housing so it does not interfere with the locking engagement between the saddle and housing. The liner extends along the housing from a distal edge of the rail to a proximal edge of the rail with a cutout along the locking clip. FIGS. 169A-169B illustrate two different cross sectional views of the liner when the saddle is engaged with the housing. The liner engages with the protrusions on the saddle as shown in FIG. 169A. The liner is configured to accommodate the locking mechanisms, e.g. cantilever locks, as shown in the cross-sectional view of FIG. 169B.

Figure 170A:
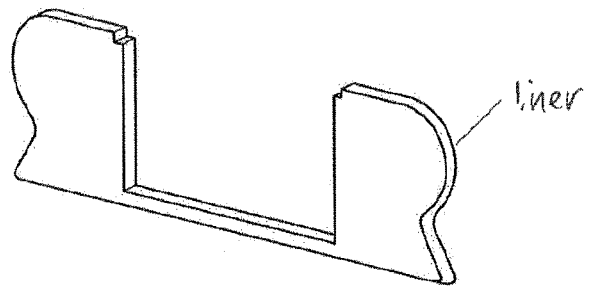
Figure 170B:
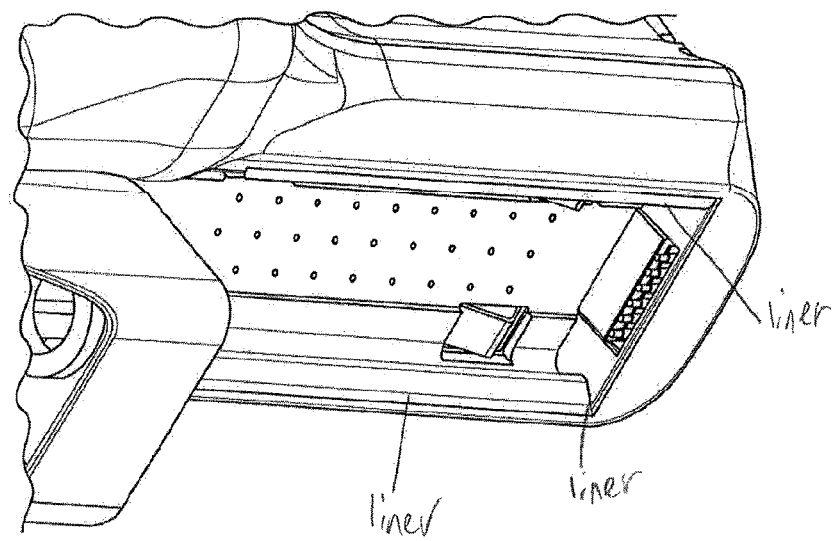

The liner can also include a portion in a proximal portion of the housing with an opening section to accommodate electrical connectors that engage with the surgical tool electrical contacts. FIG. 170A illustrates an embodiment of a section of the liner designed to accommodate the electrical connectors on the housing along. FIG. 170B illustrates the liner section attached to the housing.

Figure 171A:
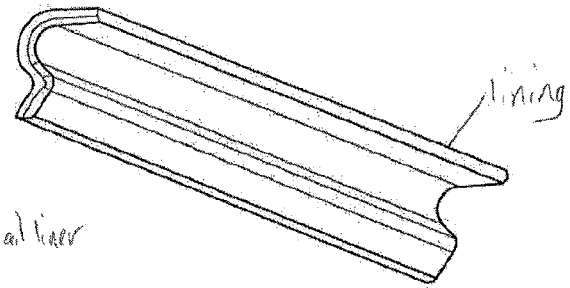
Figure 171B:
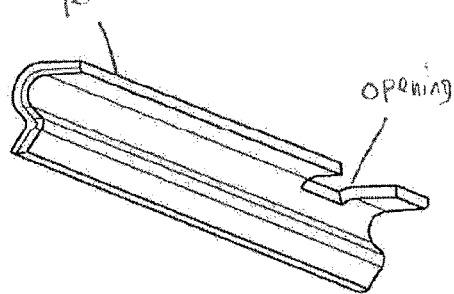
Figure 171C:
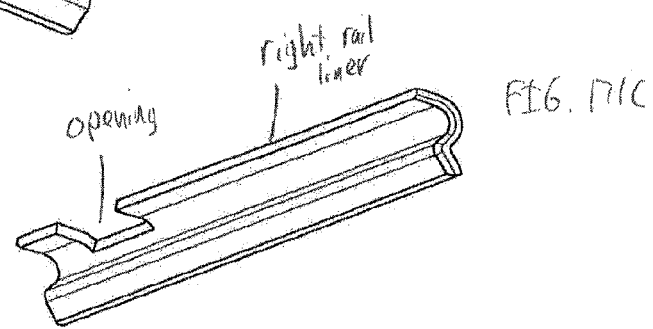
Figure 171D:
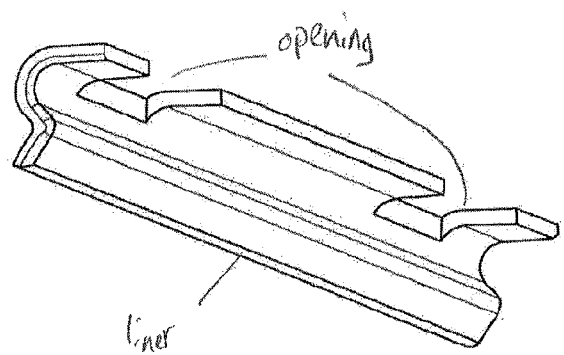
Figure 172A:
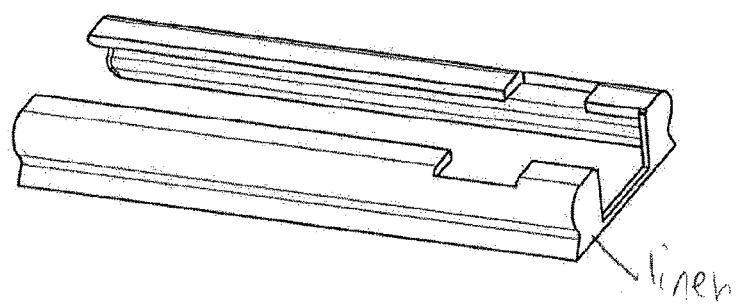
Figure 172B:
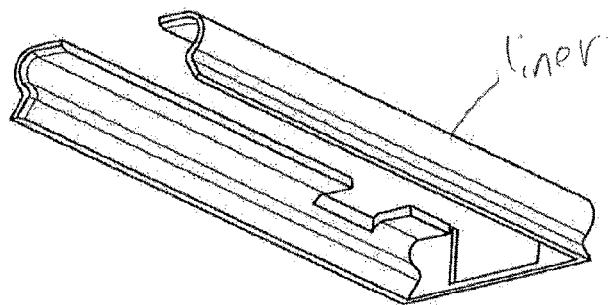
Figure 173A:
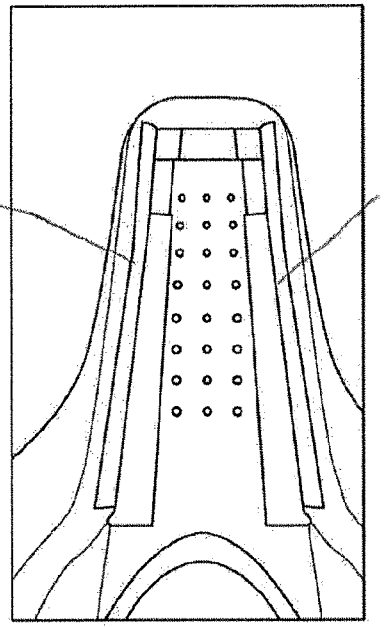
Figure 173B:
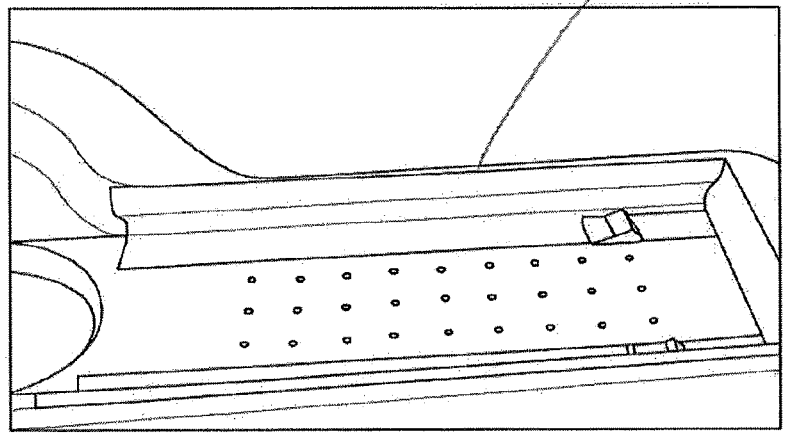

FIGS. 171A-171D illustrate various configurations for rail liners with and without openings for locking clips. FIG. 171A illustrates a lining without an opening for a lock. The opening for the cantilever lock can be made after the liner is added to the housing. FIGS. 171B-C illustrate a left and right rail, each with an opening to accommodate the lock. FIG. 171D illustrates a symmetrical rail liner with two lock openings such that can be used as either the left or right rail. FIGS. 172A-B illustrate a liner made out of a single component. FIGS. 173A-B illustrate another liner embodiment. The liners extend from a distal end of a rail towards a proximal end of the liner. The liner extends over the enter rail surface but has an interior portion that only extends from the proximal end of the rail to the locking tabs.

It is to be appreciated that these additional aspects of saddle/OTT housing engagement may be applied to any of the saddle and OTT embodiments described herein.

OTT Module Gaskets and Vibration Damping

The on-tool-tracking device can include a vibration damping material to reduce vibration between the surgical tool and the on-tool-tracking device. Elastomeric materials can be used for vibration damping. Examples of elastomeric materials that can be used include rubber, butyl/rubber, PTFE, silicone, polyurethane foam, neoprene, and nitrile. The specific material and configuration of the vibration damping material, such as the size, thickness, profile, and a discrete or continuous design, can be selected based on the desired vibration damping. Design considerations for the properties of the vibration damping material can include the elasticity and the compression of the material in use in the device. The vibration damping material or gasket can also be used in multiple discrete locations (e.g. FIGS. 177A-C) or can have a single piece construction (FIGS. 174B, 175A-C, and 176A-C). The vibration damping required can be based on design factors, such as the weight of the tool, tool speed, and natural frequency of vibration of the surgical tool.

Any of the gasket materials and configurations described herein can be used for vibration dampening (FIGS. 174-179).

The vibration damping material can be located in various locations on the inside and outside of the housing of the on-tool-tracking device. For example, any of the mating surfaces between separate parts of the devices described herein can include vibration damping pads, such as elastomeric pads. For example, vibration damping material can be provided between the mating surface of the lid assembly and the mating surface of the housing assembly, see for example the gaskets illustrated in FIG. 178A.

Figure 174A:
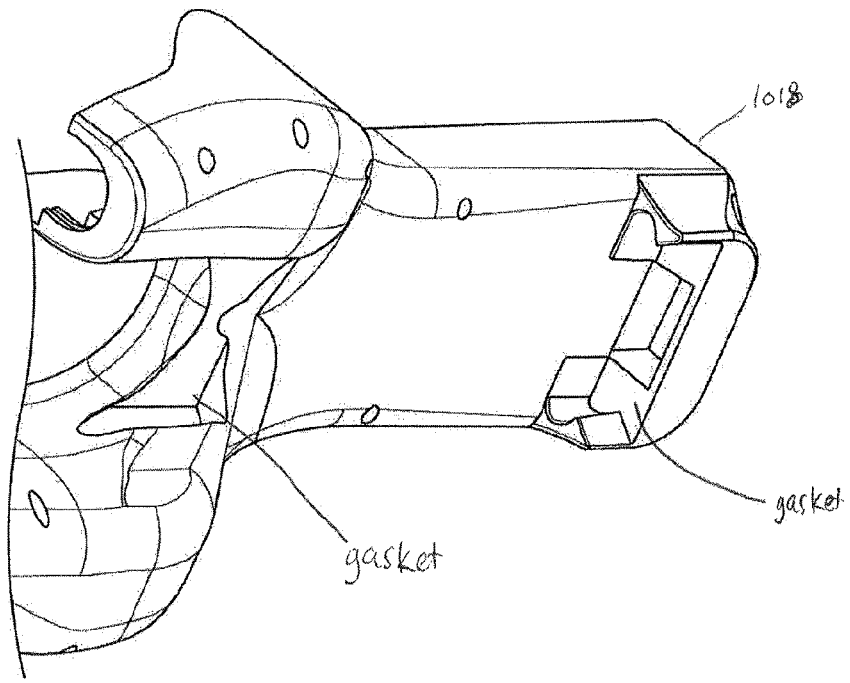
FIGS. 174A-179D illustrate various embodiments of gaskets that can be used for vibration damping.
Figure 174B:
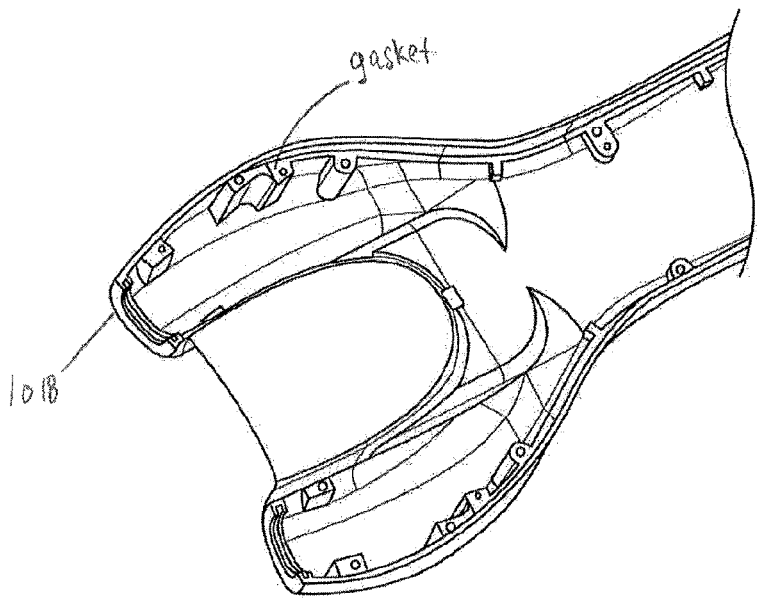
Figure 175A:
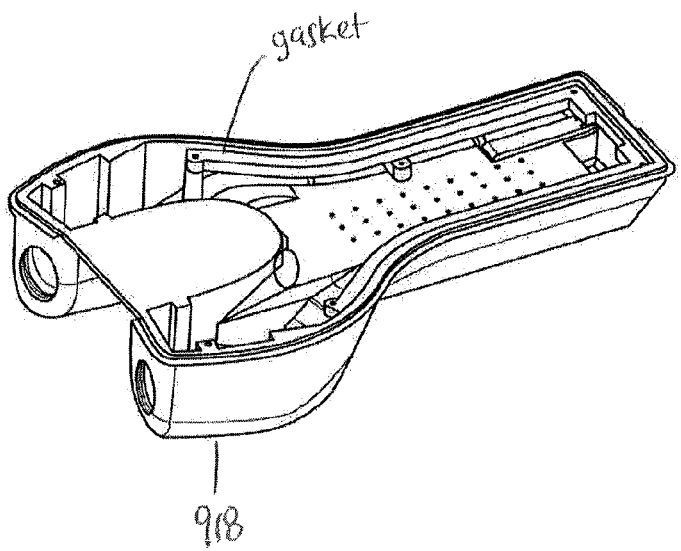
Figure 175B:
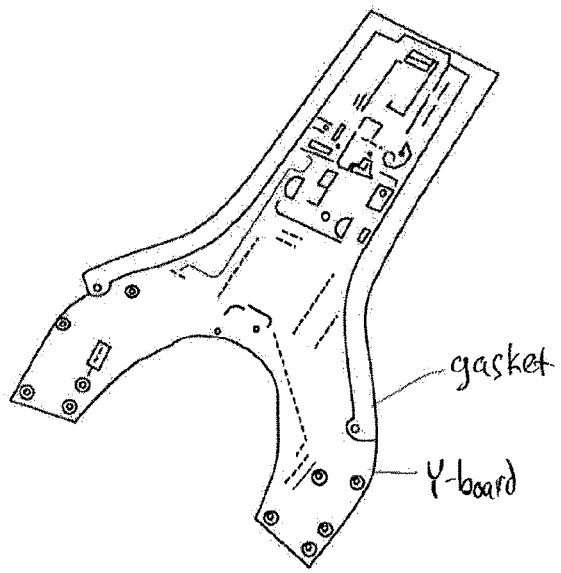
Figure 175C:
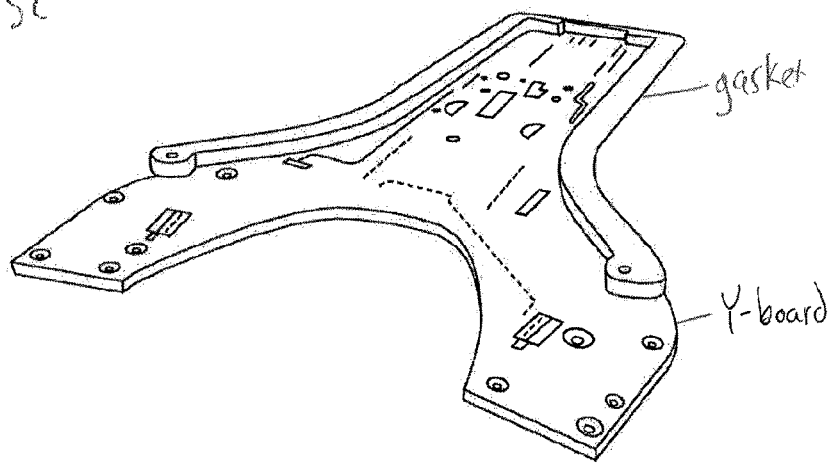
Figure 176A:
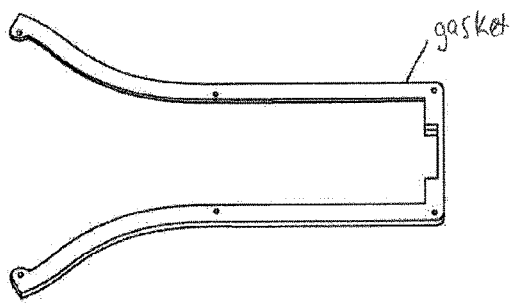
Figure 176B:
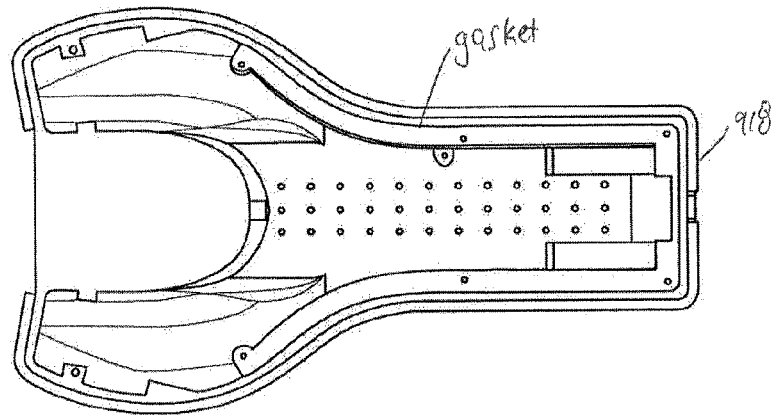
Figure 176C:
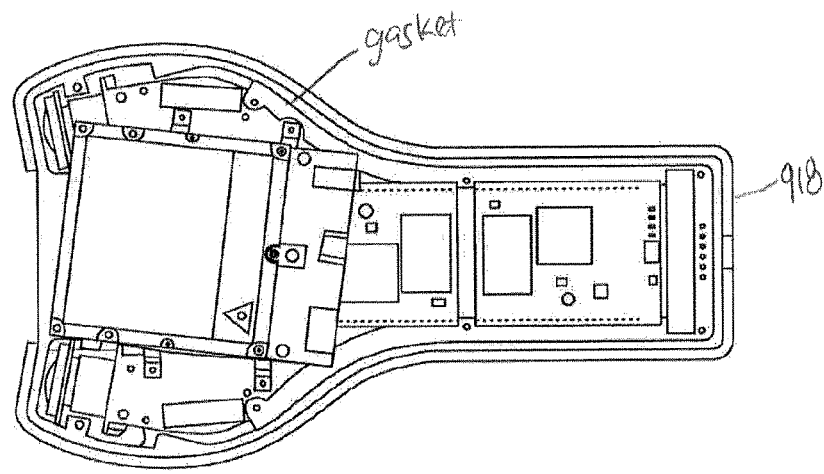

The vibration damping material can be provided between the inner housing and the support for the camera and projector, such as the Y-board assembly as shown in FIG. 174C. In this configuration the vibration material can provide vibration damping and isolation to the cameras, projectors, and any electronics supported on the Y-board assembly. A single gasket configuration can be used to isolate the Y-board assembly from the housing as illustrated in FIGS. 174B, 175A-C, and 176A-C. FIGS. 174B, 175A, and 176A-C illustrate a vibration damping material/gasket along an inside surface of the housing 918 and proximal end of the housing 918 configured to engage with the housing 918 and a bottom surface of the Y-board assembly. FIGS. 175B-C illustrate a vibration damping material along the inside surface of the housing and proximal end of the housing positioned on the Y-board assembly and configured to engage with an inner surface of the lid. The gasket/vibration damping material can also be provided between the Y-board assembly and the lid assembly as shown in FIG. 175B-C and/or between the Y-board assembly and the housing assembly as shown in FIG. 175A.

Figure 178A:
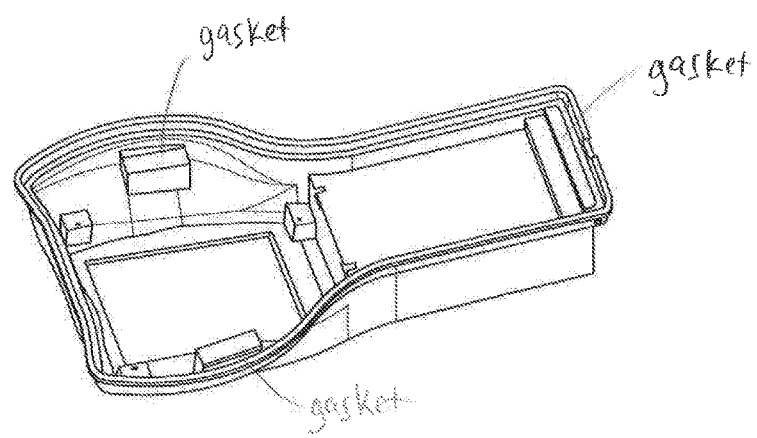
Figure 178B:
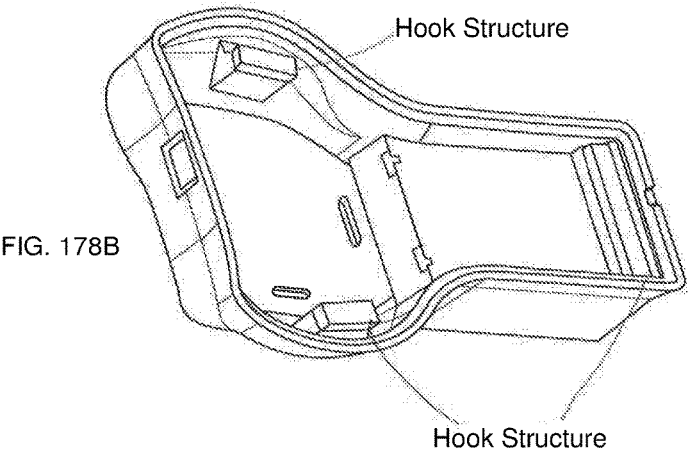

In some embodiments multiple discrete gaskets can be used as vibration damping materials as illustrated in FIGS. 177A-C, and 178A. In some embodiments an elastomeric material, such as neoprene can be used as a screw cover as illustrated in FIGS. 177A-C. The elastomeric screw covers shown in FIG. 177A provide vibration damping between the lid assembly and the Y-board and housing assembly. FIG. 178B illustrates discrete arrays of hook structures that can be used to engage with complementary structures on the housing.

Vibration damping material can also be provided around electrical contacts to reduce the possibility of vibration affecting the electrical contact between the electronic connectors and contacts. FIGS. 179A-D illustrate an embodiment of a gasket that provides vibration damping and isolation to the electrical contacts between the on-tool-tracking device housing and the surgical tool.

Vibration damping can also be provided between the saddle and the housing. FIG. 174A illustrates a gasket on the underside of the housing 1018 adjacent to the cameras and on a back end adjacent to the opening for the electrical connectors. A variety of liner configurations are illustrated in FIGS. 174C and 168A-173B and described herein. The liner can be attached to surface of the housing configured to engage with the saddle to improve the fit between the saddle and the housing and to also provide vibration damping. In some embodiments the liners can be attached to the housing instead of the surgical tool so as to not affect the sterilization process for the surgical tool.

The housing surface for releasable engagement can be designed with a small space between the saddle and housing to place a vibration damping liner as illustrated in FIGS. 96A-C and 169A-B.

OTT Module Battery Chamber

The on-tool-tracking device includes a battery with an outer shell shape configured to fit within the on-tool tracking device. The battery also includes connectors to couple to the connector type used within the on-tool-tracking device. The battery shape, size, and type can be selected based on the power, voltage, and current requirements for the elements in the on-tool-tracking device that use electrical energy. In some embodiments the battery is configured to power the on-tool-tracking device for about 1 hour or greater during a surgical procedure.

The on-tool-tracking device includes a battery chamber or compartment configured to receive the battery configured to power the on-tool-tracking device. The battery chamber can be within a part of the lid assembly of the housing (FIGS. 86D and 86E). Other locations and configurations are also possible for the battery chamber.

Figure 191A:
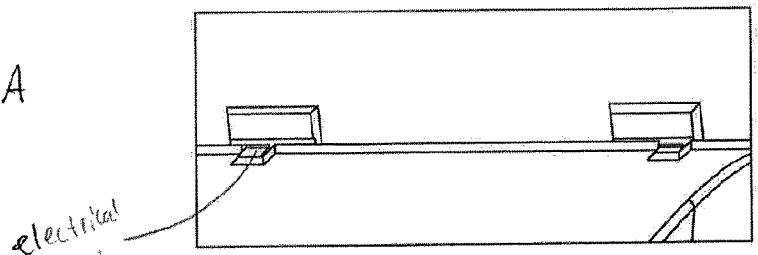
Figure 191B:
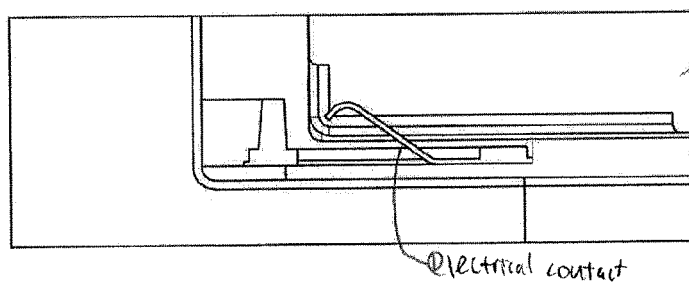
Figure 191C:
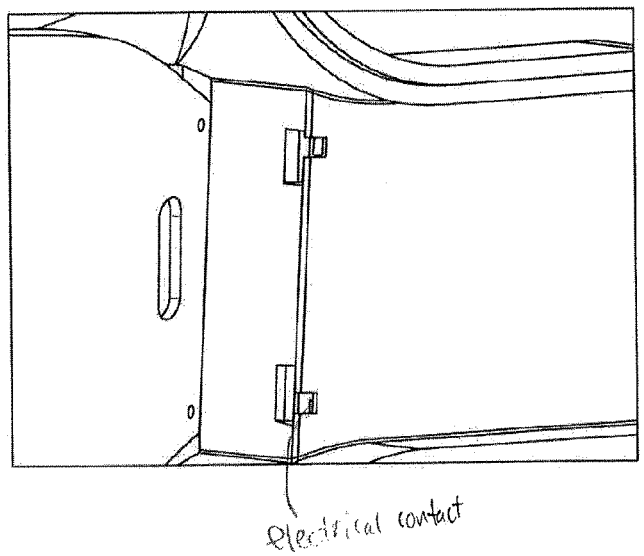

There are battery contacts within the lid of the on-tool-tracking device. An example of battery contacts within the on-tool-tracking device are illustrated in FIGS. 191A-C. Electrical contacts on the battery contact the battery contacts within the battery chamber. The battery contacts have an opposing side that can conduct the power to the device through the openings in the battery chamber.

The battery can enter the battery chamber through an opening in the housing. The battery slides into the battery chamber such that electrical contacts on the battery engage with and form an electrical connection with electrical contacts within the on-tool-tracking device as shown in FIGS. 86D-H. A battery door closes to seal the battery and battery chamber from the environment outside of the on-tool-tracking housing. A gasket can be used between the battery door and the battery chamber to seal the battery from the external environment, e.g. operating room environment.

A variety of different battery door configurations can be used with the on-tool-tracking devices disclosed herein as shown in FIGS. 180-191. The battery door opens to provide enough space for the battery to slide into the battery chamber as shown in FIGS. 86D-H. The battery door then closes to seal the battery within the battery chamber for the surgical procedure as shown in FIG. 86H. An attachment mechanism, latching mechanism, or similar structure is used to secure the battery door in the closed position to keep the battery separate from the operating room environment during the surgical procedure.

In some embodiments a sliding gate is used as the attachment mechanism for the battery door as shown in FIGS. 180A-C. The sliding gate extends to allow the battery door to open and close. The sliding gate slides down when the battery door is closed to engage with ridges in the exterior of the lid housing to lock the door in the closed position as shown in FIG. 180A. To open the locked door the sliding gate slides up to unlock the battery door as shown in FIGS. 180B-C.

Figure 182A:
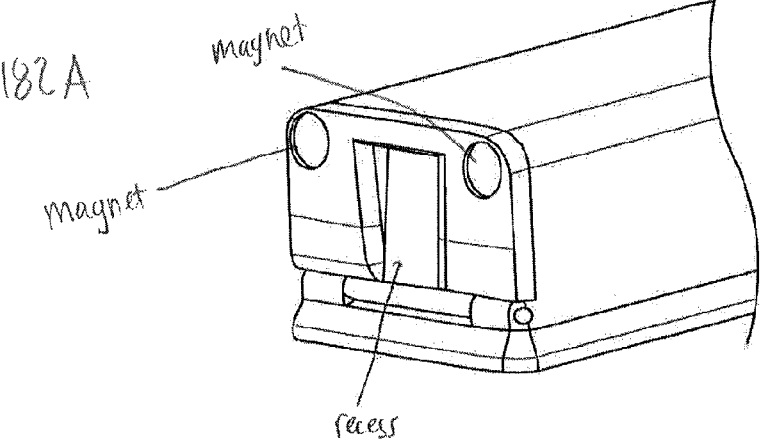
Figure 182B:
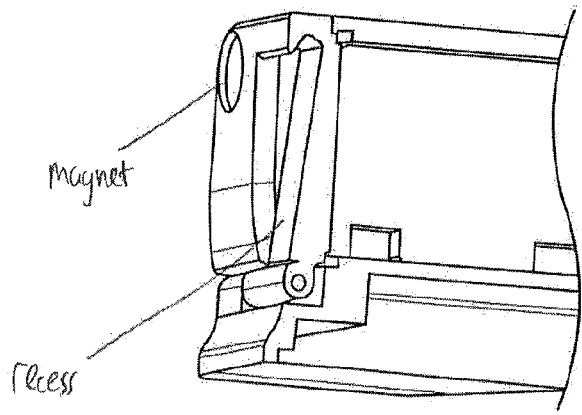
Figure 183A:
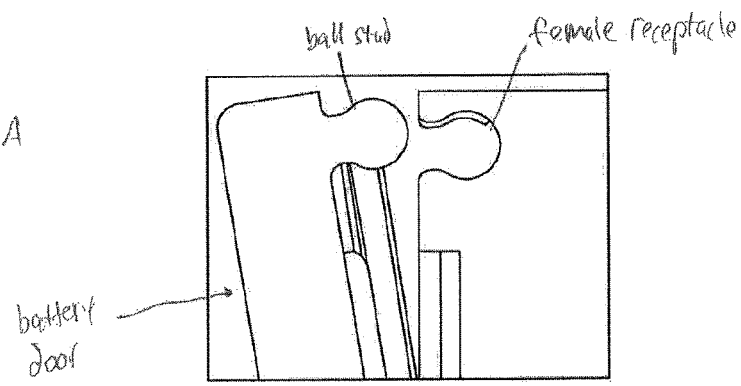
Figures 183C, 183D:
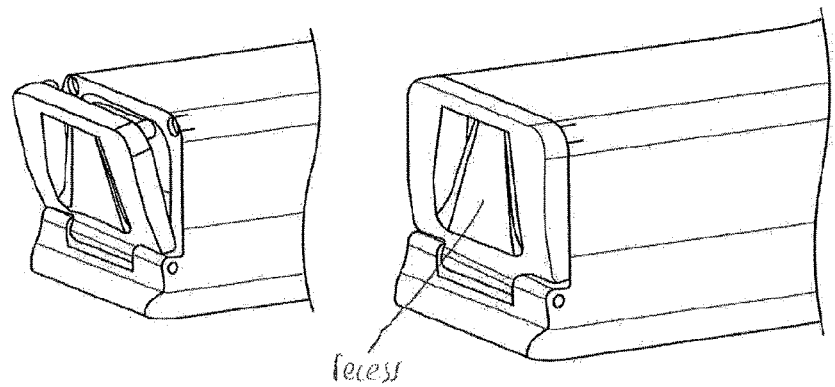
Figure 183B:
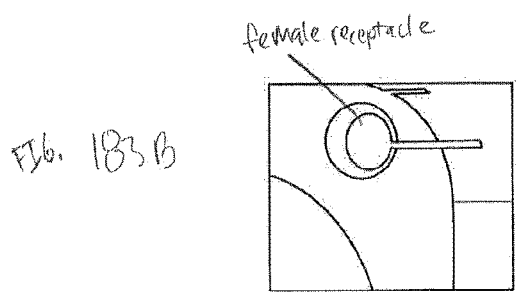

In some embodiments a magnet can be used in the battery door to secure the door in the closed position as illustrated in FIGS. 181A-B and 182A-B. FIGS. 181A-B and 182A-B illustrate two magnets in the battery door. The magnets are positioned within recesses in the battery door such that they magnetically engage with metallic elements within the housing, such as a metal screw. In one example neodymium magnets are used. In one example a nickel plated screw can be positioned in the housing adjacent to where the magnets are located in the battery door. The magnets can be covered in epoxy or outer sealing material. FIGS. 181A-B illustrates a protruding ridge in the battery door. The battery door can be opened by applying a force to the protruding ridge. FIGS. 182A-B illustrates a recess in the battery door configured such that a tool can be inserted into the ridge as a lever to force the door open.

Figure 184A:
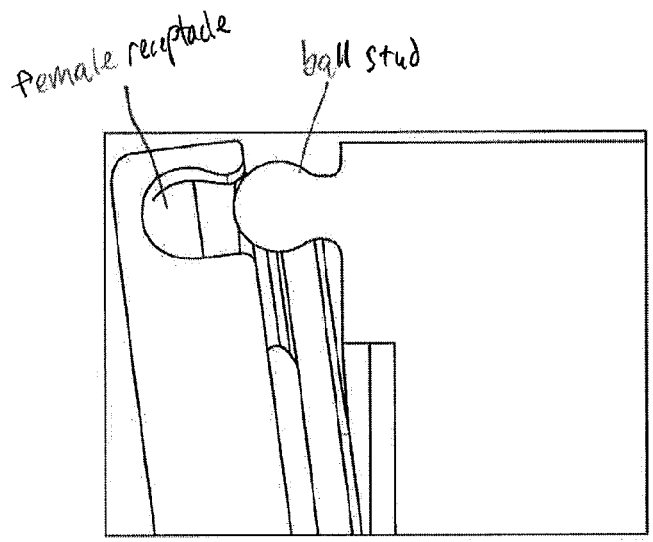
Figure 184B:
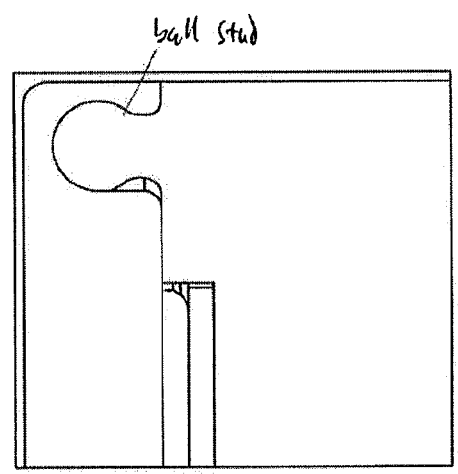

In some embodiments the attachment or latching mechanism can be built into the shape of the battery door and the lid. In some embodiments a ball stud can be used in the battery door with a corresponding female ball stud receptacle in the housing as illustrated in FIGS. 183A-183D. The ball stud protrudes from the battery door and fits into a corresponding recess in the lid housing. The battery door snaps shut and locks into place when the ball stud fits into the corresponding recess in the lid housing. A tool can be slid into a recess in the exterior of the battery door exterior to act as a lever to open the battery door. In some embodiments an attachment mechanism similar to the one illustrated in FIGS. 183A-D is used but with the ball stud protruding from the lid housing with a corresponding female receptacle in the battery chamber door as illustrated in FIGS. 184A-B.

Figure 185A:
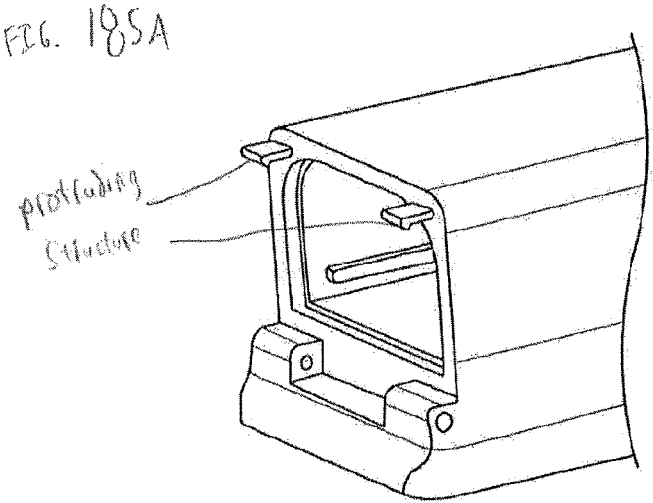
Figure 185B:
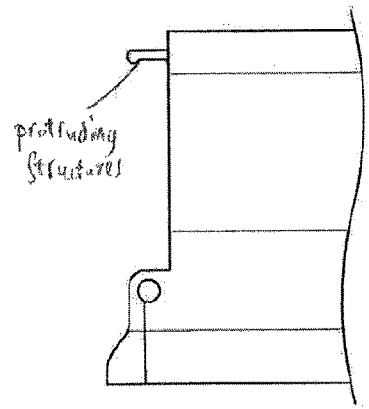
Figure 185C:
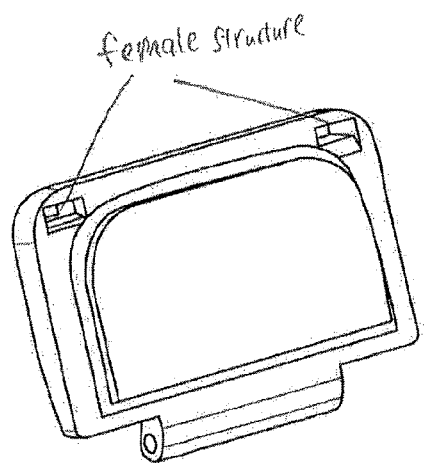
Figure 186A:
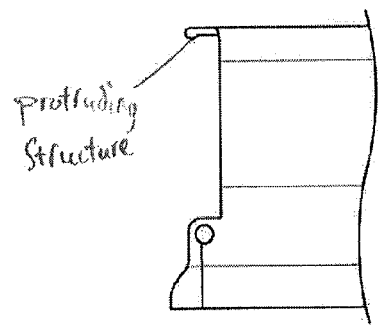
Figure 186B:
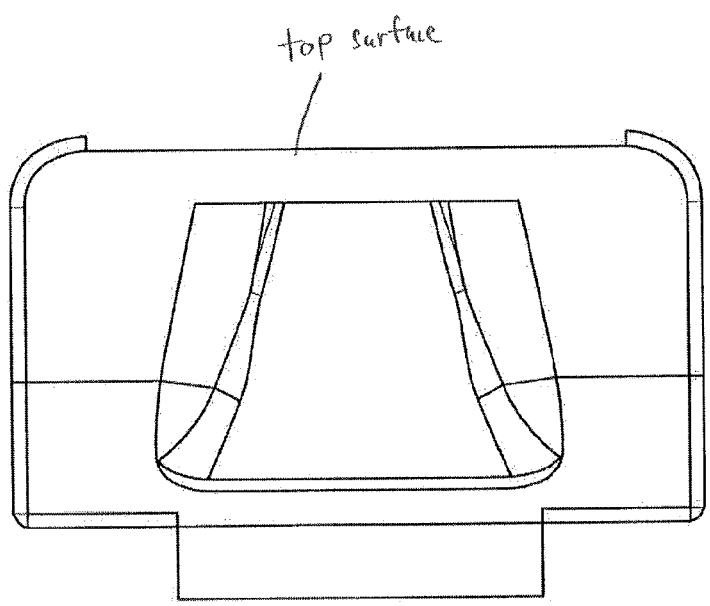
Figure 197A:
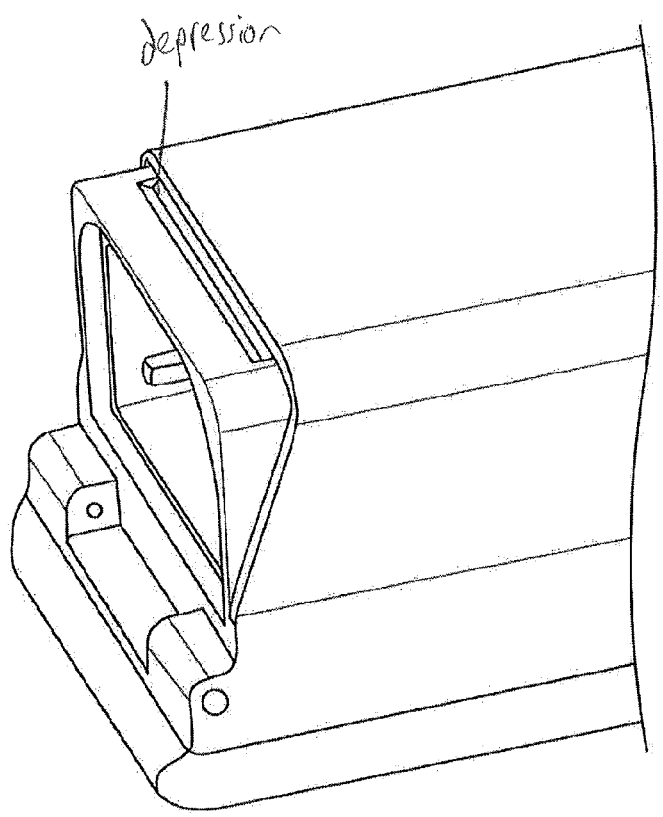
Figure 197B:
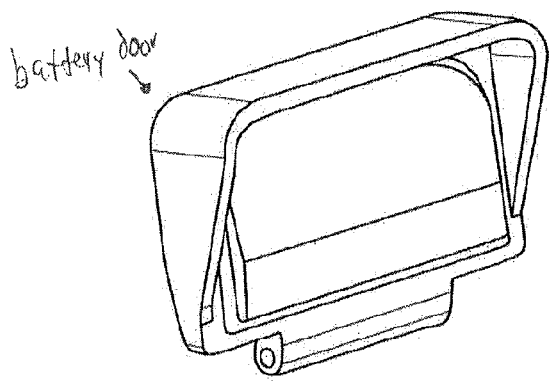
Figure 188A:
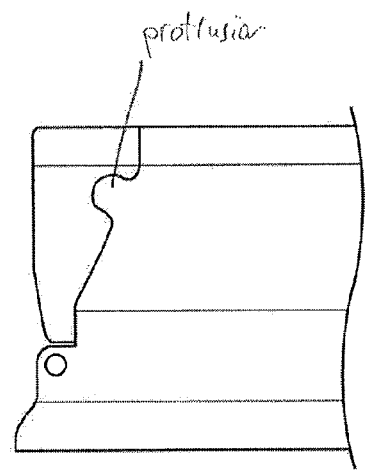
Figure 188B:
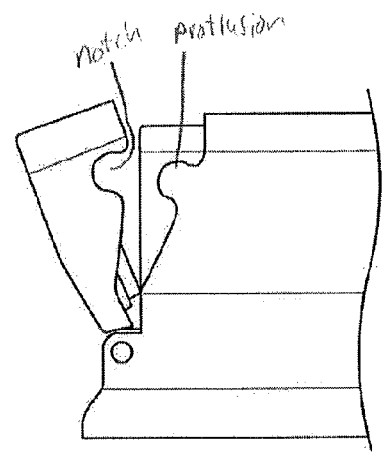

Another embodiment of a battery door attachment mechanism is illustrated in FIGS. 185A-185C. The lid housing has two protruding structures that snap into corresponding receptacles in the battery door. The male structure snaps into the female structure in the battery door to close the battery door. FIGS. 186A-186B illustrates a similar structure with a wider protruding structure that engages with a top surface of the battery door to snap the battery door closed.

In some embodiments the battery door can include a structure that fits into a complementary structure of an external surface of the lid housing. A battery door having a collar design that fits into the lid housing is illustrated in FIGS. 187A-187D. The battery door collar has a cantilever that snaps into engagement with a depression in an exterior of the housing lid to hold the battery door closed.

In some embodiments the battery door can include notches that receive complementary protrusions or projections on the lid housing, as illustrated in FIGS. 188A-188B, 189A-B, and 190A-B. FIGS. 188A-188B, 189A-B, and 190A-B illustrate battery doors having two side notches that engage with projections in the lid housing. The side notches engage with the projections to hold the battery door closed. The side notches illustrated in FIGS. 190A-B have an additional hook structure that further snaps into engagement with the projections in the lid housing to hold the battery door closed.

OTT Battery Insertion Funnel

Figure 192A:
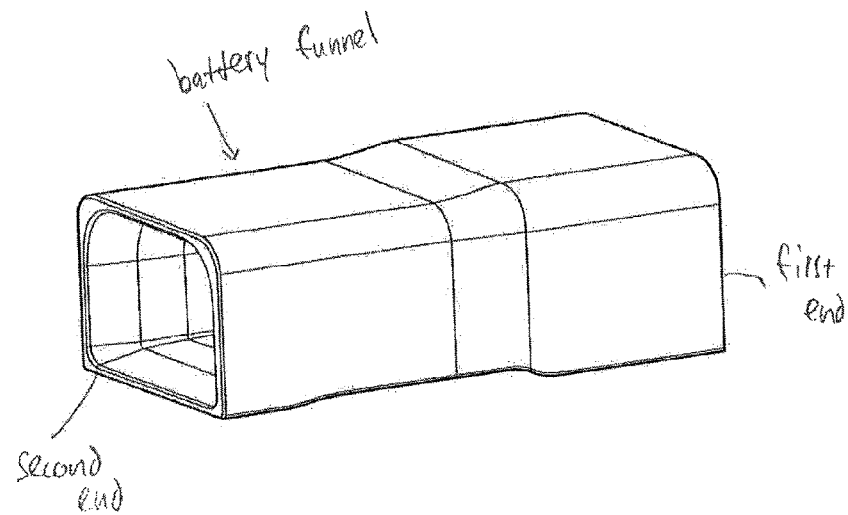
FIGS. 192A-194F illustrate various embodiments of a battery funnel along with methods of use.
Figure 192B:
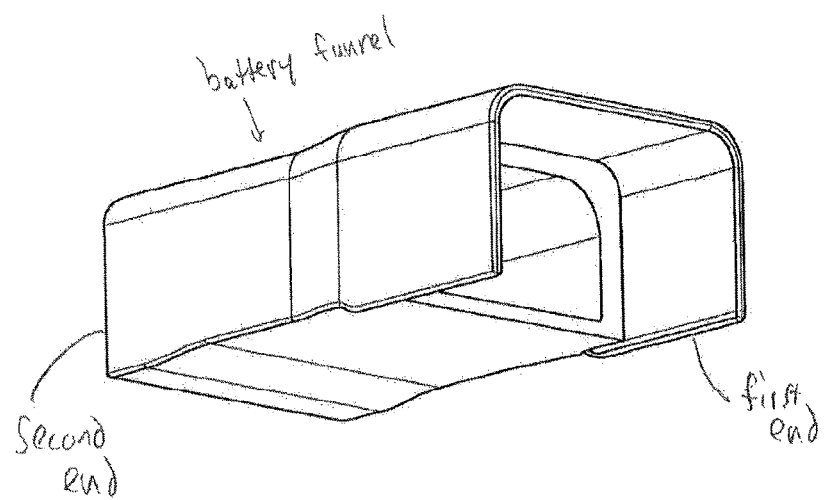
Figure 143A:
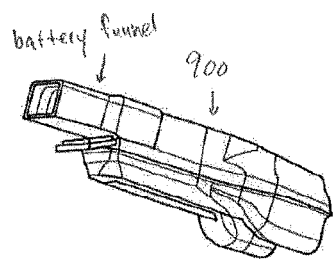

Prior to performing a surgical procedure the on-tool-tracking device can be sterilized as described herein. The battery may or may not be sterilized prior to insertion in the on-tool-tracking device. In some embodiments when a non-sterilized battery is used, the battery can be inserted into the on-tool-tracking device using a disposable sterile component, such as a funnel. The battery chamber door and sealing gasket can then seal the non-sterilized battery from the sterilized operating room environment. The disposable sterile funnel can be used to facilitate the insertion of the non-sterilized battery into the on-tool-tracking device without contaminating the sterilized external housing surfaces. An embodiment of a sterile battery funnel or chute is illustrated in FIGS. 192A-B. The sterile battery funnel has a first end configured to engage with the lid housing. The first end can have an exterior housing with three walls and an open side to allow the sterile battery chute to slide over a portion of the lid housing. The second end of the battery chute opposing the first end is configured with an opening sized to receive the battery. The sterile battery funnel illustrated in FIGS. 192A-B can be modified to engage and work with any of the battery door and battery chamber designs described herein.

Figure 193B:
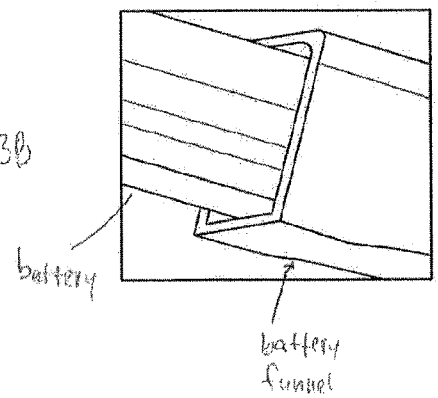
Figure 194A:
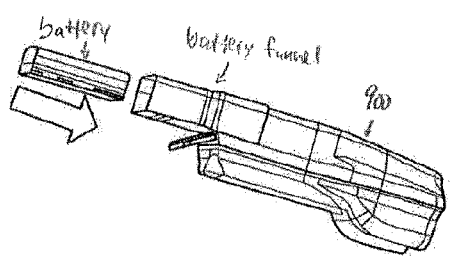
Figure 194B:
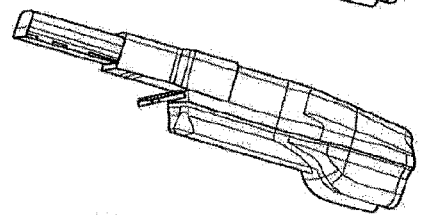
Figure 194C:
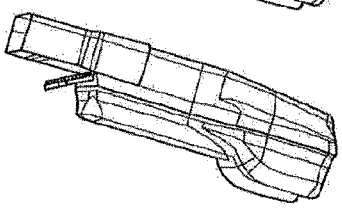
Figure 194D:
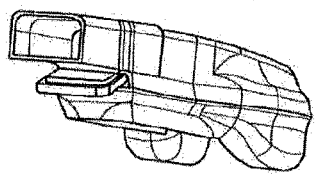
Figure 194E:
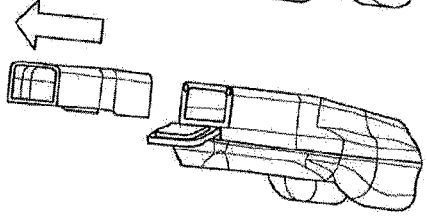
Figure 194F:
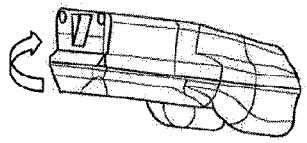

An example of inserting a non-sterile battery into the on-tool-tracking device 900 using the sterile battery funnel is illustrated in FIGS. 193A-B and 194A-194F. The sterile battery funnel is removed from the packaging and slid on to the on-tool-tracking device (FIGS. 193A, 194A). The non-sterile battery is slid into the second end of the battery funnel (FIGS. 193B, 194A-B). The battery slides through an interior volume of the funnel (FIGS. 194C, 194D). The first end of the battery funnel engages the housing lid adjacent to the battery chamber such that the battery does not contact a sterile exterior of the lid housing. The battery proceeds through the interior volume of the on-tool-tracking device into the battery chamber. After the battery is within the battery chamber the funnel slides off of the on-tool-tracking device and can be discarded (FIG. 194E). The battery door is then closed with the non-sterile battery inside the battery chamber (FIG. 194F). The sterile on-tool-tracking device is then ready for use.

OTT Power Management

Figure 107:
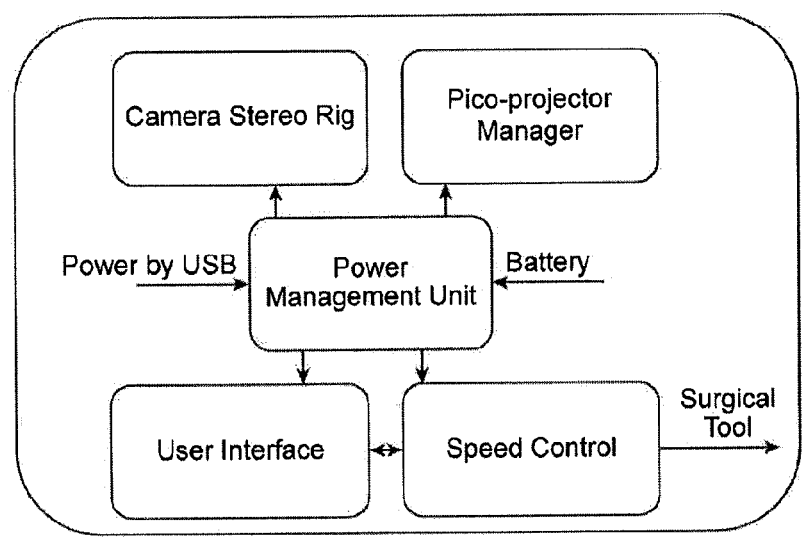
FIG. 107 is a schematic illustration of a power management unit in accordance with some embodiments.

The on tool tracking devices disclosed herein can include a power management system configure to provide power to the components on the device. FIG. 107 is a schematic illustration of a power management unit in accordance with some embodiments. The illustrated power management device is configured to control power to the pair of cameras, projector, user interface, and speed control module. The speed control module sends the signals to control the speed of the surgical instrument.

The power management unit can be configured to control the electrical components of the on tool tracking device and to apply an algorithm that takes into account the voltage, average and peak current to components, average and peak power of all of the components in the on tool tracking device along with the component demands for different processes performed during the computer assisted surgical procedure. The power management unit is also configured to cooperate with the hover CAS processing analysis and steps described herein, for example the processing methodologies illustrated in FIGS. 34-36 and 63-65 and discussed in detail herein. The power management unit is configured to support the specific processing modes described herein to supply the appropriate power levels to each component required for the selected processing mode.

The power management unit can be included on the Y-board assembly. The power management can include multiple voltage regulators at different voltages. The separate voltage regulators can be configured to power different components in the on tool tracking device.

In one example the power management can include a 5V regulator and a 3.3V regulator. The 5V regulator can be configured to power the microcontroller, cameras, projector, wireless transmission module, and other components. The 3.3V regulator can be configured to control wireless transmission module and other components.

Mating the OTT Electronics Module to the Tool with an Integrated Saddle Fitting

In another example, an existing tool is retrofitted and a portion of the tool housing is removed. The saddle is attached as a permanent replacement of the removed surface of the tool and provides governing controls for the motor and other tool functions as available. The outer mating surface of the saddle provides a standardized contour that fits the OTT electronics module. Electrical connectors are positioned on the tool and the module so that they come into contact when the module is locked into position.

"Key Fit" Saddle Variations for the Mating of the OTT Electronics Module

Another embodiment of a two-part OTT device is illustrated in FIG. 70A through FIG. 70G. These examples illustrate how variations in the mating surface of the saddle and the respective OTT electronics module can be used to physically prevent an OTT electronics module from being mated with a tool that is not intended for use with that OTT electronics module.

The need for such a key fit can be applied to a variety of scenarios, including but not limited to, the following examples:

1) A simplified OTT electronics module where providing a key fit for the module is preferable to a more complex OTT electronics module. For example, an OTT electronics module could be devised only for use with a handheld saw, and a separate OTT electronics module could be devised for use with a handheld drill. The key fit contours on the respective mating surfaces of the saddle and saw would ensure that the OTT electronics module for the handheld saw could not be mated with the handheld drill or the other way around.

2) An OTT electronics module that fits a specific revision of a tool. For example, an annual model revision where the physical characters are similar to other models, but specific tuning is still required to ensure optimal performance between the OTT electronics module and the tool.

In one such example, the inner mating surface of the OTT electronics module FIG. 70B includes a shaped channel (7002), which corresponds with a raised surface (7003) on the saddle FIG. 70C. In FIG. 70D, inner mating surface of the OTT electronics module includes a raised surface (7004) that corresponds with a recessed channel (7005) on the saddle FIG. 70E. In this combination of examples, the OTT electronics module would not fit on saddle FIG. 70C, nor would it fit on saddle FIG. 70F or saddle FIG. 70G.

Further variations could be devised to ensure a reliable fit of the OTT electronics module to the appropriate handheld tool and saddle while ensuring that the mating only occurs between the intended OTT electronics module and saddle pair.

In a further example of mating surface variations, the guiding rails on the saddle and the corresponding channels on the OTT electronics module FIG. 69A could be raised or lowered in position, or the saddle could be widened or narrowed, to move the position of the rails thus providing another elements of characteristics that can be manipulated to ensure that only a mating between an intended OTT electronics module and saddle combination can occur.

Additional Options for Governing

In another example, the OTT electronics module and the OTT saddle could provide the means of governing control between the OTT electronics module and the tool without the need for direct electrical contacts. In such an example, the tool could be devised to contain a wireless control module with which the OTT electronics module communicates in order to provide the same governing functions. This wireless module would be connected in line with the tool function circuitry to cut the motor, or slow it, upon receiving an appropriate control signal, wirelessly, from the OTT electronics module.

Electronic Identification & Verification of Electronic Guidance Module when Mated with Handheld Tool Another embodiment of a two-part OTT device is illustrated in FIG. 71A through FIG. 71D. The saddle is the component that has at least one surface for coupling to the tool to be guided by the OTT device. The saddle also includes at least one surface for mating to an OTT electronics module. The OTT electronics module includes the cameras, projector, sensors and other electronics as described herein in FIGS. 1-15B, 53-62B, 74A-C, 75C-G, 76A-B, 77A-D, 78A-78B, 79A-B, 80A-80E, 81A-81E, 82A-82C, 83A-83D, 84A-84C, 85A-85E, 86A-86H, 87A-87F, 90C-E, 91B, 92B, 93B, 95A, 95B, 96A-C, 97A, 97C, 98A, 99B, 100A, 100B, 101B, 102A-C, 103A-B, 104C-E, 112A, 112D, 116A-116C, 117A-D, 118A-C, 119A-B, 120A-120B, 122, 123, 124, 126, 128-130, 132, 133A-B, 134, 136A-136C, 137, 146A-146E, 147A-C, 148A-148D, 149A-149C, 150A-F, 151B-G, 154, 155A-D, 156A-156D, 157A-157E, 158A-B, 159A-B, 160B, 161, 162A-D, 163, 164A-B, 165A, 166B, 167B, 167C, 168A-C, 169A-B, 170B, 173A-173B, 174A-174B, 174C, 175A, 176B-C, 177B, 178A, 178B, 179C, 179D, 190A, and 190B. In the examples that follow, a plurality of alternative mechanical, electrical and mechanical and electrical connections are possible between the two components. A wide variety of different functions are made possible by the mating of these two OTT device components. Some functions relate to the use of the OTT device and the tool and others relate to the overall OTT CAS system operation. These and other details will be appreciated in the description and figures that follow.

In this embodiment, there is recognized a need to provide verification when an OTT electronics module is fitted to the saddle of a tool. This verification includes information that the OTT electronics module that is being mated with the type of tool it is expecting and that the OTT electronics module is authentic and not a forgery or an unlicensed device.

Figure 71A:
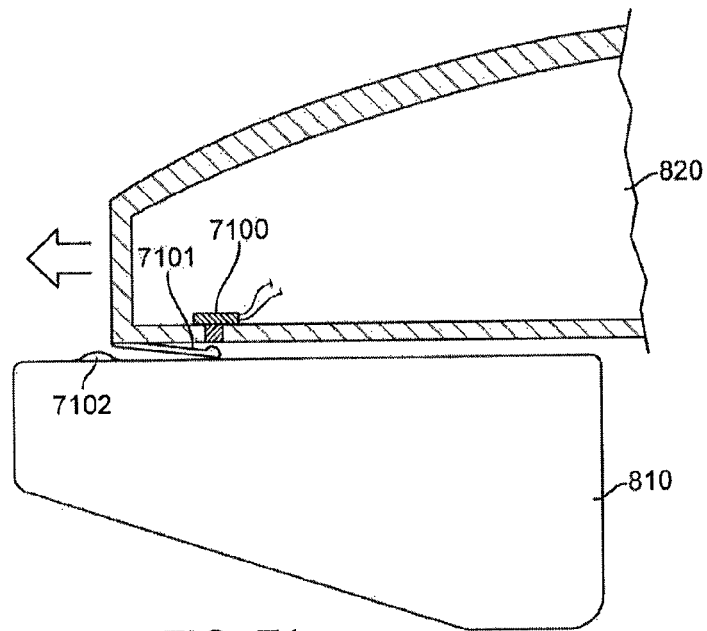
Figure 71B:
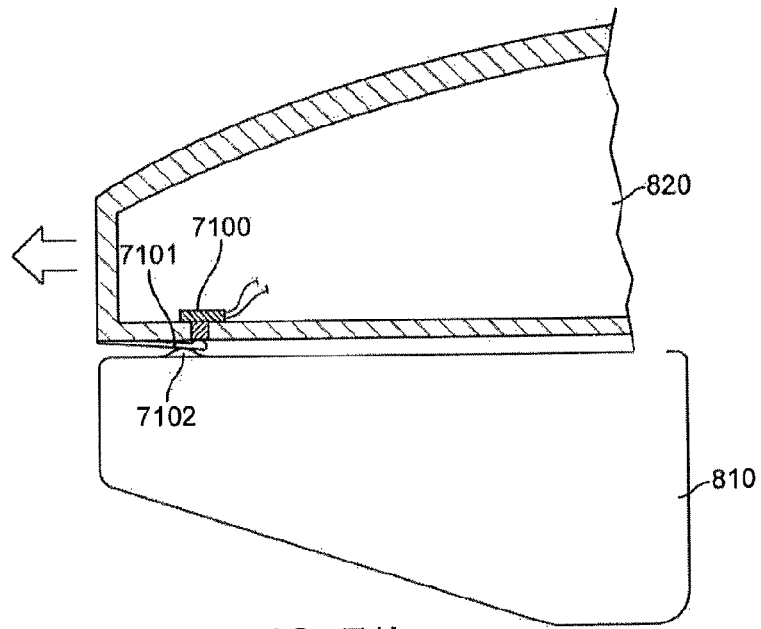

In one example, a surface feature, such as a bump (7102), can be added to activate a switch (7100) found on the mating surface of the OTT electronics module (820). As shown in FIG. 71A, the surface feature or "bump" (7102) is located on the saddle (810), while a cantilever (7101) is positioned on the OTT electronics module. As the OTT electronics module is positioned to mate with the saddle FIG. 71A, the bump pushes on the cantilever when the two features come into contact FIG. 71B. As the cantilever on the OTT electronics module raises in response to coming in contact with the bump, it depresses a switch located inside the OTT electronics module housing. This switch can provide a simple signal to positively confirm a proper mating, or can be used in more complex embodiments as described below.

Figure 71C:
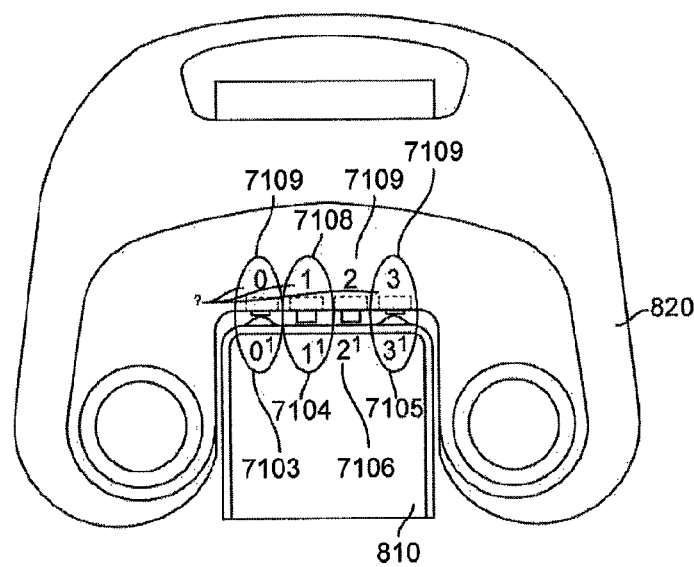

In a further example using the combination of "bump" and cantilever-activated switch described above, multiple bumps and switches can be positioned in a similar way to provide a binary code for use by the OTT electronics module and the OTT CAS system. In FIG. 71C, positions are indicated for four bumps on the saddle (7103, 0'; 7104, 1'; 7105, 2'; 7106, 3'), which correspond in position with four cantilever-activated switches found on the inner mating surface of the OTT electronics module (7107, 0; 7108, 1; 7109, 2; 7110, 3). In the example illustrated in FIG. 71C, there are bumps on the saddle in positions 0' (7103) and 3' (7106). When the OTT electronics module is properly mated with the saddle, switches 0 (7107) and 3 (7110) are therefore activated. The OTT electronics module could interpret this series of switches as a binary reading of '1001'. As described above, this signal can be used to positively signify a proper mating between a saddle and OTT electronics module. This signal can also be used to indicate what type of tool the OTT electronics module has been mated to. For example, a binary value of '1001' could be used to signify a handheld drill while a binary value of '1100' could be used to signify a handheld oscillating saw. It should be noted that the number of bump and cantilever-activated switches used can be altered depending on the number of binary digits desired.

In an alternative embodiment to the above examples, a magnet could be used to replace the bump (7102) and a magnetic reed switch could be used to replace the combination of switch (7100) and cantilever (7101). In such an embodiment, the contact of the reed switch closes a circuit when the OTT electronics module and the saddle are properly mated, thus bringing the reed switch into close proximity with the corresponding magnet on the saddle.

While the uses of the bumps and switches is a useful method for providing simple electronic feedback and unique identifiers, it may be desirous to provide a more sophisticated signaling system between the saddle and the OTT electronics module. To facilitate this, an embodiment may provide electrical contacts, which complete a circuit that may contain various components, including by not limited to, logic processors, RAM, nonvolatile storage, and sensors.

Figure 71D:
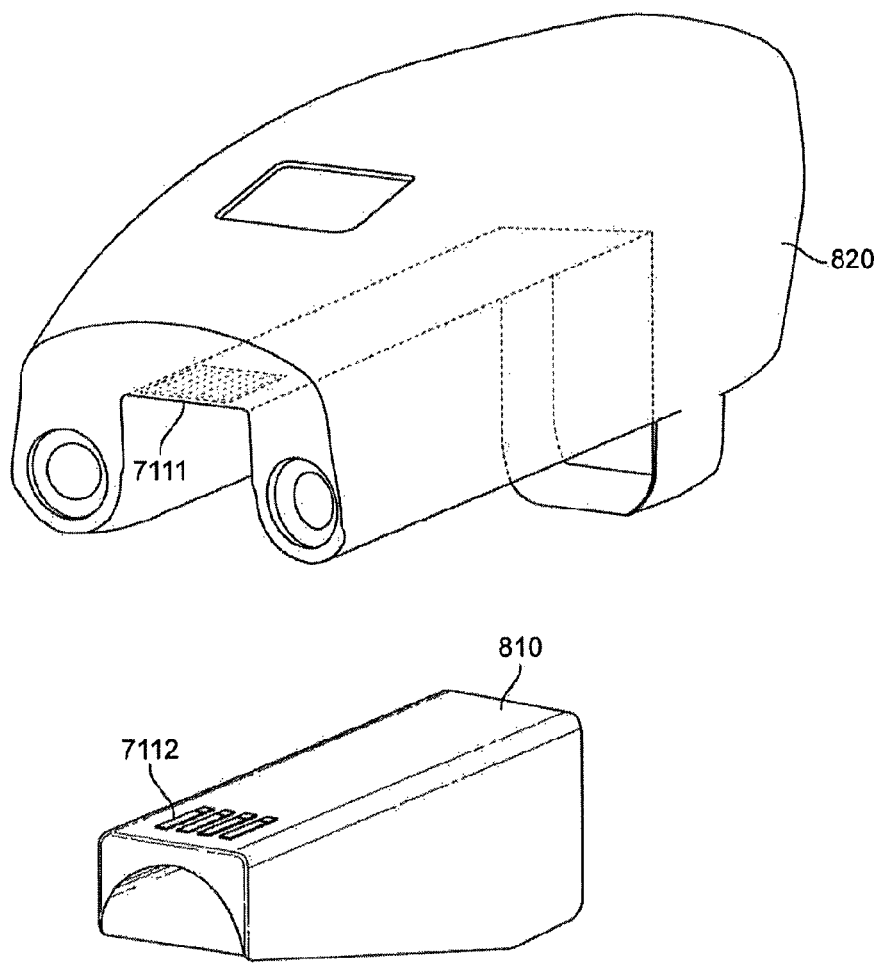

In one example FIG. 71D, the electrical connection points can be implemented through a series of exposed contacts on one mating surface (7111) and surface mounted spring contacts on the second surface (7112). As the OTT electronics module (820) and the saddle (810) are mated, the contacts meet and are held into place by the pressure applied by the spring contacts. When the OTT electronics module is powered on, the circuitry joined by these connections is activated, and the results are evaluated by the on board processor of the OTT electronics module.

In the OTT electronics module and the saddle there are electrical connection points and associated electronics to provide an electronic exchange of data between the saddle portion of a handheld tool with a computer guided module for use in computer aided surgery.

In one embodiment, circuitry found on the OTT electronics package and/or the saddle contains a logic element for determining both the type of tool to which the module has been mated as well as determining the authenticity and licensing of the system prior to use, and some sort of persistent, nonvolatile memory including but not limited to FLASH memory, a "fusible-link" PROM, or a UV-erasable PROM associated with and connected to the logic element for maintaining a log of connection attempts and usage statistics.

The type of persistent, nonvolatile memory selection used depends on the type of data to be stored. For example, metering usage in the form of times powered on or activated for a individual case could be stored in a "fusible-link" PROM. This form of storage is substantially permanent and suitable for maintaining a simple count. However, it may be impractical for larger arrays of data that are not required for unchangeable storage. One such example, includes saved device telemetry, or a metering of times, when on board devices like the projector and the cameras are switched on and off. Such data, useful for diagnostics and archiving, would be better stored in a small amount of FLASH memory.

In an example where different OTT electronics modules are made to specifically mate to a tool with which it is to be used, this validation provides additional assurance to the system that the mating is correct. In other words, the OTT electronics module would receive positive confirmation about which brand or type of tool with which it has been mated. If, for example, the OTT electronics module is mated with a drill and is expecting to be mated with a saw, the verification process will fail and the OTT electronics module will generate an error through the computer software and the operating workstation.

In an example, where the module can be mated with any tool, this validation, or handshake, provides a level of assurance that the expected tool is mated correctly with the module. The verification procedure during the mating process would, for example, identify that the OTT electronics module has been mated with a drill. This confirmation would be logged through the computer software and the operating workstation for any desired purposes of accountability, verification or analysis.

Additionally, there may be a need to verify the authenticity of the device to ensure protection against forgery, or the use of an "expired" or unlicensed device. One example of how to accomplish this is through the use of circuitry which is found on the saddle and the OTT electronics module. When mated, the OTT electronics module looks for an expected indication of variables including but not limited to the identification of the tool type and its brand, and other identifying characteristics, and a handshake, through the use of examples including but not limited to encrypted data, an embedded serial number, or a electronic signature or key that authenticates the device for use.

In the figure, the saddle and the OTT electronics module include connecting pins along the respective mating surfaces. When the OTT electronics module is mated with the saddle by sliding the two pieces together, these pins come into contact, and complete an electrical connection which connects electronic circuitry between the two devices. This circuitry may include a series of resistors, a CPU, RAM or an FPGA as well as persistent, nonvolatile storage including but not limited to FLASH, a "fusible-link" PROM or a UV-erasable PROM.

In one alternative implementation, the identification and validation circuitry may also contain an example of persistent, nonvolatile storage like FLASH memory a "fusible-link" PROM or a UV-erasable PROM to save data related to the usage of the device. This information may include, but is not limited to, the number of activations of the OTT electronics module, the number of battery exchanges, software version or revision setting, the total time of camera operation, the total time of projector operation, and total time powered on.

In one example, a fusible-link PROM is used for storing the number of times the OTT electronics module has been used. Each time the device is powered on, or activated for a procedure, a portion of memory is then "burned into" a set position on the fusible-link PROM. For simple counting, this could be a single bit location of the fusible-link PROM. This is done in a fashion similar to the way an electronic vehicle odometer stores miles. This type of storage is substantially permanent and cannot be "rolled back." Each time, one of the embedded fuses making up the fusible-link PROM is "burned out," the process cannot be undone. This use of a fusible-link PROM or other similar functioning electronic use device would allow the total uses of the module to be logged and the module can be "expired" after a pre-determined number of uses with limited risk of tampering.

Visual Tool Tip and Cutting Surface Recognition and Registration

Figure 72:
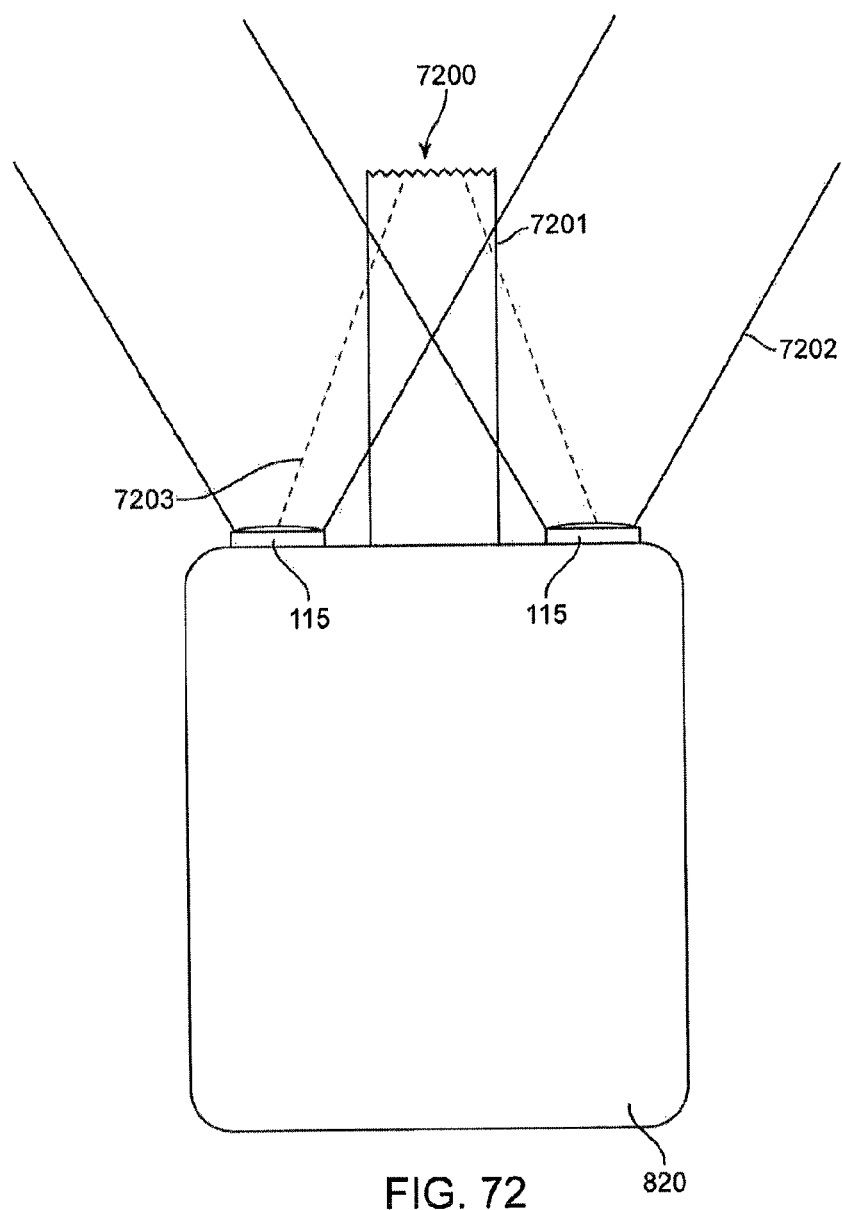

Another embodiment of a two-part OTT device is illustrated in FIG. 72. When the OTT electronics module (820) is mated with a tool, it becomes the guidance system for the cutting surfaces of the tool. For the purpose of verification and to provide additional safety measures for the operation of the systems it may be necessary to verify the type of cutting instrument to which the OTT electronics module has been mated. This method of verification and evaluation may be used in conjunction with other OTT embodiments and OTT CAS systems and operations described herein.

Using the stereo cameras (115) contained within the OTT electronics package, the tip and boundaries of the tool (7200) is visible (7203) within the field of view (7202) of the cameras. When the OTT electronics module is mated with the saddle of the tool, the OTT electronics module is powered on and initialized. During this initialization the images seen by each of the cameras is transmitted to the software package on the computer workstation.

The images are compared to the known geometry of possible tool types, including but not limited to, an oscillating saw or a drill. Relative to these two examples, the tip of the saw and the tip of the drill are calculated based on the view of the cameras and validated against the computer model associated with the respective tool.

In addition or alternatively, any of the OTT modules described herein may be modified to have additional functionality. For example, an OTT may be modified to include a display. Alternatively, the OTT may be adapted to work with a remote control to drive the main system, such as, for example, to run via an iPod, an iPad or other iOS or Android (smart phone like) device that may be removably mounted on the OTT. In other aspects, such an OTT may be described as an OTT tablet. Still further aspects of an OTT as described herein may be modified to include a new case format, a battery funnel and/or a clipping mechanism.

In still other aspects, the system operation may be modified to include the use of the OTT projector as a method of registration for navigation using an OTT enabled system. In still other aspects, there is provided a divot on one or more reference frames. In other aspects, the operation of the system or the use of an OTT enabled freehand surgical tool may be modified for use with on-bone tracking.

FIG. 73A: Illustrates the physical characteristics of a projector, with a body, a projection window or opening, and the 'projection cone' that results on a truncated pyramid volume, with the base growing larger as we move farther away from the projection opening.

FIG. 73B (left): Schematic representation of a frontal view of the projection opening. It illustrates the two main dimensions (w: width and h: height), which are two of the parameters that define the projection characteristics. While the dimension of the opening of the casing does not necessarily influence the shape of the 'projection cone', it can influence it in some cases depending on the distance and physical dimensions of the light emitting source.

FIG. 73B (right): Schematic representation of a side view of the projection opening and the projection cone. $\alpha$ and $\alpha'$ (usually the same) are the angles of the projected cone (or components of the projected angle) that define the vertical increase of the projected image along the a axis of the light beam.

Figure 73C:
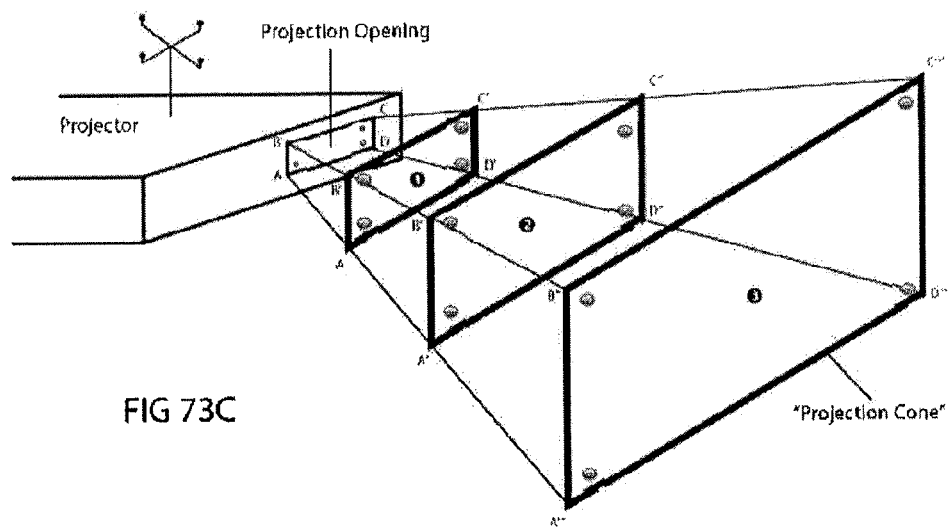

FIG. 73C: Illustrates the variation of the image size and the relative appearance of four calibration points (A, B, C, and D) while arbitrary increasing distances and changing orientation of the projected image. By indicating the position in 3D of the projected points A', B', C' and D'; A", B", C" and D"; etc., (e.g. with a navigated pointer) to calculate the projector's registration matrix as explained in the body of the invention.

Figure 73D:
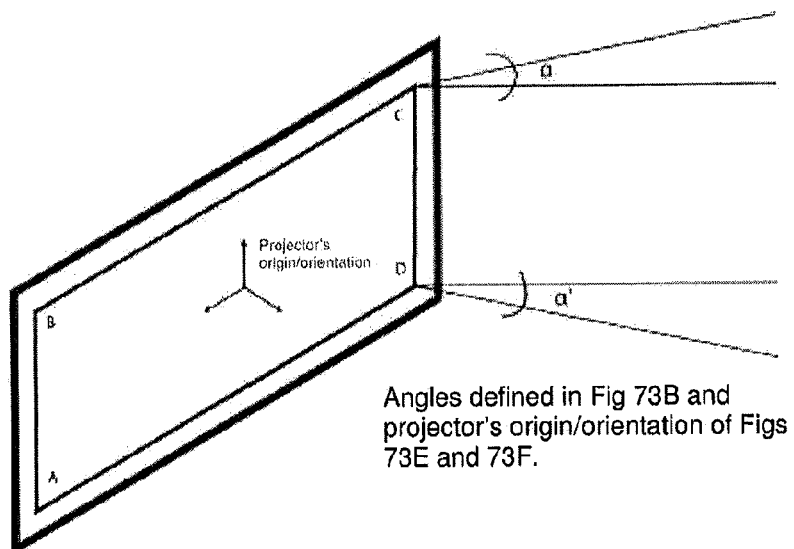

FIG. 73D: Schematic representation of the front of the projector (in pseudo-perspective) with the four calibration points A to D. It illustrates how the center of these points will vary in the vertical aspect (angles α and α') with the increase of the distance from the projector. The xyz coordinate axis in the middle illustrates the origin and orientation assigned to the projector for the calculations.

Figure 73E:
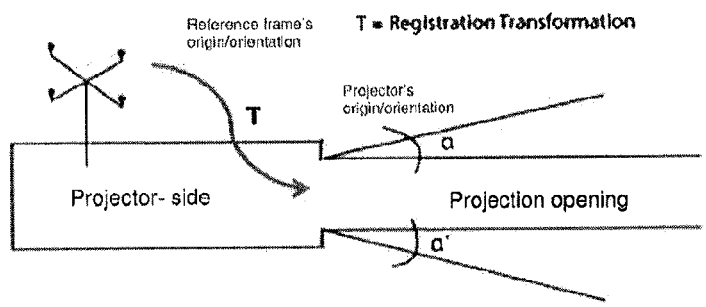

FIG. 73E: Schematic representation of the projector's side view, with a reference frame attached to it for tracking in 3D and indicates. The xyz coordinate axis on the reference frame indicates the reference frame's origin and orientation, assign to it by the navigation module. The xyz coordinate axis on the projection opening of the projector, indicates the origin and orientation assigned (arbitrarily by us) to the projector for our calculations. T represents the transformation matrix that maps one coordinate system to another.

Figure 73F:
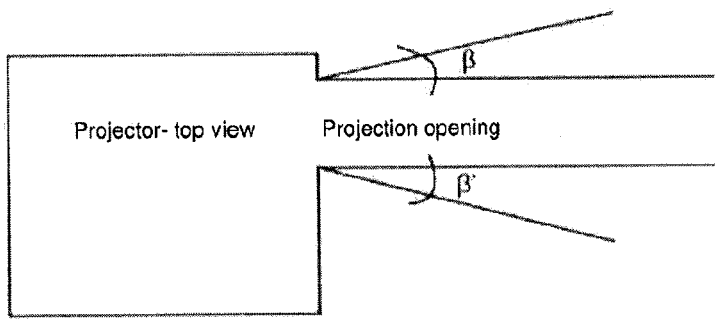

FIG. 73F (right): Schematic representation of the projector's top view and the projection opening. β and β' (usually the same) are the angles of the projected cone (or components of the projected angle) that define the horizontal increase of the projected image along the a axis of the light beam.

In addition or alternatively, any of the OTT modules described herein may be modified to have additional functionality. For example, an OTT may be modified to include a display. Alternatively, the OTT may be adapted to work with a remote control to drive the main system, such as, for example, to run via an iPod, an iPad or other iOS or Android (or smart phone like) device that may be removably mounted on the OTT, or embedded (inserted/clipped) into a recess on the top surface of the OTT device. In other aspects, such an OTT may be described as an OTT tablet. In one embodiment, an OTT module may have a screen (eg. color LCD type) or other display incorporated into a surface of the OTT housing. In an alternative embodiment, a display is provided as a detachable item. In one embodiment, the display runs on an iOS implementation and runs on iPod, iPads, etc. In addition or alternatively, an iPod or other device can be used as a 'remote control' to drive the main system. That is, the remote control device can be on-board the OTT device, or just loose. In use, an iPod, iPad or smart phone like device for this purpose is placed in a sterile bag and put it in the surgical scene, so the surgeon and/or nurse can drive the system settings from there.

Portable Display Screen

The attached screen is currently embodied as an iPhone and could be any other similarly-sized smart phone, such as a Droid or Blackberry, or a custom built touch display.

Attached to the saw, the display is typically intended for use with an attitude and offset distance display. It can also utilize a 3D rendering engine software and show 3D surface or volumetric models and provide the same guidance and selection of viewing parameters as specified in the automatic selection of view. The display can also show a mixture of 2D guidance graphs or schematics to give 3D guidance for location and orientation of the power tool on one part of the LCD screen (e.g. of the iPhone), while on the part of the screen a 3D scene is provided rendering the guidance in a 3D manner. The LCD screen can also provide a textual menu to communicate commands with the main CAS system computer, or to display or make choices by the user to the system. Both the guidance sections on the LCD screen (3D panel, and 2D panel, and the menu panel) can have borders or no borders, and can be scaled to occupy different sizes on the screen along with border dragging and scaling and textual menu choices.

Additionally, the user can move the model on the screen. Such changes are analogous to the view on the main OTT CAS screen with the advantage being the closer proximity of the attached screen compared to the terminal screen, and the implications of touching screens in the sterile environment versus main computer screens which may (optionally) or may not be sterile or conveniently close to the surgeon or assistant.

In another example, the view, or any parameters of the display, can be changed by using the touch screen interface.

The attached screen can also be removed and used as a detached display or as a remote control device.

In still another aspect, there is provided methods of using the pico projector or other projector onboard the OTT for use in an automatic, or semi-automatic bone registration technique. In one aspect, there is provided a method for calculating or determining the bone registration matrix in the context of OTT using reference frames. This can be implemented as a combination of the 3D tracking described for OTT and a dynamic 3D scanning process such as those used in commercially available image processing and tracking processes.

In one aspect, such an OTT based registration process or technique includes the steps of:

a) Obtaining a 3D model of the anatomy (e.g. bone), usually during pre-surgical planning. For example, on an image-based setup, this can be done as 3D reconstruction from the patient's computer tomography (CT) or Magnetic resonance Imaging (MRI), data or through morphing (scaling) of a generalized bone from an atlas.

b) Attaching a tracking reference frame to the bone. The tracking reference frame is visible to the OTT cameras.

c) Performing a 3D scanning of the anatomy (e.g. bone) surface by using OTT's projector to project a pattern (e.g. point(s), line(s), grid(s), text, figures (sprites), etc.) on the surface of interest and OTT's camera(s) system to capture and process the reflection of the lights on the surface of interest.

d) Simultaneously with c), the tracking in 3D the reference frame attached to the object of interest (e.g. bone), using any of the techniques described herein. While OTT cameras are used for both processes, 3D scanning and tracking, one example of how to coordinate the two processes is by switching from one function to another at high rate, and pairing each 3D scanning data sampling with a 3D tracking position/orientation.

e) Based on data from c) and d), obtaining a surface model of the anatomy (e.g. bone) surface positioned and oriented relative to the reference frame attached to the object of interest (e.g. bone).

f) Surface matching a) and c). This process calculates a transformation matrix that matches one surface into the other. The process can be done manually (with user graphical intervention or verification) or with various levels of automation. The latter harnesses image processing and pattern recognition and matching routines using correlation or other known techniques.

g) Calculating final anatomy (e.g. bone) registration matrix combining e) and f).

The process described above may be modified or enhanced using a number of different variations. Some variations of the steps outlined above include, by way of illustration and not limitation: (a) using pico projector for bone registration is similar to the steps above but optionally includes using different wavelengths filters to optimize step d); or (b) using pico projector for bone registration is similar to the steps above but optionally includes using the known anatomy shape from a) to optimize 3D scanning process on c).

OTT Tracking without Reference Frames

In this alternative embodiment, an OTT system is adapted and configured for performing reference frame-free 3D tracking with OTT. In one aspect, there is the step of projecting a known pattern with the projector (e.g. mono- or multi-chrome, infrared, etc. point(s), line(s), grid(s), etc.) on a known geometry (e.g. bone), and applying image recognition and computer vision algorithms on the reflected light to track the position and orientation of the object of interest (e.g. bone) in 3D (e.g. relative to OTT's internal origin and coordinate system). This may be considered a form of using a projected grid for navigation. One method for implementing such a freehand surgical navigation technique includes, by way of example and not limitation:

a) Obtaining a 3D model of the anatomy (e.g. bone), usually during pre-surgical planning. For example, on an image-based setup, this can be done as 3D reconstruction from the patient's computer tomography (CT) data or other methods mentioned above.
b) Dynamically projecting a known pattern with the projector (e.g. mono- or multi-chrome, infrared, etc. point(s), line(s), grid(s), etc.) on the real patient's anatomy (e.g. bone).
c) Applying image recognition and computer vision algorithms (as well as techniques presented in 2) on the images projected on the anatomy (e.g. bone) to calculate its position and orientation in space.

The process described above may be modified or enhanced using a number of different variations. Some variations of the steps outlined above include, by way of illustration and not limitation: (a) using OTT's projector for both, 3D tracking and displaying information to guide the user during cutting, drilling, etc., the system uses different color schemes to two sets of images to avoid interfering with the image processing, as well as interfering with the users' interpretation of the projected guidance; (b) using emitted infrared light for tracking patterns to avoid interfering with the users' interpretation of the visible light projected guidance; (c) using OTT's switches from grid to guidance at high rate to create a stroboscopic effect, but still preventing the two processes (object tracking and user guidance) from interfering with each other.

Multiple Reference Frames

For a particular surgical case there may not be a single location for the bone's reference frame where the instrument with the cameras can 'see' it from any location required for cutting (or drilling, or filing, etc.). In such cases, one can use a 'combination' reference frame (multi-faced): A single registration process (using any of the faces) allows the system to track the object afterwards regardless of which of the faces is visible at the time. Notwithstanding, any element of the indicator subsystem could readily be used for any approach to computer assisted surgery wherein the computer assisted surgery system establishes both the location of the tool in three dimensions and calculates where, according to a surgical plan, the surgeon intends to make a resection. In one alternative aspect, the methods, systems and procedures described herein are modified to incorporate one or more of the techniques, devices or methods described in U.S. Non Provisional patent application Ser. No. 11/764,505 filed on Jun. 18, 2007 and published as US 2008/0009697 entitled "Method and Apparatus for Computer Aided Surgery," the entirety of which is incorporated herein for all purposes.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An on tool tracking and guidance device, comprising:
   a housing having a surface for engagement with a surface on a saddle;
   a pair of cameras within or coupled to the housing wherein when the housing is coupled to the saddle the pair of cameras are in position to provide an image output having a field of view including at least a portion of an active element of a surgical tool coupled to the saddle;
   a display on the housing;
   an electronic image processor within or in communication with the housing configured to receive an output from the pair of cameras and perform an image processing operation using at least a portion of the output from the pair of cameras in furtherance of at least one step of a computer assisted surgery procedure; and
   a communication element within the housing configured to provide information related to the image processing operation to a component separate from the housing, wherein the communication element is configured to provide information wirelessly, by Bluetooth, by WiFi, or by ultra-wideband technology,
   wherein the on tool tracking device is configured to determine a computer aided surgery (CAS) processing mode based upon an evaluation of one or more of: a physical parameter within the surgical field such as a position or a combination of positions of one or more elements tracked in the field through reference frames attached to the one or more elements, a reference frame input, a projected image, a motion detected from a sensor, a motion detection from a calculation, the overall progress of a computer aided surgery procedure, a measured or predicted deviation from a previously prepared computer aided surgery plan wherein the CAS processing mode is selected from one of a number of predefined processing modes including a hover mode, a site approach mode, and an active step mode.

2. The on tool tracking and guidance device of claim 1 wherein the display includes a touch screen.

3. The on tool tracking and guidance device of claim 2 wherein the display is configured to provide a visual output comprising information from an on tool tracking CAS processing step or to provide guidance to a user of the surgical tool related to a CAS step or to provide guidance to a user of the surgical tool to adjust the speed of the surgical tool or to provide guidance to a user of the surgical tool related to CAS data collected by the on tool tracking device and assessed during the CAS procedure.

4. The on tool tracking and guidance device of claim 1 wherein the on tool tracking device is further configured to collect and process computer assisted surgery data; and the on tool tracking device or a processing system in communication with the on tool tracking device is configured to assess the CAS data in real time during the computer assisted surgery procedure.

5. The on tool tracking and guidance device of claim 4 wherein assessing the CAS data includes a comparison of data received from the on tool tracking device and data provided using a computer assisted surgery surgical plan.

6. The on tool tracking and guidance device of claim 1 wherein the on tool tracking device is configured to process data related to one or more of visual data from the pair of cameras, data from a sensor on the on tool tracking device, and data related to an operational characteristic of the surgical tool.

7. The on tool tracking and guidance device of claim 1 wherein the surgical tool is configured to receive a control signal from the on tool tracking device to adjust a performance parameter of the surgical tool based on the CAS data.

8. The on tool tracking and guidance device of claim 7 further comprising: an electronic interface between the on tool tracking device and the surgical tool to send the control signal from the on tool tracking device to the surgical tool to control the operation of the surgical tool, wherein the performance parameter includes modifying a tool cutting speed or stopping a tool operation.

9. The on tool tracking and guidance device of claim 1, further comprising: a projector within or coupled to the housing configured to provide an output at least partially within the field of view of the pair of cameras.

10. The on tool tracking and guidance device of claim 9 wherein the electronic image processor within or in communication with the housing is configured to generate an output to the projector based on the image processing operation, a step related to a computer assisted surgery procedure, an interaction with the display or a step of a freehand navigated computer assisted surgery procedure.

11. The on tool tracking and guidance device of claim 9 wherein the output from the projector is adapted for projection on a portion of the patient's anatomy.

12. The on tool tracking and guidance device of claim 1 wherein the computer assisted surgery procedure is a freehand navigated computer assisted surgery procedure.

13. The on tool tracking and guidance device of claim 1 further comprising: a second pair of cameras within or coupled to the housing wherein when the housing is coupled to the saddle the pair of cameras or the second pair of cameras are in position to provide an image output having a field of view including at least a portion of an active element of a surgical tool coupled to the saddle.

14. The on tool tracking and guidance device of claim 13 wherein the pair of cameras or the second pair of cameras comprises a physical or electronic filter for viewing within the infrared spectrum.

15. The on tool tracking and guidance device of claim 1 wherein the pair of cameras comprises a physical or electronic filter for viewing within the infrared spectrum.

16. The on tool tracking and guidance device of claim 1 wherein the saddle is shaped to form a complementary curve with a portion of the surgical tool.

17. The on tool tracking and guidance device of claim 1 wherein the saddle provides releasable mechanical engagement between the housing and the surgical tool.

18. The on tool tracking and guidance device of claim 1 wherein the saddle provides releasable electrical engagement between the housing and the surgical tool.

19. The on tool tracking and guidance device of claim 1 wherein when the housing is coupled to the saddle the at least a portion of the active segment of the surgical tool comprised the distal most portion of the active element.

20. The on tool tracking and guidance device of claim 1 wherein the visual axis of the first camera of the pair of camera and the visual axis of the second camera of the pair of camera are inclined at an angle of between about 0° to about 20° relative to a line generally parallel to a longitudinal axis of the active element.

* * * * *